US012540131B2

(12) United States Patent
Keylor et al.

(10) Patent No.: US 12,540,131 B2
(45) Date of Patent: Feb. 3, 2026

(54) N-(HETEROARYL) QUINAZOLIN-2-AMINE DERIVATIVES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: Mitchell H. Keylor, Malden, MA (US); Michael J. Ardolino, Arlington, MA (US); Ryan W. Chau, Somerville, MA (US); Peter H. Fuller, Ashland, MA (US); Anmol Gulati, Watertown, MA (US); Rebecca Elizabeth Johnson, Oakland, CA (US); Solomon D. Kattar, Wakefield, MA (US); Kaila A. Margrey, Cambridge, MA (US); Gregori J. Morriello, Randolph, NJ (US); Santhosh F. Neelamkavil, Edison, NJ (US); Xin Yan, Newton, MA (US); Elsie C. Yu, Brighton, MA (US); Cayetana Carmela Zarate Saez, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 876 days.

(21) Appl. No.: 17/769,814

(22) PCT Filed: Oct. 20, 2020

(86) PCT No.: PCT/US2020/056401
§ 371 (c)(1),
(2) Date: Apr. 18, 2022

(87) PCT Pub. No.: WO2021/080929
PCT Pub. Date: Apr. 29, 2021

(65) Prior Publication Data

US 2023/0023066 A1 Jan. 26, 2023

Related U.S. Application Data

(60) Provisional application No. 62/926,033, filed on Oct. 25, 2019.

(51) Int. Cl.

| | |
|---|---|
| ***C07D 403/14*** | (2006.01) |
| ***C07D 401/14*** | (2006.01) |
| ***C07D 403/12*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |

(52) U.S. Cl.
CPC ......... *C07D 403/14* (2013.01); *C07D 401/14* (2013.01); *C07D 403/12* (2013.01); *C07D 405/14* (2013.01); *C07D 409/14* (2013.01); *C07D 413/14* (2013.01); *C07D 417/14* (2013.01)

(58) Field of Classification Search
CPC .. C07D 403/14; C07D 401/14; C07D 403/12; C07D 405/14; C07D 409/14; C07D 413/14; C07D 417/14
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |

(Continued)

FOREIGN PATENT DOCUMENTS

| | | | |
|---|---|---|---|
| WO | 2007071348 | A1 | 6/2007 |
| WO | 2007149798 | A2 | 12/2007 |

(Continued)

OTHER PUBLICATIONS

Abdel-Magid, ACS Medicinal Chemistry Letters, Oct. 2019, 846-847 (Year: 2019).*

(Continued)

*Primary Examiner* — Andrew D Kosar
*Assistant Examiner* — Phillip Matthew Rzeczycki
(74) *Attorney, Agent, or Firm* — Sylvia A. Ayler; Catherine D. Fitch

(57) ABSTRACT

The present invention is directed to substituted certain N-(heteroaryl)quinazolin-2-amine derivatives of Formula (I): and pharmaceutically acceptable salts thereof, wherein J, $R^3$, and $R^4$, are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of diseases, such as Parkinson's disease, in which LRRK-2 kinase is involved.

(I)

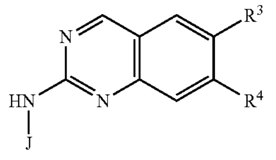

18 Claims, No Drawings

(56) References Cited

U.S. PATENT DOCUMENTS

| | | | | |
|---|---|---|---|---|
| 9,156,845 B2 | 10/2015 | Galatsis | | |
| 9,212,186 B2 | 12/2015 | Baker-glenn | | |
| 9,884,828 B2 | 2/2018 | Aubele | | |
| 2008/0293706 A1 | 11/2008 | Chaudhari | | |
| 2009/0137583 A1* | 5/2009 | Kishikawa | ................ | A61P 3/10 514/266.4 |
| 2015/0087664 A1 | 3/2015 | Blake et al. | | |
| 2016/0009689 A1 | 1/2016 | Miller et al. | | |

FOREIGN PATENT DOCUMENTS

| | | | | |
|---|---|---|---|---|
| WO | WO-2012021830 A1 * | 2/2012 | ................ | A61P 9/10 |
| WO | 2012162254 A1 | 11/2012 | | |
| WO | 2013164323 A1 | 11/2013 | | |
| WO | 2014001973 A1 | 1/2014 | | |
| WO | 2015054572 A1 | 4/2015 | | |
| WO | 2016036586 A1 | 3/2016 | | |
| WO | 2019074810 A1 | 4/2019 | | |

OTHER PUBLICATIONS

Bandmann, Neurology, 2012, 78 (11) 772-773 (Year: 2012).*

V.I. Pokrovsky, Drugs, Popular Medical Encyclopedia, 4th Edition, 317, 1997.

Ding, Xiao et al., Leucine-rich repeat kinase 2 inhibitors: a patent review (2014-present), Expert Opinion on Therapeutic Patents, 2020, 275-286, 30:4.

Aasly, J.O. et al., Clinical Features of LRRK2—Associated Parkinson's Disease in Central Norway, Ann Neurol, 2005, 762-765, 57(5).

Adams, J.R. et al., PET in LRRK2 mutations: comparison to sporadic Parkinson's disease and evidence for presymptomatic compensation, Brain, 2005, 2777-2785, 128.

Bailey, R.M. et al., LRRK2 phosphorylates novel tau epitopes and promotes tauopathy, Acta Neuropathol, 2013, 809-827, 126.

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1q32 and STAT3 with Ankylosing Spondylitis Suggests Genetic Overlap with Crohn's Disease, PLoS Genetics, Jan. 5, 2010, 6(12):e1001195.

Engel, P. et al., Therapeutic Targeting of B Cells for Rheumatic Autoimmune Diseases, Pharmacological Reviews, 2011, 127-156, 63(1).

Gilks, W.P. et al., A common LRRK2 mutation in idiopathic Parkinson's disease, Lancet, 2005, 415-416, 365.

Goedert, M. et al., Mutations causing neurodegenerative tauopathies, Biochimica et Biophysica Acta, 2005, 240-250, 1739.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS One, Jan. 9, 2012, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G Bac transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, Jan. 9, 2006, 1:17.

Zimprich, A. et al., Mutations in LRRK2 Cause Autosomal-Dominant Parkinsonism with Pleomorphic Pathology, Neuron, 2004, 601-607, 44(4).

Agalliu, I. et al., Higher Frequency of Certain Cancers in LRRK2 G2019S Mutation Carriers With Parkinson Disease, JAMA Neurology, 72(1), 58-65, 2015.

* cited by examiner

N-(HETEROARYL) QUINAZOLIN-2-AMINE DERIVATIVES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2020/056401 filed Oct. 20, 2020, which claims priority from U.S. Ser. No. 62/926,033 filed Oct. 25, 2019.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and Parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5): 1602-11). As neuroinflammation is a hallmark of a number of neurodegenerative diseases such PD, AD, MS, HIV-induced dementia, ALS, ischemic stroke, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjogren's syndrome, Delvic's disease, inflammatory myopathies (Engel at al., Pharmacol Rev. 2011 March; 63(1):127-56; Homam et al., Homam et al., Clin Neuromuscular disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain N-(heteroaryl) quinazolin-2-amine derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of Formula (I), exhibit excellent LRRK2 inhibitory activity. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

(I)

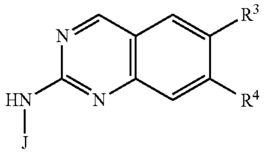

or a pharmaceutically acceptable salt thereof, wherein:

J is selected from:

a

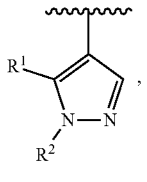

b

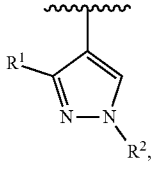

-continued c

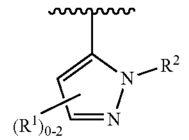

and d

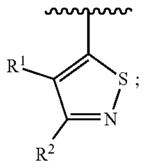

$R^1$ is independently selected from H, —$(C_1$-$C_6)$alkyl, —$(C_1$-$C_6)$haloalkyl, halogen, CN, and cyclopropyl;

$R^2$ is independently selected from —$(C_1$-$C_6)$alkyl, —$(C_1$-$C_6)$haloalkyl, —$((C_1$-$C_6)alkyl))_n(C_3$-$C_8)$cycloalkyl, bicyclopentanyl, spirohetanyl, azaspiroheptanyl, $(CH_2)n$oxetanyl, $(CH_2)_n$oxolanyl, thiazolyl, and piperidinyl, said alkyl, haloalkyl, cycloalkyl, bicyclopentanyl optionally substituted with 1, 2, or 3 groups independently selected from halogen, OH, CN, —$(C_1$-$C_6)$alkyl, —$(C_1$-$C_6)$alkylOH, O—$(C_1$-$C_6)$ alkyl, —$(C_1$-$C_6)$alkyl-O—$(C_1$-$C_6)$alkyl, and —O—$(C_1$-$C_6)$ haloalkyl, and said spiroheptanyl, azaspiroheptanyl, oxetanyl, oxolanyl, thiazolyl, and piperidinyl optionally substituted with 1, to 2 groups independently selected from halogen, OH, CN, —$(C_1$-$C_6)$alkyl, —$(CH_2)_nO(C_1$-$C_6)$alkyl, —$(C_1$-$C_6)$haloalkyl, oxolanyl, and oxetanyl, said oxolanyl and oxetanyl optionally substituted with 1 to 2 groups of $CH_3$;

$R^3$ is selected from $CH_3$, $CF_3$, $OCH_3$, Cl, CN, and cyclopropyl; and $R^4$ is selected from $(C_3$-$C_6)$cycloalkyl, piperidinyl, pyrrolidinyl, spiropentanyl, spirohexanyl, azaspiroheptanyl, azabicycloheptanyl, azabicylcooctanyl, and oxaazabicyclononanyl, said cycloalkyl, piperidinyl, pyrrolidinyl, spiropentanyl, spirohexanyl, azaspiroheptanyl, azabicycloheptanyl, azabicylcooctanyl, oxaazabicyclononanyl optionally substituted with 1 to 3 groups of $R^b$;

$R^b$ is selected from hydrogen, $(C_1$-$C_6)$alkyl, OH, $(CH_2)_n(C_3$-$C_6)$cycloalkyl, halogen, $(C_1$-$C_6)$haloalkyl, $C(O)(C_1$-$C_6)$alkyl, $(CH_2)n$oxetanyl, $(CH_2)n$oxolanyl, $(CH_2)_n$oxanyl, tetrahydrothiophenedionyl, thietanedionyl, oxaspirooctanyl, and bicyclohexanyl, said alkyl, cycloalkyl, oxetanyl, oxolanyl, tetrahydrothiophenedionyl, thietanedionyl, oxaspirooctanyl, and bicyclohexanyl optionally substituted with 1 to 3 groups of $R^{b1}$;

$R^{b1}$ is selected from $(C_1$-$C_6)$alkyl, $O(C_1$-$C_6)$alkyl, $(C_3$-$C_6)$ cycloalkyl, OH, halogen, CN, $CF_3$, phenyl, oxazolidinonyl, pyrrolidinonyl, morpholinyl, said phenyl optionally substituted with 1 to 2 groups of halogen and CN; and n is 0, 1, 2, 3, or 4.

An embodiment of Formula I is realized when n is 0. Another embodiment of Formula I is realized when n is 1. Another embodiment of Formula I is realized when n is 2. embodiment of Formula I is realized when n is 3. Another embodiment of Formula I is realized when n is 4.

An embodiment of Formula I is realized when $R^1$ is selected from the group consisting of H, —$CH_3$, —$C(CH_3)_3$, —$CHF_2$, $CF_3$, Br, Cl, CN and cyclopropyl. Another embodiment of Formula I is realized when $R^1$ is hydrogen. Another embodiment of Formula I is realized when $R^1$ is —$CH_3$. Still another embodiment of Formula I is realized when $R^1$ is Cl. Yet another embodiment of Formula I is realized when $R^1$ is —$CHF_2$ or $CF_3$.

Another embodiment of Formula I is realized when $R^2$ is unsubstituted or substituted —$(C_1\text{-}C_6)$alkyl. A subembodiment of this aspect of the invention is realized when the —$(C_1\text{-}C_6)$alkyl is selected from —$CH_3$, —$CH_2CH_3$, —$CH_2(CH_3)$—, —$CH_2(CH_3)_2$—, $C(CH_3)_2$—, —$CH_2(CH_3)$—, —$C(CH_3)_3$—, —CH—, —$(CH_2)_2$—, —$CH(CH_3)C(CH_3)_2$—, —$CH_2CH$—, —$C(CH_3)_2CH_2$—, and —$CH_2C(CH_3)(OH)$—, A subembodiment of this aspect of the invention is realized when $R^2$ is unsubstituted —$(C_1\text{-}C_6)$alkyl. Another subembodiment of this aspect of the invention is realized when $R^2$ is —$(C_1\text{-}C_6)$alkyl substituted with 1 to 3 groups of OH, $CH_3$, $OCH_3$, $OCHF_2$, $OCF_3$, CN, $CF_3$, $CH_2F$, $CHF_2$ and Fl. Another subembodiment of this aspect of the invention is realized when $R^2$ is —$CH_3$, or —$CH_2(CH_3)_2$—.

Another embodiment of Formula I is realized when $R^2$ is unsubstituted or substituted —$((C_1\text{-}C_6)alkyl)_n(C_3\text{-}C_8)$cycloalkyl. A subembodiment of this aspect of the invention is realized when —$((C_1\text{-}C_6)alkyl)_n(C_3\text{-}C_8)$cycloalkyl is selected from the group consisting of $(CH_2)_n$cyclopropyl, $(CH_2)_n$cyclobutyl, $(CH_2)_n$cyclopentyl, and $(CH_2)_n$cyclohexyl. A subembodiment of this aspect of the invention is realized when —$((C_1\text{-}C_6)alkyl)_n(C_3\text{-}C_8)$cycloalkyl of $R^2$ is unsubstituted. Another subembodiment of this aspect of the invention is realized when —$((C_1\text{-}C_6)alkyl)_n(C_3\text{-}C_8)$cycloalkyl of $R^2$ is selected from $(CH_2)_n$cyclopropyl, $(CH_2)_n$cyclobutyl, $(CH_2)_n$cyclopentyl, and $(CH_2)_n$cyclohexyl substituted with 1 to 3 groups of OH, $CH_3$, $OCH_3$, $OCHF_2$, $OCF_3$, CN, Fl, Cl, $CF_3$, $CHF_2$, and $CH_2F$. Still another subembodiment of this aspect of the invention is realized when $R^2$ is unsubstituted or substituted $(CH_2)_n$cyclopropyl or $(CH_2)_n$cyclobutyl. Still another subembodiment of this aspect of the invention is realized when $R^2$ is cyclopropyl substituted with 1 to 3 groups selected from OH, $CH_3$, $OCH_3$, $OCHF_2$, $OCF_3$, CN, Fl, Cl, $CF_3$, $CHF_2$, and $CH_2F$. Still another subembodiment of this aspect of the invention is realized when $R^2$ is cyclobutyl substituted with 1 to 3 groups selected from OH, $CH_3$, $OCH_3$, $OCHF_2$, $OCF_3$, CN, Fl, Cl, $CF_3$, $CHF_2$, and $CH_2F$.

Another embodiment of Formula I is realized when $R^2$ is unsubstituted or substituted bicyclopentanyl. A subembodiment of this aspect of the invention is realized when $R^2$ is unsubstituted bicyclopentanyl. A subembodiment of this aspect of the invention is realized when $R^2$ is bicyclopentanyl substituted with 1 to 3 groups selected from OH, $CH_3$, —$(CH_2)_nOCH_3$, —$C(CH_3)_2OCH_3$, —$OCHF_2$, —$OCF_3$, —CN, —$CF_3$, —$CH_2F$, —$CHF_2$ and —Fl.

Another embodiment of Formula I is realized when $R^2$ is unsubstituted or substituted spiroheptanyl, or azaspiroheptanyl. A subembodiment of this aspect of the invention is realized when $R^2$ is unsubstituted spiroheptanyl, or azaspiroheptanyl. A subembodiment of this aspect of the invention is realized when $R^2$ is spiroheptanyl, or azaspiroheptanyl substituted with 1 to 3 groups selected from halogen, OH, CN, —$(C_1\text{-}C_6)$alkyl, —$(CH_2)_nO(C_1\text{-}C_6)$alkyl, —$(C_1\text{-}C_6)$haloalkyl, oxolanyl, and oxetanyl, said oxolanyl and oxetanyl optionally substituted with 1 to 2 groups of $CH_3$.

Another embodiment of Formula I is realized when $R^2$ is unsubstituted or substituted $(CH_2)$noxetanyl or $(CH_2)$noxolanyl. Another embodiment of Formula I is realized when $R^2$ is unsubstituted $(CH_2)$noxetanyl or $(CH_2)$noxolanyl. A subembodiment of this aspect of the invention is realized when $R^2$ is $(CH_2)$noxetanyl or $(CH_2)$noxolanyl substituted with 1 to 3 groups selected from halogen, OH, CN, —$(C_1\text{-}C_6)$alkyl, —$(CH_2)_nO(C_1\text{-}C_6)$alkyl, —$(C_1\text{-}C_6)$haloalkyl, oxolanyl, and oxetanyl, said oxolanyl and oxetanyl optionally substituted with 1 to 2 groups of $CH_3$.

Another embodiment of Formula I is realized when $R^2$ is unsubstituted or substituted thiazolyl or piperidinyl. Another embodiment of Formula I is realized when $R^2$ is unsubstituted thiazolyl or piperidinyl. A subembodiment of this aspect of the invention is realized when $R^2$ is thiazolyl or piperidinyl substituted with 1 to 3 groups of halogen, OH, CN, —$(C_1\text{-}C_6)$alkyl, —$(CH_2)_nO(C_1\text{-}C_6)$alkyl, —$(C_1\text{-}C_6)$haloalkyl, oxolanyl, and oxetanyl, said oxolanyl and oxetanyl optionally substituted with 1 to 2 groups of $CH_3$.

An embodiment, in Formula (I) is realized when $R^3$ is selected from Cl, $CH_3$, $CF_3$, and CN. Another embodiment of this aspect of the invention is realized when $R^3$ Cl. Another embodiment of this aspect of the invention is realized when $R^3$ $CH_3$. Another embodiment of this aspect of the invention is realized when $R^3$ CN. Another embodiment of this aspect of the invention is realized when $R^3$ $CF_3$.

In an alternative of each of the preceding embodiments, in Formula (I) J is selected from

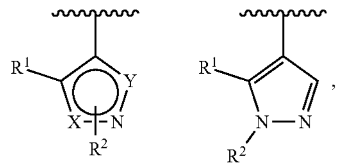

a

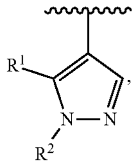

b

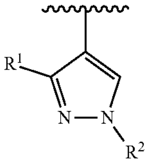

and c

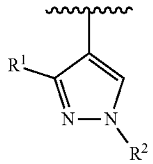

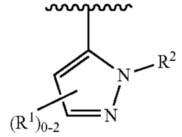

and

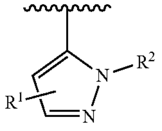

wherein $R^1$ wherein $R^1$ and $R^2$ are as defined in Formula (I). A subembodiment of this aspect of the invention is realized when J is a. A subembodiment of this aspect of the invention is realized when J is b. A subembodiment of this aspect of the invention is realized when J is c. Another subembodiment of this aspect of the invention is realized when $R^1$ of J a, b, or c is selected from H, Cl, and $CH_3$. Another subembodiment of this aspect of the invention is realized when $R^2$ of J a, b, or c is selected from —$(C_1\text{-}C_6)$alkyl, —$(C_1\text{-}C_6)$haloalkyl, —($C_1$-$C_6$)alkyl-O—($C_1$-$C_6$)alkyl, $(CH_2)_n$cyclopropyl, $(CH_2)_n$cyclobutyl, bicyclopentanyl, spiroheptanyl, azaspiroheptanyl, ($CH_2$)noxetanyl, ($CH_2$)noxolanyl, thiazolyl and piperidinyl, said —($C_1$-$C_6$)alkyl, —($C_1$-$C_6$)haloalkyl, —($C_1$-$C_6$)alkyl-O—($C_1$-$C_6$)alkyl, $(CH_2)_n$cyclopropyl, $(CH_2)_n$cyclobutyl, bicyclopentanyl, spiroheptanyl, azaspiroheptanyl, ($CH_2$)noxetanyl, ($CH_2$)noxolanyl, thiazolyl and piperidinyl optionally substituted as described herein. Another subembodiment of this aspect of the invention is realized when $R^2$ of J a, b, or c is —($C_1$-$C_6$)alkyl, optionally substituted with 1 to 3 groups of OH, $CH_3$, $OCH_3$, $OCHF_2$, $OCF_3$, CN, $CF_3$, $CH_2F$, $CHF_2$ and Fl. Another subembodiment of this aspect of the invention is realized when $R^2$ of J a, b, or c is cyclopropyl, optionally substituted with 1 to 3 groups of OH, $CH_3$, $OCH_3$, $OCHF_2$, $OCF_3$, CN, Fl, Cl, $CF_3$, $CHF_2$, and $CH_2F$. Another embodiment this aspect of the invention is realized when $R^2$ of J a, b, or c is bicyclopentanyl, optionally substituted with 1 to 3 groups of OH, $CH_3$, —$(CH_2)_n OCH_3$, —$C(CH_3)_2OCH_3$, —$OCHF_2$, —$OCF_3$, —CN, —$CF_3$, —$CH_2F$, —$CHF_2$ and —Fl.

In another alternative of each of the preceding embodiments, in Formula (I) J is:

d

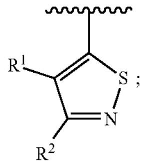

wherein $R^1$ and $R^2$ are as defined in Formula (I), or in any of the alternative embodiments for each of $R^1$ and $R^2$ described above. Another subembodiment of this aspect of the invention is realized when $R^1$ of J d is selected from H, Cl, and $CH_3$. Another subembodiment of this aspect of the invention is realized when $R^2$ of J d is selected from —($C_1$-$C_6$)alkyl, —($C_1$-$C_6$)haloalkyl, and —($C_1$-$C_6$)alkyl-O—($C_1$-$C_6$)alkyl, optionally substituted with 1 to 3 groups of OH, $CH_3$, $OCH_3$, $OCHF_2$, $OCF_3$, CN, $CF_3$, $CH_2F$, $CHF_2$ and Fl. Another subembodiment of this aspect of the invention is realized when $R^2$ of J d is cyclopropyl, optionally substituted with 1 to 3 groups of OH, $CH_3$, $OCH_3$, $OCHF_2$, $OCF_3$, CN, Fl, Cl, $CF_3$, $CHF_2$, and $CH_2F$. Another embodiment this aspect of the invention is realized when $R^2$ of J d is bicyclopentanyl, optionally substituted with 1 to 3 groups of OH, $CH_3$, —$(CH_2)_n OCH_3$, —$C(CH_3)_2OCH_3$, —$OCHF_2$, —$OCF_3$, —CN, —$CF_3$, —$CH_2F$, —$CHF_2$ and —Fl.

In another alternative of each of the preceding embodiments, in Formula (I) $R^4$ is selected from cyclopropyl, cyclohexyl, azaspiroheptanyl, spiropentanyl, spirohexanyl, azabicycloheptanyl azabicyclooctanyl, oxaazabicyclononanyl, pyrrolidinyl, and piperidinyl, said cyclopropyl, cyclohexyl, azaspiroheptanyl, spiropentanyl, spirohexanyl, azabicycloheptanyl azabicyclooctanyl, oxaazabicyclononanyl, pyrrolidinyl, and piperidinyl optionally substituted with 1 to 3 groups $R^b$. A subembodiment of this aspect of the invention is realized when $R^4$ is selected optionally substituted cyclopropyl. A subembodiment of this aspect of the invention is realized when $R^4$ is optionally substituted cyclohexyl. A subembodiment of this aspect of the invention is realized when $R^4$ is optionally substituted azaspiroheptanyl, spiropentanyl, spirohexanyl, azabicycloheptanyl azabicyclooctanyl, or oxaazabicyclononanyl. A subembodiment of this aspect of the invention is realized when $R^4$ is optionally substituted pyrrolidinyl. An aspect of this subembodiment is realized when the $R^4$ pyrrolidinyl is linked through a carbon atom. A subembodiment of this aspect of the invention is realized when $R^4$ is optionally substituted piperidinyl. An aspect of this subembodiment is realized when the $R^4$ piperidinyl is linked through a carbon atom. A subembodiment of this aspect of the invention is realized when the substituent, $R^b$, is selected from ($C_1$-$C_6$)alkyl, OH, $(CH_2)_n$($C_3$-$C_6$)cycloalkyl, halogen, ($C_1$-$C_6$)haloalkyl, C(O)($C_1$-$C_6$) alkyl, ($CH_2$)noxetanyl, ($CH_2$)noxolanyl, ($CH_2$)noxanyl, tetrahydrothiophenedionyl, thietanedionyl, oxaspirooctanyl, and bicyclohexanyl, said alkyl, cycloalkyl, oxetanyl, oxolanyl, tetrahydrothiophenedionyl, thietanedionyl, oxaspirooctanyl, and bicyclohexanyl optionally substituted with 1 to 3 groups of $R^{b1}$. Another subembodiment of this aspect of the invention is realized when $R^b$ is selected from $CH_3$, $CH_2C(CH_3)_2OH$, ($CH_2$)CH(OH)$CH_2$phenyl, $CH_2C(CH_3)$(OH)phenyl, $CH_2$CH(OH)phenyl, oxetanyl, oxolanyl, and thietanedionyl, said phenyl, oxetanyl, oxolanyl and thietanedionyl optionally substituted with 1 to 3 groups of $R^{b1}$. Another subembodiment of this invention is realized when $R^b$ is selected from $CH_3$, or $CH_2C(CH_3)_2OH$. Another subembodiment of this invention is realized when $R^b$ is selected from optionally substituted ($CH_2$)CH(OH)$CH_2$phenyl, $CH_2C(CH_3)$(OH)phenyl, or $CH_2$CH(OH)phenyl. Another subembodiment of this invention is realized when $R^b$ is optionally substituted oxetanyl. Another subembodiment of this invention is realized when $R^b$ is optionally substituted oxolanyl. Another subembodiment of this invention is realized when $R^b$ is optionally substituted thietanedionyl.

An embodiment of the invention of Formula I is realized when $R^{b1}$ is selected from $CH_3$, OH, $OCH_3$, $CF_3$, Fl, Cl, CN, $CH_2CN$, and cyclopropyl.

In another embodiment, the compounds of Formula I or a pharmaceutically acceptable salt thereof is realized, by structural Formula I':

I'

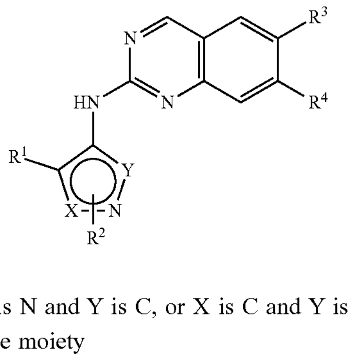

wherein X is N and Y is C, or X is C and Y is S, such that the moiety

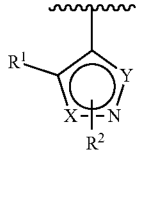

is selected from

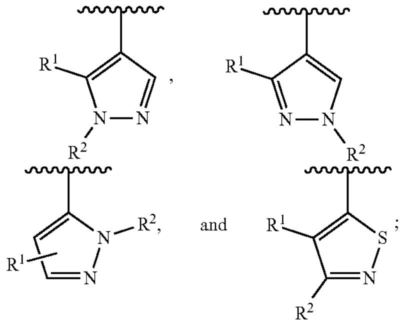

and

R¹ is selected from H, Cl, and $CH_3$;

$R^2$ is selected from —($C_1$-$C_6$)alkyl, —($C_1$-$C_6$)haloalkyl, —($C_1$-$C_6$)alkyl-OH, —($C_1$-$C_6$)haloalkyl-OH, —($C_1$-$C_6$)alkyl-CN, —($C_1$-$C_6$)alkyl-O—($C_1$-$C_6$)alkyl, —($C_1$-$C_6$)alkyl-O—($C_1$-$C_6$)haloalkyl, —($C_3$-$C_6$)cycloalkyl, —($C_3$-$C_6$)cycloalkyl which is substituted with 1, 2, or 3 groups independently selected from halogen, OH, CN, —($C_1$-$C_6$)alkyl, and —O—($C_1$-$C_6$)alkyl, —($C_1$-$C_3$)alkyl($C_3$-$C_6$)cycloalkyl, —($C_1$-$C_3$)alkyl($C_3$-$C_6$)cycloalkyl which is substituted with 1, 2, or 3 groups independently selected from halogen, OH, CN, and —($C_1$-$C_6$)alkyl, bicycloalkyl;

bicycloalkyl which is substituted with 1 or 2 groups independently selected from halogen, C(O)($C_1$-$C_6$)alkyl, C(O)O($C_1$-$C_6$)alkyl, ($C_1$-$C_6$)alkyl-OH, ($C_1$-$C_6$)alkyl-CN, C(O)NH($C_1$-$C_6$)alkyl, C(O)N(($C_1$-$C_6$)alkyl)$_2$, C(O)N(($C_1$-$C_6$)alkyl)-O—(($C_1$-$C_6$)alkyl), ($C_1$-$C_6$)haloalkyl, ($C_1$-$C_6$)alkyl-O—($C_1$-$C_6$)alkyl, ($C_1$-$C_6$)haloalkyl-O—($C_1$-$C_6$)alkyl, ($C_1$-$C_6$)alkyl-O—($C_1$-$C_6$)haloalkyl, ($C_1$-$C_6$)haloalkyl-O—($C_1$-$C_6$)haloalkyl, cyclopropyl, and cyclobutyl;

oxetanyl, oxetanyl which is substituted with 1, 2, or 3 groups independently selected from halogen, OH, CN, and —($C_1$-$C_6$)alkyl, tetrahydrofuranyl, tetrahydrofuranyl which is substituted with 1, 2, or 3 groups independently selected from halogen, OH, CN, and —($C_1$-$C_6$)alkyl, —($C_1$-$C_3$)alkyl-oxetanyl, —($C_1$-$C_3$)alkyl-oxetanyl which is substituted with 1, 2, or 3 groups independently selected from halogen, OH, CN, and —($C_1$-$C_6$)alkyl, —($C_1$-$C_3$)alkyl-tetrahydrofuranyl, —($C_1$-$C_3$)alkyl-tetrahydrofuranyl which is substituted with 1, 2, or 3 groups independently selected from halogen, OH, CN, and —($C_1$-$C_6$)alkyl,

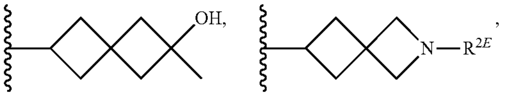

wherein R' is selected from H, —($C_1$-$C_6$)alkyl, —($C_1$-$C_6$) haloalkyl,

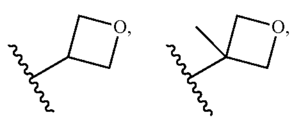

and

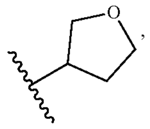

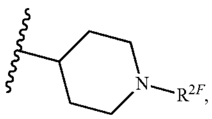

and

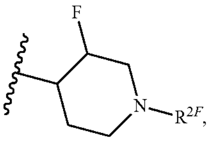

wherein:

$R^{2F}$ is selected from H, —($C_1$-$C_6$)alkyl, —($C_1$-$C_6$)fluoroalkyl, —($C_1$-$C_6$)alkyl-O—($C_1$-$C_6$)alkyl,

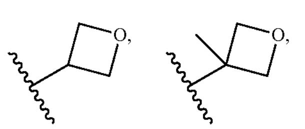

and

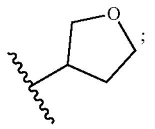

$R^3$ is selected from $CH_3$, $CF_3$, $OCH_3$, Cl, CN, and cyclopropyl; and $R^4$ is selected from ($C_1$-$C_6$)alkyl, ($C_3$-$C_6$)cycloalkyl, ($C_3$-$C_6$)cycloalkyl substituted with 1 or 2 fluorine atoms,

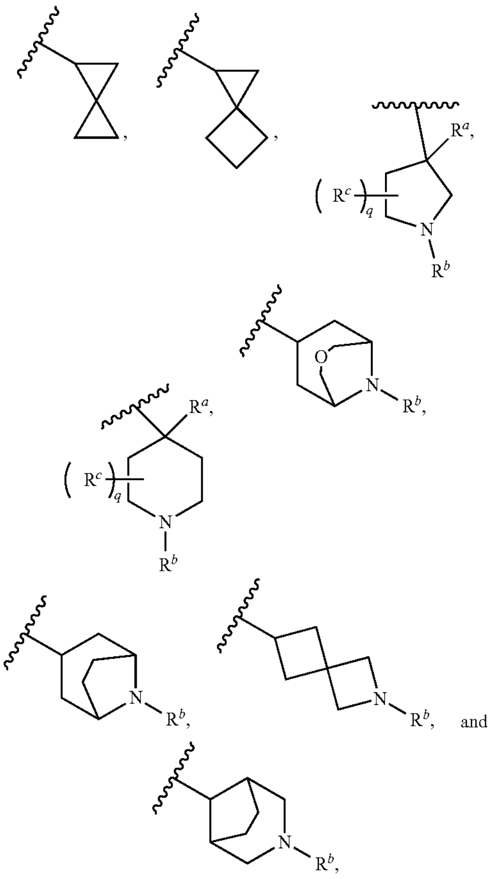

and wherein:

q is 1 or 2;

$R^a$ is selected from H, F, OH;

$R^c$ is selected from H, F, CN, OH, —$(C_1-C_6)$alkyl, and $O(C_1-C_4)$alkyl;

$R^b$ is selected from H, —$(C_1-C_6)$alkyl, —$(C_1-C_6)$haloalkyl, —$(C_1-C_6)$alkyl-OH, —$(C_1-C_6)$alkyl-CN, —$(C_1-C_6)$haloalkyl-OH, —$(C_1-C_6)$alkyl-O—$(C_1-C_6)$alkyl, —$(C_1-C_6)$alkyl-O—$(C_1-C_6)$haloalkyl, —$(C_3-C_6)$cycloalkyl, —$(C_3-C_6)$cycloalkyl which is substituted with 1, 2, or 3 groups independently selected from halogen, OH, CN, $(C_1-C_6)$alkyl, and $O(C_1-C_4)$alkyl, —$(C_1-C_3)$alkyl$(C_3-C_6)$cycloalkyl, —$(C_1-C_3)$alkyl$(C_3-C_6)$cycloalkyl which is substituted with 1, 2, or 3 groups independently selected from halogen, OH, CN, and —$(C_1-C_6)$alkyl, oxetanyl, oxetanyl which is substituted with 1, 2, or 3 groups independently selected from halogen, OH, CN, and —$(C_1-C_6)$alkyl, —$(C_1-C_3)$alkyl-oxetanyl, —$(C_1-C_3)$alkyl-oxetanyl which is substituted with 1, 2, or 3 groups independently selected from halogen, OH, CN, and —$(C_1-C_6)$alkyl, tetrahydrofuranyl, tetrahydrofuranyl which is substituted with 1, 2, or 3 groups independently selected from halogen, OH, CN, and —$(C_1-C_6)$alkyl, —$(C_1-C_3)$alkyl-tetrahydrofuranyl, —$(C_1-C_3)$alkyl-tetrahydrofuranyl which is substituted with 1, 2, or 3 groups independently selected from halogen, OH, CN, and —$(C_1-C_6)$alkyl,

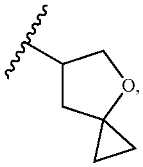,
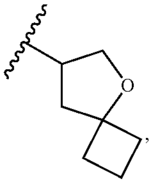,
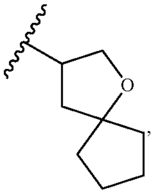, thietanyl, thietanyl which is substituted with 1, 2, or 3 groups independently selected from halogen, OH, CN, and —$(C_1-C_6)$alkyl, —$(C_1-C_3)$alkyl-thietanyl, —$(C_1-C_3)$alkyl-thietanyl which is substituted with 1, 2, or 3 groups independently selected from halogen, OH, CN, and —$(C_1-C_6)$alkyl, thietanyl 1,1-dioxide, thietanyl 1,1-dioxide which is substituted with 1, 2, or 3 groups independently selected from halogen, OH, CN, and —$(C_1-C_6)$alkyl, —$(C_1-C_3)$alkyl-thietanyl 1,1-dioxide, —$(C_1-C_3)$alkyl-thietanyl 1,1-dioxide which is substituted with 1, 2, or 3 groups independently selected from halogen, OH, CN, and —$(C_1-C_6)$alkyl, tetrahydrothiophenyl, tetrahydrothiophenyl which is substituted with 1, 2, or 3 groups independently selected from halogen, OH, CN, and —$(C_1-C_6)$alkyl, —$(C_1-C_3)$alkyl-tetrahydrothiophenyl, —$(C_1-C_3)$alkyl-tetrahydrothiophenyl which is substituted with 1, 2, or 3 groups independently selected from halogen, OH, CN, and —$(C_1-C_6)$alkyl, tetrahydrothiophenyl 1,1-dioxide, tetrahydrothiophenyl 1,1-dioxide which is substituted with 1, 2, or 3 groups independently selected from halogen, OH, CN, and —$(C_1-C_6)$alkyl, —$(C_1-C_3)$alkyl-tetrahydrothiophenyl 1,1-dioxide, and —$(C_1-C_3)$alkyl-tetrahydrothiophenyl 1,1-dioxide which is substituted with 1, 2, or 3 groups independently selected from halogen, OH, CN, and —$(C_1-C_6)$alkyl.

In another embodiment, in Formula (I):

$R^3$ is selected from Cl, $CH_3$, and CN.

In an alternative of each of the preceding embodiments, in Formula (I):

X is N and Y is C, and the moiety

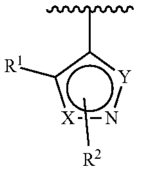

is selected from

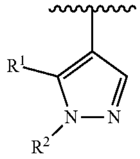

and

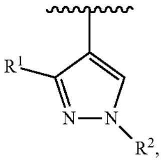, wherein:

$R^1$ and $R^2$ are as defined in Formula (I).

In another alternative of each of the preceding embodiments, in Formula (I):

X is N and Y is C, and the moiety

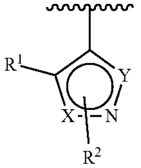

is selected from

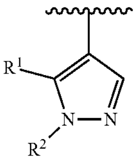

and

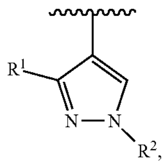

wherein:

$R^1$ is selected from H, Cl, and $CH_3$; and $R^2$ is selected from —($C_1$-$C_6$)alkyl, —($C_1$-$C_6$)haloalkyl, —($C_1$-$C_6$)alkyl-OH, —($C_1$-$C_6$)haloalkyl-OH, —($C_1$-$C_6$)alkyl-O—($C_1$-$C_6$)alkyl, —($C_1$-$C_6$)alkyl-O—($C_1$-$C_6$)haloalkyl,

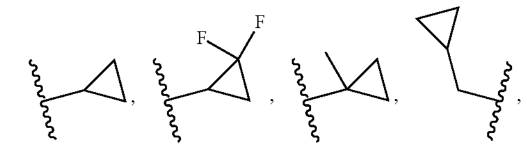

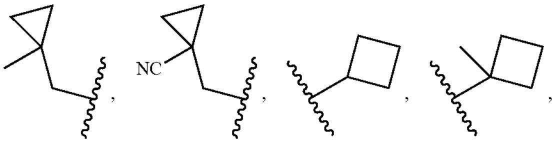

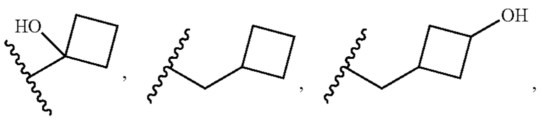

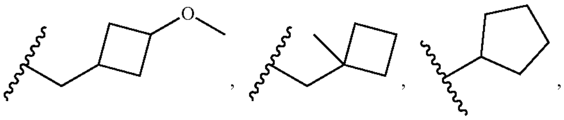

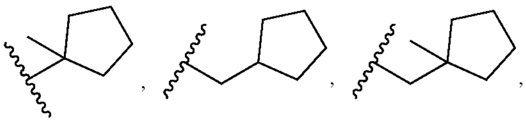

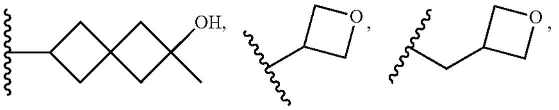

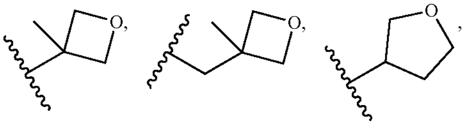

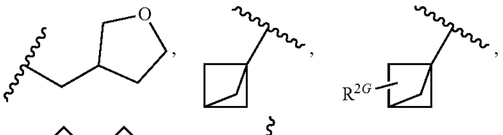

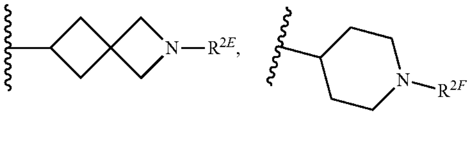

and

-continued

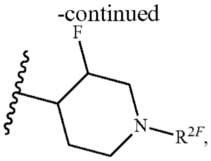

wherein:

$R^{2E}$ is selected from H, —($C_1$-$C_6$)alkyl, —($C_1$-$C_6$)haloalkyl,

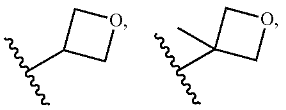

and

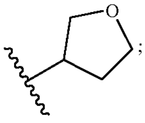

$R^{2F}$ is selected from H, —($C_1$-$C_6$)alkyl, —($C_1$-$C_6$)fluoroalkyl, —($C_1$-$C_6$)alkyl-O—($C_1$-$C_6$)alkyl,

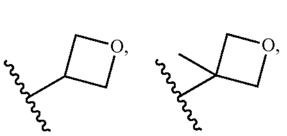

and

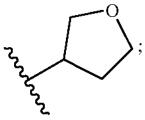

and $R^{2G}$ is 1 or 2 groups independently selected from halogen, C(O)($C_1$-$C_6$)alkyl, C(O)O($C_1$-$C_6$)alkyl, ($C_1$-$C_6$)alkyl-OH, ($C_1$-$C_6$)alkyl-CN, C(O)NH($C_1$-$C_6$)alkyl, C(O)N(($C_1$-$C_6$)alkyl)$_2$, C(O)N(($C_1$-$C_6$)alkyl)-O—(($C_1$-$C_6$)alkyl), ($C_1$-$C_6$)haloalkyl, ($C_1$-$C_6$)alkyl-O—($C_1$-$C_6$)alkyl, ($C_1$-$C_6$)haloalkyl-O—($C_1$-$C_6$)alkyl, ($C_1$-$C_6$)alkyl-O—($C_1$-$C_6$)haloalkyl, ($C_1$-$C_6$)haloalkyl-O—($C_1$-$C_6$)haloalkyl, cyclopropyl, and cyclobutyl.

Non-limiting examples of $R^2$ when, in any of the preceding embodiments, $R^2$ is a bicycloalkyl which is unsubstituted or substituted with 1 or 2 groups independently selected from halogen, C(O)($C_1$-$C_6$)alkyl, C(O)O($C_1$-$C_6$)alkyl, ($C_1$-$C_6$)alkyl-OH, ($C_1$-$C_6$)alkyl-CN, C(O)NH($C_1$-$C_6$)alkyl, C(O)N(($C_1$-$C_6$)alkyl)$_2$, C(O)N(($C_1$-$C_6$)alkyl)-O—(($C_1$-$C_6$)alkyl), ($C_1$-$C_6$)haloalkyl, ($C_1$-$C_6$)alkyl-O—($C_1$-$C_6$)alkyl, ($C_1$-$C_6$)haloalkyl-O—($C_1$-$C_6$)alkyl, ($C_1$-$C_6$)alkyl-O—($C_1$-$C_6$)haloalkyl, ($C_1$-$C_6$)haloalkyl-O—($C_1$-$C_6$)haloalkyl, cyclopropyl, and cyclobutyl include:

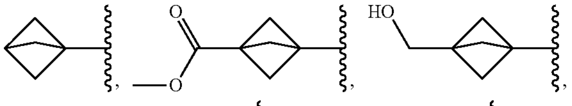

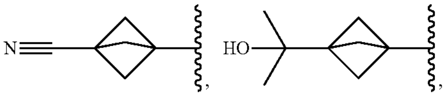

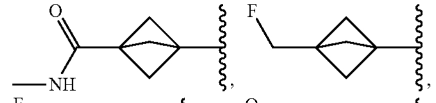

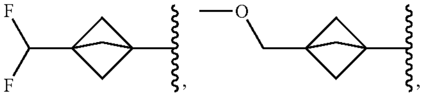

-continued

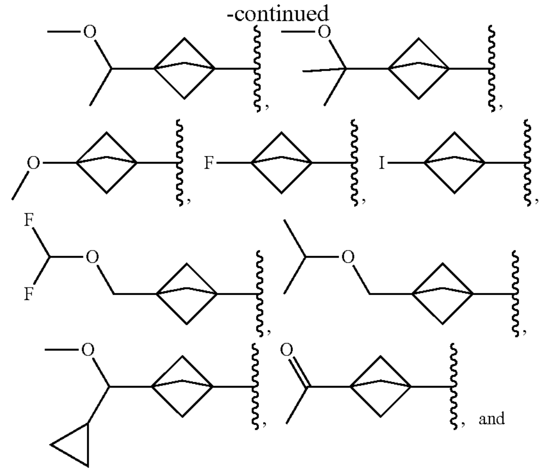

, and

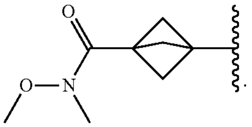

In another alternative of each of the preceding embodiments, in Formula (I):

X is C and Y is S, and the moiety

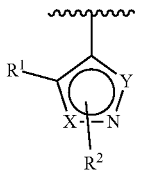

is

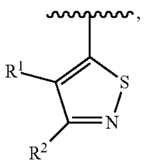

wherein:

$R^1$ and $R^2$ are as defined in Formula (I), or in any of the alternative embodiments for each of $R^1$ and $R^2$ described above.

In another alternative of each of the preceding embodiments, in Formula (I'):

X is C and Y is S, and the moiety

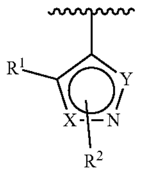

is

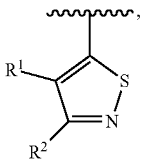

wherein:

$R^1$ is selected from H, Cl, and $CH_3$; and $R^2$ is selected from —$(C_1$-$C_6)$alkyl, —$(C_1$-$C_6)$haloalkyl, —$(C_1$-$C_6)$alkyl-OH, —$(C_1$-$C_6)$haloalkyl-OH, —$(C_1$-$C_6)$alkyl-O—$(C_1$-$C_6)$alkyl, and —$(C_1$-$C_6)$alkyl-O—$(C_1$-$C_6)$haloalkyl.

In an alternative of the immediately preceding embodiment, IV is —$(C_1$-$C_6)$alkyl.

In another alternative of each of the preceding embodiments, in Formula (I):

$R^4$ is selected from $(C_1$-$C_6)$alkyl, cyclopropyl, cyclopropyl substituted with 1 or 2 fluorine atoms, cyclobutyl, cyclobutyl substituted with 1 or 2 fluorine atoms, cyclopentyl, cyclopentyl substituted with 1 or 2 fluorine atoms,

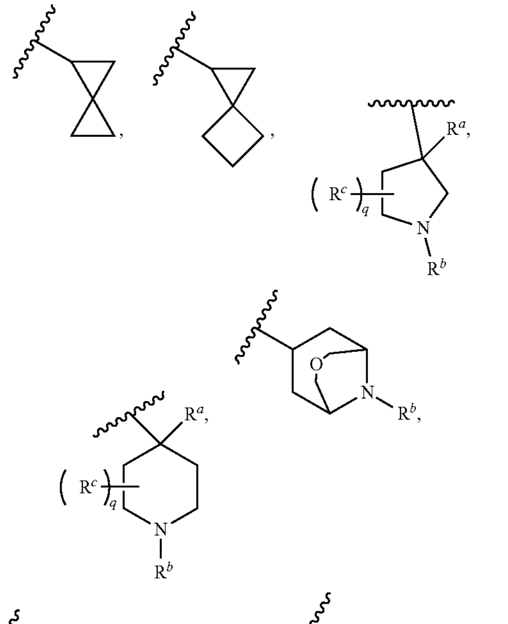

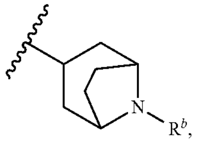

and

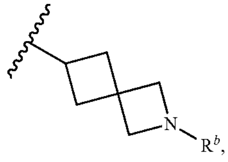

wherein:

q is 1 or 2;

$R^a$ is selected from H, F, OH;

$R^c$ is selected from H, F, —$(C_1$-$C_6)$alkyl, OH; and $R^b$ is selected from H, —$(C_1$-$C_6)$alkyl, —$(C_1$-$C_6)$haloalkyl, —$(C_1$-$C_6)$alkyl-OH, —$(C_1$-$C_6)$alkyl-CN, —$(C_1$-$C_6)$haloalkyl-OH, —$(C_1$-$C_6)$alkyl-O—$(C_1$-$C_6)$alkyl, —$(C_1$-$C_6)$alkyl-O—$(C_1$-$C_6)$haloalkyl,

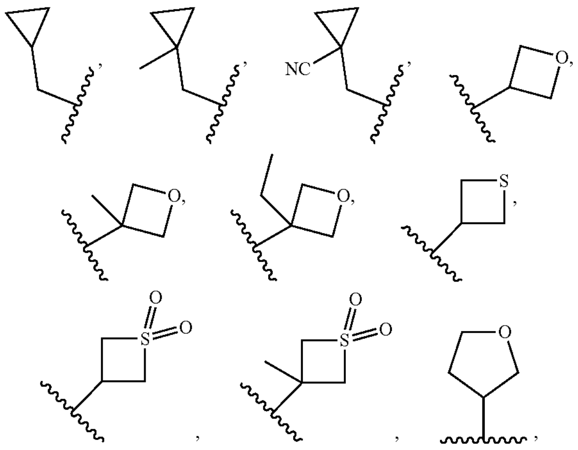

-continued

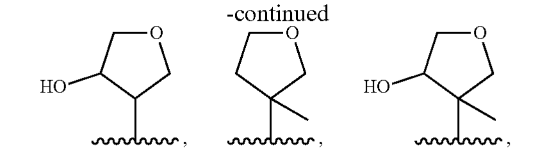

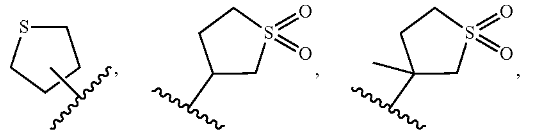

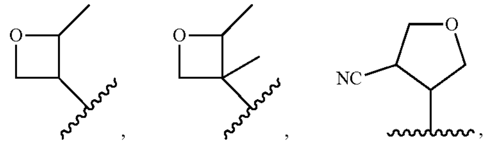

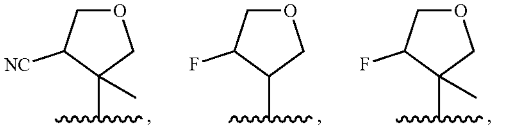

and

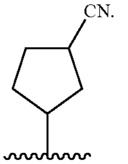

In another alternative of each of the preceding embodiments, in Formula (I'):

X is N and Y is C, or X is C and Y is S, such that the moiety

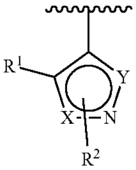

is selected from

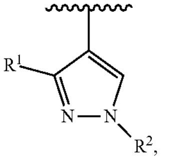

and

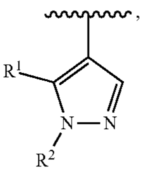

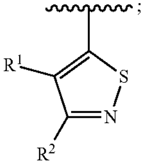

$R^1$ is selected from H, Cl, and $CH_3$;

$R^2$ is selected from —($C_1$-$C_6$)alkyl, —($C_1$-$C_6$)haloalkyl, —($C_1$-$C_6$)alkyl-OH, —($C_1$-$C_6$)haloalkyl-OH, —($C_1$-$C_6$)alkyl-O—($C_1$-$C_6$)alkyl, —($C_1$-$C_6$)alkyl-O—($C_1$-$C_6$)haloalkyl,

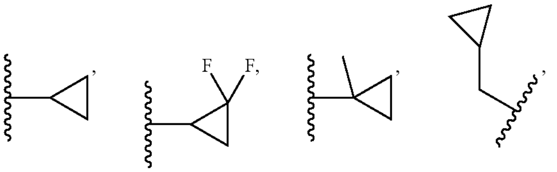

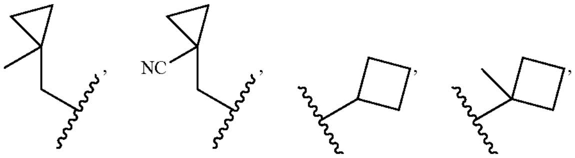

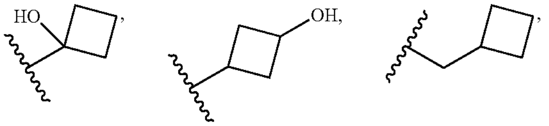

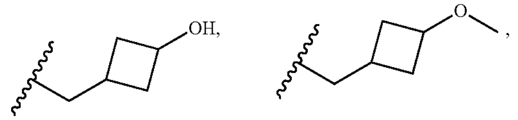

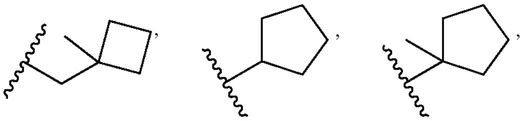

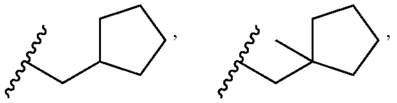

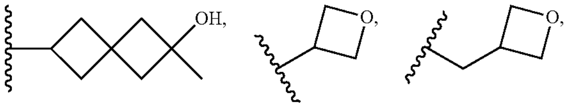

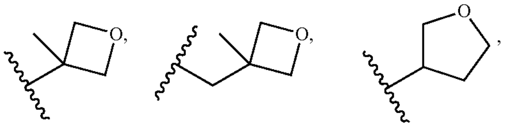

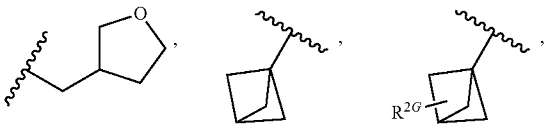

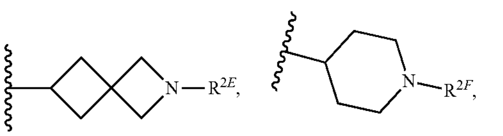

and

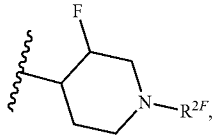

wherein:

$R^{2E}$ is selected from H, —($C_1$-$C_6$)alkyl, —($C_1$-$C_6$)haloalkyl,

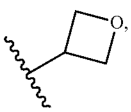, 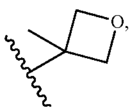, and 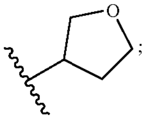;

R' is selected from H, —($C_1$-$C_6$)alkyl, —($C_1$-$C_6$)fluoroalkyl, —($C_1$-$C_6$)alkyl-O—($C_1$-$C_6$)alkyl,

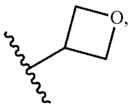, 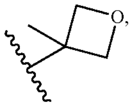, and 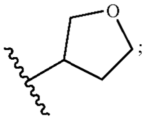;

and $R^{2G}$ is 1 or 2 groups independently selected from halogen, C(O)($C_1$-$C_6$)alkyl, C(O)O($C_1$-$C_6$)alkyl, ($C_1$-$C_6$)alkyl-OH, ($C_1$-$C_6$)alkyl-CN, C(O)NH($C_1$-$C_6$)alkyl, C(O)N(($C_1$-$C_6$)alkyl)$_2$, C(O)N(($C_1$-$C_6$)alkyl)-O—(($C_1$-$C_6$)alkyl), ($C_1$-$C_6$)haloalkyl, ($C_1$-$C_6$)alkyl-O—($C_1$-$C_6$)alkyl, ($C_1$-$C_6$)haloalkyl-O—($C_1$-$C_6$)alkyl, ($C_1$-$C_6$)alkyl-O—($C_1$-$C_6$)haloalkyl, ($C_1$-$C_6$)haloalkyl-O—($C_1$-$C_6$)haloalkyl, cyclopropyl, and cyclobutyl.

$R^3$ is selected from Cl, $CH_3$, CN, $CF_3$, $OCH_3$, and cyclopropyl; and $R^4$ is selected from ($C_1$-$C_6$)alkyl, cyclopropyl, cyclopropyl substituted with 1 or 2 fluorine atoms, cyclobutyl, cyclobutyl substituted with 1 or 2 fluorine atoms, cyclopentyl, cyclopentyl substituted with 1 or 2 fluorine atoms,

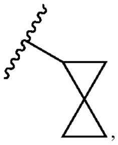, 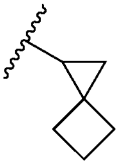, 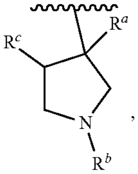, and

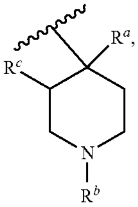

wherein:

$R^a$ is selected from H, F, OH;

$R^c$ is selected from H, F, —($C_1$-$C_6$)alkyl, OH; and $R^b$ is selected from H, —($C_1$-$C_6$)alkyl, —($C_1$-$C_6$)haloalkyl, —($C_1$-$C_6$)alkyl-OH, —($C_1$-$C_6$)alkyl-CN, —($C_1$-$C_6$)haloalkyl-OH, —($C_1$-$C_6$)alkyl-O—($C_1$-$C_6$)alkyl, —($C_1$-$C_6$)alkyl-O—($C_1$-$C_6$)haloalkyl,

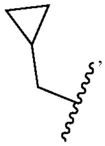, 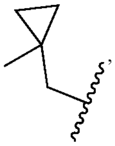, 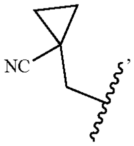, 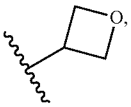,

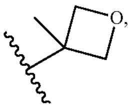, 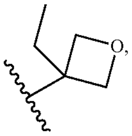, 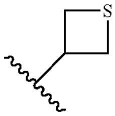,

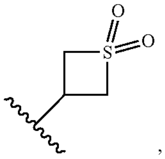, 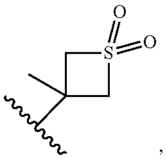, 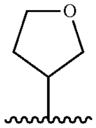,

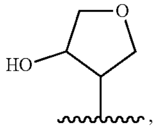, 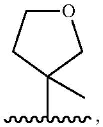, 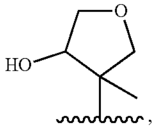,

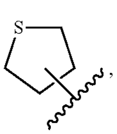, 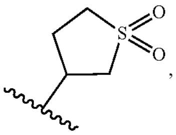, 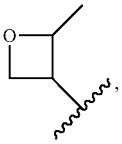, and

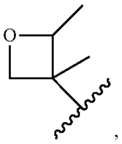, 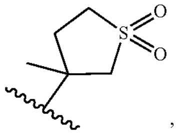, 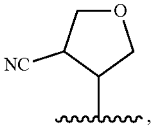,

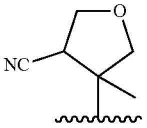, 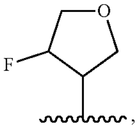, 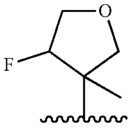,

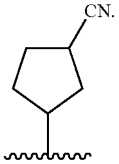

As noted above, non-limiting examples of $R^2$ when, in any of the preceding embodiments, $R^2$ is

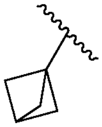 or 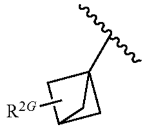

include:

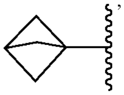, 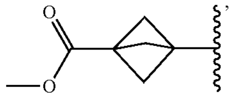,

-continued

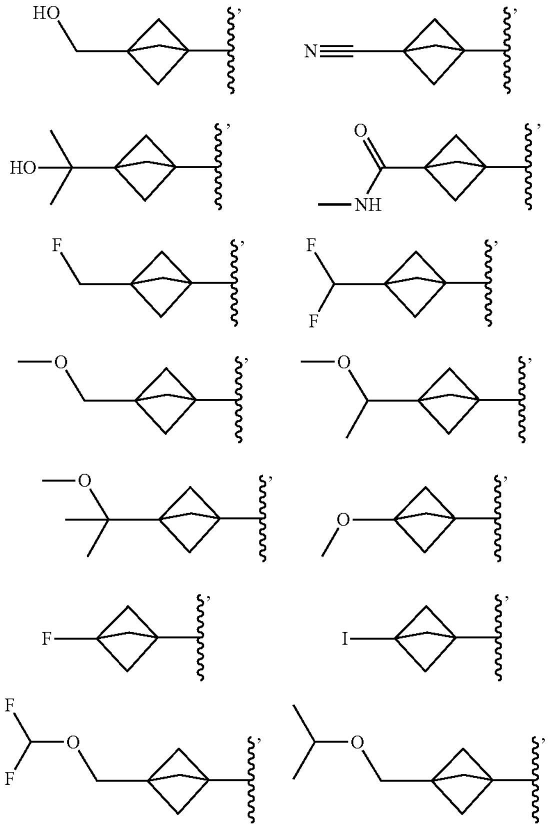

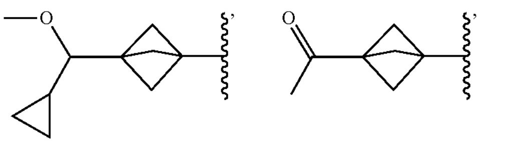

and

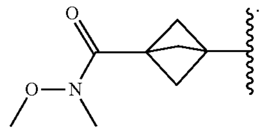

Still another embodiment of the invention of Formula I is represented by structural Formula II:

II

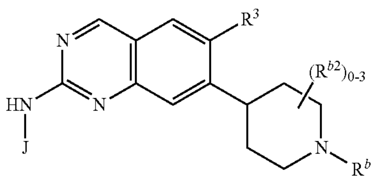

or a pharmaceutically acceptable salt thereof, wherein J, $R^3$ and $R^b$ are as described herein and $R^{b2}$ is independently selected from $C_{1-6}$ alkyl and halogen. A subembodiment of Formula II is realized when $R^{b2}$ is independently selected from $CH_3$ and fluorine.

A subembodiment of Formula II is realized when J is selected from a

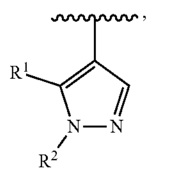

b

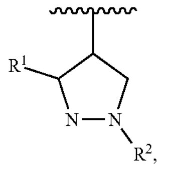

c

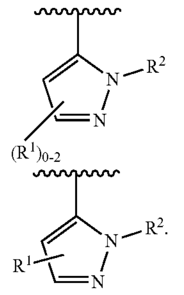

A subembodiment of this aspect of Formula II is realized when the J is a. A subembodiment of this aspect of Formula II is realized when the J is b. A subembodiment of this aspect of Formula II is realized when the J is c. Another subembodiment of Formula II is realized when $R^1$ is selected from H, —$CH_3$, —$C(CH_3)_3$, —$CHF_2$, $CF_3$, Br, Cl, CN and cyclopropyl. An aspect of this subembodiment of Formula II is realized when $R^1$ is H, —$CH_3$, or Cl. An aspect of this subembodiment of Formula II is realized when $R^1$ is H. An aspect of this subembodiment of Formula II is realized when $R^1$ is —$CH_3$. An aspect of this subembodiment of Formula II is realized when $R^1$ is Cl.

Still another subembodiment of Formula II is realized when $R^2$ of J a, b, or c is selected from —$(C_1$-$C_6)$alkyl, —$(C_1$-$C_6)$haloalkyl, —$(C_1$-$C_6)$alkyl-O—$(C_1$-$C_6)$alkyl, $(CH_2)_n$cyclopropyl, $(CH_2)_n$cyclobutyl, bicyclopentanyl, spiroheptanyl, azaspiroheptanyl, $(CH_2)$noxetanyl, $(CH_2)$noxolanyl, thiazolyl and piperidinyl, said —$(C_1$-$C_6)$alkyl, —$(C_1$-$C_6)$haloalkyl, —$(C_1$-$C_6)$alkyl-O—$(C_1$-$C_6)$alkyl, $(CH_2)_n$cyclopropyl, $(CH_2)_n$cyclobutyl, bicyclopentanyl, spiroheptanyl, azaspiroheptanyl, $(CH_2)$noxetanyl, $(CH_2)$noxolanyl, thiazolyl and piperidinyl optionally substituted as described herein. Another subembodiment of this aspect of the invention is realized when n is 0. Another subembodiment of this aspect of the invention is realized when n is 1. Another subembodiment of this aspect of the invention is realized when n is 2. Another subembodiment of this aspect of the invention is realized when n is 3. Another subembodiment of this aspect of the invention is realized when $R^2$ of J a, b, or c is —$(C_1$-$C_6)$alkyl, optionally substituted with 1 to 3 groups of OH, $CH_3$, $OCH_3$, $OCHF_2$, $OCF_3$, CN, $CF_3$, $CH_2F$, $CHF_2$ and Fl. Another subembodiment of this aspect of the invention is realized when $R^2$ of J a, b, or c is cyclopropyl, optionally substituted with 1 to 3 groups, preferably 1 to 2 groups of OH, $CH_3$, $OCH_3$, $OCHF_2$, $OCF_3$, CN, Fl, Cl, $CF_3$, $CHF_2$, and $CH_2F$. Another embodiment this aspect of the invention is realized when $R^2$ of J a, b, or c is bicyclopentanyl, optionally substituted with 1 to 3 groups, preferably 1 to 2 groups of OH, $CH_3$, $—(CH_2)_nOCH_3$, $—C(CH_3)_2OCH_3$, $—OCHF_2$, $—OCF_3$, —CN, $—CF_3$, $—CH_2F$, $—CHF_2$ and —Fl.

Another embodiment of the invention of Formula II is realized when $R^3$ is selected from Cl, $CH_3$, $CF_3$, and CN. A subembodiment of this aspect of Formula II is realized when $R^3$ is Cl. A subembodiment of this aspect of Formula II is realized when $R^3$ is $CH_3$.

Another embodiment of the invention of Formula II is realized when $R^b$ is selected from $CH_3$, $CH_2C(CH_3)_2OH$, $(CH_2)CH(OH)CH_2$phenyl, $CH_2C(CH_3)(OH)$phenyl, $CH_2CH(OH)$phenyl, oxetanyl, oxolanyl, and thietanedionyl, said phenyl, oxetanyl, oxolanyl and thietanedionyl optionally substituted with 1 to 3 groups of $R^{b1}$. A subembodiment of this aspect of Formula II is realized when $R^b$ is selected from $CH_2C(CH_3)_2OH$, or optionally substituted oxetanyl, oxolanyl, and thietanedionyl. A subembodiment of this aspect of Formula II is realized when $R^b$ is $CH_2C(CH_3)_2OH$. A subembodiment of this aspect of Formula II is realized when $R^b$ is optionally substituted oxetanyl. A subembodiment of this aspect of Formula II is realized when $R^b$ is optionally substituted oxolanyl. A subembodiment of this aspect of Formula II is realized when $R^b$ is optionally substituted thietanedionyl. A subembodiment of this aspect of Formula II is realized when $R^b$ is substituted with 1 to 3 groups of $R^{b1}$ is selected from $CH_3$, OH, $OCH_3$, $CF_3$, Fl, Cl, CN, $CH_2CN$, and cyclopropyl. A subembodiment of this aspect of Formula II is realized when $R^{b1}$ is selected from $CH_3$ and OH.

Another embodiment of the invention of Formula II is realized when $R^{b2}$ is 0 or absent. Another embodiment of the invention of Formula II is realized when 1 $R^{b2}$ is present. Another embodiment of the invention of Formula II is realized when 2 $R^{b2}$ are present. Still another embodiment of Formula II is realized when each $R^{b2}$ is independently selected from $CH_3$, OH, and Fl.

Yet another embodiment of the invention of Formula II is realized when J is a, b, or c, $R^1$ is H, $—CH_3$, or Cl, $R^2$ is selected from optionally substituted $—(C_1\text{-}C_6)$alkyl, cyclopropyl, and bicyclopentanyl, $R^3$ is selected from Cl, $CH_3$, $CF_3$, and CN, and $R^b$ is selected from $CH_2C(CH_3)_2OH$, oxetanyl, oxolanyl, and thietanedionyl, said oxetanyl, oxolanyl, and thietanedionyl optionally substituted with 1 to 3 groups of $R^{b1}$ selected from $CH_3$ and OH. A subembodiment of this aspect of the invention is realized when $R^b$ is $CH_2C(CH_3)_2OH$. A subembodiment of this aspect of the invention is realized when $R^b$ is optionally substituted oxetanyl. A subembodiment of this aspect of the invention is realized when $R^b$ is optionally substituted oxolanyl. A subembodiment of this aspect of the invention is realized when $R^b$ is optionally substituted thietanedionyl.

In each of the preceding embodiments and alternative embodiments described above and herein, pharmaceutically acceptable salts of each embodiment are also contemplated.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $—CH_2C(O)—$ groups (keto forms) may undergo tautomerism to form hydroxyl $—CH{=}C(OH)—$ groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"($C_1$-$C_n$)Alkyl" means an aliphatic hydrocarbon group, which may be straight or branched, comprising 1 to n carbon atoms. Thus, for example, "($C_1$-$C_6$)alkyl" means an aliphatic hydrocarbon group, which may be straight or branched, comprising 1 to 6 carbon atoms. Similarly, for example, "($C_1$-$C_3$)alkyl" means an aliphatic hydrocarbon group, which may be straight or branched, comprising 1 to 3 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halogen atom. As appreciated by those of skill in the art, "halo" or "halogen" as used herein is intended to include chloro (Cl), fluoro (F), bromo (Br) and iodo (I). Chloro (Cl) and fluoro(F) halogens are generally preferred.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, isopropyl, n-butyl, i-butyl, and t-butyl.

"Aryl" means an aromatic monocyclic or multicyclic ring system comprising 6 to 14 carbon atoms, preferably 6 to 10 carbon atoms. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridone, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclo pentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

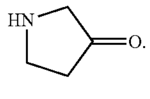

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and $S(O)_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl (also referred to herein as oxolanyl), tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

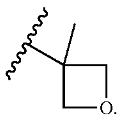 [SMILES: *C1(C)COC1]

It should be noted that in hetero-atom containing ring systems of this invention, there are no hydroxyl groups on carbon atoms adjacent to a N, O or S, as well as there are no N or S groups on carbon adjacent to another heteroatom.

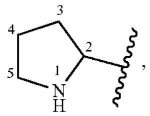

there is no —OH attached directly to carbons marked 2 and 5.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution of an available hydrogen atom of the relevant moiety with the specified groups, radicals or moieties.

When a variable appears more than once in a group, e.g., $R^6$ in $—N(R^6)_2$, or a variable appears more than once in a structure presented herein, the variables can be the same or different.

The line —, as a bond generally indicates a mixture of, or either of, the possible isomers, e.g., containing (R)- and (S)-stereochemical configuration. For example:

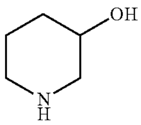

encompasses

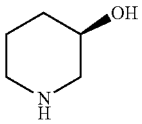

and/or

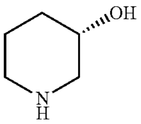

Furthermore, unwedged-bolded or unwedged-hashed lines are used in structures containing multiple stereocenters in order to depict relative configuration where it is known. For example:

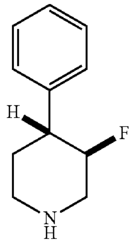

means that the fluorine and hydrogen atoms are on the same face of the piperidine ring, but represents a mixture of, or one of, the possible isomers at right
whereas:

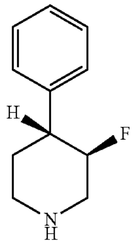 [SMILES: F[C@H]1CNCC[C@@H]1c1ccccc1]

and/or

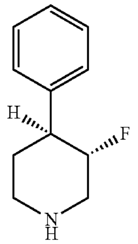

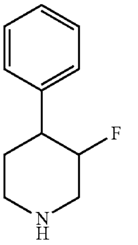

represents a mixture of, or one of, the possible isomers at right

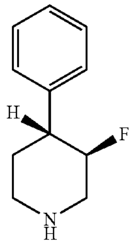

and/or

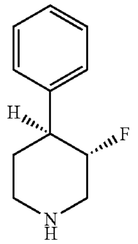

and/or

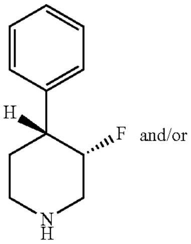

and/or

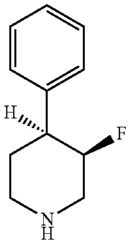

In all cases, compound name(s) accompany the structure drawn and are intended to capture each of the stereochemical permutations that are possible for a given structural isomer based on the synthetic operations employed in its preparation. Lists of discrete stereoisomers that are conjoined using or indicate that the presented compound (e.g. 'Example number') was isolated as a single stereoisomer, and that the identity of that stereoisomer corresponds to one of the possible configurations listed. Lists of discrete stereoisomers that are conjoined using and indicate that the presented compound was isolated as a racemic mixture or diastereomeric mixture.

A specific absolute configuration is indicated by use of a wedged-bolded or wedged-hashed line. Unless a specific absolute configuration is indicated, the present invention is meant to encompass all such stereoisomeric forms of these compounds.

The wavy line , as used herein, indicates a point of attachment to the rest of the compound. Lines drawn into the ring systems, such as, for example:

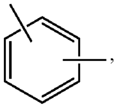, indicate that the indicated line (bond) may be attached to any of the substitutable ring carbon atoms.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

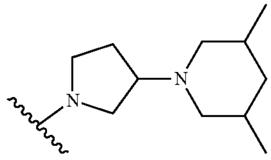 [SMILES: *N1CCC(N2CC(C)CC(C)C2)C1]

represents

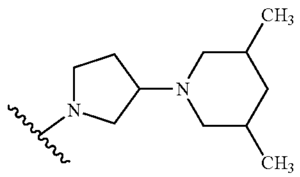 [SMILES: *N1CCC(N2CC(C)CC(C)C2)C1]

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of the invention contain one or more acidic groups or basic groups, the invention includes the corresponding pharmaceutically acceptable salts.

Thus, the compounds of the invention that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of the invention which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the invention simultaneously contain acidic and basic groups in the molecule the invention also includes, in addition to the salt forms mentioned, inner salts or betaines (zwitterions). Salts can be obtained from the compounds of the invention by customary methods which are known to the person skilled in the art, for example by combination with an organic or inorganic acid or base in a solvent or dispersant, or by anion exchange or cation exchange from other salts. The present invention also includes all salts of the compounds of the invention which, owing to low physiological compatibility, are not directly suitable for use in pharmaceuticals but which can be used, for example, as intermediates for chemical reactions or for the preparation of pharmaceutically acceptable salts.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof "Treatment" as used herein also refers to control, amelioration, or reduction of risks to the subject afflicted with a disease, disorder or condition in which LRRK2 is involved. The terms "preventing", or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjogren's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformLy and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanthin and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanthin, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the present invention can be prepared according to the following schemes and specific examples, or modifications thereof, using readily available starting materials, reagents and conventional synthesis procedures. It is also possible to make use of variants which are themselves known to those of ordinary skill in this art but are not mentioned in detail. The general procedures for making the compounds claimed in this invention can be readily understood by one skilled in the art from viewing the following schemes and descriptions. Abbreviations used in the experimentals may include, but are not limited to the following:

| | |
|---|---|
| 2-MeTHF | 2-Methyltetrahydrofuran |
| AcOH | Acetic Acid |
| Aq. | Aqueous |
| BHT | 3,5-Di-tert-4-butylhydroxytoluene |
| BINAP | (2,2'-bis(diphenylphosphino)-l,1'-binaphthyl) |
| BrettPhos Pd G3 | BrettPhos-Pd-G3, [(2-Di-cyclohexylphosphino-3,6-dimethoxy-2',4',6'-triisopropyl-1,1'-biphenyl)-2-(2'-amino-1,1'-biphenyl)]palladium (II) methanesulfonate 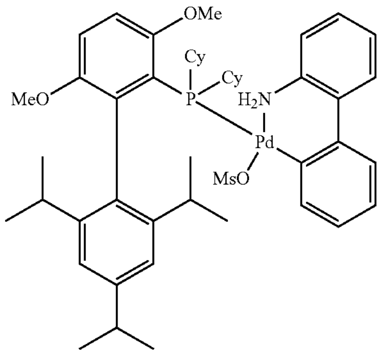 |
| $C_2Cl_6$ | Hexachloroethane |
| Cy | Cyclohexyl |
| DAST | Diethylaminosulfur trifluoride |
| DCE | Dichloroethane |
| DCM | Dichloromethane |
| DIPEA | N,N-Diisopropylethylamine |
| DMA | Dimethylacetamide |
| DMAP | 4-Dimethylaminopyridine |
| DMCDA | trans-N,N'dimethylcyclohexane-1,2-diamine |
| DMF | Dimethylformamide |
| DMSO | Dimethyl sulfoxide |
| Et | Ethyl |
| EtOAc | Ethyl acetate |
| EtOH | Ethanol |
| $Et_3N$ | Triethylamine |
| ESI | Electrospray ionization |
| Hr(s) | Hour(s) |
| $^1$H-NMR | Proton nuclear magnetic resonance |
| HPLC | High performance liquid chromatography |
| IPA | Isopropyl alcohol |
| iPr | Isopropyl |
| LCMS | Liquid chromatography-mass spectrometry |
| LiHMDS | Lithium bis(trimethylsilyl)amide |
| Me | Methyl |
| MeCN | Acetonitrile |
| MeOH | Methanol |
| Min. | Minutes |
| MS | Mass spectrometry |
| m/z | Mass to charge ratio |
| NBS | N-bromosuccinimide |
| NHP | N-hyroxyphthalimide |
| NMP | N-Methyl-2-pyrrolidone |
| Palau' Chlor ® | 2-Chloro-1,3-bis(methoxycarbonyl)guanidine |
| Pd/C | Palladium on Carbon |
| PE | Petroleum ether |
| psi | Pounds per square inch |
| RT | Room temperature |
| RuPhos Pd G4 | (2-Dicyclohexylphosphino-2',6'-diisopropoxy-1,1'-biphenyl)[2-(2'-amino-1,1'-biphenyl)]palladium (II) methanesulfonate |

-continued

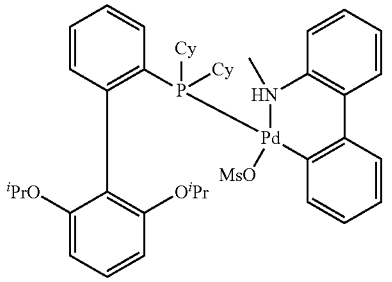

| | |
|---|---|
| Sat. | Saturated |
| SFC | Supercritical Fluid Chromatography |
| STAB | Sodium Triacetoxyborohydride |
| tBu | Tert-butyl |
| tBu BrettPhos Pd G3 | tert-BuBrettPhos-Pd-G3, [(2-Di-tert-butylphosphino-3,6-dimethoxy-2',4',6'-triisopropyl-1,1'-biphenyl)-2-(2'-amino-1,1'-biphenyl)]palladium (II) methanesulfonate |

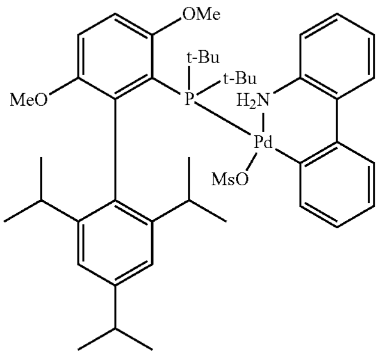

| | |
|---|---|
| TFA | Trifluoroacetic acid |
| THF | Tetrahydrofuran |
| TLC | Thin Layer Chromatography |
| $t_R$ | Retention time |
| Xphos Pd G3 | (2-Dicyclohexylphosphino-2',4',6'-triisopropyl-1,1'-biphenyl)[2-(2'-amino-1,1'-biphenyl)]palladium (II) methanesulfonate |

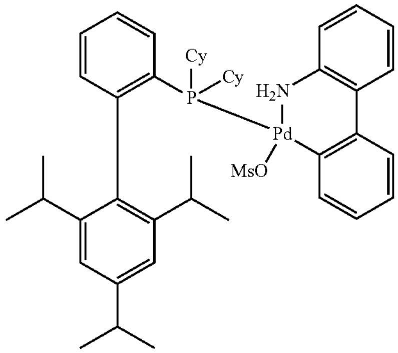

General Experimental Information:

Unless otherwise noted, all reactions are magnetically stirred. Unless otherwise noted, when diethyl ether is used in the experiments described below, it is Fisher ACS certified material and is stabilized with BHT. Unless otherwise noted, "concentrated" and/or "solvent removed under reduced pressure" means evaporating the solvent from a solution or mixture using a rotary evaporator or vacuum pump. Unless otherwise noted, flash chromatography is carried out on a Teledyne Isco (Lincoln, NE), Analogix (Burlington, WI), or Biotage (Stockholm, SWE) automated chromatography system using a commercially available cartridge as the column. Columns may be purchased from Teledyne Isco, Analogix, Biotage, Varian (Palo Alto, CA), or Supelco (Bellefonte, PA) and are usually filled with silica gel as the stationary phase. Reverse phase prep-HPLC conditions, where used, can be found at the end of each experimental section. Aqueous solutions were concentrated on a Genevac (Ipswich, ENG) or by freeze-drying/lyophilization. Unless otherwise noted, all LRRK2 $pIC_{50}$ data presented in tables refers to the LRRK2 G2019S $K_m$ ATP LanthaScreen™ assay (Life Technologies Corp., Carlsbad, CA) that is described in the Biological Assay section.

Synthesis of Common Intermediates

Scheme 1

Synthesis of 7-bromo-6-chloroquinazolin-2-amine

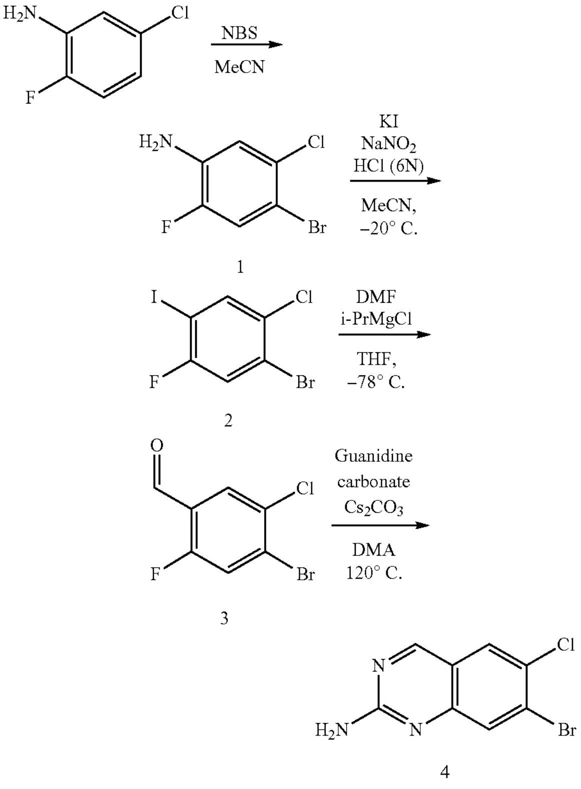

4-bromo-5-chloro-2-fluoroaniline (1)

A 5 L, 4-necked round-bottom flask was charged with 5-chloro-2-fluoroaniline (215 g, 1.48 mol) under inert atmosphere. MeCN (2.15 L) was added, followed by the portionwise addition of NBS (263 g, 1.48 mol) at RT, and the resultant solution was stirred for 2 hrs at RT. Solvent was then removed under reduced pressure, and the crude residue was diluted with EtOAc (1.5 L). This mixture was washed with water (3×500 mL), then brine (1×500 mL), then dried over anhydrous $Na_2SO_4$. The solution was filtered, and solvent removed from the collected filtrate under reduced pressure to afford the title compound 1.

1-bromo-2-chloro-5-fluoro-4-iodobenzene (2)

A 10 L, 4-necked round-bottom flask was charged with 4-bromo-5-chloro-2-fluoroaniline 1 (300 g, 1.34 mol) under inert atmosphere. MeCN (4.5 L) was added, followed by the addition of 6 N HCl (aqueous, 223 mL, 1.34 mol) at RT and stirred for 1.5 hrs. The mixture was then cooled to −20° C., and sodium nitrite (96.8 g, 1.40 mol) in water (300 mL) was added dropwise over 15 min, then stirred for 30 min. The mixture was maintained at −20° C. and treated with an aqueous (1.3 L) solution of potassium iodide (665 g, 4.01 mol) dropwise with stirring over 20 min. The resultant mixture was allowed to warm to RT and stirred for 1 hr. The mixture was then extracted with EtOAc (2×3 L), and the combined organic phases were washed with sat. aq. $Na_2S_2O_3$ (4×1.5 L) and brine (1×1.5 L). Solvent was removed under reduced pressure and the resultant crude residue was purified by flash chromatography on silica gel (100% PE) to afford the title compound 2.

4-bromo-5-chloro-2-fluorobenzaldehyde (3)

A 10 L, 4-necked round-bottom flask was charged with 1-bromo-2-chloro-5-fluoro-4-iodobenzene 2 (374 g, 1.12 mol) under inert atmosphere. To the flask was added THF (4 L), and the mixture was cooled to −78° C. Isopropylmagnesium chloride (2M in THF, 614 mL, 1.23 mol) was added dropwise with stirring, and the resultant mixture was stirred for 1 hr at −78° C. DMF (245 g, 3.35 mol) was added dropwise with stirring at −78° C., and the mixture was allowed to warm to RT and stirred for 2 hrs. After quenching with 2 L of water/ice, the mixture was extracted with EtOAc (2×2 L). The organic phase was washed with brine (1×2 L), and the solvent removed under reduced pressure. The residue was slurried with PE (500 mL) to afford the title compound 3.

7-bromo-6-chloroquinazolin-2-amine (4)

A 10 L 4-necked round-bottom flask was charged with 4-bromo-5-chloro-2-fluorobenzaldehyde 3 (200 g, 842 mmol), $Cs_2CO_3$ (823 g, 2.53 mol), and guanidine carbonate (152 g, 842 mmol) under inert atmosphere. DMA (4 L) was added, and the resultant solution was stirred for 12 hrs at 120° C. On cooling, the mixture was diluted with 15 L of water/ice. Solids were collected by filtration and slurried with EtOAc (700 mL) to afford the title compound 4. MS (ESI): m/z calc'd for $C_8H_6BrClN_3$ $[M+H]^+$: 258, found 258; $^1H$ NMR (300 MHz, DMSO-$d_6$, 25° C.) δ: 9.11 (s, 1H), 8.07 (s, 1H), 7.78 (s, 1H), 7.17 (s, 2H).

Scheme 2. Synthesis of N,N-bis(tert-butyloxycarbonyl)-7-bromo-6-chloroquinazolin-2-amine

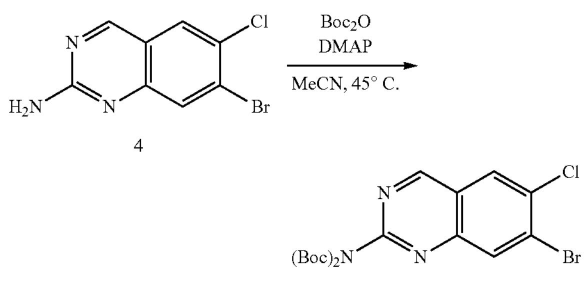

4

5

N,N-bis(tert-butyloxycarbonyl)-7-bromo-6-chloroquinazolin-2-amine (5)

A 5 L 4-necked round-bottom flask was charged with 7-bromo-6-chloroquinazolin-2-amine 4 (168 g, 650 mmol) and DMAP (79 g, 650 mmol) under inert atmosphere. MeCN (1.7 L) was added, and to the stirring mixture was added di-tert-butyl dicarbonate (426 g, 1.95 mol) dropwise with stirring at 45° C. The resultant solution was stirred for 1 hr at 45° C. The reaction was removed from the heat, diluted with water (1 L), and extracted with EtOAc (2×1 L). Solvent was removed under reduced pressure and the crude residue was purified by flash chromatography on silica gel (EtOAc/PE, 10-30%) to afford the title compound 5. MS (ESI): m/z calc'd for $C_{18}H_{22}BrClN_3O_4$ $[M+H]^+$: 458, found 458; $^1H$ NMR (400 MHz, $CDCl_3$, 25° C.) δ: 9.35 (m, 1H), 8.38 (s, 1H), 8.09 (s, 1H), 1.49 (s, 18H).

Scheme 3. Synthesis of 7-bromo-2,6-dichloroquinazoline

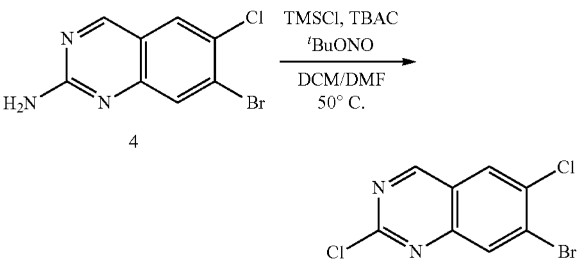

4

6

7-bromo-2,6-dichloroquinazoline (6)

A 500-mL 4-necked round-bottom flask was charged with 7-bromo-6-chloroquinazolin-2-amine 4 (6.0 g, 23 mmol) under inert atmosphere. A solution of TMSCl (9.8 g, 90 mmol) in DCM (60 mL) was added to the flask, followed by DMF (6 mL). The solution was stirred at rt for 1 hr. Tetrabutylammonium chloride (7.78 g, 28 mmol) was then added, and the resultant mixture was warmed to 50° C. To the stirring mixture at 50° C., tert-butyl nitrite (7.14 g, 69 mmol) was added dropwise, and on complete addition the mixture was stirred at this temperature for 1 hr. The reaction was then quenched by the addition of sat. aq. $NH_4Cl$ (200 mL). This mixture was extracted with DCM (2×100 mL), and the combined organic layers washed with brine (1×50 mL). The organic phase was dried over $Na_2SO_4$, filtered, and the solvent removed under reduced pressure. The crude residue was then purified by flash chromatography over silica gel (EtOAc/PE, 25%) to afford the title compound 6. MS (ESI): m/z calc'd for $C_8H_4BrCl_2N_2$ $[M+H]^+$: 277, found 277; $^1H$ NMR (300 MHz, DMSO-$d_6$, 25° C.) δ: 9.61 (s, 1H), 8.61 (s, 1H), 8.52 (s, 1H).

Scheme 4. Synthesis of tert-butyl (7-bromo-6-chloroquinazolin-2-yl)(1-cyclopropyl-5-methyl-1H-pyrazol-4-yl)carbamate

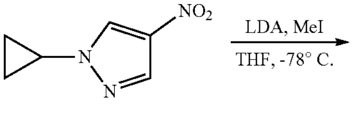

-continued

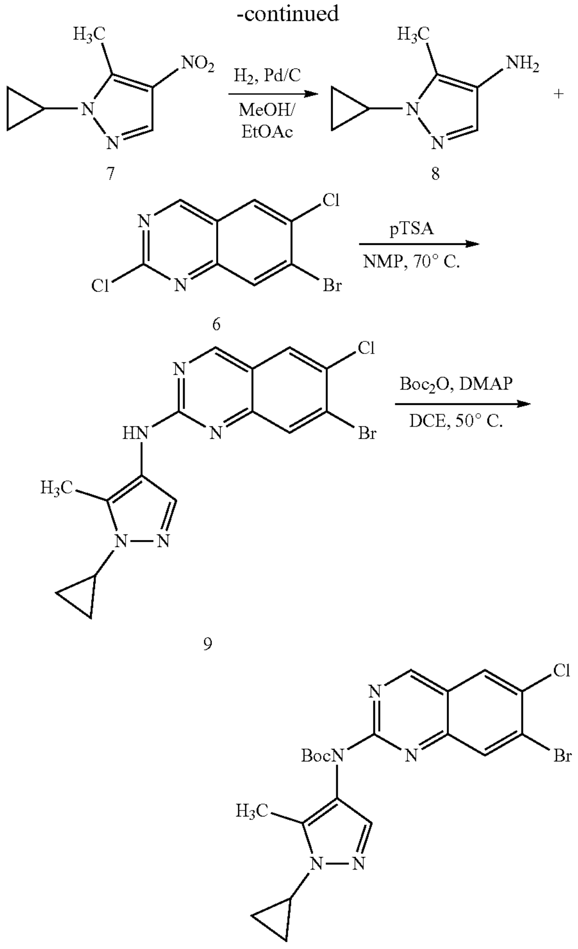

7 8 6 9 10

1-cyclopropyl-5-methyl-4-nitro-1H-pyrazole (7)

A 10-L, 4-necked round-bottom flask was charged with 1-cyclopropyl-4-nitropyrazole (280 g, 1.83 mol) under inert atmosphere. THF (2.8 L) was added, and the mixture was cooled to −78° C.

To the stirring mixture at this temperature was slowly added lithium diisopropylamide (2 M in THF/heptane/ethylbenzene, 950 mL, 1.90 mol). The resultant mixture was stirred at −78° C. for 2 hrs, at which point iodomethane (389 g, 2.74 mol) was slowly added. On complete addition, the reaction vessel was removed from the cooling bath and stirred at room temperature for 30 min. The reaction was quenched by pouring into ice water (10 L), and the mixture was extracted with EtOAc (3x2 L). The combined organic layers were dried over anhydrous $Na_2SO_4$, filtered, and solvent was removed from the collected filtrate under reduced pressure to afford the title compound 7.

1-cyclopropyl-5-methyl-1H-pyrazol-4-amine (8)

A 5-L round-bottom flask was charged with intermediate 7 (155 g, 927 mmol) and Pd/C (10 wt %, 80 g) under inert atmosphere. MeOH/EtOAc (3 L, 1:1 v/v) was added, and the vessel was evacuated and purged over 3 cycles of vacuum/inert atmosphere. Finally, the vessel was once again evacuated, but then back-filled with $H_2$ gas (1 atm) instead of inert atmosphere. The mixture was stirred at RT overnight. Solids were removed by filtration, and solvent was removed from the collected filtrate under reduced pressure. The crude residue was subjected to purification by flash chromatography over silica gel (50% EtOAc/PE) to afford the title compound 8.

7-bromo-6-chloro-N-(1-cyclopropyl-5-methyl-1H-pyrazol-4-yl)quinazolin-2-amine (9)

A 10-L, 4-necked round-bottom flask was charged with 7-bromo-2,6-dichloroquinazoline 6 (346 g, 1.24 mol) and para-toluene sulfonic acid monohydrate (53.6 g, 311 mmol) under inert atmosphere. NMP (4 L) was added, and the mixture was stirred for 1 hr at RT. To the stirring mixture at this point was added intermediate 8 (193 g, 1.41 mol). The reaction mixture was then warmed to 70° C. and stirred at this temperature for 3 hrs. The reaction was quenched by pouring into ice water (12 L), which resulted in precipitation of solids. The solids were collected by filtration to afford the title compound 9.

tert-butyl (7-bromo-6-chloroquinazolin-2-yl)(1-cyclopropyl-5-methyl-1H-pyrazol-4-yl)carbamate (10)

A 3-L, 4-necked round-bottom flask was charged with intermediate 9 (100 g, 264 mmol), di-tert-butyl dicarbonate (115 g, 528 mmol), and 4-dimethylaminopyridine (8.1 g, 66.1 mmol) under inert atmosphere. DCE (1 L) was added, and the resultant solution was warmed to 50° C. with stirring for 1 hr. The reaction was quenched by pouring into ice water (2 L), and the mixture was extracted with DCM (3x500 mL). The combined organic layers were dried over anhydrous $Na_2SO_4$, filtered, and solvent was removed from the collected filtrate under reduced pressure to afford the title compound 10. MS (ESI): m/z calc'd for $C_{20}H_{22}BrClN_5O_2$ $[M+H]^+$: 478, found 478; $^1H$ NMR (300 MHz, $CDCl_3$, 25° C.) δ: 9.25 (s, 1H), 8.27 (s, 1H), 8.00 (s, 1H), 7.46 (s, 1H), 3.39 (m, 1H), 2.28 (s, 3H), 1.50 (s, 9H), 1.31-1.18 (m, 2H), 1.18-0.96 (m, 2H).

Scheme 5
Synthesis of 7-bromo-6-chloro-N-(5-chloro-1-cyclopropyl-1H-pyrazol-4-yl)quinazolin-2-amine

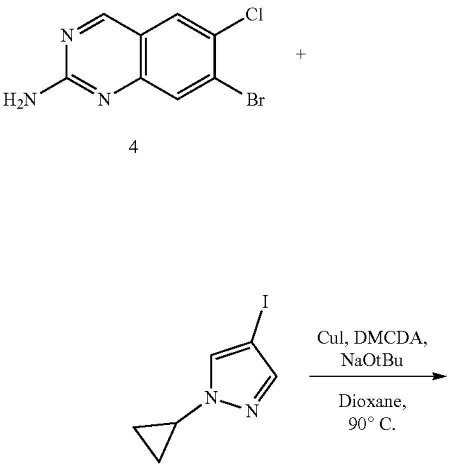

4

-continued

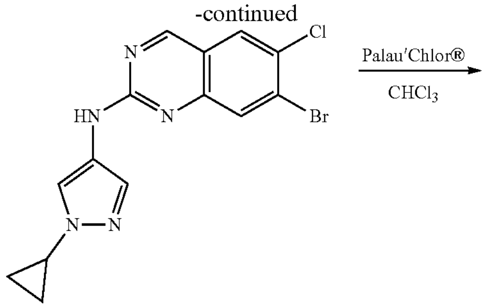

11

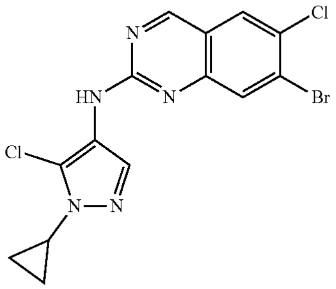

12

7-bromo-6-chloro-N-(1-cyclopropyl-1H-pyrazol-4-yl)quinazolin-2-amine (11)

A 10-L 4-necked round-bottom flask was charged with trans-N,N'-dimethyl-1,2-cyclohexanediamine (DMCDA) (39.5 g, 278 mmol) and copper (I) iodide (35.2 g, 185 mmol) under inert atmosphere. Dioxane (7 L) was added and the headspace degassed under vacuum. The mixture was stirred at RT for 5 min, at which point 7-bromo-6-chloroquinazolin-2-amine 4 (240 g, 925 mmol), 1-cyclopropyl-4-iodo-1H-pyrazole (239 g, 925 mmol), and NaOtBu (178 g, 1.85 mol) were added in sequence. The flask was degassed again, and the resultant mixture was heated to 90° C. and maintained at this temperature for 8 hrs with stirring under inert atmosphere. Upon cooling to RT, the mixture was diluted with EtOAc (5 L) and washed successively with sat. aq. $NH_4Cl$ (1.5 L) and brine (1.5 L). The organic layer was dried over anhydrous magnesium sulfate, filtered, and solvent was removed from the collected filtrate under reduced pressure. The resultant crude residue was subjected to purification by flash chromatography over silica gel (MeOH/DCM, 0-20%) to afford the title compound 11.

7-bromo-6-chloro-N-(5-chloro-1-cyclopropyl-1H-pyrazol-4-yl)quinazolin-2-amine (12)

A 5-L 4-necked round-bottom flask was charged with intermediate 11 (110 g, 302 mmol) under inert atmosphere. Chloroform (2.75 L) was added, and to the stirring mixture at RT was added Palau'Chlor® (70 g, 332 mmol). The resultant mixture was stirred at 25° C. for 2 hrs, at which point the reaction was quenched by the addition of sat. aq. sodium thiosulfate solution (110 mL, 1 V) at RT. Phases were separated and the aqueous phase was extracted with DCM (3×2 L). The combined organic layers were washed successively with 1N HCl (2×1.5 L) and brine (1.5 L), dried over $MgSO_4$, filtered, and solvent was removed from the collected filtrate under reduced pressure. The resultant crude product was upgraded by slurry overnight in PE/EtOAc (1:1, 1.1 L). The solid was collected by vacuum filtration to afford the title compound 12. MS (ESI): m/z calc'd for $C_{14}H_{11}BrCl_2N_5$ $[M+H]^+$: 398, found 398; $^1H$ NMR (400 MHz, DMSO-$d_6$, 25° C.) δ: 9.41 (s, 1H), 9.24 (s, 1H), 8.21 (s, 1H), 7.97 (s, 1H), 7.87 (s, 1H), 3.61 (m, 1H), 1.15-1.02 (m, 4H).

Scheme 6
Synthesis of N,N-bis(tert-butyloxycarbonyl)-6-chloro-7-iodoquinazolin-2-amine

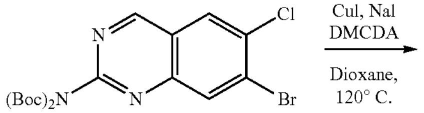

5

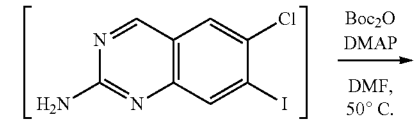

13

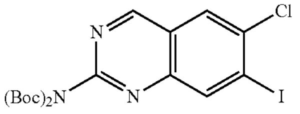

14

N,N-bis(tert-butyloxycarbonyl)-6-chloro-7-iodoquinazolin-2-amine (14)

A 5-L 4-necked round-bottom flask was charged with N,N-bis(tert-butyloxycarbonyl)-7-bromo-6-chloroquinazolin-2-amine 5 (250 g, 545 mmol), copper(I) iodide (10.3 g, 54 mmol), trans-N,N'-dimethylcyclohexane-1,2-diamine (DMCDA) (15.5 g, 109 mmol), and sodium iodide (405 g, 2.70 mol) under inert atmosphere. The mixture was then dissolved/suspended in dioxane (2.5 L) and heated to reflux overnight with stirring. Upon cooling, the mixture was diluted with ice water (5 L), and precipitated solids were collected by filtration to afford the crude 6-chloro-7-iodoquinazolin-2-amine 13, a fraction of which was carried on directly to the subsequent step. A 3-L 4-necked round-bottom flask was charged with the crude intermediate 13 (120 g, 393 mmol) and DMAP (48 g, 393 mmol) under inert atmosphere. MeCN (1 L) was added, followed by the portionwise addition of di-tert-butyl dicarbonate (429 g, 1.97 mol) at 50° C. The resultant solution was stirred for 2 hrs at this temperature. Solvent was removed under reduced pressure, and the crude residue was purified by flash chromatography over silica gel (EtOAc/hexanes, 5%) to afford the title compound 14. MS (ESI): m/z calc'd for $C_{18}H_{22}ClIN_3O_4$ $[M+H]^+$: 506, found 506; $^1H$ NMR (400 MHz, $CDCl_3$, 25° C.) δ: 9.33 (s, 1H), 8.65 (s, 1H), 8.04 (s, 1H), 1.47 (s, 18H).

Scheme 7. Synthesis of (1-(tert-butoxycarbonyl)piperidin-4-yl)zinc(II) iodide

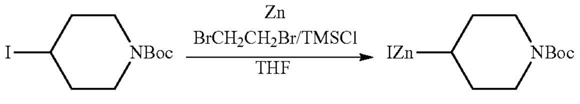

15

(1-(tert-butoxycarbonyl)piperidin-4-yl)zinc(II) iodide (15)

A 10-L 4-necked round-bottom flask was charged with zinc (378 g, 5.78 mol) under inert atmosphere. THF (5.4 L) was added and the headspace was degassed under vacuum (3×). Then, dibromoethane (36 g, 194 mmol) and chlorotrimethylsilane (21.1 g, 194 mmol) were added and the headspace was once again degassed under vacuum (3×). The mixture was then warmed to 65° C. and stirred for 20 min. Next, the mixture was cooled to RT and tert-butyl 4-iodopiperidine-1-carboxylate (900 g, 2.89 mol) was added. The headspace was once again degassed under vacuum (3×), and the resultant solution was stirred for 30 min at 45° C. The mixture was cooled to RT, stirring was stopped, and the suspension was allowed to settle overnight. The supernatant was titrated using established procedures to determine the concentration of the title compound 15.

Scheme 8. Synthesis of tert-butyl 4-(2-amino-6-chloroquinazolin-7-yl)piperidine-1-carboxylate

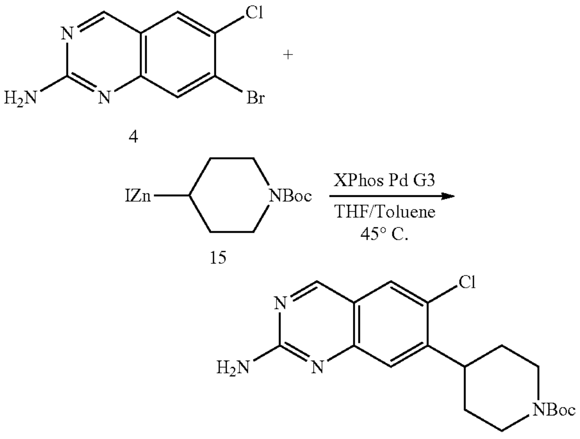

4

15

16 tert-butyl 4-(2-amino-6-chloroquinazolin-7-yl)piperidine-1-carboxylate (16)

A 20-L 4-necked round-bottom flask was charged with 7-bromo-6-chloroquinazolin-2-amine 4 (220 g, 850 mmol) and XPhos Pd G3 (72 g, 85 mmol) under inert atmosphere. Toluene (2 L) was added and the headspace degassed under vacuum (3×). Finally, [1-(tert-butoxycarbonyl)piperidin-4-yl](iodo)zinc 15 in THF (5.24 L, 2.76 mol) was added over the course of 0.5 hr at RT. The headspace was once again degassed under vacuum (3×), and the resultant solution was stirred for 12 hrs at 45° C. Upon cooling to RT, the reaction was then quenched by the addition of ice water (7.5 L). This mixture was extracted with EtOAc (3×2.5 L), and the combined organic phase was washed with water (4×1.5 L) and brine (1×1.5 L). Solvent was removed under reduced pressure, and the crude residue was purified by flash chromatography over silica gel (EtOAc/PE, 10-30%) to afford the title compound 16. This material was further purified by Flash-Prep-HPLC with the following conditions (IntelFlash-1): Column, C18 silica gel; mobile phase, $MeCN/H_2O$ $(NH_4HCO_3)$=3/2 increasing to $MeCN/H_2O(NH_4HCO_3)$=9/1 within 20 min. Final upgrade of this material by re-crystallization from MeCN afforded 16 in pure form. MS (ESI): m/z calc'd for $C_{18}H_{24}ClN_4O_2$ $[M+H]^+$: 363, found 363; $^1H$ NMR (300 MHz, DMSO-$d_6$, 25° C.) δ: 9.06 (s, 1H), 7.94 (s, 1H), 7.31 (s, 1H), 6.95 (s, 2H), 4.09 (m, 2H), 3.13 (m, 1H), 2.88 (m, 2H), 1.86 (m, 2H), 1.63-1.49 (m, 2H), 1.44 (s, 9H).

Scheme 9. Synthesis of tert-butyl (2R)-4-iodo-2-methylpiperidine-1-carboxylate

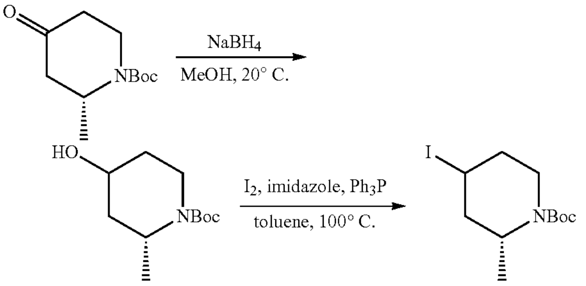

17

18 tert-butyl (2R)-4-hydroxy-2-methylpiperidine-1-carboxylate (17)

A 5-L, 3-necked round-bottom flask was charged with tert-butyl (R)-2-methyl-4-oxopiperidine-1-carboxylate (100 g, 469 mmol) under inert atmosphere. MeOH (1 L) was added, and the stirring mixture was cooled to 0° C. To the stirring mixture at this temperature this temperature was added $NaBH_4$ (17.7 g, 469 mmol) in portions. On complete addition, the reaction mixture was allowed to warm to RT and stirred at this temperature for 2 hrs. The reaction was quenched by pouring into water (1.5 L). The solution was extracted with $CH_2C12$ (2×1 L). The combined organic phase was washed with brine, dried over anhydrous $Na_2SO_4$, filtered, and solvent was removed from the collected filtrate under reduced pressure to afford the title compound 17 as a diastereomeric mixture.

tert-butyl (2R)-4-iodo-2-methylpiperidine-1-carboxylate (18)

A 5-L, 3-necked round-bottom flask was charged with tert-butyl (2R)-4-hydroxy-2-methylpiperidine-1-carboxylate 17 (100 g, 465 mmol) under inert atmosphere. Toluene (2 L) was added, and to the stirring mixture at room temperature were added imidazole (63.2 g, 929 mmol), triphenylphosphine (366 g, 1.39 mol), and iodine (177 g, 697 mmol). The reaction mixture was then heated to 100° C., and held at this temperature for 2 hrs. On cooling to RT, the reaction solution was poured into sat. aq. $Na_2S_2O_3$ (1.5 L). The phases were separated, and the aqueous phase was extracted with EtOAc (1 L). The combined organic layers were washed with brine, dried over anhydrous $Na_2SO_4$, filtered, and solvent was removed from the collected filtrate under reduced pressure. The crude residue was subjected to purification by flash chromatography over silica gel (3-40% EtOAc/PE) to afford the title compound 18 as a diastereomeric mixture. MS (ESI): m/z calc'd for $C_{11}H_{21}INO_2$ $[M+H]^+$: 326, found 270 [M+H loss of $^{t}$Bu]$^+$; $^1$H NMR (400 MHz, $CD_3OD$, 25° C.) δ: 4.11-4.51 (m, 2H), 3.84-3.85 (m, 1H), 2.88-2.91 (m, 1H), 2.22-2.33 (m, 2H), 2.04-2.08 (m, 2H), 1.45 (s, 9H), 1.32-1.72 (m, 3H).

Scheme 10. Synthesis of tert-butyl (2S)-4-iodo-2-methylpiperidine-1-carboxylate

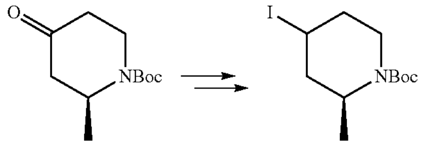

19 tert-butyl (2S)-4-iodo-2-methylpiperidine-1-carboxylate (19)

The title compound could be prepared using identical methods to those described above for the corresponding (R) isomer 18. MS (ESI): m/z calc'd for $C_{11}H_{21}INO_2$ $[M+H]^+$: 326, found 270 [M+H loss of $^{t}$Bu]$^+$; $^1$H NMR (400 MHz, $CD_3OD$, 25° C.) δ: 4.11-4.51 (m, 2H), 3.84-3.85 (m, 1H), 2.88-2.91 (m, 1H), 2.22-2.33 (m, 2H), 2.04-2.08 (m, 2H), 1.45 (s, 9H), 1.32-1.72 (m, 3H).

trans-tetrahydrofuran-3,4-diol (20)

A 10-L 4-necked round-bottom flask was charged with 3,6-dioxabicyclo[3.1.0]hexane (409 g, 4.75 mol). $H_2SO_4$ (4 L, 1.5 mol/L) was added, and the resulting solution was heated to reflux and stirred for 6 hrs. The reaction mixture was cooled to room temperature. The pH value of the solution was adjusted to 8 with $Na_2CO_3$. Solvent was removed under reduces pressure. The product was extracted with THF (5 L). THF was removed from the extract under reduced pressure to afford the title compound 20.

trans-4-((tert-butyldiphenylsilyl)oxy)tetrahydrofuran-3-ol (21)

A 3-L 4-necked round-bottom flask was charged with trans-tetrahydrofuran-3,4-diol 20 (52 g, 499 mmol), imidazole (51 g, 749 mmol), and TBDPSCl (137 g, 498 mmol) under inert atmosphere. MeCN (1.50 L) was added and the resultant solution was stirred for 4 hrs at 80° C. Solvent was removed under reduced pressure. The residue was taken up in EtOAc (1 L), and the organic phase was washed with water (2×500 mL), dried over $Na_2SO_4$, and filtered. Solvent was removed from the collected filtrate under reduced pressure. The crude residue was subjected to purification by flash chromatography over silica gel (0-3% EtOAc/PE) to afford the racemic title compound 21.

(3S,4S) and (3R,4R) 4-((tert-butyldiphenylsilyl)oxy) tetrahydrofuran-3-ol (22 and 23)

The racemic material 21 could be resolved to its component enantiomers by chiral preparative SFC (Column &

Scheme 11

Synthesis of (R)- and (S)-4-((tert-butyldiphenylsilyl)oxy)-dihydrofuran-3-(2H)-one

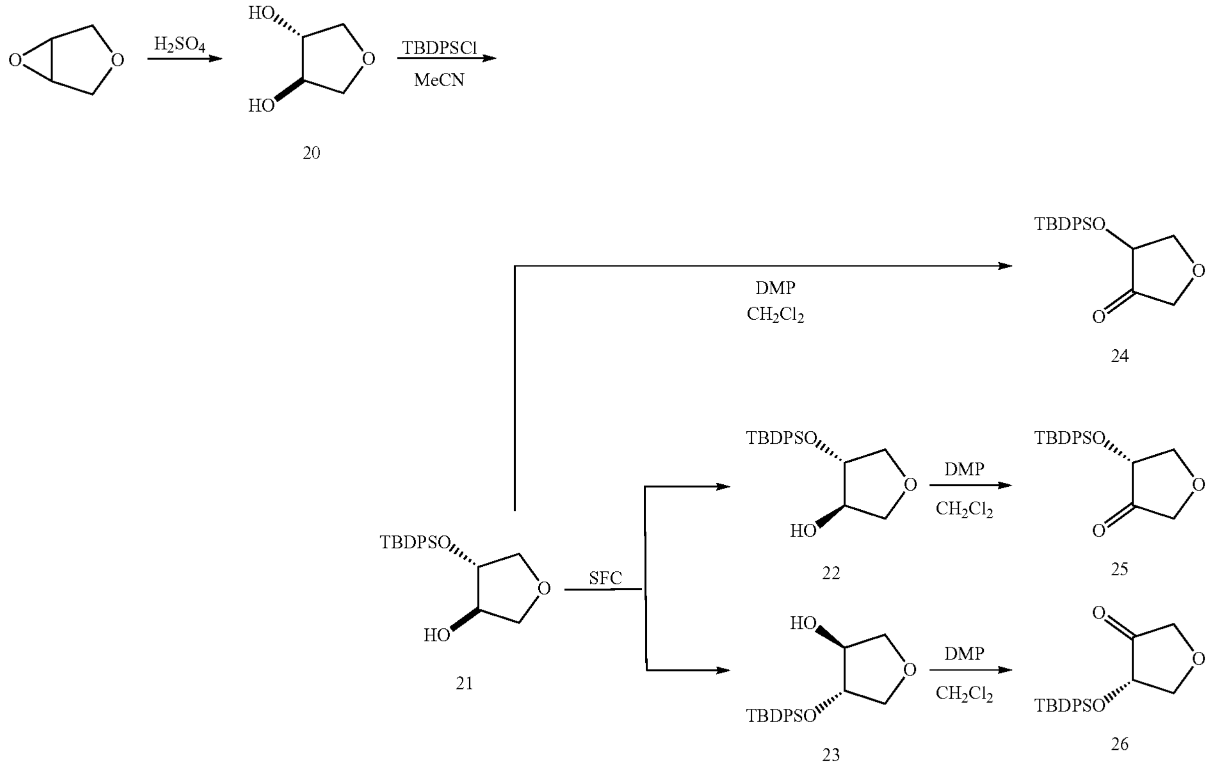

dimensions: AS-H, 50 mm×250 mm; Mobile phase A: $CO_2$; Mobile phase B: 2% DEA in IPA) to afford the title compounds 22 (tR=2.9 min) and 23 (tR=5.4 min).

4-((tert-butyldiphenylsilyl)oxy)dihydrofuran-3(2H)-one (24)

A 500-mL 4-necked round-bottom flask was charged with intermediate 21 (85.7 g, 250 mmol) under inert atmosphere. DCM (1.7 L) was added, and to the resulting solution was added Dess-Martin periodinane (117 g, 275 mmol) in portions at room temperature. The reaction mixture was stirred for 3 hrs at 30-35° C. The reaction was then quenched by the addition of 1.5 L of aqueous $NaHCO_3/Na_2S_2O_3$ (1:1). Phases were separated, and the aqueous phase was extracted with additional DCM (3×500 mL). The combined organic phase was then washed with brine (1×500 mL), dried over anhydrous $Na_2SO_4$, filtered, and solvent was removed from the collected filtrate under reduced pressure. The crude residue was subjected to purification by flash chromatography over silica gel (1% EtOAc/PE) to afford the title compound 24. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H).

(R)- and (S)-4-((tert-butyldiphenylsilyl)oxy)dihydrofuran-3(2H)-one (25 and 26)

By substituting alcohol 22 in an identical procedure to that described above, the enantiopure compound 25 was prepared. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H).

By substituting alcohol 23 in an identical procedure to that described above, the enantiopure compound 26 was prepared. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H).

Scheme 12. Synthesis of (3S,4S) and (3R,4R) 1-(4-((tert-butyldiphenylsilyl)oxy)-3-methyltetrahydrofuran-3-yl)-4-iodopiperidine

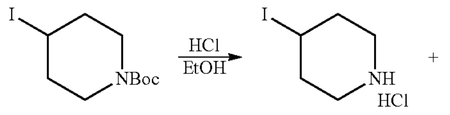

27

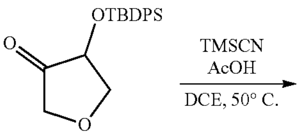

24

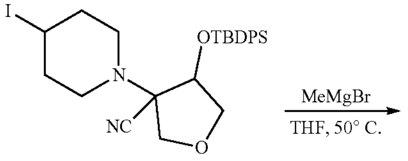

28

-continued

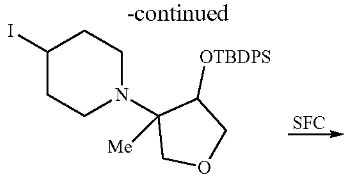

28

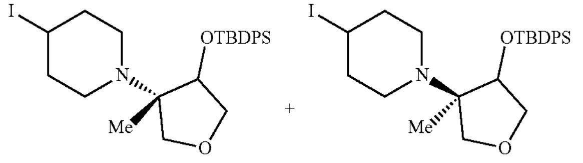

30 31

4-iodopiperidine hydrochloride (27)

A 10-L 4-necked round-bottom flask was charged with tert-butyl 4-iodopiperidine-1-carboxylate (400 g) and EtOH (3.2 L) under inert atmosphere. This was followed by the addition of HCl (gas) in 1,4-dioxane (1.6 L) dropwise with stirring at room temperature. The resulting solution was stirred for 16 hrs at room temperature. Solvent was removed under reduced pressure to afford the title compound 27.

4-((tert-butyldiphenylsilyl)oxy)-3-(4-iodopiperidin-1-yl)tetrahydrofuran-3-carbonitrile (28)

A 3-L 4-necked round-bottom flask was charged with 4-iodopiperidine hydrochloride 27 (250 g, 1.01 mol) and KOAc (110 g, 1.12 mol) under inert atmosphere. DCE (1.25 L) was added, and the resultant mixture was stirred for 1 hr at 50° C. At this point, racemic 4-((tert-butyldiphenylsilyl)oxy)dihydrofuran-3(2H)-one 24 (370 g, 1.09 mol) was added at RT. The resultant solution was stirred for 1 hr at 50° C. This was followed by the addition of TMSCN (150 g, 1.51 mol) dropwise with stirring at 50° C. The reaction mixture was stirred for 16 hrs at 50° C. The reaction was then quenched by the addition of 1 L of sat. aq. $NaHCO_3$. The phases were separated, and the aqueous phase was extracted with $CH_2C12$ (1 L). The combined organic layers were dried over anhydrous $Na_2SO_4$, filtered, and solvent was removed from the collected filtrate under reduced pressure to afford the title compound 28.

1-(4-((tert-butyldiphenylsilyl)oxy)-3-methyltetrahydrofuran-3-yl)-4-iodopiperidine (29)

A 5-L 4-necked round-bottom flask was charged with 4-[(tert-butyldiphenylsilyl)oxy]-3-(4-iodopiperidin-1-yl)oxolane-3-carbonitrile 28 (700 g, 1.249 mol) under inert atmosphere. THF (2 L) was added, and the solution was cooled to 0° C. To the stirring mixture at this temperature was dropwise added MeMgBr (1.20 L) (3 M in THF) maintaining the internal reaction temperature at or below 10° C. The resulting solution was warmed to 50° C. and stirred for 3 hrs at this temperature. The reaction was then quenched by the addition of sat. aq. $NaHCO_3$. The biphasic mixture was extracted with EtOAc (2×1 L). The combined organic layers were dried over anhydrous $Na_2SO_4$, filtered, and solvent was removed from the collected filtrate under reduced pressure. The crude residue was subjected to purification by flash chromatography over silica gel (2-10% EtOAc/PE) to afford semi-pure material. This material was further upgraded by preparative reverse-phase HPLC with the following conditions (IntelFlash-1): silica gel; MeCN: $H_2O$ 0-100% over 20 min, to afford the racemic title compound 29. MS (ESI): m/z calc'd for $C_{26}H_{36}INO_2Si$ $[M+H]^+$: 550, found 550; $^1H$ NMR (400 MHz, $CDCl_3$, 25° C.) δ: 7.80 (m, 2H), 7.71 (m, 2H), 7.53-7.35 (m, 6H), 4.28 (s, 1H), 4.09-3.96 (m, 2H), 3.90-3.76 (m, 2H), 3.65 (m, 1H), 2.62-2.52 (m, 1H), 2.42 (s, 1H), 2.24 (m, 1H), 2.06 (m, 4H), 1.11 (s, 9H), 0.94 (s, 3H).

(3S,4S) and (3R,4R) 1-(4-((tert-butyldiphenylsilyl) oxy)-3-methyltetrahydrofuran-3-yl)-4-iodopiperidine (30 and 31)

The racemic material 29 could be resolved to its component enantiomers by chiral preparative SFC (Column & dimensions: AD-H, 50 mm×250 mm; Mobile phase A: $CO_2$; Mobile phase B: 2 mM $NH_3$-MeOH in IPA) to afford the title compounds 30 (tR=5.0 min) and 31 (tR=5.8 min). MS (ESI): m/z calc'd for $C_{26}H_{36}INO_2Si$ $[M+H]^+$: 550, found 550; $^1H$ NMR (400 MHz, $CDCl_3$, 25° C.) δ: 7.80 (m, 2H), 7.71 (m, 2H), 7.53-7.35 (m, 6H), 4.28 (s, 1H), 4.09-3.96 (m, 2H), 3.90-3.76 (m, 2H), 3.65 (m, 1H), 2.62-2.52 (m, 1H), 2.42 (s, 1H), 2.24 (m, 1H), 2.06 (m, 4H), 1.11 (s, 9H), 0.94 (s, 3H). MS (ESI): m/z calc'd for $C_{26}H_{36}INO_2Si$ $[M+H]^+$: 550, found 550; $^1H$ NMR (400 MHz, $CDCl_3$, 25° C.) δ: 7.80 (m, 2H), 7.71 (m, 2H), 7.53-7.35 (m, 6H), 4.28 (s, 1H), 4.09-3.96 (m, 2H), 3.90-3.76 (m, 2H), 3.65 (m, 1H), 2.62-2.52 (m, 1H), 2.42 (s, 1H), 2.24 (m, 1H), 2.06 (m, 4H), 1.11 (s, 9H), 0.94 (s, 3H).

Scheme 13. Synthesis of 4-iodo-1-(3-methyloxetan-3-yl)piperidine

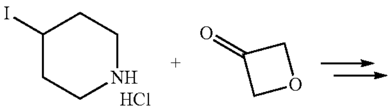

27

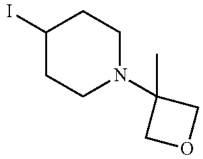

32

4-iodo-1-(3-methyloxetan-3-yl)piperidine (32)

The title compound was prepared using an identical sequence to that which was used for the preparation of 29, substituting 3-oxetanone for intermediate 24. MS (ESI): m/z calc'd for $C_9H_{17}INO$ $[M+H]^+$: 282, found 282; $^1H$ NMR (400 MHz, $CDCl_3$, 25° C.) δ: 4.55 (m, 2H), 4.33 (m, 1H), 4.21 (m, 2H), 2.43 (m, 2H), 2.20 (m, overlap, 6H), 1.37 (s, 3H).

Scheme 14. Synthesis of (3S,4S) and (3R,4R) 1-(4-((tert-butyldiphenylsilyl)oxy)tetrahydrofuran-3-yl)-4-iodopiperidine

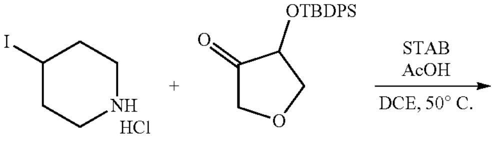

27 24

-continued

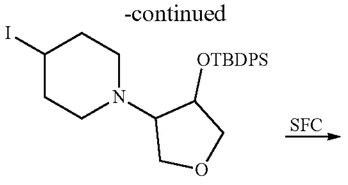

33

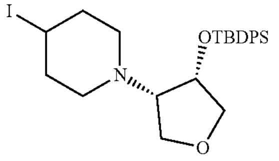

+

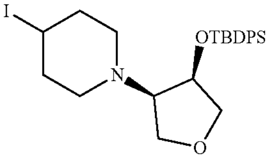

34 35

1-(4-((tert-butyldiphenylsilyl)oxy)tetrahydrofuran-3-yl)-4-iodopiperidine (33)

A 5-L 3-necked round-bottom flask was charged with 4-iodopiperidine hydrochloride 27 (121 g, 489 mmol), 4-((tert-butyldiphenylsilyl)oxy)dihydrofuran-3(2H)-one 24 (200 g, 587 mmol), and 4 Å molecular sieves (480 g) under inert atmosphere. DCE (2.5 L) was added, and the suspension was stirred for 15 minutes at RT. To the stirring mixture at RT were then added AcOH (33.6 mL, 587 mmol) and $NaBH(OAc)_3$ (259 g, 1.22 mol). The reaction mixture was then warmed to 65° C. and stirred at this temperature for 3 hrs. On cooling to RT, the reaction mixture was diluted with DCM and washed with sat. aq. $NH_4Cl$ (6 L). The organic layer was then dried over $MgSO_4$, filtered, and solvent was removed from the collected filtrate under reduced pressure. The crude residue was subjected to purification by flash chromatography over silica gel (5-100% EtOAc/PE) to afford the racemic title compound 33. MS (ESI): m/z calc'd for $C_{25}H_{35}INO_2Si$ $[M+H]^+$: 536, found 536; $^1H$ NMR (400 MHz, $CDCl_3$, 25° C.) δ: 7.77-7.79 (m, 2H), 7.66-7.68 (m, 2H), 7.38-7.45 (m, 6H), 4.24-4.25 (m, 2H), 3.90-3.98 (m, 2H), 3.68-3.80 (m, 2H), 2.57-2.63 (m, 3H), 2.05-2.10 (m, 6H), 1.09 (s, 9H).

(3S,4S) and (3R,4R) 1-(4-((tert-butyldiphenylsilyl) oxy)tetrahydrofuran-3-yl)-4-iodopiperidine (34 and 35)

The racemic material 33 could be resolved to its component enantiomers by chiral preparative SFC (Column & dimensions: OJ, 50 mm×250 mm; Mobile phase A: $CO_2$; Mobile phase B: 0.1% $NH_4OH$ in EtOH) to afford the title compounds 34 (tR=3.4 min) and 35 (tR=5.7 min). MS (ESI): m/z calc'd for $C_{25}H_{35}INO_2Si$ $[M+H]^+$: 536, found 536; $^1H$ NMR (400 MHz, $CDCl_3$, 25° C.) δ: 7.77-7.79 (m, 2H), 7.66-7.68 (m, 2H), 7.38-7.45 (m, 6H), 4.24-4.25 (m, 2H), 3.90-3.98 (m, 2H), 3.68-3.80 (m, 2H), 2.57-2.63 (m, 3H), 2.05-2.10 (m, 6H), 1.09 (s, 9H).

Scheme 15. Synthesis of 4-iodo-1-(oxetan-3-yl)piperidine

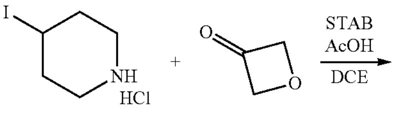

27

-continued

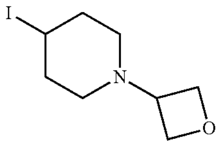

36

4-iodo-1-(oxetan-3-yl)piperidine (36)

The title compound was prepared using a slightly modified procedure from that which was used for the preparation of 33, substituting 3-oxetanone for intermediate 24. The only other modification is that the reaction was conducted at room temperature instead of at 50° C. MS (ESI): m/z calc'd for $C_8H_{15}INO$ $[M+H]^+$: 268, found 268; $^1H$ NMR (300 MHz, $CDCl_3$, 25° C.) δ: 4.61 (m, 4H), 4.46-4.17 (m, 1H), 3.49 (m, 1H), 2.61-2.35 (m, 2H), 2.16 (m, 6H).

Scheme 16. Synthesis of 6-chloro-7-(1-(oxetan-3-yl)piperidin-4-yl) quinazolin-2-amine

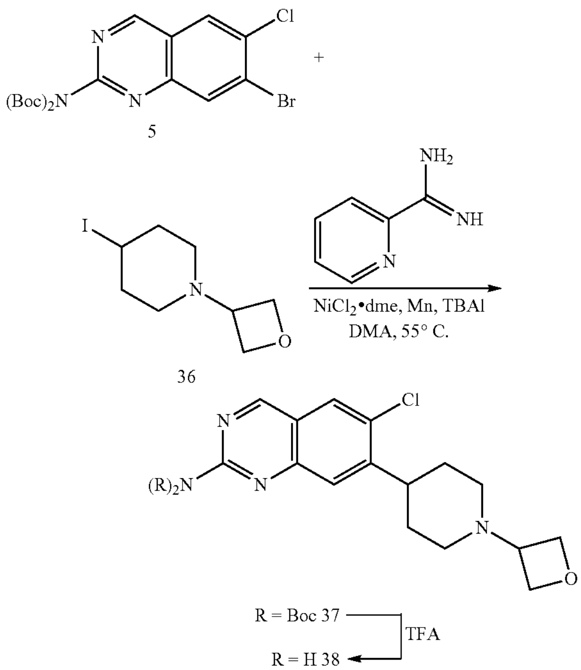

N,N-bis(tert-butyloxycarbonyl)-6-chloro-7-(1-(oxetan-3-yl)piperidin-4-yl)quinazolin-2-amine (37)

A 1-L round-bottom flask was charged with $NiCl_2DME$ (14.4 g, 65.5 mmol) and picolinimidamide hydrochloride (10.3 g, 65.6 mmol) under inert atmosphere. DMA (600 mL) was added, and the mixture was stirred for 30 min at RT. A separate 2-L, 3-necked round-bottom flask was charged with intermediate 5 (120 g, 262 mmol), intermediate 36 (84 g, 314 mmol), TBAI (24.2 g, 65.5 mmol), and Mn (43.3 g, 788 mmol) under inert atmosphere. DMA (1.2 L) was added, and the resultant mixture was stirred at RT. The nickel-ligand mixture was then transferred into this flask at RT. The reaction mixture was then warmed to 55° C. and stirred at this temperature for 3 hrs. On cooling to RT, the mixture was diluted with EtOAc (2 L), then washed with brine (3×1 L). The organic phase was dried over anhydrous $Na_2SO_4$, filtered, and solvent was removed from the collected filtrate under reduced pressure. The crude residue was subjected to purification by flash chromatography over silica gel (5-30% EtOAc/PE) to afford the title compound 37.

6-chloro-7-(1-(oxetan-3-yl)piperidin-4-yl)quinazolin-2-amine (38)

A 3-L, 3-necked round-bottom flask was charged with intermediate 37 (100 g, 193 mmol) under inert atmosphere. DCM (1 L) was added, and the resultant solution was cooled to 0° C. To the stirring mixture was added TFA (500 mL, 6.73 mol) dropwise, maintaining the internal reaction temperature at or below 10° C. On complete addition, the reaction was allowed to stir at RT for 3 hrs. All volatiles were removed under reduced pressure, and the resultant residue was taken up in water (500 mL). To the stirring mixture was carefully added $Na_2CO_3$ until the pH had stabilized at 9. Solids were then collected by filtration and washed with iPrOH (300 mL). Further drying afforded the title compound 38. MS (ESI): m/z calc'd for $C_{16}H_{20}ClN_4O$ [M+H]+: 319, found 319; $^1H$ NMR (300 MHz, $CDCl_3$, 25° C.) δ: 8.89 (s, 1H), 7.70 (s, 1H), 7.45 (s, 1H), 4.74-4.61 (m, 4H), 3.54 (m, 1H), 3.13-2.98 (m, 1H), 2.91 (m, 2H), 2.87 (m, 2H), 2.10-1.99 (m, overlap, 4H), 1.79 (m, 2H).

Scheme 17. Synthesis of 6-chloro-7-(1-(3-methyloxetan-3-yl)piperidin-4-yl)quinazolin-2-amine

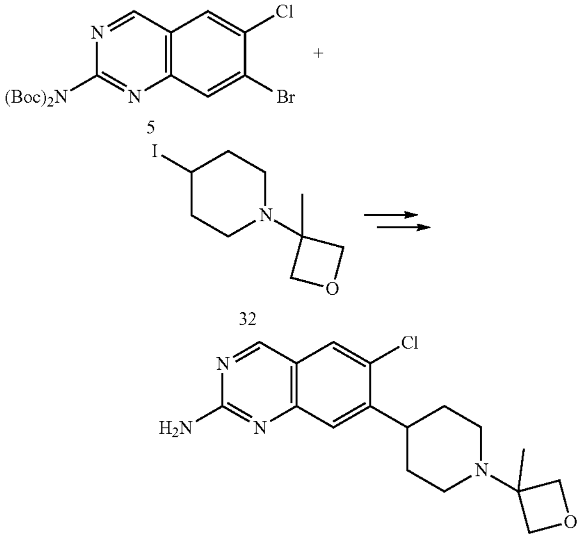

39

6-chloro-7-(1-(3-methyloxetan-3-yl)piperidin-4-yl) quinazolin-2-amine (39)

The title compound was prepared using an identical method to that which was used for the preparation of 38, substituting intermediate 32 for intermediate 36. MS (ESI): m/z calc'd for $C_{17}H_{22}ClN_4O$ [M+H]+: 333, found 333; $^1H$ NMR (300 MHz, $CDCl_3$, 25° C.) δ: 8.91 (s, 1H), 7.71 (s, 1H), 7.49 (s, 1H), 4.64 (d, J=5.7 Hz, 2H), 4.26 (d, J=5.7 Hz, 2H), 3.05 (m, 1H), 2.69 (m, 2H), 2.34 (m, 2H), 1.98 (m, 2H), 1.81 (m, 2H), 1.43 (s, 3H).

Scheme 18. Synthesis of (3R,4R) and (3S,4S) 4-(4-(2-amino-6-chloroquinazolin-7-yl)piperidin-1-yl)-4-methyltetrahydrofuran-3-ol

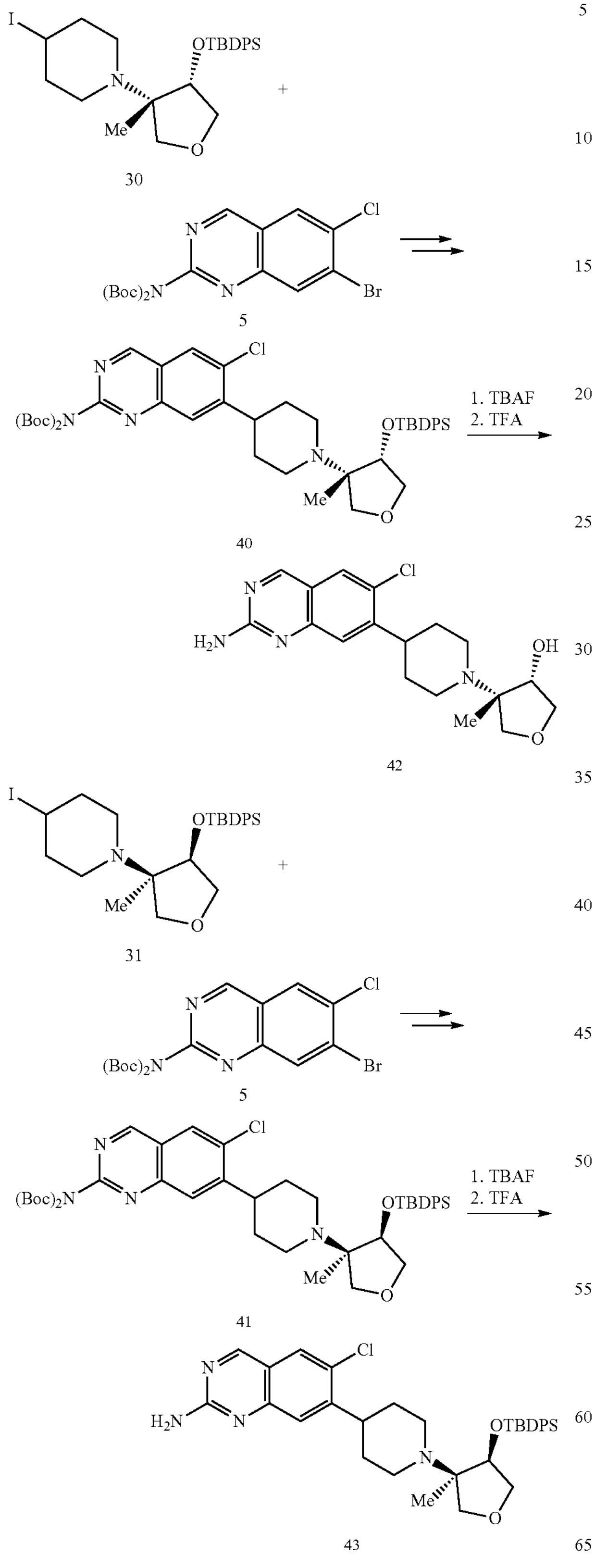

30 5 40 42 31 5 41 43

(3R,4R) and (3S,4S) N,N-di((tertbutyloxycarbonyl)-7-(1-(4-((tert-butyldiphenylsilyl)oxy)-3-methyltetrahydrofuran-3-yl)piperidin-4-yl)-6-chloroquinazolin-2-amine (40 and 41)

The title compounds were prepared using an identical method to that which was used for the preparation of 37, substituting intermediates 30 and 31 for intermediate 36. $^1$H NMR (400 MHz, $CDCl_3$, 25° C.) δ: 9.29 (s, 1H), 7.96 (s, 1H), 7.82 (br d, J=6.8 Hz, 2H), 7.72 (br d, J=6.4 Hz, 2H), 7.35-7.51 (m, 8H), 4.09-4.18 (m, 2H), 4.02 (br d, J=2.8 Hz, 1H), 3.83-3.93 (m, 3H), 3.70 (d, J=6.8 Hz, 1H), 3.03 (br t, J=11.2 Hz, 2H), 2.68 (br d, J=9.6 Hz, 3H), 2.53-2.63 (m, 2H), 2.24-2.47 (m, 2H), 1.78-2.01 (m, 4H), 1.67 (br d, J=10.0 Hz, 2H), 1.50 (s, 18H), 0.97 (s, 3H); $^1$H NMR (400 MHz, $CDCl_3$, 25° C.) δ: 9.29 (s, 1H), 7.96 (s, 1H), 7.82 (br d, J=6.8 Hz, 2H), 7.72 (br d, J=6.4 Hz, 2H), 7.35-7.51 (m, 8H), 4.09-4.18 (m, 2H), 4.02 (br d, J=2.8 Hz, 1H), 3.83-3.93 (m, 3H), 3.70 (d, J=6.8 Hz, 1H), 3.03 (br t, J=11.2 Hz, 2H), 2.68 (br d, J=9.6 Hz, 3H), 2.53-2.63 (m, 2H), 2.24-2.47 (m, 2H), 1.78-2.01 (m, 4H), 1.67 (br d, J=10.0 Hz, 2H), 1.50 (s, 18H), 0.97 (s, 3H).

(3R,4R) and (3S,4S) 4-(4-(2-amino-6-chloroquinazolin-7-yl)piperidin-1-yl)-4-methyltetrahydrofuran-3-ol (42 and 43)

A 1-L round bottom flask was charged with either 40 or 41 (35 g, 43.7 mmol) under inert atmosphere. The material was dissolved in THF (350 mL) and cooled to 0° C. with stirring. To the stirring mixture at this temperature was added TBAF (1 M in THF, 87.3 mL) dropwise. On complete addition, the ice bath was removed, and the reaction was allowed to stir at RT for 12 hrs. To the mixture was added an aqueous solution of EDTA (0.5 wt %, 500 mL). The mixture was stirred for several minutes at RT, then transferred to a separatory funnel where it was extracted with EtOAc (3×150 mL). The combined organic layers were dried over anhydrous $Na_2SO_4$, filtered, and the solvent removed from the collected filtrate under reduced pressure to afford the corresponding desilylated compounds (not drawn). These intermediates (40 g, 71 mmol) were separately dissolved in DCM (300 mL) in 1-L round bottom flasks. To each mixture was added TFA (26.3 mL, 355 mmol) at RT, and the resultant mixture was stirred at RT for 12 hrs. Volatiles were removed under reduced pressure to afford the crude residues. Each residue was separately taken into DCM (1 L) and carefully washed with sat. aq. $NaHCO_3$ (2×500 mL). Each organic layer was dried over anhydrous $Na_2SO_4$, filtered, and the solvent removed from the collected filtrates under reduced pressure to afford the corresponding deprotected crude materials. The crude products were purified either by recrystallization from DCM (500 mL) at 40° C. or trituration with EtOAc (300 mL) followed by collection by vacuum filtration. This afforded the title compounds 42 and 43, and additional material could be recovered from the filtrate by preparative RP-HPLC Phenomenex luna c18 250 mm*100 mm*15 um; mobile phase: [water (0.1% TFA)-ACN]; B %: 2%-25%, 20 min Scheme 19. Synthesis of (3R,4R) and (3S,4S) tert-butyl 4-(2-amino-6-chloroquinazolin-7-yl)-3-fluoropiperidine-1-carboxylate

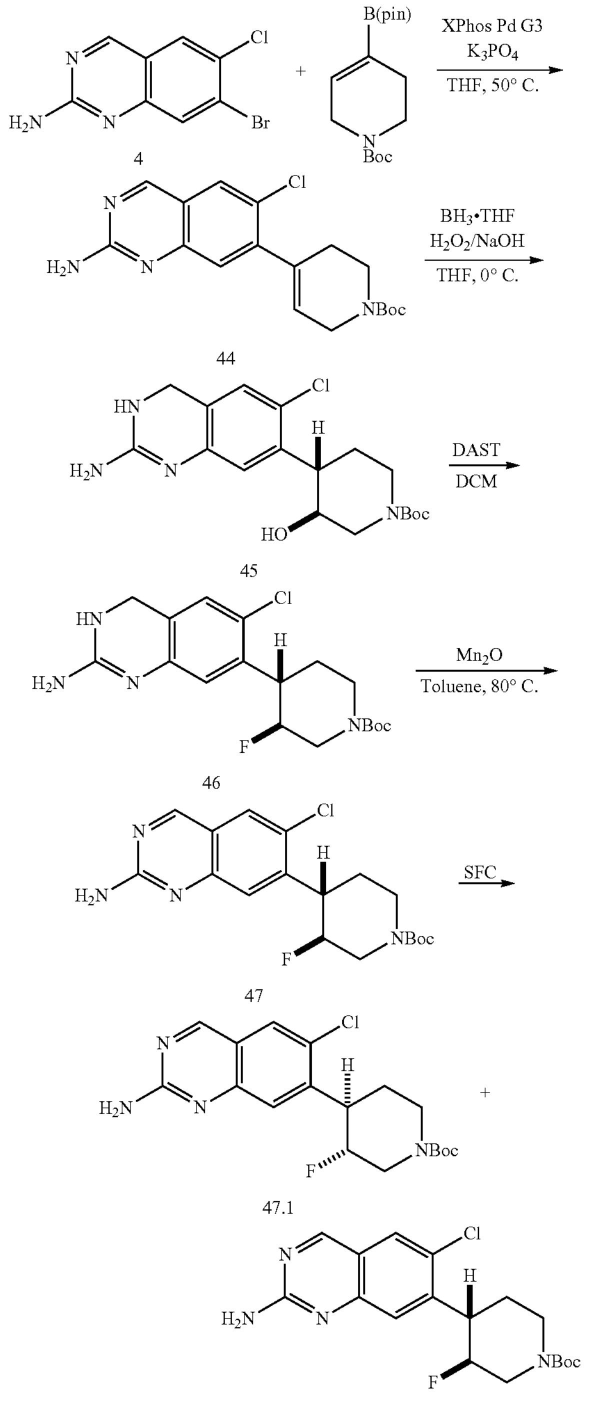

4

44

45

46

47

47.1

47.2 tert-butyl 4-(2-amino-6-chloroquinazolin-7-yl)-3,6-dihydropyridine-1(2H)-carboxylate (44)

A 5-L 4-necked round-bottom flask was charged with 7-bromo-6-chloroquinazolin-2-amine 4 (350 g, 1.35 mol), tert-butyl 4-(4,4,5,5-tetramethyl-1,3,2-dioxaborolan-2-yl)-3,6-dihydro-2H-pyridine-1-carboxylate (544 g, 1.76 mol), and tribasic potassium phosphate (575 g, 2.71 mol) under inert atmosphere. THF (3.5 L), then XPhos Pd G3 (115 g, 135 mmol) were added, and the headspace was degassed under vacuum (2×). The resultant solution was stirred for 12 hrs at 50° C. Upon cooling to RT, the reaction mixture was diluted with water (3 L). The phases were separated, and the aqueous phase was extracted with EtOAc (2×2 L). The organic layers were combined, solvent was removed under reduced pressure, and the resultant crude residue was subjected to purification by flash chromatography over silica gel (EtOAc/DCM, 0-50%) to provide the desired tert-butyl 4-(2-amino-6-chloroquinazolin-7-yl)-3,6-dihydro-2H-pyridine-1-carboxylate 44.

(3R,4R) and (3S,4S) tert-butyl 4-(2-amino-6-chloro-3,4-dihydroquinazolin-7-yl)-3-hydroxypiperidine-1-carboxylate (45)

A 20-L 4-necked round-bottom flask was charged with tert-butyl 4-(2-amino-6-chloroquinazolin-7-yl)-3,6-dihydropyridine-1(2H)-carboxylate 44 (300 g, 831 mmol) under inert atmosphere. THF (3 L) was added, the mixture was cooled to 0° C., and $BH_3$.THF (4.2 L, 4.16 mol) was added dropwise with stirring. Upon complete addition, the reaction was stirred for an additional 12 hrs. The mixture was then cooled to 0° C., and to the stirring reaction were added sequentially 1.75 N sodium hydroxide (2.4 L, 4.16 mol) dropwise with stirring, then $H_2O_2$ (720 mL, 4.16 mol) dropwise with stirring. The resultant solution was stirred for 2 hrs at RT then diluted with water (2 L). The mixture was extracted with EtOAc (2×1 L), and the combined organic phases were washed with brine (1 L). Solvent was removed under reduced pressure and the resultant crude residue was upgraded by slurry with MTBE to afford the title compound 45.

(3R,4R) and (3S,4S) tert-butyl 4-(2-amino-6-chloro-3,4-dihydroquinazolin-7-yl)-3-fluoropiperidine-1-carboxylate (46)

A 10-L 4-necked round-bottom flask was charged with tert-butyl 4-(2-amino-6-chloro-3,4-dihydroquinazolin-7-yl)-3-hydroxypiperidine-1-carboxylate 44 (240 g, 630 mmol) under inert atmosphere. DCM (4.8 L) was added and the solution was cooled to −78° C. To the stirring mixture at this temperature was then added DAST (254 g, 1.58 mmol) dropwise. The resultant solution was allowed warm to RT and stirred for 2 hrs. The reaction was then quenched by the addition of sat. aq. $NaHCO_3$(1 L) and water (1 L). Phases were separated, and the aqueous phase was extracted with additional DCM (2×2 L). The combined organic phase was washed with brine (500 mL), and solvent was removed under reduced pressure to afford the title compound 46, which was carried forward in its crude form.

(3R,4R) and (3S,4S) tert-butyl 4-(2-amino-6-chloroquinazolin-7-yl)-3-fluoropiperidine-1-carboxylate (47)

A 5-L 4-necked round-bottom flask was charged with tert-butyl 4-(2-amino-6-chloro-3,4-dihydroquinazolin-7-yl)-3-fluoropiperidine-1-carboxylate 46 (283 g, 739 mmol) and $MnO_2$ (643 g, 7.39 mol) under inert atmosphere. Toluene (2.83 L) was added, and the resultant solution was stirred for 12 hrs at 80° C. Upon cooling to RT, solids were removed by filtration and the filtrate collected. Solvent was removed under reduced pressure to afford a crude residue, which was subjected to purification by flash chromatography over silica gel (MeOH/DCM, 0-2%) to afford semi-pure material. This material was then upgraded by achiral preparative SFC (Column & dimensions: Chiral ART Amylose-SA, 250 mm×50 mm; Mobile phase A: $CO_2$; Mobile phase B: 2 mM $NH_3$-MeOH) to afford the racemic title compound 47 in pure form. The racemic material could be resolved to its component enantiomers by chiral preparative SFC(Column & dimensions: Chiral PAK IF, 250 mm×50 mm; Mobile phase A: $CO_2$; Mobile phase B: 8 mM $NH_3$-MeOH) to afford 47.1 and 47.2. MS (ESI): m/z calc'd for $C_{18}H_{23}ClFN_4O_2$ $[M+H]^+$: 381, found 381; $^1H$ NMR (400 MHz, acetone-$d_6$, 25° C.) δ: 9.08 (s, 1H), 7.93 (s, 1H), 7.60 (s, 1H), 6.34 (br s, 2H), 4.97 (m, 1H), 4.53 (br s, 1H), 4.18 (m, 1H), 3.57 (m, 1H), 2.97 (br s, 2H), 2.02 (m, 1H), 1.70 (m, 1H), 1.50 (s, 9H). MS (ESI): m/z calc'd for $C_{18}H_{23}ClFN_4O_2$ $[M+H]^+$: 381, found 381; $^1H$ NMR (400 MHz, acetone-$d_6$, 25° C.) δ: 9.08 (s, 1H), 7.93 (s, 1H), 7.60 (s, 1H), 6.34 (br s, 2H), 4.97 (m, 1H), 4.53 (br s, 1H), 4.18 (m, 1H), 3.57 (m, 1H), 2.97 (br s, 2H), 2.02 (m, 1H), 1.70 (m, 1H), 1.50 (s, 9H).

Scheme 20. Synthesis of (3R,4R) and (3S,4S) tert-butyl 4-(2-amino-6-methylquinazolin-7-yl)-3-fluoropiperidine-1-carboxylate

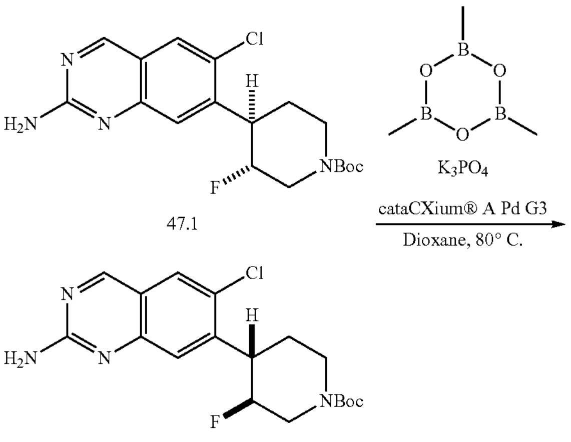

47.1

47.2

-continued

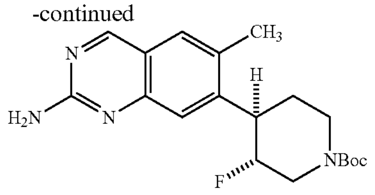

48

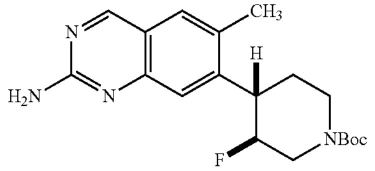

49

(3R,4R) and (3S,4S) tert-butyl 4-(2-amino-6-methylquinazolin-7-yl)-3-fluoropiperidine-1-carboxylate (48 and 49)

A 2-L, 4-necked round-bottom flask was charged with intermediate 47.1 (68.7 g, 180 mmol), $K_3PO_4$ (153 g, 721 mmol), trimethylboroxine (113 g, 901 mmol), and cat-aCXium® Pd G3 (26.3 g, 36.1 mmol) under inert atmosphere. Dioxane (700 mL) was added, and the resultant solution was warmed to 80° C. and stirred for 12 hrs at this temperature. On cooling to RT, the mixture was diluted with EtOAc (500 mL) and filtered. Solvent was removed from the collected filtrate under reduced pressure. The crude residue was subjected to purification by flash chromatography over silica gel (0-100% EtOAc/hexanes) to afford the title compound 48. MS (ESI): m/z calc'd for $C_{19}H_{26}FN_4O_2$ $[M+H]^+$: 361, found 361; $^1H$ NMR (400 MHz, DMSO-$d_6$, 25° C.) δ: 8.97 (s, 1H), 7.56 (s, 1H), 7.40 (s, 1H), 6.70 (m, 2H), 4.81 (m, 1H), 4.33 (s, 1H), 4.04-3.89 (m, 1H), 3.27-3.14 (m, 1H), 2.91 (s, 2H), 2.39 (s, 3H), 1.89-1.79 (m, 1H), 1.59 (m, 1H), 1.44 (s, 9H). Enantiomeric title compound 49 was prepared using an identical procedure substituting starting material 47.2. MS (ESI): m/z calc'd for $C_{19}H_{26}FN_4O_2$ $[M+H]^+$: 361, found 361; $^1H$ NMR (400 MHz, DMSO-$d_6$, 25° C.) δ: 8.97 (s, 1H), 7.56 (s, 1H), 7.40 (s, 1H), 6.70 (m, 2H), 4.81 (m, 1H), 4.33 (s, 1H), 4.04-3.89 (m, 1H), 3.27-3.14 (m, 1H), 2.91 (s, 2H), 2.39 (s, 3H), 1.89-1.79 (m, 1H), 1.59 (m, 1H), 1.44 (s, 9H).

GENERAL SYNTHETIC SCHEMES AND PREPARATIVE EXAMPLES

The compounds of the invention may be prepared by methods known in the art of organic synthesis as set forth in part by the following general synthetic schemes and specific preparative examples. Starting materials are available commercially or may be prepared by known methods.

General Scheme 1

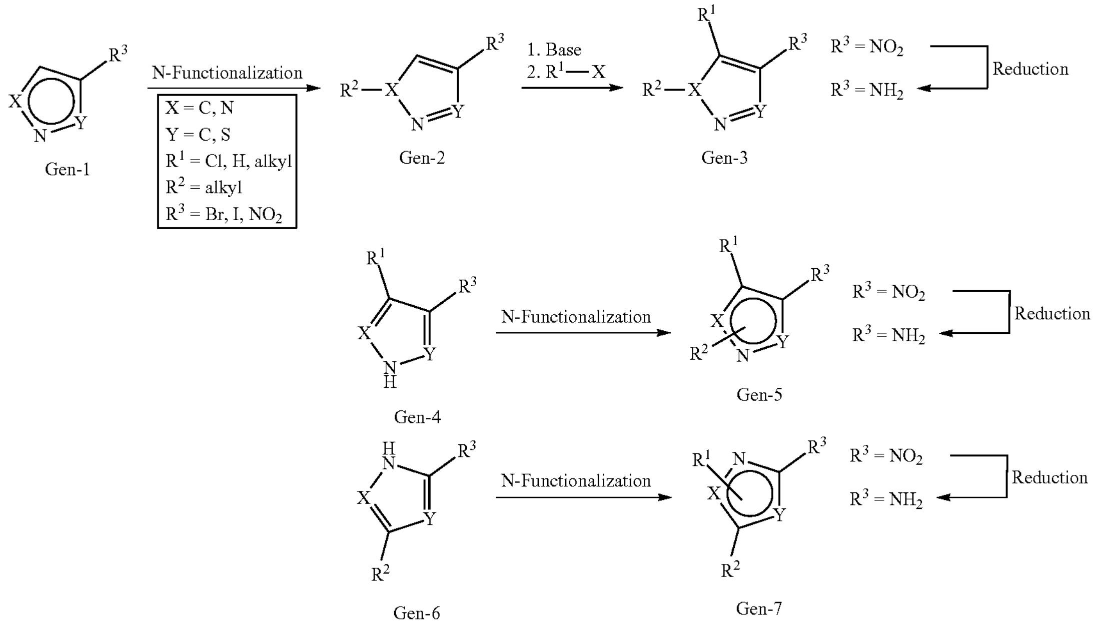

Gen-1 Gen-2 Gen-3 Gen-4 Gen-5 Gen-6 Gen-7

In General Scheme 1, commercially available or synthetically prepared 4-substituted pyrazoles Gen-1 could be alkylated using a number of synthetic transformations commonly known to those skilled in the art, including, but not limited to, base-mediated alkylation, a Mitsunobu reaction, an epoxide-opening reaction, or a Chan-Lam coupling reaction to afford N-alkyl pyrazoles Gen-2. A number of intermediates of the form Gen-2 are available commercially, including isothiazoles of the depicted substitution pattern. Likewise, isothiazoles in this substitution pattern can be accessed synthetically by known methods. In cases where Gen-2 is a pyrazole, it could optionally be functionalized at the 5-position by treatment with strong base followed by reaction with an electrophile (chlorination or methylation, for example) to form Gen-3. In instances of Gen-3 where $R^1$=$NO_2$, reduction to the corresponding aniline was performed. In an alternate route, commercially available or synthetically prepared 3,4-disubstituted pyrazoles Gen-4 could be alkylated using similar transformations to those performed on Gen-1. These transformations typically afforded a mixture of 1,4,5-trisubstituted-pyrazoles (i.e. Gen-3), and 1,3,4-trisubstituted-pyrazoles, which together are represented as Gen-5. Finally, commercially available or synthetically prepared 3,5-disubstituted pyrazoles Gen-6 could be alkylated using similar transformations to those performed on Gen-1. These transformations typically afforded a mixture of the two regioisomeric products, which together are represented as Gen-7. Representative preparative examples are described in more detail below.

Scheme 21. Synthesis of 5-chloro-1-(2,2-difluoroethyl)-1H-pyrazol-4-amine

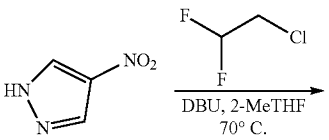

-continued

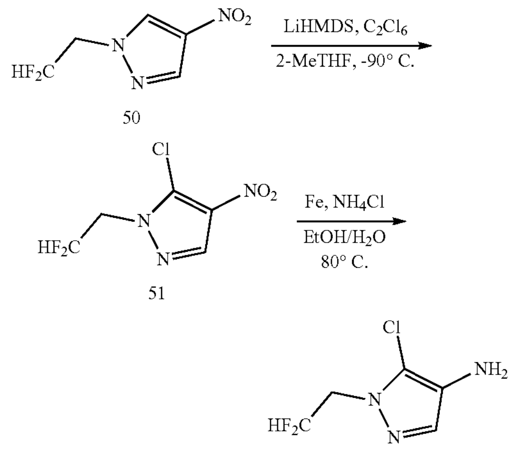

50

51

52

1-(2,2-difluoroethyl)-4-nitro-1H-pyrazole (50)

A 10-L 4-necked round-bottom flask was charged with 4-nitropyrazole (300 g, 2.65 mol) under inert atmosphere. 2-MeTHF (3 L) was added, followed by DBU (808 g, 5.31 mol), and ultimately 2-chloro-1,1-difluoroethane (653 g, 7.96 mol). The resultant solution was warmed to 70° C. and stirred overnight at this temperature. Upon cooling to RT, the reaction was quenched by the addition of ice water. Phases were separated, and the aqueous phase was extracted with 2-MeTHF (2×1 L). The combined organic layers were dried over $MgSO_4$ and filtered. Solvent volume was reduced to 3.3 L [Note: 2988 J/g; onset temperature 291° C.; SS=0.128; EP=0.262>0]. This form of the title compound 50 was used directly in the next step without further purification.

5-chloro-1-(2,2-difluoroethyl)-4-nitro-1H-pyrazole (51)

A 10-L 4-necked round-bottom flask was charged with a solution of 1-(2,2-difluoroethyl)-4-nitropyrazole 50 in 2-MeTHF (3.3 L) and hexachloroethane (529 g, 2.24 mol) under inert atmosphere. The solution was cooled to −90° C., and to the stirring mixture was added LiHMDS (1 M, 2.23 L) dropwise over 2 hrs. The resultant solution was stirred for an additional 1 hr at this temperature, then quenched by the addition of $NH_4Cl$. Phases were separated, and the aqueous phase was extracted with 2-MeTHF (2×1 L). The combined organic layers were washed with $H_2O$ (2×1 L), dried over $MgSO_4$, and filtered. Solvent volume was reduced to 3 L [Note: 2221 J/g; onset temperature 301° C.; SS=−0.013; EP=0.127>0]. The solution was shown by NMR assay to contain the desired 5-chloro-1-(2,2-difluoroethyl)-4-nitro-1H-pyrazole 51, and this form of the title compound was used without further purification. MS (ESI): m/z calc'd for $C_5H_5ClF_2N_3O_2$ $[M+H]^+$: 212, found 212; $^1H$ NMR (400 MHz, $CDCl_3$, 25° C.) δ: 8.57 (s, 1H), 6.48 (m, 1H), 4.81 (m, 2H).

5-chloro-1-(2,2-difluoroethyl)-1H-pyrazol-4-amine (52)

A 30-mL scintillation vial equipped with a magnetic stirrer was charged with 5-chloro-1-(2,2-difluoroethyl)-4-nitro-1H-pyrazole 51 (1.60 g, 7.56 mmol), iron dust (3.01 g, 54.0 mmol), and ammonium chloride (2.89 g, 54.0 mmol). To the vial was added EtOH (10 mL) then water (2 mL), the vial was sealed with a pressure release cap, and the mixture was heated to 80° C. for 3 hrs. Upon cooling to RT, the reaction mixture was diluted into EtOAc, and the resultant mixture was treated with $Na_2SO_4$ to remove water. This mixture was then filtered first through a fritted pad to remove iron, and subsequently the filtrate was taken through a fritted Celite® (diatomaceous earth) pad to remove residual inorganics and water. Solvent was removed from the resultant filtrate under reduced pressure to afford the desired 52. Note that 52 and related aminopyrazole intermediates were stable for a period of days under inert atmosphere and protected from light at 4° C., but typically were only prepared in quantities as needed. MS (ESI): m/z calc'd for $C_5H_7ClF_2N_3$ $[M+H]^+$: 181, found 181; $^1H$ NMR (400 MHz, acetone-$d_6$, 25° C.) δ: 7.38 (s, 1H), 6.31 (m, 1H), 4.57 (m, 2H), 2.85 (br s, 2H).

Scheme 22. Synthesis of trans-4-(5-chloro-4-nitro-1H-pyrazol-1-yl)-3-fluoro-1-(3-methyloxetan-3-yl)piperidine

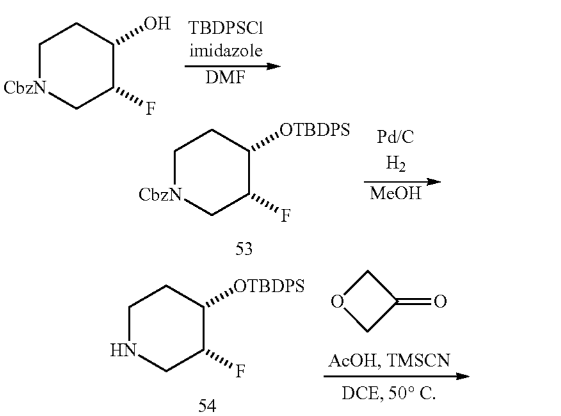

53

54

-continued

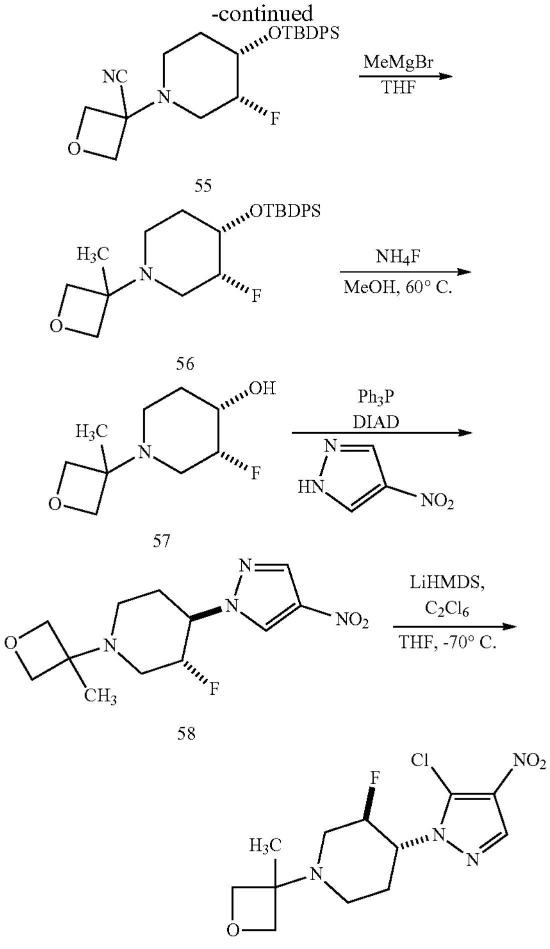

55

56

57

58

59 benzyl cis-4-((tert-butyldiphenylsilyl)oxy)-3-fluoropiperidine-1-carboxylate (53)

A 20-L 4-necked round-bottom flask was charged with benzyl (3R,4S) and (3S,4R) 3-fluoro-4-hydroxypiperidine-1-carboxylate (260 g, 1.03 mol) and imidazole (210 g, 3.08 mol) under inert atmosphere. THF (4 L) was added, and to the stirring mixture at RT was then added TBDPS-Cl (296 g, 1.08 mol). The resultant solution was stirred at RT overnight. The reaction mixture was poured into ice/EtOAc/$H_2O$ and the phases separated. The aqueous phase was extracted with EtOAc (3×4 L), and the combined organic phases were washed with brine (2×4 L), dried over $Na_2SO_4$, and filtered. Solvent was removed under reduced pressure to afford the title compound 53. The product was used in the next step directly without further purification.

cis-4-((tert-butyldiphenylsilyl)oxy)-3-fluoropiperidine (54)

A 20-L 1-necked round-bottom flask was charged with (3R,4S) and (3S,4R) 4-[(tert-butyldiphenylsilyl)oxy]-3-fluoropiperidine-1-carboxylate 53 (350 g, 711 mmol) and Pd/C (10%, 150 g) under inert atmosphere. MeOH (10 L) was added, and the inert atmosphere was exchanged for $H_2$ (1 atm). The resultant solution was stirred at RT 15-20 hrs, at which point it was filtered, washing the filter cake with MeOH (2×1 L) and EtOAc (1 L) before eventually quenching the Pd-containing filter cake with water prior to disposal. Solvent was removed from the organic filtrate under reduced pressure to afford the title compound 54, which was used in the next step directly without further purification.

cis-3-(4-((tert-butyldiphenylsilyl)oxy)-3-fluoropiperidin-1-yl)oxetane-3-carb ° nitrite (55)

A 20-L 4-necked round-bottom flask was charged with (3R,4S) and (3S,4R) 4-((tert-butyldiphenylsilyl)oxy)-3-fluoropiperidine 54 (400 g, 1.12 mol) under inert atmosphere. DCE (10 L) was added and the solution warmed to 50° C. To the stirring mixture at this temperature were added oxetan-3-one (97 g, 1.34 mol) and AcOH (81 g, 1.34 mol), and the resultant mixture was stirred for 30 minutes. Finally, TMSCN (133 g, 1.34 mol) was added dropwise, and the reaction was warmed to 70° C. with stirring for 20 hrs. Upon cooling to RT, the reaction was diluted with aqueous KOH (1 M, 5 L). This mixture was extracted with DCM (3×2.5 L), and the combined organic phases were washed with $H_2O$ (1×5 L), dried over $Na_2SO_4$, and the solvent removed under reduced pressure. The crude residue was subjected to purification by flash chromatography over silica gel (EtOAc/PE=10-30%) to afford the title compound 55.

cis-4-((tert-butyldiphenylsilyl)oxy)-3-fluoro-1-(3-methyloxetan-3-yl)piperidine (56)

A 20-L 3-necked round-bottom flask was charged with (3R,4S) and (3S,4R) 3-(4-((tert-butyldiphenylsilyl)oxy)-3-fluoropiperidin-1-yl)oxetane-3-carbonitrile 55 (350 g, 798 mmol) under inert atmosphere. THF (10 L) was added and the solution cooled to −5° C. Then, MeMgBr (1 M, 1.6 L) was added slowly over the course of 1 hr. Upon complete addition, the reaction was allowed to warm to RT and stirred at this temperature for 3 days. The reaction was cooled to 0° C. and quenched by the careful addition of MeOH, followed by sat. aq. $NH_4Cl$ (2 L). This mixture was diluted with aqueous potassium sodium tartrate (5 L), and THF was removed from the biphasic mixture under reduced pressure. The remaining aqueous phase was extracted with EtOAc (4×5 L), and the combined organic phases dried over $Na_2SO_4$ and filtered. Solvent was removed under reduced pressure, and the crude residue was subjected to purification by flash chromatography over silica gel (EtOAc/PE, 10-30%) to afford the title compound 56.

cis-3-fluoro-1-(3-methyloxetan-3-yl)piperidin-4-ol (57)

A 10-L 1-necked round-bottom flask was charged with (3R,4S) and (3S,4R) 4-((tert-butyldiphenylsilyl)oxy)-3-fluoro-1-(3-methyloxetan-3-yl)piperidine 56 (103 g, 241 mmol) under inert atmosphere. MeOH (3 L) was added, and to the stirring solution was then added $NH_4F$ (135 g, 3.65 mol). The resultant mixture was then warmed to 60° C. and stirred at this temperature for 18 hrs. Upon cooling to RT, solids were removed by filtration, and solvent removed from the filtrate under reduced pressure. The crude residue was then subjected to purification by flash chromatography over silica gel (EtOAc/PE, 10-50%) to afford the title compound 57.

trans-3-fluoro-1-(3-methyloxetan-3-yl)-4-(4-nitro-1H-pyrazol-1-yl)piperidine (58)

A 10-L 3-necked round-bottom flask was charged with (3R,4S) and (3S,4R) 3-fluoro-1-(3-methyloxetan-3-yl)piperidin-4-ol 57 (31 g, 164 mmol), 4-nitro-1H-pyrazole (47 g, 412 mmol), and $Ph_3P$ (133 g, 507 mmol) under inert atmosphere. THF (3 L) was added and the solution was cooled to 0° C. DIAD (109 g, 539 mmol) was then added dropwise to the stirring mixture at this temperature. Upon complete addition, the mixture was allowed to warm to RT and stirred at this temperature for 20 hrs, at which point solvent was removed under reduced pressure. The crude residue was subjected to purification via flash chromatography over silica gel (EtOAc/PE, 10-50%) to afford the title compound 58.

trans-4-(5-chloro-4-nitro-1H-pyrazol-1-yl)-3-fluoro-1-(3-methyloxetan-3-yl)piperidine (59)

A 10-L 3-necked round-bottom flask was charged with (3R,4R) and (3S,4S) 3-fluoro-1-(3-methyloxetan-3-yl)-4-(4-nitro-1H-pyrazol-1-yl)piperidine 58 (15 g, 47 mmol) under inert atmosphere. THF (2 L) was then added and the solution cooled to −70° C. Then, LiHMDS (0.2 M, 320 mL) was added, and the resultant mixture was stirred for 2 hrs at −70° C. Hexachloroethane (76 g, 320 mmol) was then introduced dropwise at this temperature as a solution in THF. Upon complete addition the reaction was allowed to warm to RT and stirring was continued at this temperature for 2 hrs. The mixture was then cooled to 0° C. and carefully quenched with brine. THF was removed from the biphasic mixture under reduced pressure, and the remaining aqueous phase was extracted with EtOAc (4×2 L). The combined organic phases were dried over $Na_2SO_4$ and filtered. Solvent was removed under reduced pressure, and the crude residue was subjected to purification by flash chromatography over silica gel (EtOAc/DCM=10-25%) to afford the title compound 59. MS (ESI): m/z calc'd for $C_{12}H_{17}ClFN_4O_3$ $[M+H]^+$: 319, found 319; $^1H$ NMR (400 MHz, $CDCl_3$, 25° C.) δ: 8.25 (s, 1H), 5.15-4.95 (m, 1H), 4.57 (m, 2H), 4.42 (m, 1H), 4.26 (m, 2H), 3.04 (m, 1H), 2.66 (m, 1H), 2.42-2.25 (m, 3H), 2.03 (m, 1H), 1.43 (s, 3H).

Scheme 23. Synthesis of 1-(4-bromo-5-chloro-1H-pyrazol-1-yl)-2-methylpropan-2-ol

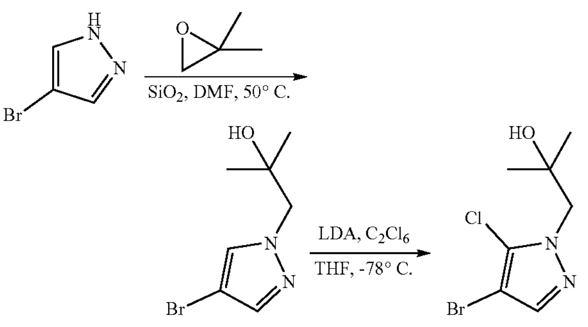

60

61

1-(4-bromo-1H-pyrazol-1-yl)-2-methylpropan-2-ol (60)

A 10-L pressure vessel was charged with 4-bromo-1H-pyrazole (180 g, 1.22 mol), 2,2-dimethyloxirane (883 g, 12.3 mol), and $SiO_2$ (2.21 g, 36.7 mmol) under inert atmosphere. DMF (900 mL) was added and the vessel was purged with inert atmosphere and the pressure increased to 50 psi. The mixture was then warmed to 50° C. with stirring for 24 hrs.

On completion, MTBE (200 mL) was added and the mixture slurried for 2 hrs, at which point the solid was collected by filtration and dried to afford the title compound 60.

1-(4-bromo-5-chloro-1H-pyrazol-1-yl)-2-methylpropan-2-ol (61)

A 5-L 3-necked round-bottom flask was charged with 1-(4-bromo-1H-pyrazol-1-yl)-2-methylpropan-2-ol 60 (87.5 g, 399 mmol) under inert atmosphere. THF (613 mL) was added, and the stirring solution was cooled to −78° C. To the stirring mixture at this temperature lithium diisopropylamide (2M, 409 mL) was added dropwise. The reaction was stirred at −78° C. for 1 hr, at which point a solution of hexachloroethane (114 g, 479 mmol) in THF (262 mL) was added dropwise. Upon complete addition the reaction was allowed to stir for an additional 0.5 hrs. The mixture was then carefully quenched with sat. aq. $NH_4Cl$ (2.5 L), and then extracted with MTBE (3×1.0 L). The organic phases were combined, and solvent was removed under reduced pressure. The resultant crude residue was subjected to purification by flash chromatography over silica gel (EtOAc/PE, 1-100%) to afford the title compound 61. MS (ESI): m/z calc'd for $C_7H_{11}BrClN_2O$ $[M+H]^+$: 252, found 252; $^1H$ NMR (400 MHz, $CDCl_3$, 25° C.) δ: 7.50 (s, 1H), 4.05 (s, 2H), 3.62 (s, 1H), 1.11 (s, 6H).

Scheme 24. Synthesis of 1-(4-bromo-5-methyl-1H-pyrazol-1-yl)-2-methylpropan-2-ol

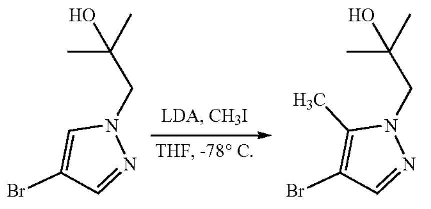

60 62

Synthesis of 1-(4-bromo-5-methyl-1H-pyrazol-1-yl)-2-methylpropan-2-ol (62)

A 20-mL, scintillation vial was charged with 1-(4-bromo-1H-pyrazol-1-yl)-2-methylpropan-2-ol 60 (150 mg, 0.69 mmol) under inert atmosphere. THF (3.5 mL) was added, and the stirring solution was cooled to −78° C. To the stirring mixture at this temperature was added lithium diisopropylamide (1M, 1.58 mL) dropwise. The reaction was stirred at −78° C. for 1 hr, at which point iodomethane (65 μL, 1.03 mmol) was added. The mixture was allowed to slowly warm to RT overnight, then carefully quenched by the addition of sat. aq. $NH_4Cl$. The mixture was extracted with EtOAc (3×20 mL), the combined organic phases dried over $Na_2SO_4$, and the solvent removed under reduced pressure. The resultant crude residue was subjected to purification by flash chromatography over silica gel (3:1 EtOAc/EtOH in Hexanes, 0-80%) to afford the title compound 62. MS (ESI): m/z calc'd for $C_8H_{14}BrN_2O$ $[M+H]^+$: 233, found 233.

Scheme 25. Synthesis of 4-bromo-5-chloro-1-(1-methylcyclopropyl)-1H-pyrazole

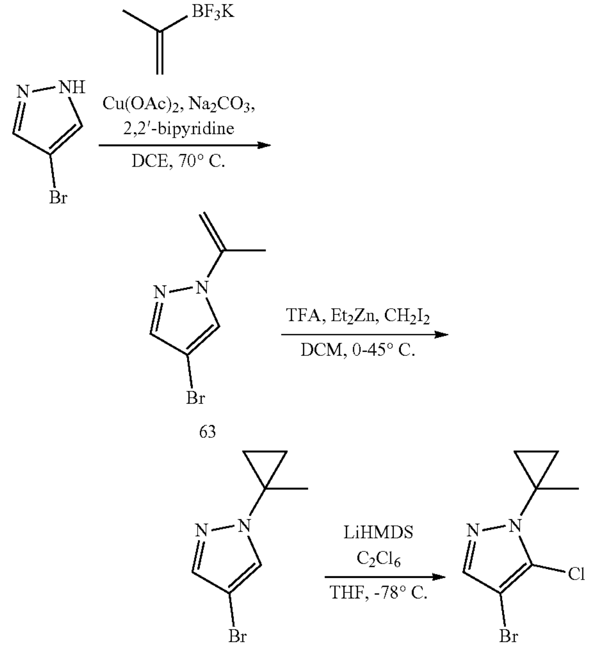

63 64 65

4-bromo-1-(prop-1-en-2-yl)-1H-pyrazole (63)

A 20-L 4-necked round-bottom flask was charged with 4-bromo-1H-pyrazole (600 g, 4.08 mol), potassium isopropenyltrifluoroborate (1.03 kg, 6.94 mol), and $Na_2CO_3$ (865 g, 8.16 mol) under inert atmosphere. DCE (6 L) was added, and the solution was cooled to 15° C. A suspension of $Cu(OAc)_2$ (742 g, 4.08 mol) and 2,2'-bipyridine (956 g, 6.12 mol) in DCE (4 L) was then added to the reaction mixture at this temperature. Upon complete addition, the reaction was warmed to 70° C., and stirring was continued at this temperature for 5 hrs. The mixture was allowed to cool to RT and filtered to remove solids. Solvent was removed from the collected filtrate under reduced pressure, and the resultant crude residue was subjected to purification by flash chromatography over silica gel (EtOAc/PE, 0-10%) to afford the title compound 63.

4-bromo-1-(1-methylcyclopropyl)-1H-pyrazole (64)

A 10-L 3-necked round-bottom flask was charged with DCM (1.2 L) under inert atmosphere. The solvent was cooled to 0° C., and Et2Zn (1 M, 1.07 L) was added. The mixture was again equilibrated to 0° C., and TFA (122 g, 1.07 mol) was carefully added. The resultant mixture was stirred at this temperature for 30 minutes, at which point a solution of $CH_2I_2$ (286 g, 1.07 mol) in DCM (500 mL) was added dropwise, maintaining the temperature at or below 5° C. Upon complete addition, the mixture was stirred for an additional 30 minutes, at which point a solution of 4-bromo-1-(prop-1-en-2-yl)-1H-pyrazole 63 (100 g, 535 mmol) in DCM (600 mL) was added. The reaction mixture was then warmed to 45° C. and stirred at this temperature for 72 hrs. The reaction was cooled to 15° C., and carefully quenched by the addition of sat. aq. $NH_4Cl$ (4 L). The phases were separated, and the aqueous phase extracted with EtOAc (3×2 L). The combined organic phases were washed with $H_2O$(1 L), dried over $Na_2SO_4$, and the solvent removed under reduced pressure. The crude residue was subjected to purification by flash chromatography over silica gel (EtOAc/PE, 0-5%) to afford the title compound 64.

4-bromo-5-chloro-1-(1-methylcyclopropyl)-1H-pyrazole (65)

A 10-L 3-necked round-bottom flask was charged with 4-bromo-1-(1-methylcyclopropyl)-1H-pyrazole 64 (200 g, 995 mmol) under inert atmosphere. THF (1.2 L) was added, and the solution was cooled to −78° C. To the stirring mixture at this temperature was added LDA (2 M, 746 mL), and stirring was continued for 2 hrs at this temperature. A solution of hexachloroethane (283 g, 1.19 mol) in THF (800 mL) was then added dropwise at −78° C. over the course of 2 hrs. Upon complete addition, the mixture was allowed to warm to 15° C. and stirred at this temperature for 4 hrs. The mixture was quenched by pouring carefully into sat. aq. $NH_4Cl$ (2.5 L) at 0° C. The phases were separated, and the aqueous phase extracted with EtOAc (3×800 mL). The combined organic layers were washed with brine (2×800 mL), dried over $Na_2SO_4$, and filtered. Solvent was removed under reduced pressure and the crude residue was subjected to purification by flash chromatography over silica gel (EtOAc/PE, 0-10%) to afford the title compound 65. MS (ESI): m/z calc'd for $C_7H_9BrClN_2$ $[M+H]^+$: 235, found 235; $^1H$ NMR (400 MHz, DMSO-$d_6$, 25° C.) δ: 7.69 (s, 1H), 1.44 (s, 3H), 1.19-1.16 (m, 2H), 1.04-1.00 (m, 2H).

Scheme 26. Synthesis of 1-((4-bromo-5-methyl-1H-pyrazol-1-yl)methyl) cyclopropane-1-carbonitrile and 1-((4-bromo-3-methyl-1H-pyrazol-1-yl) methyl)cyclopropane-1-carbonitrile

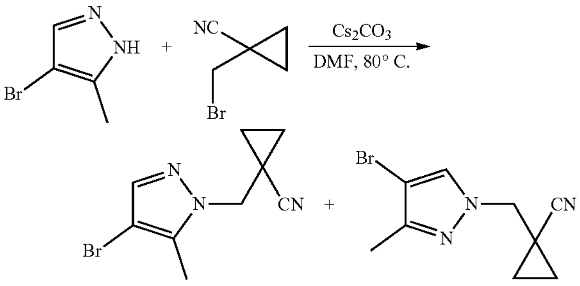

66 67

1-((4-bromo-5-methyl-1H-pyrazol-1-yl)methyl)cyclopropane-1-carbonitrile (66) and 14(4-bromo-3-methyl-1H-pyrazol-1-yl)methyl)cyclopropane-1-carbonitrile (67)

A 20-mL scintillation vial was charged with 4-bromo-5-methyl-1H-pyrazole (500 mg, 3.11 mmol) and $Cs_2CO_3$ (2.53 g, 7.76 mmol) under inert atmosphere. DMF (7.8 mL) was added, and to the stirring mixture at RT was added 1-(bromomethyl)cyclopropane-1-carbonitrile (500 mg, 3.12 mmol). The resultant mixture was heated to 80° C. and allowed to stir at this temperature overnight. Upon cooling to RT, the mixture was diluted with EtOAc and filtered over a pad of Celite 0 (diatomaceous earth). Solvent was removed from the collected filtrate under reduced pressure, and the resultant crude residue was subjected to purification by flash chromatography over silica gel (3:1 EtOAc/EtOH in hexanes, 0-60%), to afford a mixture of the title compounds 66 and 67. Final compounds derived from these, or related isomeric mixtures, could ultimately be resolved into their isomerically pure forms by preparative SFC purification. MS (ESI): m/z calc'd for $C_9H_{11}BrN_3$ $[M+H]^+$: 240, found 240.

Scheme 27. Synthesis of (R)-and (S)-4-bromo-5-chloro-1-(2,2-difluorocyclopropyl)-1H-pyrazole

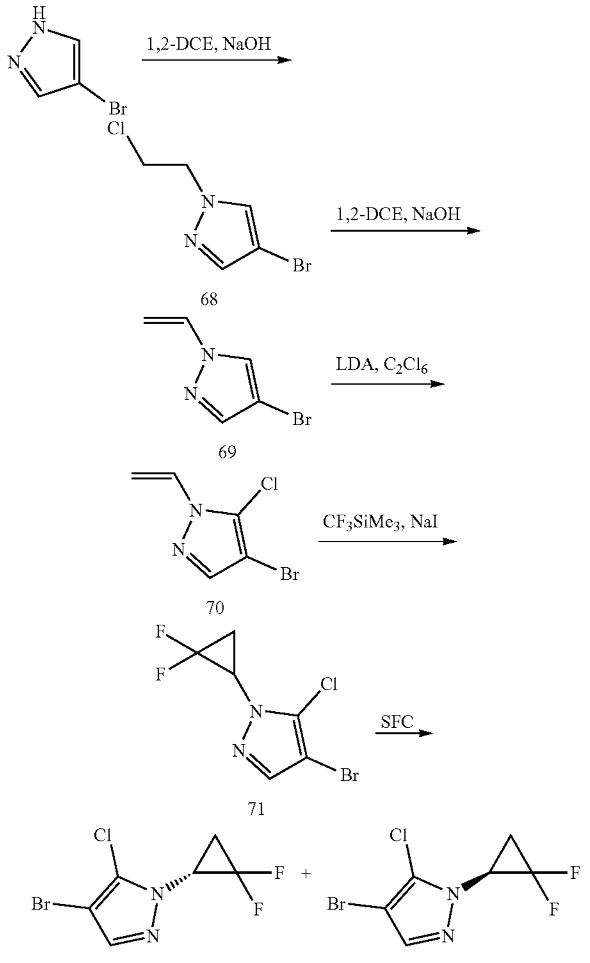

68 69 70 71 71.1 71.2

4-bromo-1-(2-chloroethyl)-1H-pyrazole (68)

A 10-L 3-necked round-bottom flask was charged with a solution of NaOH (201 g, 5.03 mol) in $H_2O$(1.2 L). DCE (1.73 kg, 17.4 mol), 4-bromopyrazole (493 g, 3.35 mol) and benzyl triethylammonium chloride (38.4 g, 0.17 mol) were then added at RT. The reaction mixture was warmed to 80° C. and stirred for 3 hrs at this temperature. On cooling to RT, the reaction mixture was poured into water (1.00 L), and layers were separated. The aqueous phase was extracted with DCM (3×1 L). The combined organic phase was washed with $H_2O$(3×1 L) and brine (3×1 L), dried over anhydrous $Na_2SO_4$ and filtered. Solvent was removed from the collected filtrate under reduced pressure to afford the title compound 68.

4-bromo-1-vinyl-1H-pyrazole (69)

A 10-L 3-necked round-bottom flask was charged with a solution of KOH (372 g, 6.6 mol) in $H_2O$ (800 mL). To the stirring mixture at room temperature were added 1,4-hydroquinone (62 g, 0.56 mol), benzyl triethylammonium chloride (23 g, 0.1 mol), and 4-bromo-1-(2-chloroethyl)-1H-pyrazole 68 (534 g, 2.55 mol). After stirring at RT for 3 hrs, the reaction mixture was warmed to 80° C. and stirred for an additional 3 hrs. The reaction mixture was poured into water (1 L), and layers were separated. The reaction mixture was extracted with ether (3×1 L). The combined organic phase was washed with HCl (1 N, 2×500 mL) and brine (2×500 mL), dried over anhydrous $Na_2SO_4$, and filtered. Solvent was removed from the collected filtrate under reduced pressure to afford a crude residue. The crude product was distilled in vacuum (70° C., 10 mmHg pressure) to afford the title compound 69.

4-bromo-5-chloro-1-vinyl-1H-pyrazole (70)

A 10-L 3-necked round-bottom flask was charged with diisopropylamine (300 g, 2.9 mol) under inert atmosphere and cooled to −78° C. To the stirring mixture at this temperature was slowly added n-butyllithium (1.08 L, 2.5 M in hexanes, 2.69 mol), and the resultant mixture was stirred for 20 minutes at this temperature. A solution of 4-bromo-1-vinyl-1H-pyrazole 69 (343 g, 1.9 mol) in THF (1 L) was then slowly added, and on complete addition the solution was allowed to warm to RT. The resulting solution was stirred for 40 mins at RT then cooled to −78° C., and hexachloroethane (558 g, 2.35 mol) was added. The mixture was stirred at −78° C. for 2 hrs. The reaction mixture was poured into sat. aq. $NH_4Cl$ (1 L) and extracted with ether (3×1.5 L). The combined organic phase was washed with HCl (1 N, 3×1.5 L), sat. aq. $NaHCO_3$(3×1 L), and brine (3×1 L). The collected organic phase was dried over $Na_2SO_4$ and filtered. Solvent was removed from the collected filtrate under reduced pressure to afford a crude residue. The crude residue was subjected to purification by flash chromatography over silica gel (100% PE) to afford the title compound 70.

(R)- and (S)-4-bromo-5-chloro-1-(2,2-difluorocyclopropyl)-1H-pyrazole (71.1 and 71.2)

A 10-L 3-necked round-bottom flask was charged with 4-bromo-5-chloro-1-vinyl-1H-pyrazole 70 (288 g, 1.39 mol) and NaI (833 g, 5.56 mol) under inert atmosphere. MeCN (3 L) was added, and the mixture was warmed to 80° C. To the stirring mixture at this temperature was added trifluoromethyltrimethylsilane (850 g, 5.97 mol) dropwise. The reaction mixture was stirred at 80° C. for 3 hrs. Upon cooling, the reaction mixture was filtered, and solvent was removed from the collected filtrate under reduced pressure. The crude residue was subjected to purification by flash chromatography over silica gel (1-10% EtOAc/PE) to afford the racemic title compound 71. The racemic material could be resolved to its component enantiomers by chiral preparative SFC (Column & dimensions: OD-5H, 4.6 mm×150 mm; Mobile phase A: $CO_2$; Mobile phase B: 1:1 n-heptane/IPA with 0.1% $NH_4OH$) to afford the title compounds 71.1 (tR=3.6 min) and 71.2 (tR=5.2 min). MS (ESI): m/z calc'd for $C_6H_5BrClF_2N_2$ $[M+H]^+$: 256, found 256; $^1H$ NMR (300 MHz, $CDCl_3$, 25° C.) δ: 7.55 (s, 1H), 3.98 (m, 1H), 2.47 (m, 1H), 2.16 (m, 1H).

Scheme 28. Synthesis of (R)-and (S)-4-bromo-1-(2,2-difluorocyclopropyl)-5-methyl-1H-pyrazole

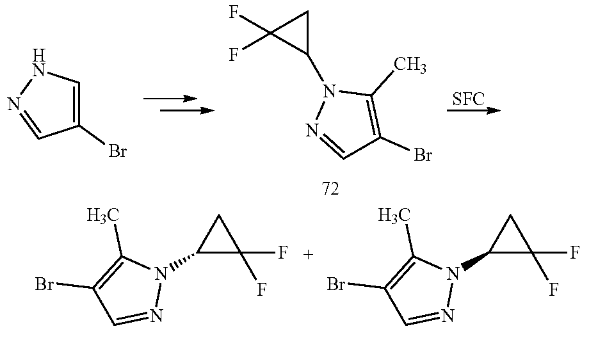

72

72.1

72.2

(R)- and (S)-4-bromo-1-(2,2-difluorocyclopropyl)-5-methyl-1H-pyrazole (72.1 and 72.2)

The title compounds were prepared analogously to compounds 71.1 and 71.2, substituting iodomethane for hexachloroethane. At the final reaction, the racemic title compound was purified from the crude residue by recrystallization from petroleum ether. The racemic material could be resolved to its component enantiomers by chiral preparative SFC(Column & dimensions: AD, 50 mm×250 mm; Mobile phase A: $CO_2$; Mobile phase B: 1:1 n-heptane/IPA with 0.1% $NH_4OH$) to afford the title compounds 72.1 (tR=3.5 min) and 72.2 (tR=4.7 min). MS (ESI): m/z calc'd for $C_7H_8BrF_2N_2$ $[M+H]^+$: 237, found 237; $^1H$ NMR (400 MHz, $CDCl_3$, 25° C.) δ: 7.43 (s, 1H), 3.89-3.83 (m, 1H), 2.42-2.38 (m, 1H), 2.33 (s, 3H), 2.14-2.09 (m, 1H).

Scheme 29. Synthesis of 1-(bicyclo[1.1.1]pentan-1-yl)-4-iodo-1H-pyrazole

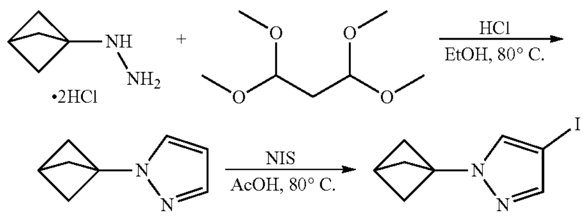

73

74

1-(bicyclo[1.1.1]pentan-1-yl)-1H-pyrazole (73)

A 5-L, 3-necked round-bottom flask was charged with bicyclo[1.1.1]pentan-1-ylhydrazine hydrochloride (1:2) (345 g, 2.02 mol) and 1,1,3,3-tetramethoxypropane (331 g, 2.02 mol) under inert atmosphere. EtOH (1.70 L) was added, and to the stirring mixture at room temperature was added concentrated HCl (521 mL). The resultant mixture was warmed to 80° C. and stirred at this temperature for 6 hrs. On cooling to RT, solvent and water were removed under reduced pressure. The crude residue was taken into $H_2O$(800 mL) and extracted with DCM (3×1 L). The combined organic layers were dried over $Na_2SO_4$, filtered, and solvent was removed from the collected filtrate under reduced pressure to afford the title compound 73.

1-(bicyclo[1.1.1]pentan-1-yl)-4-iodo-1H-pyrazole (74)

A 3-L, 3-necked round-bottom flask was charged with intermediate 73 (270 g, 2.02 mol) under inert atmosphere. AcOH (1.35 L) was added, and to the stirring mixture at room temperature was added NIS (499 g, 2.22 mol). The reaction mixture was warmed to 80° C. and stirred at this temperature for 1 hr. On cooling to RT, solvent was removed under reduced pressure. The crude residue was taken into $H_2O$(1 L) and extracted with DCM (3×1.5 L). The combined organic layers were dried over $Na_2SO_4$, filtered, and solvent was removed from the collected filtrate under reduced pressure. The crude residue was subjected to purification by flash chromatography over silica gel (0-10% EtOAc/PE) to afford the title compound 74. MS (ESI): m/z calc'd for $C_8H_{10}IN_2$ [M+H]$^+$: 261, found 261; $^1$H NMR (400 MHz, $CDCl_3$, 25° C.) δ: 7.52 (s, 1H), 7.47 (s, 1H), 2.62 (s, 1H), 2.29 (s, 6H).

Scheme 30. Synthesis of 1-(3-fluorobicyclo[1.1.1]pentan-1-yl)-4-iodo-1H-pyrazole

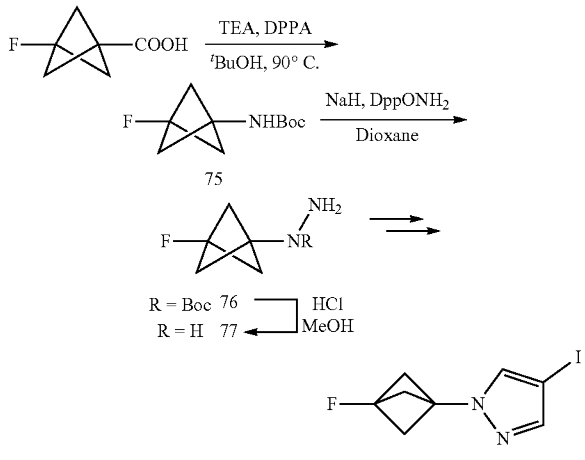

78 tert-butyl (3-fluorobicyclo[1.1.1]pentan-1-yl)carbamate (75)

A 250-mL round-bottom flask was charged with triethylamine (2.04 g, 20.0 mmol) and fluorobicyclo[1.1.1]pentane-1-carboxylic acid (2.50 g, 19.2 mmol) under inert atmosphere. $^t$BuOH (25 mL) was added, and to the stirring mixture at room temperature was added diphenyl azidooxyphosphonate (5.71 g, 19.6 mmol) slowly over the course of 20 min. The reaction was stirred at RT for 2 hrs, at which point it was warmed to 90° C. and stirred for an additional 3 hrs. Solvent was removed under reduced pressure at 40° C., and the residue was diluted with MTBE. The organic phase was washed with sat. aq. $NaHCO_3$ (3×), dried over anhydrous $Na_2SO_4$, filtered, and solvent was removed from the collected filtrate under reduced pressure. The crude residue was subjected to purification by flash chromatography over silica gel (0-100% EtOAc/PE) to afford the title compound 75. $^1$H NMR (400 MHz, $CDCl_3$, 25° C.) δ: 2.33 (s, 6H), 1.45 (s, 9H).

tert-butyl 1-(3-fluorobicyclo[1.1.1]pentan-1-yl)hydrazine-1-carboxylate (76)

A 250-mL round-bottom flask was charged with intermediate 75 (1.0 g, 4.97 mmol) under inert atmosphere. Dioxane (20 mL) was added, and to the stirring mixture at room temperature was added NaH (65% dispersion in mineral oil, 390 mg, 9.94 mmol), and the reaction was stirred for 3 hrs. At this point, O-(diphenylphosphinyl)hydroxylamine (1.51 g, 6.46 mmol) was added, and the resultant mixture was stirred overnight. The reaction was then diluted with EtOAc and washed with water (75 mL). The aqueous phase was then extracted with additional EtOAc (3×30 mL). The combined organic layers were dried over $Na_2SO_4$, filtered, and solvent was removed from the collected filtrate under reduced pressure. The crude residue was subjected to purification by flash chromatography over silica gel (0-50% EtOAc/PE) to afford the title compound 76. $^1$H NMR (400 MHz, DMSO-$d_6$, 25° C.) δ: 4.50 (s, 2H), 2.28 (m, 6H), 1.41 (s, 9H).

(3-fluorobicyclo[1.1.1]pentan-1-yl)hydrazine (77)

A 100-mL round-bottom flask was charged with intermediate 76 (720 mg, 3.33 mmol) under inert atmosphere. HCl (4 M solution in MeOH, 14.4 mL) was added, and the mixture was stirred for 6 hrs at RT. Solvent was removed under reduced pressure to afford the title compound 77. $^1$H NMR (400 MHz, DMSO-$d_6$, 25° C.) δ: 2.18 (m, 6H).

1-(3-fluorobicyclo[1.1.1]pentan-1-yl)-4-iodo-1H-pyrazole (78)

An identical sequence to that described for the preparation of intermediate 74 was performed, substituting intermediate 77. This afforded the title compound 78. MS (ESI): m/z calc'd for $C_8H_9FIN_2$ [M+H]$^+$: 279, found 279; $^1$H NMR (400 MHz, DMSO-$d_6$, 25° C.) δ: 8.05 (s, 1H), 7.62 (s, 1H), 2.61 (m, 6H).

Scheme 31. Synthesis of methyl 3-(4-bromo-1H-pyrazol-1-yl)bicyclo[1.1.1]pentane-1-carboxylate

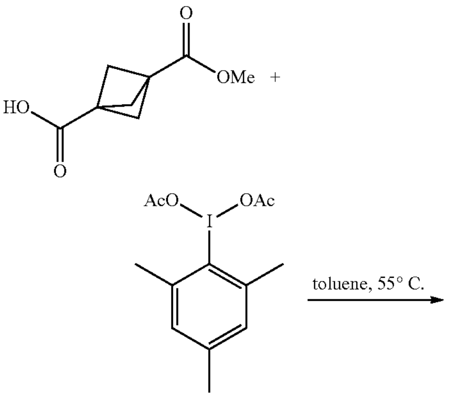

-continued

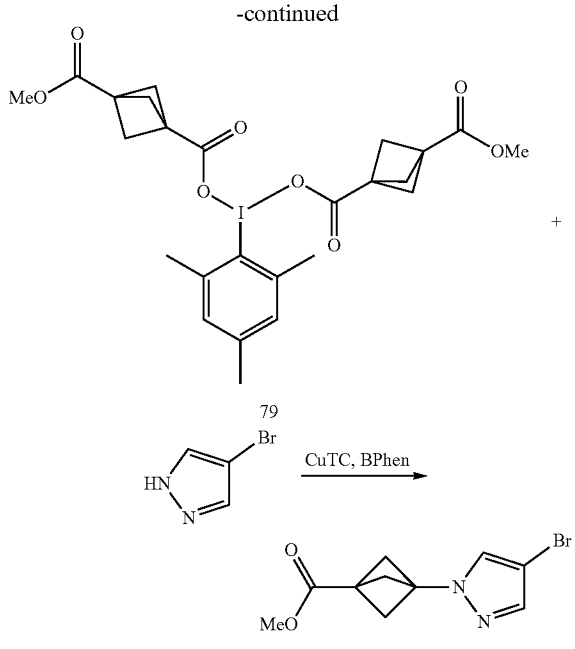

79

80

O'[1],O'[1]-(mesityl-$\lambda^3$-iodanediyl) 3,3'-dimethyl bis (bicyclo[1.1.1]pentane-1,3-dicarboxylate) (79)

A 5-L, 3-necked round-bottom flask was charged with iodomesitylene diacetate (321 g, 881 mmol) and 3-(methoxycarbonyl)bicyclo[1.1.1]pentane-1-carboxylic acid (300 g, 1.76 mol) under inert atmosphere. Toluene (2.0 L) was added, and the the flask was attached to a rotary evaporator with the water bath heated to 55° C. and the solvent (and the generated acetic acid) was removed under reduced pressure. The evaporation process was then repeated with three additional aliquots (2 L each) of toluene to afford the title compound 79. $^1$H NMR (500 MHz, $CDCl_3$, 25° C.) δ: 7.08 (s, 2H), 3.65 (s, 6H), 2.69 (s, 6H), 2.38 (s, 3H), 2.20 (s, 12H).

methyl 3-(4-bromo-1H-pyrazol-1-yl)bicyclo[1.1.1]pentane-1-carboxylate (80)

A 10-L, 3-necked round-bottom flask was charged with 4-bromo-1H-pyrazole (100 g, 680 mmol), intermediate 79 (497 g, 850 mmol), and 4,7-diphenyl-1,10-phenanthroline (33.9 g, 102 mmol) under inert atmosphere. Dioxane (3.0 L) was added, and to the stirring mixture at room temperature was added copper (I) thiophene-2-carboxylate (38.9 g, 204 mmol). The resultant mixture was stirred at RT for 16 hrs. The reaction was then filtered, and solvent was removed from the collected filtrate under reduced pressure. The crude residue was subjected to purification by flash chromatography over silica gel (5-50% EtOAc/PE) to afford the title compound 80. MS (ESI): m/z calc'd for $C_{10}H_{12}BrN_2O_2$ $[M+H]^+$: 271, found 271; $^1$H NMR (400 MHz, $CDCl_3$, 25° C.) δ: 7.51 (s, 1H), 7.46 (s, 1H), 3.75 (s, 3H), 2.56 (s, 5H), 2.49-2.64 (m, 1H).

Scheme 32. Synthesis of 3-(4-bromo-1H-pyrazol-1-yl)bicyclo[1.1.1]pentane-1-carbonitrile

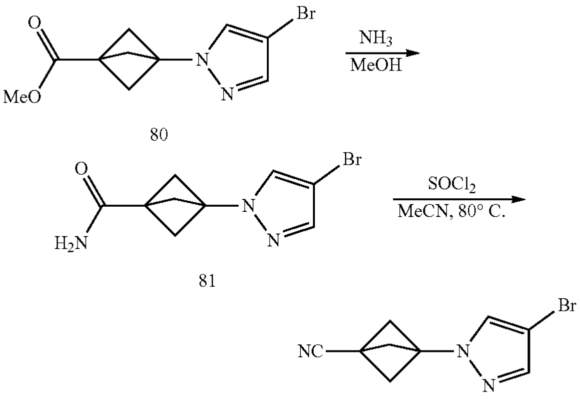

80

81

82

3-(4-bromo-1H-pyrazol-1-yl)bicyclo[1.1.1]pentane-1-carboxamide (81)

A 20-mL scintillation vial was charged with intermediate 80 (200 mg, 0.738 mmol) under inert atmosphere. Ammonia (7 N in MeOH, 2.1 mL, 14.7 mmol) was added, and the mixture was stirred at RT for 18 hrs. Solvent was removed under reduced pressure to afford the title compound 81. MS (ESI): m/z calc'd for $C_9H_{11}BrN_3O$ $[M+H]^+$: 256, found 256.

3-(4-bromo-1H-pyrazol-1-yl)bicyclo[1.1.1]pentane-1-carbonitrile (82)

A 50-mL round-bottom flask was charged with intermediate 81 (189 mg, 0.738 mmol) under inert atmosphere. MeCN (9 mL) was added, and to the stirring mixture at RT was added thionyl chloride (1.0 mL, 14 mmol). The solution was heated to reflux for 3 hrs. Volatiles were removed under reduced pressure (caution: HCl gas evolves). The resulting residue was azeotroped several times with THF to afford the title compound 82. MS (ESI): m/z calc'd for $C_9H_9BrN_3$ $[M+H]^+$: 238, found 238.

Scheme 33. Synthesis of (3-(4-bromo-1H-pyrazol-1-yl)bicyclo[1.1.1]pentan-1-yl)methanol

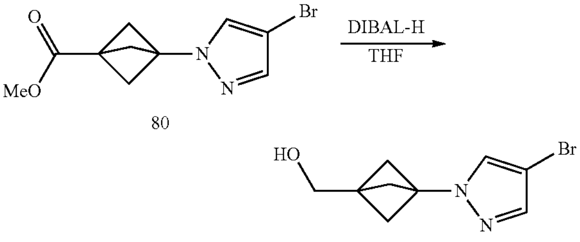

80

83

(3-(4-bromo-1H-pyrazol-1-yl)bicyclo[1.1.1]pentan-1-yl)methanol (83)

A 500-mL round-bottom flask was charged with intermediate 80 (5.0 g, 18 mmol) under inert atmosphere. THF (75 mL) was added, and the resultant solution was cooled to 0° C. To the stirring mixture at this temperature was added DIBAL-H (1 M in hexane, 55.3 mL, 55.3 mmol) and the resultant solution was stirred at 0° C. for 2 hrs. The reaction was quenched by slowly pouring it into sat. aq. $NH_4Cl$ (100 mL), and then allowed to stir vigorously at room temperature. A slurry was formed, and the material was then filtered through Celite. The phases of the filtrate were separated, and the organic layer was dried over anhydrous $Na_2SO_4$, filtered, and solvent was removed from the collected filtrate under reduced pressure. The crude residue was subjected to purification by flash chromatography over silica gel (0-80% EtOAc/hexanes) to afford the title compound 83. MS (ESI): m/z calc'd for $C_9H_{12}BrN_2O$ $[M+H]^+$: 243, found 243.

Scheme 34. Synthesis of 4-bromo-1-(3-((difluoromethoxy) methyl)bicyclo[1.1.1]pentan-1-yl)1H-pyrazole

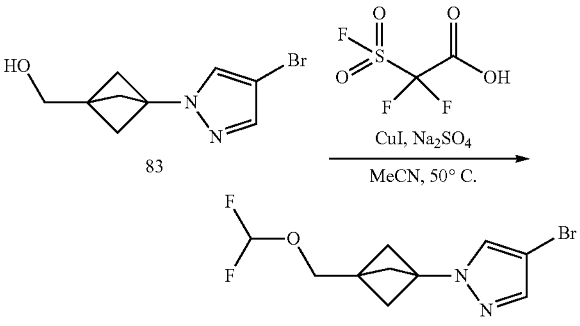

83

84

4-bromo-1-(3-((difluoromethoxy)methyl)bicyclo [1.1.1]pentan-1-yl)-1H-pyrazole (84)

A 5-mL microwave vial was charged with intermediate 83 (250 mg, 1.03 mmol), sodium sulfate (73 mg, 0.51 mmol), and copper (I) iodide (98 mg, 0.51 mmol). MeCN (3.5 mL) was added, and the mixture was warmed to 50° C. To the stirring mixture at this temperature was added 2,2-difluoro-2-(fluorosulfonyl)acetic acid (201 mg, 1.13 mmol), and the reaction was stirred for an additional 7 hrs at 50° C. The crude reaction mixture was then concentrated in vacuo and the resulting residue was partitioned between diethyl ether and 1N aq. NaOH. The organic layer was separated and washed further with 1N aq. HCl, water, and brine. The organic layer was then dried over anhydrous $Na_2SO_4$, filtered, and solvent was removed from the collected filtrate under reduced pressure. The crude residue was subjected to purification by flash chromatography over silica gel (0-50% EtOAc/hexanes) to afford the title compound 84. MS (ESI): m/z calc'd for $C_{10}H_{12}BrF_2N_2O$ $[M+H]^+$: 293, found 293.

Scheme 35. Synthesis of 4-bromo-1-(3-(methoxymethyl)bicyclo[1.1.1]pentan-1-yl)1H-pyrazole

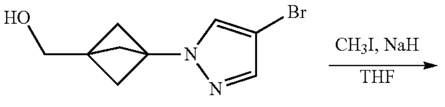

83

-continued

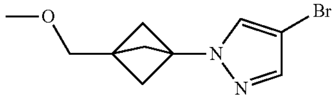

85

4-bromo-1-(3-(methoxymethyl)bicyclo[1.1.1]pentan-1-yl)-1H-pyrazole (85)

A 100-mL round-bottom flask was charged with intermediate 83 (1.0 g, 4.11 mmol) under inert atmosphere. THF (20 mL) was added and the solution was cooled to 0° C. To the stirring mixture at this temperature was added NaH (200 mg, 5.00 mmol), and the mixture was stirred for 30 minutes at 0° C. Iodomethane (514 µL, 8.23 mmol) was then added. The reaction mixture was allowed to warm to RT and stirred for an additional 2 hrs. The reaction was quenched by addition to sat. aq. $NH_4Cl$ (25 mL) and diluted with ethyl acetate (25 mL). The phases were separated, and the aqueous phase was extracted once more with EtOAc. The combined organic layer was washed with brine (1×50 mL), dried over anhydrous $Na_2SO_4$, filtered, and solvent was removed from the collected filtrate under reduced pressure. The crude residue was subjected to purification by flash chromatography over silica gel (0-50% EtOAc/hexanes) to afford the title compound 85. MS (ESI): m/z calc'd for $C_{10}H_{14}BrN_2O$ $[M+H]^+$: 257, found 257.

Scheme 36. Synthesis of 3-(4-bromo-1H-pyrazol-1-yl)bicyclo[1.1.1]pentane-1-carbaldehyde

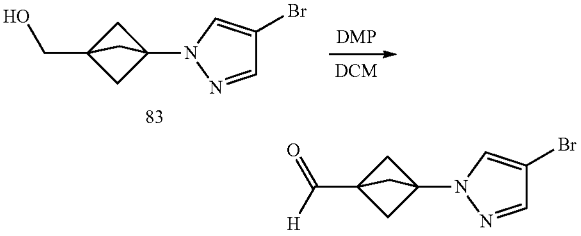

83

86

3-(4-bromo-1H-pyrazol-1-yl)bicyclo[1.1.1]pentane-1-carbaldehyde (86)

A 25-mL round-bottom flask was charged with intermediate 83 (500 mg, 2.06 mmol) under inert atmosphere. DCM (8 mL) was added, and the solution was cooled to 0° C. To the stirring mixture at this temperature was added Dess-Martin periodinane (960 mg, 2.62 mmol), and the reaction mixture was stirred for an additional 1 hr at this temperature. The solution was diluted with DCM (25 mL) and poured into sat. aq. $Na_2CO_3$ (100 mL). The phases were separated and the aqueous phase was extracted with DCM (2×25 mL). The combined organic layers were dried over anhydrous $Na_2SO_4$, filtered, and solvent was removed from the collected filtrate under reduced pressure. The crude residue was subjected to purification by flash chromatography over silica gel (0-100% EtOAc/hexanes) to afford the title compound 86. MS (ESI): m/z calc'd for $C_9H_{10}BrN_2O$ $[M+H]^+$: 241, found 241.

Scheme 37. Synthesis of 4-bromo-1-(3-(difluoromethyl)bicyclo[1.1.1]pentan-1-yl)1H-pyrazole

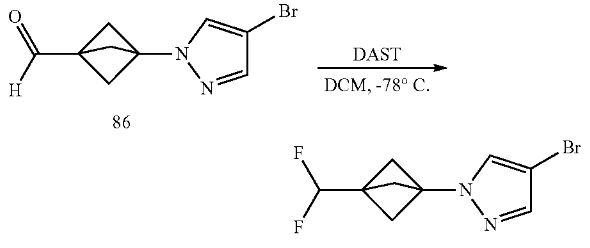

86

87

4-bromo-1-(3-(difluoromethyl)bicyclo[1.1.1]pentan-1-yl)-1H-pyrazole (87)

A 50-mL round-bottom flask was charged with intermediate 86 (300 mg, 1.24 mmol) under inert atmosphere. DCM (12 mL) was added, and the solution was cooled to −78° C. To the stirring mixture at this temperature was added DAST (658 μL, 4.98 mmol), and the reaction was stirred for an additional 30 min at −78° C. The reaction was then allowed to warm to RT and diluted with additional DCM (15 mL). The organic layer was washed with water (20 mL) and 4 M aq. NaOH (20 mL), then dried over anhydrous $Na_2SO_4$, filtered, and solvent was removed from the collected filtrate under reduced pressure. The crude residue was subjected to purification by flash chromatography over silica gel (0-40% EtOAc/hexanes) to afford the title compound 87. MS (ESI): m/z calc'd for $C_9H_{10}BrF_2N_2$ $[M+H]^+$: 263, found 263.

Scheme 38. Synthesis of 1-(3-(4-bromo-1H-pyrazol-1-yl)bicyclo[1.1.1]pentan-1-yl)-N,N-dimethylmethanamine (88)

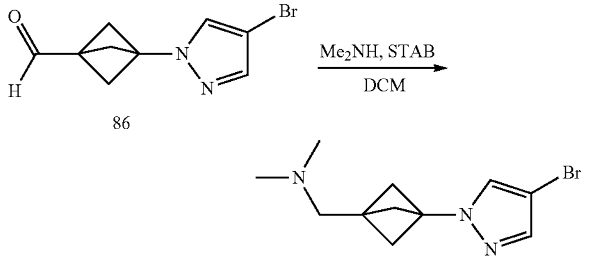

86

89

1-(3-(4-bromo-1H-pyrazol-1-yl)bicyclo[1.1.1]pentan-1-yl)-N,N-dimethylmethanamine (89)

A 4 dram vial was charged with intermediate 86 (250 mg, 1.04 mmol), dimethylamine (518 μL, 1.04 mmol), and 4 Å molecular sieves under inert atmosphere. DCM (3 mL) was added, and the mixture was stirred at room temperature for 1 hr. To the mixture was then added STAB (440 mg, 2.07 mmol), and the solution was stirred at room temperature overnight. On cooling to RT, solids were removed by filtration, and the filtrate was washed with sat. aq. $NaHCO_3$ (2×10 mL). The organic layer was dried over anhydrous $Na_2SO_4$, filtered, and solvent was removed from the collected filtrate under reduced pressure. The crude residue was subjected to purification by flash chromatography over silica gel (0-100% 3:1 EtOAc:EtOH in hexanes) to afford the title compound 89. MS (ESI): m/z calc'd for $C_{11}H_{17}BrN_3$ $[M+H]^+$: 270, found 270.

Scheme 39. Synthesis of 1-(3-(4-bromo-1H-pyrazol-1-yl)bicyclo[1.1.1]pentan-1-yl)ethan-1-ol

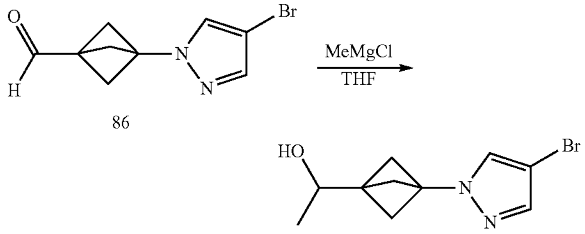

86

90

1-(3-(4-bromo-1H-pyrazol-1-yl)bicyclo[1.1.1]pentan-1-yl)ethan-1-ol (90)

A 20-mL scintillation vial was charged with intermediate 86 (300 mg, 1.24 mmol) under inert atmosphere. THF (5 mL) is added, and the solution was cooled to 0° C. To the stirring mixture at this temperature was added MeMgCl (3.4 M in THF, 366 μL, 1.24 mmol), the reaction was stirred at this temperature for 1 hr. The mixture is quenched using sat. aq. $NH_4Cl$, and mixture was diluted with EtOAc and additional sat. aq. $NH_4C1$. The phases were separated and the aqueous phase was extracted with additional EtOAc (2×10 mL). The combined organic layers are dried over anhydrous $Na_2SO_4$, filtered, and solvent was removed from the collected filtrat under reduced pressure. The crude residue was subjected to purification by flash chromatography over silica gel (0-60% EtOAc/hexanes) to afford the title compound 90. MS (ESI): m/z calc'd for $C_{10}H_{14}BrN_2O$ $[M+H]^+$: 257, found 257.

Scheme 40. Synthesis of 4-bromo-1-(3-methoxybicyclo[1.1.1]pentan-1-yl)-1H-pyrazole

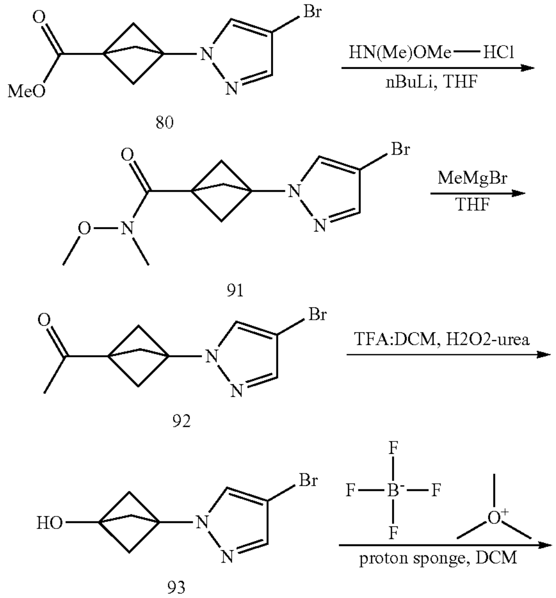

80

91

92

93

-continued

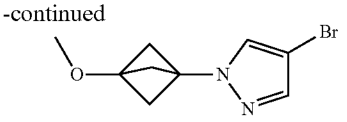

94

3-(4-bromo-1H-pyrazol-1-yl)-N-methoxy-N-methyl-bicyclo[1.1.1]pentane-1-carboxamide (91)

A 500-mL round-bottom flask was charged with N,O-dimethylhydroxylamine, HCl (1.38 g, 14.2 mmol). THF (75 mL) was added, and the resultant solution was cooled to −78° C. To the stirring mixture at this temperature was added n-butyllithium (2.5 M solution in hexanes, 11.3 mL, 28.3 mmol), and the mixture was stirred for 45 minutes, or until all solid was dissolved. At this point, intermediate 80 (3.20 g, 11.8 mmol) was added as a solution in THF (5 mL), slowly over 5 minutes. The reaction was then allowed to warm to room temperature and stirred for 2 hrs. The mixture was quenched by the addition of sat. aq. $NaHCO_3$ (200 mL) and diluted with DCM (200 mL). The phases were separated, and the aqueous phase was extracted with additional DCM (2x75 mL). The combined organic layers were dried over anhydrous $Na_2SO_4$, filtered, and solvent was removed from the collected filtrate under reduced pressure. The crude residue was subjected to purification by flash chromatography over silica gel (0-100% 3:1 EtOAc:EtOH in hexanes) to afford the title compound 91. MS (ESI): m/z calc'd for $C_{11}H_{15}BrN_3O_2$ $[M+H]^+$: 300, found 300.

1-(3-(4-bromo-1H-pyrazol-1-yl)bicyclo[1.1.1]pentan-1-yl)ethan-1-one (92)

A 500-mL round-bottom flask was charged with intermediate 91 (2.3 g, 7.7 mmol) under inert atmosphere. THF (50 mL) was added, and the solution was cooled to −5° C. To the stirring mixture at this temperature was added MeMgBr (3.4 M solution in 2-MeTHF, 2.64 mL, 9.2 mmol). The resultant mixture was stirred for 2 hrs at this temperature, then quenched by the addition of sat. aq. $NaHCO_3$ (50 mL). The mixture was diluted with DCM (100 mL) and the phases were separated. The aqueous phase was extracted with additional DCM (2x75 mL), and the combined organic layers were dried over anhydrous $Na_2SO_4$, filtered, and solvent was removed from the collected filtrate under reduced pressure. The crude residue was subjected to purification by flash chromatography over silica gel (0-100% 3:1 EtOAc:EtOH in hexanes) to afford the title compound 92. MS (ESI): m/z calc'd for $C_{10}H_{12}BrN_2O$ $[M+H]^+$: 255, found 255.

3-(4-bromo-1H-pyrazol-1-yl)bicyclo[1.1.1]pentan-1-ol (93)

A 50-mL round-bottom flask was charged with intermediate 92 (500 mg, 1.96 mmol) under inert atmosphere. DCM (10 mL) and TFA (10.5 mL) were then added at RT, and to the stirring mixture at this temperature was then added urea-hydrogen peroxide (1.10 g, 11.8 mmol). The mixture was then warmed to 32° C. and stirred for 5 hrs at this temperature. The mixture was then diluted with water (15 mL) and stirred for 15 min. The phases were separated, and the aqueous phase was extracted with additional DCM (2x15 mL). The combined organic layers were washed with 10% aq. $Na_2S_2O_3$ (50 mL), dried over anhydrous $Na_2SO_4$, filtered, and solvent was removed from the collected filtrate under reduced pressure. The crude residue was subjected to purification by flash chromatography over silica gel (0-50% 3:1 EtOAc:EtOH in hexanes) to afford the title compound 93. MS (ESI): m/z calc'd for $C_8H_{10}BrN_2O$ $[M+H]^+$: 229, found 229.

4-bromo-1-(3-methoxybicyclo[1.1.1]pentan-1-yl)-1H-pyrazole (94)

A 50-mL round-bottom flask was charged with intermediate 93 (500 mg, 2.18 mmol), proton sponge (1.4 g, 6.6 mmol), and trimethyloxonium tetrafluoroborate (807 mg, 5.46 mmol) under inert atmosphere. DCM (20 mL) was added, and the mixture was stirred at RT for 2 hrs. The reaction was then diluted with 0.5 N aq. HCl (15 mL), and stirred for 1 hr at RT. The phases were separated, and the aqueous phase was extracted with additional DCM (2x15 mL). The combined organic layers were dried over anhydrous $Na_2SO_4$, filtered, and solvent was removed from the collected filtrate under reduced pressure. The crude residue was subjected to purification by flash chromatography over silica gel (0-50% 3:1 EtOAc:EtOH in hexanes) to afford the title compound 94. MS (ESI): m/z calc'd for $C_9H_{11}BrN_2O$ $[M+H]^+$: 243, found 243.

Scheme 41. Synthesis of 5-bromo-1,3-dimethyl-1H-pyrazole

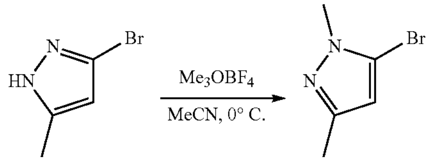

95

5-bromo-1,3-dimethyl-1H-pyrazole (95)

A 50-mL round-bottom flask was charged with 3-bromo-5-methyl-1H-pyrazole (2.00 g, 12.4 mmol) under inert atmosphere. MeCN (5 mL) was added, and the mixture was cooled to 0° C. To the stirring mixture at this temperature was added trimethyloxonium tetrafluoroborate (2.71 g, 14.3 mmol). The resultant mixture was held at 0° C. for 3 hrs, then warmed to RT and stirred for an additional 15 hrs. The reaction was quenched by pouring into sat. aq. $NaHCO_3$ (30 mL). The mixture was extracted with EtOAc (3x20 mL), and the combined organic phases were washed with brine (1x50 mL), dried over anhydrous $Na_2SO_4$, filtered, and solvent was removed from the collected filtrate under reduced pressure. The crude residue was subjected to purification by flash chromatography over silica gel (0-20% EtOAc/PE) to afford the title compound 95. MS (ESI): m/z calc'd for $C5H_8BrN_2$ $[M+H]^+$: 175, found 175.

Scheme 42. Synthesis of 4-bromo-1-cyclopropyl-5-(difluoromethyl)-1H-pyrazole

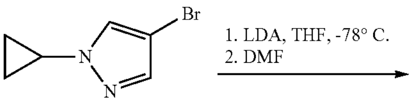

-continued

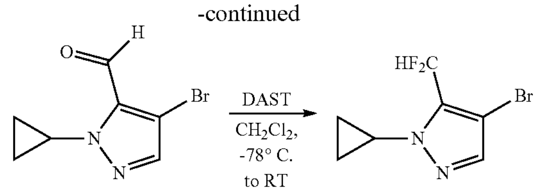

96 97

4-bromo-1-cyclopropyl-1H-pyrazole-5-carbaldehyde (96)

A 250-mL round-bottom flask was charged with 4-bromo-1-cyclopropyl-1H-pyrazole (2.50 g, 13.4 mmol) under inert atmosphere. THF (10 mL) was added, and the mixture was cooled to −78° C. with stirring. To the mixture at this temperature was slowly added lithium diisopropylamide (1 M in THF/hexanes, 20.0 mL). The mixture was held at this temperature with stirring for 1.5 hrs, at which point DMF (1.55 mL) was slowly added. The mixture was stirred overnight, allowing the dry ice bath to warm to RT. Water (20 mL) was added, and the mixture was stirred for 20 min.

The mixture was then transferred to a separatory funnel where it was diluted into additional water (50 mL) and extracted with DCM (3×50 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 96. MS (ESI): m/z calc'd for $C_7H_8BrN_2O$ $[M+H]^+$: 215, found 215.

4-bromo-1-cyclopropyl-5-(difluoromethyl)-1H-pyrazole (97)

A 50-mL Corning™ Falcon™ tube was charged with 4-bromo-1-cyclopropyl-1H-pyrazole-5-carbaldehyde 96 (1.00 g, 4.65 mmol) under inert atmosphere. DCM (10 mL) was added, and the mixture was cooled to −78° C. To the mixture at this temperature was slowly added DAST (1 M in DCM, 14.0 mL). Upon complete addition, the reaction was stirred overnight, allowing the dry ice bath to warm to RT. Water (20 mL) was added, and the mixture was transferred to a separatory funnel containing an excess of sat. aq. $NaHCO_3$. The phases were mixed vigorously, then separated. The aqueous phase was then extracted with additional DCM (2×40 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 97. MS (ESI): m/z calc'd for $C_7H_8BrF_2N_2$ [M+H]+: 236, found 236.

Each of the substituted heterocycles presented in Table 1 below are either commercially available, or were prepared in accordance with the synthetic routes in General Scheme 1, using procedures analogous to those described above.

TABLE 1

| Intermediate | Structure |
| --- | --- |
| 98 | 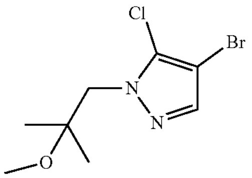 |
| 99 | 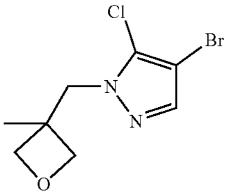 |
| 100 | 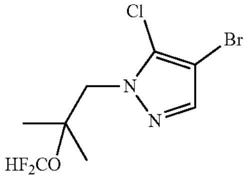 |
| 101 | 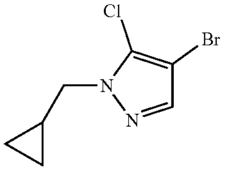 [SMILES: Clc1c(Br)cnn1CC1CC1] |
| 102 | 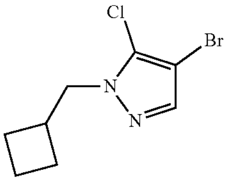 [SMILES: Clc1c(Br)cnn1CC1CCC1] |
| 103 | 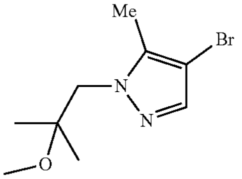 |
| 104 | 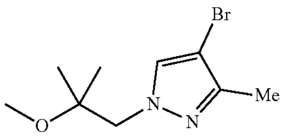 |
| 105 | 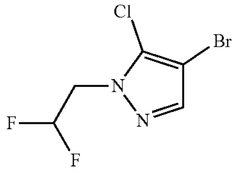 [SMILES: FC(F)Cn1ncc(Br)c1Cl] |

TABLE 1-continued
| Intermediate | Structure |
|---|---|
| 106 | 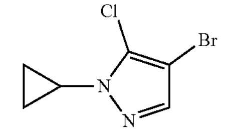 |
| 107 | 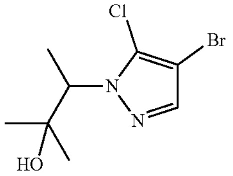 |
| 108 | 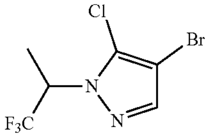 |
| 109 | 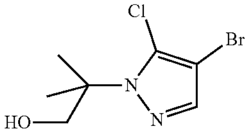 |
| 110 | 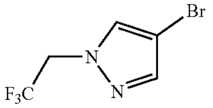 |
| 111 | 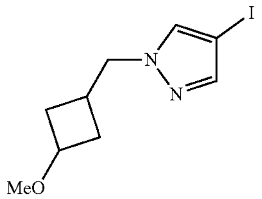 [SMILES: COC1CC(Cn2cc(I)cn2)C1] |
| 112 | 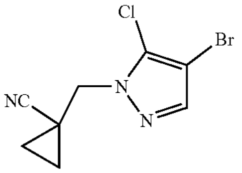 [SMILES: N#CC1(Cn2ncc(Br)c2Cl)CC1] |
| 113 | 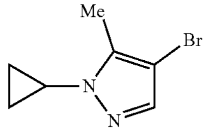 |
| 114 | 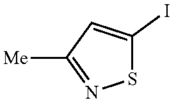 |
| 115 | 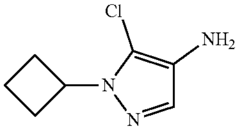 [SMILES: Nc1cnn(C2CCC2)c1Cl] |
| 116 | 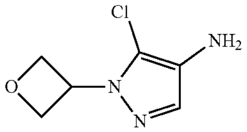 [SMILES: Nc1cnn(C2COC2)c1Cl] |
| 117 | 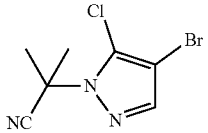 |
| 118 | 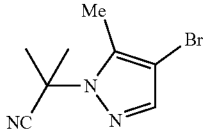 |
| 119 | 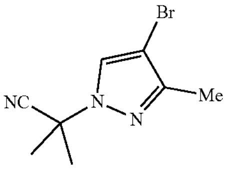 |
| 120 | 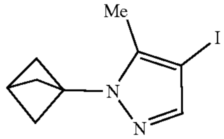 [SMILES: Cc1c(I)cnn1C12CC(C1)C2] |
| 121 | 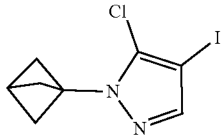 [SMILES: Clc1c(I)cnn1C12CC(C1)C2] |
| 122 | 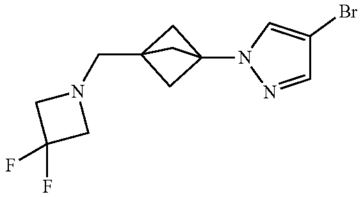 [SMILES: FC1(F)CN(CC23CC(n4cc(Br)cn4)(C2)C3)C1] |
| 123 | 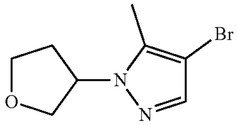 |
| 124 | 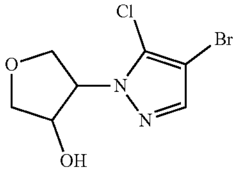 [SMILES: OC1COCC1n1ncc(Br)c1Cl] |
| 125 | 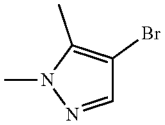 |

TABLE 1-continued
| Intermediate | Structure |
|---|---|
| 126 | 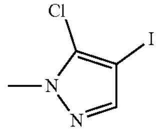 |
| 127 | 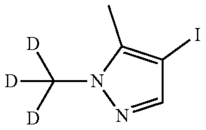 |
| 128 | 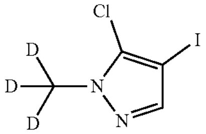 [SMILES: [2H]C([2H])([2H])n1ncc(I)c1Cl] |
| 129 | 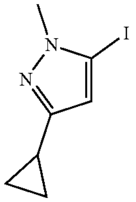 |
| 130 | 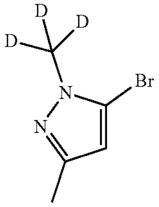 |
| 131 | 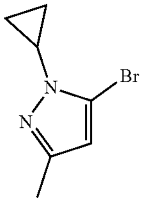 |
| 132 | 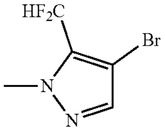 |
| 133 | 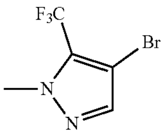 |
TABLE 1-continued
| Intermediate | Structure |
|---|---|
| 134 | 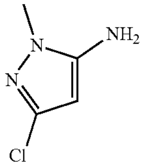 |
| 135 | 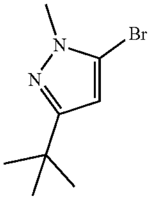 |
| 136 | 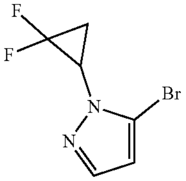 |
| 137 | 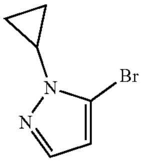 |
| 138 | 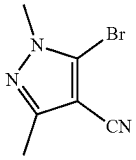 |
| 139 | 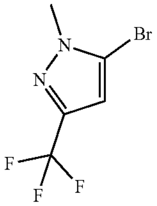 |

General Scheme 2

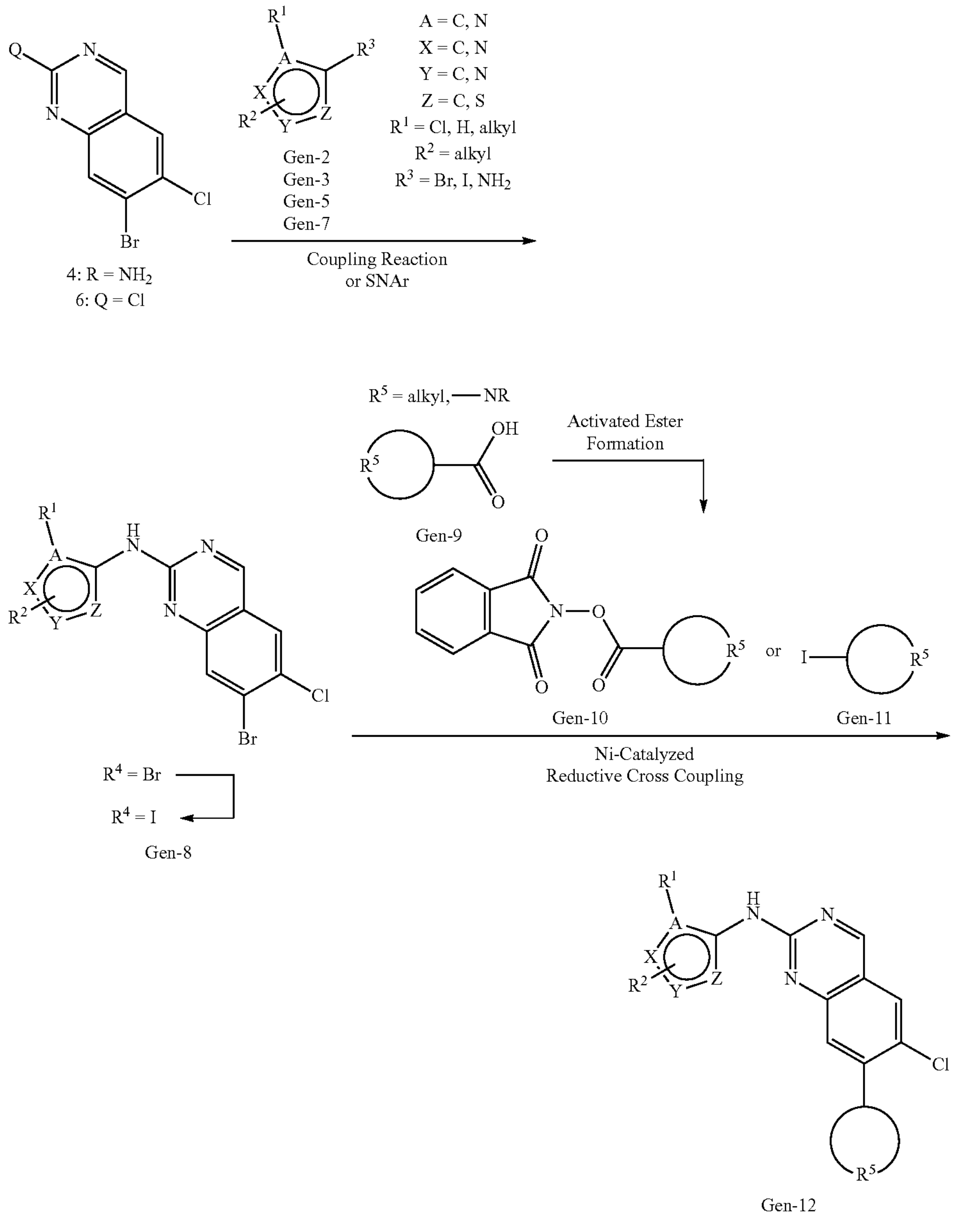

In General Scheme 2, commercially available or synthetically prepared intermediates 4 and/or 6 were coupled with commercially available or synthetically prepared aryl amines Gen-2/Gen-3/Gen-5/Gen-7 through either a cross coupling reaction, or SNAr reaction, to provide Gen-8. Copper-catalyzed halogen exchange could optionally be performed to generate the corresponding aryl iodide. Commercially available or synthetically prepared carboxylic acids Gen-9 were transformed to activated esters Gen-10 by condensation with N-hydroxyphthalimide. The aryl halide Gen-8 could ultimately be transformed under nickel-catalyzed reductive cross coupling with either Gen-10, or commercially available or synthetically prepared alkyl iodides Gen-11, to afford elaborated compounds of the form Gen-12. The representative compounds are described in more detail below.

Preparation of Examples 1.1 and 1.2

Scheme 43. Synthesis of (S) and (R) 1,3-dioxoisoindolin-2-yl spiro[2.2]pentane-1-carboxylate

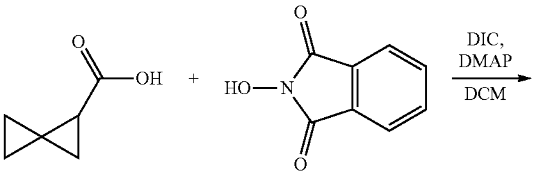

-continued

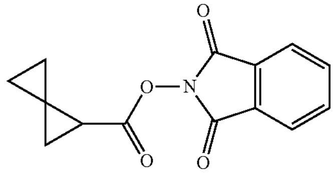

140

(S) and (R) 1,3-dioxoisoindolin-2-yl spiro[2.2]pentane-1-carboxylate (140)

A 250 mL round-bottom flask was charged with (S) and (R) spiro[2.2]pentane-1-carboxylic acid (3 g, 26.8 mmol), N-hydroxyphthalimide (4.80 g, 29.4 mmol), DMAP (0.327 g, 2.68 mmol), and DCM (100 mL). To the stirring mixture at RT was added N,N'-diisopropylcarbodiimide (4.56 mL, 29.4 mmol). The resultant mixture was stirred at RT overnight. The reaction mixture was filtered, solvent was removed under reduced pressure, and the resultant crude residue was subjected to purification by flash chromatography over silica gel (EtOAc/hexanes, 0-20%) to afford the title compound 140. $^1H$ NMR (400 MHz, DMSO-$d_6$, 25° C.) δ: 8.05-7.87 (m, 4H), 2.51-2.47 (m, 1H), 1.82-1.76 (m, 1H), 1.65-1.59 (m, 1H), 1.21-1.12 (m, 1H), 1.07-0.97 (m, 2H), 0.93-0.86 (m, 1H).

Scheme 44. Synthesis of (S) or (R) 6-chloro-N-(1-ethyl-5-methyl-1H-pyrazol-4-yl)-7-(spiro[2.2]pentan-1-yl)quinazolin-2-amine

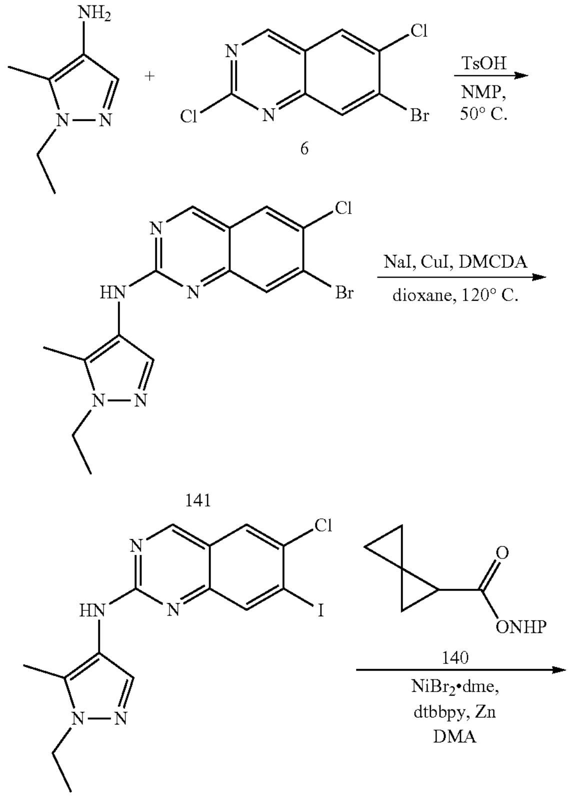

-continued

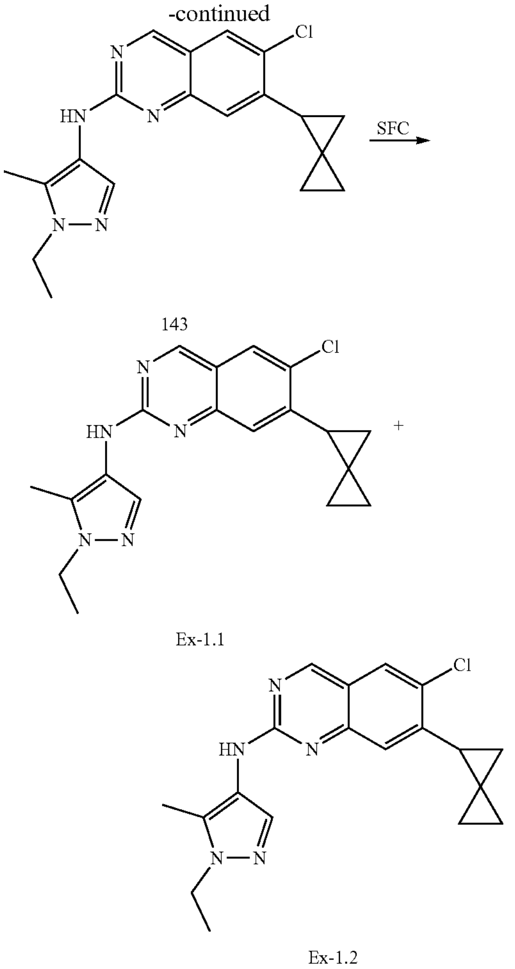

7-bromo-6-chloro-N-(1-ethyl-5-methyl-1H-pyrazol-4-yl)quinazolin-2-amine (141)

A 50 mL round-bottom flask was charged with 1-ethyl-5-methyl-1H-pyrazol-4-amine, HCl (337 mg, 2.09 mmol), 7-bromo-2,6-dichloroquinazoline 6 (290 mg, 1.04 mmol), p-toluenesulfonic acid (298 mg, 1.57 mmol), and NMP (3 mL). The resultant mixture was allowed to stir at 50° C. overnight. Solvent was then removed under reduced pressure and the resultant crude residue was subjected to purification by flash chromatography over silica gel (gradient elution: 0-25% 3:1 EtOAc/EtOH in hexanes) to afford the title compound 141. MS (ESI): m/z calc'd for $C_{14}H_{13}BrClN_5$ $[M+H]^+$: 366, found 366.

6-chloro-N-(1-ethyl-5-methyl-1H-pyrazol-4-yl)-7-iodoquinazolin-2-amine (142)

A vial was charged with 7-bromo-6-chloro-N-(1-ethyl-5-methyl-1H-pyrazol-4-yl)quinazolin-2-amine 141 (380 mg, 1.04 mmol), sodium iodide (777 mg, 5.18 mmol), copper(I) iodide (19.7 mg, 0.10 mmol), and 1,4-dioxane (8 mL). Trans-N,N-dimethylcyclohexane-1,2-diamine (DMCDA) (33 μL, 0.21 mmol) was added, the vial was sealed, purged with nitrogen, and then stirred at 120° C. overnight. The reaction mixture was diluted with MeOH, filtered over a pad of Celite, and solvent was removed under reduced pressure.

The crude residue was subjected to purification by flash chromatography over silica gel (3:1 EtOAc/EtOH in hexanes, 0-50%) to afford the title compound 142. MS (ESI): m/z calc'd for $C_{14}H_{13}ClIN_5$ [M+H]$^+$: 414, found 414.

(S) or (R) 6-chloro-N-(1-ethyl-5-methyl-1H-pyrazol-4-yl)-7-(spiro[2.2]pentan-1-yl)quinazolin-2-amine (Ex-1.1 and Ex-1.2)

A vial was charged with nickel(II) bromide 2-methoxyethyl ether complex (9.2 mg, 0.03 mmol) 4,4'-di-tert-butyl-2,2'-bipyridine (7 mg, 0.03 mmol), and DMA (500 μL). The vial was purged with nitrogen and then stirred at rt for 15 minutes. The resultant catalyst mixture was added to a nitrogen purged solution of 6-chloro-N-(1-ethyl-5-methyl-1H-pyrazol-4-yl)-7-iodoquinazolin-2-amine 142 (54 mg, 0.131 mmol), 1,3-dioxoisoindolin-2-yl spiro[2.2]pentane-1-carboxylate (50.4 mg, 0.196 mmol) 140, and zinc (17.07 mg, 0.261 mmol) in DMA (1 mL). The resultant mixture was purged with nitrogen and allowed to stir at RT overnight. The reaction mixture was diluted with EtOAc, filtered, and solvent removed under reduced pressure. The crude residue was subjected to purification by reversed phase HPLC, eluting with water (0.1% TFA)-MeCN, to afford the racemic title compound 143. The racemic material could be resolved to its component enantiomers by chiral preparative SFC (Column & dimensions: AD-H, 21 mm×250 mm; Mobile phase A: $CO_2$; Mobile phase B: MeOH with 0.1% $NH_4OH$) to afford the title compounds Ex-1.1 (tR=4.2 min) and Ex-1.2 (tR=5.5 min). MS (ESI): m/z calc'd for $C_{19}H_{20}ClN_5$ [M+H]$^+$: 354, found 354; $^1$H NMR (400 MHz, DMSO-$d_6$, 25° C.) δ: 9.11 (s, 1H), 9.04 (s, 1H), 7.95 (s, 1H), 7.72 (s, 1H), 7.21 (s, 1H), 4.06 (q, J=7.2 Hz, 2H), 2.72-2.59 (m, 1H), 2.22 (s, 3H), 1.69-1.57 (m, 1H), 1.46-1.37 (m, 1H), 1.32 (t, J=7.2 Hz, 3H), 1.07-1.01 (m, 1H), 1.01-0.94 (m, 1H), 0.94-0.85 (m, 1H), 0.70-0.57 (m, 1H). MS (ESI): m/z calc'd for $C_{19}H_{20}ClN_5$ [M+H]+: 354, found 354; $^1$H NMR (400 MHz, DMSO-$d_6$, 25° C.) δ: 9.11 (s, 1H), 9.03 (s, 1H), 7.95 (s, 1H), 7.72 (s, 1H), 7.21 (s, 1H), 4.06 (q, J=7.2 Hz, 2H), 2.73-2.61 (m, 1H), 2.22 (s, 3H), 1.68-1.54 (m, 1H), 1.48-1.37 (m, 1H), 1.32 (t, J=7.2 Hz, 3H), 1.10-1.01 (m, 1H), 1.01-0.94 (m, 1H), 0.94-0.83 (m, 1H), 0.69-0.56 (m, 1H).

Preparation of Examples 1.3 and 1.4

Scheme 45. Synthesis of (S) or (R) 1-(3-(6-chloro-2-((1-cyclopropyl-1H-pyrazol-4-yl)amino)quinazolin-7-yl)pyrrolidin-1-yl)-2-methylpropan-2-ol

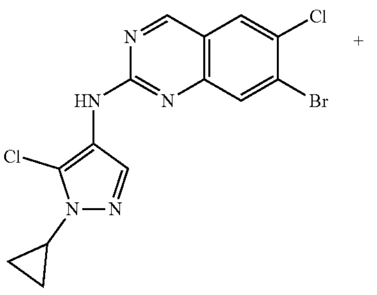

12

-continued

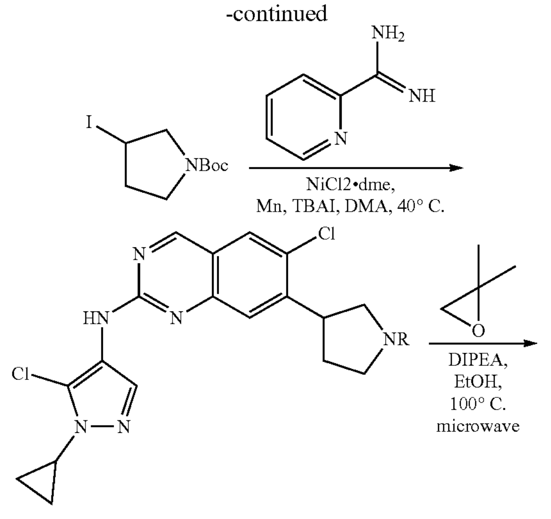

144 R = Boc
145 R = H
TFA

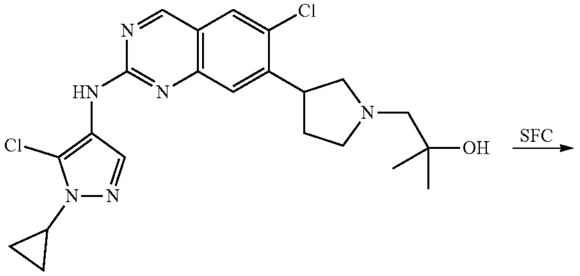

146

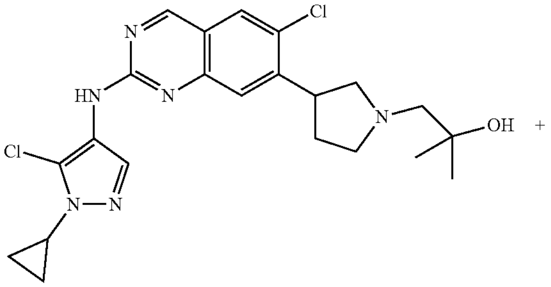

Ex-1.3

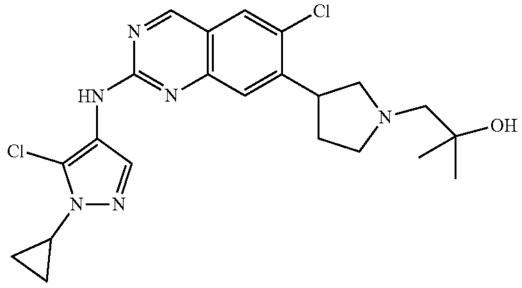

Ex-1.4 tert-butyl 3-(6-chloro-2-((5-chloro-1-cyclopropyl-1H-pyrazol-4-yl)amino)quinazolin-7-yl)pyrrolidine-1-carboxylate (144)

A 20-mL scintillation vial was charged with 7-bromo-6-chloro-N-(5-chloro-1-cyclopropyl-1H-pyrazol-4-yl)quinazolin-2-amine 12 (100 mg, 0.251 mmol), tert-butyl 3-iodopyrrolidine-1-carboxylate (149 mg, 0.501 mmol), picolinimidamide hydrochloride (12 mg, 0.075 mmol), $NiCl_2$.dme (17 mg, 0.075 mmol), manganese (28 mg, 0.501 mmol) and TBAI (93 mg, 0.251 mmol) under inert atmosphere. DMA (2 mL) was added, and the resultant mixture was stirred at 35° C. for 7 h. The reaction was quenched with sat. aq. $NH_4Cl$ (20 mL) and extracted with EtOAc (3×10 mL). The combined organic phases were washed with brine (20 mL), dried over $Na_2SO_4$, filtered, and the solvent removed from the collected filtrate under reduced pressure. The resultant crude 144 was used in the next step without further purification.

6-chloro-N-(5-chloro-1-cyclopropyl-1H-pyrazol-4-yl)-7-(pyrrolidin-3-yl)quinazolin-2-amine (145)

A 20-mL scintillation vial was charged with tert-butyl 3-(6-chloro-2-((5-chloro-1-cyclopropyl-1H-pyrazol-4-yl) amino)quinazolin-7-yl)pyrrolidine-1-carboxylate 144 (crude from previous step) under inert atmosphere. DCM (5 mL), then TFA (1 mL) were added, and the resultant mixture was stirred at RT for 5 hrs. The reaction was quenched using sat. aq. $NaHCO_3$ (20 mL), the phases were separated, and the aqueous phase extracted with EtOAc (3×20 mL). The combined organic phases were washed with brine (50 mL), dried over $Na_2SO_4$, filtered, and the solvent removed from the collected filtrate under reduced pressure. The resultant crude residue was purified by reversed phase HPLC, eluting with water (0.1% TFA)-MeCN to afford the title compound 145.

(S) or (R) 1-(3-(6-chloro-2-((1-cyclopropyl-1H-pyrazol-4-yl)amino)quinazolin-7-yl)pyrrolidin-1-yl)-2-methylpropan-2-ol (Ex-1.3 and Ex-1.4)

A 5-mL microwave vial was charged with (S) and (R) 6-chloro-N-(5-chloro-1-cyclopropyl-1H-pyrazol-4-yl)-7-(pyrrolidin-3-yl)quinazolin-2-amine 145 (30 mg, 0.077 mmol), DIPEA (27 μL, 0.154 mmol) and 2,2-dimethyloxirane (0.103 mL, 1.156 mmol) under inert atmosphere. EtOH (1 mL) was added, and the vial was sealed and heated to 100° C. with stirring under microwave irradiation for 1 hr. Upon cooling, the solvent was removed under reduced pressure. The resultant crude residue was purified by reversed phase HPLC, eluting with water (0.1% TFA)-MeCN to afford the racemic title compound 146 in pure form. The racemic material could be resolved to its component enantiomers by chiral preparative SFC(Column & dimensions: DAICEL CHIRALPAK AD, 250 mm×30 mm; Mobile phase A: $CO_2$; Mobile phase B: 0.1% $NH_3.H_2O$ IPA) to afford the title compounds Ex-1.3 (tR=0.90 min) and Ex-1.4 (tR=1.83 min). MS (ESI): m/z calc'd for $C_{22}H_{27}C_{12}N_6O$ $[M+H]^+$: 461, found 461; $^1H$ NMR (400 MHz, $CDCl_3$, 25° C.) δ: 8.96 (s, 1H), 8.24 (br s, 1H), 7.74 (s, 1H), 7.71 (s, 1H), 6.80 (s, 1H), 3.92-3.84 (m, 1H), 3.50-3.44 (m, 1H), 3.27-3.22 (m, 1H), 3.07-2.96 (m, 3H), 2.93-2.87 (m, 1H), 2.64-2.56 (m, 2H), 2.45-2.36 (m, 1H), 2.02-1.94 (m, 1H), 1.26-1.21 (m, 8H), 1.13-1.08 (m, 2H). MS (ESI): m/z calc'd for $C_{22}H_{27}C_{12}N_6O$ $[M+H]^+$: 461, found 461; $^1H$ NMR (400 MHz, $CDCl_3$, 25° C.) δ: 8.96 (s, 1H), 8.24 (br s, 1H), 7.74 (s, 1H), 7.71 (s, 1H), 6.80 (br s, 1H), 3.94-3.83 (m, 1H), 3.47 (s, 1H), 3.28-3.21 (m, 1H), 3.08-2.95 (m, 3H), 2.91 (m, 1H), 2.64-2.54 (m, 2H), 2.44-2.36 (m, 1H), 2.02-1.93 (m, 1H), 1.25-1.22 (m, 8H), 1.13-1.07 (m, 2H).

Preparation of Examples 1.5 and 1.6

Scheme 46. Synthesis of (1R,2S) or (1R,2R) or (1S,2S) or (1S,2R) 2-(4-(6-chloro-2-((1-cyclopropyl-5-methyl-1H-pyrazol-4-yl)amino)quinazolin-7-yl)piperidin-1-yl)cyclobutan-1-ol

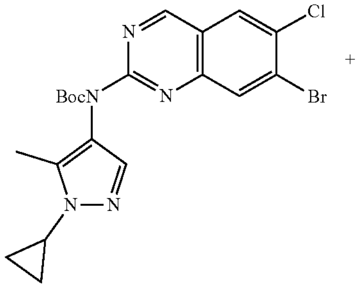

10

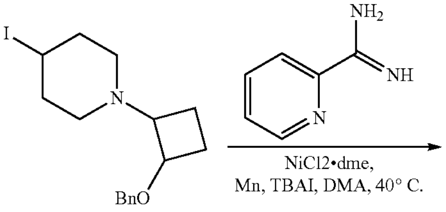

148

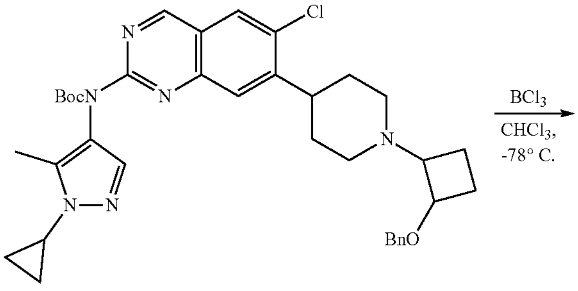

147

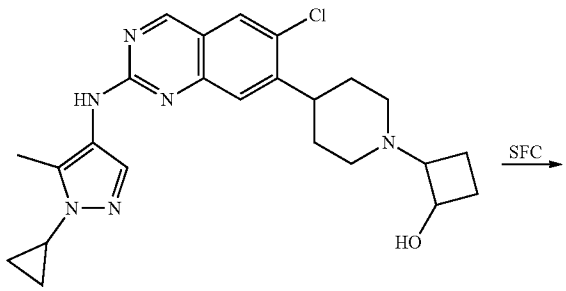

149

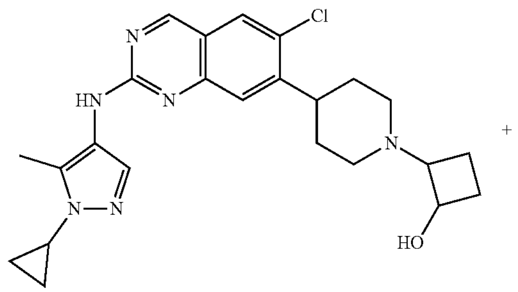

Ex-1.5

-continued

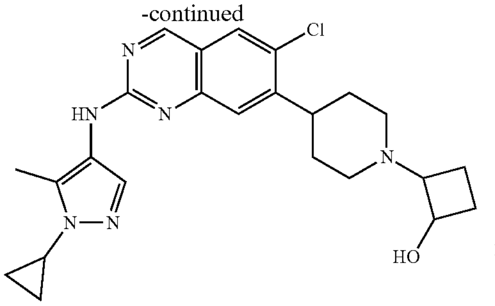

Ex-1.6 tert-butyl (7-(1-(2-(benzyloxy)cyclobutyl)piperidin-4-yl)-6-chloroquinazolin-2-yl)(1-cyclopropyl-5-methyl-1H-pyrazol-4-yl)carbamate (147)

Starting 1-(2-(benzyloxy)cyclobutyl)-4-iodopiperidine 148 was prepared using amine 27 and the corresponding ketone in accordance with previously described procedures (vide supra). A 4-dram vial was charged with pyridine-2-carboximidamide, HCl (43 mg, 0.27 mmol) and $NiCl_2$dme (60 mg, 0.27 mmol) under inert atmosphere. MeCN (2 mL) was added, and the mixture was stirred at RT under inert atmosphere. A separate 20-mL scintillation vial was charged with intermediate 10 (520 mg, 1.09 mmol), intermediate 148 (605 mg, 1.63 mmol), zinc (149 mg, 2.28 mmol), and tetrabutylammonium iodide (602 mg, 1.63 mmol) under inert atmosphere. MeCN (3.5 mL) was added and the mixture was stirred vigorously. The nickel-ligand mixture was then transferred to the stirring reagents under inert atmosphere, and the reaction was stirred at RT for 3 hrs. The mixture was filtered, and solvent was removed from the collected filtrate under reduced pressure. The crude residue was subjected to purification by flash chromatography over silica gel (0-70% EtOAc/hexanes) to afford the title compound 147.

(1R,2S) or (1R,2R) or (1S,2S) or (1S,2R) 2-(4-(6-chloro-2-((1-cyclopropyl-5-methyl-1H-pyrazol-4-yl)amino)quinazolin-7-yl)piperidin-1-yl)cyclobutan-1-ol (Ex-1.5 and Ex-1.6)

A 30 mL scintillation vial was charged with intermediate 147 (200 mg, 0.311 mmol) under inert atmosphere. Chloroform (1.5 mL) was added, and to the stirring mixture at −78° C. was added boron trichloride (1 M in DCM, 620 μL, 0.62 mmol). The resultant mixture was stirred at −78° C. for 6 hrs. At 6 hrs, the reaction was diluted with DCM (25 mL) and quenched by dropwise addition of sat. aq. $NaHCO_3$(25 mL). The phases were separated and the aqueous phase was extracted with DCM (3×25 mL). The combined organic phases were washed with $H_2O$(50 mL), dried over anhydrous $Na_2SO_4$, filtered, and solvent was removed from the collected filtrate under reduced pressure. The resultant crude residue was subjected to purification by silica gel chromatography (0-100% 3:1 EtOAc:EtOH in hexanes) to afford the racemic title compound 149. The racemic material could be resolved to its component enantiomers by chiral preparative SFC(Column & dimensions: CCA F4, 21 mm×250 mm; Mobile phase A: $CO_2$; Mobile phase B: MeOH with 0.1% $NH_4OH$) to afford Ex-1.5 (tR=2.6 min) and Ex-1.6 (tR=3.6 min). MS (ESI) m/z calc'd for $C_{23}H_{28}ClN_6O_2$ [M+H]+: 454, found 454; $^1H$ NMR (400 MHz, DMSO-$d_6$, 25° C.) δ: 9.15

(s, 1H), 9.10 (s, 1H), 8.01 (s, 1H), 7.71 (s, 1H), 7.38 (s, 1H), 4.21 (s, 1H), 3.50 (m, 2H), 2.30 (s, 3H), 2.17-1.80 (m, 6H), 1.49 (m, 2H), 1.34-1.09 (m, 2H), 1.07-0.92 (m, 5H), 0.82 (m, 1H). MS (ESI) m/z calc'd for $C_{23}H_{28}ClN_6O_2$ [M+H]+: 454, found 454; $^1H$ NMR (400 MHz, DMSO-$d_6$, 25° C.) δ: 9.15 (s, 1H), 9.10 (s, 1H), 8.01 (s, 1H), 7.71 (s, 1H), 7.38 (s, 1H), 4.21 (s, 1H), 3.50 (m, 2H), 2.30 (s, 3H), 2.17-1.80 (m, 6H), 1.49 (m, 2H), 1.34-1.09 (m, 2H), 1.07-0.92 (m, 5H), 0.82 (m, 1H).

Scheme 47. Synthesis of (3R,4R)- or (3S,4S)- 4-(4-(6-chloro-2-((5-chloro-1-cyclopropyl-1H-pyrazol-4-yl)amino)quinazolin-7-yl)piperidin-1-yl)-4-methyltetrahydrofuran-3-ol

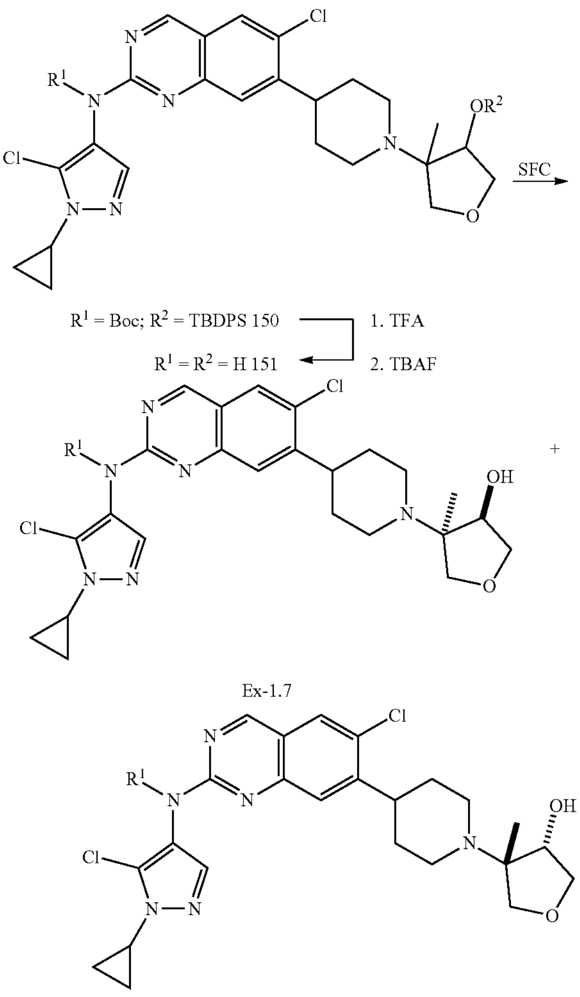

Ex-1.7

Ex-1.8

Synthesis of (3R,4R)- or (3S,4S)-4-(4-(6-chloro-2-((5-chloro-1-cyclopropyl-1H-pyrazol-4-yl)amino)quinazolin-7-yl)piperidin-1-yl)-4-methyltetrahydrofuran-3-ol (Ex-1.7 and Ex-1.8)

Starting tert-butyl(7-(1-(4-((tert-butyldiphenylsilyl)oxy)-3-methyltetrahydrofuran-3-yl)piperidin-4-yl)-6-chloroquinazolin-2-yl)(5-chloro-1-cyclopropyl-1H-pyrazol-4-yl)carbamate 150 was prepared by the same method used for the synthesis of 147, substituting intermediates 12 and 29 as starting materials. A 20-mL scintillation vial was charged with 150 (148 mg, 0.176 mmol) under inert atmosphere. DCM (2 mL) was added, and to the resultant mixture at RT was added TFA (203 μL, 2.64 mmol). The reaction was allowed to stir overnight. Volatiles were removed under reduced pressure to afford a residue, which was carried directly on to the subsequent step. The residue was dissolved in THF (3 mL), and to the stirring mixture at RT was added TBAF (1 M in THF, 352 μL, 0.352 mmol). The resultant mixture was stirred overnight. Volatiles were removed under reduced pressure to give a residue, which was subjected to purification by flash chromatography over silica gel (0-10% MeOH/DCM). The resultant material was further purified by reversed phase HPLC, eluting with water (0.1% TFA)-MeCN to afford the racemic title compound 151. The racemic material could be resolved to its component enantiomers by chiral preparative SFC (Column & dimensions: Lux-3, 21 mm×250 mm; Mobile phase A: $CO_2$; Mobile phase B: MeOH with 0.1% $NH_4OH$) to afford Ex-1.7 (tR=4.3 min) and Ex-1.8 (tR=6.3 min). MS (ESI) m/z calc'd for $C_{24}H_{29}Cl_2N_6O_2$ [M+H]+: 503, found 503; $^1$H NMR (500 MHz, DMSO-$d_6$, 25° C.) δ: 9.18 (s, overlap, 2H), 8.02 (s, 1H), 7.89 (br s, 1H), 7.52 (s, 1H), 4.53 (m, 1H), 4.36 (m, 1H), 3.96 (m, 1H), 3.78 (m, 1H), 3.71 (m, 1H), 3.61 (m, 2H), 3.54 (m, 1H), 3.17 (m, 1H), 3.00 (m, 1H), 2.83 (m, 1H), 2.40 (m, 1H), 1.85 (m, overlap, 4H), 1.2-0.8 (m, overlap, 7H). MS (ESI) m/z calc'd for $C_{24}H_{29}Cl_2N_6O_2$ [M+H]+: 503, found 503; $^1$H NMR (500 MHz, DMSO-$d_6$, 25° C.) δ: 9.18 (s, overlap, 2H), 8.02 (s, 1H), 7.89 (br s, 1H), 7.52 (s, 1H), 4.53 (m, 1H), 4.36 (m, 1H), 3.96 (m, 1H), 3.78 (m, 1H), 3.71 (m, 1H), 3.61 (m, 2H), 3.54 (m, 1H), 3.17 (m, 1H), 3.00 (m, 1H), 2.83 (m, 1H), 2.40 (m, 1H), 1.85 (m, overlap, 4H), 1.2-0.8 (m, overlap, 7H).

Compounds in Table 2 below were prepared in accordance with the synthetic sequence illustrated in General Scheme 2 and Scheme 45 using the corresponding starting materials.

TABLE 2

| Ex | Structure | Name | Exact Mass [M + H]$^+$ |
|---|---|---|---|
| Ex-1.9 | 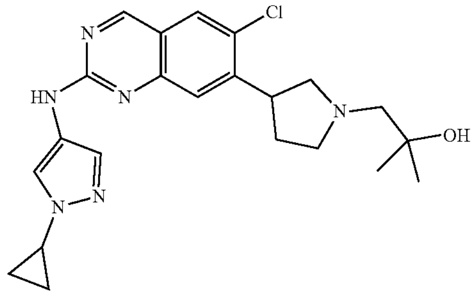 [SMILES: CC(C)(O)CN1CCC(c2cc3nc(Nc4cnn(C5CC5)c4)ncc3cc2Cl)C1] | (S) or (R) 1-(3-{6-chloro-2-[(1-cyclopropyl-1H-pyrazol-4-yl)amino]quinazolin-7-yl}pyrrolidin-1-yl)-2-methylpropan-2-ol | Calc'd 427, found 427 |
| Ex-1.10 | 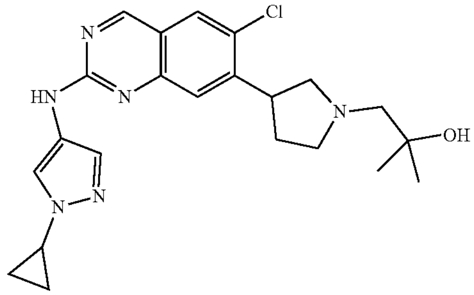 [SMILES: CC(C)(O)CN1CCC(c2cc3nc(Nc4cnn(C5CC5)c4)ncc3cc2Cl)C1] | (S) or (R) 1-(3-{6-chloro-2-[(1-cyclopropyl-1H-pyrazol-4-yl)amino]quinazolin-7-yl}pyrrolidin-1-yl)-2-methylpropan-2-ol | Calc'd 427, found 427 |
| Ex-1.11 | 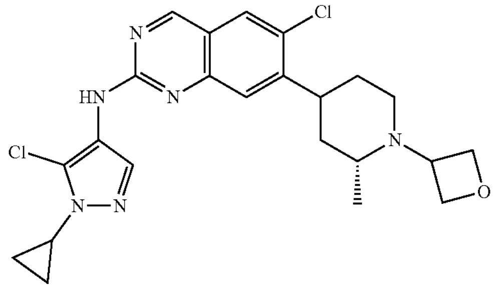 [SMILES: C[C@@H]1CC(c2cc3nc(Nc4cnn(C5CC5)c4Cl)ncc3cc2Cl)CCN1C1COC1] | (S) or (R) 6-chloro-N-(5-chloro-1-cyclopropyl-1H-pyrazol-4-yl)-7-(2-methyl-1-(oxetan-3-yl)piperidin-4-yl)quinazolin-2-amine | Calc'd 473, found 473 |

TABLE 2-continued

| Ex | Structure | Name | Exact Mass [M + H]+ |
|---|---|---|---|
| Ex-1.12 | 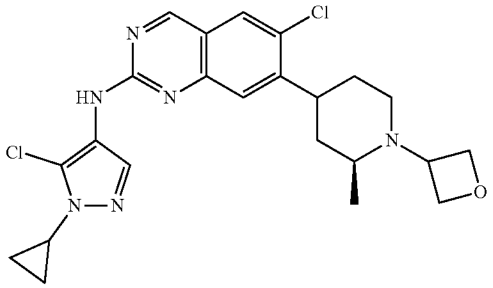 [SMILES: C[C@H]1CC(c2cc3nc(Nc4cnn(C5CC5)c4Cl)ncc3cc2Cl)CCN1C1COC1] | (S) or (R) 6-chloro-N-(5-chloro-1-cyclopropyl-1H-pyrazol-4-yl)-7-(2-methyl-1-(oxetan-3-yl)piperidin-4-yl)quinazolin-2-amine | Calc'd 473, found 473 |
| Ex-1.13 | 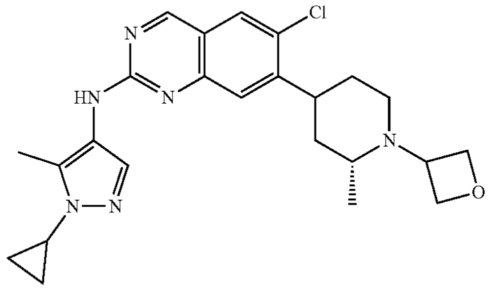 [SMILES: Cc1c(Nc2ncc3cc(Cl)c(C4CCN(C5COC5)[C@H](C)C4)cc3n2)cnn1C1CC1] | (S) or (R) 6-chloro-N-(1-cyclopropyl-5-methyl-1H-pyrazol-4-yl)-7-(2-methyl-1-(oxetan-3-yl)piperidin-4-yl)quinazolin-2-amine | Calc'd 453, found 453 |
| Ex-1.14 | 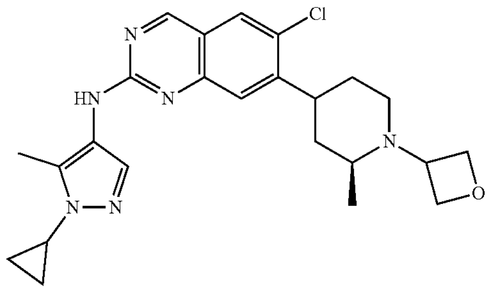 [SMILES: Cc1c(Nc2ncc3cc(Cl)c(C4CCN(C5COC5)[C@@H](C)C4)cc3n2)cnn1C1CC1] | (S) or (R) 6-chloro-N-(1-cyclopropyl-5-methyl-1H-pyrazol-4-yl)-7-(2-methyl-1-(oxetan-3-yl)piperidin-4-yl)quinazolin-2-amine | Calc'd 453, found 453 |
| Ex-1.15 | 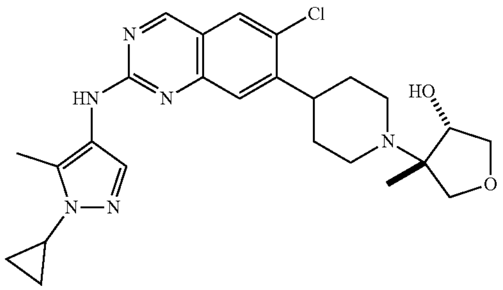 [SMILES: Cc1c(Nc2ncc3cc(Cl)c(C4CCN([C@@]5(C)COC[C@H]5O)CC4)cc3n2)cnn1C1CC1] | (3S,4S) or (3R,4R) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol | Calc'd 483, found 483 |
| Ex-1.16 | 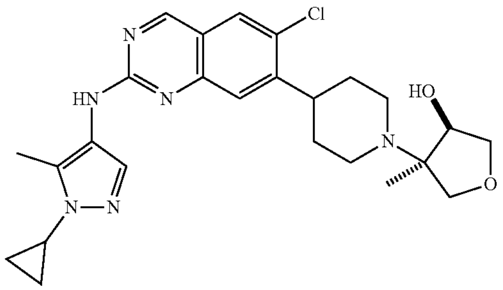 [SMILES: Cc1c(Nc2ncc3cc(Cl)c(C4CCN([C@]5(C)COC[C@@H]5O)CC4)cc3n2)cnn1C1CC1] | (3S,4S) or (3R,4R) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol | Calc'd 483, found 483 |

TABLE 2-continued

| Ex | Structure | Name | Exact Mass [M + H]+ |
|---|---|---|---|
| Ex-1.17 | 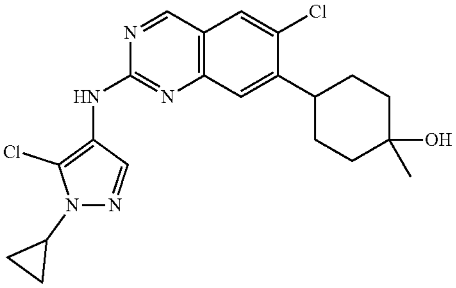 [SMILES: CC1(O)CCC(c2cc3nc(Nc4cnn(C5CC5)c4Cl)ncc3cc2Cl)CC1] | cis-or trans-4-(6-chloro-2-((5-chloro-1-cyclopropyl-1H-pyrazol-4-yl)amino)quinazolin-7-yl)-1-methylcyclohexan-1-ol | Calc'd 432, found 432 |
| Ex-1.18 | 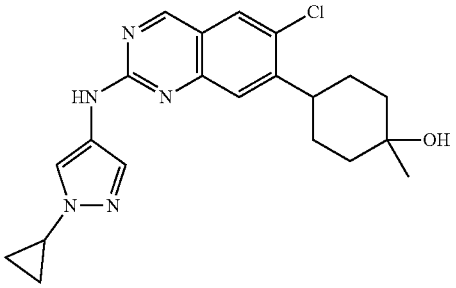 [SMILES: CC1(O)CCC(c2cc3nc(Nc4cnn(C5CC5)c4)ncc3cc2Cl)CC1] | cis-or trans-4-(6-chloro-2-((1-cyclopropyl-1H-pyrazol-4-yl)amino)quinazolin-7-yl)-1-methylcyclohexan-1-ol | Calc'd 398, found 398 |
| Ex-1.19 | 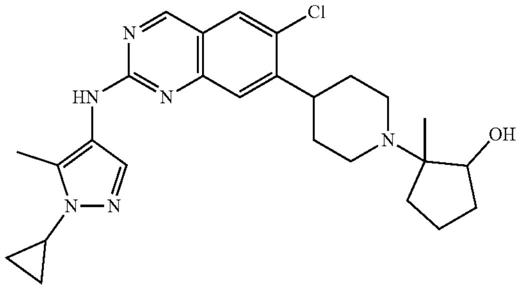 [SMILES: Cc1c(Nc2ncc3cc(Cl)c(C4CCN(C5(C)CCCC5O)CC4)cc3n2)cnn1C1CC1] | (1R,2S) or (1S,2R) or (1S,2S) or (1R,2R) 2-(4-(6-chloro-2-((1-cyclopropyl-5-methyl-1H-pyrazol-4-yl)amino)quinazolin-7-yl)piperidin-1-yl)-2-methylcyclopentan-1-ol | Calc'd 481, found 481 |
| Ex-1.20 | 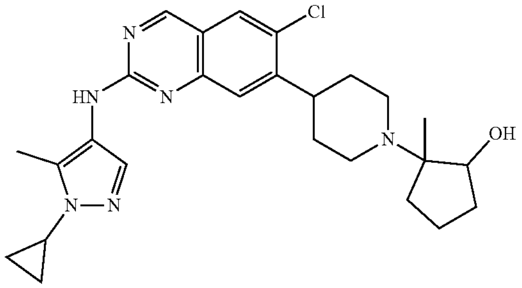 [SMILES: Cc1c(Nc2ncc3cc(Cl)c(C4CCN(C5(C)CCCC5O)CC4)cc3n2)cnn1C1CC1] | (1R,2S) or (1S,2R) or (1S,2S) or (1R,2R) 2-(4-(6-chloro-2-((1-cyclopropyl-5-methyl-1H-pyrazol-4-yl)amino)quinazolin-7-yl)piperidin-1-yl)-2-methylcyclopentan-1-ol | Calc'd 481, found 481 |
| Ex-1.21 | 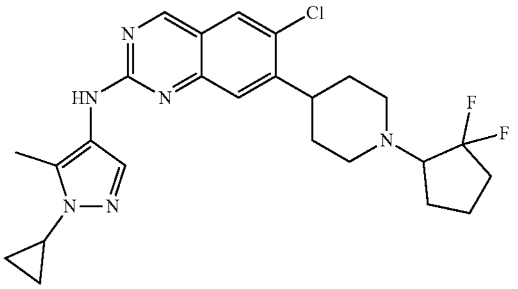 [SMILES: Cc1c(Nc2ncc3cc(Cl)c(C4CCN(C5CCCC5(F)F)CC4)cc3n2)cnn1C1CC1] | (S) or (R) 6-chloro-N-(1-cyclopropyl-5-methyl-1H-pyrazol-4-yl)-7-[1-(2,2-difluorocyclopentyl)piperidin-4-yl]quinazolin-2-amine | Calc'd 487, found 487 |

TABLE 2-continued

| Ex | Structure | Name | Exact Mass [M + H]⁺ |
|---|---|---|---|
| Ex-1.22 | 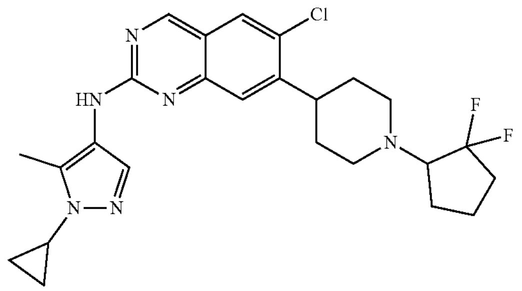 [SMILES: Cc1c(Nc2ncc3cc(Cl)c(C4CCN(C5CCCC5(F)F)CC4)cc3n2)cnn1C1CC1] | (S) or (R) 6-chloro-N-(1-cyclopropyl-5-methyl-1H-pyrazol-4-yl)-7-[1-(2,2-difluorocyclopentyl)piperidin-4-yl]quinazolin-2-amine | Calc'd 487, found 487 |
| Ex-1.23 | 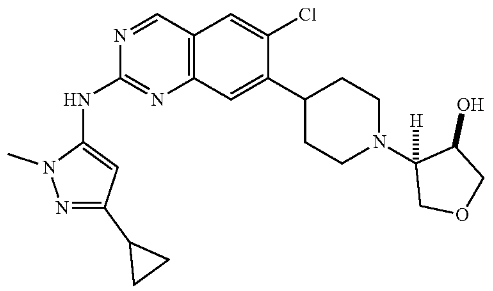 [SMILES: Cn1nc(C2CC2)cc1Nc1ncc2cc(Cl)c(C3CCN([C@@H]4COC[C@@H]4O)CC3)cc2n1] | (3S,4S) or (3R,4R) 4-(4-{6-chloro-2-[(3-cyclopropyl-1-methyl-1H-pyrazol-5-yl)amino]quinazolin-7-yl}piperidin-1-yl)oxolan-3-ol | Calc'd 469, found 469 |
| Ex-1.24 | 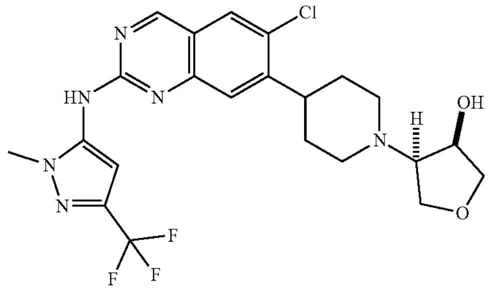 [SMILES: Cn1nc(C(F)(F)F)cc1Nc1ncc2cc(Cl)c(C3CCN([C@@H]4COC[C@@H]4O)CC3)cc2n1] | (3S,4S) or (3R,4R) 4-[4-(6-chloro-2-{[1-methyl-3-(trifluoromethyl)-1H-pyrazol-5-yl]amino}quinazolin-7-yl)piperidin-1-yl]oxolan-3-ol | Calc'd 497, found 497 |
| Ex-1.25 | 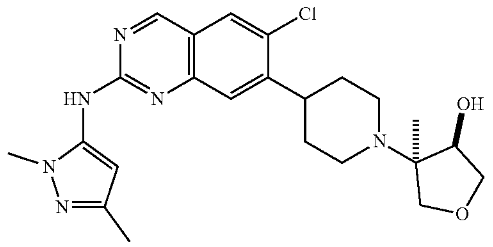 [SMILES: Cc1cc(Nc2ncc3cc(Cl)c(C4CCN([C@]5(C)COC[C@@H]5O)CC4)cc3n2)n(C)n1] | (3S,4S) or (3R,4R) 4-(4-{6-chloro-2-[(1,3-dimethyl-1H-pyrazol-5-yl)amino]quinazolin-7-yl}piperidin-1-yl)-4-methyloxolan-3-ol | Calc'd 457, found 457 |
| Ex-1.26 | 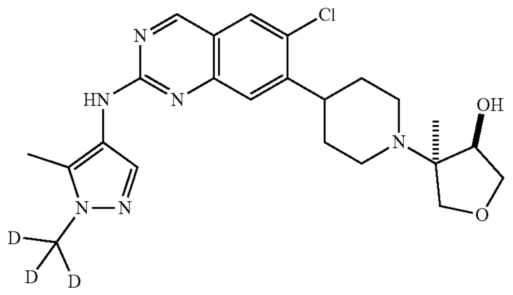 [SMILES: [2H]C([2H])([2H])n1ncc(Nc2ncc3cc(Cl)c(C4CCN([C@]5(C)COC[C@@H]5O)CC4)cc3n2)c1C] | (3S,4S) or (3R,4R)-4-(4-(6-chloro-2-((5-methyl-1-(methyl-d3)-1H-pyrazol-4-yl)amino)quinazolin-7-yl)piperidin-1-yl)-4-methyltetrahydrofuran-3-ol | Calc'd 460, found 460 |

TABLE 2-continued

| Ex | Structure | Name | Exact Mass [M + H]$^+$ |
|---|---|---|---|
| Ex-1.27 | 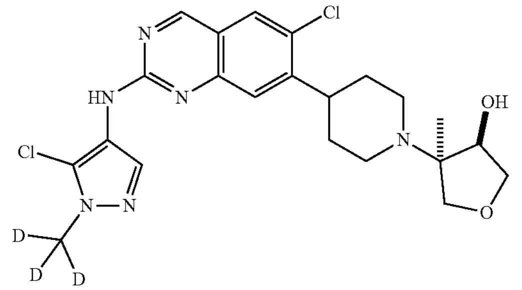 [SMILES: [2H]C([2H])([2H])n1ncc(Nc2ncc3cc(Cl)c(C4CCN([C@]5(C)COC[C@@H]5O)CC4)cc3n2)c1Cl] | (3S,4S) or (3R,4R)-4-(4-(6-chloro-2-((5-chloro-1-(methyl-d3)-1H-pyrazol-4-yl)amino)quinazolin-7-yl)piperidin-1-yl)-4-methyltetrahydrofuran-3-ol | Calc'd 480, found 480 |
| Ex-1.28 | 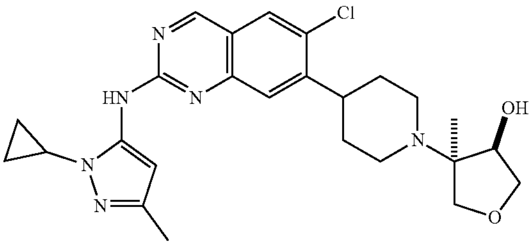 [SMILES: Cc1cc(Nc2ncc3cc(Cl)c(C4CCN([C@]5(C)COC[C@@H]5O)CC4)cc3n2)n(C2CC2)n1] | (3S,4S) or (3R,4R) 4-(4-{6-chloro-2-[(1-cyclopropyl-3-methyl-1H-pyrazol-5-yl)amino]quinazolin-7-yl}piperidin-1-yl)-4-methyloxolan-3-ol | Calc'd 483, found 483 |

General Scheme 3

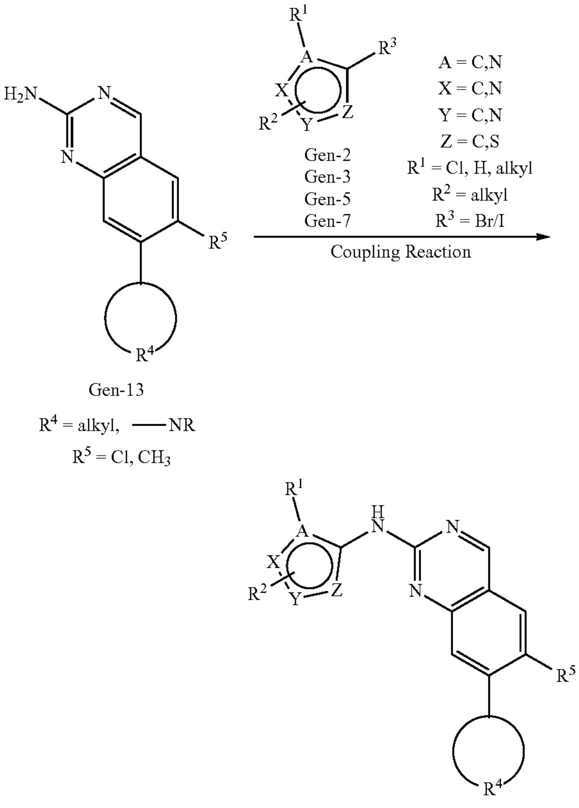

Gen-14

In General Scheme 3, intermediates of type Gen-13, prepared as described in Scheme 8, Scheme 19, Scheme 20, or alternatively by reaction of intermediates 5 or 14 with intermediates of type Gen-10 or Gen-11 under reductive nickel catalysis as exemplified in General Scheme 2, Scheme 44, and Scheme 45, could be coupled with commercially available or synthetically prepared (hetero)aryl (pseudo)halides Gen-2/Gen-3/Gen-5/Gen-7 using standard palladium- or copper-catalyzed amine acylation methodology to afford elaborated compounds of the form Gen-14. The representative compounds are described in more detail below.

Preparation of Examples 2.1 and 2.2

Scheme 48

Synthesis of (3S,4S) or (3R,4R) 1-(5-chloro-4-((6-chloro-7-(3-fluoro-1-(3-methyloxetan-3-yl)piperidin-4-yl)quinazolin-2-yl)amino)-1H-pyrazol-1-yl)-2-methylpropan-2-ol

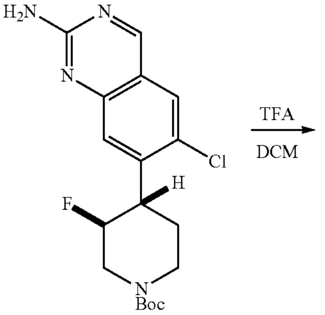

47

-continued

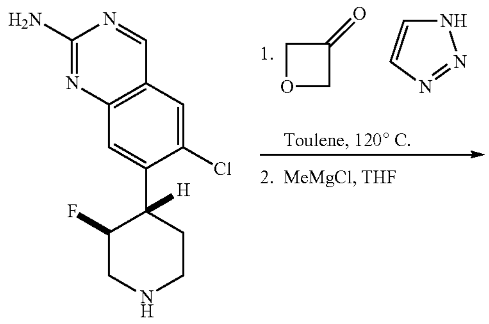

152

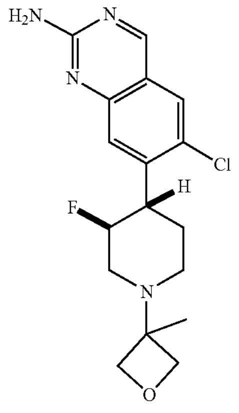

+

153

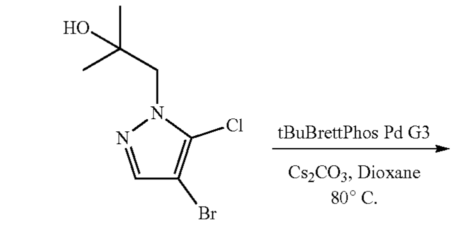

61

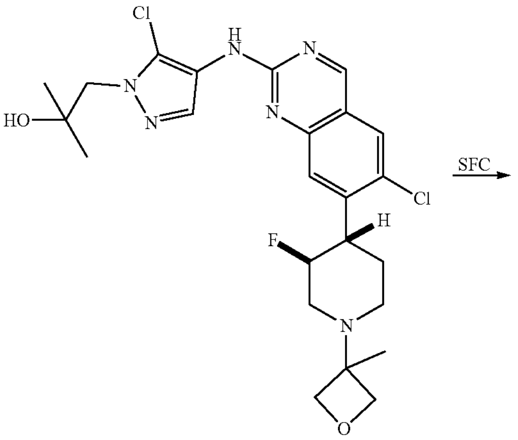

154

-continued

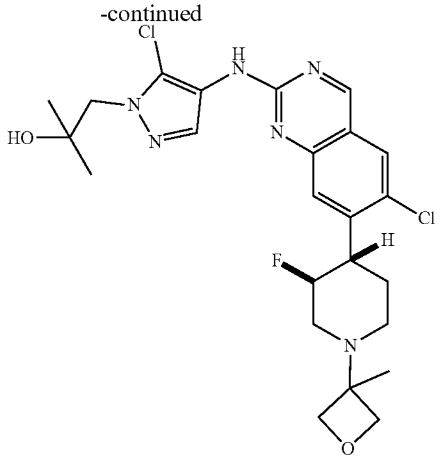

Ex-2.1

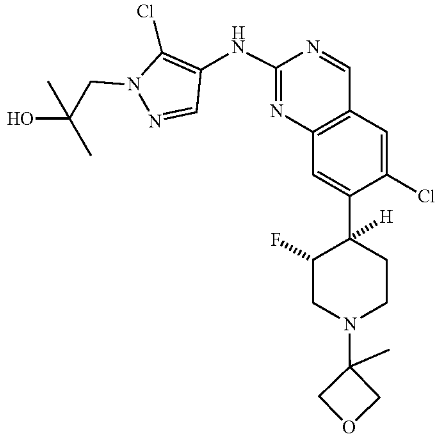

Ex-2.2

6-chloro-7-(3-fluoropiperidin-4-yl)quinazolin-2-amine (152)

A 100 mL round-bottom flask was charged with tert-butyl 4-(2-amino-6-chloroquinazolin-7-yl)-3-fluoropiperidine-1-carboxylate 47 (2.00 g, 5.25 mmol). DCM (52.5 mL) was added, and to the stirring mixture at RT was added TFA (4.05 mL, 52.5 mmol). The resultant mixture was stirred at 20° C. for 3 hrs. The reaction mixture was poured into an Erlenmeyer flask containing sat. aq. $NaHCO_3$ and a light yellow solid was precipitated. The solid was filtered and washed with deionized water. The precipitate was dried under high vacuum overnight to yield 6-chloro-7-(3-fluoropiperidin-4-yl)quinazolin-2-amine 152. MS (ESI): m/z calc'd for $C_{13}H_{15}ClFN_4$ $[M+H]^+$: 281, found 281.

6-chloro-7-(3-fluoro-1-(3-methyloxetan-3-yl)piperidin-4-yl)quinazolin-2-amine (153)

A 30 mL scintillation vial was charged with 6-chloro-7-(3-fluoropiperidin-4-yl)quinazolin-2-amine 152 (100 mg, 0.356 mmol) under inert atmosphere. Toluene (1.43 mL) was added, and to the stirring mixture at RT was added 1H-1,2,3-triazole (23 μL, 0.392 mmol) and oxetan-3-one (25 μL, 0.427 mmol). The resultant mixture was stirred at 120° C. for 2 hrs. A separate 30 mL scintillation vial containing methylmagnesium chloride (3.0 M in THF) (593 μL, 1.78 mmol) was cooled to 0° C. under inert atmosphere. On cooling to RT, the above reaction mixture was transferred via syringe to the MeMgCl-containing vial under inert atmosphere. After 5 minutes the ice bath was removed, and the mixture allowed to warm to RT. After 2 hrs, the reaction was quenched by the addition of sat. aq. $NH_4Cl$ (50 mL). The phases were separated, and the aqueous phase extracted with EtOAc (3×25 mL). The combined organic phases were washed with $H_2O$ (50 mL), dried over $Na_2SO_4$, and the solvent removed under reduced pressure. The resultant crude residue was subjected to purification by flash chromatography over silica gel (MeOH/DCM, 0-30%) to afford the title compound 153. MS (ESI): m/z calc'd for $C_{17}H_{21}ClFN_4O$ $[M+H]^+$: 351, found 351.

(3S,4S) or (3R,4R) 1-(5-chloro-4-((6-chloro-7-(3-fluoro-1-(3-methyloxetan-3-yl)piperidin-4-yl)quinazolin-2-yl)amino)-1H-pyrazol-1-yl)-2-methylpropan-2-ol (Ex-2.1 and Ex-2.2)

A 20 mL scintillation vial was charged with 6-chloro-7-(3-fluoro-1-(3-methyloxetan-3-yl)piperidin-4-yl)quinazolin-2-amine 153 (54 mg, 0.154 mmol), 1-(4-bromo-5-chloro-1H-pyrazol-1-yl)-2-methylpropan-2-ol 61 (98 mg, 0.385 mmol), tBuBrettPhos Pd G3 (66 mg, 0.077 mmol), and cesium carbonate (251 mg, 0.770 mmol) under inert atmosphere. Dioxane (770 μL) was added, and the resultant mixture was heated to 80° C. and maintained at this temperature with stirring for 12 hrs. On cooling to RT, the crude reaction mixture was diluted in DCM and directly loaded onto a silica gel column for purification by flash chromatography (3:1 EtOAc/EtOH in Hexanes, 0-100%) to afford the racemic title compound 154. This material was then resolved into its component enantiomers by chiral preparative SFC(Column & dimensions: OJ-H, 21×250; Mobile phase A: $CO_2$; Mobile phase B: MeOH with 0.1% $NH_4OH$) to afford Ex-2.1 (tR=7.7 min) and Ex-2.2 (tR=9.1 min). MS (ESI): m/z calc'd for $C_{24}H_{30}Cl_2FN_6O_2$ $[M+H]^+$: 523, found 523; $^1H$ NMR (400 MHz, DMSO-$d_6$, 25° C.) δ: 9.23 (s, 1H), 9.21 (s, 1H), 8.12 (s, 1H), 8.06 (s, 1H), 7.76 (s, 1H) 5.09 (m, 1H), 4.75 (s, 1H), 4.47 (d, J=4 Hz, 1H), 4.42 (d, J=4 Hz, 1H), 4.16 (t, J=8 Hz, 2H), 4.04 (s, 2H), 3.26 (m, 1H), 3.01 (m, 1H), 2.57 (m, 1H), 2.22 (m, 2H), 1.94 (m, 1H), 1.66 (m, 1H), 1.34 (s, 3H), 1.16 (m, 6H). MS (ESI): m/z calc'd for $C_{24}H_{30}Cl_2FN_6O_2$ $[M+H]^+$: 523, found 523; $^1H$ NMR (400 MHz, DMSO-$d_6$, 25° C.) δ: 9.23 (s, 1H), 9.21 (s, 1H), 8.12 (s, 1H), 8.06 (s, 1H), 7.76 (s, 1H) 5.09 (m, 1H), 4.75 (s, 1H), 4.47 (d, J=4 Hz, 1H), 4.42 (d, J=4 Hz, 1H), 4.16 (t, J=8 Hz, 2H), 4.04 (s, 2H), 3.26 (m, 1H), 3.01 (m, 1H), 2.57 (m, 1H), 2.22 (m, 2H), 1.94 (m, 1H), 1.66 (m, 1H), 1.34 (s, 3H), 1.16 (m, 6H).

Preparation of Example 2.3

Scheme 49. Synthesis of 6-chloro-N-(1-(3-(methoxymethyl)bicyclo[1.1.1]pentan-1-yl)-1H-pyrazol-4-yl)-7-(1-(3-methyloxetan-3-yl)piperidin-4-yl)quinazolin-2-amine

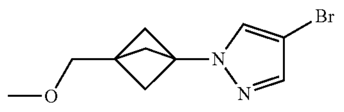

85

+

-continued

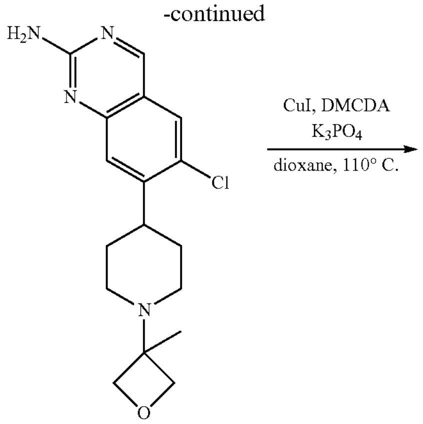

39

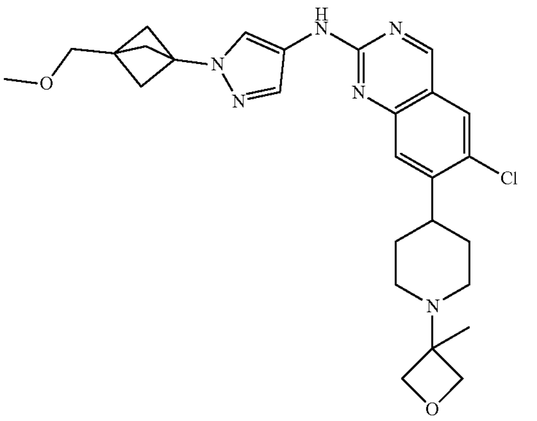

Ex-2.3

6-chloro-N-(1-(3-(methoxymethyl)bicyclo[1.1.1]pentan-1-yl)-1H-pyrazol-4-yl)-7-(1-(3-methyloxetan-3-yl)piperidin-4-yl)quinazolin-2-amine (Ex-2.3)

A 5-mL microwave vial was charged with intermediate 39 (50 mg, 0.150 mmol), copper (I) iodide (9 mg, 0.045 mmol), tribasic potassium phosphate (96 mg, 0.451 mmol), and trans-N-dimethylcyclohexane-1,2-diamine (DMCDA) (13 mg, 0.09 mmol) under inert atmosphere. Then, a solution of intermediate 85 (40 mg, 0.156 mmol) in anhydrous dioxane (1.5 mL) was added to the reaction vessel. The resultant mixture was heated to 110° C. and stirred at this temperature overnight. On cooling, the mixture was diluted with EtOAc (5 mL) and filtered, washing with additional EtOAc. Solvent was removed from the collected filtrate under reduced pressure. The crude residue was subjected to purification by flash chromatography over silica gel (0-80% 3:1 EtOAc: Ethanol in hexanes) to afford the title compound Ex-2.3. MS (ESI): m/z calc'd for $C_{27}H_{34}ClN_6O_2$ $[M+H]^+$: 509, found 509; $^1H$ NMR (500 MHz, DMSO-$d_6$, 25° C.) δ: 9.87 (s, 1H); 9.16 (s, 1H); 8.25 (s, 1H); 8.00 (s, 1H); 7.65 (s, 1H); 5.76 (s, 2H), 4.46 (d, J=6.0 Hz, 2H); 4.16 (d, J=6.0 Hz, 2H); 3.56 (s, 3H), 3.06-2.89 (m, 1H), 2.72-2.55 (m, 4H), 2.25-2.14 (m, 6H), 1.91-1.78 (m, 5H), 1.34 (s, 3H).

Preparation of Example 2.4

Scheme 50. Synthesis of (3S,4S) or (3R,3R)-(4-(4-(2-((5-chloro-1-cyclopropyl-1H-pyrazol-4-yl)amino)-6-methylquinazolin-7-yl)piperidin-1-yl)tetrahydrofuran-3-ol

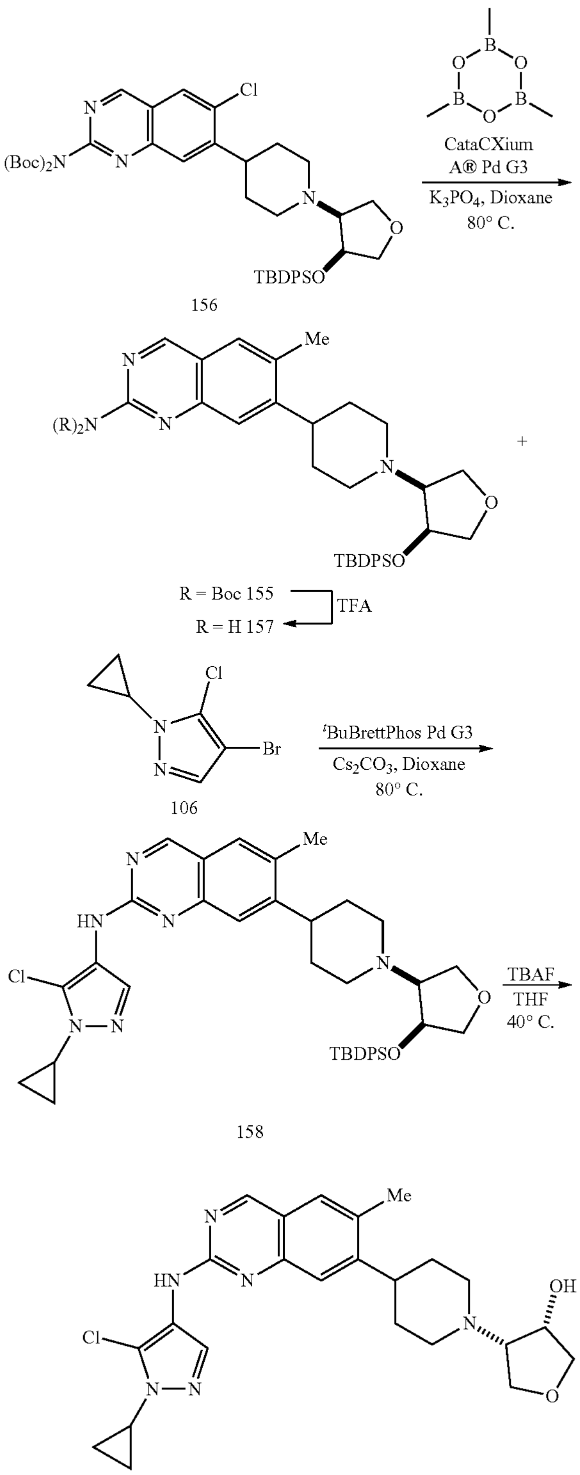

156

R = Boc 155

R = H 157

106

158

Ex-2.4

(3S,4S) or (3R,4R) N,N-bis(tert-butyloxycarbonyl)-7-(1-(4-((tert-butyldiphenylsilyl)oxy)tetrahydrofuran-3-yl)piperidin-4-yl)-6-methylquinazolin-2-amine (155)

Starting (3S,4S) or (3R,4R) 7-(1-(-4-((tert-butyldiphenylsilyl)oxy)tetrahydrofuran-3-yl)piperidin-4-yl)-6-chloroquinazolin-2-amine 156 was prepared by the same method used for the synthesis of 147, substituting intermediates 5 and 35 as starting materials. A 50-mL round-bottom flask was charged with intermediate 156 (600 mg, 0.762 mmol), cataCXium A® Pd G3 (111 mg, 0.152 mmol), and tribasic potassium phosphate (647 mg, 3.05 mmol) under inert atmosphere. Dioxane (3.8 mL) was added, and to the stirring mixture at RT was added trimethylboroxine (533 μL, 3.81 mmol). The resultant mixture was stirred at 80° C. for 16 hrs. At 16 hrs, the reaction was diluted with DCM, filtered, and solvent was removed from the collected filtrate under reduced pressure.

The resultant crude residue was subjected to purification by silica gel chromatography (0-100% 3:1 EtOAc:EtOH in hexanes) to afford the title compound 155. MS (ESI) m/z calc'd for $C_{44}H_{59}N_4O_6Si$ $[M+H]^+$: 767, found 767.

(3S,4S) or (3R,4R) 7-(1-(-4-((tert-butyldiphenylsilyl)oxy)tetrahydrofuran-3-yl)piperidin-4-yl)-6-methylquinazolin-2-amine (157)

A 20-mL microwave vial was charged with intermediate 155 (300 mg, 0.391 mmol) inert atmosphere. DCM (2 mL) was added, and to the stirring mixture at RT was added TFA (300 μL, 3.89 mmol). The resultant mixture was stirred at RT for 3 hrs. At 3 hrs, the reaction was diluted with DCM (25 mL) and quenched by dropwise addition of sat. aq. $NaHCO_3$ (25 mL). The phases were separated, and the aqueous phase was extracted with DCM (3×50 mL). The combined organic phases were washed with $H_2O$(50 mL), dried over anhydrous $Na_2SO_4$, and the solvent removed under reduced pressure to afford the title compound 157. MS (ESI) m/z calc'd for $C_{34}H_{43}N_4O_2Si$ $[M+H]^+$: 567, found 567.

(3S,4S) or (3R,4R) 7-(1-(-4-((tert-butyldiphenylsilyl)oxy)tetrahydrofuran-3-yl)piperidin-4-yl)-N-(5-chloro-1-cyclopropyl-1H-pyrazol-4-yl)-6-methylquinazolin-2-amine (158)

A 5-mL microwave vial was charged with 4-bromo-5-chloro-1-cyclopropyl-1H-pyrazole 106 (138 mg, 0.621 mmol), intermediate 157 (160 mg, 0.282 mmol), cesium carbonate (460 mg, 1.411 mmol), and tBuBrettPhos Pd G3 (72 mg, 0.085 mmol) under inert atmosphere. To the stirring mixture at RT was added dioxane (1.4 mL). The resultant mixture was stirred at 80° C. for 16 hrs. At 16 hrs, the reaction mixture was diluted in DCM, filtered, and concentrated. The resultant crude residue was subjected to purification by silica gel chromatography (0-50% 3:1 EtOAc:EtOH in hexanes) to afford the title compound 158. MS (ESI) m/z calc'd for $C_{40}H_{48}ClN_6O_2Si$ $[M+H]^+$: 707, found 707.

(3S,4S) or (3R,4R)-(4-(4-(2-((5-chloro-1-cyclopropyl-1H-pyrazol-4-yl)amino)-6-methylquinazolin-7-yl)piperidin-1-yl)tetrahydrofuran-3-ol (Ex-2.4)

A 5-mL microwave vial was charged with intermediate 158 (110 mg, 0.156 mmol) and DCM (1 mL) under inert atmosphere. To the stirring mixture at RT was added TBAF (1M in THF, 800 μL, 0.8 mmol). The resultant mixture was stirred at 40° C. for 16 hrs. At 16 hrs, the reaction mixture was concentrated. The resultant crude residue was subjected to purification by silica gel chromatography (0-70% 3:1 EtOAc:EtOH in hexanes) to afford the title compound Ex-2.4. MS (ESI) m/z calc'd for $C_{24}H_{30}ClN_6O_2$ $[M+H]^+$: 469, found 469. $^1H$ NMR (400 MHz, DMSO-$d_6$, 25° C.) δ: 9.08 (s, 1H), 8.90 (s, 1H), 7.87 (s, 1H), 7.63 (s, 1H), 7.37 (s, 1H), 4.22 (m, 2H), 3.90-3.83 (m, 2H), 3.70 (d, J=9.5 Hz, 1H), 3.61 (m, 2H), 3.18 (m, 1H), 2.82-2.65 (m, 3H), 2.42 (s, 3H), 2.33-2.26 (m, 1H), 2.19 (m, 1H), 1.86-1.80 (m, 1H), 1.76 (m, 3H), 1.11-1.05 (m, 4H)

Compounds in Table 3 below were prepared in accordance with the synthetic sequence illustrated in General Scheme 3 using the corresponding starting materials.

TABLE 3

| Ex | Structure | Name | Exact Mass $[M + H]^+$ |
|---|---|---|---|
| Ex-2.5 | 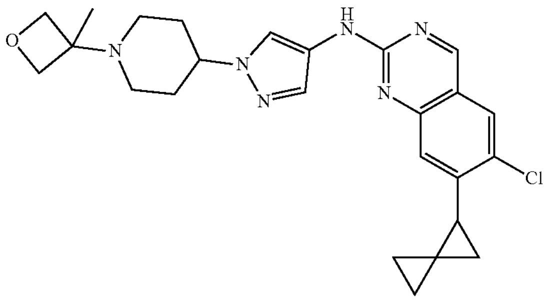 [SMILES: CC1(N2CCC(n3cc(Nc4ncc5cc(Cl)c(C6CC67CC7)cc5n4)cn3)CC2)COC1] | (S) or (R) 6-chloro-N-{1-[1-(3-methyloxetan-3-yl)piperidin-4-yl]-1H-pyrazol-4-yl}-7-(spiro[2.2]pentan-1-yl)quinazolin-2-amine | Calc'd 465, found 465 |
| Ex-2.6 | 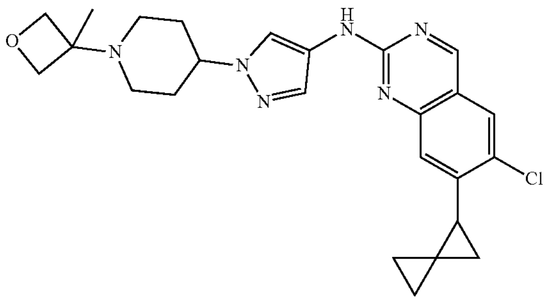 [SMILES: CC1(N2CCC(n3cc(Nc4ncc5cc(Cl)c(C6CC67CC7)cc5n4)cn3)CC2)COC1] | (S) or (R) 6-chloro-N-{1-[1-(3-methyloxetan-3-yl)piperidin-4-yl]-1H-pyrazol-4-yl}-7-(spiro[2.2]pentan-1-yl)quinazolin-2-amine | Calc'd 465, found 465 |
| Ex-2.7 | 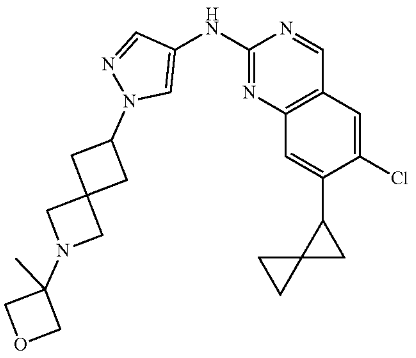 [SMILES: CC1(N2CC3(CC(n4cc(Nc5ncc6cc(Cl)c(C7CC78CC8)cc6n5)cn4)C3)C2)COC1] | (S) or (R) 6-chloro-N-{1-[2-(3-methyloxetan-3-yl)-2-azaspiro[3.3]heptan-6-yl]-1H-pyrazol-4-yl}-7-(spiro[2.2]pentan-1-yl)quinazolin-2-amine | Calc'd 477, found 477 |
| Ex-2.8 | 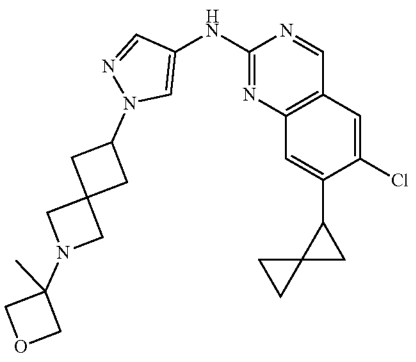 [SMILES: CC1(N2CC3(CC(n4cc(Nc5ncc6cc(Cl)c(C7CC78CC8)cc6n5)cn4)C3)C2)COC1] | (S) or (R) 6-chloro-N-{1-[2-(3-methyloxetan-3-yl)-2-azaspiro[3.3]heptan-6-yl]-1H-pyrazol-4-yl}-7-(spiro[2.2]pentan-1-yl)quinazolin-2-amine | Calc'd 477, found 477 |

TABLE 3-continued

| Ex | Structure | Name | Exact Mass [M + H]+ |
|---|---|---|---|
| Ex-2.9 | 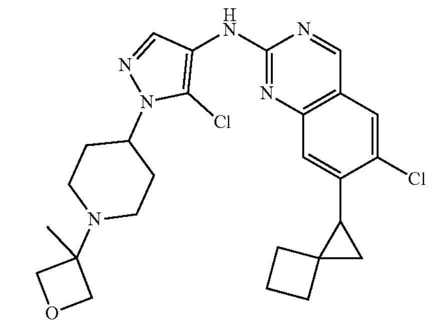 [SMILES: CC1(N2CCC(n3ncc(Nc4ncc5cc(Cl)c(C6CC67CCC7)cc5n4)c3Cl)CC2)COC1] | (S) or (R) 6-chloro-N-{5-chloro-1-[1-(3-methyloxetan-3-yl)piperidin-4-yl]-1H-pyrazol-4-yl}-7-(spiro[2.3]hexan-1-yl)quinazolin-2-amine | Calc'd 513, found 513 |
| Ex-2.10 | 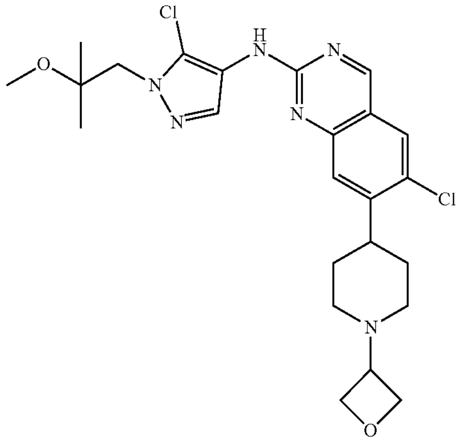 [SMILES: COC(C)(C)Cn1ncc(Nc2ncc3cc(Cl)c(C4CCN(C5COC5)CC4)cc3n2)c1Cl] | 6-chloro-N-[5-chloro-1-(2-methoxy-2-methylpropyl)-1H-pyrazol-4-yl]-7-[1-(oxetan-3-yl)piperidin-4-yl]quinazolin-2-amine | Calc'd 505, found 505 |
| Ex-2.11 | 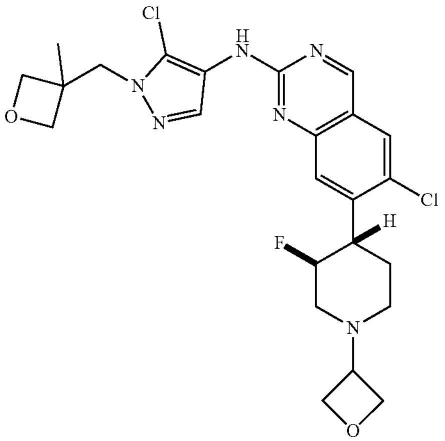 [SMILES: CC1(Cn2ncc(Nc3ncc4cc(Cl)c([C@@H]5CCN(C6COC6)C[C@H]5F)cc4n3)c2Cl)COC1] | (3S,4S) or (3R,4R) 6-chloro-N-{5-chloro-1-[(3-methyloxetan-3-yl)methyl]-1H-pyrazol-4-yl}-7-[3-fluoro-1-(oxetan-3-yl)piperidin-4-yl]quinazolin-2-amine | Calc'd 521, found 521 |

TABLE 3-continued

| Ex | Structure | Name | Exact Mass [M + H]+ |
|---|---|---|---|
| Ex-2.12 | 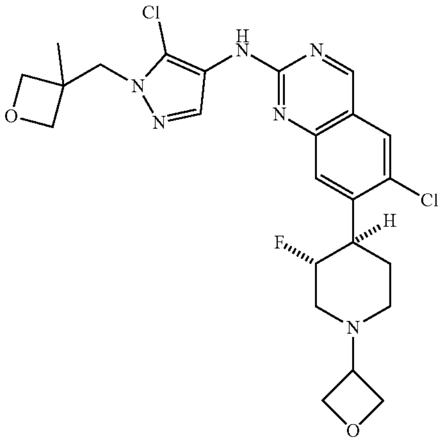 [SMILES: CC1(Cn2ncc(Nc3ncc4cc(Cl)c([C@H]5CCN(C6COC6)C[C@@H]5F)cc4n3)c2Cl)COC1] | (3S,4S) or (3R,4R) 6-chloro-N-{5-chloro-1-[(3-methyloxetan-3-yl)methyl]-1H-pyrazol-4-yl}-7-[3-fluoro-1-(oxetan-3-yl)piperidin-4-yl]quinazolin-2-amine | Calc'd 521, found 521 |
| Ex-2.13 | 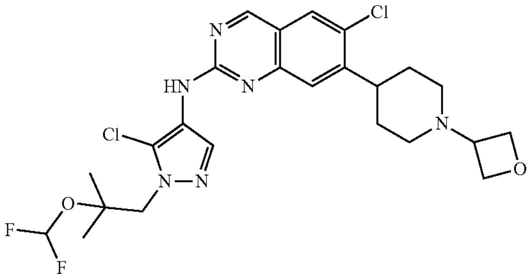 [SMILES: CC(C)(Cn1ncc(Nc2ncc3cc(Cl)c(C4CCN(C5COC5)CC4)cc3n2)c1Cl)OC(F)F] | 6-chloro-N-{5-chloro-1-[2-(difluoromethoxy)-2-methylpropyl]-1H-pyrazol-4-yl}-7-[1-(oxetan-3-yl)piperidin-4-yl]quinazolin-2-amine | Calc'd 541, found 541 |
| Ex-2.14 | 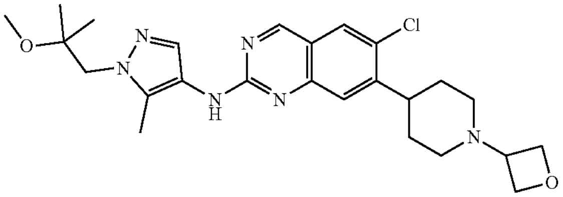 [SMILES: COC(C)(C)Cn1ncc(Nc2ncc3cc(Cl)c(C4CCN(C5COC5)CC4)cc3n2)c1C] | 6-chloro-N-[1-(2-methoxy-2-methylpropyl)-5-methyl-1H-pyrazol-4-yl]-7-[1-(oxetan-3-yl)piperidin-4-yl]quinazolin-2-amine | Calc'd 485, found 485 |
| Ex-2.15 | 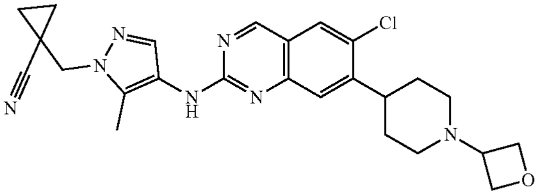 [SMILES: Cc1c(Nc2ncc3cc(Cl)c(C4CCN(C5COC5)CC4)cc3n2)cnn1CC1(C#N)CC1] | 1-{[4-({6-chloro-7-[1-(oxetan-3-yl)piperidin-4-yl]quinazolin-2-yl}amino)-5-methyl-1H-pyrazol-1-yl]methyl}cyclopropane-1-carbonitrile | Calc'd 478, found 478 |
| Ex-2.16 | 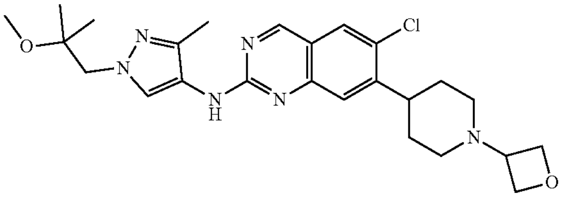 [SMILES: COC(C)(C)Cn1cc(Nc2ncc3cc(Cl)c(C4CCN(C5COC5)CC4)cc3n2)c(C)n1] | 6-chloro-N-[1-(2-methoxy-2-methylpropyl)-3-methyl-1H-pyrazol-4-yl]-7-[1-(oxetan-3-yl)piperidin-4-yl]quinazolin-2-amine | Calc'd 485, found 485 |
| Ex-2.17 | 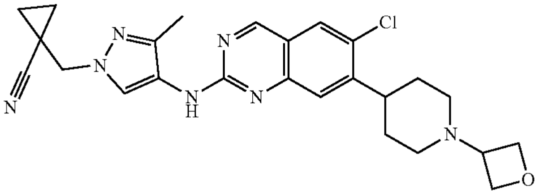 [SMILES: Cc1nn(CC2(C#N)CC2)cc1Nc1ncc2cc(Cl)c(C3CCN(C4COC4)CC3)cc2n1] | 1-{[4-({6-chloro-7-[1-(oxetan-3-yl)piperidin-4-yl]quinazolin-2-yl}amino)-3-methyl-1H-pyrazol-1-yl]methyl}cyclopropane-1-carbonitrile | Calc'd 478, found 478 |

TABLE 3-continued

| Ex | Structure | Name | Exact Mass $[M + H]^+$ |
|---|---|---|---|
| Ex-2.18 | 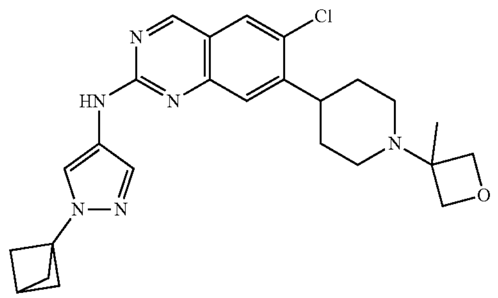 | N-(1-(bicyclo[1.1.1]pentan-1-yl)-1H-pyrazol-4-yl)-6-chloro-7-(1-(3-methyloxetan-3-yl)piperidin-4-yl)quinazolin-2-amine | Calc'd 465, found 465 |
| Ex-2.19 | 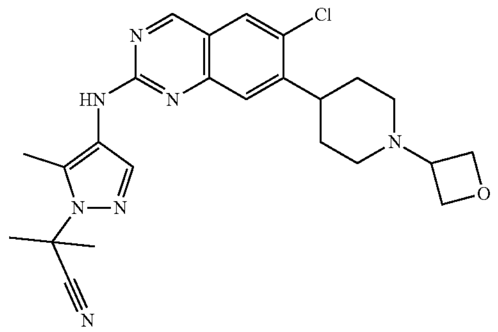 [SMILES: Cc1c(Nc2ncc3cc(Cl)c(C4CCN(C5COC5)CC4)cc3n2)cnn1C(C)(C)C#N] | 2-[4-({6-chloro-7-[1-(oxetan-3-yl)piperidin-4-yl]quinazolin-2-yl}amino)-5-methyl-1H-pyrazol-1-yl]-2-methylpropanenitrile | Calc'd 466, found 466 |
| Ex-2.20 | 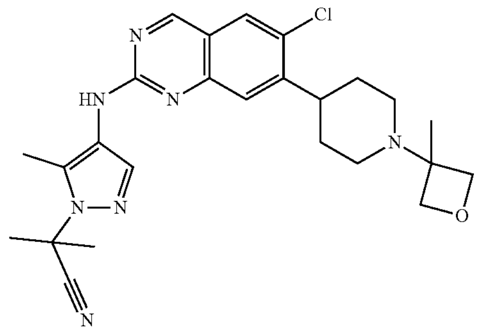 [SMILES: Cc1c(Nc2ncc3cc(Cl)c(C4CCN(C5(C)COC5)CC4)cc3n2)cnn1C(C)(C)C#N] | 2-[4-({6-chloro-7-[1-(3-methyloxetan-3-yl)piperidin-4-yl]quinazolin-2-yl}amino)-5-methyl-1H-pyrazol-1-yl]-2-methylpropanenitrile | Calc'd 480, found 480 |
| Ex-2.21 | 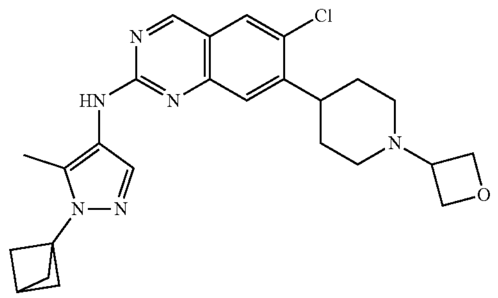 | N-[1-(bicyclo[1.1.1]pentan-1-yl)-5-methyl-1H-pyrazol-4-yl]-6-chloro-7-[1-(oxetan-3-yl)piperidin-4-yl]quinazolin-2-amine | Calc'd 465, found 465 |
| Ex-2.22 | 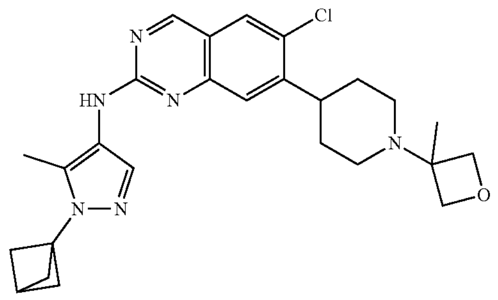 | N-[1-(bicyclo[1.1.1]pentan-1-yl)-5-methyl-1H-pyrazol-4-yl]-6-chloro-7-[1-(3-methyloxetan-3-yl)piperidin-4-yl]quinazolin-2-amine | Calc'd 479, found 479 |

TABLE 3-continued

| Ex | Structure | Name | Exact Mass [M + H]$^+$ |
|---|---|---|---|
| Ex-2.23 | 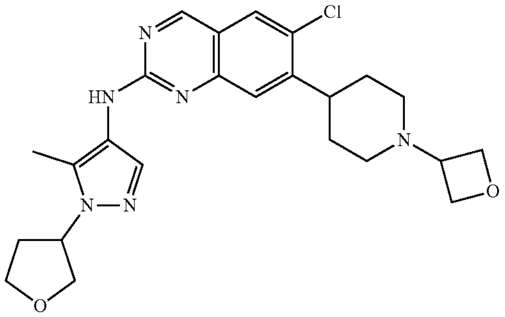 [SMILES: Cc1c(Nc2ncc3cc(Cl)c(C4CCN(C5COC5)CC4)cc3n2)cnn1C1CCOC1] | (S) or (R) 6-chloro-N-[5-methyl-1-(oxolan-3-yl)-1H-pyrazol-4-yl]-7-[1-(oxetan-3-yl)piperidin-4-yl]quinazolin-2-amine | Calc'd 469, found 469 |
| Ex-2.24 | 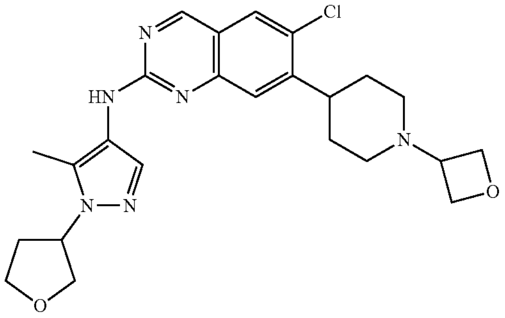 [SMILES: Cc1c(Nc2ncc3cc(Cl)c(C4CCN(C5COC5)CC4)cc3n2)cnn1C1CCOC1] | (S) or (R) 6-chloro-N-[5-methyl-1-(oxolan-3-yl)-1H-pyrazol-4-yl]-7-[1-(oxetan-3-yl)piperidin-4-yl]quinazolin-2-amine | Calc'd 469, found 469 |
| Ex-2.25 | 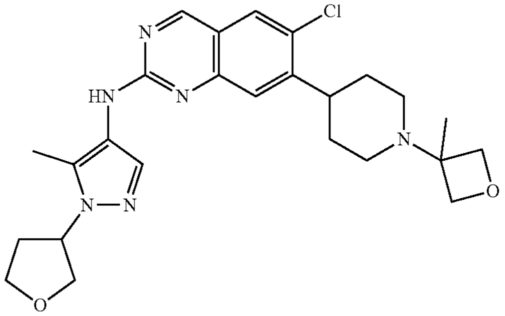 [SMILES: Cc1c(Nc2ncc3cc(Cl)c(C4CCN(C5(C)COC5)CC4)cc3n2)cnn1C1CCOC1] | (S) or (R) 6-chloro-7-[1-(3-methyloxetan-3-yl)piperidin-4-yl]-N-[5-methyl-1-(oxolan-3-yl)-1H-pyrazol-4-yl]quinazolin-2-amine | Calc'd 483, found 483 |
| Ex-2.26 | 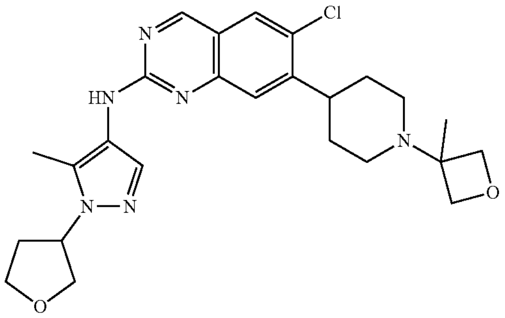 [SMILES: Cc1c(Nc2ncc3cc(Cl)c(C4CCN(C5(C)COC5)CC4)cc3n2)cnn1C1CCOC1] | (S) or (R) 6-chloro-7-[1-(3-methyloxetan-3-yl)piperidin-4-yl]-N-[5-methyl-1-(oxolan-3-yl)-1H-pyrazol-4-yl]quinazolin-2-amine | Calc'd 483, found 483 |
| Ex-2.27 | 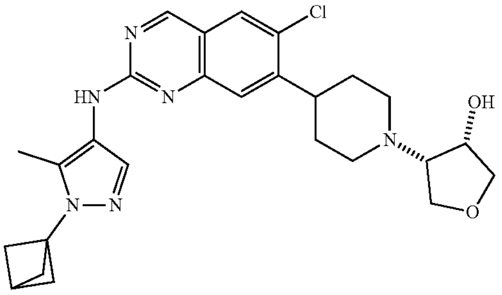 | (3S,4S) or (3R,4R) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol | Calc'd 495, found 495 |

TABLE 3-continued

| Ex | Structure | Name | Exact Mass [M + H]+ |
|---|---|---|---|
| Ex-2.28 | 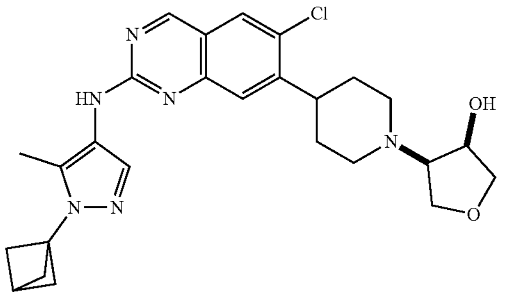 | (3S,4S) or (3R,4R) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol | Calc'd 495, found 495 |
| Ex-2.29 | 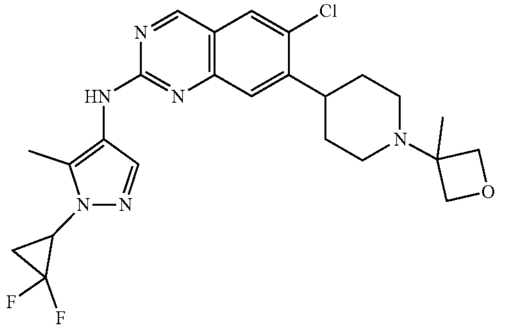 [SMILES: Cc1c(Nc2ncc3cc(Cl)c(C4CCN(C5(C)COC5)CC4)cc3n2)cnn1C1CC1(F)F] | (S) or (R) 6-chloro-N-[1-(2,2-difluorocyclopropyl)-5-methyl-1H-pyrazol-4-yl]-7-[1-(3-methyloxetan-3-yl)piperidin-4-yl]quinazolin-2-amine | Calc'd 489, found 489 |
| Ex-2.30 | 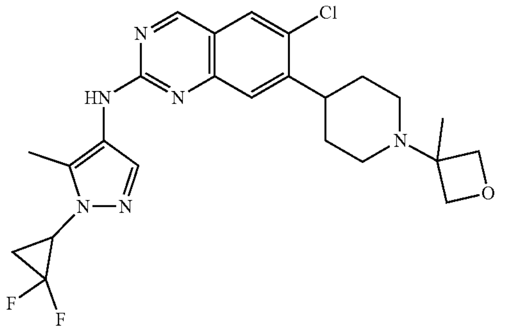 [SMILES: Cc1c(Nc2ncc3cc(Cl)c(C4CCN(C5(C)COC5)CC4)cc3n2)cnn1C1CC1(F)F] | (S) or (R) 6-chloro-N-[1-(2,2-difluorocyclopropyl)-5-methyl-1H-pyrazol-4-yl]-7-[1-(3-methyloxetan-3-yl)piperidin-4-yl]quinazolin-2-amine | Calc'd 489, found 489 |
| Ex-2.31 | 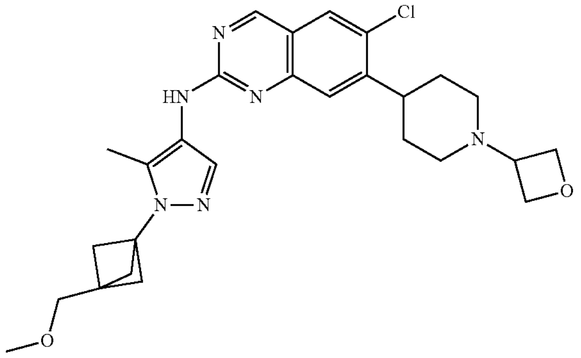 [SMILES: COCC12CC(n3ncc(Nc4ncc5cc(Cl)c(C6CCN(C7COC7)CC6)cc5n4)c3C)(C1)C2] | 6-chloro-N-{1-[3-(methoxymethyl)bicyclo[1.1.1]pentan-1-yl]-5-methyl-1H-pyrazol-4-yl}-7-[1-(oxetan-3-yl)piperidin-4-yl]quinazolin-2-amine | Calc'd 509, found 509 |

TABLE 3-continued

| Ex | Structure | Name | Exact Mass [M + H]$^+$ |
|---|---|---|---|
| Ex-2.32 | 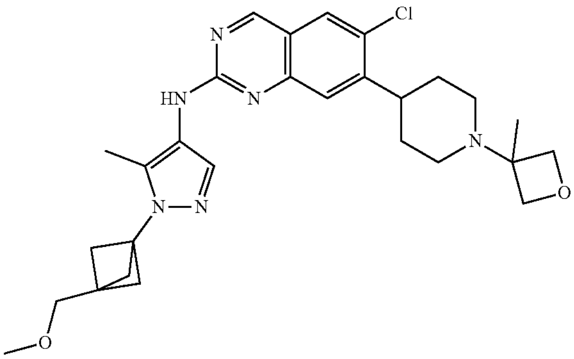 [SMILES: COCC12CC(n3ncc(Nc4ncc5cc(Cl)c(C6CCN(C7(C)COC7)CC6)cc5n4)c3C)(C1)C2] | 6-chloro-N-{1-[3-(methoxymethyl)bicyclo[1.1.1]pentan-1-yl]-5-methyl-1H-pyrazol-4-yl}-7-[1-(3-methyloxetan-3-yl)piperidin-4-yl]quinazolin-2-amine | Calc'd 523, found 523 |
| Ex-2.33 | 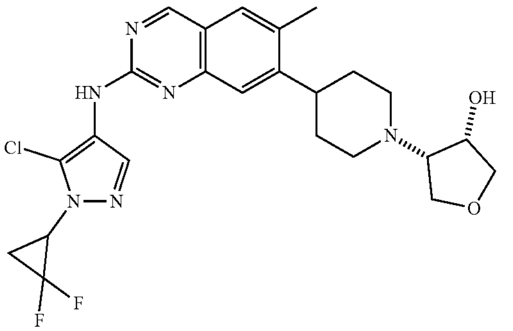 [SMILES: Cc1cc2cnc(Nc3cnn(C4CC4(F)F)c3Cl)nc2cc1C1CCN([C@H]2COC[C@H]2O)CC1] | (R)(3S,4S) or (R)(3R,4R) or (S)(3S,4S) or (S)(3R,4R) 4-[4-(2-{[5-chloro-1-(2,2-difluorocyclopropyl)-1H-pyrazol-4-yl]amino}-6-methylquinazolin-7-yl)piperidin-1-yl]oxolan-3-ol | Calc'd 505, found 505 |
| Ex-2.34 | 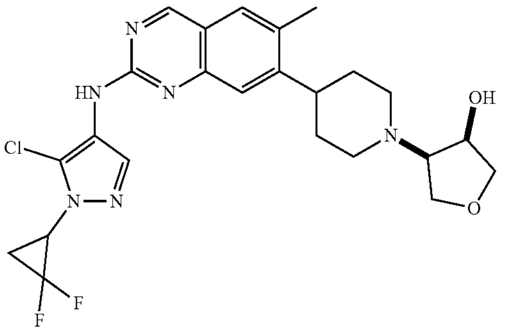 [SMILES: Cc1cc2cnc(Nc3cnn(C4CC4(F)F)c3Cl)nc2cc1C1CCN([C@@H]2COC[C@@H]2O)CC1] | 4-[4-(2-{[5-chloro-1-(2,2-difluorocyclopropyl)-1H-pyrazol-4-yl]amino}-6-methylquinazolin-7-yl)piperidin-1-yl]oxolan-3-ol | Calc'd 505, found 505 |
| Ex-2.35 | 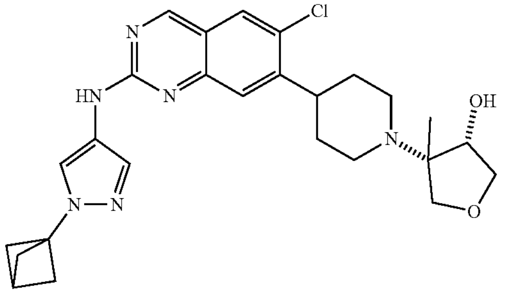 | (3S,4S) or (3R,4R) 4-[4-(2-{[1-(bicyclo[1.1.1]pentan-1-yl)-1H-pyrazol-4-yl]amino}-6-chloroquinazolin-7-yl)piperidin-1-yl]-4-methyloxolan-3-ol | Calc'd 495, found 495 |

TABLE 3-continued

| Ex | Structure | Name | Exact Mass [M + H]+ |
| --- | --- | --- | --- |
| Ex-2.36 | 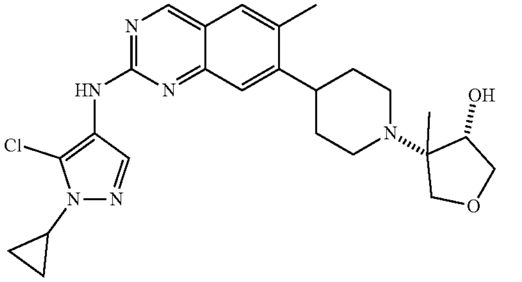 | (3S,4S) or (3R,4R) 4-(4-{2-[(5-chloro-1-cyclopropyl-1H-pyrazol-4-yl)amino]-6-methylquinazolin-7-yl}piperidin-1-yl)-4-methyloxolan-3-ol | Calc'd 483, found 483 |
| Ex-2.37 | 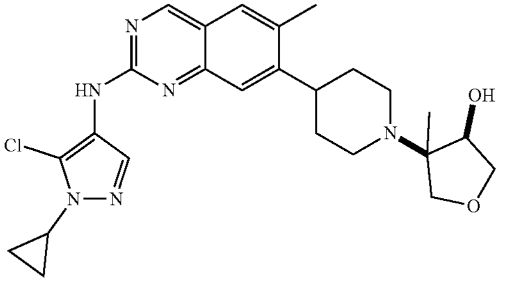 | (3S,4S) or (3R,4R) 4-(4-{2-[(5-chloro-1-cyclopropyl-1H-pyrazol-4-yl)amino]-6-methylquinazolin-7-yl}piperidin-1-yl)-4-methyloxolan-3-ol | Calc'd 483, found 483 |
| Ex-2.38 | 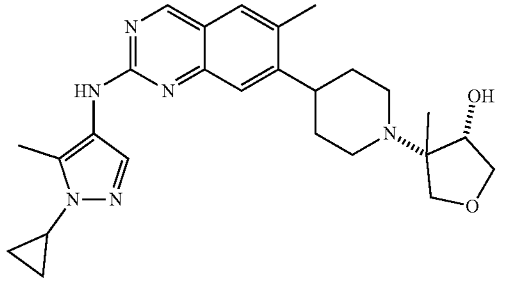 | (3S,4S) or (3R,4R) 4-(4-{2-[(1-cyclopropyl-5-methyl-1H-pyrazol-4-yl)amino]-6-methylquinazolin-7-yl}piperidin-1-yl)-4-methyloxolan-3-ol | Calc'd 463, found 463 |
| Ex-2.39 | 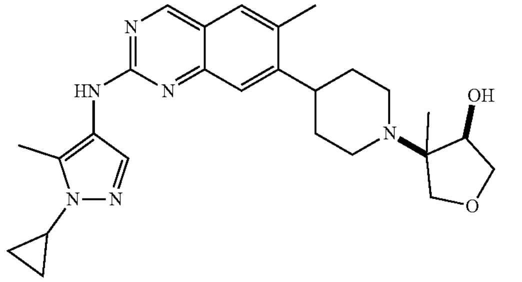 | (3S,4S) or (3R,4R) 4-(4-{2-[(1-cyclopropyl-5-methyl-1H-pyrazol-4-yl)amino]-6-methylquinazolin-7-yl}piperidin-1-yl)-4-methyloxolan-3-ol | Calc'd 463, found 463 |
| Ex-2.40 | 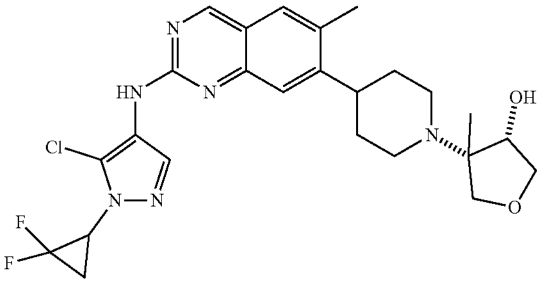 | (R)(3S,4S) or (R)(3R,4R) or (S)(3S,4S) or (S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol | Calc'd 519, found 519 |

TABLE 3-continued

| Ex | Structure | Name | Exact Mass [M + H]+ |
|---|---|---|---|
| Ex-2.41 | 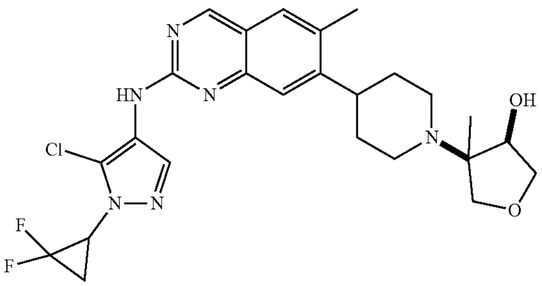 | (R)(3S,4S) or (R)(3R,4R) or (S)(3S,4S) or (S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol | Calc'd 519, found 519 |
| Ex-2.42 | 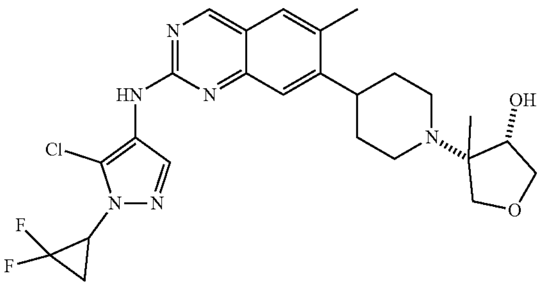 | (R)(3S,4S) or (R)(3R,4R) or (S)(3S,4S) or (S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol | Calc'd 519, found 519 |
| Ex-2.43 | 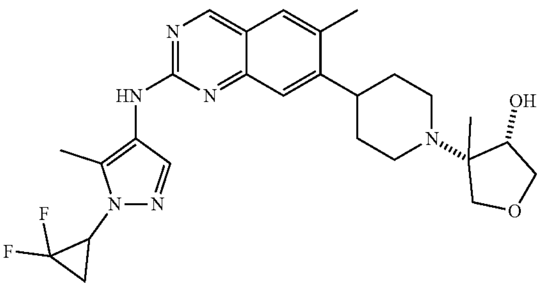 | (R)(3S,4S) or (R)(3R,4R) or (S)(3S,4S) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol | Calc'd 499, found 499 |
| Ex-2.44 | 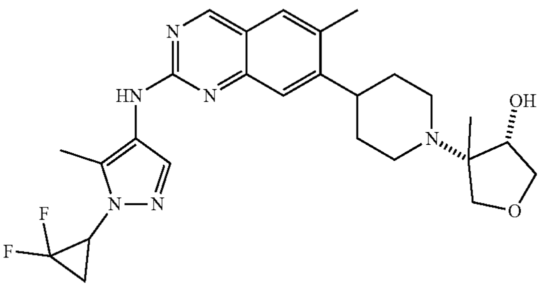 | (R)(3S,4S) or (R)(3R,4R) or (S)(3S,4S) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol | Calc'd 499, found 499 |
| Ex-2.45 | 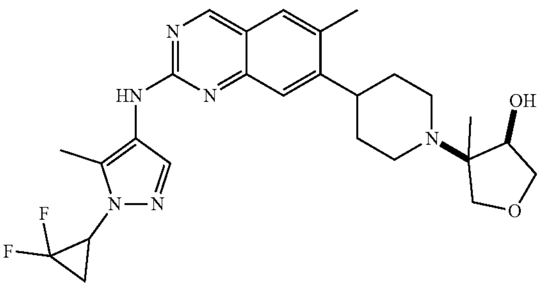 | (R)(3S,4S) or (R)(3R,4R) or (S)(3S,4S) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol | Calc'd 499, found 499 |

TABLE 3-continued

| Ex | Structure | Name | Exact Mass [M + H]+ |
|---|---|---|---|
| Ex-2.46 | 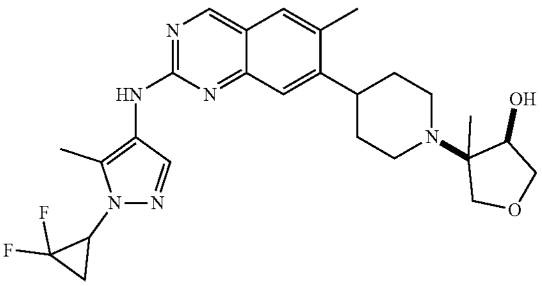 | (R)(3S,4S) or (R)(3R,4R) or (S)(3S,4S) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol | Calc'd 499, found 499 |
| Ex-2.47 | 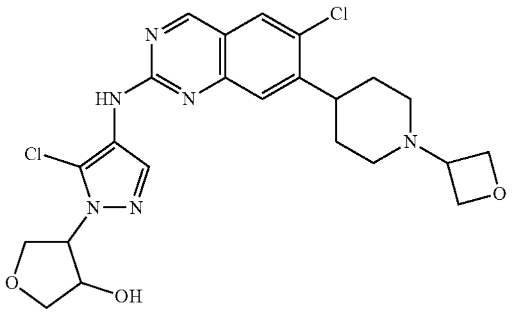 [SMILES: OC1COCC1n1ncc(Nc2ncc3cc(Cl)c(C4CCN(C5COC5)CC4)cc3n2)c1Cl] | (3S,4S) or (3R,4R) or (3S,4R) or (3R,4S) 4-[5-chloro-4-({6-chloro-7-[1-(oxetan-3-yl)piperidin-4-yl]quinazolin-2-yl}amino)-1H-pyrazol-1-yl]oxolan-3-ol | Calc'd 505, found 505 |
| Ex-2.48 | 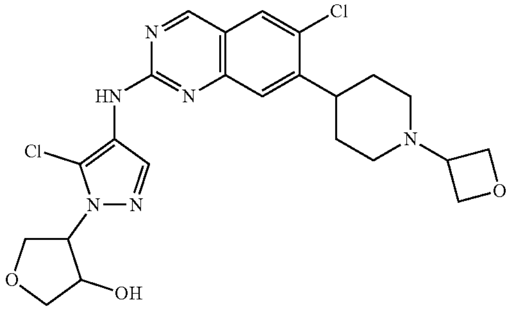 [SMILES: OC1COCC1n1ncc(Nc2ncc3cc(Cl)c(C4CCN(C5COC5)CC4)cc3n2)c1Cl] | 4-[5-chloro-4-({6-chloro-7-[1-(oxetan-3-yl)piperidin-4-yl]quinazolin-2-yl}amino)-1H-pyrazol-1-yl]oxolan-3-ol | Calc'd 505, found 505 |
| Ex-2.49 | 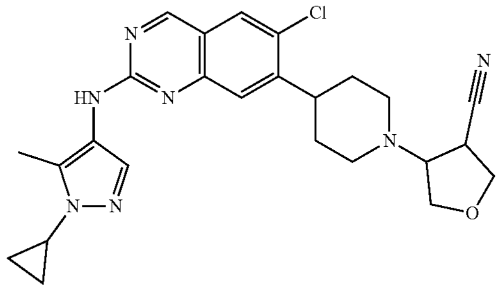 [SMILES: Cc1c(Nc2ncc3cc(Cl)c(C4CCN(C5COCC5C#N)CC4)cc3n2)cnn1C1CC1] | (3S,4S) or (3R,4R) or (3S,4R) or (3R,4S) 4-(4-{6-chloro-2-[(1-cyclopropyl-5-methyl-1H-pyrazol-4-yl)amino]quinazolin-7-yl}piperidin-1-yl)oxolane-3-carbonitrile | Calc'd 478, found 478 |
| Ex-2.50 | 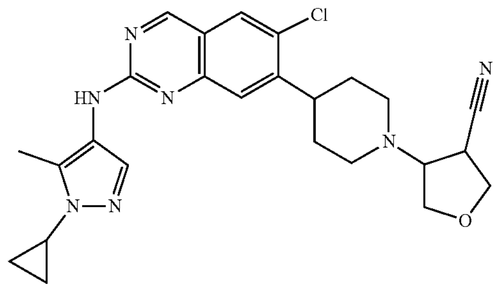 [SMILES: Cc1c(Nc2ncc3cc(Cl)c(C4CCN(C5COCC5C#N)CC4)cc3n2)cnn1C1CC1] | (3S,4S) or (3R,4R) or (3S,4R) or (3R,4S) 4-(4-{6-chloro-2-[(1-cyclopropyl-5-methyl-1H-pyrazol-4-yl)amino]quinazolin-7-yl}piperidin-1-yl)oxolane-3-carbonitrile | Calc'd 478, found 478 |

TABLE 3-continued

| Ex | Structure | Name | Exact Mass [M + H]+ |
|---|---|---|---|
| Ex-2.51 | 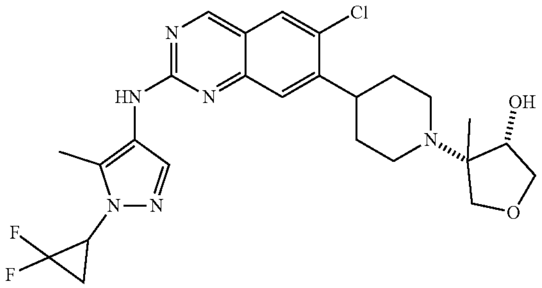 | (R)(3S,4S) or (R)(3R,4R) or (S)(3S,4S) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol | Calc'd 519, found 519 |
| Ex-2.52 | 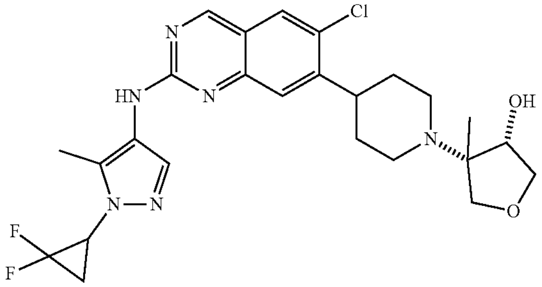 | (R)(3S,4S) or (R)(3R,4R) or (S)(3S,4S) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol | Calc'd 519, found 519 |
| Ex-2.53 | 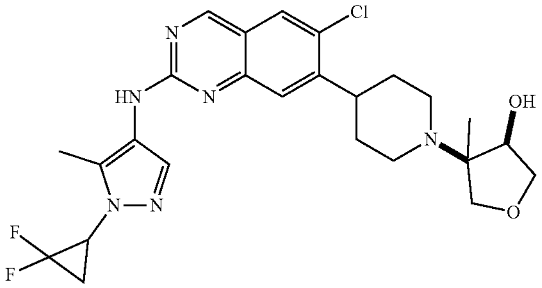 | (R)(3S,4S) or (R)(3R,4R) or (S)(3S,4S) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol | Calc'd 519, found 519 |
| Ex-2.54 | 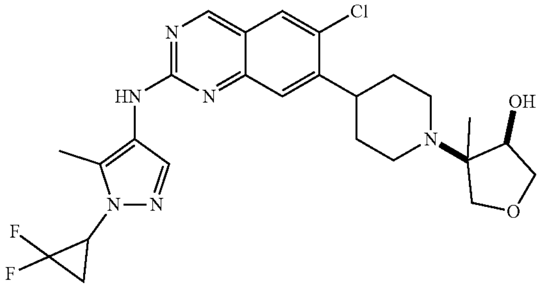 | (R)(3S,4S) or (R)(3R,4R) or (S)(3S,4S) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol | Calc'd 519, found 519 |
| Ex-2.55 | 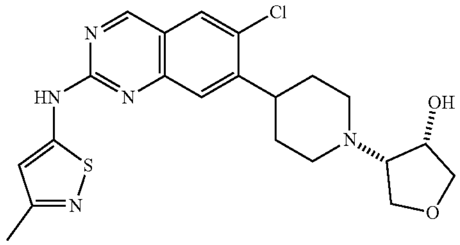 [SMILES: Cc1cc(Nc2ncc3cc(Cl)c(C4CCN([C@H]5COC[C@H]5O)CC4)cc3n2)sn1] | (3S,4S) or (3R,4R)4-(4-{6-chloro-2-[(3-methyl-1,2-thiazol-5-yl)amino]quinazolin-7-yl}piperidin-1-yl)oxolan-3-ol | Calc'd 446, found 446 |

TABLE 3-continued

| Ex | Structure | Name | Exact Mass [M + H]+ |
|---|---|---|---|
| Ex-2.56 | 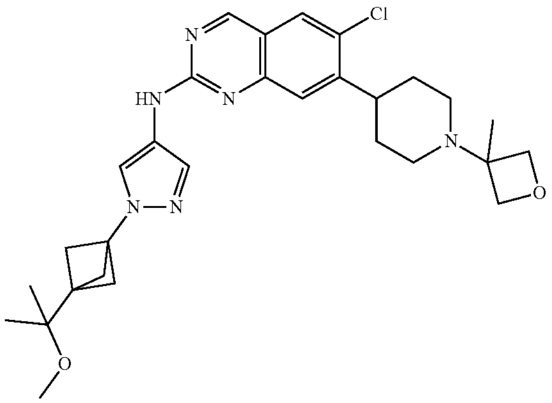 [SMILES: COC(C)(C)C12CC(n3cc(Nc4ncc5cc(Cl)c(C6CCN(C7(C)COC7)CC6)cc5n4)cn3)(C1)C2] | 6-chloro-N-{1-[3-(2-methoxypropan-2-yl)bicyclo[1.1.1]pentan-1-yl]-1H-pyrazol-4-yl}-7-[1-(3-methyloxetan-3-yl)piperidin-4-yl]quinazolin-2-amine | Calc'd 537, found 537 |
| Ex-2.57 | 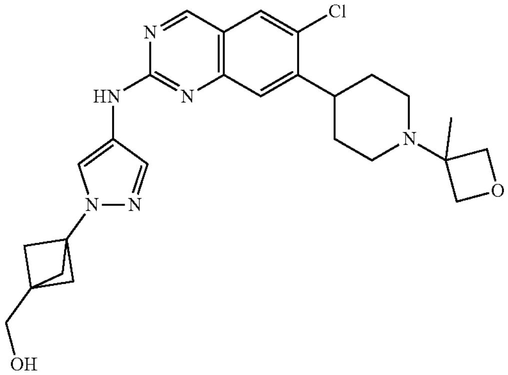 [SMILES: CC1(N2CCC(c3cc4nc(Nc5cnn(C67CC(CO)(C6)C7)c5)ncc4cc3Cl)CC2)COC1] | {3-[4-({6-chloro-7-[1-(3-methyloxetan-3-yl)piperidin-4-yl]quinazolin-2-yl}amino)-1H-pyrazol-1-yl]bicyclo[1.1.1]pentan-1-yl}methanol | Calc'd 495, found 495 |
| Ex-2.58 | 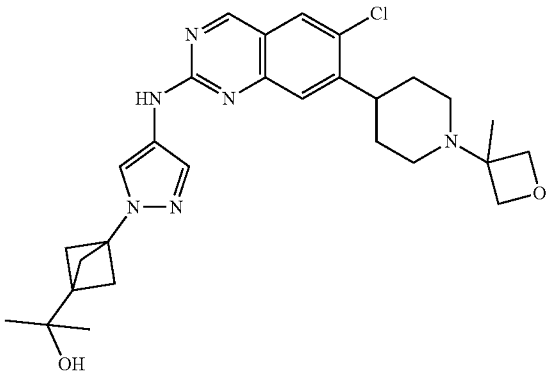 [SMILES: CC1(N2CCC(c3cc4nc(Nc5cnn(C67CC(C(C)(C)O)(C6)C7)c5)ncc4cc3Cl)CC2)COC1] | 2-{3-[4-({6-chloro-7-[1-(3-methyloxetan-3-yl)piperidin-4-yl]quinazolin-2-yl}amino)-1H-pyrazol-1-yl]bicyclo[1.1.1]pentan-1-yl}propan-2-ol | Calc'd 523, found 523 |
| Ex-2.59 | 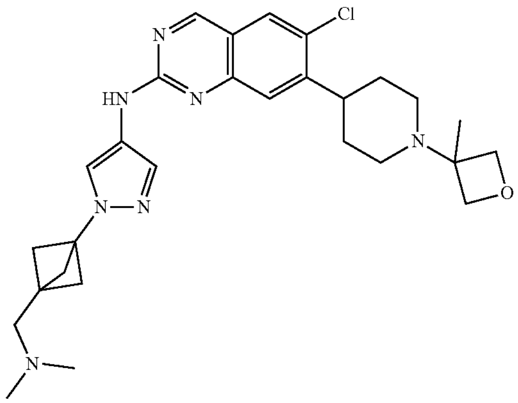 [SMILES: CN(C)CC12CC(n3cc(Nc4ncc5cc(Cl)c(C6CCN(C7(C)COC7)CC6)cc5n4)cn3)(C1)C2] | 6-chloro-N-(1-{3-[(dimethylamino)methyl]bicyclo[1.1.1]pentan-1-yl}-1H-pyrazol-4-yl)-7-[1-(3-methyloxetan-3-yl)piperidin-4-yl]quinazolin-2-amine | Calc'd 522, found 522 |

TABLE 3-continued

| Ex | Structure | Name | Exact Mass [M + H]+ |
|---|---|---|---|
| Ex-2.60 | 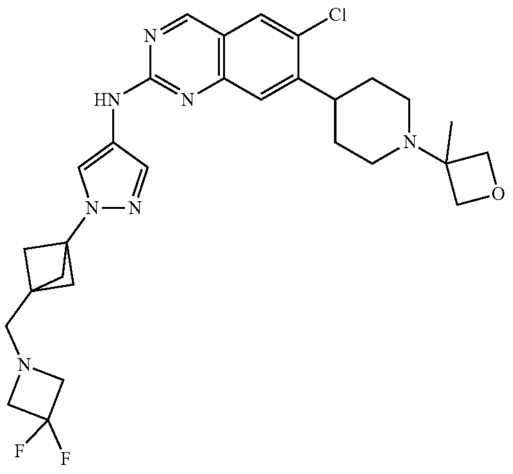 [SMILES: CC1(N2CCC(c3cc4nc(Nc5cnn(C67CC(CN8CC(F)(F)C8)(C6)C7)c5)ncc4cc3Cl)CC2)COC1] | 6-chloro-N-(1-{3-[(3,3-difluoroazetidin-1-yl)methyl]bicyclo[1.1.1]pentan-1-yl}-1H-pyrazol-4-yl)-7-[1-(3-methyloxetan-3-yl)piperidin-4-yl]quinazolin-2-amine | Calc'd 570, found 570 |
| Ex-2.61 | 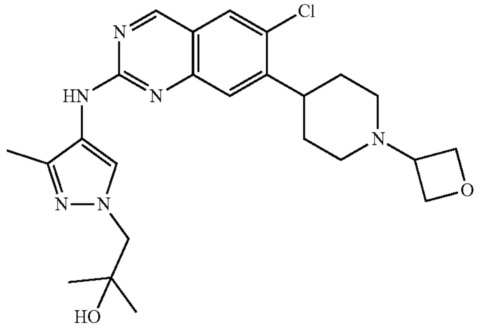 [SMILES: Cc1nn(CC(C)(C)O)cc1Nc1ncc2cc(Cl)c(C3CCN(C4COC4)CC3)cc2n1] | 1-[4-({6-chloro-7-[1-(oxetan-3-yl)piperidin-4-yl]quinazolin-2-yl}amino)-3-methyl-1H-pyrazol-1-yl]-2-methylpropan-2-ol | Calc'd 471, found 471 |
| Ex-2.62 | 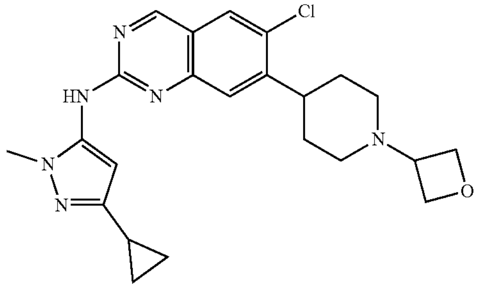 [SMILES: Cn1nc(C2CC2)cc1Nc1ncc2cc(Cl)c(C3CCN(C4COC4)CC3)cc2n1] | 6-chloro-N-(3-cyclopropyl-1-methyl-1H-pyrazol-5-yl)-7-[1-(oxetan-3-yl)piperidin-4-yl]quinazolin-2-amine | Calc'd 439, found 439 |
| Ex-2.63 | 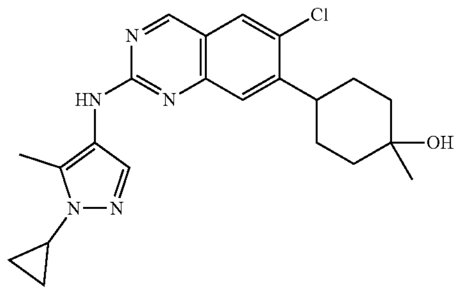 [SMILES: Cc1c(Nc2ncc3cc(Cl)c(C4CCC(C)(O)CC4)cc3n2)cnn1C1CC1] | cis- or trans- 4-{6-chloro-2-[(1-cyclopropyl-5-methyl-1H-pyrazol-4-yl)amino]quinazolin-7-yl}-1-methylcyclohexan-1-ol | Calc'd 412, found 412 |

TABLE 3-continued

| Ex | Structure | Name | Exact Mass [M + H]+ |
|---|---|---|---|
| Ex-2.64 | 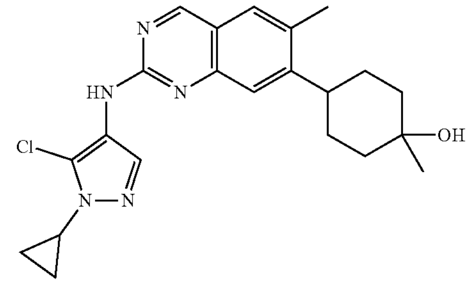 [SMILES: Cc1cc2cnc(Nc3cnn(C4CC4)c3Cl)nc2cc1C1CCC(C)(O)CC1] | cis- or trans- 4-{2-[(5-chloro-1-cyclopropyl-1H-pyrazol-4-yl)amino]-6-methylquinazolin-7-yl}-1-methylcyclohexan-1-ol | Calc'd 412, found 412 |
| Ex-2.65 | 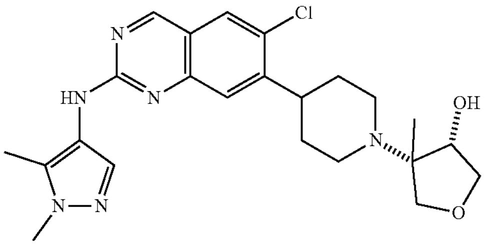 [SMILES: Cc1c(Nc2ncc3cc(Cl)c(C4CCN([C@@]5(C)COC[C@H]5O)CC4)cc3n2)cnn1C] | (3S,4S) or (3R,4R) 4-(4-{6-chloro-2-[(1,5-dimethyl-1H-pyrazol-4-yl)amino]quinazolin-7-yl}piperidin-1-yl)-4-methyloxolan-3-ol | Calc'd 457, found 457 |
| Ex-2.66 | 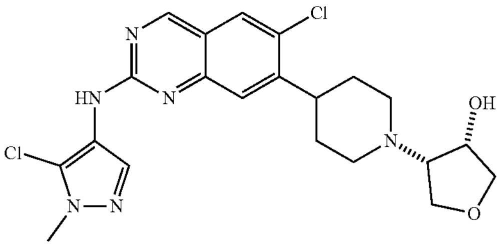 [SMILES: Cn1ncc(Nc2ncc3cc(Cl)c(C4CCN([C@H]5COC[C@H]5O)CC4)cc3n2)c1Cl] | (3S,4S) or (3R,4R) 4-(4-{6-chloro-2-[(5-chloro-1-methyl-1H-pyrazol-4-yl)amino]quinazolin-7-yl}piperidin-1-yl)oxolan-3-ol | Calc'd 463, found 463 |
| Ex-2.67 | 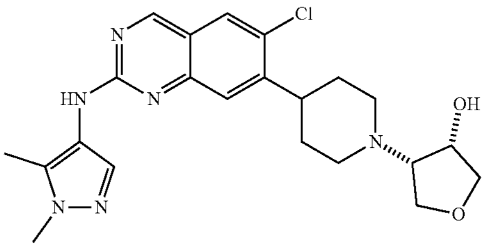 [SMILES: Cc1c(Nc2ncc3cc(Cl)c(C4CCN([C@H]5COC[C@H]5O)CC4)cc3n2)cnn1C] | (3S,4S) or (3R,4R) 4-(4-{6-chloro-2-[(1,5-dimethyl-1H-pyrazol-4-yl)amino]quinazolin-7-yl}piperidin-1-yl)oxolan-3-ol | Calc'd 443, found 443 |
| Ex-2.68 | 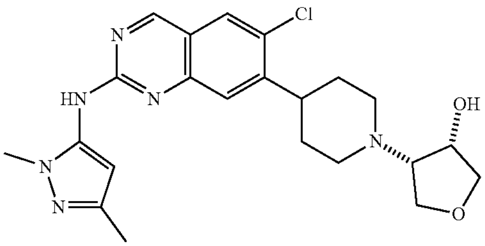 [SMILES: Cc1cc(Nc2ncc3cc(Cl)c(C4CCN([C@H]5COC[C@H]5O)CC4)cc3n2)n(C)n1] | (3S,4S) or (3R,4R) 4-(4-{6-chloro-2-[(1,3-dimethyl-1H-pyrazol-5-yl)amino]quinazolin-7-yl}piperidin-1-yl)oxolan-3-ol | Calc'd 443, found 443 |
| Ex-2.69 | 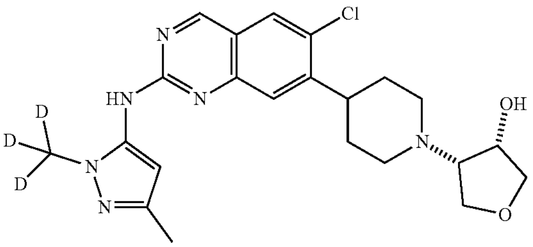 [SMILES: [2H]C([2H])([2H])n1nc(C)cc1Nc1ncc2cc(Cl)c(C3CCN([C@H]4COC[C@H]4O)CC3)cc2n1] | (3S,4S) or (3R,4R) 4-(4-(6-chloro-2-((3-methyl-1-(methyl-$d_3$)-1H-pyrazol-5-yl)amino)quinazolin-7-yl)piperidin-1-yl)tetrahydrofuran-3-ol | Calc'd 446, found 446 |

TABLE 3-continued

| Ex | Structure | Name | Exact Mass [M + H]+ |
|---|---|---|---|
| Ex-2.70 | 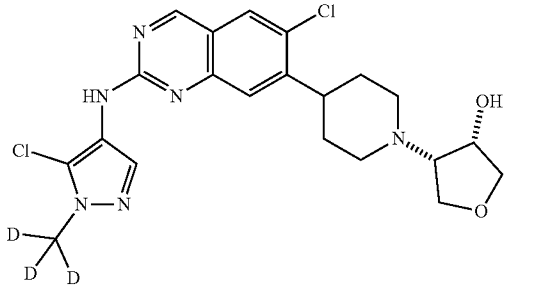 [SMILES: [2H]C([2H])([2H])n1ncc(Nc2ncc3cc(Cl)c(C4CCN([C@H]5COC[C@H]5O)CC4)cc3n2)c1Cl] | (3S,4S) or (3R,4R) 4-(4-(6-chloro-2-((5-chloro-1-(methyl-$d_3$)-1H-pyrazol-4-yl)amino)quinazolin-7-yl)piperidin-1-yl)tetrahydrofuran-3-ol | Calc'd 466, found 466 |
| Ex-2.71 | 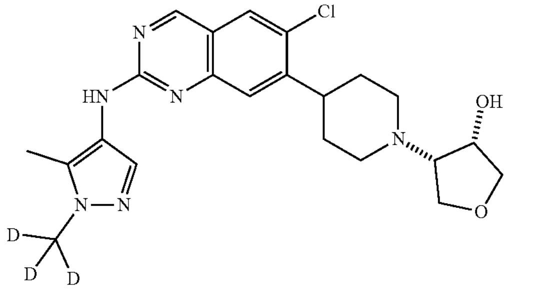 [SMILES: [2H]C([2H])([2H])n1ncc(Nc2ncc3cc(Cl)c(C4CCN([C@H]5COC[C@H]5O)CC4)cc3n2)c1C] | (3S,4S) or (3R,4R) 4-(4-(6-chloro-2-((5-methyl-1-(methyl-$d_3$)-1H-pyrazol-4-yl)amino)quinazolin-7-yl)piperidin-1-yl)tetrahydrofuran-3-ol | Calc'd 466, found 466 |
| Ex-2.72 | 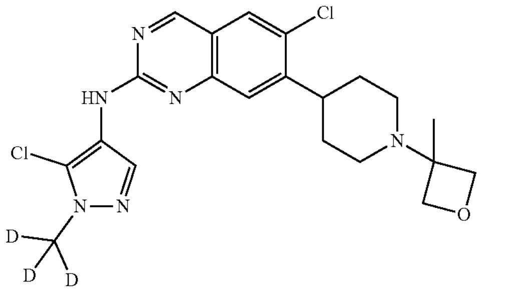 [SMILES: [2H]C([2H])([2H])n1ncc(Nc2ncc3cc(Cl)c(C4CCN(C5(C)COC5)CC4)cc3n2)c1Cl] | 6-chloro-N-(5-chloro-1-(methyl-$d_3$)-1H-pyrazol-4-yl)-7-(1-(3-methyloxetan-3-yl)piperidin-4-yl)quinazolin-2-amine | Calc'd 450, found 450 |
| Ex-2.73 | 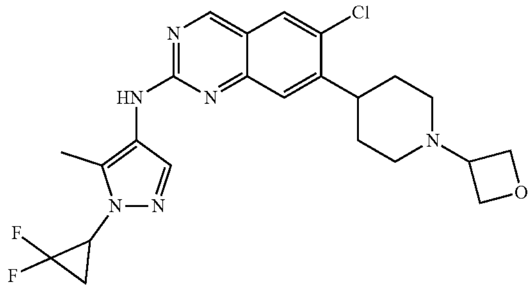 [SMILES: Cc1c(Nc2ncc3cc(Cl)c(C4CCN(C5COC5)CC4)cc3n2)cnn1C1CC1(F)F] | (S) or (R) 6-chloro-N-[1-(2,2-difluorocyclopropyl)-5-methyl-1H-pyrazol-4-yl]-7-[1-(oxetan-3-yl)piperidin-4-yl]quinazolin-2-amine | Calc'd 475, found 475 |
| Ex-2.74 | 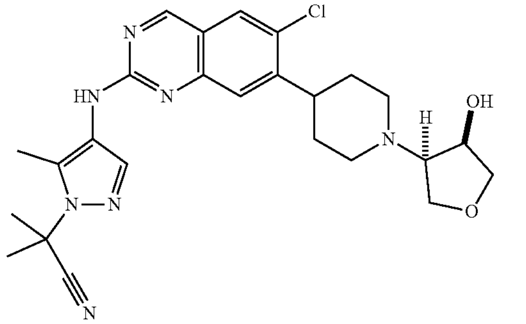 [SMILES: Cc1c(Nc2ncc3cc(Cl)c(C4CCN([C@@H]5COC[C@@H]5O)CC4)cc3n2)cnn1C(C)(C)C#N] | (3S,4S) or (3R,4R) 2-[4-({6-chloro-7-[1-(4-hydroxyoxolan-3-yl)piperidin-4-yl]quinazolin-2-yl}amino)-5-methyl-1H-pyrazol-1-yl]-2-methylpropanenitrile | Calc'd 496, found 496 |

TABLE 3-continued

| Ex | Structure | Name | Exact Mass [M + H]+ |
|---|---|---|---|
| Ex-2.75 | 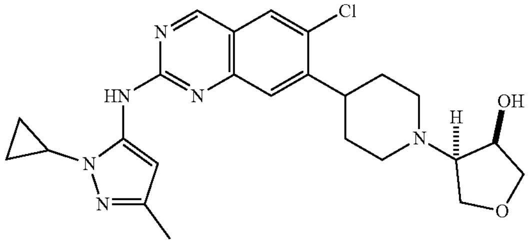 [SMILES: Cc1cc(Nc2ncc3cc(Cl)c(C4CCN([C@@H]5COC[C@@H]5O)CC4)cc3n2)n(C2CC2)n1] | (3S,4S) or (3R,4R)4-(4-{6-chloro-2-[(1-cyclopropyl-3-methyl-1H-pyrazol-5-yl)amino]quinazolin-7-yl}piperidin-1-yl)oxolan-3-ol | Calc'd 469, found 469 |
| Ex-2.76 | 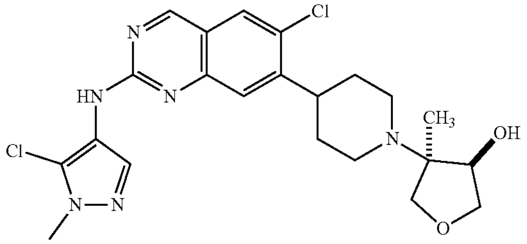 [SMILES: Cn1ncc(Nc2ncc3cc(Cl)c(C4CCN([C@]5(C)COC[C@@H]5O)CC4)cc3n2)c1Cl] | (3S,4S) or (3R,4R) 4-(4-(6-chloro-2-((5-chloro-1-methyl-1H-pyrazol-4-yl)amino)quinazolin-7-yl)piperidin-1-yl)-4-methyltetrahydrofuran-3-ol | Calc'd 477, found 477 |
| Ex-2.77 | 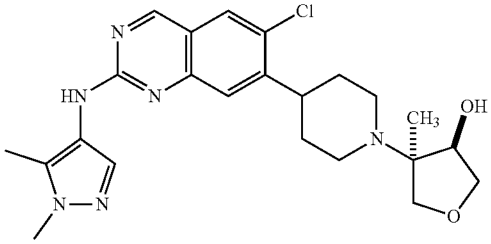 [SMILES: Cc1c(Nc2ncc3cc(Cl)c(C4CCN([C@]5(C)COC[C@@H]5O)CC4)cc3n2)cnn1C] | (3S,4S) or (3R,4R) 4-(4-{6-chloro-2-[(1,5-dimethyl-1H-pyrazol-4-yl)amino]quinazolin-7-yl}piperidin-1-yl)-4-methyloxolan-3-ol | Calc'd 457, found 457 |
| Ex-2.78 | 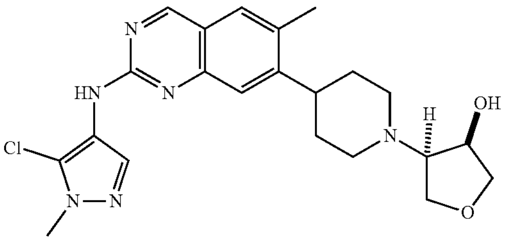 [SMILES: Cc1cc2cnc(Nc3cnn(C)c3Cl)nc2cc1C1CCN([C@@H]2COC[C@@H]2O)CC1] | (3S,4S) or (3R,4R) 4-(4-{2-[(5-chloro-1-methyl-1H-pyrazol-4-yl)amino]-6-methylquinazolin-7-yl}piperidin-1-yl)oxolan-3-ol | Calc'd 443, found 443 |
| Ex-2.79 | 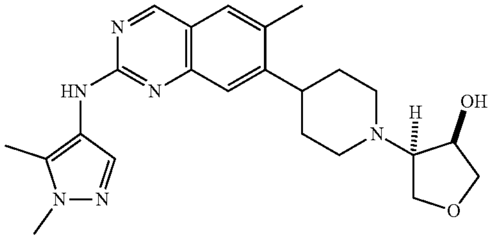 [SMILES: Cc1cc2cnc(Nc3cnn(C)c3C)nc2cc1C1CCN([C@@H]2COC[C@@H]2O)CC1] | (3S,4S) or (3R,4R) 4-(4-{2-[(1,5-dimethyl-1H-pyrazol-4-yl)amino]-6-methylquinazolin-7-yl}piperidin-1-yl)oxolan-3-ol | Calc'd 423, found 423 |
| Ex-2.80 | 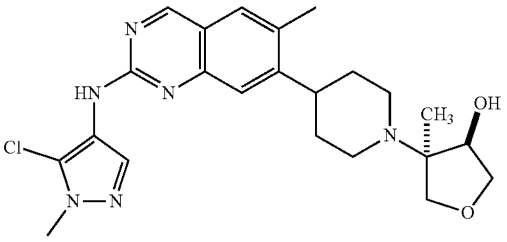 [SMILES: Cc1cc2cnc(Nc3cnn(C)c3Cl)nc2cc1C1CCN([C@]2(C)COC[C@@H]2O)CC1] | (3S,4S) or (3R,4R) 4-(4-{2-[(5-chloro-1-methyl-1H-pyrazol-4-yl)amino]-6-methylquinazolin-7-yl}piperidin-1-yl)-4-methyloxolan-3-ol | Calc'd 457, found 457 |

TABLE 3-continued

| Ex | Structure | Name | Exact Mass [M + H]$^+$ |
|---|---|---|---|
| Ex-2.81 | 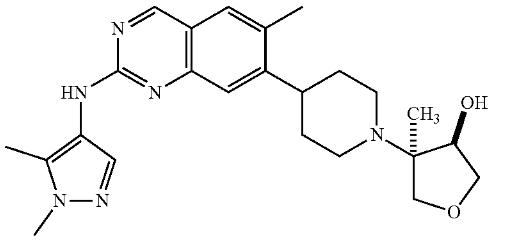 [SMILES: Cc1cc2cnc(Nc3cnn(C)c3C)nc2cc1C1CCN([C@]2(C)COC[C@@H]2O)CC1] | (3S,4S) or (3R,4R) 4-(4-{2-[(1,5-dimethyl-1H-pyrazol-4-yl)amino]-6-methylquinazolin-7-yl}piperidin-1-yl)-4-methyloxolan-3-ol | Calc'd 437, found 437 |
| Ex-2.82 | 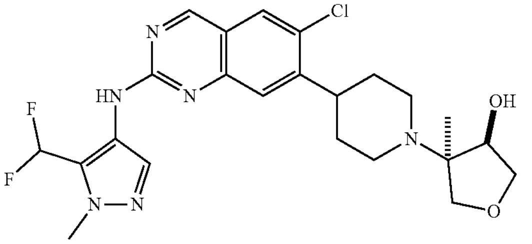 [SMILES: Cn1ncc(Nc2ncc3cc(Cl)c(C4CCN([C@]5(C)COC[C@@H]5O)CC4)cc3n2)c1C(F)F] | (3S,4S) or (3R,4R) 4-[4-(6-chloro-2-{[5-(difluoromethyl)-1-methyl-1H-pyrazol-4-yl]amino}quinazolin-7-yl)piperidin-1-yl]-4-methyloxolan-3-ol | Calc'd 493, found 493 |
| Ex-2.83 | 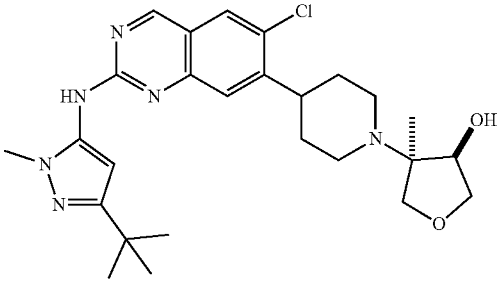 [SMILES: Cn1nc(C(C)(C)C)cc1Nc1ncc2cc(Cl)c(C3CCN([C@]4(C)COC[C@@H]4O)CC3)cc2n1] | (3S,4S) or (3R,4R) 4-(4-{2-[(3-tert-butyl-1-methyl-1H-pyrazol-5-yl)amino]-6-chloroquinazolin-7-yl}piperidin-1-yl)-4-methyloxolan-3-ol | Calc'd 499, found 499 |
| Ex-2.84 | 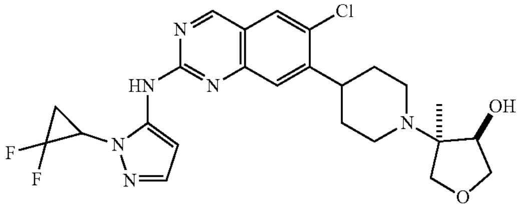 [SMILES: C[C@@]1(N2CCC(c3cc4nc(Nc5ccnn5C5CC5(F)F)ncc4cc3Cl)CC2)COC[C@@H]1O] | (S)(3S,4S) or (S)(3R,4R) or (R)(3S,4S) or (R)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol | Calc'd 505, found 505 |
| Ex-2.85 | 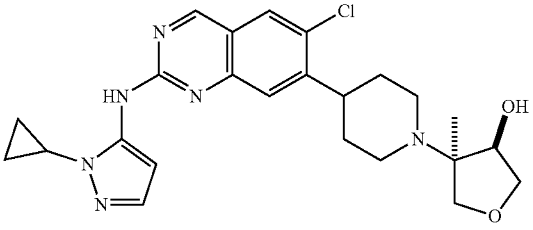 [SMILES: C[C@@]1(N2CCC(c3cc4nc(Nc5ccnn5C5CC5)ncc4cc3Cl)CC2)COC[C@@H]1O] | (3S,4S) or (3R,4R) 4-(4-{6-chloro-2-[(1-cyclopropyl-1H-pyrazol-5-yl)amino]quinazolin-7-yl}piperidin-1-yl)-4-methyloxolan-3-ol | Calc'd 469, found 469 |
| Ex-2.86 | 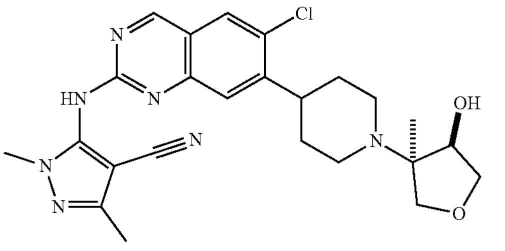 [SMILES: Cc1nn(C)c(Nc2ncc3cc(Cl)c(C4CCN([C@]5(C)COC[C@@H]5O)CC4)cc3n2)c1C#N] | (3S,4S) or (3R,4R) 5-({6-chloro-7-[1-(4-hydroxy-3-methyloxolan-3-yl)piperidin-4-yl]quinazolin-2-yl}amino)-l,3-dimethyl-1H-pyrazole-4-carbonitrile | Calc'd 482, found 482 |

TABLE 3-continued

| Ex | Structure | Name | Exact Mass [M + H]+ |
|---|---|---|---|
| Ex-2.87 | 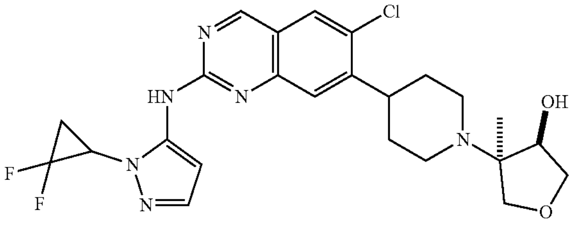 [SMILES: C[C@@]1(N2CCC(c3cc4nc(Nc5ccnn5C5CC5(F)F)ncc4cc3Cl)CC2)COC[C@@H]1O] | (S)(3S,4S) or (S)(3R,4R) or (R)(3S,4S) or (R)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol | Calc'd 505, found 505 |
| Ex-2.88 | 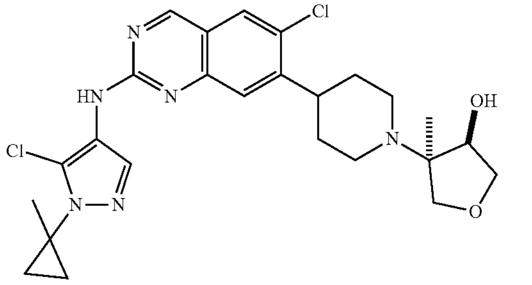 [SMILES: CC1(n2ncc(Nc3ncc4cc(Cl)c(C5CCN([C@]6(C)COC[C@@H]6O)CC5)cc4n3)c2Cl)CC1] | (3S,4S) or (3R,4R) 4-[4-(6-chloro-2-{[5-chloro-1-(1-methylcyclopropyl)-1H-pyrazol-4-yl]amino}quinazolin-7-yl)piperidin-1-yl]-4-methyloxolan-3-ol | Calc'd 517, found 517 |
| Ex-2.89 | 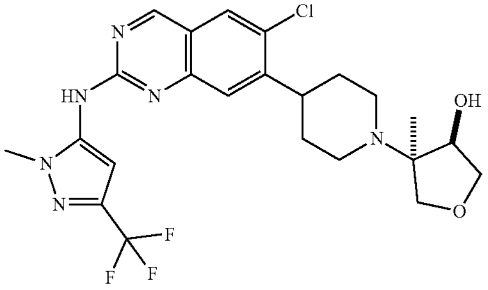 [SMILES: Cn1nc(C(F)(F)F)cc1Nc1ncc2cc(Cl)c(C3CCN([C@]4(C)COC[C@@H]4O)CC3)cc2n1] | (3S,4S) or (3R,4R) 4-[4-(6-chloro-2-{[1-methyl-3-(trifluoromethyl)-1H-pyrazol-5-yl]amino}quinazolin-7-yl)piperidin-1-yl]-4-methyloxolan-3-ol | Calc'd 511, found 511 |
| Ex-2.90 | 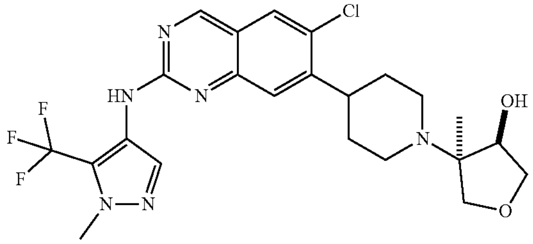 [SMILES: Cn1ncc(Nc2ncc3cc(Cl)c(C4CCN([C@]5(C)COC[C@@H]5O)CC4)cc3n2)c1C(F)(F)F] | (3S,4S) or (3R,4R) 4-(4-(6-chloro-2-((1-methyl-5-(trifluoromethyl)-1H-pyrazol-4-yl)amino)quinazolin-7-yl)piperidin-1-yl)-4-methyltetrahydrofuran-3-olyl)piperidin-1-yl]-4-methyloxolan-3-ol | Calc'd 511, found 511 |
| Ex-2.91 | 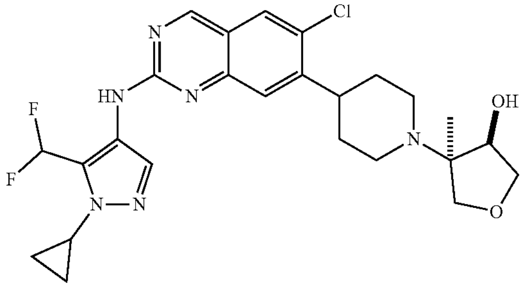 [SMILES: C[C@@]1(N2CCC(c3cc4nc(Nc5cnn(C6CC6)c5C(F)F)ncc4cc3Cl)CC2)COC[C@@H]1O] | (3S,4S) or (3R,4R) 4-[4-(6-chloro-2-{[1-cyclopropyl-5-(difluoromethyl)-1H-pyrazol-4-yl]amino}quinazolin-7-yl)piperidin-1-yl]-4-methyloxolan-3-ol | Calc'd 519, found 519 |

General Scheme 4

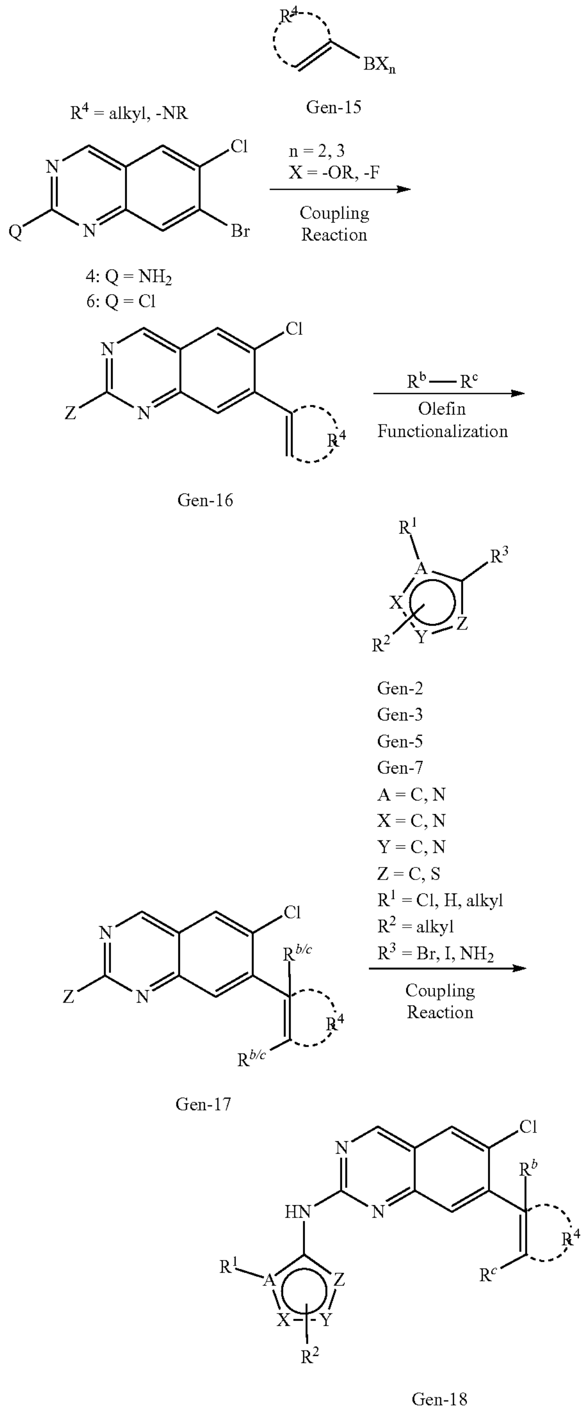

Gen-15

Gen-16

Gen-2
Gen-3
Gen-5
Gen-7

Gen-17

Gen-18

In General Scheme 4, intermediate 4 or 6 was coupled with commercially available or synthetically prepared vinyl boronic acids, boronic esters, or potassium trifluoroborate salts Gen-15 to provide Gen-16. Intermediates of the form Gen-16 could then optionally be subjected to number of olefin functionalization reactions commonly known to those skilled in the art, including, but not limited to, catalytic hydrogenation, hydroboration (cf. Scheme 19), concerted/nonconcerted cheletropic reactions, etc. to afford Gen-17. In the case of hydroboration, subsequent functional group interconversions commonly known to those skilled in the art (e.g. oxidation, fluorination, etc.) could be performed. In the case of cheletropic reactions (e.g. cyclopropanation), by definition the vicinal substituents in Gen-17 are either both $R_b$ or both $R_c$, and represent a single atom bonded to each of the carbon atoms that formerly comprised the olefin in Gen-16. Intermediate Gen-17 could in turn be converted to Gen-18 through palladium catalyzed cross coupling with intermediates of the form Gen-2/Gen-3/Gen-5/Gen-7. The representative compounds are described in more detail below.

Preparation of Examples 3.1 and 3.2

Scheme 51. Synthesis of (3R,4R)(7S) or (3R,4R)(7R) or (3S,4S)(7S) or (3S,4S)(7R) 6-chloro-N-(N-chloro-1-(-3-fluoro-1-(3-methyloxetan-3-yl) piperidin-4-yl)-1H-pyrazol-4-yl)-7-(2,2-difluorocyclopropyl)quinazolin-2-amine

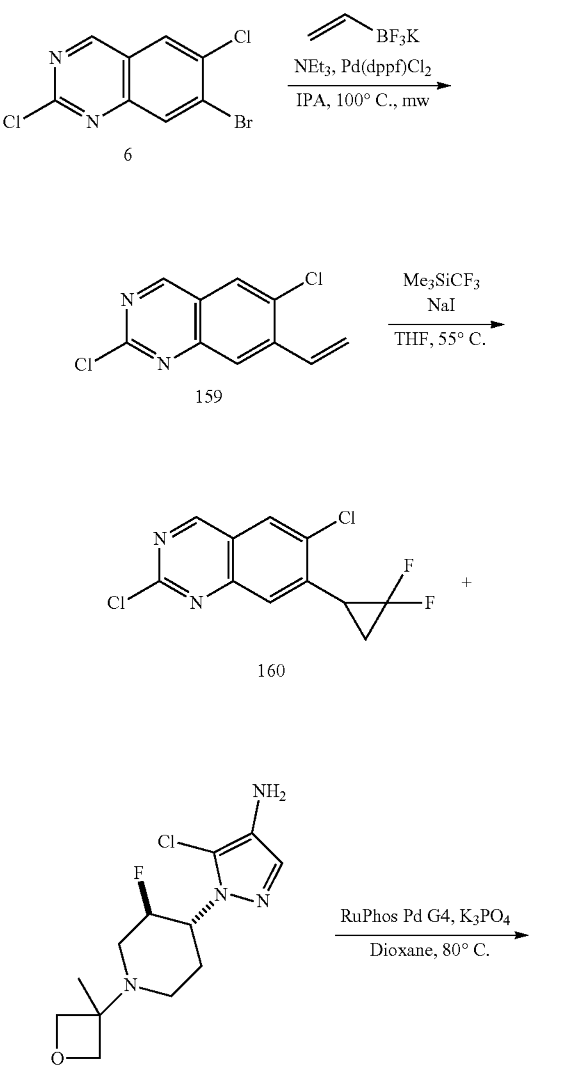

6

159

160

161

-continued

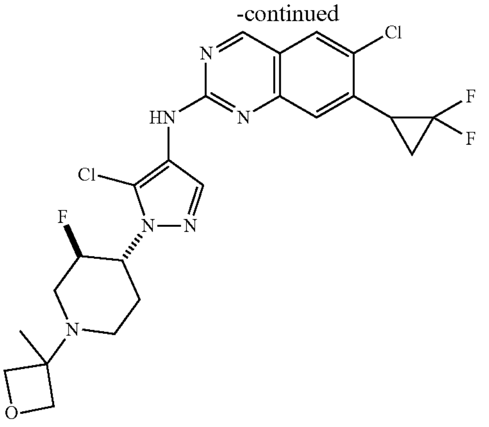

162

SFC

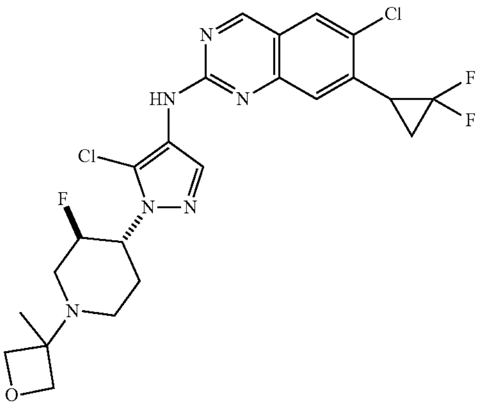

Ex-3.1

+

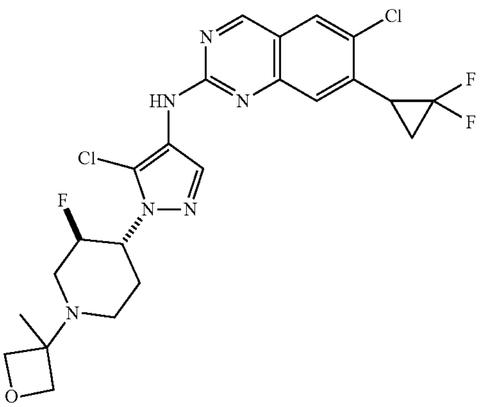

Ex-3.2

2,6-dichloro-7-vinylquinazoline (159)

A 20-mL microwave vial was charged with 7-bromo-2, 6-dichloroquinazoline 6 (300 mg, 1.08 mmol), Pd(dppf) Cl2.$CH_2Cl_2$ (44 mg, 0.054 mmol) and trifluoro(vinyl)-14-borane, potassium salt (145 mg, 1.08 mmol) under inert atmosphere. IPA (10.8 mL) was then added, and to the stirring mixture at RT was added Et3N (608 μL, 4.39 mmol). The resultant mixture was placed in the microwave and stirred at 100° C. for 1 hr. Upon cooling to RT, solvent was removed under reduced pressure and the resultant crude residue was subjected to purification by flash chromatography on silica gel (EtOAc/hexanes, 0-40%) to afford title compound 159. MS (ESI): m/z calc'd for $C_{10}H_7Cl_2N_2$ $[M+H]^+$: 225, found 225.

2,6-dichloro-7-(2,2-difluorocyclopropyl)quinazoline (160)

A 20-mL vial was charged with 2,6-dichloro-7-vinylquinazoline 159 (190 mg, 0.84 mmol) and NaI (25 mg, 0.17 mmol) under inert atmosphere. To this mixture at RT, a THF solution of trimethyl(trifluoromethyl)silane (0.50 M, 4.2 mL) was added. The resultant mixture was then warmed to 55° C. and stirred at this temperature for 72 hrs. Upon cooling to RT, solvent was removed under reduced pressure and the resultant crude residue was subjected to purification by flash chromatography on silica gel (3:1 EtOAc/EtOH in hexanes, 0-20%) to afford the title compound 160. MS (ESI): m/z calc'd for $C_{11}H_7Cl_2F_2N_2$ $[M+H]^+$: 275, found 275.

(3R,4R)(7S) or (3R,4R)(7R) or (3S,4S)(7S) or (3S,4S)(7R) 6-chloro-N-(5-chloro-1-(3-fluoro-1-(3-methyloxetan-3-yl)piperidin-4-yl)-1H-pyrazol-4-yl)-7-(2,2-difluorocyclopropyl)quinazolin-2-amine (Ex-3.1 and Ex-3.2)

A 5-mL microwave vial was charged with $K_3PO_4$ (15 mg, 0.073 mmol) and RuPhos Pd G4 (3.1 mg, 3.6 μmol) under inert atmosphere. 2,6-Dichloro-7-(2,2-difluorocyclopropyl) quinazoline 160 (10 mg, 0.036 mmol) was added as a solution in dioxane (0.5 mL). 5-chloro-1-(3-fluoro-1-(3-methyloxetan-3-yl)piperidin-4-yl)-1H-pyrazol-4-amine 161 (26 mg, 0.091 mmol), which was prepared by reduction of intermediate 59 using a procedure equivalent to that described in Scheme 21 for the preparation of 52, was then added as a solution in dioxane (0.7 mL). The resultant mixture was heated to 80° C. and stirred at this temperature for 18 hrs. Upon cooling to RT, the reaction mixture was filtered through a Celite plug eluting with EtOAc. Solvent was removed from the collected filtrate under reduced pressure, and the resultant crude residue was subjected to purification by flash chromatography on silica gel (3:1 EtOAc/EtOH in hexanes, 0-30%) to afford the racemic title compound 162 in pure form. The racemic material could be resolved to its component enantiomers by chiral preparative SFC(Column & dimensions: OJ-H, 21×250 mm; Mobile phase A: $CO_2$; Mobile phase B: MeOH with 0.1% $NH_4OH$) to afford the title compounds Ex-3.1 (tR=6.0 min) and Ex-3.2 (tR=7.3 min). $^1$H-NMR data below corresponds to Ex-3.1. MS (ESI): m/z calc'd for $C_{19}H_{20}Cl_2FN_6$ $[M+H]^+$: 421, found 421; $^1$H NMR (400 MHz, DMSO-$d_6$, 25° C.) δ: 9.29 (s, 1H), 9.23 (s, 1H), 8.09 (s, 2H), 7.55 (s, 1H), 5.01-4.87 (m, 1H), 4.48-4.38 (m, 3H), 4.16-4.14 (m, 2H), 3.18 (q, J=11.9 Hz, 1H), 3.03-3.01 (m, 1H), 2.64-2.58 (m, 1H), 2.36-2.28 (m, 3H), 2.14-2.04 (m, 2H), 2.00-1.96 (m, 1H), 1.32 (s, 3H).

General Scheme 5.

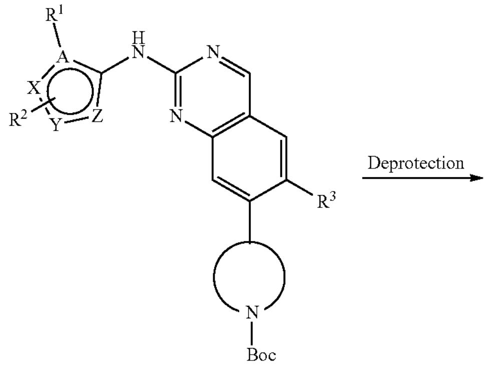

Gen-19

A = C,N
X = C,N
Y = C,N
Z = C,S
$R^1$ = Cl, H, alkyl
$R^2$ = alkyl
$R^3$ = Cl, $CH_3$

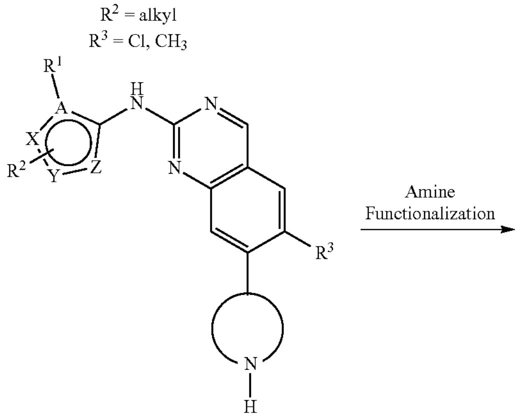

Gen-20

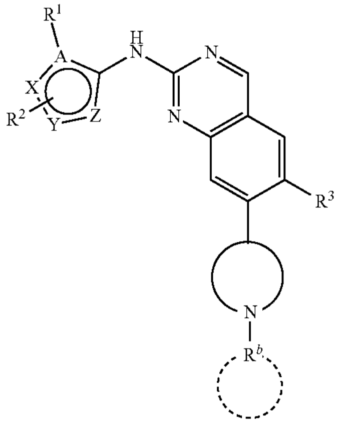

Gen-21

In General Scheme 5, compounds of the form Gen-19 are encompassing of, but not limited to, Gen-12/Gen-14/Gen-18, and specifically refers to instances of these compounds in which the fragment denoted with a circle bears a protected aliphatic amine (—Boc is offered as a protecting group example). Deprotection of Gen-19 under standard conditions reveals the free amine Gen-20. Subsequent functionalization of Gen-20 can be achieved by a number of transformations commonly known to those skilled in the art, including, but not limited to, reductive amination, base-mediated alkylation or conjugate addition, a two-step sequence involving a Strecker reaction followed by a Bruylants reaction (cf. Scheme), a nucleophilic epoxide-opening reaction, or a two-step sequence involving thiocarbamoyl fluoride formation and in situ desulfurization-fluorination, to arrive at compounds of the form Gen-21. In instances of Gen-21 where $R^b$ is an aliphatic thioether-containing fragment, oxidation to the corresponding sulfone was performed. One could contemplate substituents about either of the fragments denoted with a circle (solid or dashed). The representative compounds are described in more detail below.

Preparation of Examples 4.1 and 4.2

Scheme 52. Synthesis of (3S,4S) or (3R,4R) 6-chloro-N-(5-chloro-1-cyclopropyl-1H-pyrazol-4-yl)-7-(3-fluoropiperidin-4-yl)quinazolin-2-amine

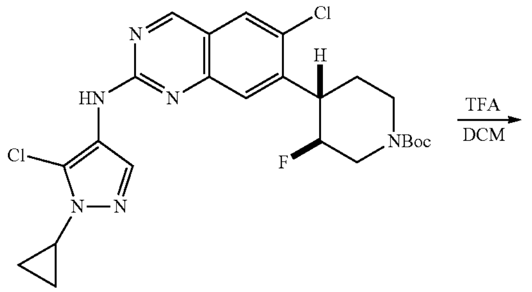

163

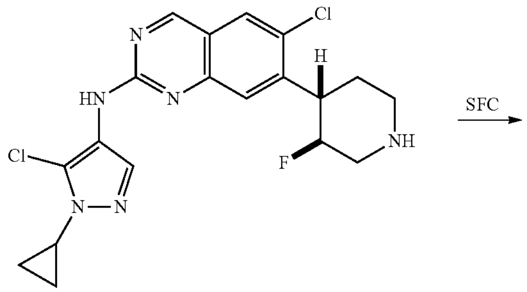

164

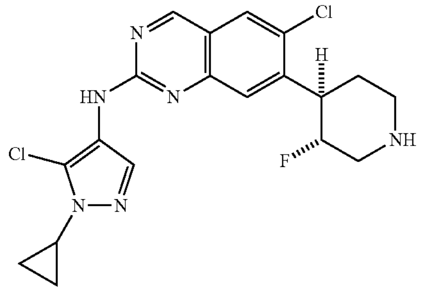

+

Ex-4.1

-continued

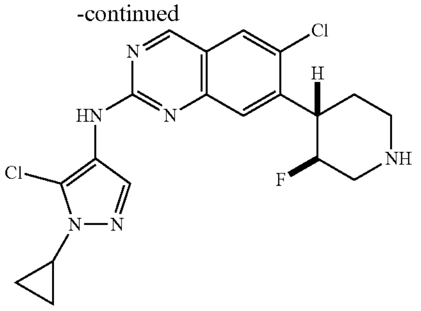

Ex-4.2

(3S,4S) or (3R,4R) 6-chloro-N-(5-chloro-1-cyclopropyl-1H-pyrazol-4-yl)-7-(3-fluoropiperidin-4-yl) quinazolin-2-amine (Ex-4.1 and Ex-4.2)

Starting (3S,4S) and (3R,4R) tert-butyl 4-(6-chloro-2-((5-chloro-1-cyclopropyl-1H-pyrazol-4-yl)amino)quinazolin-7-yl)-3-fluoropiperidine-1-carboxylate 163 was prepared in accordance with the synthetic protocol described in Scheme and the accompanying text, substituting aminoquinazoline 47 for 153, and substituting bromopyrazole 106 for 61. A 100-mL round bottomed flask was charged with 163 (1.5 g, 2.9 mmol). DCM (29 mL) was added, and to the stirring mixture at RT was added TFA (2.2 mL, 29 mmol). The resultant mixture was stirred at RT for 3 hrs, at which point the reaction was quenched by the addition of sat. aq. $NaHCO_3$ (50 mL). The phases were separated, and the aqueous phase extracted with DCM (3×50 mL). The combined organic phases were washed with brine (50 mL), dried over $Na_2SO_4$, and the solvent removed under reduced pressure. The crude residue was subjected to purification by flash chromatography over silica gel (3:1 EtOAc/EtOH in hexanes, 0-100%) to afford the racemic title compound 164 in pure form. The racemic material could be resolved to its component enantiomers by chiral preparative SFC(Column & dimensions: IC, 21 mm×250 mm; Mobile phase A: $CO_2$; Mobile phase B: MeOH with 0.1% $NH_4OH$) to afford the title compounds Ex-4.1 (tR=5.0 min) and Ex-4.2 (tR=5.9 min). MS (ESI): m/z calc'd for $C_{23}H_{24}Cl_2F_3N_6O$ $[M+H]^+$: 527, found 527; $^1H$ NMR (400 MHz, DMSO-$d_6$, 25° C.) δ: 9.19 (s, 2H), 8.03 (s, 1H), 7.90 (bs, 1H), 7.66 (s, 1H), 4.99-4.85 (m, 1H), 3.63-3.59 (m, 1H), 3.37-3.27 (m, 3H), 2.91 (d, J=11.8 Hz, 1H), 2.63-2.53 (m, 1H), 2.46-2.36 (m, 1H), 1.87-1.84 (m, 1H), 1.59-1.52 (m, 1H), 1.11-1.04 (m, 4H).

Preparation of Example 4.3

Scheme 53. Synthesis of 1-(5-chloro-4-((6-chloro-7-(1-(oxetan-3-yl)piperidin-4-yl)quinazolin-2-yl)amino)-1H-pyrazol-1-yl)-2-methylpropan-2-ol

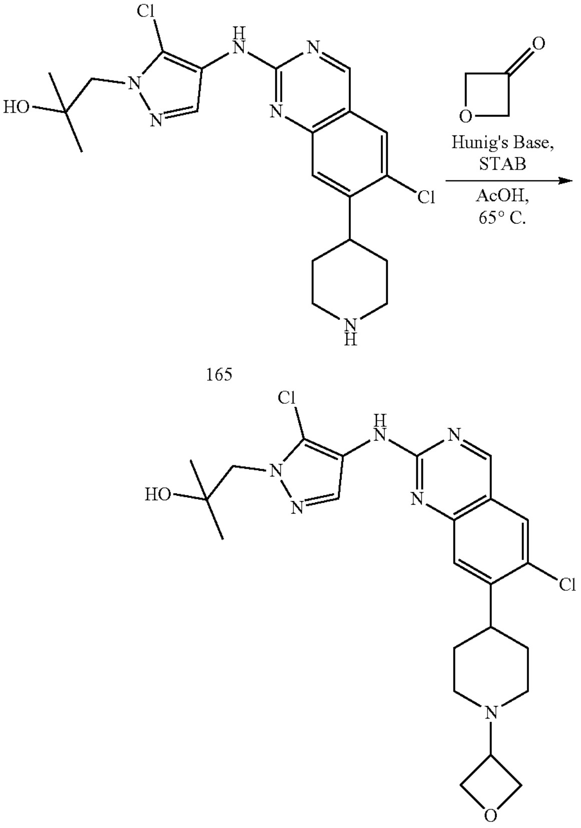

165

Ex-4.3

1-(5-chloro-4-((6-chloro-7-(1-(oxetan-3-yl)piperidin-4-yl)quinazolin-2-yl)amino)-1H-pyrazol-1-yl)-2-methylpropan-2-ol (Ex-4.3)

The Boc-protected precursor (not shown) to starting 1-(5-chloro-4-((6-chloro-7-(piperidin-4-yl)quinazolin-2-yl) amino)-1H-pyrazol-1-yl)-2-methylpropan-2-ol 165 was prepared in accordance with the synthetic protocol described in Scheme and the accompanying text, substituting aminoquinazoline 16 for 153. Removal of the Boc-group was achieved by treatment with TFA in accordance with the synthetic protocol described in Scheme and the accompanying text and provided intermediate 165. A 20-mL scintillation vial was charged with intermediate 165 (40 mg, 0.092 mmol), STAB (49 mg, 0.23 mmol), and activated 4 Å molecular sieves under an inert atmosphere. DCE (459 μL) was added, followed by 3-oxetanone (15 μL, 0.23 mmol), and finally AcOH (8 μL, 0.138 mmol). The reaction mixture was warmed to 65° C. and stirred at this temperature for 6 hrs. On cooling to RT, the crude reaction mixture was filtered, and solvent was removed from the collected filtrate under reduced pressure. The resultant crude residue was purified by reversed phase HPLC, eluting with water (0.1% TFA)-MeCN to afford the title compound Ex-4.3. MS (ESI):

m/z calc'd for $C_{23}H_{29}Cl_2N_6O_2$ $[M+H]^+$: 491, found 491; $^1H$ NMR (400 MHz, DMSO-$d_6$, 25° C.) δ: 9.18 (s, 1H), 9.17 (s, 1H), 8.02 (m, 2H), 7.49 (s, 1H) 4.75 (s, 1H), 4.56 (t, J=4 Hz 2H), 4.47 (t, J=4 Hz, 2H), 4.04 (s, 2H), 3.46 (m, 1H), 2.98 (m, 1H), 2.86 (m, 2H), 1.94 (m, 2H), 1.85 (m, 2H), 1.74 (m, 2H), 1.15 (s, 6H)

Preparation of Examples 4.4 and 4.5

Scheme 54. Synthesis of (3S,4S) or (3R,4R) 1-(5-chloro-4-((6-chloro-7-(1-ethylpiperidin-4-yl)quinazolin-2-yl)amino)-1H-pyrazol-1-yl)-2-methylpropan-2-ol

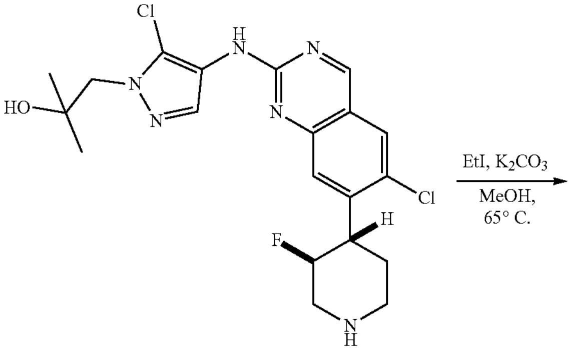

166

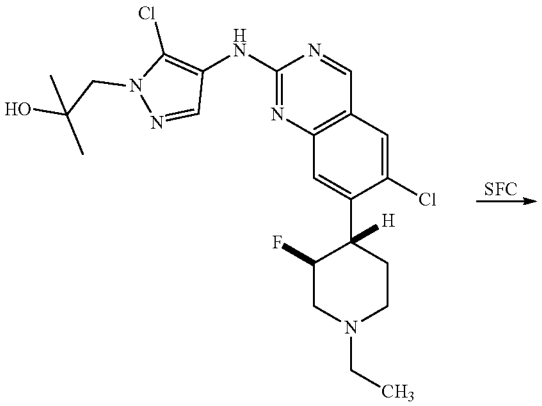

167

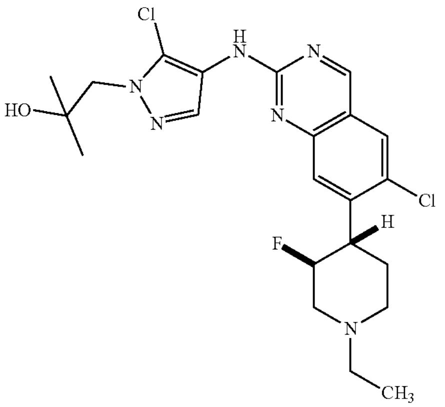

+

Ex-4.4

-continued

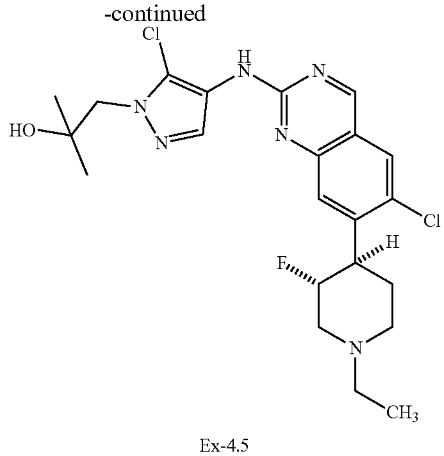

Ex-4.5

(3S,4S) or (3R,4R) 1-(5-chloro-4-((6-chloro-7-(1-ethyl-3-fluoropiperidin-4-yl)quinazolin-2-yl)amino)-1H-pyrazol-1-yl)-2-methylpropan-2-ol (Ex-4.4 and Ex-4.5)

The Boc-protected precursor (not shown) to starting (3S, 4S) and (3R,4R) 1-(5-chloro-4-((6-chloro-7-(3-fluoropiperidin-4-yl)quinazolin-2-yl)amino)-1H-pyrazol-1-yl)-2-methylpropan-2-ol 166 was prepared in accordance with the synthetic protocol described in Scheme and the accompanying text, substituting aminoquinazoline 47 for 153. Removal of the Boc-group was achieved by treatment with TFA in accordance with the synthetic protocol described in Scheme and the accompanying text to provide compound 166. A 20-mL scintillation vial was charged with racemic compound 166, (200 mg, 0.22 mmol), 4 Å molecular sieves, and potassium carbonate (243 mg, 1.76 mmol), under inert atmosphere. MeCN (1.1 mL) was added, and to the stirring mixture at RT was added iodoethane (53 uL, 0.66 mmol). The resultant mixture was stirred at 30° C. for 30 min, at which point the reaction was diluted with DCM and washed with sat. aq. $NaHCO_3$. The combined organic layers were dried over $Na_2SO_4$, and the solvent was removed under reduced pressure. The resultant crude residue was subjected to purification by silica gel chromatography (3:1 EtOAc/EtOH in hexanes, 0-100%) to afford the racemic title compound 167 in pure form. The racemic material could be resolved to its component enantiomers by chiral preparative SFC (Column & dimensions: OJ-H, 21 mm×250 mm; Mobile phase A: $CO_2$; Mobile phase B: MeOH with 0.1% $NH_4OH$) to afford the title compounds Ex-4.4 (tR=5.5 min) and Ex-4.5 (tR=6.6 min). MS (ESI): m/z calc'd for $C22H_{28}Cl_2FN_6O$ $[M+H]^+$: 481, found 481; $^1H$ NMR (400 MHz, DMSO-$d_6$, 25° C.) δ: 9.20 (s, 2H), 8.07 (bs, 1H), 8.05 (s, 1H), 7.73 (s, 1H), 5.12 (m, 1H), 5.01 (m, 1H), 4.75 (s, 1H), 4.04 (s, 2H), 3.36 (m, 1H), 3.24 (m, 1H), 2.92 (m, 1H), 2.50 (m, 1H), 2.13-2.02 (m, 2H), 1.91 (m, 1H), 1.64 (m, 1H), 1.16 (s, 6H), 1.06-1.04 (m, 3H). MS (ESI): m/z calc'd for $C_{22}H_{28}Cl_2FN_6O$ $[M+H]^+$: 481, found 481; $^1H$ NMR (400 MHz, DMSO-$d_6$, 25° C.) δ: 9.20 (s, 2H), 8.07 (bs, 1H), 8.05 (s, 1H), 7.73 (s, 1H), 5.12 (m, 1H), 5.01 (m, 1H), 4.75 (s, 1H), 4.04 (s, 2H), 3.36 (m, 1H), 3.24 (m, 1H), 2.92 (m, 1H), 2.50 (m, 1H), 2.13-2.02 (m, 2H), 1.91 (m, 1H), 1.64 (m, 1H), 1.16 (s, 6H), 1.06-1.04 (m, 3H).

Preparation of Example 4.6

Scheme 55. Synthesis of (S) and (R) 3-(4-(6-chloro-2-((5-chloro-1-(2,2-difluoroethyl)-1H-pyrazol-4-yl)amino)quinzolin-7-yl)piperidin-1-yl)tetrahydrothiophene 1,1-dioxide

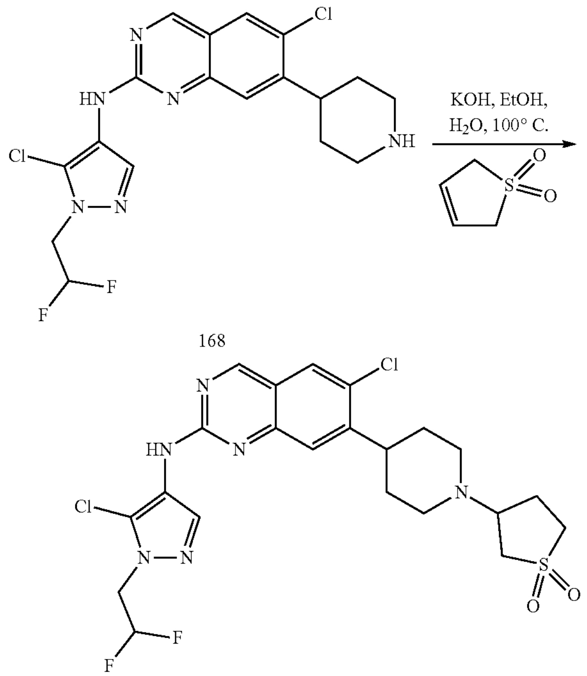

168

Ex-4.6

(S) and (R) 3-(4-(6-chloro-2-((5-chloro-1-(2,2-difluoroethyl)-1H-pyrazol-4-yl)amino)quinazolin-7-yl) piperidin-1-yl)tetrahydrothiophene 1,1-dioxide (Ex-4.6)

The Boc-protected precursor (not shown) to starting 6-chloro-N-(5-chloro-1-(2,2-difluoroethyl)-1H-pyrazol-4-yl)-7-(piperidin-4-yl)quinazolin-2-amine 168 was prepared by reacting the corresponding intermediate of type Gen-8 (cf. General Scheme 2) with intermediate 15 in accordance with the synthetic protocol described in Scheme 8 and the accompanying text. Removal of the Boc-group was achieved by treatment with TFA in accordance with the synthetic protocol described in Scheme and the accompanying text to provide compound 168. A 20-mL scintillation vial was charged with compound 168 (75 mg, 0.14 mmol) under inert atmosphere. EtOH (2 mL) and water (1 mL) were added, followed by addition of 3-sulfolene (34 mg, 0.284 mmol) and aqueous 1N potassium hydroxide (570 µl, 0.57 mmol). The resultant mixture was heated to 100° C. and stirred at this temperature overnight. Upon cooling to RT, the reaction was quenched with sat. aq. $NaHCO_3$ and diluted with DCM. The phases were separated, and the aqueous phase extracted with DCM (2×25 mL). The combined organic phases were dried over $MgSO_4$, filtered, and solvent was removed from the collected filtrate under reduced pressure. The resultant crude residue was subjected to purification by flash chromatography over silica gel (MeOH/DCM, 0-10%) to afford the racemic title compound Ex-4.6.

MS (ESI): m/z calc'd for $C_{22}H_{24}Cl_2F_2N_6O_2S$ $[M+H]^+$: 545, found 545; $^1H$ NMR (400 MHz, DMSO-$d_6$, 25° C.) δ: 9.40-9.16 (m, 2H), 8.10 (s, 1H), 8.03 (s, 1H), 7.48 (s, 1H), 6.41 (t, J=54.3 Hz, 1H), 4.65 (t, J=14.9 Hz, 2H), 3.44-3.33 (m, 2H), 3.30-3.21 (m, 1H), 3.16-3.05 (m, 2H), 3.05-2.89 (m, 3H), 2.41-2.30 (m, 1H), 2.31-2.16 (m, 2H), 2.10-1.94 (m, 1H), 1.93-1.81 (m, 2H), 1.77-1.63 (m, 2H).

Preparation of Example 4.7

Scheme 56. Synthesis of 6-chloro-N-(5-chloro-1-(1-methylcyclopropyl)-1H-pyrazol-4-yl)-7-(1-(trifluoromethyl)piperidin-4-yl)quinazolin-2-amine

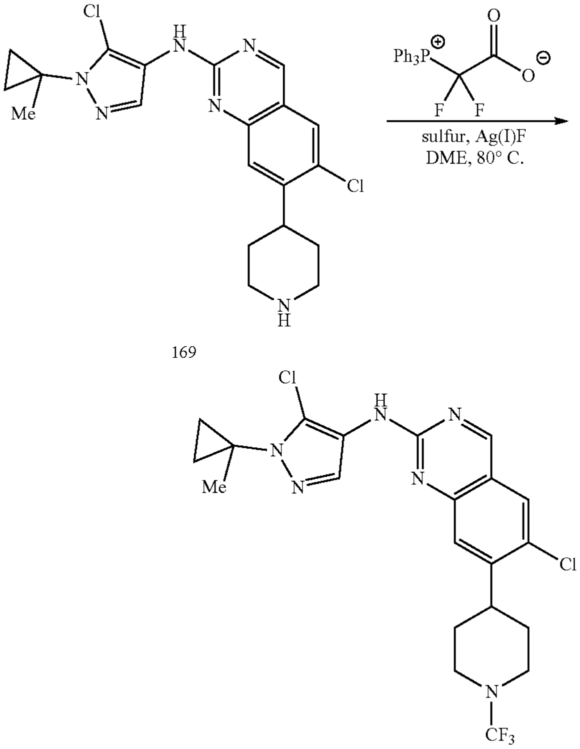

169

Ex-4.7

6-chloro-N-(5-chloro-1-(1-methylcyclopropyl)-1H-pyrazol-4-yl)-7-(1-(trifluoromethyl)piperidin-4-yl) quinazolin-2-amine (Ex-4.7)

The Boc-protected precursor (not shown) to starting 6-chloro-N-(5-chloro-1-(1-methylcyclopropyl)-1H-pyrazol-4-yl)-7-(piperidin-4-yl)quinazolin-2-amine 169 was prepared by reacting intermediates 16 and 65 in accordance with the sequence illustrated in General Scheme 3 using an analogous synthetic protocol to that described in Scheme and the accompanying text for the preparation of intermediate 154. Removal of the Boc-group was achieved by treatment with TFA in accordance with the synthetic protocol described in Scheme and the accompanying text to provide intermediate 169. A 4-mL scintillation vial was charged with intermediate 169 (150 mg, 0.36 mmol), 2,2-difluoro-2-(triphenylphosphonio)acetate (160 mg, 0.45 mmol), and sulfur (23 mg, 0.72 mmol), under inert atmosphere. DME (2.7 mL) was added, and the resultant mixture was stirred at 50° C. for 30 minutes. The reaction was cooled to RT, then silver (I) fluoride (205 mg, 1.62 mmol) was added, and the resultant mixture was stirred at 80° C. for 12 hrs. On cooling to RT, the reaction was diluted with DCM and the mixture was filtered through Celite 0 (diatomaceous earth). Solvent was removed from the collected filtrate under reduced pressure, and the resultant crude residue was subjected to purification by flash chromatography over silica gel (3:1 EtOAc/EtOH in hexanes, 0-60%) to afford the title compound Ex-4.7. MS (ESI): m/z calc'd for $C_{21}H_{21}Cl_2F_3N_6$ $[M+H]^+$: 485, found 485; $^1H$ NMR (400 MHz, DMSO-$d_6$, 25° C.) δ: 9.19 (s, 2H), 8.04 (s, 1H), 7.94 (bs, 1H), 7.53 (s, 1H), 4.01-3.97 (m, 2H), 3.25-3.16 (m, 3H), 1.93-1.87 (m, 2H), 1.81-1.75 (m, 2H), 1.49 (s, 3H), 1.21 (s, 2H), 1.04 (s, 2H).

Preparation of Example 4.8

Scheme 57. Synthesis of 1-((2S)-4-(6-chloro-2-((5-chloro-1-cyclopropyl-1H-pyrazol-4-yl)amino)quinazolin-7-yl)-2-methylpiperidin-1-yl)ethan-1-one

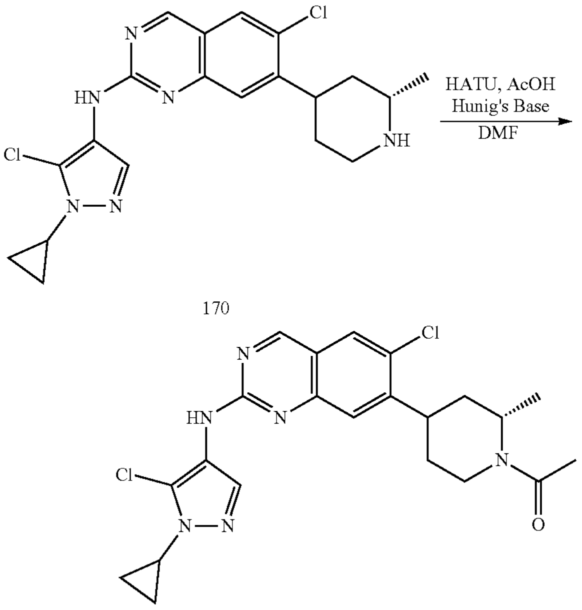

170

Ex-4.8

1-42S)-4-(6-chloro-2-((5-chloro-1-cyclopropyl-1H-pyrazol-4-yl)amino)quinazolin-7-yl)-2-methylpiperidin-1-yl)ethan-1-one (Ex-4.8)

Starting 6-chloro-N-(5-chloro-1-cyclopropyl-1H-pyrazol-4-yl)-7-42S)-2-methylpiperidin-4-yl)quinazolin-2-amine 170 was prepared by the same method used for the synthesis of 147, substituting intermediates 12 and 19 as starting materials. A 5-mL microwave vial was charged with intermediate 170 (250 mg, 0.253 mmol) and HATU (241 mg, 0.633 mmol) under inert atmosphere. DMF (1.26 mL) was added, and to the stirring mixture at RT was added Hunig's base (177 μL, 1.01 mmol). Finally, acetic acid (30 mg, 0.506 mmol) was added, and the resultant mixture was stirred at rt for 2 hrs. At 2 hrs, the reaction was diluted with DCM and quenched by slow addition of sat. aq. $NaHCO_3$ (50 mL). The phases were separated and the aqueous phase extracted with DCM (3×50 mL). The combined organic phases were washed with $H_2O$(50 mL), dried over anhydrous $Na_2SO_4$, filtered, and solvent was removed from the collected filtrate under reduced pressure. The crude residue was subject to purification by reversed phase HPLC, eluting with water (0.1% $NH_4OH$)-MeCN to afford the title compound Ex-4.8. MS (ESI) m/z calc'd for $C_{22}H_{25}O_2N_6O$ [M+H]+: 459, found 459. $^1H$ NMR (400 MHz, DMSO-$d_6$, 25° C.) δ: 9.19 (s, overlap, 2H), 8.03 (s, 1H), 7.88 (s, 1H), 7.45 (s, 1H), 4.93-4.83 (m, 1H), 4.52-4.26 (m, 1H), 3.81 (m, 1H), 3.61 (m, 1H), 3.51-3.41 (m, 1H), 2.83 (m, 1H), 2.05 (m, 3H), 1.88-1.75 (m, 3H), 1.63-1.53 (m, 1H), 1.33 (d, 1H), 1.21 (d, 1H), 1.11-1.04 (m, 4H).

Preparation of Example 4.9

Scheme 58. Synthesis of (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) (4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol

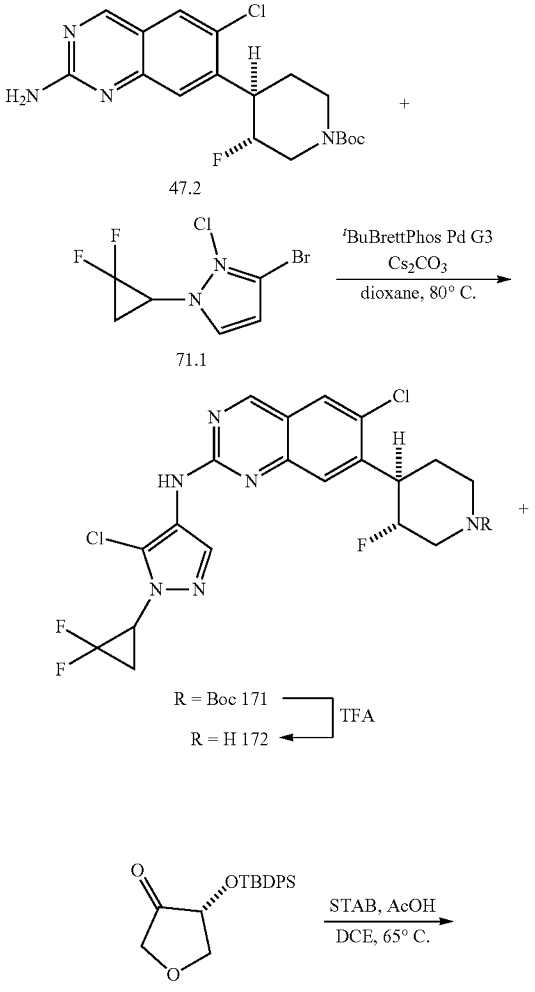

47.2

71.1

R = Boc 171

R = H 172

25

-continued

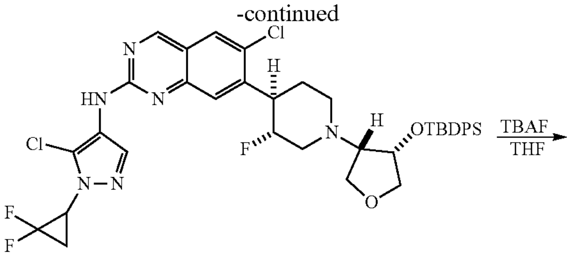

173

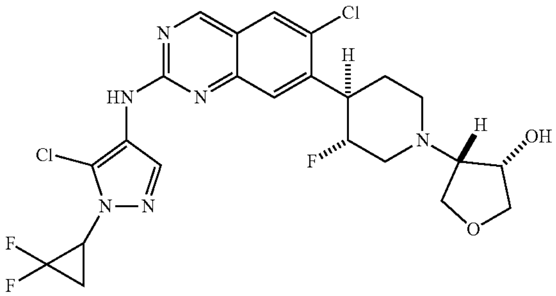

Ex-4.9

(R)(3S,4S) or (R)(3R,4R) or (S)(3S,4S) or (S)(3R, 4R) tert-butyl 4-(6-chloro-2-((5-chloro-1-(2,2-difluorocyclopropyl)-1H-pyrazol-4-yl)amino)quinazolin-7-yl)-3-fluoropiperidine-1-carboxylate (171)

A 20 mL oven-dried microwave vial was charged with (3S,4S) or (3R,4R) tert-butyl 4-(2-amino-6-chloroquinazolin-7-yl)-3-fluoropiperidine-1-carboxylate 47.2 (500 mg, 1.31 mmol), (R) or (S) 4-bromo-5-chloro-1-(2,2-difluorocyclopropyl)-1H-pyrazole 71.1 (507 mg, 1.97 mmol), cesium carbonate (2.14 g, 6.56 mmol), and $^{t}$BuBrettPhos Pd G3 (337 mg, 0.394 mmol) under inert atmosphere. The vial was evacuated and purged with argon (3×). Dioxane (4.4 mL) was added and the reaction mixture was warmed to 80° C. with stirring and maintained at this temperature overnight. Upon cooling to RT, the mixture was diluted with EtOAc (10 mL) and filtered through Celite, eluting with additional EtOAc (2×20 mL). Solvent was removed from the collected filtrate under reduced pressure. The crude residue was subjected to purification by flash chromatography over silica gel (10-85% EtOAc/DCM) to afford the title compound 171. MS (ESI): m/z calc'd for $C_{24}H_{26}Cl_2F_3N_6O_2$ $[M+H]^+$: 557, found 557.

(R)(3S,4S) or (R)(3R,4R) or (S)(3S,4S) or (S)(3R, 4R) 6-chloro-N-(5-chloro-1-(2,2-difluorocyclopropyl)-1H-pyrazol-4-yl)-7-(3-fluoropiperidin-4-yl) quinazolin-2-amine (172)

A 30 mL scintillation vial was charged with intermediate 171 (505 mg, 0.906 mmol) under inert atmosphere. DCM (9.1 mL) was added, and to the stirring solution at RT was added trifluoroacetic acid (698 μL, 9.1 mmol). At 3 hrs, the reaction mixture was diluted with DCM (15 mL) and transferred to a separatory funnel containing sat. aq. $NaHCO_3$ (50 mL). The phases were separated and the aqueous phase was extracted once more using 3:1 $CHCl_3$/IPA (40 mL). The combined organic layers were dried over anhydrous $Na_2SO_4$, filtered, and the solvent removed from the collected filtrate under reduced pressure to afford the title compound 172. MS (ESI): m/z calc'd for $C_{19}H_{18}Cl_2F_3N_6$ $[M+H]^+$: 457, found 457.

(R)(3S,4S)(3S,4S) or (R)(3S,4S)(3R,4R) or (R)(3R, 4R)(3S,4S) or (R)(3R,4R)(3R,4R) or (S)(3S,4S)(3S, 4S) or (S)(3S,4S)(3R,4R) or (S)(3R,4R)(3S,4S) or (S)(3R,4R)(3R,4R) 74144-((tert-butyldiphenylsilyl) oxy)tetrahydrofuran-3-yl)-3-fluoropiperidin-4-yl)-6-chloro-N-(5-chloro-1-(2,2-difluorocyclopropyl)-1H-pyrazol-4-yl)quinazolin-2-amine (173)

A 3-necked 250-mL round-bottom flask fitted with a reflux condenser was charged with intermediate 172 (414 mg, 0.905 mmol), (R) or (S) 4-((tert-butyldiphenylsilyl)oxy) dihydrofuran-3(2H)-one 25 (462 mg, 1.36 mmol), sodium triacetoxyborohydride (575 mg, 2.72 mmol), and approximately ~1 weight equivalent of oven-dried 4-angstrom molecular sieves under inert atmosphere. DCE (18 mL) was added and to the stirring mixture at RT was added acetic acid (155 μL, 2.72 mmol), and the reaction was heated to 70° C. At 2 hrs the mixture was diluted with DCM (50 mL) and filtered through a medium porosity frit to remove debris from the molecular sieves as well as some inorganics. The filtrate was then carefully transferred to an Erlenmeyer flask containing sat. aq. $NaHCO_3$ (100 mL) where it was mixed thoroughly. This mixture was then transferred to a separatory funnel where the phases were separated and the aqueous phase extracted with DCM (2×30 mL). The combined organic layers were dried over anhydrous $Na_2SO_4$, filtered, and solvent was removed from the collected filtrate under reduced pressure. The crude residue was subjected to purification by flash chromatography over silica gel (10-85% EtOAc/DCM) to afford the title compound 173. MS (ESI): m/z calc'd for $C_{39}H_{42}Cl_2F_3N_6O_2Si$ $[M+H]^+$: 781, found 781.

(R)(3S,4S)(3S,4S) or (R)(3S,4S)(3R,4R) or (R)(3R, 4R)(3S,4S) or (R)(3R,4R)(3R,4R) or (S)(3S,4S)(3S, 4S) or (S)(3S,4S)(3R,4R) or (S)(3R,4R)(3S,4S) or (S)(3R,4R)(3R,4R) 4-(4-(6-chloro-2-((5-chloro-1-(2, 2-difluorocyclopropyl)-1H-pyrazol-4-yl)amino)quinazolin-7-yl)-3-fluoropiperidin-1-yl)tetrahydrofuran-3-ol (Ex-4.9)

A 30 mL scintillation vial equipped with a magnetic stirrer was charged with intermediate 173 (472 mg, 0.604 mmol) under inert atmosphere. THF (12 mL) was added and to the stirring mixture at RT was added tetra-n-butylammonium fluoride (1 M in THF, 3.00 mL, 3.00 mmol). After stirring overnight, the reaction was diluted with EtOAc (25 mL) and transferred to a separatory funnel containing sat. aq. $NH_4Cl$ (60 mL). Phases were separated and the aqueous phase was extracted with EtOAc (2×25 mL). The combined organic phases were then washed with brine (75 mL), dried over anhydrous $Na_2SO_4$, filtered, and solvent was removed from the collected filtrate under reduced pressure. The crude material was subjected to purification by flash chromatography over silica gel (Solvent A=DCM, Solvent B=80:20:1 DCM:MeOH:7 N $NH_3$ in MeOH; 5-20%) to afford the title compound Ex-4.9. MS (ESI): m/z calc'd for $C_{23}H_{24}Cl_2F_3N_6O_2$ [M+H]+: 543, found 543; $^1$H NMR (500 MHz, DMSO-$d_6$, 25° C.) δ: 9.40 (s, 1H), 9.23 (s, 1H), 8.11

(s, 1H), 8.07 (s, 1H), 7.74 (s, 1H), 5.17 (dtd, J=48.7, 9.8, 4.5 Hz, 1H), 4.51 (dd, J=8.9, 8.4 Hz, 1H), 4.43 (s, 1H), 4.28-4.16 (m, 1H), 3.87 (d, overlap, J=10.8 Hz, 1H), 3.85 (d, overlap, J=9.5 Hz, 1H), 3.69 (d, J=9.5 Hz, 1H), 3.59 (dd, J=10.0, 7.6 Hz, 1H), 3.54-3.46 (m, 1H), 3.33-3.24 (m, 1H),
2.81 (ddd, J=10.5, 7.2, 4.2 Hz, 1H), 2.65 (br d, J=10.5 Hz, 1H), 2.49-2.39 (m, 2H), 2.33-2.21 (m, 2H), 1.93-1.86 (m, 1H), 1.76-1.62 (m, 1H).
Preparation of Examples 4.10 and 4.11
Scheme 59. Synthesis of (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
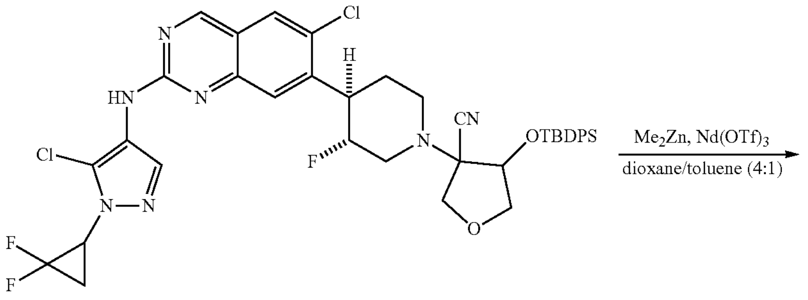
175
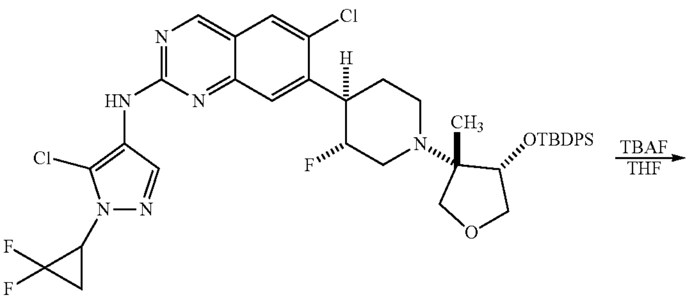
174
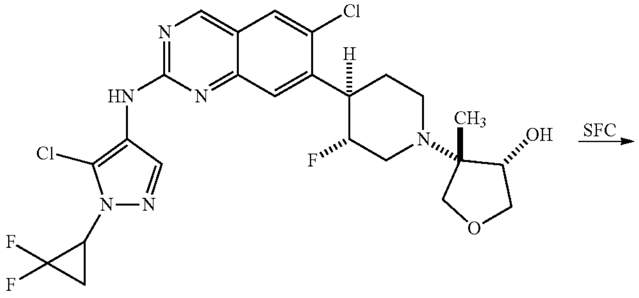
176
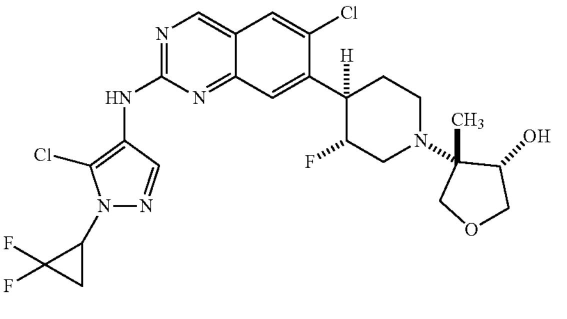
+
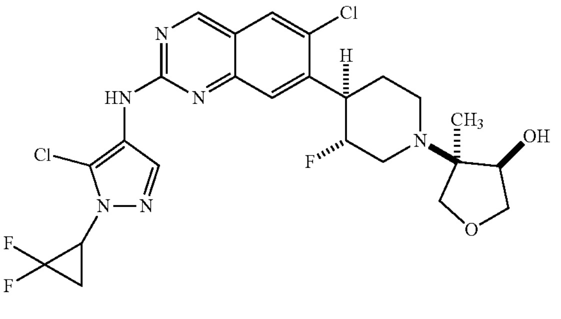
Ex-4.10
Ex-4.11

4-((tert-butyldiphenylsilyl)oxy)-3-methyltetrahydrofuran-3-yl)-3-fluoropiperidin-4-yl)-6-chloro-N-(5-chloro-1-(2,2-difluorocyclopropyl)-1H-pyrazol-4-yl)quinazolin-2-amine (174)

Starting aminonitrile 175 was prepared by reacting the corresponding NH-piperidine precursor with ketone 25 under standard Strecker reaction conditions as were described for the preparation of intermediate 28. A 30-mL scintillation vial was charged with intermediate 175 (800 mg, 0.992 mmol) and neodymium (III) triflate (147 mg, 0.248 mmol) under inert atmosphere. Dioxane (2 mL) and toluene (500 μL) were added, and the mixture was stirred and cooled to 0° C. To the stirring mixture at this temperature was slowly added dimethylzinc (2 M in toluene, 2.48 mL, 4.96 mmol). On complete addition, the mixture was stirred at 0° C. for 15 minutes, at which point the reaction was warmed to 50° C. and stirred at this temperature overnight. The reaction was cooled to RT, then carefully quenched by pouring into 1 M aq. NaOH (40 mL). The mixture was then extracted with DCM (3×25 mL). The combined organic layers were washed with a sat. aq. solution of Rochelle's salt (2×75 mL), brine (1×75 mL), dried over anhydrous $Na_2SO_4$, filtered, and the solvent removed from the collected filtrate under reduced pressure. The crude residue was subjected to purification by flash chromatography over silica gel (10-65% EtOAc/DCM) to afford the title compound 174. MS (ESI): m/z calc'd for $C_{40}H_{44}Cl_2F_3N_6O_2Si$ $[M+H]^+$: 795, found 795.

(R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol (Ex-4.10 and Ex-4.11)

A 30 mL scintillation vial was charged with intermediate 174 (188 mg, 0.236 mmol) under inert atmosphere. THF (2.4 mL) was added, and to the stirring mixture at RT was then added TBAF (1 M in THF, 1.18 mL, 1.18 mmol) via syringe. After stirring for 3.5 hrs, the reaction was diluted with EtOAc (30 mL) and transferred to a separatory funnel containing sat. aq. $NH_4Cl$ (50 mL). Phases were separated and the aqueous phase was extracted once more with EtOAc (30 mL). The combined organic phases were then added back to the separatory funnel and washed with brine (1×50 mL). The combined organic layers were dried over $Na_2SO_4$, filtered, and concentrated to dryness in vacuo. The crude material was subjected to purification by flash chromatography over silica gel (Solvent A=DCM, Solvent B=80:20:1 DCM:MeOH:7 N $NH_3$ in MeOH; 5-20%) to afford the title compound 176 as a mixture of major and minor diastereomers This material could be resolved to its component stereoisomers by chiral preparative SFC(Column & dimensions: AS-H, 21 mm×250 mm; Mobile phase A: $CO_2$; Mobile phase B: MeOH with 0.1% $NH_4OH$) to afford the title compounds Ex-4.10 (tR=4.2 min) and Ex-4.11 (tR=5.5 min). MS (ESI): m/z calc'd for $C_{24}H_{26}Cl_2F_3N_6O_2$ $[M+H]^+$: 557, found 557; $^1H$ NMR (500 MHz, DMSO-$d_6$, 25° C.) δ: 9.33 (s, 1H), 9.23 (s, 1H), 8.06 (s, overlap, 2H), 7.82 (s, 1H), 5.28 (dtd, J=49.1, 9.9, 4.8 Hz, 1H), 4.51 (dd, J=8.6, 8.0 Hz, 1H), 4.33 (s, 1H), 3.95 (dd, J=9.7, 3.3 Hz, 1H), 3.85 (m, br, 1H), 3.70 (d, J=9.6 Hz, 1H), 3.60 (d, J=7.3 Hz, 1H), 3.53 (d, J=7.3 Hz, 1H), 3.27 (m, 1H), 3.23-3.13 (m, 1H), 2.50-2.35 (m, overlap, 5H), 1.95-1.81 (m, 1H), 1.81-1.66 (m, 1H), 1.05 (s, 3H). MS (ESI): m/z calc'd for $C_{24}H_{26}Cl_2F_3N_6O_2$ $[M+H]^+$: 557, found 557; $^1H$ NMR (500 MHz, DMSO-$d_6$, 25° C.) δ: 9.34 (s, 1H), 9.23 (s, 1H), 8.07 (s, overlap, 2H), 7.83 (s, 1H), 5.12 (dtd, J=49.1, 9.8, 5.0 Hz, 1H), 4.51 (dd, J=8.6, 8.2 Hz, 1H), 4.32 (s, 1H), 3.95 (dd, J=9.6, 3.2 Hz, 1H), 3.78 (s, 1H), 3.70 (d, J=9.6 Hz, 1H), 3.65 (d, J=7.3 Hz, 1H), 3.58 (d, J=7.3 Hz, 1H), 2.89-2.80 (m, 1H), 2.80-2.72 (m, 1H), 2.61-2.53 (m, 1H), 2.48-2.43 (m, overlap, 2H), 1.85 (m, 2H), 1.30-1.13 (m, 2H), 1.05 (s, 3H).

Preparation of Examples 4.12 and 4.13

Scheme 60. Synthesis of (R) or (S) 3-(4-(6-chloro-2-((1-cyclopropyl-5-methyl-1H-pyrazol-4-yl)amino)quinazolin-7-yl)piperidin-1-yl)-1,1,1-trifluoropropan-2-ol

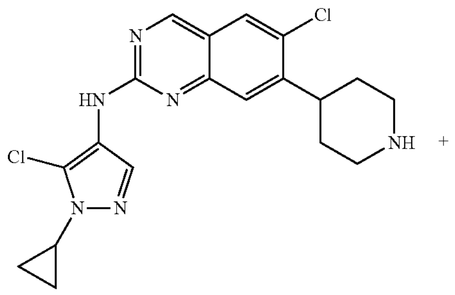

177

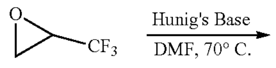

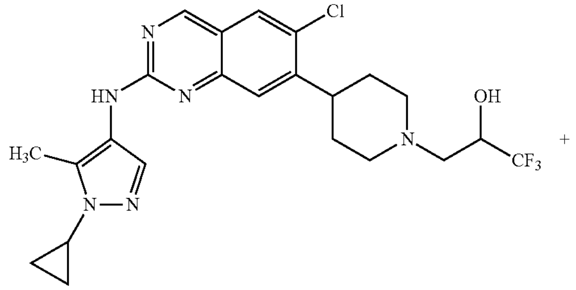

Ex.-4.12

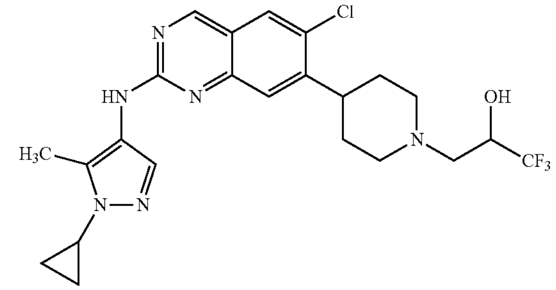

Ex.-4.13

(R) or (S) 3-(4-(6-chloro-2-((1-cyclopropyl-5-methyl-1H-pyrazol-4-yl)amino)quinazolin-7-yl) piperidin-1-yl)-1,1,1-trifluoropropan-2-ol (Ex-4.12 and Ex-4.13)

A 5-mL microwave vial was charged with 6-chloro-N-(1-cyclopropyl-5-methyl-1H-pyrazol-4-yl)-7-(piperidin-4-yl) quinazolin-2-amine 177 (100 mg, 0.261 mmol) and 2-(trifluoromethyl)oxirane (146 mg, 1.306 mmol) under inert atmosphere. DMF (1.75 mL) was added. Finally, to the stirring mixture at RT was added Hunig's base (228 μL, 1.31 mmol). The sealed reaction mixture was heated to 70° C. and maintained at this temperature for 30 min. On cooling to RT, the mixture was diluted with DMSO(6 mL) and aliquots subjected to purification by reversed phase HPLC, eluting with water (0.1% TFA)-MeCN to afford the title compound as a racemic mixture. The material was then free-based by liquid-liquid extraction (sat. aq. $NaHCO_3$/3:1 $CHCl_3$:IPA). The purified racemate could be resolved to its component enantiomers by chiral preparative SFC(Column & dimensions: CCA F4, 21 mm×250 mm; Mobile phase A: $CO_2$; Mobile phase B: MeOH with 0.1% $NH_4OH$) to afford the title compounds Ex-4.12 (tR=2.5 min) and Ex-4.13 (tR=3.1 min). MS (ESI) m/z calc'd for $C_{23}H_{27}ClF_3N_{60}$ $[M+H]^+$: 495, found 495. $^1H$ NMR (500 MHz, DMSO-$d_6$, 25° C.) δ: 9.13 (s, 1H), 9.06 (s, 1H), 7.97 (s, 1H), 7.71 (s, 1H), 7.41 (s, 1H), 4.16 (m, 1H), 3.50 (m, 2H), 3.08 (t, J=11.0 Hz, 2H), 2.95 (m, 1H), 2.65-2.53 (m, 2H), 2.30 (s, 3H), 2.28-2.16 (m, 2H), 1.84 (m, 2H), 1.78-1.63 (m, 2H), 1.08-1.02 (m, 2H), 0.99 (m, 2H). MS (ESI) m/z calc'd for $C_{23}H_{27}ClF_3N_{60}$ $[M+H]^+$: 495, found 495. $^1H$ NMR (500 MHz, DMSO-$d_6$, 25° C.) δ: 9.13 (s, 1H), 9.06 (s, 1H), 7.97 (s, 1H), 7.71 (s, 1H), 7.41 (s, 1H), 4.16 (m, 1H), 3.50 (m, 2H), 3.08 (t, J=11.0 Hz, 2H), 2.95 (m, 1H), 2.65-2.53 (m, 2H), 2.30 (s, 3H), 2.28-2.16 (m, 2H), 1.84 (m, 2H), 1.78-1.63 (m, 2H), 1.08-1.02 (m, 2H), 0.99 (m, 2H).

Preparation of Example 4.14

Scheme 61. Synthesis of 3-(4-(6-chloro-2-((5-chloro-1-(2,2-difluoroethyl)-1H-pyrazol-4-yl) amino)quinazolin-7-yl)piperidin-1-yl)thietane 1,1-dioxide

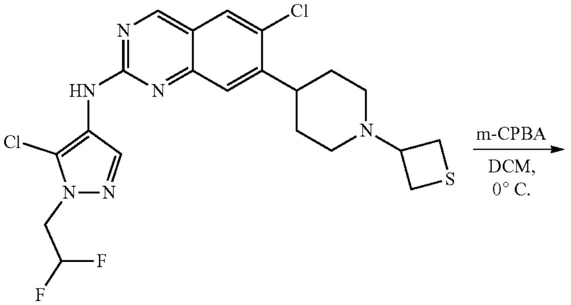

178

-continued

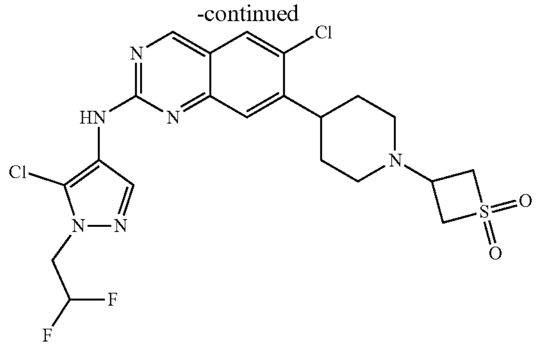

Ex.-4.14

3-(4-(6-chloro-2-((5-chloro-1-(2,2-difluoroethyl)-1H-pyrazol-4-yl)amino)quinazolin-7-yl)piperidin-1-yl)thietane 1,1-dioxide (Ex-4.14)

Starting 6-chloro-N-(5-chloro-1-(2,2-difluoroethyl)-1H-pyrazol-4-yl)-7-(1-(thietan-3-yl)piperidin-4-yl)quinazolin-2-amine 178 was prepared by reaction of intermediate 168 (cf. Scheme 55) under the reductive amination conditions described in Scheme, substituting thietan-3-one for oxetan-3-one. A 20-mL scintillation vial was charged with intermediate 178 (19 mg, 0.038 mmol) under inert atmosphere. DCM (2 mL) was added, and the solution was cooled to 0° C. To the stirring mixture at this temperature was added m-CPBA (22 mg, 0.13 mmol) and the resultant mixture was allowed to stir at 0° C. for 1 hr. The reaction mixture was quenched with sat. aq. sodium metabisulfite and sat. aq. $NaHCO_3$ and diluted with DCM. The phases were separated, and the aqueous phase extracted with DCM (2×25 mL). The combined organic phases were dried over $Na_2SO_4$, filtered, and solvent was removed from the collected filtrate under reduced pressure. The resultant crude residue was subjected to purification by reversed phase HPLC, eluting with water (0.1% TFA)-MeCN to afford the title compound Ex-4.14. MS (ESI): m/z calc'd for $C_{21}H_{22}Cl_2F_2N_6O_2S$ $[M+H]^+$: 531, found 531; $^1H$ NMR (400 MHz, DMSO-$d_6$, 25° C.) δ: 9.34 (s, 1H), 9.24 (s, 1H), 8.09 (s, 1H), 8.05 (s, 1H), 7.43 (s, 1H), 6.60-6.27 (m, 1H), 4.81-4.51 (m, 2H), 4.31-4.10 (m, 1H), 3.87-3.75 (m, 1H), 3.63-3.45 (m, 2H), 3.45-3.38 (m, 2H), 3.39-3.26 (m, 2H), 3.25-3.05 (m, 2H), 2.23-2.04 (m, 2H), 2.04-1.84 (m, 2H).

Compounds in Table 4 below were prepared in accordance with the synthetic sequence illustrated in General Scheme 5 using the corresponding starting materials.

TABLE 4
| Ex | Structure | Name | Exact Mass [M + H]+ |
|---|---|---|---|
| Ex-4.15 | 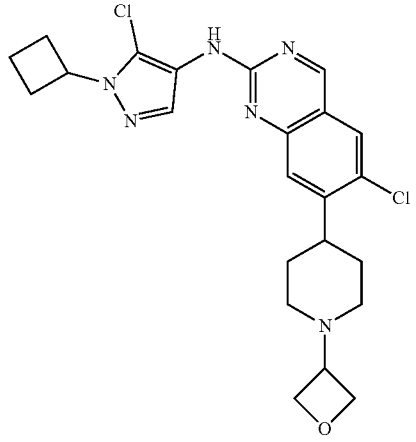 [SMILES: Clc1cc2cnc(Nc3cnn(C4CCC4)c3Cl)nc2cc1C1CCN(C2COC2)CC1] | 6-chloro-N-(5-chloro-1-cyclobutyl-1H-pyrazol-4-yl)-7-[1-(oxetan-3-yl)piperidin-4-yl]quinazolin-2-amine | Calc'd 473, found 473 |
| Ex-4.16 | 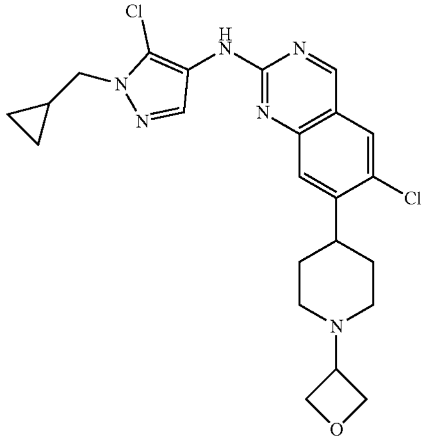 [SMILES: Clc1cc2cnc(Nc3cnn(CC4CC4)c3Cl)nc2cc1C1CCN(C2COC2)CC1] | 6-chloro-N-[5-chloro-1-(cyclopropylmethyl)-1H-pyrazol-4-yl]-7-[1-(oxetan-3-yl)piperidin-4-yl]quinazolin-2-amine | Calc'd 473, found 473 |
| Ex-4.17 | 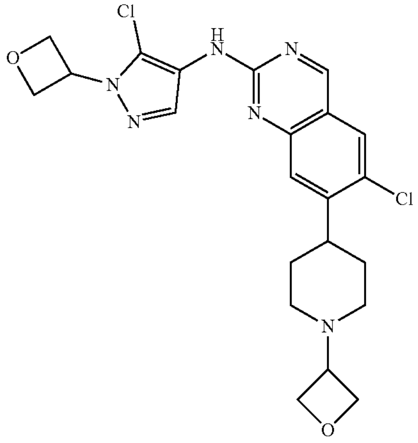 [SMILES: Clc1cc2cnc(Nc3cnn(C4COC4)c3Cl)nc2cc1C1CCN(C2COC2)CC1] | 6-chloro-N-[5-chloro-1-(oxetan-3-yl)-1H-pyrazol-4-yl]-7-[1-(oxetan-3-yl)piperidin-4-yl]quinazolin-2-amine | Calc'd 475, found 475 |

TABLE 4-continued
| Ex | Structure | Name | Exact Mass [M + H]+ |
|---|---|---|---|
| Ex-4.18 | 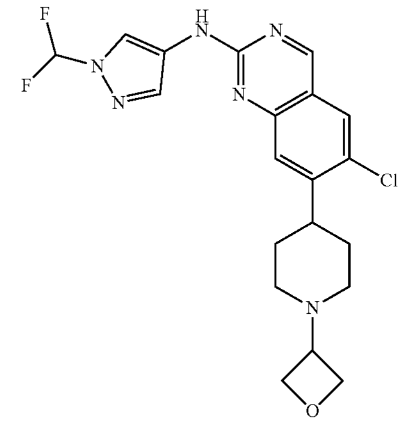 [SMILES: FC(F)n1cc(Nc2ncc3cc(Cl)c(C4CCN(C5COC5)CC4)cc3n2)cn1] | 6-chloro-N-[1-(difluoromethyl)-1H-pyrazol-4-yl]-7-[1-(oxetan-3-yl)piperidin-4-yl]quinazolin-2-amine | Calc'd 435, found 435 |
| Ex-4.19 | 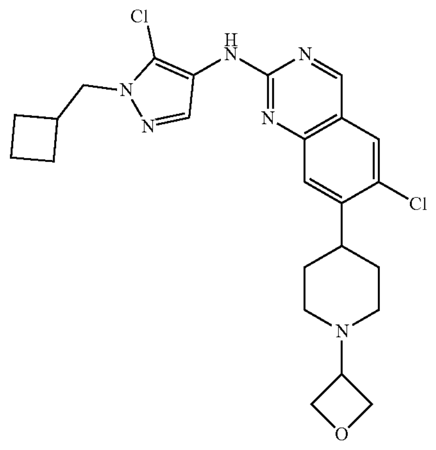 [SMILES: Clc1cc2cnc(Nc3cnn(CC4CCC4)c3Cl)nc2cc1C1CCN(C2COC2)CC1] | 6-chloro-N-[5-chloro-1-(cyclobutylmethyl)-1H-pyrazol-4-yl]-7-[1-(oxetan-3-yl)piperidin-4-yl]quinazolin-2-amine | Calc'd 487, found 487 |
| Ex-4.20 | 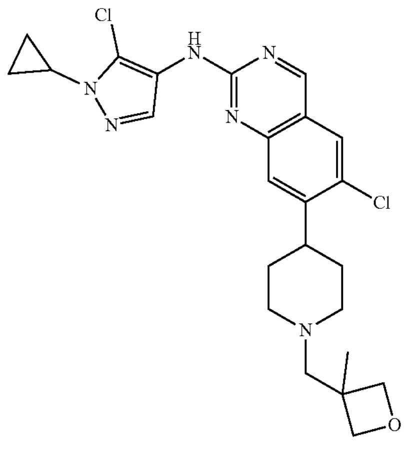 [SMILES: CC1(CN2CCC(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-{1-[(3-methyloxetan-3-yl)methyl]piperidin-4-yl}quinazolin-2-amine | Calc'd 487, found 487 |

TABLE 4-continued

| Ex | Structure | Name | Exact Mass $[M + H]^+$ |
|---|---|---|---|
| Ex-4.21 | 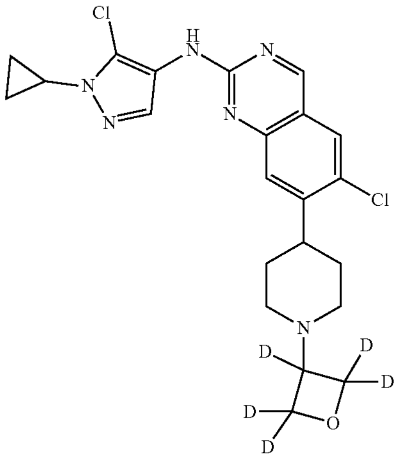 [SMILES: [2H]C1([2H])OC([2H])([2H])C1([2H])N1CCC(c2cc3nc(Nc4cnn(C5CC5)c4Cl)ncc3cc2Cl)CC1] | 6-chloro-N-(5-chloro-1-cyclopropyl-1H-pyrazol-4-yl)-7-(1-(oxetan-3-yl-2,2,4,4-d4)piperidin-4-yl)quinazolin-2-amine | Calc'd 464, found 464 |
| Ex-4.22 | 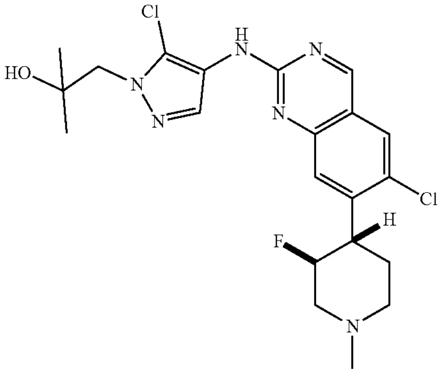 [SMILES: CN1CC[C@@H](c2cc3nc(Nc4cnn(CC(C)(C)O)c4Cl)ncc3cc2Cl)[C@H](F)C1] | (3S,4S) or (3R,4R) 1-(5-chloro-4-{[6-chloro-7-(3-fluoro-1-methylpiperidin-4-yl)quinazolin-2-yl]amino}-1H-pyrazol-1-yl)-2-methylpropan-2-ol | Calc'd 467, found 467 |
| Ex-4.23 | 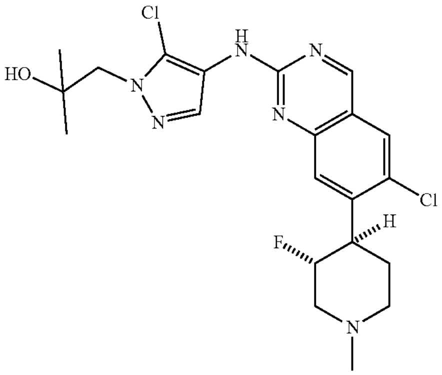 [SMILES: CN1CC[C@H](c2cc3nc(Nc4cnn(CC(C)(C)O)c4Cl)ncc3cc2Cl)[C@@H](F)C1] | (3S,4S) or (3R,4R) 1-(5-chloro-4-{[6-chloro-7-(3-fluoro-1-methylpiperidin-4-yl)quinazolin-2-yl]amino}-1H-pyrazol-1-yl)-2-methylpropan-2-ol | Calc'd 467, found 467 |
| Ex-4.24 | 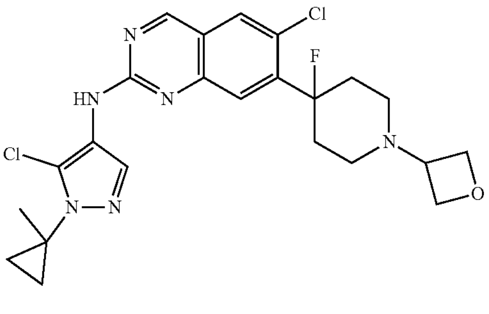 [SMILES: CC1(n2ncc(Nc3ncc4cc(Cl)c(C5(F)CCN(C6COC6)CC5)cc4n3)c2Cl)CC1] | 6-chloro-N-[5-chloro-1-(1-methylcyclopropyl)-1H-pyrazol-4-yl]-7-[4-fluoro-1-(oxetan-3-yl)piperidin-4-yl]quinazolin-2-amine | Calc'd 491, found 491 |

TABLE 4-continued

| Ex | Structure | Name | Exact Mass [M + H]+ |
|---|---|---|---|
| Ex-4.25 | 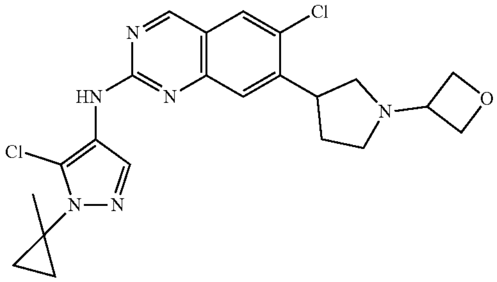 [SMILES: CC1(n2ncc(Nc3ncc4cc(Cl)c(C5CCN(C6COC6)C5)cc4n3)c2Cl)CC1] | (S) or (R) 6-chloro-N-[5-chloro-1-(1-methylcyclopropyl)-1H-pyrazol-4-yl]-7-[1-(oxetan-3-yl)pyrrolidin-3-yl]quinazolin-2-amine | Calc'd 459, found 459 |
| Ex-4.26 | 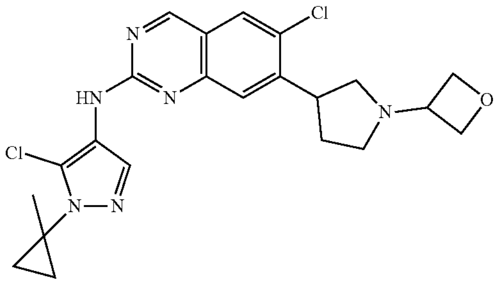 [SMILES: CC1(n2ncc(Nc3ncc4cc(Cl)c(C5CCN(C6COC6)C5)cc4n3)c2Cl)CC1] | (S) or (R) 6-chloro-N-[5-chloro-1-(1-methylcyclopropyl)-1H-pyrazol-4-yl]-7-[1-(oxetan-3-yl)pyrrolidin-3-yl]quinazolin-2-amine | Calc'd 459, found 459 |
| Ex-4.27 | 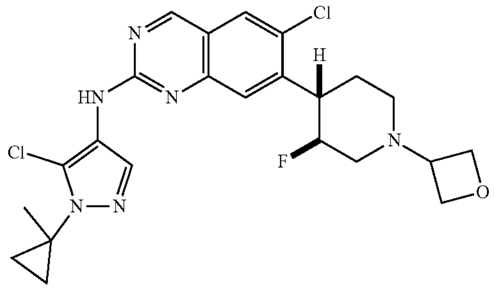 [SMILES: CC1(n2ncc(Nc3ncc4cc(Cl)c([C@@H]5CCN(C6COC6)C[C@H]5F)cc4n3)c2Cl)CC1] | (3S,4S) or (3R,4R) 6-chloro-N-[5-chloro-1-(1-methylcyclopropyl)-1H-pyrazol-4-yl]-7-[3-fluoro-1-(oxetan-3-yl)piperidin-4-yl]quinazolin-2-amine | Calc'd 491, found 491 |
| Ex-4.28 | 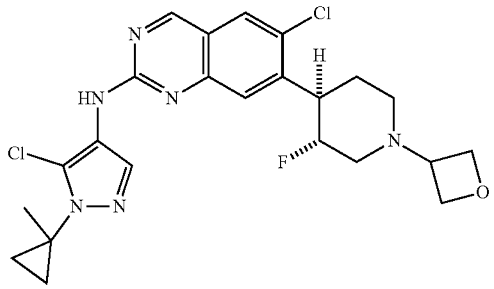 [SMILES: CC1(n2ncc(Nc3ncc4cc(Cl)c([C@H]5CCN(C6COC6)C[C@@H]5F)cc4n3)c2Cl)CC1] | (3S,4S) or (3R,4R) 6-chloro-N-[5-chloro-1-(1-methylcyclopropyl)-1H-pyrazol-4-yl]-7-[3-fluoro-1-(oxetan-3-yl)piperidin-4-yl]quinazolin-2-amine | Calc'd 491, found 491 |
| Ex-4.29 | 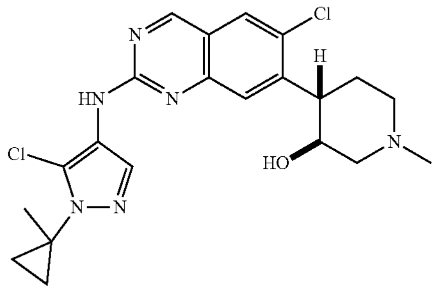 [SMILES: CN1CC[C@@H](c2cc3nc(Nc4cnn(C5(C)CC5)c4Cl)ncc3cc2Cl)[C@H](O)C1] | (3S,4S) or (3R,4R) 4-(6-chloro-2-{[5-chloro-1-(1-methylcyclopropyl)-1H-pyrazol-4-yl]amino}quinazolin-7-yl)-1-methylpiperidin-3-ol | Calc'd 447, found 447 |

TABLE 4-continued

| Ex | Structure | Name | Exact Mass [M + H]+ |
|---|---|---|---|
| Ex-4.30 | 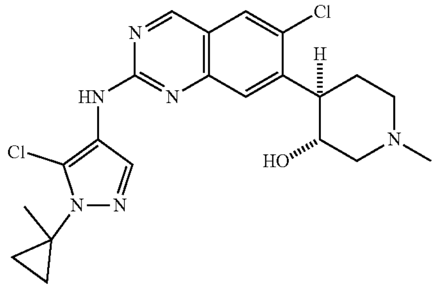 [SMILES: CN1CC[C@H](c2cc3nc(Nc4cnn(C5(C)CC5)c4Cl)ncc3cc2Cl)[C@@H](O)C1] | (3S,4S) or (3R,4R) 4-(6-chloro-2-{[5-chloro-1-(1-methylcyclopropyl)-1H-pyrazol-4-yl]amino}quinazolin-7-yl)-1-methylpiperidin-3-ol | Calc'd 447, found 447 |
| Ex-4.31 | 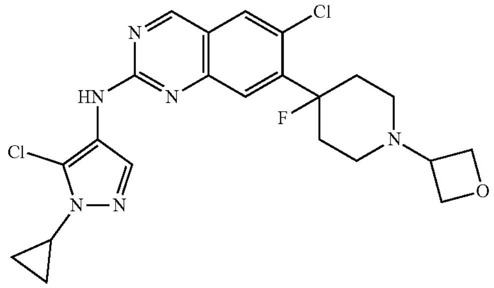 [SMILES: FC1(c2cc3nc(Nc4cnn(C5CC5)c4Cl)ncc3cc2Cl)CCN(C2COC2)CC1] | 6-chloro-N-(5-chloro-1-cyclopropyl-1H-pyrazol-4-yl)-7-[4-fluoro-1-(oxetan-3-yl)piperidin-4-yl]quinazolin-2-amine | Calc'd 477, found 477 |
| Ex-4.32 | 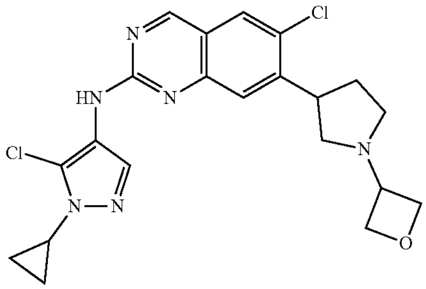 [SMILES: Clc1cc2cnc(Nc3cnn(C4CC4)c3Cl)nc2cc1C1CCN(C2COC2)C1] | (S) or (R) 6-chloro-N-(5-chloro-1-cyclopropyl-1H-pyrazol-4-yl)-7-[1-(oxetan-3-yl)pyrrolidin-3-yl]quinazolin-2-amine | Calc'd 445, found 445 |
| Ex-4.33 | 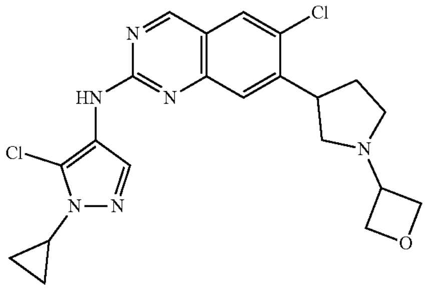 [SMILES: Clc1cc2cnc(Nc3cnn(C4CC4)c3Cl)nc2cc1C1CCN(C2COC2)C1] | (S) or (R) 6-chloro-N-(5-chloro-1-cyclopropyl-1H-pyrazol-4-yl)-7-[1-(oxetan-3-yl)pyrrolidin-3-yl]quinazolin-2-amine | Calc'd 445, found 445 |
| Ex-4.34 | 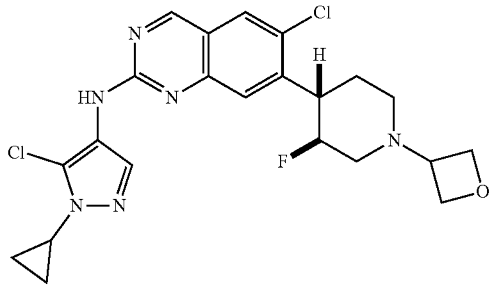 [SMILES: F[C@@H]1CN(C2COC2)CC[C@H]1c1cc2nc(Nc3cnn(C4CC4)c3Cl)ncc2cc1Cl] | (3S,4S) or (3R,4R) 6-chloro-N-(5-chloro-1-cyclopropyl-1H-pyrazol-4-yl)-7-[3-fluoro-1-(oxetan-3-yl)piperidin-4-yl]quinazolin-2-amine | Calc'd 477, found 477 |

TABLE 4-continued

| Ex | Structure | Name | Exact Mass [M + H]+ |
|---|---|---|---|
| Ex-4.35 | 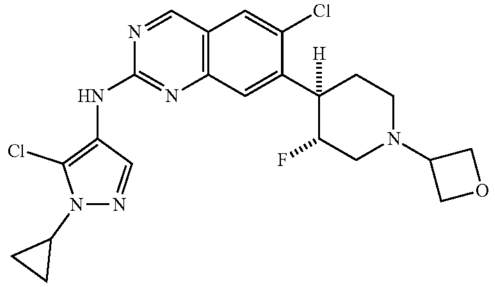 [SMILES: F[C@H]1CN(C2COC2)CC[C@@H]1c1cc2nc(Nc3cnn(C4CC4)c3Cl)ncc2cc1Cl] | (3S,4S) or (3R,4R) 6-chloro-N-(5-chloro-1-cyclopropyl-1H-pyrazol-4-yl)-7-[3-fluoro-1-(oxetan-3-yl)piperidin-4-yl]quinazolin-2-amine | Calc'd 477, found 477 |
| Ex-4.36 | 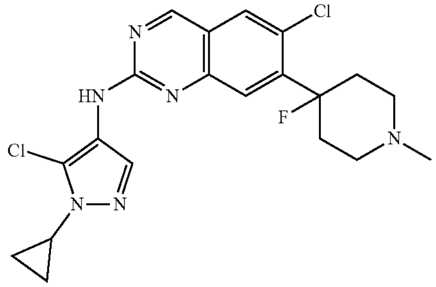 [SMILES: CN1CCC(F)(c2cc3nc(Nc4cnn(C5CC5)c4Cl)ncc3cc2Cl)CC1] | 6-chloro-N-(5-chloro-1-cyclopropyl-1H-pyrazol-4-yl)-7-(4-fluoro-1-methylpiperidin-4-yl)quinazolin-2-amine | Calc'd 435, found 435 |
| Ex-4.37 | 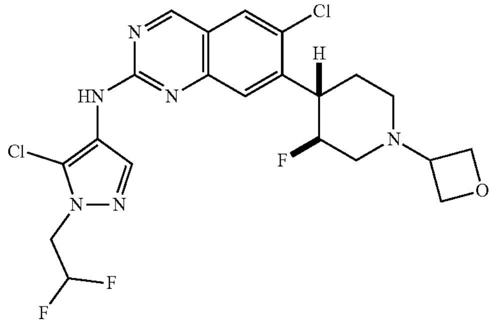 [SMILES: FC(F)Cn1ncc(Nc2ncc3cc(Cl)c([C@@H]4CCN(C5COC5)C[C@H]4F)cc3n2)c1Cl] | (3S,4S) or (3R,4R) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine | Calc'd 501, found 501 |
| Ex-4.38 | 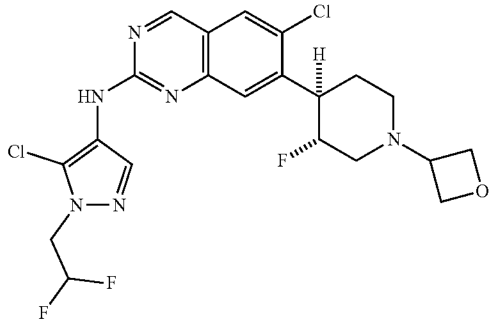 [SMILES: FC(F)Cn1ncc(Nc2ncc3cc(Cl)c([C@H]4CCN(C5COC5)C[C@@H]4F)cc3n2)c1Cl] | (3S,4S) or (3R,4R) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine | Calc'd 501, found 501 |
| Ex-4.39 | 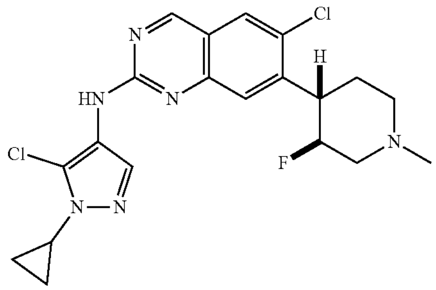 [SMILES: CN1CC[C@@H](c2cc3nc(Nc4cnn(C5CC5)c4Cl)ncc3cc2Cl)[C@H](F)C1] | (3S,4S) or (3R,4R) 6-chloro-N-(5-chloro-1-cyclopropyl-1H-pyrazol-4-yl)-7-(3-fluoro-1-methylpiperidin-4-yl)quinazolin-2-amine | Calc'd 435, found 435 |

TABLE 4-continued

| Ex | Structure | Name | Exact Mass [M + H]$^+$ |
|---|---|---|---|
| Ex-4.40 | 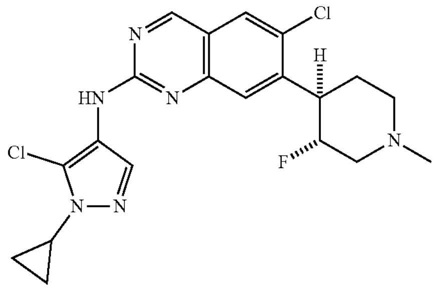 [SMILES: CN1CC[C@H](c2cc3nc(Nc4cnn(C5CC5)c4Cl)ncc3cc2Cl)[C@@H](F)C1] | (3S,4S) or (3R,4R) 6-chloro-N-(5-chloro-1-cyclopropyl-1H-pyrazol-4-yl)-7-(3-fluoro-1-methylpiperidin-4-yl)quinazolin-2-amine | Calc'd 435, found 435 |
| Ex-4.41 | 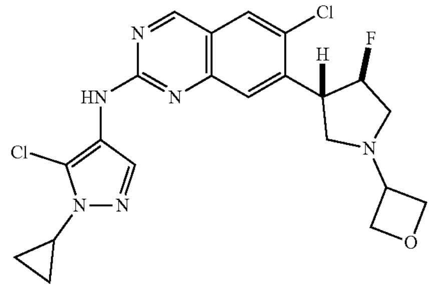 [SMILES: F[C@H]1CN(C2COC2)C[C@@H]1c1cc2nc(Nc3cnn(C4CC4)c3Cl)ncc2cc1Cl] | (3S,4R) or (3R,4S) 6-chloro-N-(5-chloro-1-cyclopropyl-1H-pyrazol-4-yl)-7-[4-fluoro-1-(oxetan-3-yl)pyrrolidin-3-yl]quinazolin-2-amine | Calc'd 463, found 463 |
| Ex-4.42 | 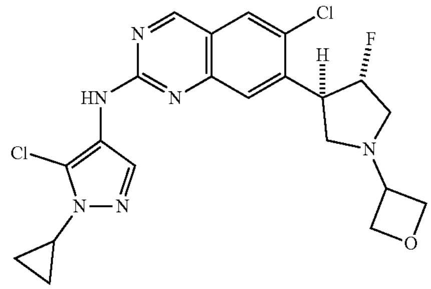 [SMILES: F[C@@H]1CN(C2COC2)C[C@H]1c1cc2nc(Nc3cnn(C4CC4)c3Cl)ncc2cc1Cl] | (3S,4R) or (3R,4S) 6-chloro-N-(5-chloro-1-cyclopropyl-1H-pyrazol-4-yl)-7-[4-fluoro-1-(oxetan-3-yl)pyrrolidin-3-yl]quinazolin-2-amine | Calc'd 463, found 463 |
| Ex-4.43 | 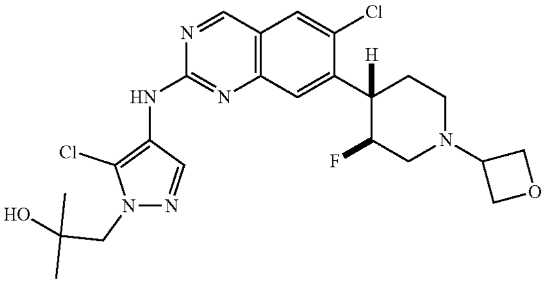 [SMILES: CC(C)(O)Cn1ncc(Nc2ncc3cc(Cl)c([C@@H]4CCN(C5COC5)C[C@H]4F)cc3n2)c1Cl] | (3S,4S) or (3R,4R) 1-[5-chloro-4-({6-chloro-7-[3-fluoro-1-(oxetan-3-yl)piperidin-4-yl]quinazolin-2-yl}amino)-1H-pyrazol-1-yl]-2-methylpropan-2-ol | Calc'd 509, found 509 |
| Ex-4.44 | 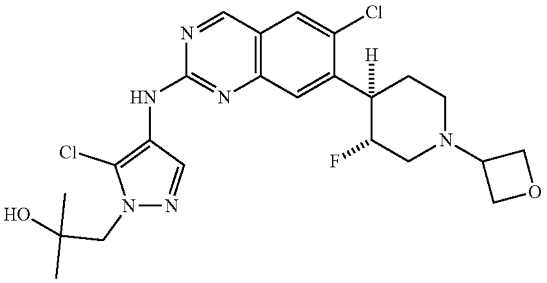 [SMILES: CC(C)(O)Cn1ncc(Nc2ncc3cc(Cl)c([C@H]4CCN(C5COC5)C[C@@H]4F)cc3n2)c1Cl] | (3S,4S) or (3R,4R) 1-[5-chloro-4-({6-chloro-7-[3-fluoro-1-(oxetan-3-yl)piperidin-4-yl]quinazolin-2-yl}amino)-1H-pyrazol-1-yl]-2-methylpropan-2-ol | Calc'd 509, found 509 |

TABLE 4-continued

| Ex | Structure | Name | Exact Mass [M + H]$^+$ |
|---|---|---|---|
| Ex-4.45 | 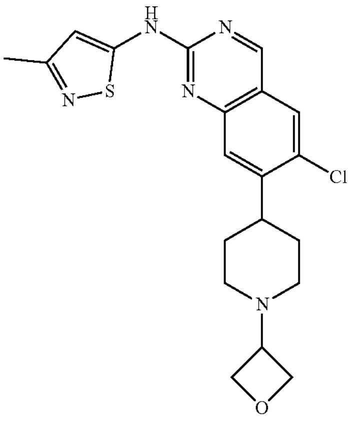 [SMILES: Cc1cc(Nc2ncc3cc(Cl)c(C4CCN(C5COC5)CC4)cc3n2)sn1] | 6-chloro-N-(3-methyl-1,2-thiazol-5-yl)-7-[1-(oxetan-3-yl)piperidin-4-yl]quinazolin-2-amine | Calc'd 416, found 416 |
| Ex-4.46 | 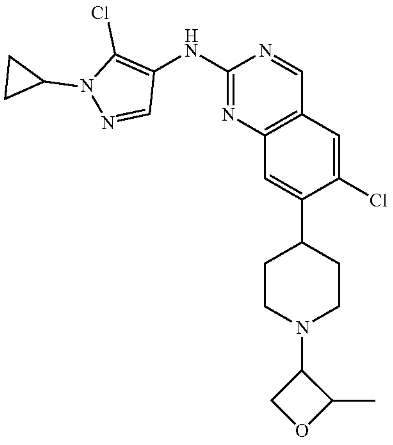 [SMILES: CC1OCC1N1CCC(c2cc3nc(Nc4cnn(C5CC5)c4Cl)ncc3cc2Cl)CC1] | (2R,3R) or (2S,3S) or (2S,3R) or (2R,3S) 6-chloro-N-(5-chloro-1-cyclopropyl-1H-pyrazol-4-yl)-7-[1-(2-methyloxetan-3-yl)piperidin-4-yl]quinazolin-2-amine | Calc'd 473, found 473 |
| Ex-4.47 | 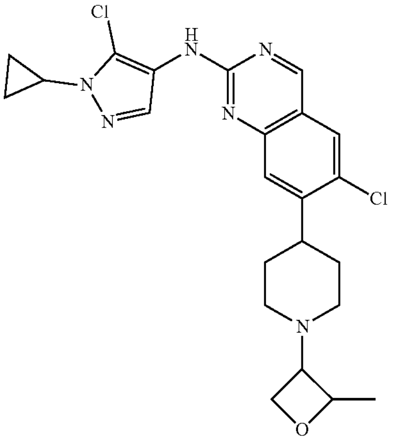 [SMILES: CC1OCC1N1CCC(c2cc3nc(Nc4cnn(C5CC5)c4Cl)ncc3cc2Cl)CC1] | (2R,3R) or (2S,3S) or (2S,3R) or (2R,3S) 6-chloro-N-(5-chloro-1-cyclopropyl-1H-pyrazol-4-yl)-7-[1-(2-methyloxetan-3-yl)piperidin-4-yl]quinazolin-2-amine | Calc'd 473, found 473 |

TABLE 4-continued
| Ex | Structure | Name | Exact Mass [M + H]+ |
|---|---|---|---|
| Ex-4.48 | 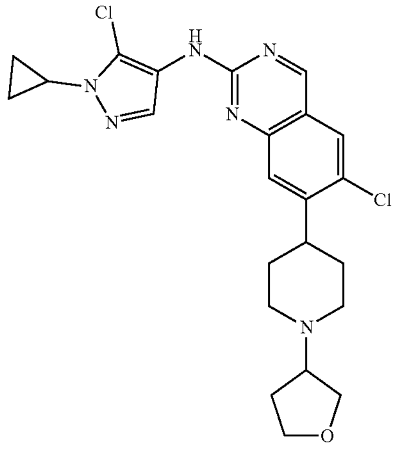 [SMILES: Clc1cc2cnc(Nc3cnn(C4CC4)c3Cl)nc2cc1C1CCN(C2CCOC2)CC1] | (S) or (R) 6-chloro-N-(5-chloro-1-cyclopropyl-1H-pyrazol-4-yl)-7-[1-(oxolan-3-yl)piperidin-4-yl]quinazolin-2-amine | Calc'd 473, found 473 |
| Ex-4.49 | 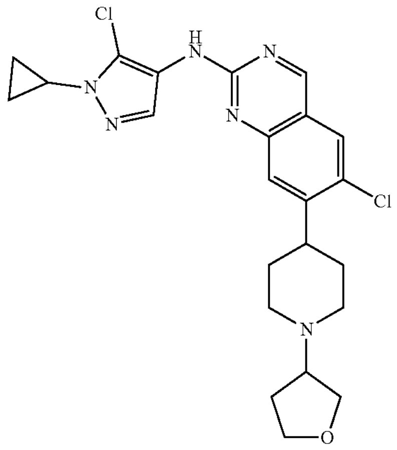 [SMILES: Clc1cc2cnc(Nc3cnn(C4CC4)c3Cl)nc2cc1C1CCN(C2CCOC2)CC1] | (S) or (R) 6-chloro-N-(5-chloro-1-cyclopropyl-1H-pyrazol-4-yl)-7-[1-(oxolan-3-yl)piperidin-4-yl]quinazolin-2-amine | Calc'd 473, found 473 |
| Ex-4.50 | 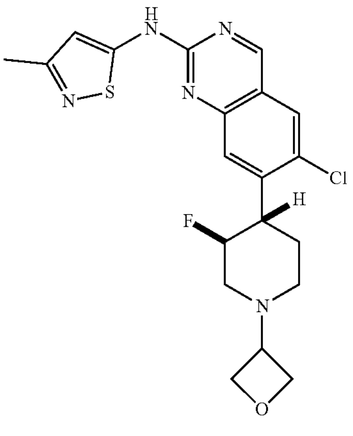 [SMILES: Cc1cc(Nc2ncc3cc(Cl)c([C@@H]4CCN(C5COC5)C[C@H]4F)cc3n2)sn1] | (3S,4S) or (3R,4R) 6-chloro-7-[3-fluoro-1-(oxetan-3-yl)piperidin-4-yl]-N-(3-methyl-1,2-thiazol-5-yl)quinazolin-2-amine | Calc'd 434, found 434 |

TABLE 4-continued

| Ex | Structure | Name | Exact Mass [M + H]+ |
|---|---|---|---|
| Ex-4.51 | 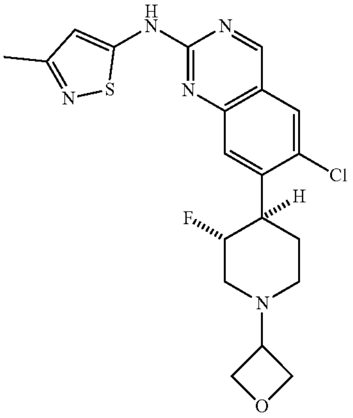 [SMILES: Cc1cc(Nc2ncc3cc(Cl)c([C@H]4CCN(C5COC5)C[C@@H]4F)cc3n2)sn1] | (3S,4S) or (3R,4R) 6-chloro-7-[3-fluoro-1-(oxetan-3-yl)piperidin-4-yl]-N-(3-methyl-1,2-thiazol-5-yl)quinazolin-2-amine | Calc'd 434, found 434 |
| Ex-4.52 | 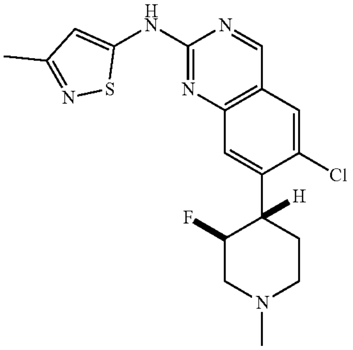 [SMILES: Cc1cc(Nc2ncc3cc(Cl)c([C@@H]4CCN(C)C[C@H]4F)cc3n2)sn1] | (3S,4R) or (3R,4R) 6-chloro-7-(3-fluoro-1-methylpiperidin-4-yl)-N-(3-methyl-1,2-thiazol-5-yl)quinazolin-2-amine | Calc'd 392, found 392 |
| Ex-4.53 | 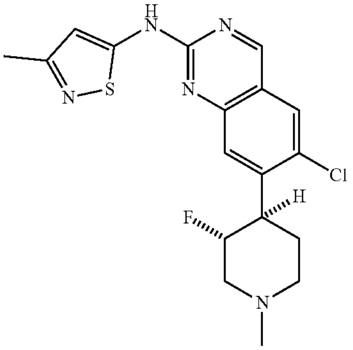 [SMILES: Cc1cc(Nc2ncc3cc(Cl)c([C@H]4CCN(C)C[C@@H]4F)cc3n2)sn1] | (3S,4S) or (3R,4R) 6-chloro-7-(3-fluoro-1-methylpiperidin-4-yl)-N-(3-methyl-1,2-thiazol-5-yl)quinazolin-2-amine | Calc'd 392, found 392 |
| Ex-4.54 | 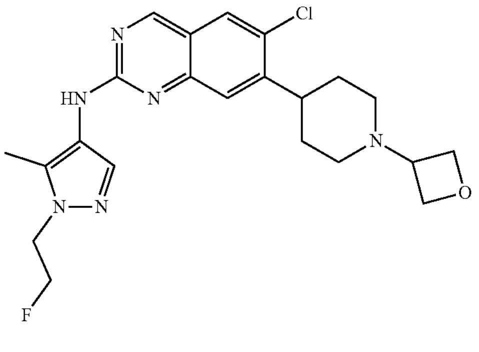 [SMILES: Cc1c(Nc2ncc3cc(Cl)c(C4CCN(C5COC5)CC4)cc3n2)cnn1CCF] | 6-chloro-N-[1-(2-fluoroethyl)-5-methyl-1H-pyrazol-4-yl]-7-[1-(oxetan-3-yl)piperidin-4-yl]quinazolin-2-amine | Calc'd 445, found 445 |

TABLE 4-continued

| Ex | Structure | Name | Exact Mass [M + H]+ |
|---|---|---|---|
| Ex-4.55 | 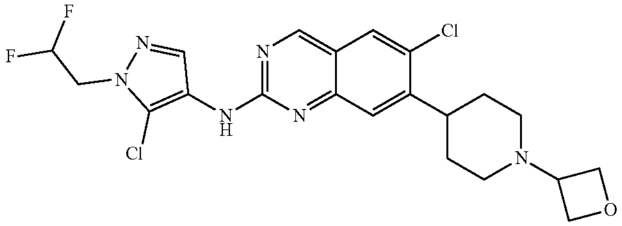 [SMILES: FC(F)Cn1ncc(Nc2ncc3cc(Cl)c(C4CCN(C5COC5)CC4)cc3n2)c1Cl] | 6-chloro-N-[5-chloro-1-(2,2-difluoroethyl)-1H-pyrazol-4-yl]-7-[1-(oxetan-3-yl)piperidin-4-yl]quinazolin-2-amine | Calc'd 483, found 483 |
| Ex-4.56 | 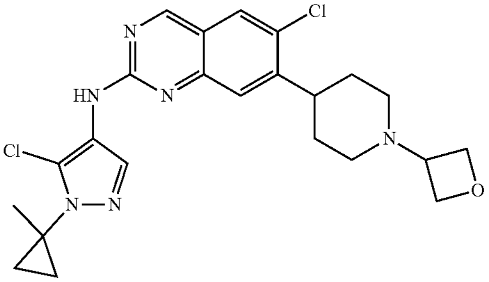 [SMILES: CC1(n2ncc(Nc3ncc4cc(Cl)c(C5CCN(C6COC6)CC5)cc4n3)c2Cl)CC1] | 6-chloro-N-[5-chloro-1-(1-methylcyclopropyl)-1H-pyrazol-4-yl]-7-[1-(oxetan-3-yl)piperidin-4-yl]quinazolin-2-amine | Calc'd 473, found 473 |
| Ex-4.57 | 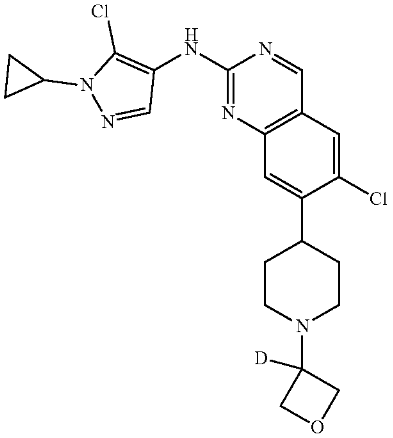 [SMILES: [2H]C1(N2CCC(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-(1-(oxetan-3-yl-3-d)piperidin-4-yl)quinazolin-2-amine | Calc'd 460, found 460 |
| Ex-4.58 | 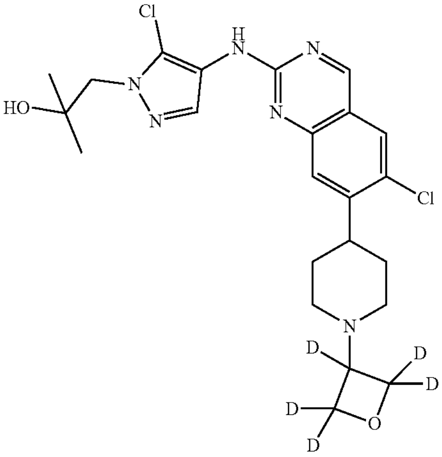 [SMILES: [2H]C1([2H])OC([2H])([2H])C1([2H])N1CCC(c2cc3nc(Nc4cnn(CC(C)(C)O)c4Cl)ncc3cc2Cl)CC1] | 1-(5-chloro-4-((6-chloro-7-(1-(oxetan-3-yl-d5)piperidin-4-yl)quinazolin-2-yl)amino)-1H-pyrazol-1-yl)-2-methylpropan-2-ol | Calc'd 496, found 496 |

TABLE 4-continued

| Ex | Structure | Name | Exact Mass [M + H]$^+$ |
|---|---|---|---|
| Ex-4.59 | 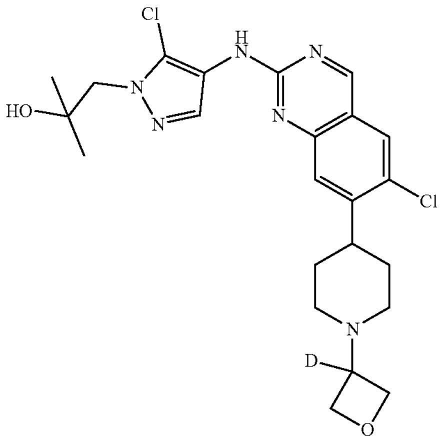 [SMILES: [2H]C1(N2CCC(c3cc4nc(Nc5cnn(CC(C)(C)O)c5Cl)ncc4cc3Cl)CC2)COC1] | 1-(5-chloro-4-((6-chloro-7-(1-(oxetan-3-yl-3-d)piperidin-4-yl)quinazolin-2-yl)amino)-1H-pyrazol-1-yl)-2-methylpropan-2-ol | Calc'd 492, found 492 |
| Ex-4.60 | 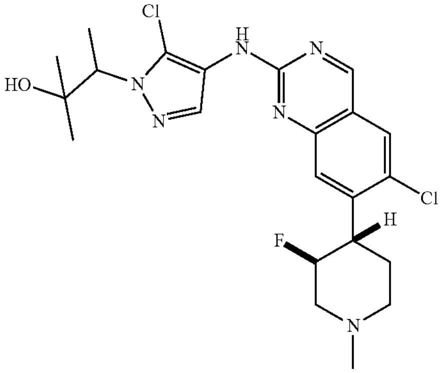 [SMILES: CC(n1ncc(Nc2ncc3cc(Cl)c([C@@H]4CCN(C)C[C@H]4F)cc3n2)c1Cl)C(C)(C)O] | (R)(3S,4S) or (R)(3R,4R) or (S)(3S,4S) or (S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol | Calc'd 481, found 481 |
| Ex-4.61 | 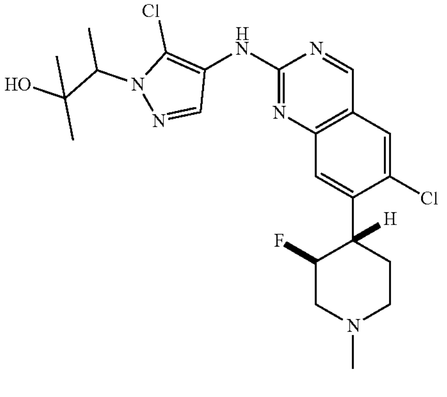 [SMILES: CC(n1ncc(Nc2ncc3cc(Cl)c([C@@H]4CCN(C)C[C@H]4F)cc3n2)c1Cl)C(C)(C)O] | (R)(3S,4S) or (R)(3R,4R) or (S)(3S,4S) or (S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol | Calc'd 481, found 481 |

TABLE 4-continued

| Ex | Structure | Name | Exact Mass [M + H]+ |
|---|---|---|---|
| Ex-4.62 | 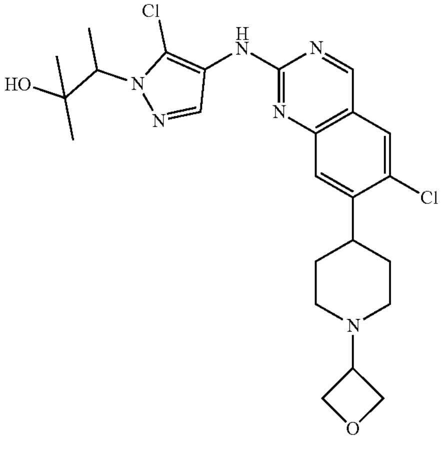 [SMILES: CC(n1ncc(Nc2ncc3cc(Cl)c(C4CCN(C5COC5)CC4)cc3n2)c1Cl)C(C)(C)O] | (8) or (R) 3-[5-chloro-4-({6-chloro-7-[1-(oxetan-3-yl)piperidin-4-yl]quinazolin-2-yl}amino)-1H-pyrazol-1-yl]-2-methylbutan-2-ol | Calc'd 505, found 505 |
| Ex-4.63 | 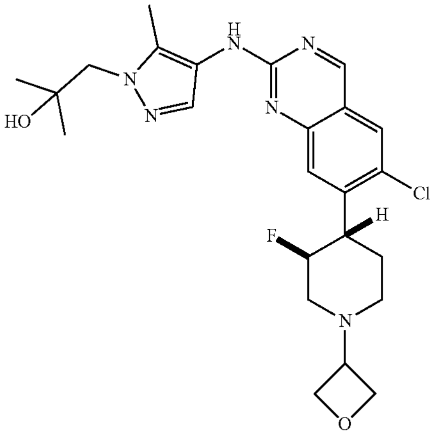 [SMILES: Cc1c(Nc2ncc3cc(Cl)c([C@@H]4CCN(C5COC5)C[C@H]4F)cc3n2)cnn1CC(C)(C)O] | (3S,4S) or (3R,4R) 1-[4-({6-chloro-7-[3-fluoro-1-(oxetan-3-yl)piperidin-4-yl]quinazolin-2-yl}amino)-5-methyl-1H-pyrazol-1-yl]-2-methylpropan-2-ol | Calc'd 489, found 489 |
| Ex-4.64 | 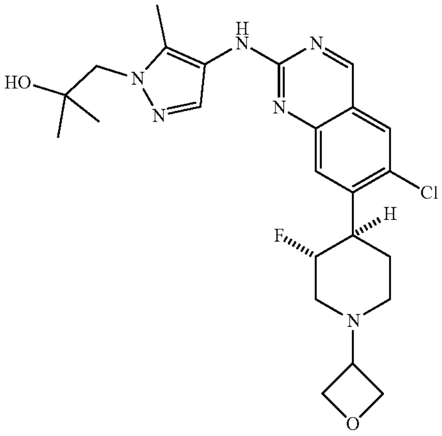 [SMILES: Cc1c(Nc2ncc3cc(Cl)c([C@H]4CCN(C5COC5)C[C@@H]4F)cc3n2)cnn1CC(C)(C)O] | (3S,4S) or (3R,4R) 1-[4-({6-chloro-7-[3-fluoro-1-(oxetan-3-yl)piperidin-4-yl]quinazolin-2-yl}amino)-5-methyl-1H-pyrazol-1-yl]-2-methylpropan-2-ol | Calc'd 489, found 489 |

TABLE 4-continued

| Ex | Structure | Name | Exact Mass [M + H]+ |
|---|---|---|---|
| Ex-4.65 | 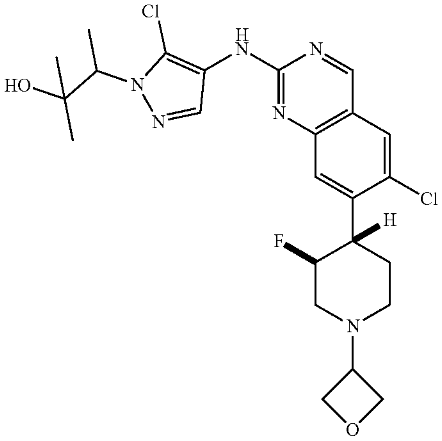 [SMILES: CC(n1ncc(Nc2ncc3cc(Cl)c([C@@H]4CCN(C5COC5)C[C@H]4F)cc3n2)c1Cl)C(C)(C)O] | (R)(3S,4S) or (R)(3R,4R) or (S)(3S,4S) or (S)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol | Calc'd 523, found 523 |
| Ex-4.66 | 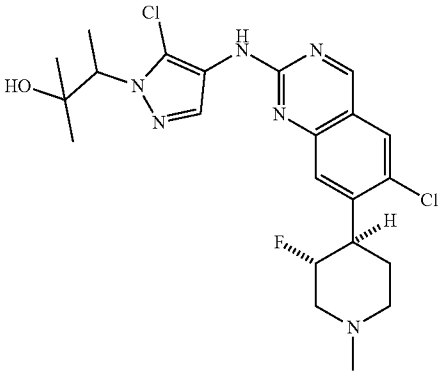 [SMILES: CC(n1ncc(Nc2ncc3cc(Cl)c([C@H]4CCN(C)C[C@@H]4F)cc3n2)c1Cl)C(C)(C)O] | (R)(3S,4S) or (R)(3R,4R) or (S)(3S,4S) or (S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol | Calc'd 481, found 481 |
| Ex-4.67 | 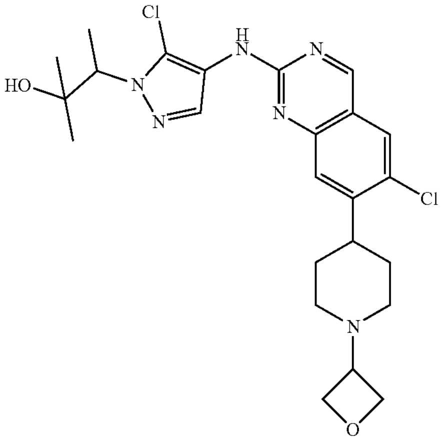 [SMILES: CC(n1ncc(Nc2ncc3cc(Cl)c(C4CCN(C5COC5)CC4)cc3n2)c1Cl)C(C)(C)O] | (S) or (R) 3-[5-chloro-4-({6-chloro-7-[1-(oxetan-3-yl)piperidin-4-yl]quinazolin-2-yl}amino)-1H-pyrazol-1-yl]-2-methylbutan-2-ol | Calc'd 505, found 505 |

TABLE 4-continued

| Ex | Structure | Name | Exact Mass [M + H]+ |
| --- | --- | --- | --- |
| Ex-4.68 | 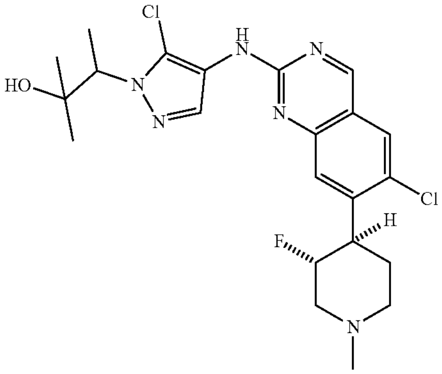 [SMILES: CC(n1ncc(Nc2ncc3cc(Cl)c([C@H]4CCN(C)C[C@@H]4F)cc3n2)c1Cl)C(C)(C)O] | (R)(3S,4S) or (R)(3R,4R) or (S)(3S,4S) or (S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol | Calc'd 481, found 481 |
| Ex-4.69 | 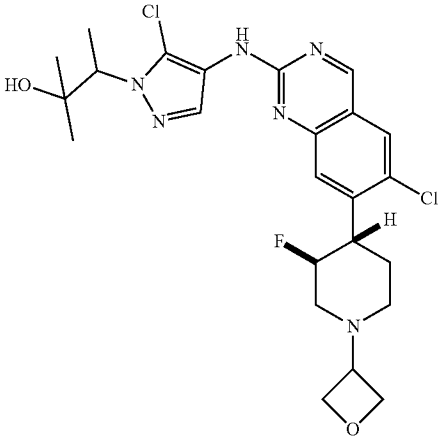 [SMILES: CC(n1ncc(Nc2ncc3cc(Cl)c([C@@H]4CCN(C5COC5)C[C@H]4F)cc3n2)c1Cl)C(C)(C)O] | (R)(3S,4S) or (R)(3R,4R) or (S)(3S,4S) or (S)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol | Calc'd 523, found 523 |
| Ex-4.70 | 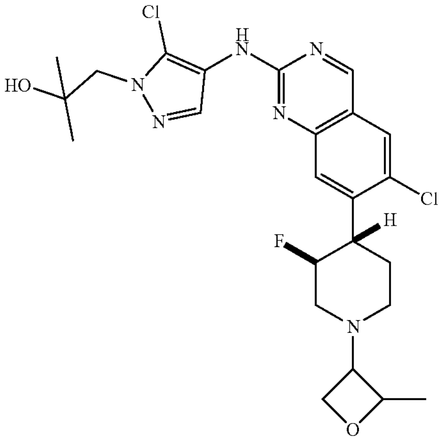 [SMILES: CC1OCC1N1CC[C@@H](c2cc3nc(Nc4cnn(CC(C)(C)O)c4Cl)ncc3cc2Cl)[C@H](F)C1] | (3S,4S)(2R,3R) or (3S,4S)(2S,3S) or (3R,4R)(2R,3R) or (3R,4R)(2S,3S) or (3R,4R)(2S,3R) or (3R,4R)(2R,3S) or (3S,4S)(2S,3R) or (3S,4S)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol | Calc'd 523, found 523 |

TABLE 4-continued

| Ex | Structure | Name | Exact Mass [M + H]+ |
| --- | --- | --- | --- |
| Ex-4.71 | 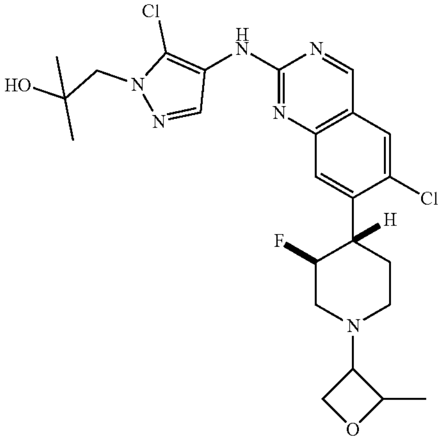 [SMILES: CC1OCC1N1CC[C@@H](c2cc3nc(Nc4cnn(CC(C)(C)O)c4Cl)ncc3cc2Cl)[C@H](F)C1] | (3S,4S)(2R,3R) or (3S,4S)(2S,3S) or (3R,4R)(2R,3R) or (3R,4R)(2S,3S) or (3R,4R)(2S,3R) or (3R,4R)(2R,3S) or (3S,4S)(2S,3R) or (3S,4S)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol | Calc'd 523, found 523 |
| Ex-4.72 | 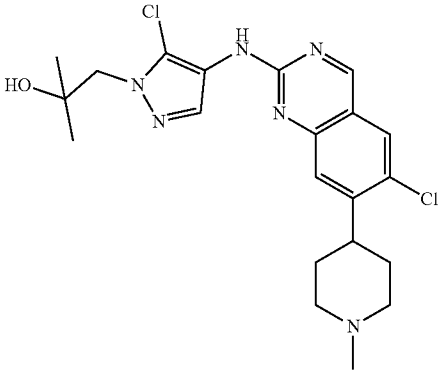 [SMILES: CN1CCC(c2cc3nc(Nc4cnn(CC(C)(C)O)c4Cl)ncc3cc2Cl)CC1] | 1-(5-chloro-4-{[6-chloro-7-(1-methylpiperidin-4-yl)quinazolin-2-yl]amino}-1H-pyrazol-1-yl)-2-methylpropan-2-ol | Calc'd 449, found 449 |
| Ex-4.73 | 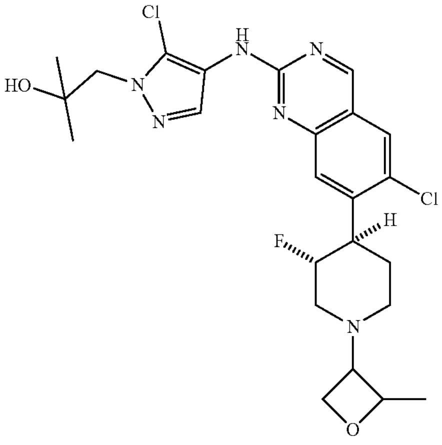 [SMILES: CC1OCC1N1CC[C@H](c2cc3nc(Nc4cnn(CC(C)(C)O)c4Cl)ncc3cc2Cl)[C@@H](F)C1] | (3S,4S)(2R,3R) or (3S,4S)(2S,3S) or (3R,4R)(2R,3R) or (3R,4R)(2S,3S) or (3R,4R)(2S,3R) or (3R,4R)(2R,3S) or (3S,4S)(2S,3R) or (3S,4S)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol | Calc'd 523, found 523 |

TABLE 4-continued

| Ex | Structure | Name | Exact Mass [M + H]+ |
|---|---|---|---|
| Ex-4.74 | 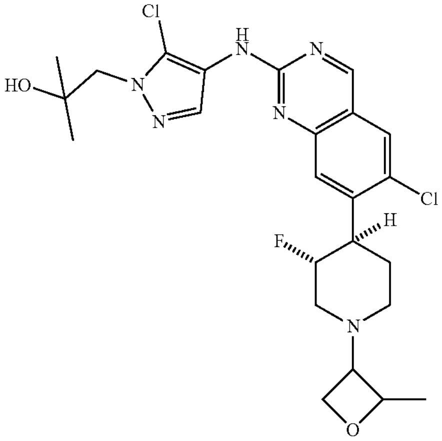 [SMILES: CC1OCC1N1CC[C@H](c2cc3nc(Nc4cnn(CC(C)(C)O)c4Cl)ncc3cc2Cl)[C@@H](F)C1] | (3S,4S)(2R,3R) or (3S,4S)(2S,3S) or (3R,4R)(2R,3R) or (3R,4R)(2S,3S) or (3R,4R)(2S,3R) or (3R,4R)(2R,3S) or (3S,4S)(2S,3R) or (3S,4S)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol | Calc'd 523, found 523 |
| Ex-4.75 | 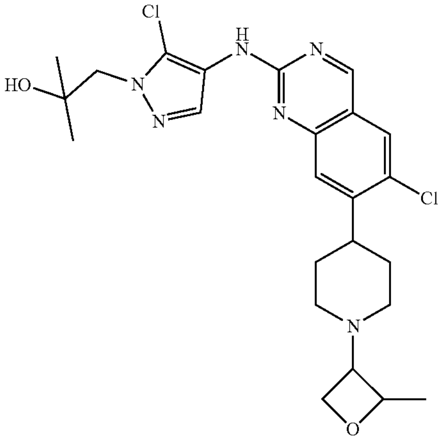 [SMILES: CC1OCC1N1CCC(c2cc3nc(Nc4cnn(CC(C)(C)O)c4Cl)ncc3cc2Cl)CC1] | (2R,3R) or (2S,3S) or (2S,3R) or (2R,3S) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol | Calc'd 505, found 505 |
| Ex-4.76 | 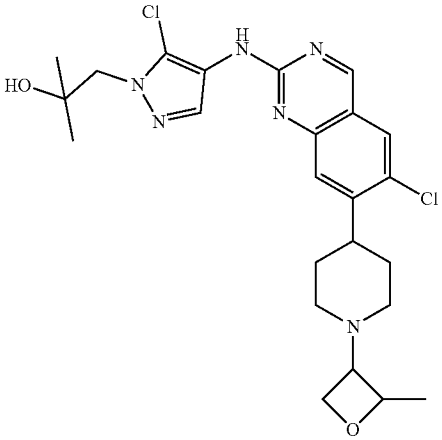 [SMILES: CC1OCC1N1CCC(c2cc3nc(Nc4cnn(CC(C)(C)O)c4Cl)ncc3cc2Cl)CC1] | (2R,3R) or (2S,3S) or (2S,3R) or (2R,3S) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol | Calc'd 505, found 505 |

TABLE 4-continued

| Ex | Structure | Name | Exact Mass [M + H]+ |
|---|---|---|---|
| Ex-4.77 | 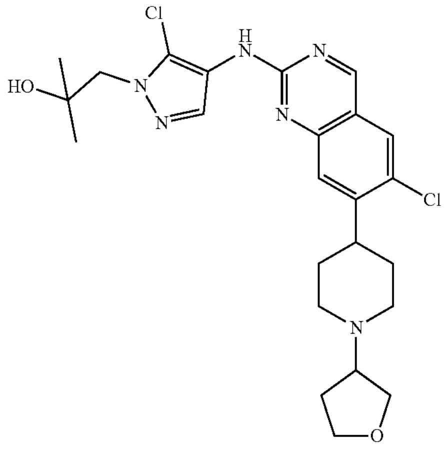 [SMILES: CC(C)(O)Cn1ncc(Nc2ncc3cc(Cl)c(C4CCN(C5CCOC5)CC4)cc3n2)c1Cl] | (S) or (R) 1-[5-chloro-4-({6-chloro-7-[1-(oxolan-3-yl)piperidin-4-yl]quinazolin-2-yl}amino)-1H-pyrazol-1-yl]-2-methylpropan-2-ol | Calc'd 505, found 505 |
| Ex-4.78 | 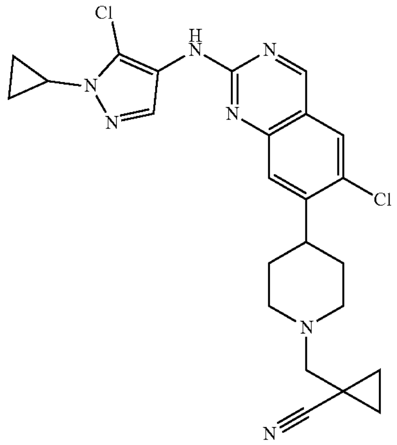 [SMILES: N#CC1(CN2CCC(c3cc4nc(Nc5cnn(C6CC6)c5Cl)ncc4cc3Cl)CC2)CC1] | 1-[(4-{6-chloro-2-[(5-chloro-1-cyclopropyl-1H-pyrazol-4-yl)amino]quinazolin-7-yl}piperidin-1-yl)methyl]cyclopropane-1-carbonitrile | Calc'd 482, found 482 |
| Ex-4.79 | 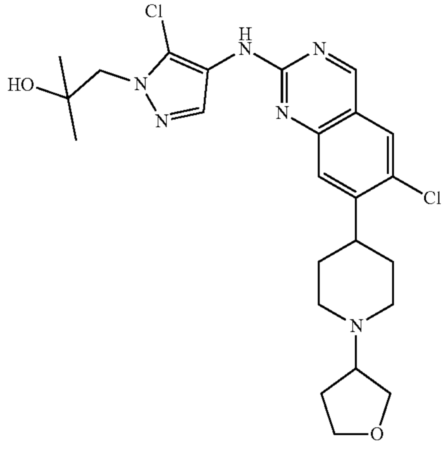 [SMILES: CC(C)(O)Cn1ncc(Nc2ncc3cc(Cl)c(C4CCN(C5CCOC5)CC4)cc3n2)c1Cl] | (S) or (R) 1-[5-chloro-4-({6-chloro-7-[1-(oxolan-3-yl)piperidin-4-yl]quinazolin-2-yl}amino)-1H-pyrazol-1-yl]-2-methylpropan-2-ol | Calc'd 505, found 505 |

TABLE 4-continued

| Ex | Structure | Name | Exact Mass [M + H]+ |
|---|---|---|---|
| Ex-4.80 | 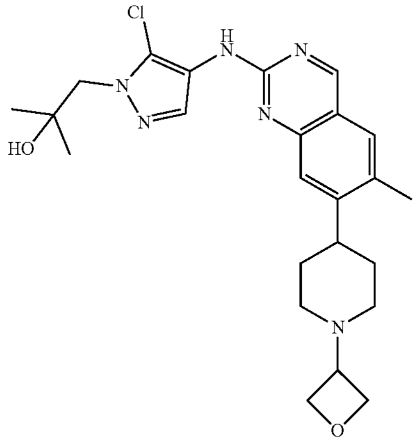 [SMILES: Cc1cc2cnc(Nc3cnn(CC(C)(C)O)c3Cl)nc2cc1C1CCN(C2COC2)CC1] | 1-[5-chloro-4-({6-methyl-7-[1-(oxetan-3-yl)piperidin-4-yl]quinazolin-2-yl}amino)-1H-pyrazol-1-yl]-2-methylpropan-2-ol | Calc'd 471, found 471 |
| Ex-4.81 | 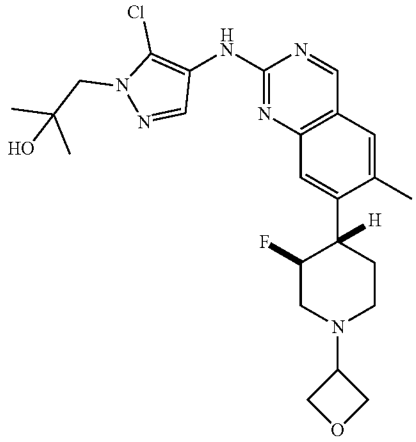 [SMILES: Cc1cc2cnc(Nc3cnn(CC(C)(C)O)c3Cl)nc2cc1[C@@H]1CCN(C2COC2)C[C@H]1F] | (3S,4S) or (3R,4R) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol | Calc'd 489, found 489 |
| Ex-4.82 | 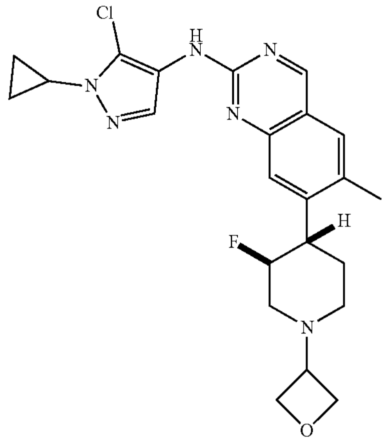 [SMILES: Cc1cc2cnc(Nc3cnn(C4CC4)c3Cl)nc2cc1[C@@H]1CCN(C2COC2)C[C@H]1F] | (3S,4S) or (3R,4R) N-(5-chloro-1-cyclopropyl-1H-pyrazol-4-yl)-7-[3-fluoro-1-(oxetan-3-yl)piperidin-4-yl]-6-methylquinazolin-2-amine | Calc'd 457, found 457 |

TABLE 4-continued

| Ex | Structure | Name | Exact Mass [M + H]+ |
|---|---|---|---|
| Ex-4.83 | 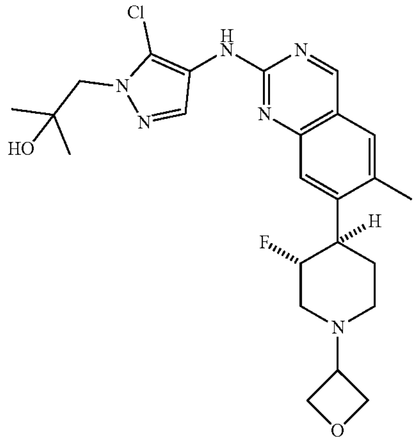 [SMILES: Cc1cc2cnc(Nc3cnn(CC(C)(C)O)c3Cl)nc2cc1[C@H]1CCN(C2COC2)C[C@@H]1F] | (3S,4S) or (3R,4R) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol | Calc'd 489, found 489 |
| Ex-4.84 | 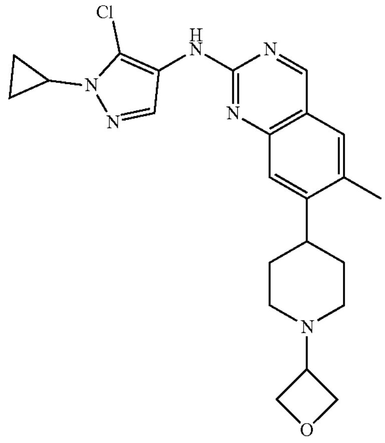 [SMILES: Cc1cc2cnc(Nc3cnn(C4CC4)c3Cl)nc2cc1C1CCN(C2COC2)CC1] | N-(5-chloro-1-cyclopropyl-1H-pyrazol-4-yl)-6-methyl-7-[1-(oxetan-3-yl)piperidin-4-yl]quinazolin-2-amine | Calc'd 439, found 439 |
| Ex-4.85 | 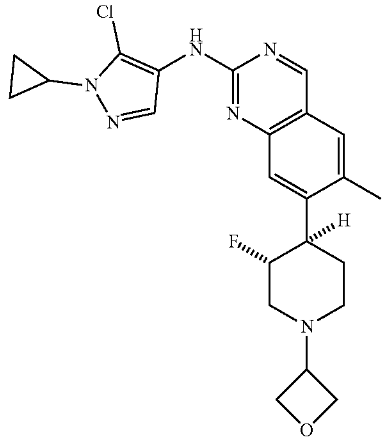 [SMILES: Cc1cc2cnc(Nc3cnn(C4CC4)c3Cl)nc2cc1[C@H]1CCN(C2COC2)C[C@@H]1F] | (3S,4S) or (3R,4R) N-(5-chloro-1-cyclopropyl-1H-pyrazol-4-yl)-7-[3-fluoro-1-(oxetan-3-yl)piperidin-4-yl]-6-methylquinazolin-2-amine | Calc'd 457, found 457 |

TABLE 4-continued

| Ex | Structure | Name | Exact Mass [M + H]+ |
|---|---|---|---|
| Ex-4.86 | 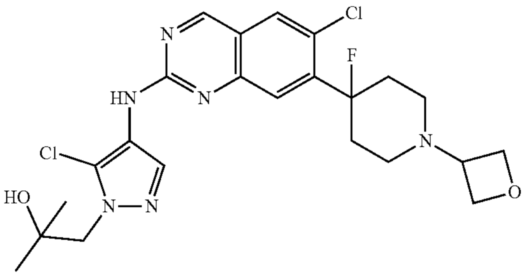 [SMILES: CC(C)(O)Cn1ncc(Nc2ncc3cc(Cl)c(C4(F)CCN(C5COC5)CC4)cc3n2)c1Cl] | 1-[5-chloro-4-({6-chloro-7-[4-fluoro-1-(oxetan-3-yl)piperidin-4-yl]quinazolin-2-yl}amino)-1H-pyrazol-1-yl]-2-methylpropan-2-ol | Calc'd 509, found 509 |
| Ex-4.87 | 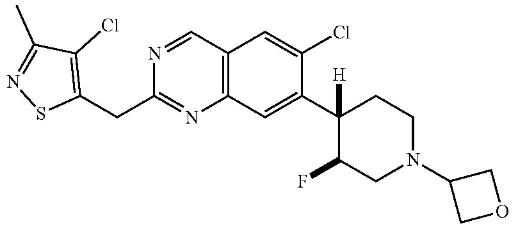 [SMILES: Cc1nsc(Cc2ncc3cc(Cl)c([C@@H]4CCN(C5COC5)C[C@H]4F)cc3n2)c1Cl] | (3S,4S) or (3R,4R) 6-chloro-N-(4-chloro-3-methyl-1,2-thiazol-5-yl)-7-[3-fluoro-1-(oxetan-3-yl)piperidin-4-yl]quinazolin-2-amine | Calc'd 468, found 468 |
| Ex-4.88 | 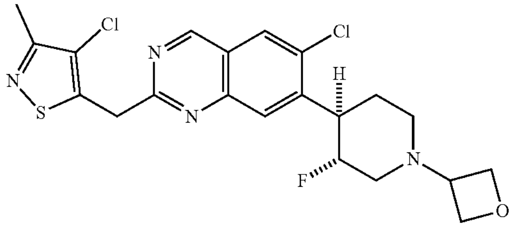 [SMILES: Cc1nsc(Cc2ncc3cc(Cl)c([C@H]4CCN(C5COC5)C[C@@H]4F)cc3n2)c1Cl] | (3S,4S) or (3R,4R) 6-chloro-N-(4-chloro-3-methyl-1,2-thiazol-5-yl)-7-[3-fluoro-1-(oxetan-3-yl)piperidin-4-yl]quinazolin-2-amine | Calc'd 468, found 468 |
| Ex-4.89 | 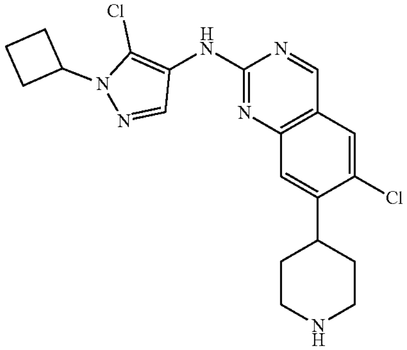 [SMILES: Clc1cc2cnc(Nc3cnn(C4CCC4)c3Cl)nc2cc1C1CCNCC1] | 6-chloro-N-(5-chloro-1-cyclobutyl-1H-pyrazol-4-yl)-7-(piperidin-4-yl)quinazolin-2-amine | Calc'd 417, found 417 |
| Ex-4.90 | 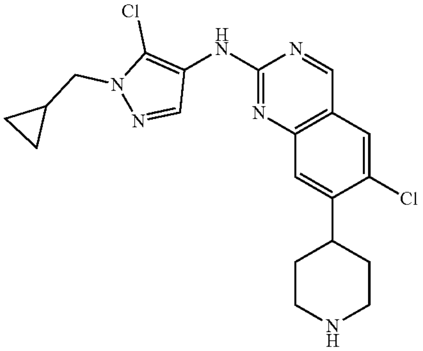 [SMILES: Clc1cc2cnc(Nc3cnn(CC4CC4)c3Cl)nc2cc1C1CCNCC1] | 6-chloro-N-[5-chloro-1-(cyclopropylmethyl)-1H-pyrazol-4-yl]-7-(piperidin-4-yl)quinazolin-2-amine | Calc'd 417, found 417 |

TABLE 4-continued

| Ex | Structure | Name | Exact Mass [M + H]+ |
|---|---|---|---|
| Ex-4.91 | 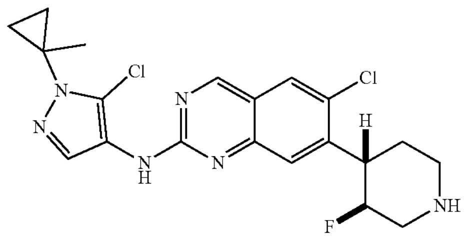 [SMILES: CC1(n2ncc(Nc3ncc4cc(Cl)c([C@@H]5CCNC[C@H]5F)cc4n3)c2Cl)CC1] | (3S,4S) or (3R,4R) 6-chloro-N-[5-chloro-1-(1-methylcyclopropyl)-1H-pyrazol-4-yl]-7-(3-fluoropiperidin-4-yl)quinazolin-2-amine | Calc'd 435, found 435 |
| Ex-4.92 | 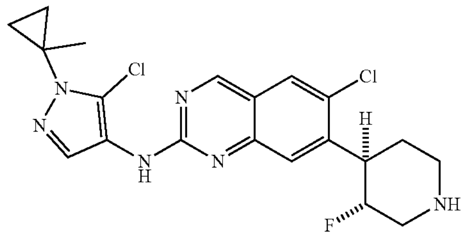 [SMILES: CC1(n2ncc(Nc3ncc4cc(Cl)c([C@H]5CCNC[C@@H]5F)cc4n3)c2Cl)CC1] | (3S,4S) or (3R,4R) 6-chloro-N-[5-chloro-1-(1-methylcyclopropyl)-1H-pyrazol-4-yl]-7-(3-fluoropiperidin-4-yl)quinazolin-2-amine | Calc'd 435, found 435 |
| Ex-4.93 | 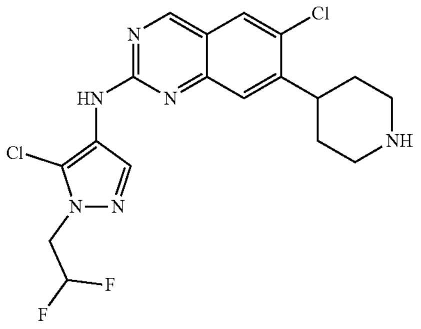 [SMILES: FC(F)Cn1ncc(Nc2ncc3cc(Cl)c(C4CCNCC4)cc3n2)c1Cl] | 6-chloro-N-[5-chloro-1-(2,2-difluoroethyl)-1H-pyrazol-4-yl]-7-(piperidin-4-yl)quinazolin-2-amine | Calc'd 427, found 427 |
| Ex-4.94 | 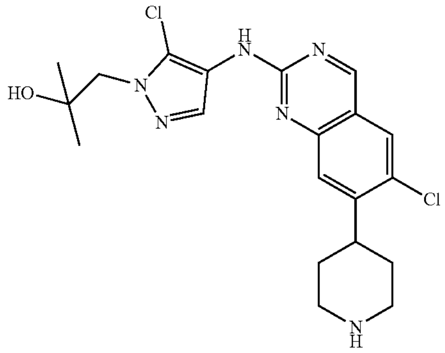 [SMILES: CC(C)(O)Cn1ncc(Nc2ncc3cc(Cl)c(C4CCNCC4)cc3n2)c1Cl] | 1-(5-chloro-4-{[6-chloro-7-(piperidin-4-yl)quinazolin-2-yl]amino}-1H-pyrazol-1-yl)-2-methylpropan-2-ol | Calc'd 435, found 435 |
| Ex-4.95 | 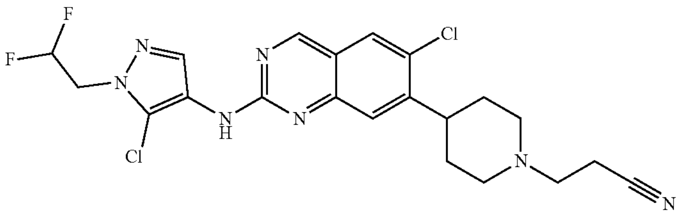 [SMILES: N#CCCN1CCC(c2cc3nc(Nc4cnn(CC(F)F)c4Cl)ncc3cc2Cl)CC1] | 3-[4-(6-chloro-2-{[5-chloro-1-(2,2-difluoroethyl)-1H-pyrazol-4-yl]amino}quinazolin-7-yl)piperidin-1-yl]propanenitrile | Calc'd 480, found 480 |

TABLE 4-continued

| Ex | Structure | Name | Exact Mass [M + H]+ |
|---|---|---|---|
| Ex-4.96 | 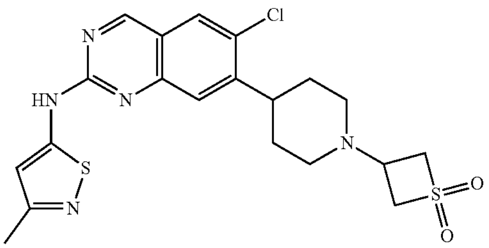 [SMILES: Cc1cc(Nc2ncc3cc(Cl)c(C4CCN(C5CS(=O)(=O)C5)CC4)cc3n2)sn1] | 3-(4-(6-chloro-2-((3-methylisothiazol-5-yl)amino)quinazolin-7-yl)piperidin-1-yl)thietane 1,1-dioxide | Calc'd 464, found 464 |
| Ex-4.97 | 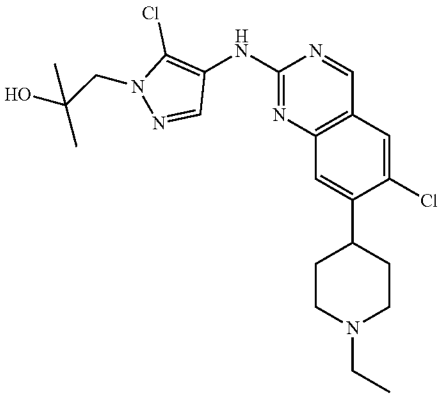 [SMILES: CCN1CCC(c2cc3nc(Nc4cnn(CC(C)(C)O)c4Cl)ncc3cc2Cl)CC1] | 1-(5-chloro-4-{[6-chloro-7-(1-ethylpiperidin-4-yl)quinazolin-2-yl]amino}-1H-pyrazol-1-yl)-2-methylpropan-2-ol | Calc'd 463, found 463 |
| Ex-4.98 | 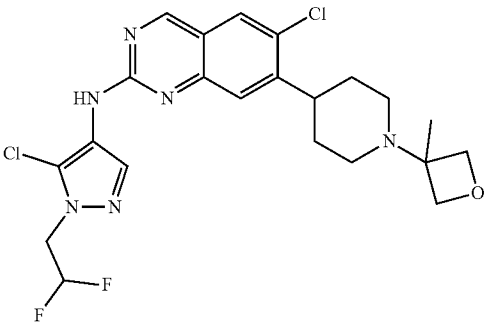 [SMILES: CC1(N2CCC(c3cc4nc(Nc5cnn(CC(F)F)c5Cl)ncc4cc3Cl)CC2)COC1] | 6-chloro-N-[5-chloro-1-(2,2-difluoroethyl)-1H-pyrazol-4-yl]-7-[1-(3-methyloxetan-3-yl)piperidin-4-yl]quinazolin-2-amine | Calc'd 497, found 497 |
| Ex-4.99 | 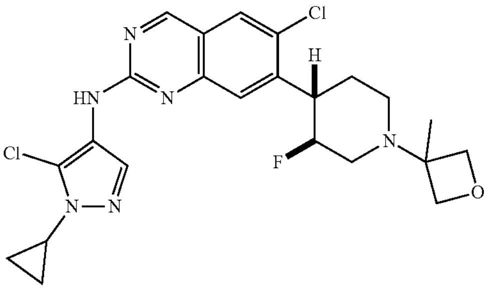 [SMILES: CC1(N2CC[C@@H](c3cc4nc(Nc5cnn(C6CC6)c5Cl)ncc4cc3Cl)[C@H](F)C2)COC1] | (3S,4S) or (3R,4R) 6-chloro-N-(5-chloro-1-cyclopropyl-1H-pyrazol-4-yl)-7-[3-fluoro-1-(3-methyloxetan-3-yl)piperidin-4-yl]quinazolin-2-amine | Calc'd 491, found 491 |
| Ex-4.100 | 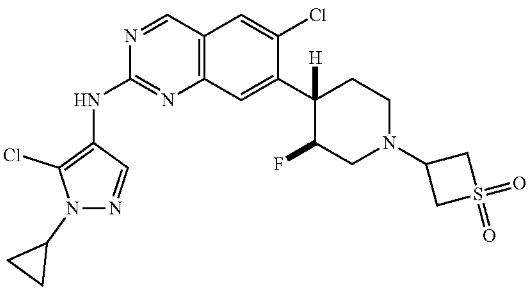 [SMILES: O=S1(=O)CC(N2CC[C@@H](c3cc4nc(Nc5cnn(C6CC6)c5Cl)ncc4cc3Cl)[C@H](F)C2)C1] | (3S,4S) or (3R,4R) 3-(4-{6-chloro-2-[(5-chloro-1-cyclopropyl-1H-pyrazol-4-yl)amino]quinazolin-7-yl}-3-fluoropiperidin-1-yl)thietane 1,1-dioxide | Calc'd 525, found 525 |

TABLE 4-continued

| Ex | Structure | Name | Exact Mass [M + H]+ |
|---|---|---|---|
| Ex-4.101 | 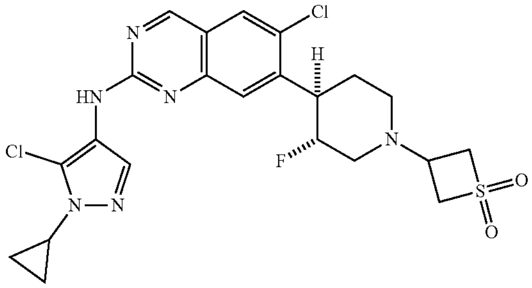 [SMILES: O=S1(=O)CC(N2CC[C@H](c3cc4nc(Nc5cnn(C6CC6)c5Cl)ncc4cc3Cl)[C@@H](F)C2)C1] | (3S,4S) or (3R,4R) 4-(4-(6-chloro-2-((5-chloro-1-cyclopropyl-1H-pyrazol-4-yl)amino)quinazolin-7-yl)piperidin-1-yl)tetrahydrofuran-3-carbonitrile | Calc'd 525, found 525 |
| Ex-4.102 | 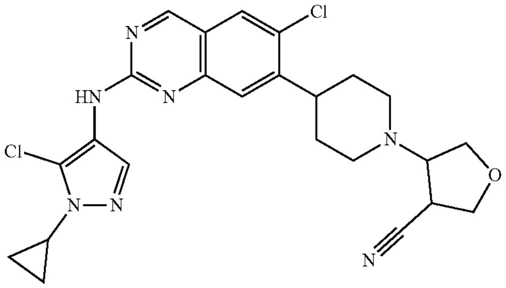 [SMILES: N#CC1COCC1N1CCC(c2cc3nc(Nc4cnn(C5CC5)c4Cl)ncc3cc2Cl)CC1] | (3S,4S) or (3R,4R) or (3S,4R) or (3R,4S) 4-(4-(6-chloro-2-((5-chloro-1-cyclopropyl-1H-pyrazol-4-yl)amino)quinazolin-7-yl)piperidin-1-yl)tetrahydrofuran-3-carbonitrile | Calc'd 498, found 498 |
| Ex-4.103 | 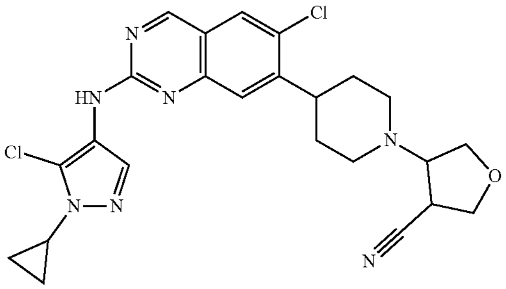 [SMILES: N#CC1COCC1N1CCC(c2cc3nc(Nc4cnn(C5CC5)c4Cl)ncc3cc2Cl)CC1] | (3S,4S) or (3R,4R) or (3S,4R) or (3R,4S) 4-(4-(6-chloro-2-((5-chloro-1-cyclopropyl-1H-pyrazol-4-yl)amino)quinazolin-7-yl)piperidin-1-yl)tetrahydrofuran-3-carbonitrile | Calc'd 498, found 498 |
| Ex-4.104 | 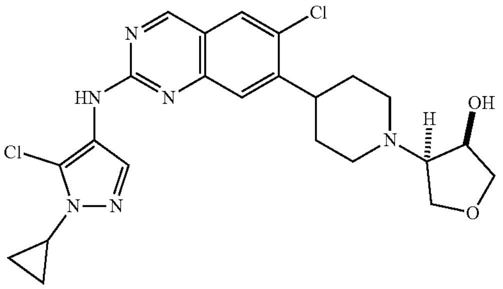 [SMILES: O[C@H]1COC[C@H]1N1CCC(c2cc3nc(Nc4cnn(C5CC5)c4Cl)ncc3cc2Cl)CC1] | (3S,4S) or (3R,4R) 4-(4-(6-chloro-2-((5-chloro-1-cyclopropyl-1H-pyrazol-4-yl)amino)quinazolin-7-yl)piperidin-1-yl)tetrahydrofuran-3-ol | Calc'd 489, found 489 |
| Ex-4.105 | 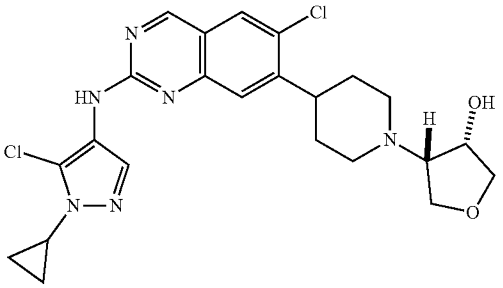 [SMILES: O[C@@H]1COC[C@@H]1N1CCC(c2cc3nc(Nc4cnn(C5CC5)c4Cl)ncc3cc2Cl)CC1] | (3S,4S) or (3R,4R) 4-(4-(6-chloro-2-((5-chloro-1-cyclopropyl-1H-pyrazol-4-yl)amino)quinazolin-7-yl)piperidin-1-yl)tetrahydrofuran-3-ol | Calc'd 489, found 489 |

TABLE 4-continued

| Ex | Structure | Name | Exact Mass [M + H]+ |
|---|---|---|---|
| Ex-4.106 | 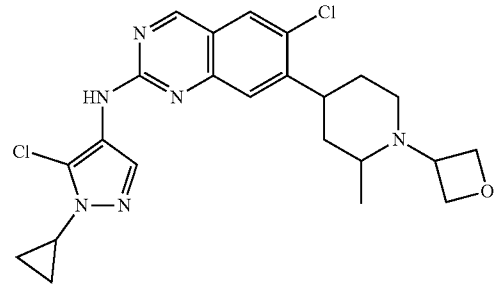 | (2S,4S) or (2R,4R) or (2S,4R) or (2R,4S) 6-chloro-N-(5-chloro-1-cyclopropyl-1H-pyrazol-4-yl)-7-(2-methyl-1-(oxetan-3-yl)piperidin-4-yl)quinazolin-2-amine | Calc'd 473, found 473 |
| Ex-4.107 | 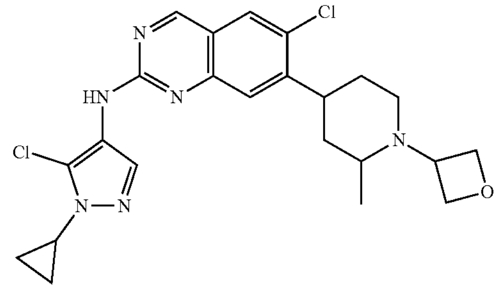 [SMILES: CC1CC(c2cc3nc(Nc4cnn(C5CC5)c4Cl)ncc3cc2Cl)CCN1C1COC1] | (2S,4S) or (2R,4R) or (2S,4R) or (2R,4S) 6-chloro-N-(5-chloro-1-cyclopropyl-1H-pyrazol-4-yl)-7-(2-methyl-1-(oxetan-3-yl)piperidin-4-yl)quinazolin-2-amine | Calc'd 473, found 473 |
| Ex-4.108 | 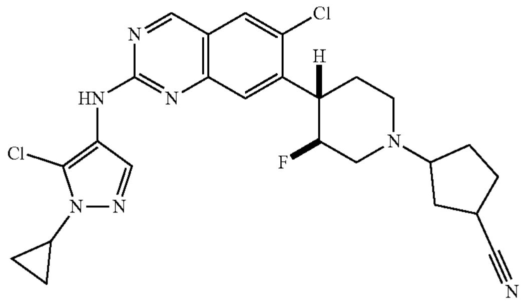 [SMILES: N#CC1CCC(N2CC[C@@H](c3cc4nc(Nc5cnn(C6CC6)c5Cl)ncc4cc3Cl)[C@H](F)C2)C1] | (1R,3S)-3-((3S,4S) or (1S,3R)-3-((3S,4S) or (1R,3R)-3-((3S,4S) or (1S,3S)-3-((3S,4S) or (1R,3S)-3-((3R,4R) or (1S,3R)-3-((3R,4R) or (1R,3R)-3-((3R,4R) or 1S,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile | Calc'd 514, found 514 |
| Ex-4.109 | 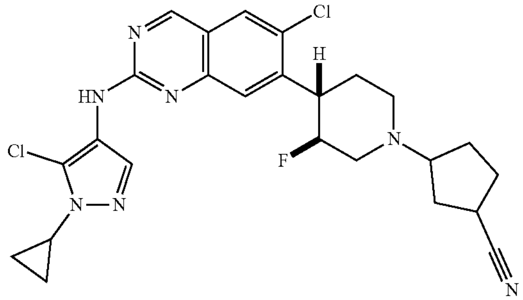 [SMILES: N#CC1CCC(N2CC[C@@H](c3cc4nc(Nc5cnn(C6CC6)c5Cl)ncc4cc3Cl)[C@H](F)C2)C1] | (1R,3S)-3-((3S,4S) or (1S,3R)-3-((3S,4S) or (1R,3R)-3-((3S,4S) or (1S,3S)-3-((3S,4S) or (1R,3S)-3-((3R,4R) or (1S,3R)-3-((3R,4R) or (1R,3R)-3-((3R,4R) or 1S,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile | Calc'd 514, found 514 |
| Ex-4.110 | 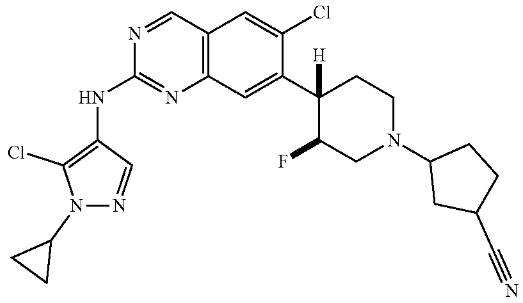 [SMILES: N#CC1CCC(N2CC[C@@H](c3cc4nc(Nc5cnn(C6CC6)c5Cl)ncc4cc3Cl)[C@H](F)C2)C1] | (1R,3S)-3-((3S,4S) or (1S,3R)-3-((3S,4S) or (1R,3R)-3-((3S,4S) or (1S,3S)-3-((3S,4S) or (1R,3S)-3-((3R,4R) or (1S,3R)-3-((3R,4R) or (1R,3R)-3-((3R,4R) or 1S,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile | Calc'd 514, found 514 |

TABLE 4-continued

| Ex | Structure | Name | Exact Mass [M + H]+ |
| --- | --- | --- | --- |
| Ex-4.111 | 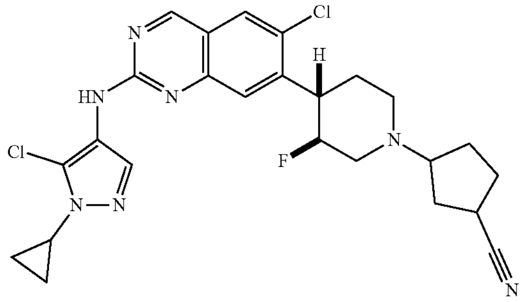 [SMILES: N#CC1CCC(N2CC[C@@H](c3cc4nc(Nc5cnn(C6CC6)c5Cl)ncc4cc3Cl)[C@H](F)C2)C1] | (1R,3S)-3-((3S,4S) or (1S,3R)-3-((3S,4S) or (1R,3R)-3-((3S,4S) or (1S,3S)-3-((3S,4S) or (1R,3S)-3-((3R,4R) or (1S,3R)-3-((3R,4R) or (1R,3R)-3-((3R,4R) or 1S,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile | Calc'd 514, found 514 |
| Ex-4.112 | 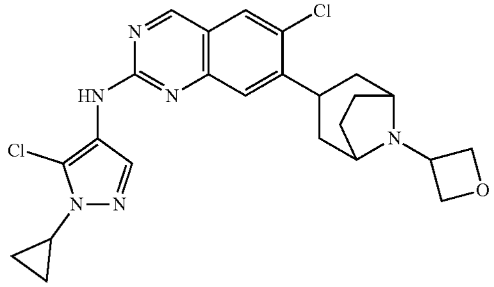 [SMILES: Clc1cc2cnc(Nc3cnn(C4CC4)c3Cl)nc2cc1C1CC2CCC(C1)N2C1COC1] | cis or trans 6-chloro-N-(5-chloro-1-cyclopropyl-1H-pyrazol-4-yl)-7-(8-(oxetan-3-yl)-8-azabicyclo[3.2.1]octan-3-yl)quinazolin-2-amine | Calc'd 485, found 485 |
| Ex-4.113 | 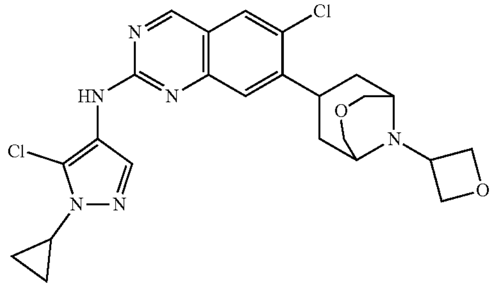 [SMILES: Clc1cc2cnc(Nc3cnn(C4CC4)c3Cl)nc2cc1C1CC2COCC(C1)N2C1COC1] | cis or trans 6-chloro-N-(5-chloro-1-cyclopropyl-1H-pyrazol-4-yl)-7-(9-(oxetan-3-yl)-3-oxa-9-azabicyclo[3.3.1]nonan-7-yl)quinazolin-2-amine | Calc'd 501, found 501 |
| Ex-4.114 | 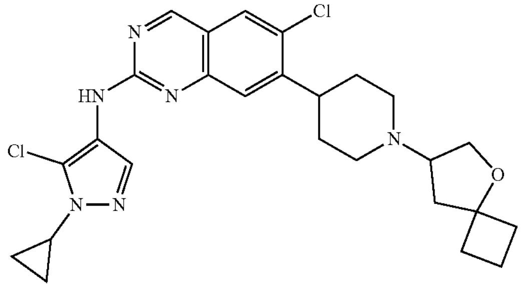 [SMILES: Clc1cc2cnc(Nc3cnn(C4CC4)c3Cl)nc2cc1C1CCN(C2COC3(CCC3)C2)CC1] | (R) or (S) 7-(1-(5-oxaspiro[3.4]octan-7-yl)piperidin-4-yl)-6-chloro-N-(5-chloro-1-cyclopropyl-1H-pyrazol-4-yl)quinazolin-2-amine | Calc'd 513, found 513 |
| Ex-4.115 | 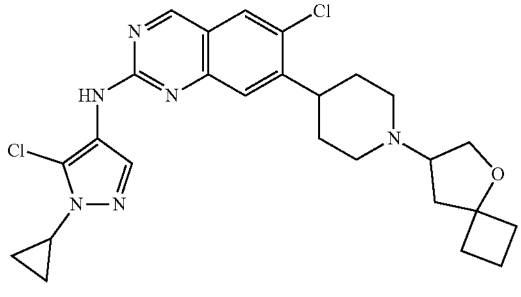 [SMILES: Clc1cc2cnc(Nc3cnn(C4CC4)c3Cl)nc2cc1C1CCN(C2COC3(CCC3)C2)CC1] | (R) or (S) 7-(1-(5-oxaspiro[3.4]octan-7-yl)piperidin-4-yl)-6-chloro-N-(5-chloro-1-cyclopropyl-1H-pyrazol-4-yl)quinazolin-2-amine | Calc'd 513, found 513 |

TABLE 4-continued

| Ex | Structure | Name | Exact Mass [M + H]$^+$ |
|---|---|---|---|
| Ex-4.116 | 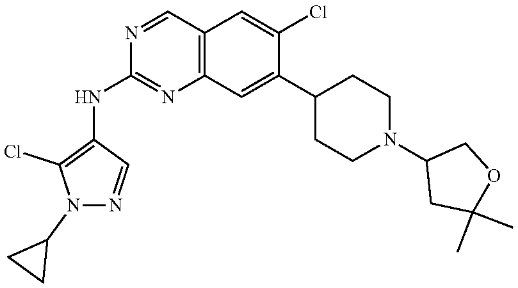 [SMILES: CC1(C)CC(N2CCC(c3cc4nc(Nc5cnn(C6CC6)c5Cl)ncc4cc3Cl)CC2)CO1] | (R) or (S) 6-chloro-N-(5-chloro-1-cyclopropyl-1H-pyrazol-4-yl)-7-(1-(5,5-dimethyltetrahydrofuran-3-yl)piperidin-4-yl)quinazolin-2-amine | Calc'd 501, found 501 |
| Ex-4.117 | 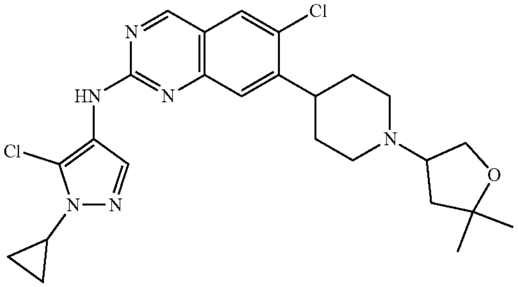 [SMILES: CC1(C)CC(N2CCC(c3cc4nc(Nc5cnn(C6CC6)c5Cl)ncc4cc3Cl)CC2)CO1] | (R) or (S) 6-chloro-N-(5-chloro-1-cyclopropyl-1H-pyrazol-4-yl)-7-(1-(5,5-dimethyltetrahydrofuran-3-yl)piperidin-4-yl)quinazolin-2-amine | Calc'd 501, found 501 |
| Ex-4.118 | 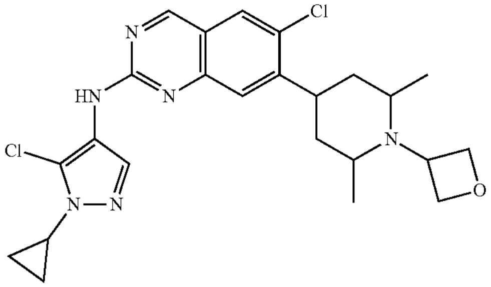 [SMILES: CC1CC(c2cc3nc(Nc4cnn(C5CC5)c4Cl)ncc3cc2Cl)CC(C)N1C1COC1] | cis or trans 6-chloro-N-(5-chloro-1-cyclopropyl-1H-pyrazol-4-yl)-7-(2,6-dimethyl-1-(oxetan-3-yl)piperidin-4-yl)quinazolin-2-amine | Calc'd 487, found 487 |
| Ex-4.119 | 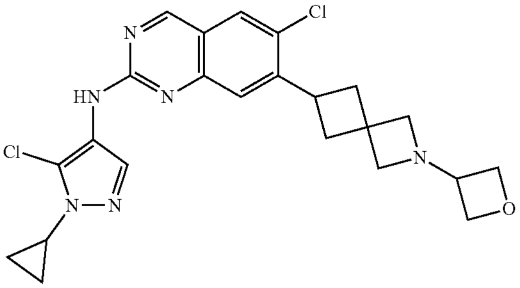 [SMILES: Clc1cc2cnc(Nc3cnn(C4CC4)c3Cl)nc2cc1C1CC2(C1)CN(C1COC1)C2] | 6-chloro-N-(5-chloro-1-cyclopropyl-1H-pyrazol-4-yl)-7-(2-(oxetan-3-yl)-2-azaspiro[3.3]heptan-6-yl)quinazolin-2-amine | Calc'd 471, found 471 |
| Ex-4.120 | 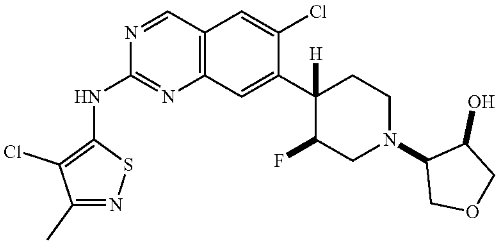 | (3S,4S)(3S,4S) or (3S,4S)(3R,4R) or (3R,4R)(3S,4S) or (3R,4R)(3R,4R) 4-{6-chloro-2-[(4-chloro-3-methyl-1,2-thiazol-5-yl)amino]quinazolin-7-yl}-3-fluoropiperidin-1-yl]oxolan-3-ol | Calc'd 498, found 498 |

TABLE 4-continued

| Ex | Structure | Name | Exact Mass [M + H]+ |
|---|---|---|---|
| Ex-4.121 | 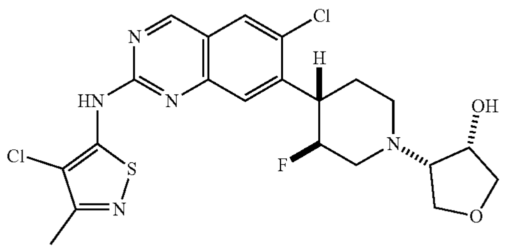 | (3S,4S)(3S,4S) or (3S,4S)(3R,4R) or (3R,4R)(3S,4S) or (3R,4R)(3R,4R) 4-{6-chloro-2-[(4-chloro-3-methyl-1,2-thiazol-5-yl)amino]quinazolin-7-yl}-3-fluoropiperidin-1-yl]oxolan-3-ol | Calc'd 498, found 498 |
| Ex-4.122 | 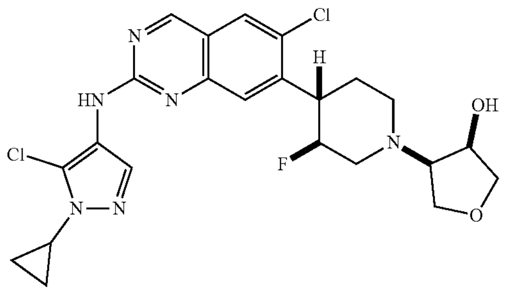 | (3S,4S)(3S,4S) or (3S,4S)(3R,4R) or (3R,4R)(3S,4S) or (3R,4R)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol | Calc'd 507, found 507 |
| Ex-4.123 | 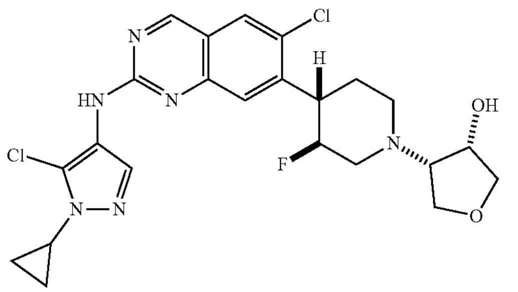 | (3S,4S)(3S,4S) or (3S,4S)(3R,4R) or (3R,4R)(3S,4S) or (3R,4R)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol | Calc'd 507, found 507 |
| Ex-4.124 | 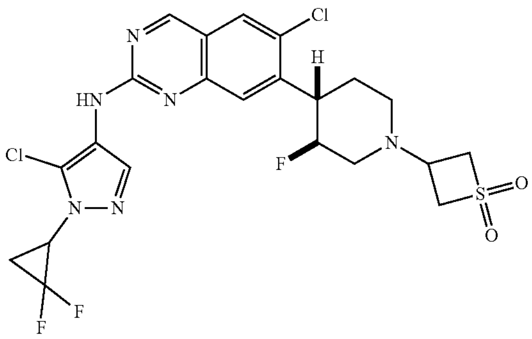 [SMILES: O=S1(=O)CC(N2CC[C@@H](c3cc4nc(Nc5cnn(C6CC6(F)F)c5Cl)ncc4cc3Cl)[C@H](F)C2)C1] | (S)(3S,4S) or (S)(3R,4R) or (R)(3S,4S) or (R)(3R,4R) 3-[4-(6-chloro-2-{[5-chloro-1-(2,2-difluorocyclopropyl)-1H-pyrazol-4-yl]amino}quinazolin-7-yl)-3-fluoropiperidin-1-yl]thietane 1,1-dioxide | Calc'd 561, found 561 |
| Ex-4.125 | 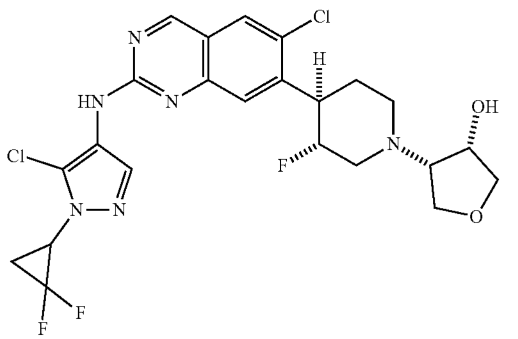 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol | Calc'd 543, found 543 |

TABLE 4-continued

| Ex | Structure | Name | Exact Mass [M + H]+ |
|---|---|---|---|
| Ex-4.126 | 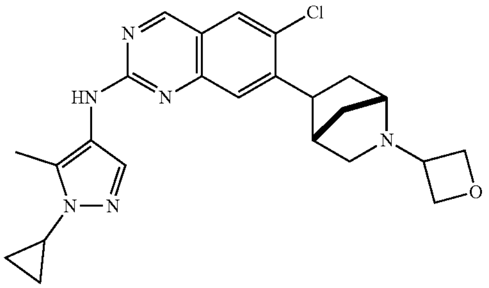 [SMILES: Cc1c(Nc2ncc3cc(Cl)c(C4C[C@H]5C[C@@H]4CN5C4COC4)cc3n2)cnn1C1CC1] | (1S,4S) or (1R,4R) 6-chloro-N-(1-cyclopropyl-5-methyl-1H-pyrazol-4-yl)-7-[2-(oxetan-3-yl)-2-azabicyclo[2.2.1]heptan-5-yl]quinazolin-2-amine | Calc'd 451, found 451 |
| Ex-4.127 | 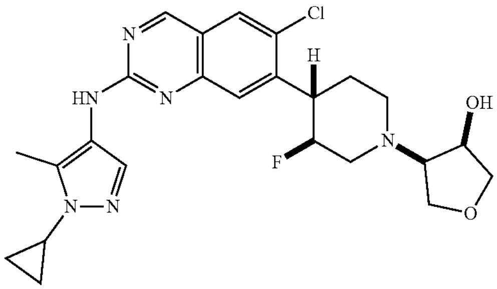 | (3S,4S)(3S,4S) or (3S,4S)(3R,4R) or (3R,4R)(3S,4S) or (3R,4R)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol | Calc'd 487, found 487 |
| Ex-4.128 | 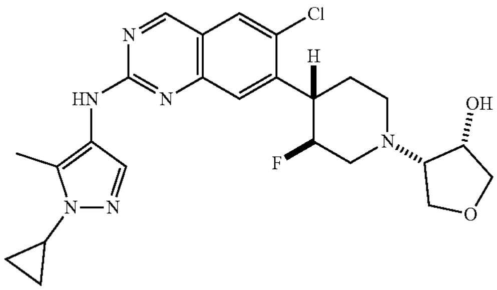 | (3S,4S)(3S,4S) or (3S,4S)(3R,4R) or (3R,4R)(3S,4S) or (3R,4R)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol | Calc'd 487, found 487 |
| Ex-4.129 | 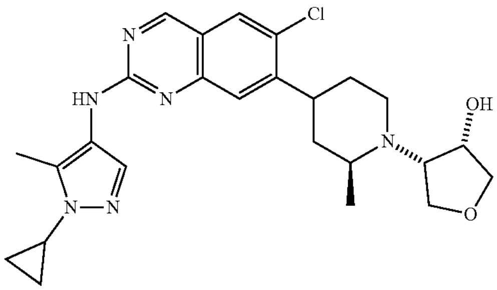 | (3S,4S)(2S,4R) or (3S,4S)(2S,4S) or (3R,4R)(2S,4R) or (3R,4R)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol | Calc'd 483, found 483 |
| Ex-4.130 | 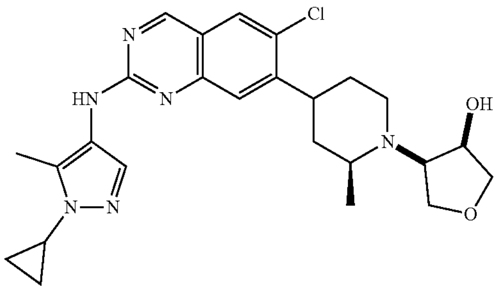 | (3S,4S)(2S,4R) or (3S,4S)(2S,4S) or (3R,4R)(2S,4R) or (3R,4R)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol | Calc'd 483, found 483 |

TABLE 4-continued

| Ex | Structure | Name | Exact Mass [M + H]$^+$ |
| --- | --- | --- | --- |
| Ex-4.131 | 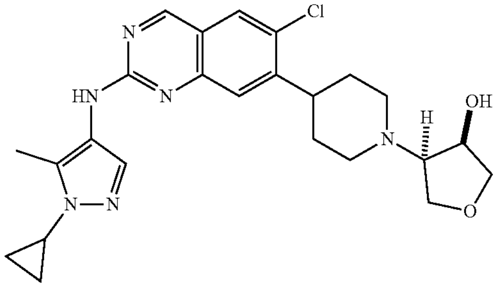 [SMILES: Cc1c(Nc2ncc3cc(Cl)c(C4CCN([C@@H]5COC[C@@H]5O)CC4)cc3n2)cnn1C1CC1] | (3S,4S) or (3R,4R) 4-(4-{6-chloro-2-[(1-cyclopropyl-5-methyl-1H-pyrazol-4-yl)amino]quinazolin-7-yl}piperidin-1-yl)oxolan-3-ol | Calc'd 469, found 469 |
| Ex-4.132 | 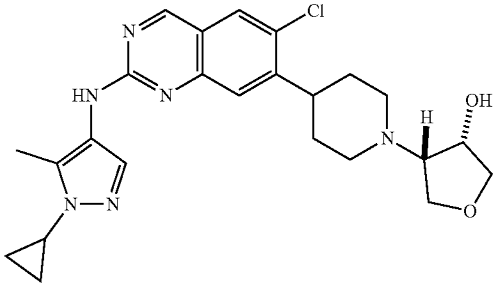 [SMILES: Cc1c(Nc2ncc3cc(Cl)c(C4CCN([C@H]5COC[C@H]5O)CC4)cc3n2)cnn1C1CC1] | (3S,4S) or (3R,4R) 4-(4-{6-chloro-2-[(1-cyclopropyl-5-methyl-1H-pyrazol-4-yl)amino]quinazolin-7-yl}piperidin-1-yl)oxolan-3-ol | Calc'd 469, found 469 |
| Ex-4.133 | 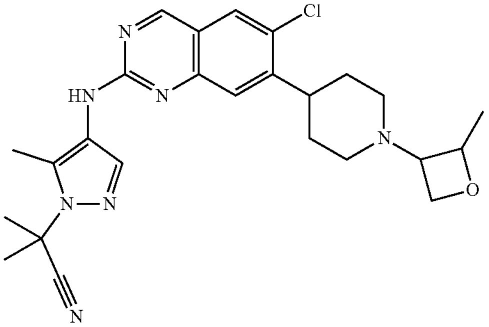 [SMILES: Cc1c(Nc2ncc3cc(Cl)c(C4CCN(C5COC5C)CC4)cc3n2)cnn1C(C)(C)C#N] | (2R,3R) or (2S,3S) or (2S,3R) or (2R,3S) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile | Calc'd 480, found 480 |
| Ex-4.134 | 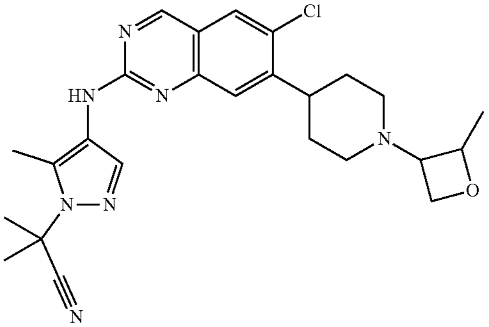 [SMILES: Cc1c(Nc2ncc3cc(Cl)c(C4CCN(C5COC5C)CC4)cc3n2)cnn1C(C)(C)C#N] | (2R,3R) or (2S,3S) or (2S,3R) or (2R,3S) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile | Calc'd 480, found 480 |
| Ex-4.135 | 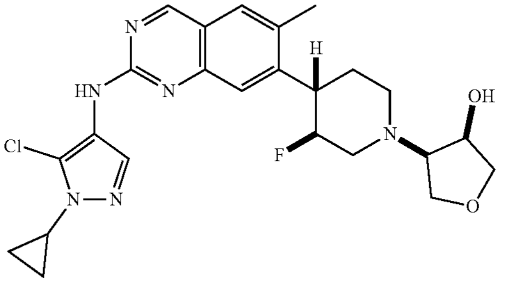 | (3S,4S)(3S,4S) or (3S,4S)(3R,4R) or (3R,4R)(3S,4S) or (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol | Calc'd 487, found 487 |

TABLE 4-continued

| Ex | Structure | Name | Exact Mass [M + H]+ |
|---|---|---|---|
| Ex-4.136 | 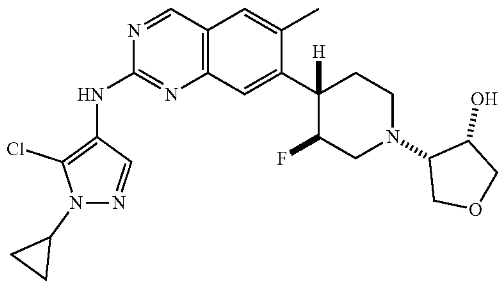 | (3S,4S)(3S,4S) or (3S,4S)(3R,4R) or (3R,4R)(3S,4S) or (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol | Calc'd 487, found 487 |
| Ex-4.137 | 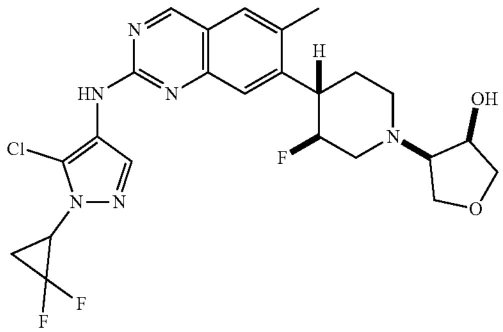 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol | Calc'd 523, found 523 |
| Ex-4.138 | 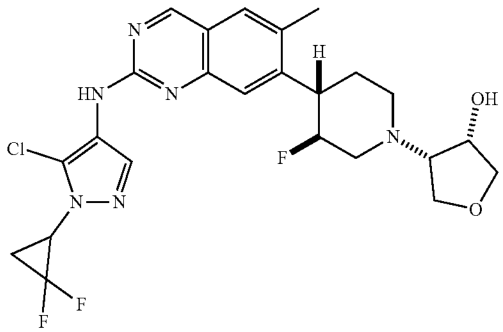 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol | Calc'd 523, found 523 |
| Ex-4.139 | 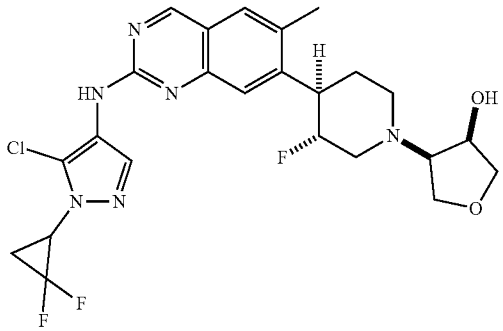 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol | Calc'd 523, found 523 |

TABLE 4-continued

| Ex | Structure | Name | Exact Mass [M + H]+ |
|---|---|---|---|
| Ex-4.140 | 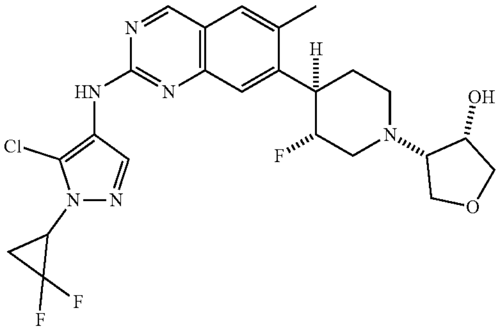 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol | Calc'd 523, found 523 |
| Ex-4.141 | 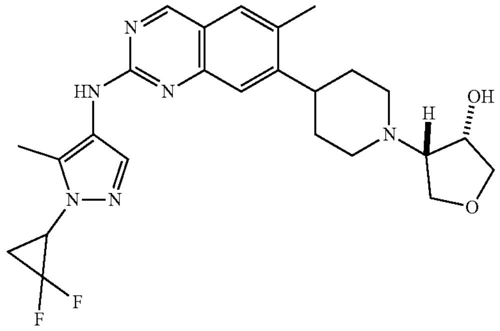 [SMILES: Cc1cc2cnc(Nc3cnn(C4CC4(F)F)c3C)nc2cc1C1CCN([C@H]2COC[C@H]2O)CC1] | (R)(3S,4S) or (S)(3S,4S) or (R)(3R,4R) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]oxolan-3-ol | Calc'd 485, found 485 |
| Ex-4.142 | 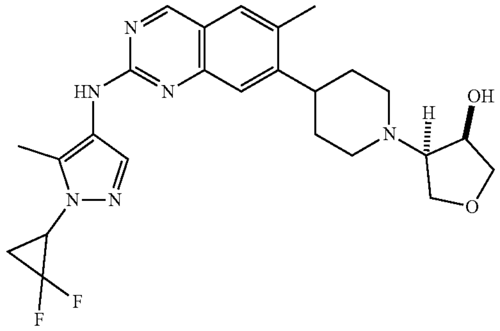 [SMILES: Cc1cc2cnc(Nc3cnn(C4CC4(F)F)c3C)nc2cc1C1CCN([C@@H]2COC[C@@H]2O)CC1] | (R)(3S,4S) or (S)(3S,4S) or (R)(3R,4R) or (S)(3R,4R) 4-[4-(2-{[1-(2,2-difluorocyclopropyl)-5-methyl-1H-pyrazol-4-yl]amino}-6-methylquinazolin-7-yl)piperidin-1-yl]oxolan-3-ol | Calc'd 485, found 485 |
| Ex-4.143 | 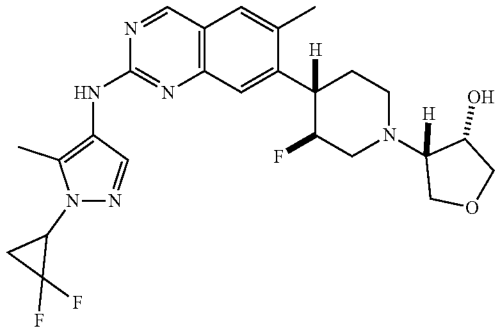 [SMILES: Cc1cc2cnc(Nc3cnn(C4CC4(F)F)c3C)nc2cc1[C@@H]1CCN([C@H]2COC[C@H]2O)C[C@H]1F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol | Calc'd 503, found 503 |

TABLE 4-continued

| Ex | Structure | Name | Exact Mass [M + H]+ |
|---|---|---|---|
| Ex-4.144 | 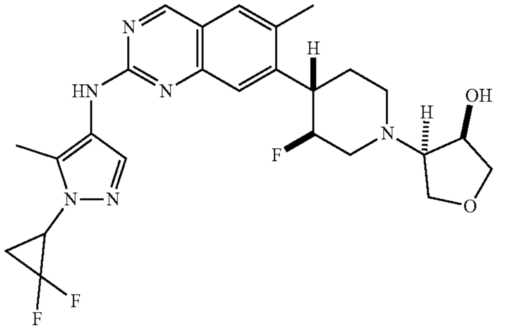 [SMILES: Cc1cc2cnc(Nc3cnn(C4CC4(F)F)c3C)nc2cc1[C@@H]1CCN([C@@H]2COC[C@@H]2O)C[C@H]1F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol | Calc'd 503, found 503 |
| Ex-4.145 | 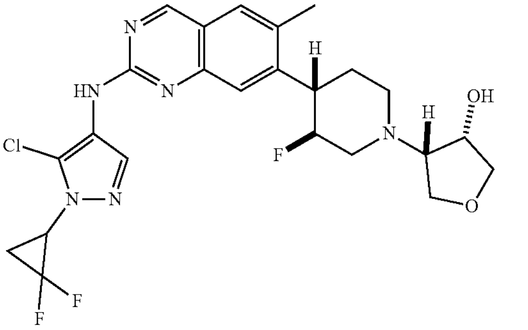 [SMILES: Cc1cc2cnc(Nc3cnn(C4CC4(F)F)c3Cl)nc2cc1[C@@H]1CCN([C@H]2COC[C@H]2O)C[C@H]1F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol | Calc'd 523, found 523 |
| Ex-4.146 | 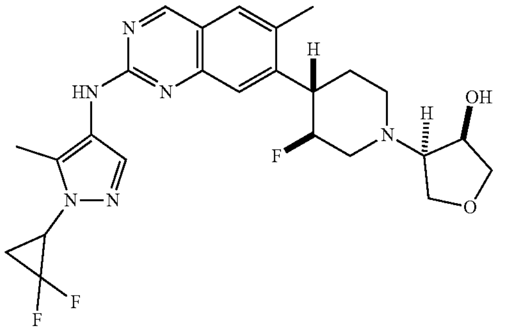 [SMILES: Cc1cc2cnc(Nc3cnn(C4CC4(F)F)c3C)nc2cc1[C@@H]1CCN([C@@H]2COC[C@@H]2O)C[C@H]1F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol | Calc'd 503, found 503 |
| Ex-4.147 | 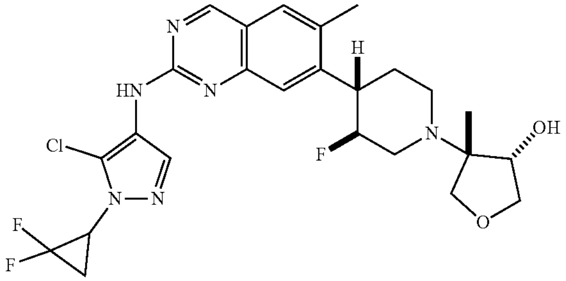 [SMILES: Cc1cc2cnc(Nc3cnn(C4CC4(F)F)c3Cl)nc2cc1[C@@H]1CCN([C@@]2(C)COC[C@H]2O)C[C@H]1F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol | Calc'd 537, found 537 |
| Ex-4.148 | 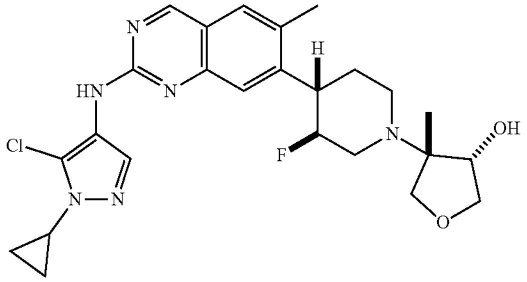 [SMILES: Cc1cc2cnc(Nc3cnn(C4CC4)c3Cl)nc2cc1[C@@H]1CCN([C@@]2(C)COC[C@H]2O)C[C@H]1F] | (3S,4S)(3S,4S) or (3S,4S)(3R,4R) or (3R,4R)(3S,4S) or (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol | Calc'd 501, found 501 |

TABLE 4-continued

| Ex | Structure | Name | Exact Mass [M + H]+ |
|---|---|---|---|
| Ex-4.149 | 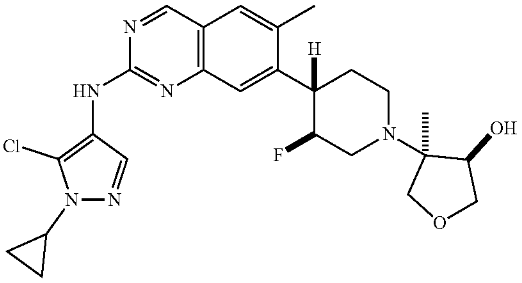 [SMILES: Cc1cc2cnc(Nc3cnn(C4CC4)c3Cl)nc2cc1[C@@H]1CCN([C@]2(C)COC[C@@H]2O)C[C@H]1F] | (3S,4S)(3S,4S) or (3S,4S)(3R,4R) or (3R,4R)(3S,4S) or (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol | Calc'd 501, found 501 |
| Ex-4.150 | 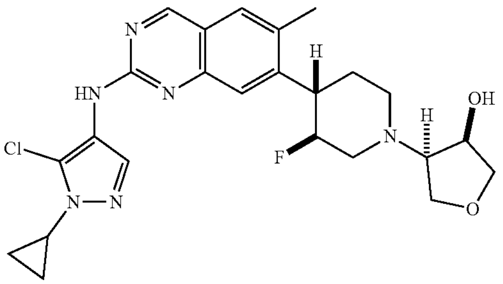 [SMILES: Cc1cc2cnc(Nc3cnn(C4CC4)c3Cl)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol | Calc'd 487, found 487 |
| Ex-4.151 | 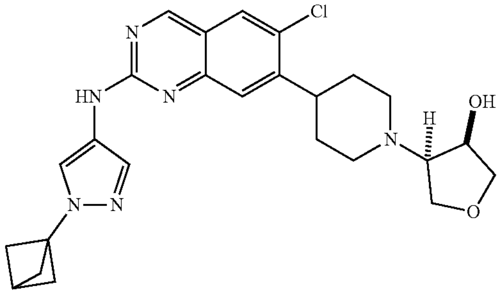 [SMILES: O[C@H]1COC[C@H]1N1CCC(c2cc3nc(Nc4cnn(C56CC(C5)C6)c4)ncc3cc2Cl)CC1] | (3S,4S) or (3R,4R) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol | Calc'd 481, found 481 |
| Ex-4.152 | 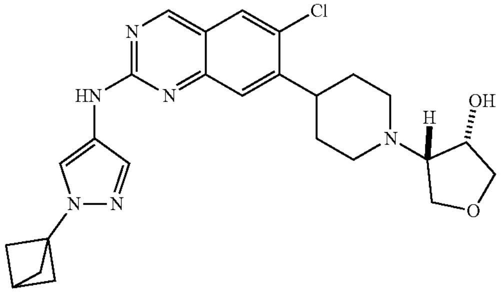 [SMILES: O[C@@H]1COC[C@@H]1N1CCC(c2cc3nc(Nc4cnn(C56CC(C5)C6)c4)ncc3cc2Cl)CC1] | (3S,4S) or (3R,4R) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol | Calc'd 481, found 481 |
| Ex-4.153 | 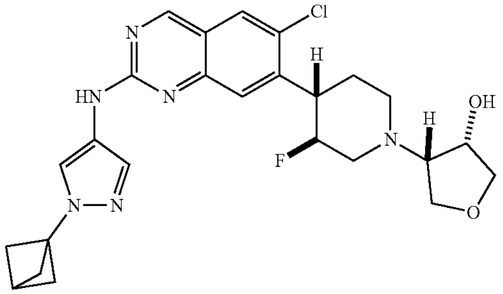 [SMILES: O[C@@H]1COC[C@@H]1N1CC[C@@H](c2cc3nc(Nc4cnn(C56CC(C5)C6)c4)ncc3cc2Cl)[C@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol | Calc'd 499, found 499 |

TABLE 4-continued

| Ex | Structure | Name | Exact Mass [M + H]+ |
|---|---|---|---|
| Ex-4.154 | 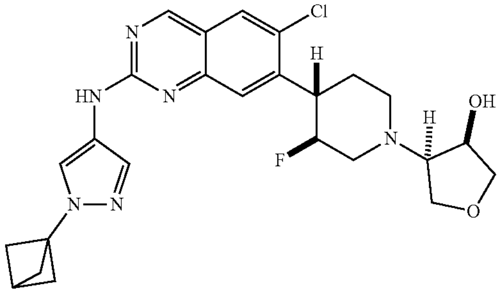 [SMILES: O[C@H]1COC[C@H]1N1CC[C@@H](c2cc3nc(Nc4cnn(C56CC(C5)C6)c4)ncc3cc2Cl)[C@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol | Calc'd 499, found 499 |
| Ex-4.155 | 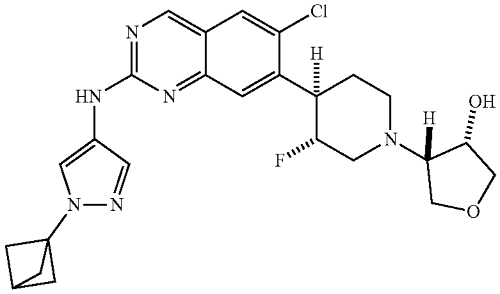 [SMILES: O[C@@H]1COC[C@@H]1N1CC[C@H](c2cc3nc(Nc4cnn(C56CC(C5)C6)c4)ncc3cc2Cl)[C@@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol | Calc'd 499, found 499 |
| Ex-4.156 | 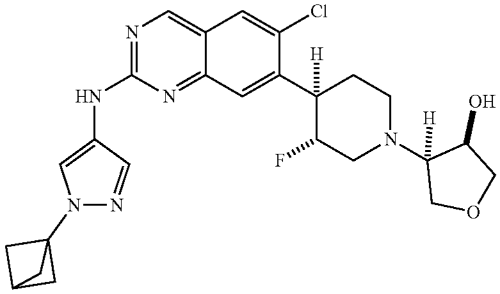 [SMILES: O[C@H]1COC[C@H]1N1CC[C@H](c2cc3nc(Nc4cnn(C56CC(C5)C6)c4)ncc3cc2Cl)[C@@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol | Calc'd 499, found 499 |
| Ex-4.157 | 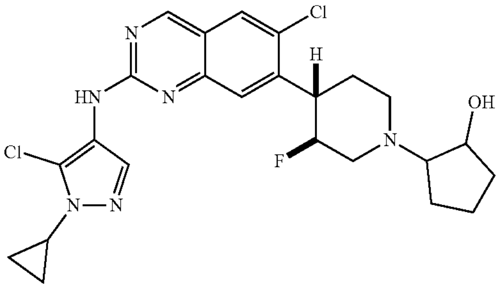 [SMILES: OC1CCCC1N1CC[C@@H](c2cc3nc(Nc4cnn(C5CC5)c4Cl)ncc3cc2Cl)[C@H](F)C1] | (1S,2R)(3S,4S) or (1R,2S)(3S,4S) or (1R,2R)(3S,4S) or (1S,2S)(3S,4S) or (1S,2R)(3R,4R) or (1R,2S)(3R,4R) or (1R,2R)(3R,4R) or (1S,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol | Calc'd 505, found 505 |
| Ex-4.158 | 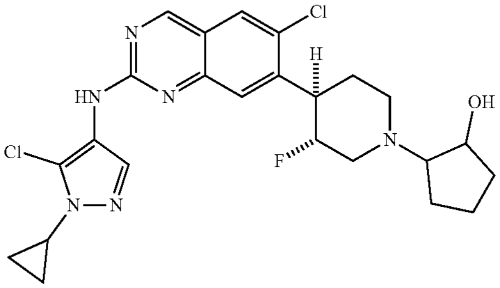 [SMILES: OC1CCCC1N1CC[C@H](c2cc3nc(Nc4cnn(C5CC5)c4Cl)ncc3cc2Cl)[C@@H](F)C1] | (1S,2R)(3S,4S) or (1R,2S)(3S,4S) or (1R,2R)(3S,4S) or (1S,2S)(3S,4S) or (1S,2R)(3R,4R) or (1R,2S)(3R,4R) or (1R,2R)(3R,4R) or (1S,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol | Calc'd 505, found 505 |

TABLE 4-continued

| Ex | Structure | Name | Exact Mass [M + H]+ |
|---|---|---|---|
| Ex-4.159 | 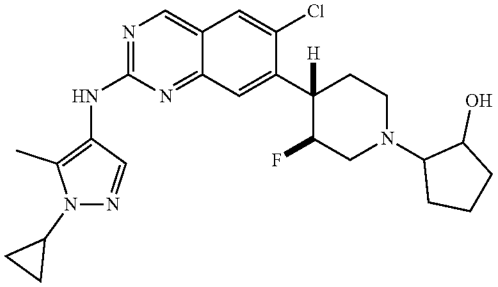 [SMILES: Cc1c(Nc2ncc3cc(Cl)c([C@@H]4CCN(C5CCCC5O)C[C@H]4F)cc3n2)cnn1C1CC1] | (1S,2R)(3S,4S) or (1R,2S)(3S,4S) or (1R,2R)(3S,4S) or (1S,2S)(3S,4S) or (1S,2R)(3R,4R) or (1R,2S)(3R,4R) or (1R,2R)(3R,4R) or (1S,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol | Calc'd 485, found 485 |
| Ex-4.160 | 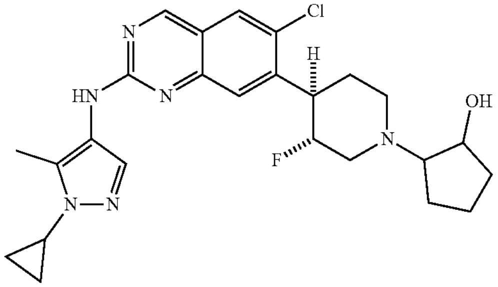 [SMILES: Cc1c(Nc2ncc3cc(Cl)c([C@H]4CCN(C5CCCC5O)C[C@@H]4F)cc3n2)cnn1C1CC1] | (1S,2R)(3S,4S) or (1R,2S)(3S,4S) or (1R,2R)(3S,4S) or (1S,2S)(3S,4S) or (1S,2R)(3R,4R) or (1R,2S)(3R,4R) or (1R,2R)(3R,4R) or (1S,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol | Calc'd 485, found 485 |
| Ex-4.161 | 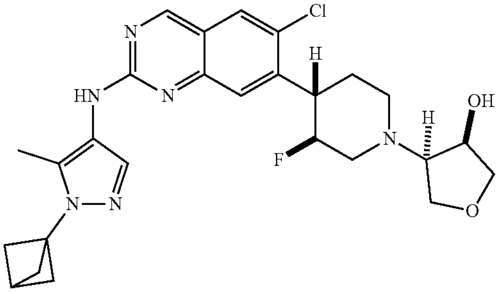 [SMILES: Cc1c(Nc2ncc3cc(Cl)c([C@@H]4CCN([C@@H]5COC[C@@H]5O)C[C@H]4F)cc3n2)cnn1C12CC(C1)C2] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol | Calc'd 513, found 513 |
| Ex-4.162 | 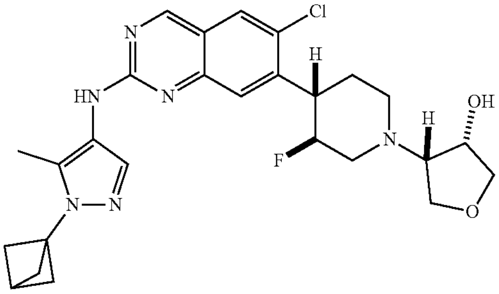 [SMILES: Cc1c(Nc2ncc3cc(Cl)c([C@@H]4CCN([C@H]5COC[C@H]5O)C[C@H]4F)cc3n2)cnn1C12CC(C1)C2] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol | Calc'd 513, found 513 |
| Ex-4.163 | 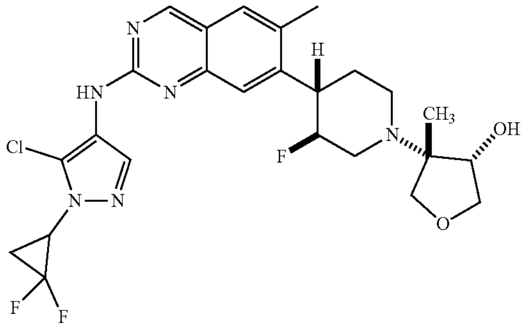 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol | Calc'd 537, found 537 |

TABLE 4-continued

| Ex | Structure | Name | Exact Mass [M + H]+ |
|---|---|---|---|
| Ex-4.164 | 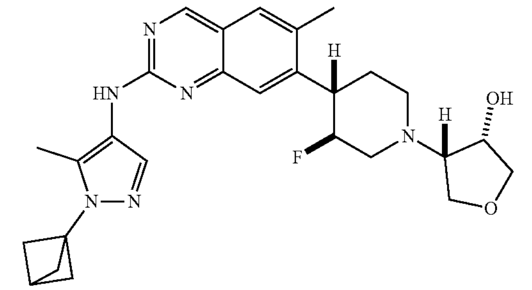 [SMILES: Cc1cc2cnc(Nc3cnn(C45CC(C4)C5)c3C)nc2cc1[C@@H]1CCN([C@H]2COC[C@H]2O)C[C@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol | Calc'd 493, found 493 |
| Ex-4.165 | 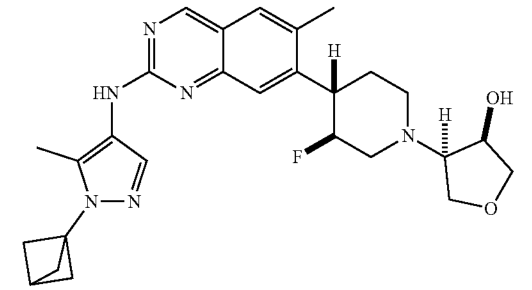 [SMILES: Cc1cc2cnc(Nc3cnn(C45CC(C4)C5)c3C)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol | Calc'd 493, found 493 |
| Ex-4.166 | 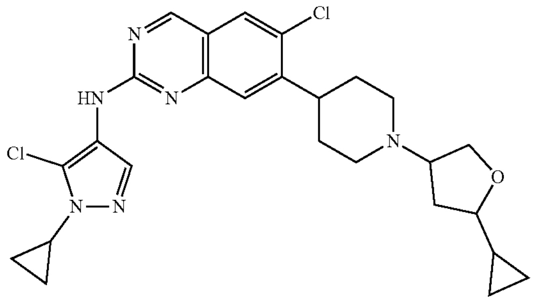 [SMILES: Clc1cc2cnc(Nc3cnn(C4CC4)c3Cl)nc2cc1C1CCN(C2COC(C3CC3)C2)CC1] | (3R,5R) or (3S,5R) or (3R,5S) or (3S,5S) 6-chloro-N-(5-chloro-1-cyclopropyl-1H-pyrazol-4-yl)-7-[1-(5-cyclopropyloxolan-3-yl)piperidin-4-yl]quinazolin-2-amine | Calc'd 513, found 513 |
| Ex-4.167 | 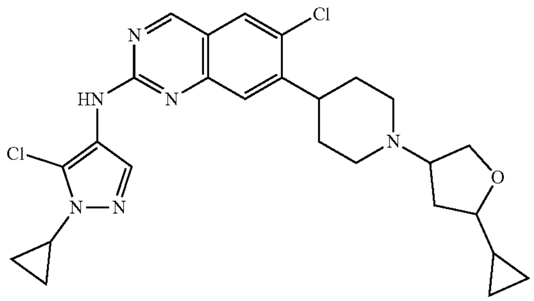 [SMILES: Clc1cc2cnc(Nc3cnn(C4CC4)c3Cl)nc2cc1C1CCN(C2COC(C3CC3)C2)CC1] | (3R,5R) or (3S,5R) or (3R,5S) or (3S,5S) 6-chloro-N-(5-chloro-1-cyclopropyl-1H-pyrazol-4-yl)-7-[1-(5-cyclopropyloxolan-3-yl)piperidin-4-yl]quinazolin-2-amine | Calc'd 513, found 513 |
| Ex-4.168 | 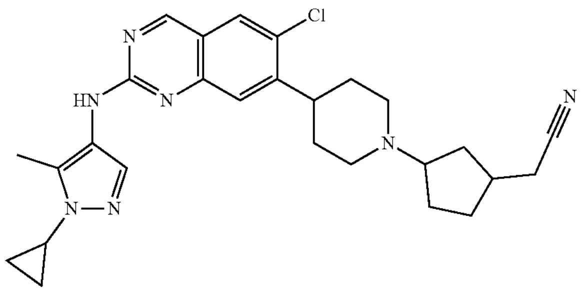 [SMILES: Cc1c(Nc2ncc3cc(Cl)c(C4CCN(C5CCC(CC#N)C5)CC4)cc3n2)cnn1C1CC1] | (1R,3R) or (1S,3R) or (1R,3S) or (1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile | Calc'd 490, found 490 |

TABLE 4-continued

| Ex | Structure | Name | Exact Mass [M + H]+ |
|---|---|---|---|
| Ex-4.169 | 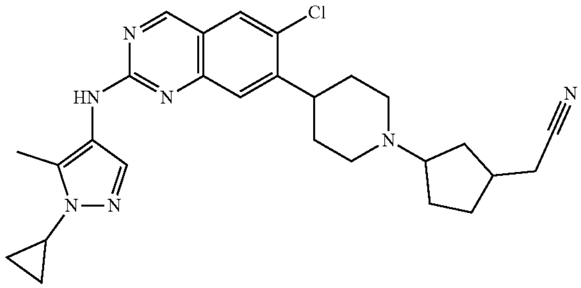 [SMILES: Cc1c(Nc2ncc3cc(Cl)c(C4CCN(C5CCC(CC#N)C5)CC4)cc3n2)cnn1C1CC1] | (1R,3R) or (1S,3R) or (1R,3S) or (1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile | Calc'd 490, found 490 |
| Ex-4.170 | 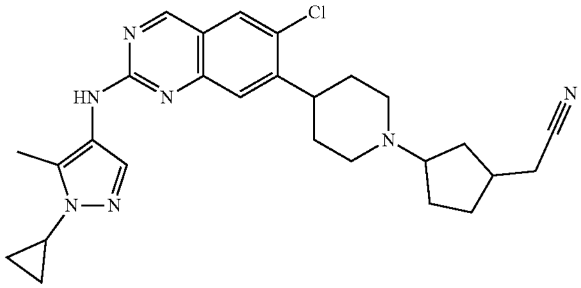 [SMILES: Cc1c(Nc2ncc3cc(Cl)c(C4CCN(C5CCC(CC#N)C5)CC4)cc3n2)cnn1C1CC1] | (1R,3R) or (1S,3R) or (1R,3S) or (1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile | Calc'd 490, found 490 |
| Ex-4.171 | 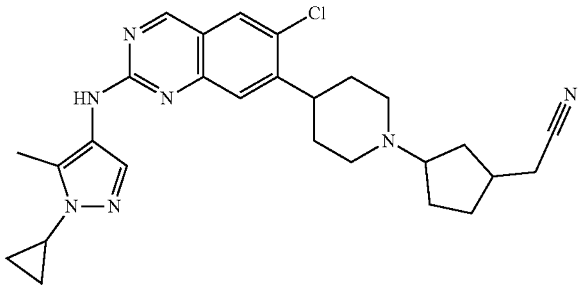 [SMILES: Cc1c(Nc2ncc3cc(Cl)c(C4CCN(C5CCC(CC#N)C5)CC4)cc3n2)cnn1C1CC1] | (1R,3R) or (1S,3R) or (1R,3S) or (1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile | Calc'd 490, found 490 |
| Ex-4.172 | 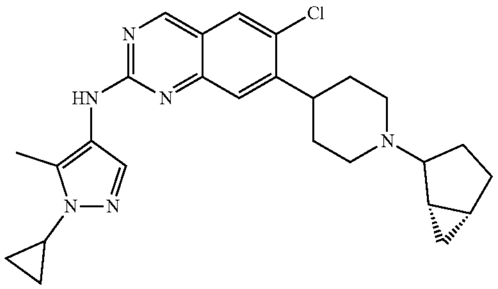 [SMILES: Cc1c(Nc2ncc3cc(Cl)c(C4CCN(C5CC[C@@H]6C[C@H]56)CC4)cc3n2)cnn1C1CC1] | 7-{1-[(1S,5R)-bicyclo[3.1.0]hexan-2-yl]piperidin-4-yl}-6-chloro-N-(1-cyclopropyl-5-methyl-1H-pyrazol-4-yl)quinazolin-2-amine | Calc'd 463, found 463 |
| Ex-4.173 | 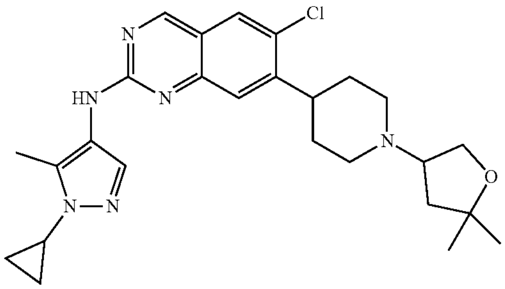 [SMILES: Cc1c(Nc2ncc3cc(Cl)c(C4CCN(C5COC(C)(C)C5)CC4)cc3n2)cnn1C1CC1] | (R) or (S) 6-chloro-N-(1-cyclopropyl-5-methyl-1H-pyrazol-4-yl)-7-[1-(5,5-dimethyloxolan-3-yl)piperidin-4-yl]quinazolin-2-amine | Calc'd 481, found 481 |

TABLE 4-continued

| Ex | Structure | Name | Exact Mass [M + H]+ |
|---|---|---|---|
| Ex-4.174 | 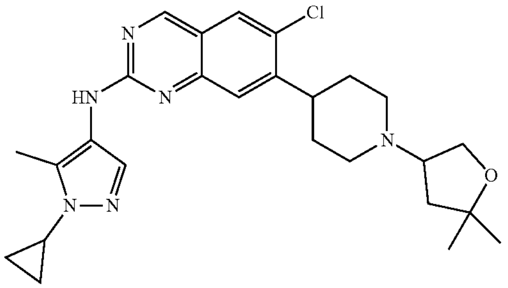 [SMILES: Cc1c(Nc2ncc3cc(Cl)c(C4CCN(C5COC(C)(C)C5)CC4)cc3n2)cnn1C1CC1] | (R) or (S) 6-chloro-N-(1-cyclopropyl-5-methyl-1H-pyrazol-4-yl)-7-[1-(5,5-dimethyloxolan-3-yl)piperidin-4-yl]quinazolin-2-amine | Calc'd 481, found 481 |
| Ex-4.175 | 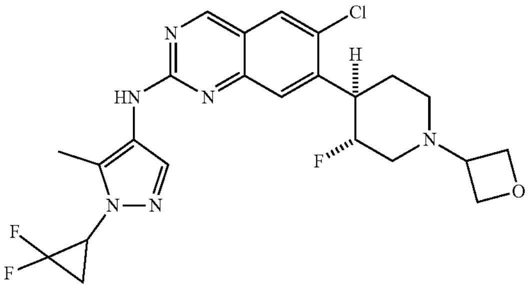 [SMILES: Cc1c(Nc2ncc3cc(Cl)c([C@H]4CCN(C5COC5)C[C@@H]4F)cc3n2)cnn1C1CC1(F)F] | (R)(3S,4S) or (S)(3S,4S) or (R)(3R,4R) or (S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine | Calc'd 493, found 493 |
| Ex-4.176 | 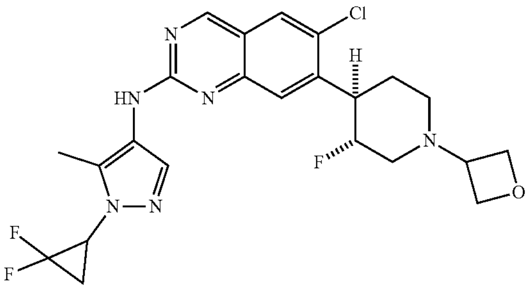 [SMILES: Cc1c(Nc2ncc3cc(Cl)c([C@H]4CCN(C5COC5)C[C@@H]4F)cc3n2)cnn1C1CC1(F)F] | (R)(3S,4S) or (S)(3S,4S) or (R)(3R,4R) or (S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine | Calc'd 493, found 493 |
| Ex-4.177 | 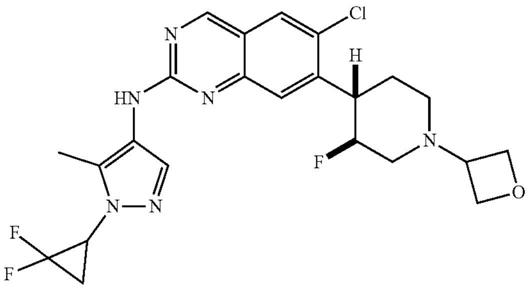 [SMILES: Cc1c(Nc2ncc3cc(Cl)c([C@@H]4CCN(C5COC5)C[C@H]4F)cc3n2)cnn1C1CC1(F)F] | (R)(3S,4S) or (S)(3S,4S) or (R)(3R,4R) or (S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine | Calc'd 493, found 493 |
| Ex-4.178 | 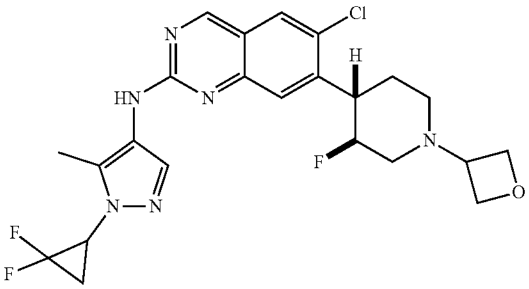 [SMILES: Cc1c(Nc2ncc3cc(Cl)c([C@@H]4CCN(C5COC5)C[C@H]4F)cc3n2)cnn1C1CC1(F)F] | (R)(3S,4S) or (S)(3S,4S) or (R)(3R,4R) or (S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine | Calc'd 493, found 493 |

TABLE 4-continued

| Ex | Structure | Name | Exact Mass [M + H]$^+$ |
|---|---|---|---|
| Ex-4.179 | 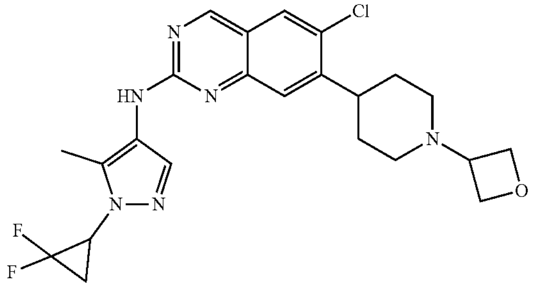 [SMILES: Cc1c(Nc2ncc3cc(Cl)c(C4CCN(C5COC5)CC4)cc3n2)cnn1C1CC1(F)F] | (R) or (S) 6-chloro-N-[1-(2,2-difluorocyclopropyl)-5-methyl-1H-pyrazol-4-yl]-7-[1-(oxetan-3-yl)piperidin-4-yl]quinazolin-2-amine | Calc'd 475, found 475 |
| Ex-4.180 | 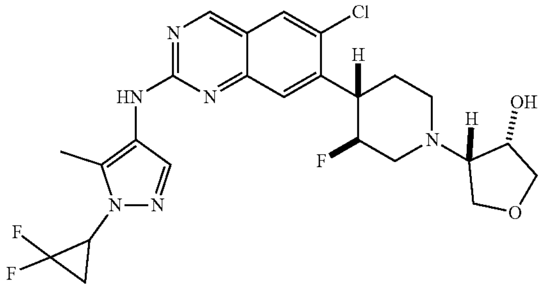 [SMILES: Cc1c(Nc2ncc3cc(Cl)c([C@@H]4CCN([C@H]5COC[C@H]5O)C[C@H]4F)cc3n2)cnn1C1CC1(F)F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol | Calc'd 523, found 523 |
| Ex-4.181 | 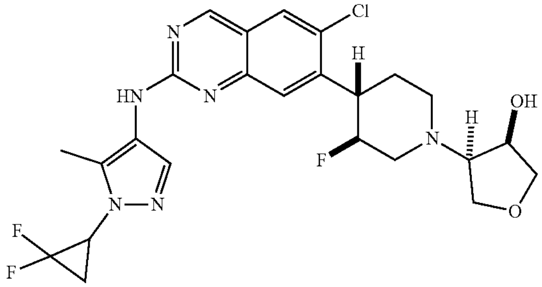 [SMILES: Cc1c(Nc2ncc3cc(Cl)c([C@@H]4CCN([C@@H]5COC[C@@H]5O)C[C@H]4F)cc3n2)cnn1C1CC1(F)F] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol | Calc'd 523, found 523 |
| Ex-4.182 | 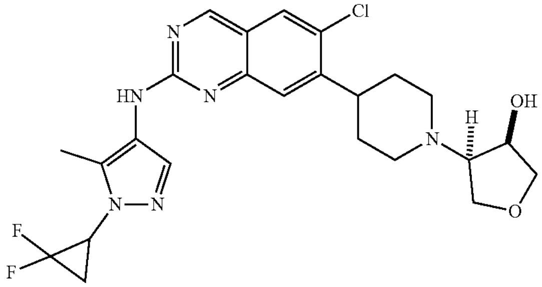 [SMILES: Cc1c(Nc2ncc3cc(Cl)c(C4CCN([C@@H]5COC[C@@H]5O)CC4)cc3n2)cnn1C1CC1(F)F] | (R)(3S,4S) or (S)(3S,4S) or (R)(3R,4R) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol | Calc'd 505, found 505 |
| Ex-4.183 | 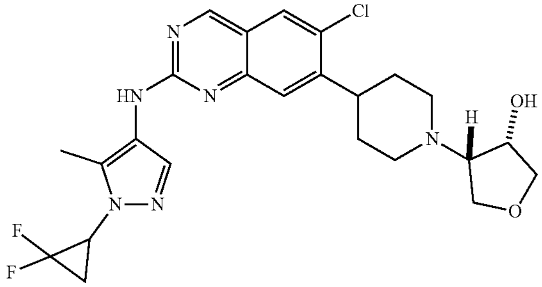 [SMILES: Cc1c(Nc2ncc3cc(Cl)c(C4CCN([C@H]5COC[C@H]5O)CC4)cc3n2)cnn1C1CC1(F)F] | (R)(3S,4S) or (S)(3S,4S) or (R)(3R,4R) or (S)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol | Calc'd 505, found 505 |

TABLE 4-continued

| Ex | Structure | Name | Exact Mass [M + H]+ |
|---|---|---|---|
| Ex-4.184 | 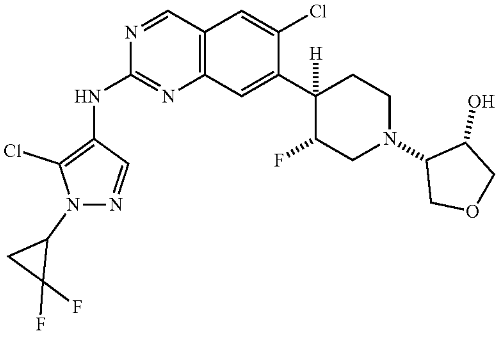 | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol | Calc'd 543, found 543 |
| Ex-4.185 | 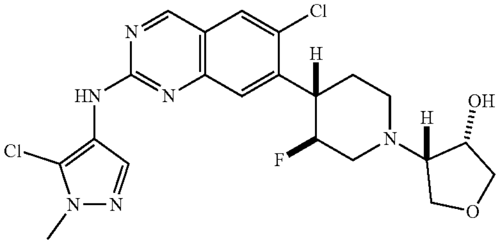 [SMILES: Cn1ncc(Nc2ncc3cc(Cl)c([C@@H]4CCN([C@H]5COC[C@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol | Calc'd 481, found 481 |
| Ex-4.186 | 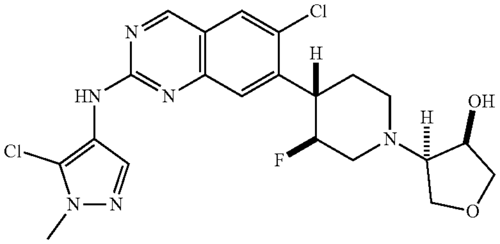 [SMILES: Cn1ncc(Nc2ncc3cc(Cl)c([C@@H]4CCN([C@@H]5COC[C@@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol | Calc'd 481, found 481 |
| Ex-4.187 | 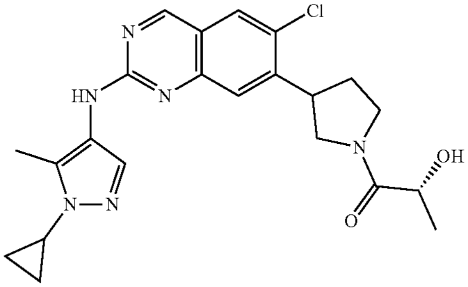 [SMILES: Cc1c(Nc2ncc3cc(Cl)c(C4CCN(C(=O)[C@@H](C)O)C4)cc3n2)cnn1C1CC1] | (2R)(3S) or (2R)(3R) 1-(3-{6-chloro-2-[(1-cyclopropyl-5-methyl-1H-pyrazol-4-yl)amino]quinazolin-7-yl}pyrrolidin-1-yl)-2-hydroxypropan-1-one | Calc'd 441, found 441 |
| Ex-4.188 | 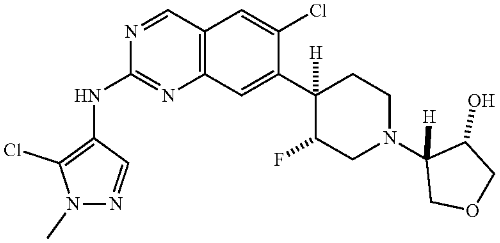 [SMILES: Cn1ncc(Nc2ncc3cc(Cl)c([C@H]4CCN([C@H]5COC[C@H]5O)C[C@@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol | Calc'd 481, found 481 |

TABLE 4-continued

| Ex | Structure | Name | Exact Mass [M + H]+ |
|---|---|---|---|
| Ex-4.189 | 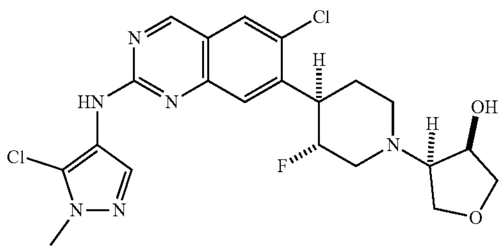 [SMILES: Cn1ncc(Nc2ncc3cc(Cl)c([C@H]4CCN([C@@H]5COC[C@@H]5O)C[C@@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol | Calc'd 481, found 481 |
| Ex-4.190 | 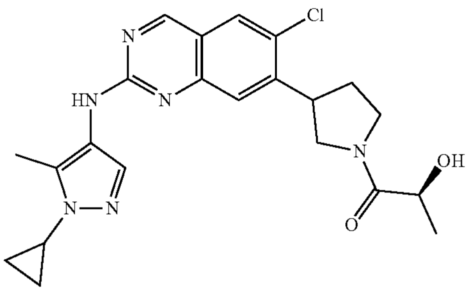 [SMILES: Cc1c(Nc2ncc3cc(Cl)c(C4CCN(C(=O)[C@H](C)O)C4)cc3n2)cnn1C1CC1] | (2S)(3S) or (2S)(3R) 1-(3-{6-chloro-2-[(1-cyclopropyl-5-methyl-1H-pyrazol-4-yl)amino]quinazolin-7-yl}pyrrolidin-1-yl)-2-hydroxypropan-1-one | Calc'd 441, found 441 |
| Ex-4.191 | 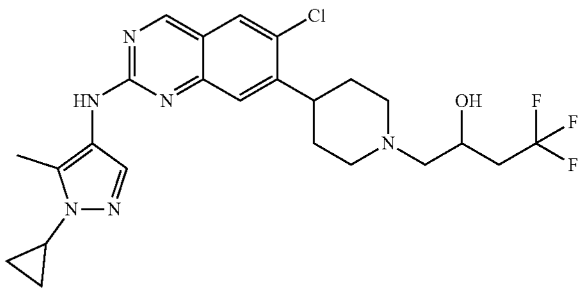 [SMILES: Cc1c(Nc2ncc3cc(Cl)c(C4CCN(CC(O)CC(F)(F)F)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol | Calc'd 509, found 509 |
| Ex-4.192 | 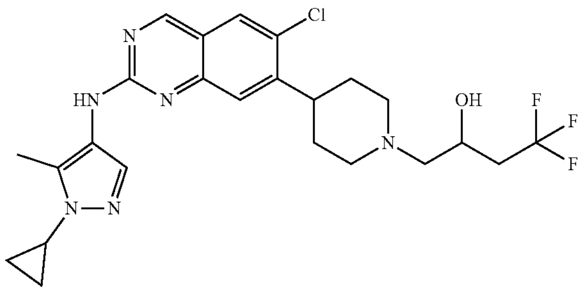 [SMILES: Cc1c(Nc2ncc3cc(Cl)c(C4CCN(CC(O)CC(F)(F)F)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol | Calc'd 509, found 509 |
| Ex-4.193 | 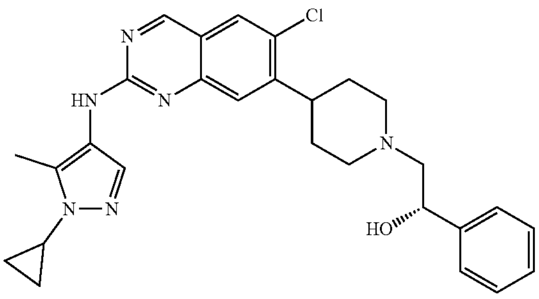 [SMILES: Cc1c(Nc2ncc3cc(Cl)c(C4CCN(C[C@@H](O)c5ccccc5)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-phenylethan-1-ol | Calc'd 503, found 503 |

TABLE 4-continued

| Ex | Structure | Name | Exact Mass [M + H]+ |
| --- | --- | --- | --- |
| Ex-4.194 | 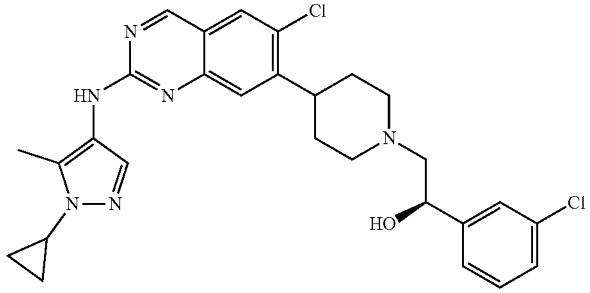 [SMILES: Cc1c(Nc2ncc3cc(Cl)c(C4CCN(C[C@H](O)c5cccc(Cl)c5)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(3-chlorophenyl)ethan-1-ol | Calc'd 537, found 537 |
| Ex-4.195 | 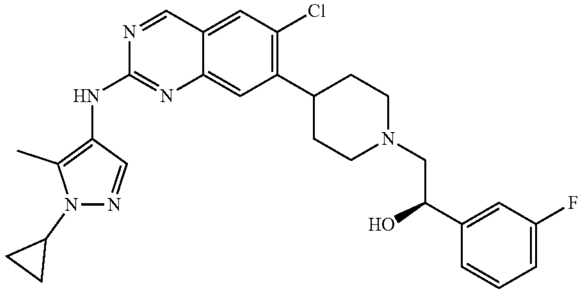 [SMILES: Cc1c(Nc2ncc3cc(Cl)c(C4CCN(C[C@H](O)c5cccc(F)c5)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(3-fluorophenyl)ethan-1-ol | Calc'd 521, found 521 |
| Ex-4.196 | 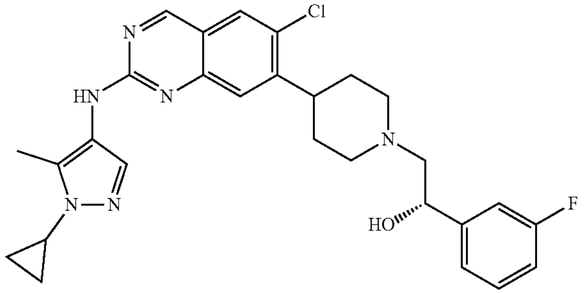 [SMILES: Cc1c(Nc2ncc3cc(Cl)c(C4CCN(C[C@@H](O)c5cccc(F)c5)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(3-fluorophenyl)ethan-1-ol | Calc'd 521, found 521 |
| Ex-4.197 | 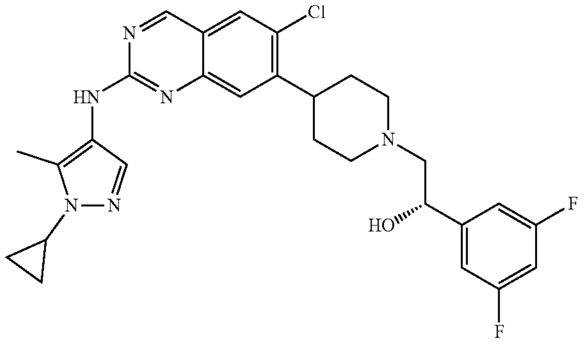 [SMILES: Cc1c(Nc2ncc3cc(Cl)c(C4CCN(C[C@@H](O)c5cc(F)cc(F)c5)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(3,5-difluorophenyl)ethan-1-ol | Calc'd 539, found 539 |

TABLE 4-continued

| Ex | Structure | Name | Exact Mass [M + H]+ |
|---|---|---|---|
| Ex-4.198 | 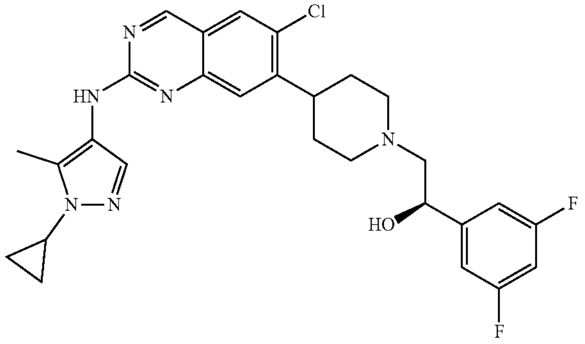 [SMILES: Cc1c(Nc2ncc3cc(Cl)c(C4CCN(C[C@H](O)c5cc(F)cc(F)c5)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(3,5-difluorophenyl)ethan-1-ol | Calc'd 539, found 539 |
| Ex-4.199 | 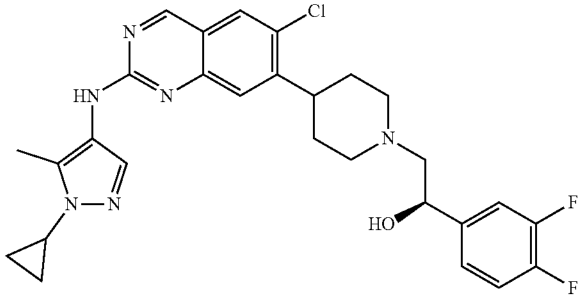 [SMILES: Cc1c(Nc2ncc3cc(Cl)c(C4CCN(C[C@H](O)c5ccc(F)c(F)c5)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(3,4-difluorophenyl)ethan-1-ol | Calc'd 539, found 539 |
| Ex-4.200 | 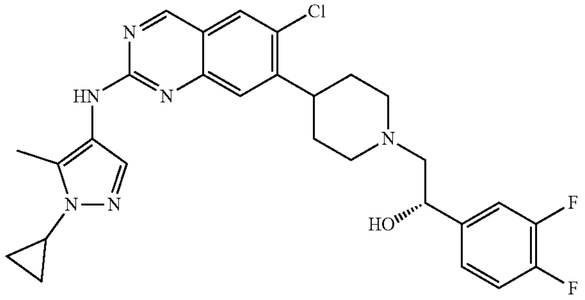 [SMILES: Cc1c(Nc2ncc3cc(Cl)c(C4CCN(C[C@@H](O)c5ccc(F)c(F)c5)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(3,4-difluorophenyl)ethan-1-ol | Calc'd 539, found 539 |
| Ex-4.201 | 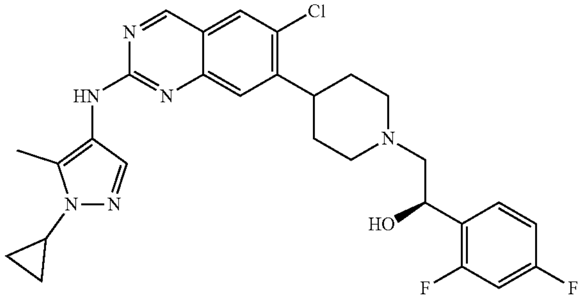 [SMILES: Cc1c(Nc2ncc3cc(Cl)c(C4CCN(C[C@H](O)c5ccc(F)cc5F)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(2,4-difluorophenyl)ethan-1-ol | Calc'd 539, found 539 |
| Ex-4.202 | 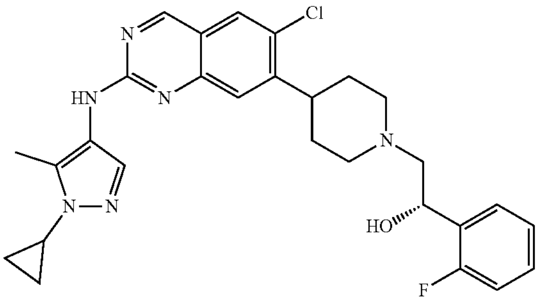 [SMILES: Cc1c(Nc2ncc3cc(Cl)c(C4CCN(C[C@@H](O)c5ccccc5F)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(2-fluorophenyl)ethan-1-ol | Calc'd 521, found 521 |

TABLE 4-continued

| Ex | Structure | Name | Exact Mass [M + H]+ |
|---|---|---|---|
| Ex-4.203 | 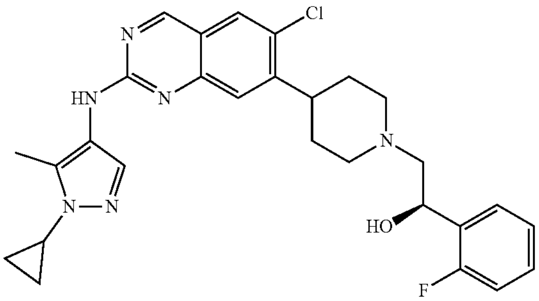 [SMILES: Cc1c(Nc2ncc3cc(Cl)c(C4CCN(C[C@H](O)c5ccccc5F)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(2-fluorophenyl)ethan-1-ol | Calc'd 521, found 521 |
| Ex-4.204 | 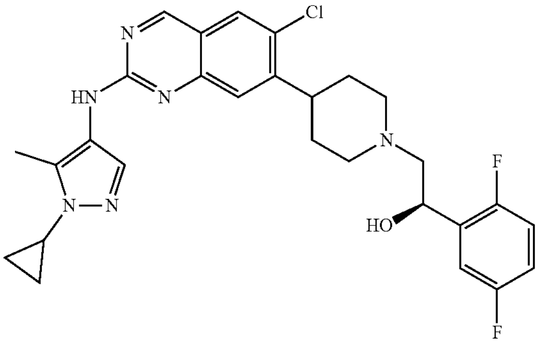 [SMILES: Cc1c(Nc2ncc3cc(Cl)c(C4CCN(C[C@H](O)c5cc(F)ccc5F)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(2,5-difluorophenyl)ethan-1-ol | Calc'd 539, found 539 |
| Ex-4.205 | 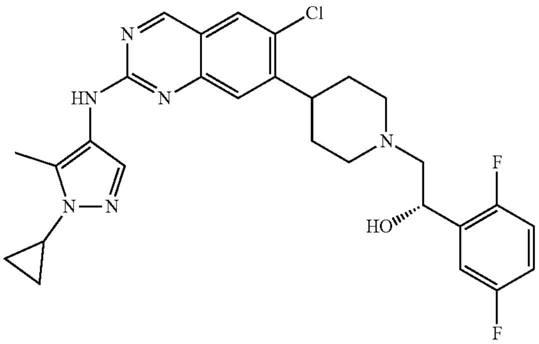 [SMILES: Cc1c(Nc2ncc3cc(Cl)c(C4CCN(C[C@@H](O)c5cc(F)ccc5F)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(2,5-difluorophenyl)ethan-1-ol | Calc'd 539, found 539 |
| Ex-4.206 | 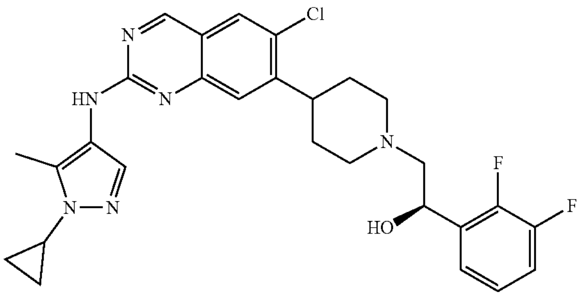 [SMILES: Cc1c(Nc2ncc3cc(Cl)c(C4CCN(C[C@H](O)c5cccc(F)c5F)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(2,3-difluorophenyl)ethan-1-ol | Calc'd 539, found 539 |

TABLE 4-continued

| Ex | Structure | Name | Exact Mass [M + H]+ |
| --- | --- | --- | --- |
| Ex-4.207 | 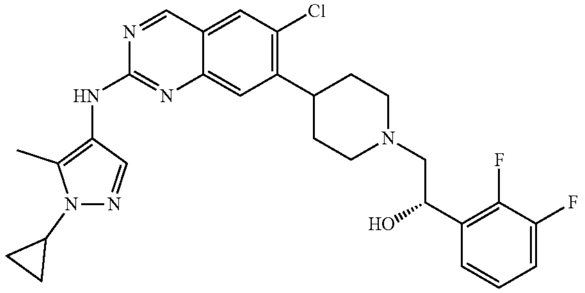 [SMILES: Cc1c(Nc2ncc3cc(Cl)c(C4CCN(C[C@@H](O)c5cccc(F)c5F)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(2,3-difluorophenyl)ethan-1-ol | Calc'd 539, found 539 |
| Ex-4.208 | 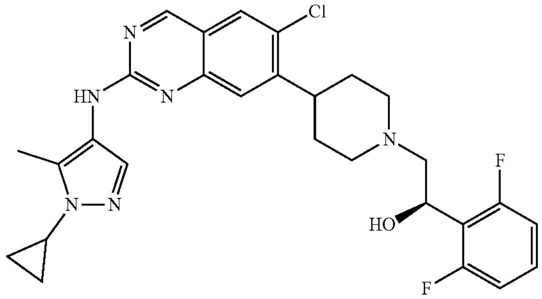 [SMILES: Cc1c(Nc2ncc3cc(Cl)c(C4CCN(C[C@H](O)c5c(F)cccc5F)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(2,6-difluorophenyl)ethan-1-ol | Calc'd 539, found 539 |
| Ex-4.209 | 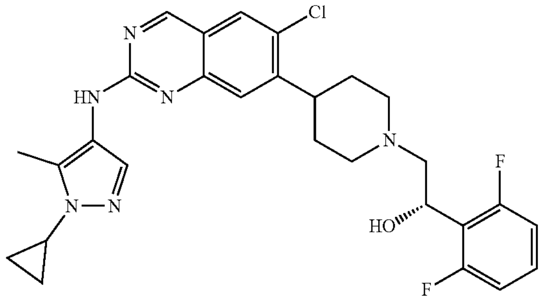 [SMILES: Cc1c(Nc2ncc3cc(Cl)c(C4CCN(C[C@@H](O)c5c(F)cccc5F)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(2,6-difluorophenyl)ethan-1-ol | Calc'd 539, found 539 |
| Ex-4.210 | 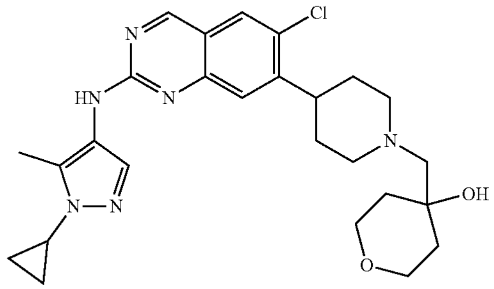 [SMILES: Cc1c(Nc2ncc3cc(Cl)c(C4CCN(CC5(O)CCOCC5)CC4)cc3n2)cnn1C1CC1] | 4-[(4-{6-chloro-2-[(1-cyclopropyl-5-methyl-1H-pyrazol-4-yl)amino]quinazolin-7-yl}piperidin-1-yl)methyl]oxan-4-ol | Calc'd 497, found 497 |
| Ex-4.211 | 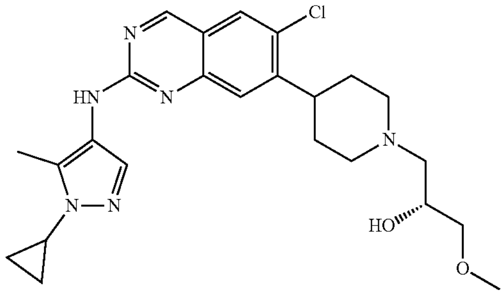 [SMILES: COC[C@H](O)CN1CCC(c2cc3nc(Nc4cnn(C5CC5)c4C)ncc3cc2Cl)CC1] | (2R)-1-(4-{6-chloro-2-[(1-cyclopropyl-5-methyl-1H-pyrazol-4-yl)amino]quinazolin-7-yl}piperidin-1-yl)-3-methoxypropan-2-ol | Calc'd 471, found 471 |

TABLE 4-continued

| Ex | Structure | Name | Exact Mass [M + H]+ |
|---|---|---|---|
| Ex-4.212 | 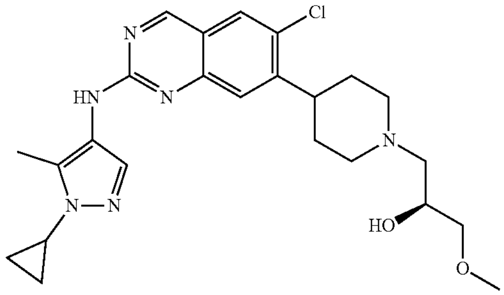 [SMILES: COC[C@@H](O)CN1CCC(c2cc3nc(Nc4cnn(C5CC5)c4C)ncc3cc2Cl)CC1] | (2S)-1-(4-{6-chloro-2-[(1-cyclopropyl-5-methyl-1H-pyrazol-4-yl)amino]quinazolin-7-yl}piperidin-1-yl)-3-methoxypropan-2-ol | Calc'd 471, found 471 |
| Ex-4.213 | 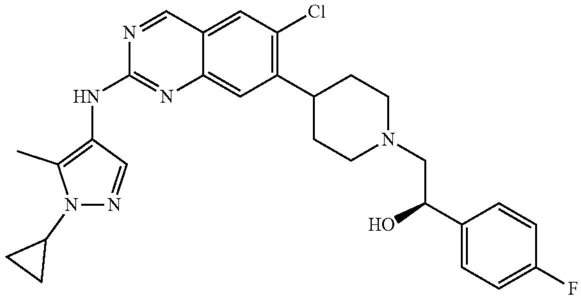 [SMILES: Cc1c(Nc2ncc3cc(Cl)c(C4CCN(C[C@H](O)c5ccc(F)cc5)CC4)cc3n2)cnn1C1CC1] | (1R)-2-(4-{6-chloro-2-[(1-cyclopropyl-5-methyl-1H-pyrazol-4-yl)amino]quinazolin-7-yl}piperidin-1-yl)-1-(4-fluorophenyl)ethan-1-ol | Calc'd 521, found 521 |
| Ex-4.214 | 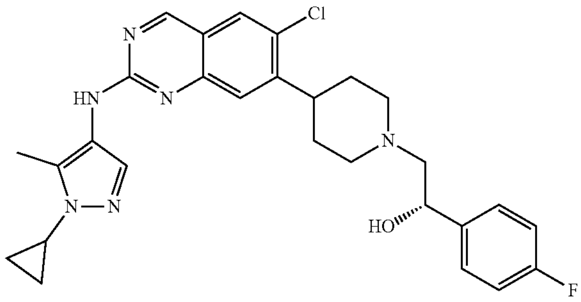 [SMILES: Cc1c(Nc2ncc3cc(Cl)c(C4CCN(C[C@@H](O)c5ccc(F)cc5)CC4)cc3n2)cnn1C1CC1] | (1S)-2-(4-{6-chloro-2-[(1-cyclopropyl-5-methyl-1H-pyrazol-4-yl)amino]quinazolin-7-yl}piperidin-1-yl)-1-(4-fluorophenyl)ethan-1-ol | Calc'd 521, found 521 |
| Ex-4.215 | 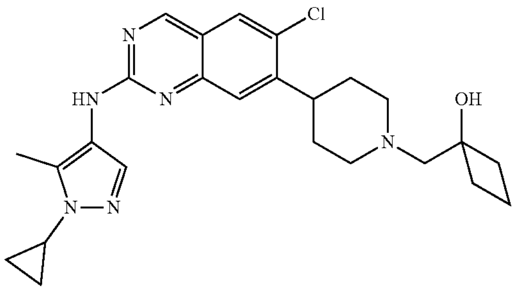 [SMILES: Cc1c(Nc2ncc3cc(Cl)c(C4CCN(CC5(O)CCC5)CC4)cc3n2)cnn1C1CC1] | 1-[(4-{6-chloro-2-[(1-cyclopropyl-5-methyl-1H-pyrazol-4-yl)amino]quinazolin-7-yl}piperidin-1-yl)methyl]cyclobutan-1-ol | Calc'd 467, found 467 |
| Ex-4.216 | 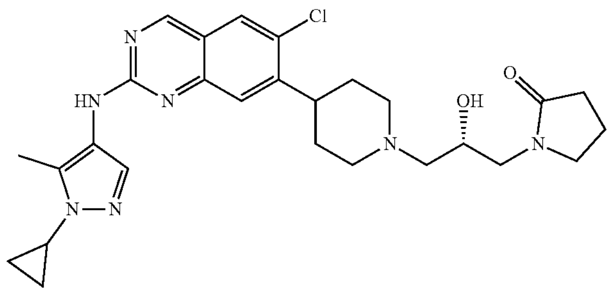 [SMILES: Cc1c(Nc2ncc3cc(Cl)c(C4CCN(C[C@H](O)CN5CCCC5=O)CC4)cc3n2)cnn1C1CC1] | 1-[(2S)-3-(4-{6-chloro-2-[(1-cyclopropyl-5-methyl-1H-pyrazol-4-yl)amino]quinazolin-7-yl}piperidin-1-yl)-2-hydroxypropyl]pyrrolidin-2-one | Calc'd 524, found 524 |

TABLE 4-continued

| Ex | Structure | Name | Exact Mass [M + H]+ |
|---|---|---|---|
| Ex-4.217 | 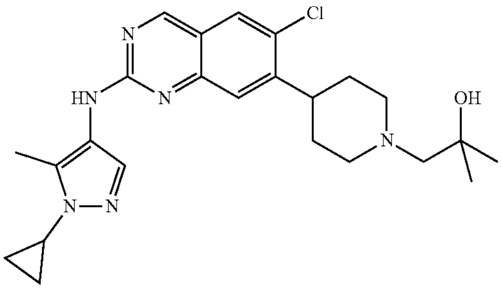 [SMILES: Cc1c(Nc2ncc3cc(Cl)c(C4CCN(CC(C)(C)O)CC4)cc3n2)cnn1C1CC1] | 1-(4-{6-chloro-2-[(1-cyclopropyl-5-methyl-1H-pyrazol-4-yl)amino]quinazolin-7-yl}piperidin-1-yl)-2-methylpropan-2-ol | Calc'd 455, found 455 |
| Ex-4.218 | 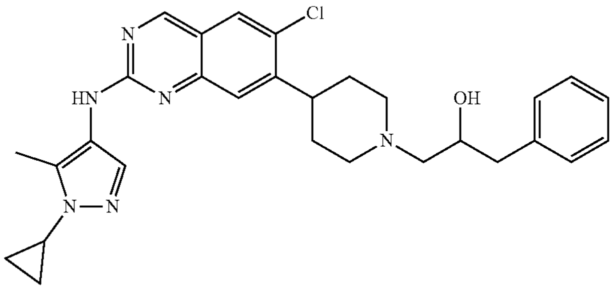 [SMILES: Cc1c(Nc2ncc3cc(Cl)c(C4CCN(CC(O)Cc5ccccc5)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-3-phenylpropan-2-ol | Calc'd 517, found 517 |
| Ex-4.219 | 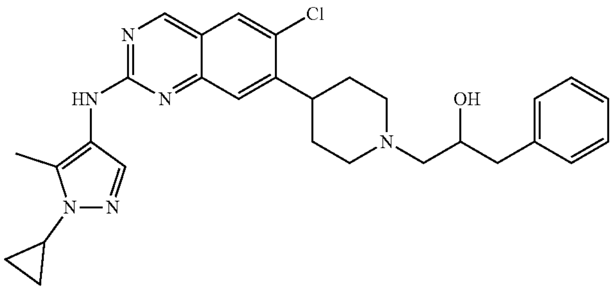 [SMILES: Cc1c(Nc2ncc3cc(Cl)c(C4CCN(CC(O)Cc5ccccc5)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-3-phenylpropan-2-ol | Calc'd 517, found 517 |
| Ex-4.220 | 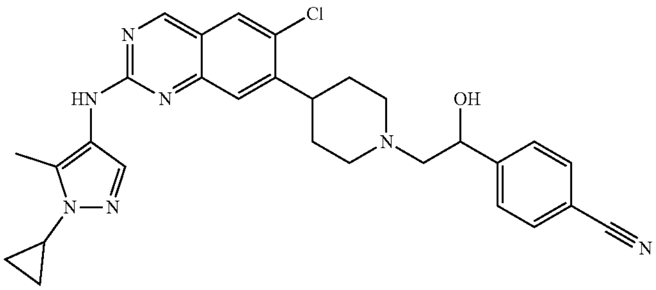 [SMILES: Cc1c(Nc2ncc3cc(Cl)c(C4CCN(CC(O)c5ccc(C#N)cc5)CC4)cc3n2)cnn1C1CC1] | (S) or (R) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile | Calc'd 528, found 528 |
| Ex-4.221 | 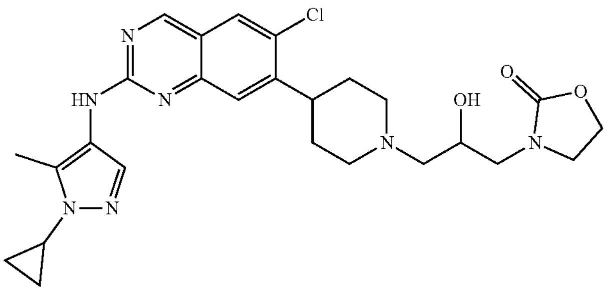 [SMILES: Cc1c(Nc2ncc3cc(Cl)c(C4CCN(CC(O)CN5CCOC5=O)CC4)cc3n2)cnn1C1CC1] | (S) or (R) 3-[3-(4-{6-chloro-2-[(1-cyclopropyl-5-methyl-1H-pyrazol-4-yl)amino]quinazolin-7-yl}piperidin-1-yl)-2-hydroxypropyl]-1,3-oxazolidin-2-one | Calc'd 526, found 526 |

TABLE 4-continued

| Ex | Structure | Name | Exact Mass [M + H]+ |
|---|---|---|---|
| Ex-4.222 | 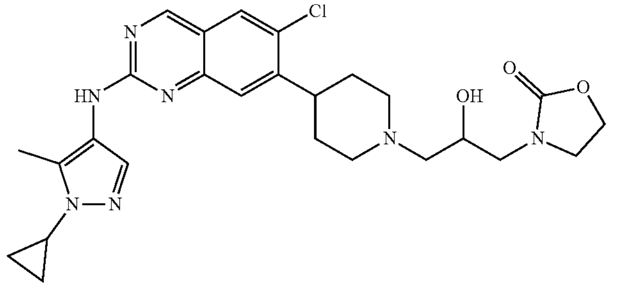 [SMILES: Cc1c(Nc2ncc3cc(Cl)c(C4CCN(CC(O)CN5CCOC5=O)CC4)cc3n2)cnn1C1CC1] | (S) or (R) 3-[3-(4-{6-chloro-2-[(1-cyclopropyl-5-methyl-1H-pyrazol-4-yl)amino]quinazolin-7-yl}piperidin-1-yl)-2-hydroxypropyl]-1,3-oxazolidin-2-one | Calc'd 526, found 526 |
| Ex-4.223 | 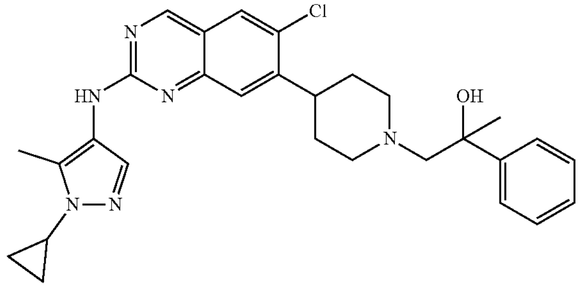 [SMILES: Cc1c(Nc2ncc3cc(Cl)c(C4CCN(CC(C)(O)c5ccccc5)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-2-phenylpropan-2-ol | Calc'd 517, found 517 |
| Ex-4.224 | 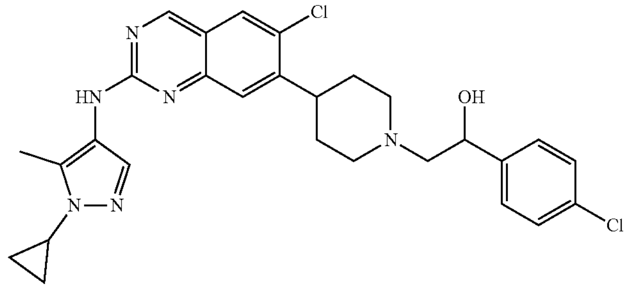 [SMILES: Cc1c(Nc2ncc3cc(Cl)c(C4CCN(CC(O)c5ccc(Cl)cc5)CC4)cc3n2)cnn1C1CC1] | (S) or (R) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol | Calc'd 537, found 537 |
| Ex-4.225 | 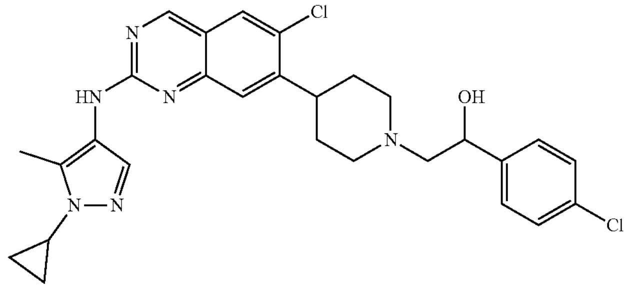 [SMILES: Cc1c(Nc2ncc3cc(Cl)c(C4CCN(CC(O)c5ccc(Cl)cc5)CC4)cc3n2)cnn1C1CC1] | (S) or (R) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol | Calc'd 537, found 537 |
| Ex-4.226 | 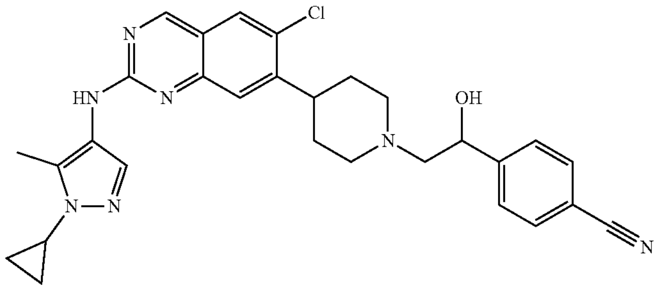 [SMILES: Cc1c(Nc2ncc3cc(Cl)c(C4CCN(CC(O)c5ccc(C#N)cc5)CC4)cc3n2)cnn1C1CC1] | (S) or (R) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile | Calc'd 528, found 528 |

TABLE 4-continued

| Ex | Structure | Name | Exact Mass [M + H]+ |
|---|---|---|---|
| Ex-4.227 | 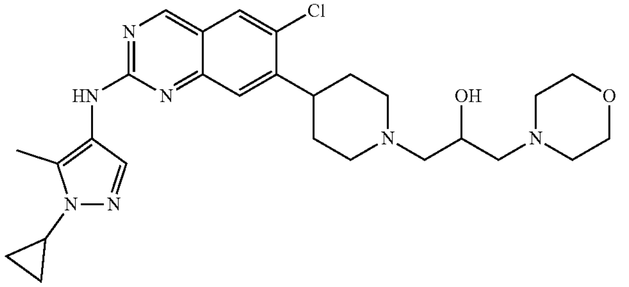 [SMILES: Cc1c(Nc2ncc3cc(Cl)c(C4CCN(CC(O)CN5CCOCC5)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-3-(morpholin-4-yl)propan-2-ol | Calc'd 526, found 526 |
| Ex-4.228 | 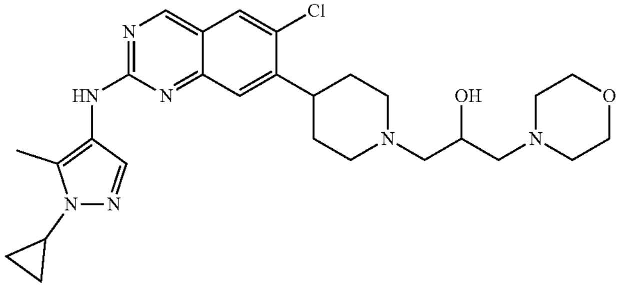 [SMILES: Cc1c(Nc2ncc3cc(Cl)c(C4CCN(CC(O)CN5CCOCC5)CC4)cc3n2)cnn1C1CC1] | (S) or (R) 1-(4-{6-chloro-2-[(1-cyclopropyl-5-methyl-1H-pyrazol-4-yl)amino]quinazolin-7-yl}piperidin-1-yl)-3-(morpholin-4-yl)propan-2-ol | Calc'd 526, found 526 |
| Ex-4.229 | 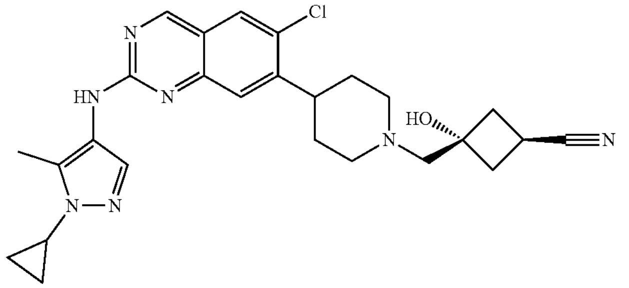 [SMILES: Cc1c(Nc2ncc3cc(Cl)c(C4CCN(C[C@]5(O)C[C@H](C#N)C5)CC4)cc3n2)cnn1C1CC1] | trans-3-[(4-{6-chloro-2-[(1-cyclopropyl-5-methyl-1H-pyrazol-4-yl)amino]quinazolin-7-yl}piperidin-1-yl)methyl]-3-hydroxycyclobutane-1-carbonitrile | Calc'd 492, found 492 |
| Ex-4.230 | 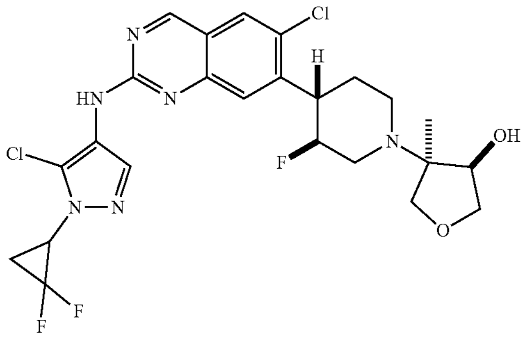 [SMILES: C[C@@]1(N2CC[C@@H](c3cc4nc(Nc5cnn(C6CC6(F)F)c5Cl)ncc4cc3Cl)[C@H](F)C2)COC[C@@H]1O] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol | Calc'd 557, found 557 |
| Ex-4.231 | 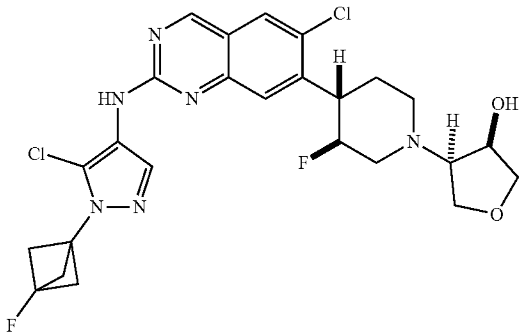 [SMILES: O[C@H]1COC[C@H]1N1CC[C@@H](c2cc3nc(Nc4cnn(C56CC(F)(C5)C6)c4Cl)ncc3cc2Cl)[C@H](F)C1] | (3S,4S)(3S,4S) or (3S,4S)(3R,4R) or (3R,4R)(3S,4S) or (3R,4R)(3R,4R) 4-[4-(6-chloro-2-{[5-chloro-1-(3-fluorobicyclo[1.1.1]pentan-1-yl)-1H-pyrazol-4-yl]amino}quinazolin-7-yl)-3-fluoropiperidin-1-yl]oxolan-3-ol | Calc'd 551, found 551 |

TABLE 4-continued

| Ex | Structure | Name | Exact Mass [M + H]+ |
|---|---|---|---|
| Ex-4.232 | 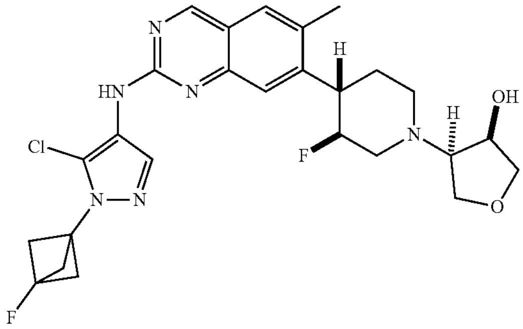 [SMILES: Cc1cc2cnc(Nc3cnn(C45CC(F)(C4)C5)c3Cl)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-[4-(2-{[5-chloro-1-(3-fluorobicyclo[1.1.1]pentan-1-yl)-1H-pyrazol-4-yl]amino}-6-methylquinazolin-7-yl)-3-fluoropiperidin-1-yl]oxolan-3-ol | Calc'd 531, found 531 |
| Ex-4.233 | 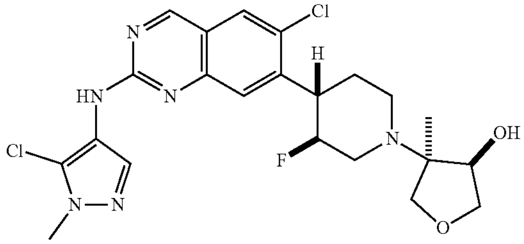 [SMILES: Cn1ncc(Nc2ncc3cc(Cl)c([C@@H]4CCN([C@]5(C)COC[C@@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol | Calc'd 495, found 495 |
| Ex-4.234 | 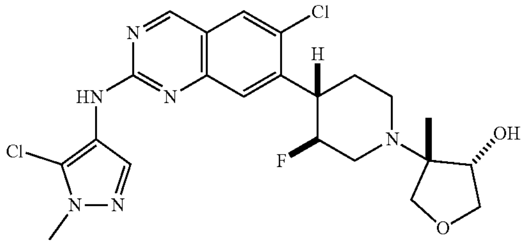 [SMILES: Cn1ncc(Nc2ncc3cc(Cl)c([C@@H]4CCN([C@@]5(C)COC[C@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol | Calc'd 495, found 495 |
| Ex-4.235 | 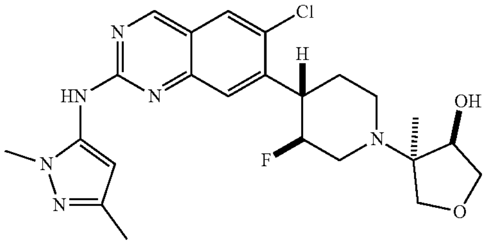 [SMILES: Cc1cc(Nc2ncc3cc(Cl)c([C@@H]4CCN([C@]5(C)COC[C@@H]5O)C[C@H]4F)cc3n2)n(C)n1] | (3S,4S)(3S,4S) or (3S,4S)(3R,4R) or (3R,4R)(3S,4S) or (3R,4R)(3R,4R) 4-(4-{6-chloro-2-[(1,3-dimethyl-1H-pyrazol-5-yl)amino]quinazolin-7-yl}-3-fluoropiperidin-1-yl)oxolan-3-ol | Calc'd 461, found 461 |
| Ex-4.236 | 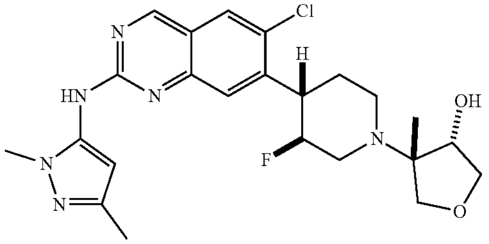 [SMILES: Cc1cc(Nc2ncc3cc(Cl)c([C@@H]4CCN([C@@]5(C)COC[C@H]5O)C[C@H]4F)cc3n2)n(C)n1] | (3S,4S)(3S,4S) or (3S,4S)(3R,4R) or (3R,4R)(3S,4S) or (3R,4R)(3R,4R) 4-(4-{6-chloro-2-[(1,3-dimethyl-1H-pyrazol-5-yl)amino]quinazolin-7-yl}-3-fluoropiperidin-1-yl)oxolan-3-ol | Calc'd 461, found 461 |

TABLE 4-continued

| Ex | Structure | Name | Exact Mass [M + H]+ |
|---|---|---|---|
| Ex-4.237 | 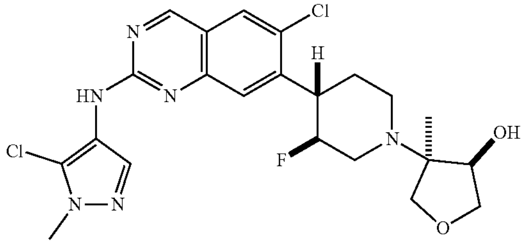 [SMILES: Cn1ncc(Nc2ncc3cc(Cl)c([C@@H]4CCN([C@]5(C)COC[C@@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol | Calc'd 495, found 495 |
| Ex-4.238 | 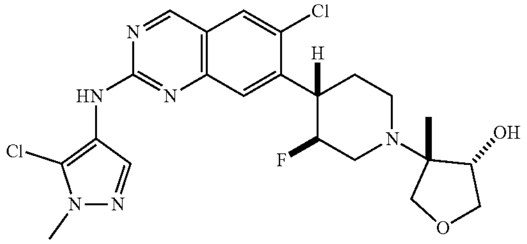 [SMILES: Cn1ncc(Nc2ncc3cc(Cl)c([C@@H]4CCN([C@@]5(C)COC[C@H]5O)C[C@H]4F)cc3n2)c1Cl] | (3S,4S)(3S,4S) or (3S,4S)(3R,4R) or (3R,4R)(3S,4S) or (3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol | Calc'd 495, found 495 |
| Ex-4.239 | 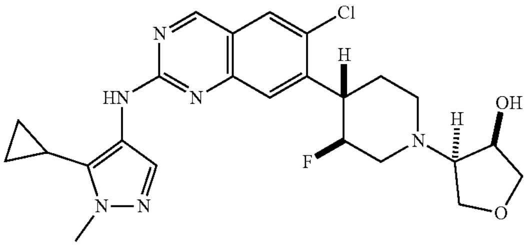 [SMILES: Cn1ncc(Nc2ncc3cc(Cl)c([C@@H]4CCN([C@@H]5COC[C@@H]5O)C[C@H]4F)cc3n2)c1C1CC1] | (3S,4S)(3S,4S) or (3S,4S)(3R,4R) or (3R,4R)(3S,4S) or (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol | Calc'd 487, found 487 |
| Ex-4.240 | 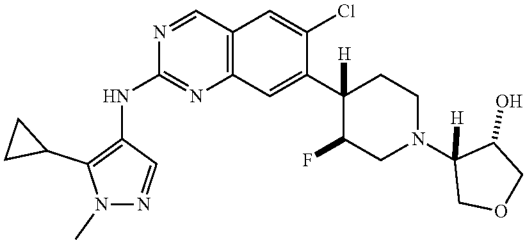 [SMILES: Cn1ncc(Nc2ncc3cc(Cl)c([C@@H]4CCN([C@H]5COC[C@H]5O)C[C@H]4F)cc3n2)c1C1CC1] | (3S,4S)(3S,4S) or (3S,4S)(3R,4R) or (3R,4R)(3S,4S) or (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol | Calc'd 487, found 487 |
| Ex-4.241 | 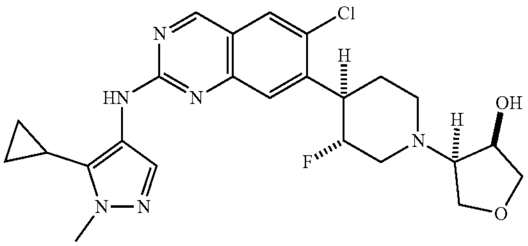 [SMILES: Cn1ncc(Nc2ncc3cc(Cl)c([C@H]4CCN([C@@H]5COC[C@@H]5O)C[C@@H]4F)cc3n2)c1C1CC1] | (3S,4S)(3S,4S) or (3S,4S)(3R,4R) or (3R,4R)(3S,4S) or (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol | Calc'd 487, found 487 |
| Ex-4.242 | 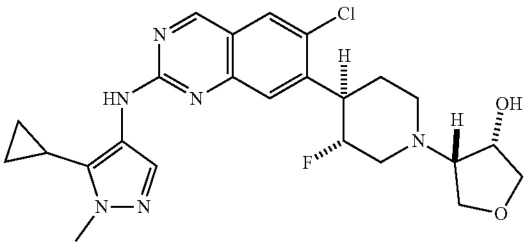 [SMILES: Cn1ncc(Nc2ncc3cc(Cl)c([C@H]4CCN([C@H]5COC[C@H]5O)C[C@@H]4F)cc3n2)c1C1CC1] | (3S,4S)(3S,4S) or (3S,4S)(3R,4R) or (3R,4R)(3S,4S) or (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol | Calc'd 487, found 487 |

TABLE 4-continued

| Ex | Structure | Name | Exact Mass [M + H]+ |
|---|---|---|---|
| Ex-4.243 | 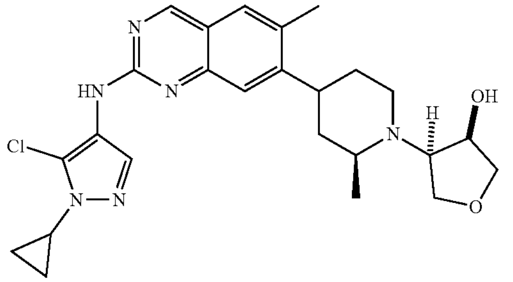 [SMILES: Cc1cc2cnc(Nc3cnn(C4CC4)c3Cl)nc2cc1C1CCN([C@@H]2COC[C@@H]2O)[C@@H](C)C1] | (3S,4S)(2S) or (3R,4R)(2S) 4-[4-{2-[(5-chloro-1-cyclopropyl-1H-pyrazol-4-yl)amino]-6-methylquinazolin-7-yl}-2-methylpiperidin-1-yl]oxolan-3-ol | Calc'd 483, found 483 |
| Ex-4.244 | 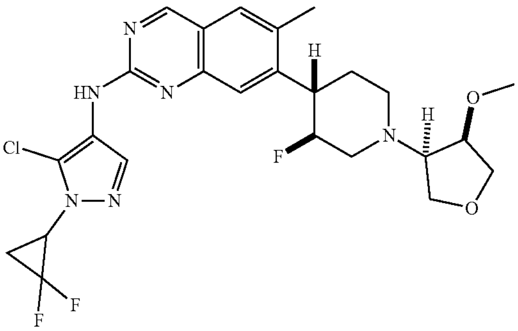 [SMILES: CO[C@H]1COC[C@H]1N1CC[C@@H](c2cc3nc(Nc4cnn(C5CC5(F)F)c4Cl)ncc3cc2C)[C@H](F)C1] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine | Calc'd 537, found 537 |
| Ex-4.245 | 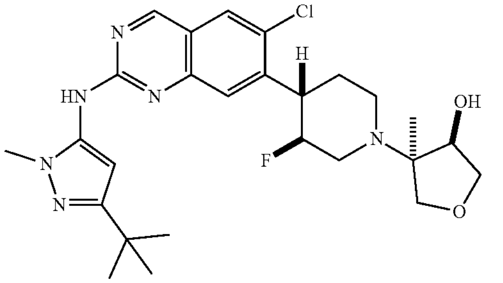 [SMILES: Cn1nc(C(C)(C)C)cc1Nc1ncc2cc(Cl)c([C@@H]3CCN([C@]4(C)COC[C@@H]4O)C[C@H]3F)cc2n1] | (3S,4S)(3S,4S) or (3S,4S)(3R,4R) or (3R,4R)(3S,4S) or (3R,4R)(3R,4R) 4-(4-{2-[(3-tert-butyl-1-methyl-1H-pyrazol-5-yl)amino]-6-chloroquinazolin-7-yl}-3-fluoropiperidin-1-yl)-4-methyloxolan-3-ol | Calc'd 517, found 517 |
| Ex-4.246 | 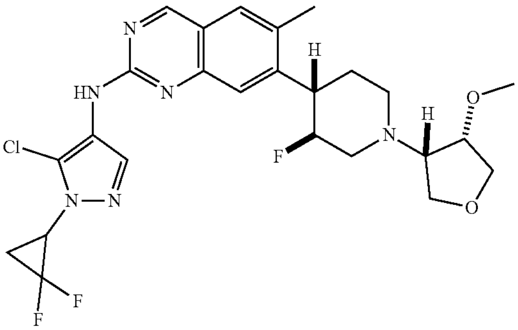 [SMILES: CO[C@@H]1COC[C@@H]1N1CC[C@@H](c2cc3nc(Nc4cnn(C5CC5(F)F)c4Cl)ncc3cc2C)[C@H](F)C1] | (R)(3S,4S)(3S,4S) or (R)(3S,4S)(3R,4R) or (R)(3R,4R)(3S,4S) or (R)(3R,4R)(3R,4R) or (S)(3S,4S)(3S,4S) or (S)(3S,4S)(3R,4R) or (S)(3R,4R)(3S,4S) or (S)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine | Calc'd 537, found 537 |
| Ex-4.247 | 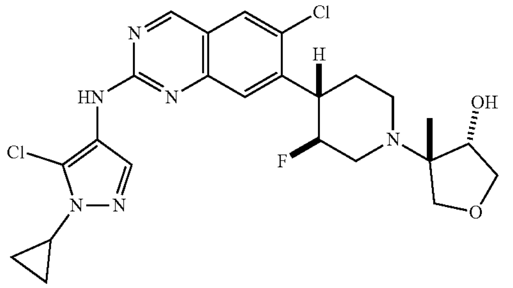 [SMILES: C[C@]1(N2CC[C@@H](c3cc4nc(Nc5cnn(C6CC6)c5Cl)ncc4cc3Cl)[C@H](F)C2)COC[C@H]1O] | (3S,4S)(3S,4S) or (3S,4S)(3R,4R) or (3R,4R)(3S,4S) or (3R,4R)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol | Calc'd 521, found 521 |

TABLE 4-continued

| Ex | Structure | Name | Exact Mass [M + H]+ |
|---|---|---|---|
| Ex-4.248 | 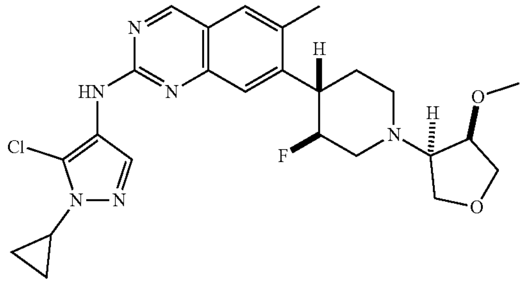 [SMILES: CO[C@H]1COC[C@H]1N1CC[C@@H](c2cc3nc(Nc4cnn(C5CC5)c4Cl)ncc3cc2C)[C@H](F)C1] | (3S,4S)(3S,4S) or (3S,4S)(3R,4R) or (3R,4R)(3S,4S) or (3R,4R)(3R,4R)N-(5-chloro-1-cyclopropyl-1H-pyrazol-4-yl)-7-[3-fluoro-1-(4-methoxy oxolan-3-yl)piperidin-4-yl]-6-methylquinazolin-2-amine | Calc'd 501, found 501 |
| Ex-4.249 | 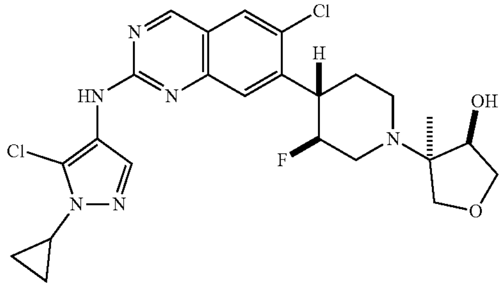 [SMILES: C[C@@]1(N2CC[C@@H](c3cc4nc(Nc5cnn(C6CC6)c5Cl)ncc4cc3Cl)[C@H](F)C2)COC[C@@H]1O] | (3S,4S)(3S,4S) or (3S,4S)(3R,4R) or (3R,4R)(3S,4S) or (3R,4R)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol | Calc'd 521, found 521 |
| Ex-4.250 | 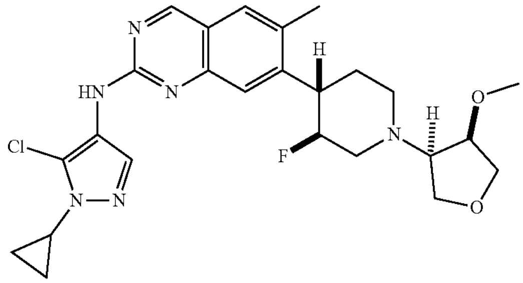 [SMILES: CO[C@H]1COC[C@H]1N1CC[C@@H](c2cc3nc(Nc4cnn(C5CC5)c4Cl)ncc3cc2C)[C@H](F)C1] | (3S,4S)(3S,4S) or (3S,4S)(3R,4R) or (3R,4R)(3S,4S) or (3R,4R)(3R,4R) N-(5-chloro-1-cyclopropyl-1H-pyrazol-4-yl)-7-[3-fluoro-1-(4-methoxy oxolan-3-yl)piperidin-4-yl]-6-methylquinazolin-2-amine | Calc'd 501, found 501 |
| Ex-4.251 | 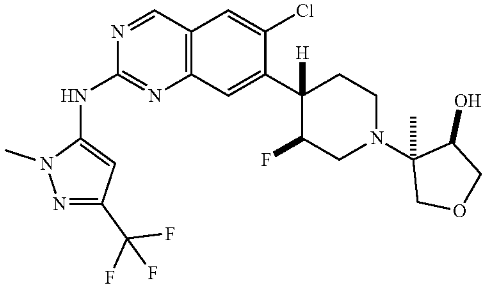 [SMILES: Cn1nc(C(F)(F)F)cc1Nc1ncc2cc(Cl)c([C@@H]3CCN([C@]4(C)COC[C@@H]4O)C[C@H]3F)cc2n1] | (3S,4S)(3S,4S) or (3S,4S)(3R,4R) or (3R,4R)(3S,4S) or (3R,4R)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol | Calc'd 529, found 529 |
| Ex-4.252 | 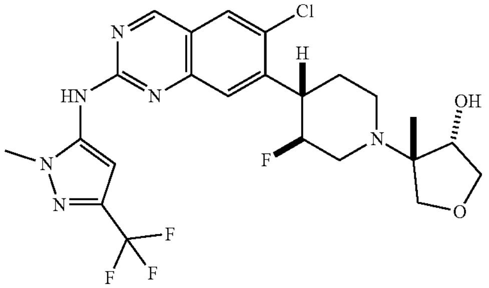 [SMILES: Cn1nc(C(F)(F)F)cc1Nc1ncc2cc(Cl)c([C@@H]3CCN([C@@]4(C)COC[C@H]4O)C[C@H]3F)cc2n1] | (3S,4S)(3S,4S) or (3S,4S)(3R,4R) or (3R,4R)(3S,4S) or (3R,4R)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol | Calc'd 529, found 529 |

TABLE 4-continued

| Ex | Structure | Name | Exact Mass [M + H]$^+$ |
|---|---|---|---|
| Ex-4.253 | 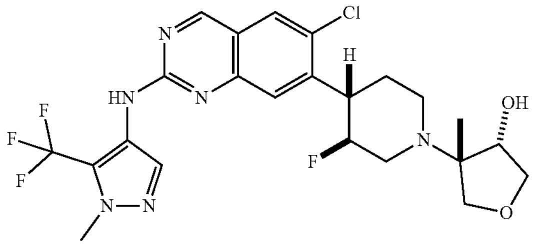 [SMILES: Cn1ncc(Nc2ncc3cc(Cl)c([C@@H]4CCN([C@@]5(C)COC[C@H]5O)C[C@H]4F)cc3n2)c1C(F)(F)F] | (3S,4S)(3S,4S) or (3S,4S)(3R,4R) or (3R,4R)(3S,4S) or (3R,4R)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol | Calc'd 529, found 529 |
| Ex-4.254 | 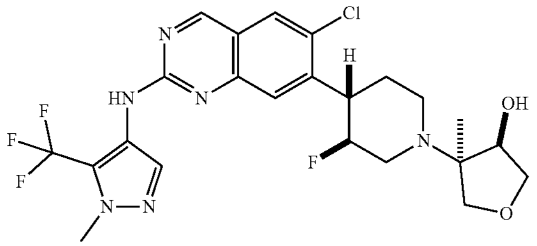 [SMILES: Cn1ncc(Nc2ncc3cc(Cl)c([C@@H]4CCN([C@]5(C)COC[C@@H]5O)C[C@H]4F)cc3n2)c1C(F)(F)F] | (3S,4S)(3S,4S) or (3S,4S)(3R,4R) or (3R,4R)(3S,4S) or (3R,4R)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol | Calc'd 529, found 529 |
| Ex-4.255 | 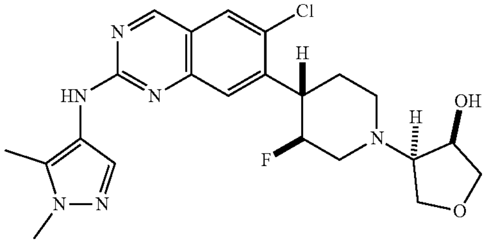 [SMILES: Cc1c(Nc2ncc3cc(Cl)c([C@@H]4CCN([C@@H]5COC[C@@H]5O)C[C@H]4F)cc3n2)cnn1C] | (3S,4S)(3S,4S) or (3S,4S)(3R,4R) or (3R,4R)(3S,4S) or (3R,4R)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol | Calc'd 461, found 461 |
| Ex-4.256 | 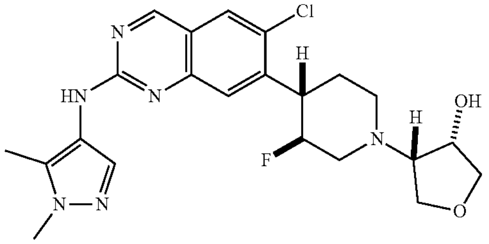 [SMILES: Cc1c(Nc2ncc3cc(Cl)c([C@@H]4CCN([C@H]5COC[C@H]5O)C[C@H]4F)cc3n2)cnn1C] | (3S,4S)(3S,4S) or (3S,4S)(3R,4R) or (3R,4R)(3S,4S) or (3R,4R)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol | Calc'd 461, found 461 |
| Ex-4.257 | 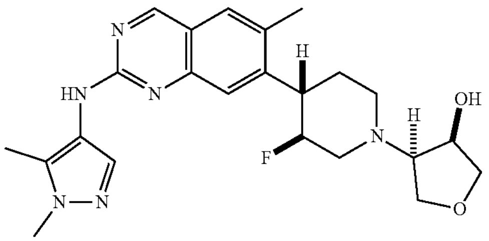 [SMILES: Cc1cc2cnc(Nc3cnn(C)c3C)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol | Calc'd 441, found 441 |
| Ex-4.258 | 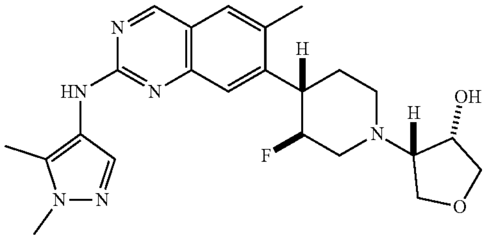 [SMILES: Cc1cc2cnc(Nc3cnn(C)c3C)nc2cc1[C@@H]1CCN([C@H]2COC[C@H]2O)C[C@H]1F] | (3S,4S)(3S,4S) or (3S,4S)(3R,4R) or (3R,4R)(3S,4S) or (3R,4R)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol | Calc'd 441, found 441 |

TABLE 4-continued

| Ex | Structure | Name | Exact Mass [M + H]+ |
|---|---|---|---|
| Ex-4.259 | 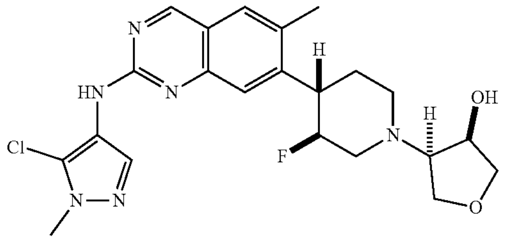 [SMILES: Cc1cc2cnc(Nc3cnn(C)c3Cl)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol | Calc'd 461, found 461 |
| Ex-4.260 | 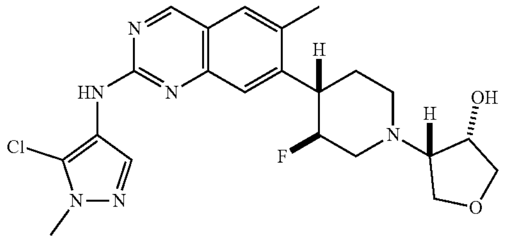 [SMILES: Cc1cc2cnc(Nc3cnn(C)c3Cl)nc2cc1[C@@H]1CCN([C@H]2COC[C@H]2O)C[C@H]1F] | (3S,4S)(3S,4S) or (3S,4S)(3R,4R) or (3R,4R)(3S,4S) or (3R,4R)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol | Calc'd 461, found 461 |
| Ex-4.261 | 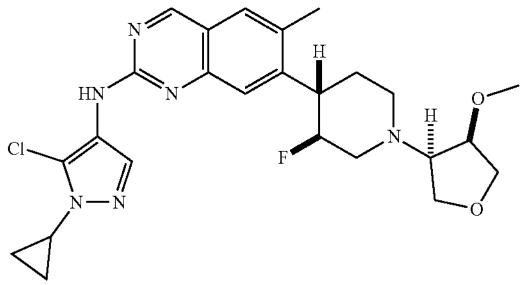 [SMILES: CO[C@H]1COC[C@H]1N1CC[C@@H](c2cc3nc(Nc4cnn(C5CC5)c4Cl)ncc3cc2C)[C@H](F)C1] | (3S,4S)(3S,4S) or (3S,4S)(3R,4R) or (3R,4R)(3S,4S) or (3R,4R)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine | Calc'd 501, found 501 |
| Ex-4.262 | 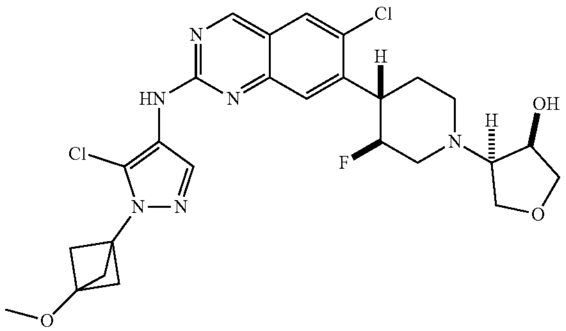 [SMILES: COC12CC(n3ncc(Nc4ncc5cc(Cl)c([C@@H]6CCN([C@@H]7COC[C@@H]7O)C[C@H]6F)cc5n4)c3Cl)(C1)C2] | (3S,4S)(3S,4S) or (3S,4S)(3R,4R) or (3R,4R)(3S,4S) or (3R,4R)(3R,4R) 4-(4-(6-chloro-2-((5-chloro-1-(3-methoxybicyclo[1.1.1]pentan-1-yl)-1H-pyrazol-4-yl)amino)quinazolin-7-yl)-3-fluoropiperidin-1-yl)tetrahydrofuran-3-ol | Calc'd 563, found 563 |

General Scheme 6.

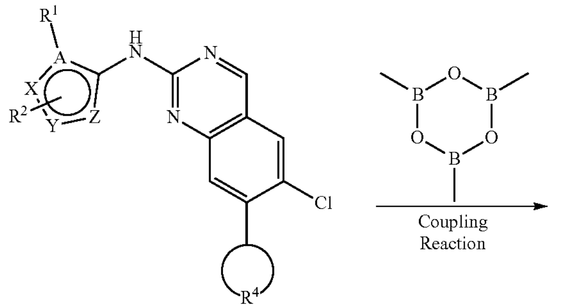

Gen-12/Gen-14/Gen-18/Gen-21

A = C,N
X = C,N
Y = C,N
Z = C,S
$R^1$ = Cl, H, alkyl
$R^2$ = alkyl
$R^4$ = alkyl, —NR

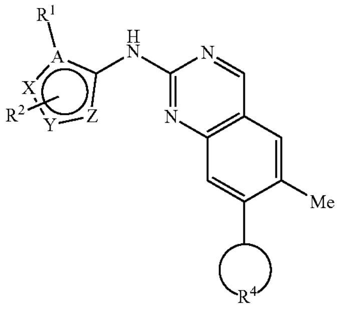

Gen-22

In General Scheme 6, previously described intermediates of the form Gen-12/Gen-14/Gen-18/Gen-21 were converted to Gen-22 via palladium catalyzed reaction with trimethylboroxin.

Preparation of Example 5.1

Scheme 62. Synthesis of 3-(4-(6-methyl-2-((5-methyl-1-(1-methylcyclopropyl)-1H-pyrazol4-yl)amino)quinazolin-7-yl)piperidin-1-yl)propanenitrile

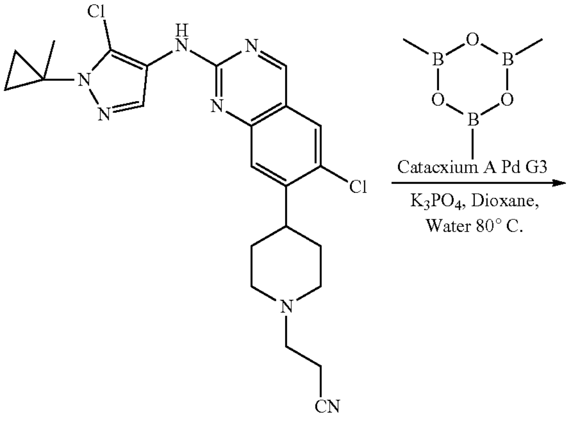

Ex-8.14

-continued

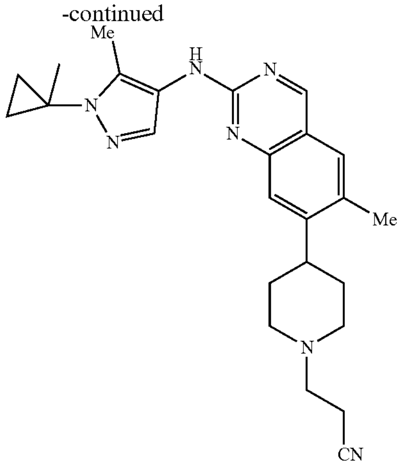

Ex-5.1

3-(4-(6-methyl-2-((5-methyl-1-(1-methylcyclopropyl)-1H-pyrazol4-yl)amino)quinazolin-7-yl)piperidin-1-yl)propanenitrile (Ex-5.1)

A 4-mL scintillation vial was charged with Ex-8.13 (30 mg, 0.064 mmol), CataCXium A Pd G3 (9.3 mg, 0.013 mmol), and potassium phosphate (54 mg, 0.26 mmol) under inert atmosphere. Dioxane (580 μL), Water (58 μL), and trimethylboroxin (36 μL, 0.26 mmol) were added and the reaction mixture was stirred at 80° C. for 12 hrs. On cooling to RT, the crude product was filtered over a pad of Celite® (diatomaceous earth), eluting with EtOAc, and solvent was removed from the collected filtrate under reduced pressure. The resultant crude residue was subjected to purification by reversed phase HPLC, eluting with water (0.1% TFA)-MeCN to afford the title compound Ex-5.1. MS (ESI): m/z calc'd for $C_{25}H_{31}N_7$ $[M+H]^+$: 430, found 430; $^1H$ NMR (400 MHz, DMSO-$d_6$, 25° C.) δ: 9.47 (s, 1H), 9.11 (s, 1H), 7.72 (m, 1H), 7.67 (s, 1H) 7.28 (s, 1H), 3.64 (m, 2H), 3.51 (m, 2H), 3.23 (m, 2H), 3.12 (m, 2H), 2.44 (s, 3H), 2.31 (s, 3H), 2.04 (m, 2H), 1.92 (m, 2H), 1.45 (s, 3H), 1.16 (s, 2H), 0.97 (m, 2H)

Preparation of Example 5.2

Scheme 63. Synthesis of 3-(4-(2-((5-chloro-1-(1-methylcyclopropyl)-1H-pyrazol-4-yl)amino)-6-methylquinazolin-7-yl)piperidin-1-yl)propanenitrile

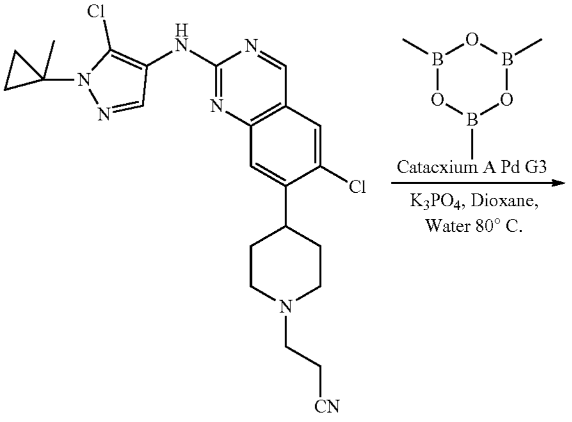

Ex-8.14

-continued

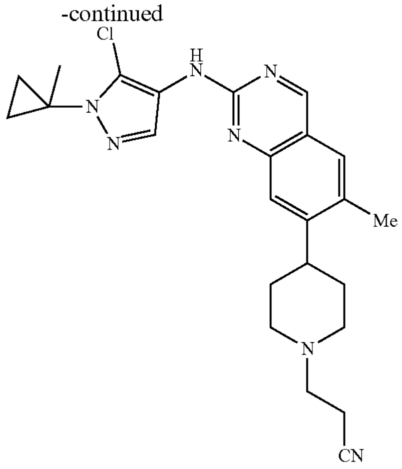

Ex-5.2

3-(4-(2-((5-chloro-1-(1-methylcyclopropyl)-1H-pyrazol-4-yl)amino)-6-methylquinazolin-7-yl)piperidin-1-yl)propanenitrile (Ex-5.2)

This compound was prepared in an analogous manner to Ex-5.1 with the following changes: 1 equivalent of trimethylboroxin was used instead of 4 equivalents, and the reaction was run for 3 hrs instead of 12 hrs. Purification by reversed phase HPLC, eluting with water (0.1% TFA)-MeCN afforded the title compound Ex-5.2. MS (ESI): m/z calc'd for $C_{24}H_{29}ClN_7$ $[M+H]^+$: 450, found 450; $^1H$ NMR (400 MHz, DMSO-$d_6$, 25° C.) δ: 9.13 (s, 1H), 8.99 (s, 1H), 7.68 (s, 1H) 7.29 (s, 1H), 3.64 (m, 2H), 3.51 (m, 2H), 3.22 (m, 2H), 3.13 (m, 3H), 2.45 (s, 3H) 2.04 (m, 2H), 1.93 (m, 2H), 1.49 (s, 3H), 1.21 (m, 3H), 1.05 (m, 2H)

Compounds in Table 5 below were prepared in accordance with the synthetic sequence illustrated in General Scheme 6 using the corresponding starting materials.

TABLE 5

| Ex | Structure | Name | Exact Mass $[M + H]^+$ |
|---|---|---|---|
| Ex-5.3 | 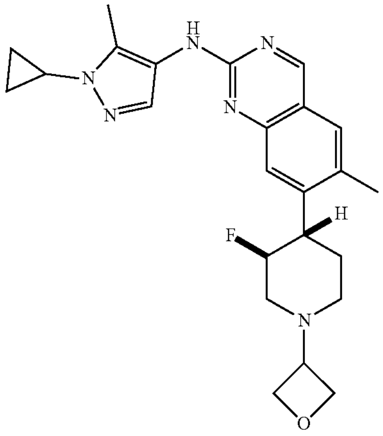 [SMILES: Cc1cc2cnc(Nc3cnn(C4CC4)c3C)nc2cc1[C@@H]1CCN(C2COC2)C[C@H]1F] | (3S,4S) or (3R,4R) N-(1-cyclopropyl-5-methyl-1H-pyrazol-4-yl)-7-[3-fluoro-1-(oxetan-3-yl)piperidin-4-yl]-6-methylquinazolin-2-amine | Calc'd 437, found 437 |
| Ex-5.4 | 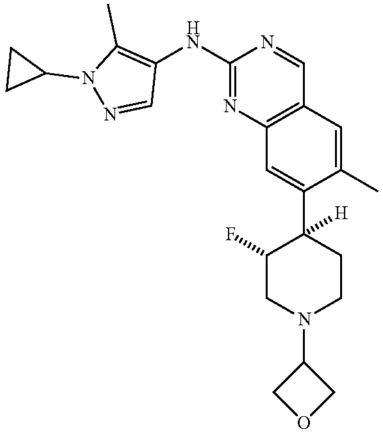 [SMILES: Cc1cc2cnc(Nc3cnn(C4CC4)c3C)nc2cc1[C@H]1CCN(C2COC2)C[C@@H]1F] | (3S,4S) or (3R,4R) N-(1-cyclopropyl-5-methyl-1H-pyrazol-4-yl)-7-[3-fluoro-1-(oxetan-3-yl)piperidin-4-yl]-6-methylquinazolin-2-amine | Calc'd 437, found 437 |

TABLE 5-continued

| Ex | Structure | Name | Exact Mass [M + H]+ |
|---|---|---|---|
| Ex-5.5 | 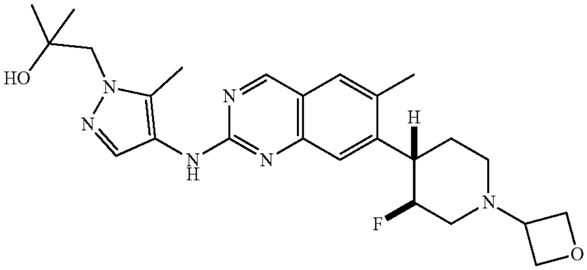 [SMILES: Cc1cc2cnc(Nc3cnn(CC(C)(C)O)c3C)nc2cc1[C@@H]1CCN(C2COC2)C[C@H]1F] | (3S,4S) or (3R,4R) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol | Calc'd 469, found 469 |
| Ex-5.6 | 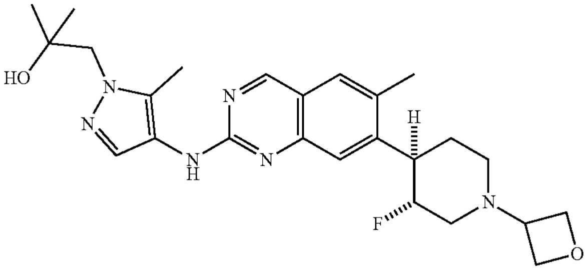 [SMILES: Cc1cc2cnc(Nc3cnn(CC(C)(C)O)c3C)nc2cc1[C@H]1CCN(C2COC2)C[C@@H]1F] | (3S,4S) or (3R,4R) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol | Calc'd 469, found 469 |
| Ex-5.7 | 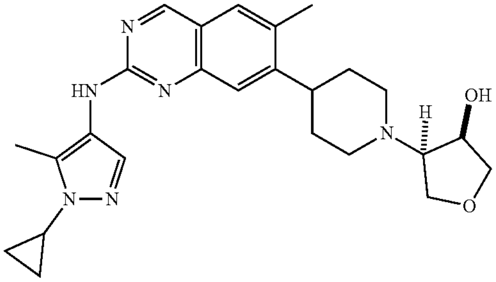 [SMILES: Cc1cc2cnc(Nc3cnn(C4CC4)c3C)nc2cc1C1CCN([C@@H]2COC[C@@H]2O)CC1] | (3S,4S) or (3R,4R) 4-(4-{2-[(1-cyclopropyl-5-methyl-1H-pyrazol-4-yl)amino]-6-methylquinazolin-7-yl}piperidin-1-yl)oxolan-3-ol | Calc'd 449, found 449 |
| Ex-5.8 | 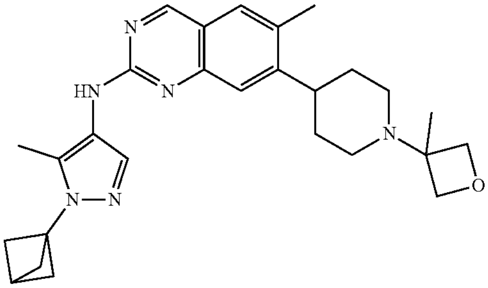 [SMILES: Cc1cc2cnc(Nc3cnn(C45CC(C4)C5)c3C)nc2cc1C1CCN(C2(C)COC2)CC1] | N-[1-(bicyclo[1.1.1]pentan-1-yl)-5-methyl-1H-pyrazol-4-yl]-6-methyl-7-[1-(3-methyloxetan-3-yl)piperidin-4-yl]quinazolin-2-amine | Calc'd 459, found 459 |
| Ex-5.9 | 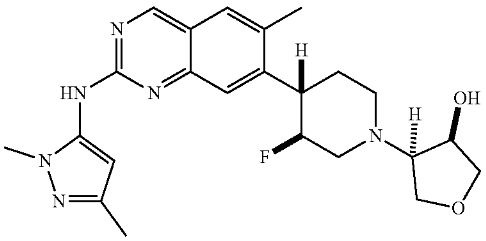 [SMILES: Cc1cc(Nc2ncc3cc(C)c([C@@H]4CCN([C@@H]5COC[C@@H]5O)C[C@H]4F)cc3n2)n(C)n1] | (3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol | Calc'd 441, found 441 |

TABLE 5-continued

| Ex | Structure | Name | Exact Mass [M + H]+ |
|---|---|---|---|
| Ex-5.10 | 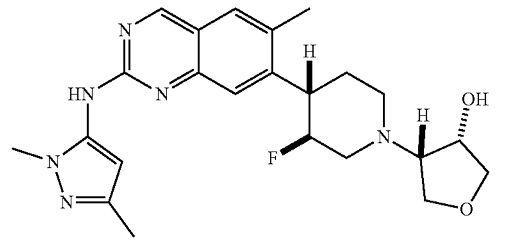 [SMILES: Cc1cc(Nc2ncc3cc(C)c([C@@H]4CCN([C@H]5COC[C@H]5O)C[C@H]4F)cc3n2)n(C)n1] | (3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol | Calc'd 441, found 441 |
| Ex-5.11 | 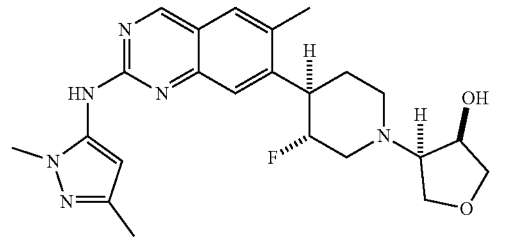 [SMILES: Cc1cc(Nc2ncc3cc(C)c([C@H]4CCN([C@@H]5COC[C@@H]5O)C[C@@H]4F)cc3n2)n(C)n1] | (3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol | Calc'd 441, found 441 |
| Ex-5.12 | 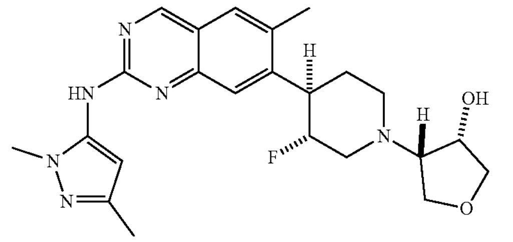 [SMILES: Cc1cc(Nc2ncc3cc(C)c([C@H]4CCN([C@H]5COC[C@H]5O)C[C@@H]4F)cc3n2)n(C)n1] | (3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol | Calc'd 441, found 441 |
| Ex-5.13 | 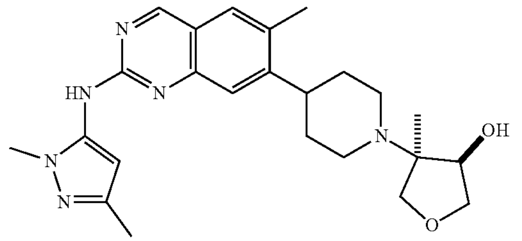 [SMILES: Cc1cc(Nc2ncc3cc(C)c(C4CCN([C@]5(C)COC[C@@H]5O)CC4)cc3n2)n(C)n1] | (3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}piperidin-1-yl)-4-methyloxolan-3-ol | Calc'd 437, found 437 |
| Ex-5.14 | 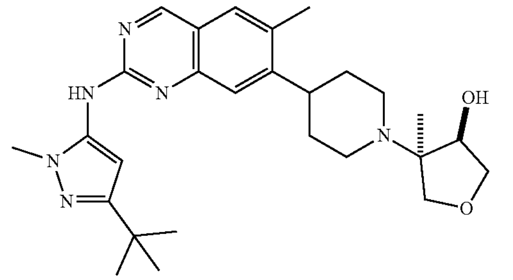 [SMILES: Cc1cc2cnc(Nc3cc(C(C)(C)C)nn3C)nc2cc1C1CCN([C@]2(C)COC[C@@H]2O)CC1] | (3S,4S) or (3R,4R) 4-(4-{2-[(3-tert-butyl-1-methyl-1H-pyrazol-5-yl)amino]-6-methylquinazolin-7-yl}piperidin-1-yl)-4-methyloxolan-3-ol | Calc'd 479, found 479 |
| Ex-5.15 | 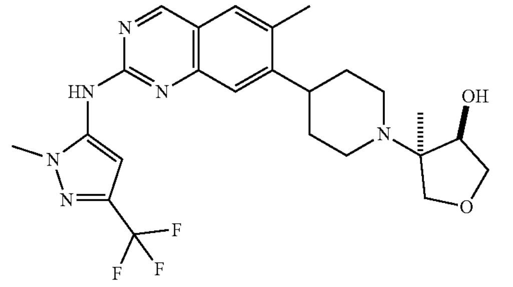 [SMILES: Cc1cc2cnc(Nc3cc(C(F)(F)F)nn3C)nc2cc1C1CCN([C@]2(C)COC[C@@H]2O)CC1] | (3S,4S) or (3R,4R) 4-methyl-4-[4-(6-methyl-2-{[1-methyl-3-(trifluoromethyl)-1H-pyrazol-5-yl]amino}quinazolin-7-yl)piperidin-1-yl]oxolan-3-ol | Calc'd 491, found 491 |

TABLE 5-continued

| Ex | Structure | Name | Exact Mass $[M + H]^+$ |
|---|---|---|---|
| Ex-5.16 | 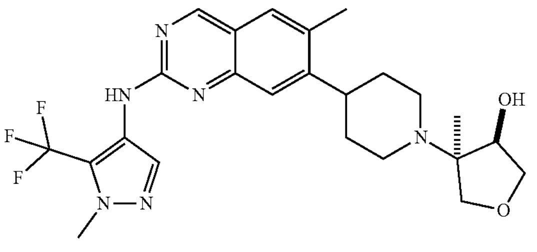 [SMILES: Cc1cc2cnc(Nc3cnn(C)c3C(F)(F)F)nc2cc1C1CCN([C@]2(C)COC[C@@H]2O)CC1] | (3S,4S) or (3R,4R) 4-methyl-4-(4-(6-methyl-2-((1-methyl-5-(trifluoromethyl)-1H-pyrazol-4-yl)amino)quinazolin-7-yl)piperidin-1-yl)tetrahydrofuran-3-ol | Calc'd 491, found 491 |

General Scheme 7.

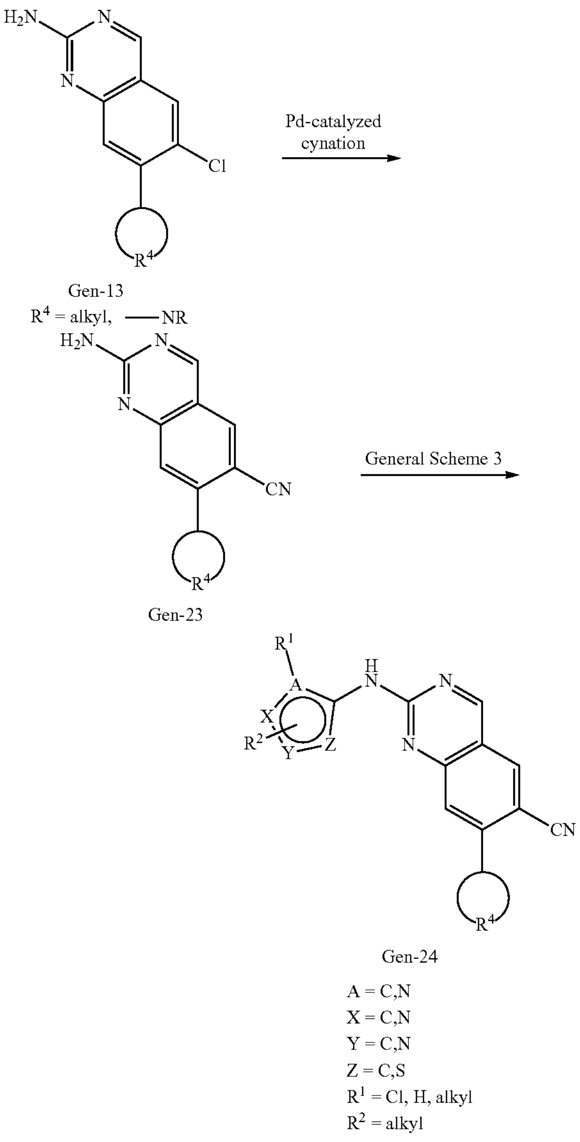

Gen-13

$R^4$ = alkyl, —NR

Gen-23

Gen-24

A = C,N

X = C,N

Y = C,N

Z = C,S $R^1$ = Cl, H, alkyl $R^2$ = alkyl

In General Scheme 7, intermediates of type Gen-13, prepared as previously described (cf General Scheme 3), could be converted to the corresponding C6-benzonitriles Gen-23 using standard palladium-catalyzed aryl cyanation methodology. Subjecting compounds Gen-23 to standard palladium-catalyzed amine arylation methodology as described in General Scheme 3 afforded elaborated compounds of the form Gen-24. The representative compounds are described in more detail below.

Preparation of Examples 6.1 and 6.2

Scheme 64

Synthesis of (3R,4R) or (3S,4S) 2-((5-chloro-1-cyclopropyl-1H-pyrazol-4-yl)amino)-7-(3-fluoro-1-(oxetan-3-yl)piperidin-4-yl)quinazoline-6-carbonite

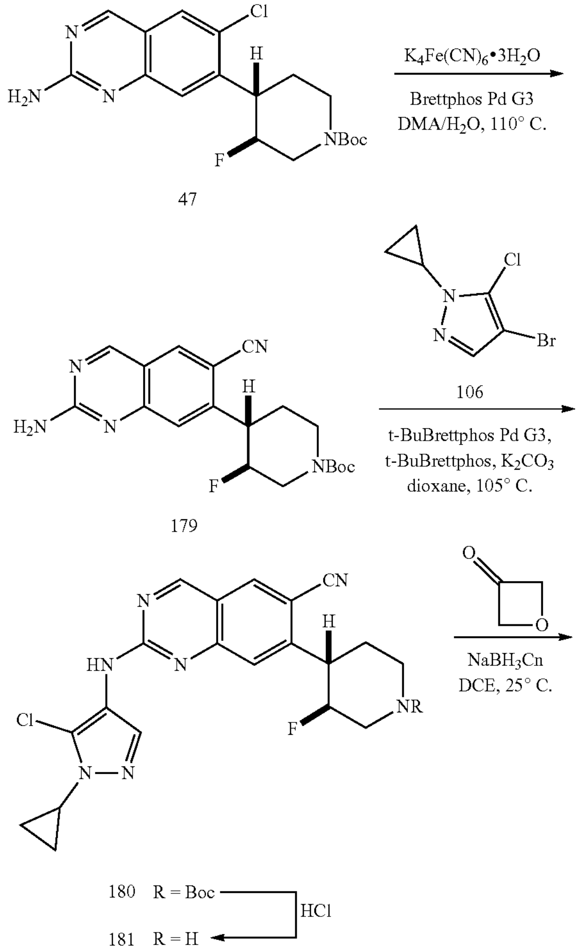

47

179

180 R = Boc

181 R = H

-continued

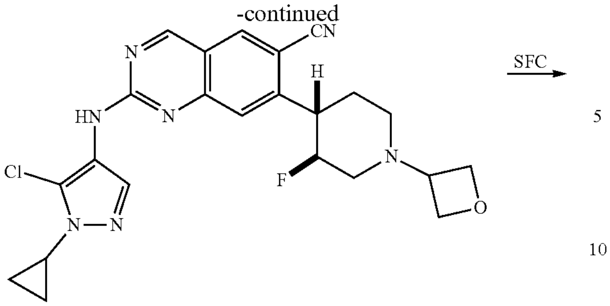

182

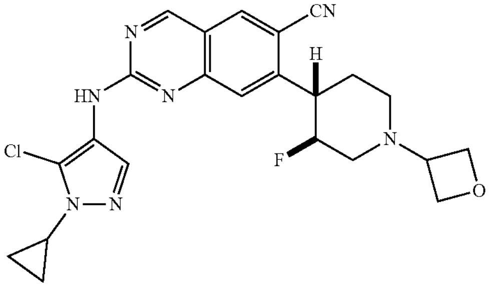

+

Ex-6.1

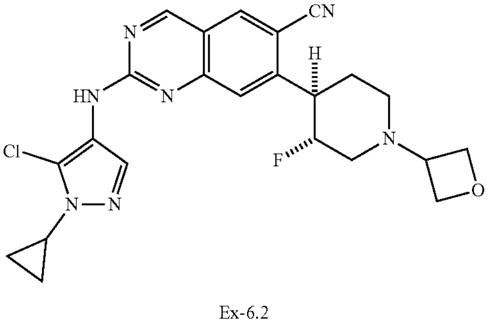

Ex-6.2

(3R,4R) and (3S,4S) tert-butyl 4-(2-amino-6-cyano-quinazolin-7-yl)-3-fluoropiperidine-1-carboxylate (179)

A 10-mL round bottom flask was charged with trans-racemic tert-butyl 4-(2-amino-6-chloroquinazolin-7-yl)-3-fluoropiperidine-1-carboxylate 47 (200 mg, 0.525 mmol), Brettphos Pd G3 (48 mg, 0.053 mmol) and $K_4Fe(CN)_6.3H_2O$(1.11 g, 2.63 mmol) under inert atmosphere. DMA (3 mL) and Water (1 mL) were added, and the resultant mixture was heated to 110° C. with stirring for 40 hrs. Upon cooling to RT, saturated $NH_4Cl$ (50 mL) was added, the phases were separated, and the aqueous phase was extracted with EtOAc (3x20 mL). The combined organic phases were washed with brine (50 mL), dried over anhydrous $Na_2SO_4$, filtered, and solvent removed from the collected filtrate under reduced pressure. The resultant crude residue was subjected to purification by reversed phase HPLC eluting with water (0.1% $NH_4HCO_3$)-MeCN, to afford the title compound 179.

(3R,4R) and (3S,4S) tert-butyl 4-(2-((5-chloro-1-cyclopropyl-1H-pyrazol-4-yl)amino)-6-cyanoquinazolin-7-yl)-3-fluoropiperidine-1-carboxylate (180)

A 25-mL round bottom flask was charged with trans-racemic tert-butyl 4-(2-amino-6-cyanoquinazolin-7-yl)-3-fluoropiperidine-1-carboxylate 179 (110 mg, 0.296 mmol), 4-bromo-5-chloro-1-cyclopropyl-1H-pyrazole 106 (127 μL, 0.889 mmol), tBuBrettPhos Pd G3 (38.0 mg, 0.044 mmol), tBuBrettPhos (43.1 mg, 0.089 mmol) and $K_2CO_3$ (164 mg, 1.185 mmol) under inert atmosphere. Dioxane (5 mL) was added and the resultant mixture was heated to 105° C. with stirring for 16 hrs. Upon cooling to RT, saturated $NH_4Cl$ (50 mL) was added, the phases were separated, and the aqueous phase was extracted with EtOAc (3x20 mL). The combined organic phases were washed with brine (50 mL), dried over anhydrous $Na_2SO_4$, filtered, and solvent removed from the collected filtrate under reduced pressure. The resultant crude residue was subjected to purification by reversed phase HPLC eluting with water (0.1% $NH_4HCO_3$)-MeCN, to afford the title compound 180.

(3R,4R) and (3S,4S) 2-((5-chloro-1-cyclopropyl-1H-pyrazol-4-yl)amino)-7-(3-fluoropiperidin-4-yl) quinazoline-6-carbonitrile (181)

A 30-mL scintillation vial was charged with trans-racemic tert-butyl 4-(2-((5-chloro-1-cyclopropyl-1H-pyrazol-4-yl) amino)-6-cyanoquinazolin-7-yl)-3-fluoropiperidine-1-carboxylate 180 (60 mg, 0.117 mmol) under inert atmosphere. MeOH (1 mL) was added, and to the stirring mixture was added a solution of HCl in dioxane (4M, 1.00 mL). The reaction was stirred at RT for 2 hrs. The reaction mixture was quenched by the careful addition of sat. aq. $NaHCO_3$ (20 mL) and extracted with EtOAc (3x10 mL). The combined organic phases were washed with brine (30 mL), dried over anhydrous $Na_2SO_4$, filtered, and solvent removed from the collected filtrate under reduced pressure to afford the title compound 181.

(3R,4R) or (3S,4S) 2-((5-chloro-1-cyclopropyl-1H-pyrazol-4-yl)amino)-7-(3-fluoro-1-(oxetan-3-yl)piperidin-4-yl)quinazoline-6-carbonitrile (Ex-6.1 and Ex-6.2)

A 20-mL scintillation vial was charged with trans-racemic 2-((5-chloro-1-cyclopropyl-1H-pyrazol-4-yl)amino)-7-(3-fluoropiperidin-4-yl)quinazoline-6-carbonitrile 181 (50 mg, 0.121 mmol), oxetan-3-one (18 mg, 0.243 mmol) and $NaBH_3CN$ (23 mg, 0.364 mmol) under inert atmosphere. DCE (3 mL) was added, and the resultant mixture was stirred at RT for 25 hrs. The reaction mixture was quenched by the addition of sat. aq. $NH_4Cl$ (20 mL) and extracted with EtOAc (3x15 mL). The combined organic phases were washed with brine (50 mL), dried over anhydrous $Na_2SO_4$, filtered, and solvent removed from the collected filtrate under reduced pressure. The resultant crude residue was subjected to purification by reversed phase HPLC eluting with water (0.1% $NH_4HCO_3$)-MeCN, to afford the title compound 182 in racemic form. The racemic material could be resolved to its component enantiomers by chiral preparative SFC (Column & dimensions: DAICEL CHIRALCEL OJ-H, 250 mmx30 mm; Mobile phase A: $CO_2$;

Mobile phase B: 0.1% $NH_3$-EtOH) to afford the title compounds Ex-6.1 (tR=4.1 min) and Ex-6.2 (tR=4.6 min). MS (ESI): m/z calc'd for $C_{23}H_{24}ClFN_{70}$ $[M+H]^+$: 468, found 468; $^1H$ NMR (500 MHz, $CDCl_3$, 25° C.) δ: 9.07 (br s, 1H), 8.25 (br s, 1H), 8.11 (s, 1H), 7.72 (s, 1H), 7.08 (s, 1H), 4.99-4.81 (m, 1H), 4.75-4.69 (m, 2H), 4.68-4.62 (m, 2H), 3.67 (m, 1H), 3.49 (m, 1H), 3.32-3.22 (m, 2H), 2.85 (m, 1H), 2.16 (m, 1H), 2.13-2.06 (m, 2H), 1.97-1.87 (m, 1H), 1.28-1.23 (m, 2H), 1.15-1.09 (m, 2H). MS (ESI): m/z calc'd for $C_{23}H_{24}ClFN_{70}$ $[M+H]^+$: 468, found 468; $^1H$ NMR (500 MHz, $CDCl_3$, 25° C.) δ: 9.07 (br s, 1H), 8.25 (br s, 1H), 8.11 (s, 1H), 7.72 (s, 1H), 7.12 (s, 1H), 4.99-4.80 (m, 1H), 4.75-4.62 (m, 2H), 4.68-4.62 (m, 2H), 3.67 (m, 1H), 3.49 (m, 1H), 3.33-3.20 (m, 2H), 2.85 (m, 1H), 2.16 (m, 1H), 2.19-2.04 (m, 2H), 1.98-1.86 (m, 1H), 1.29-1.22 (m, 2H), 1.15-1.09 (m, 2H).

Compounds in Table 6 below were prepared in accordance with the synthetic sequence illustrated in General Scheme 7 using the corresponding starting materials.

TABLE 6

| Ex | Structure | Name | Exact Mass $[M + H]^+$ |
| --- | --- | --- | --- |
| Ex-6.3 | 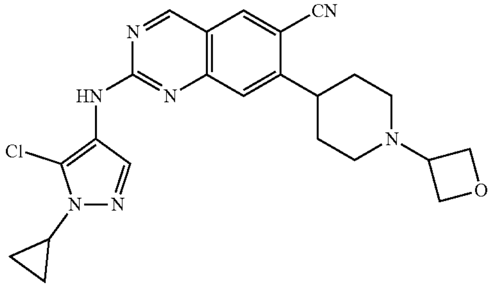 [SMILES: N#Cc1cc2cnc(Nc3cnn(C4CC4)c3Cl)nc2cc1C1CCN(C2COC2)CC1] | 2-((5-chloro-1-cyclopropyl-1H-pyrazol-4-yl)amino)-7-(1-(oxetan-3-yl)piperidin-4-yl)quinazoline-6-carbonitrile | Calc'd 450, found 450 |
| Ex-6.4 | 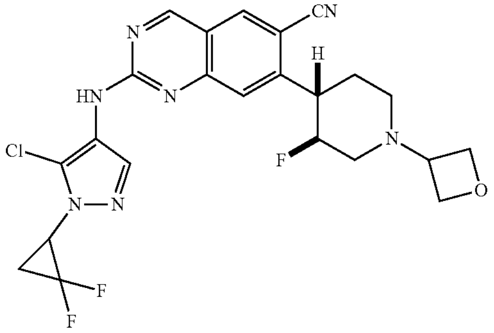 [SMILES: N#Cc1cc2cnc(Nc3cnn(C4CC4(F)F)c3Cl)nc2cc1[C@@H]1CCN(C2COC2)C[C@H]1F] | (R)(3S,4S) or (S)(3S,4S) or (R)(3R,4R) or (S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile | Calc'd 504, found 504 |
| Ex-6.5 | 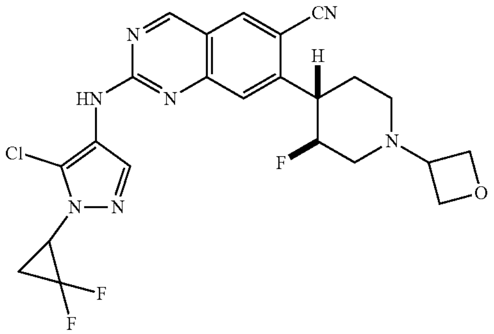 [SMILES: N#Cc1cc2cnc(Nc3cnn(C4CC4(F)F)c3Cl)nc2cc1[C@@H]1CCN(C2COC2)C[C@H]1F] | (R)(3S,4S) or (S)(3S,4S) or (R)(3R,4R) or (S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile | Calc'd 504, found 504 |
| Ex-6.6 | 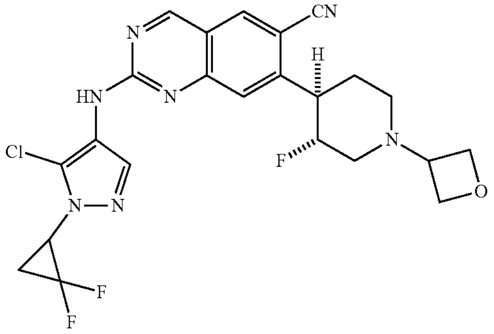 [SMILES: N#Cc1cc2cnc(Nc3cnn(C4CC4(F)F)c3Cl)nc2cc1[C@H]1CCN(C2COC2)C[C@@H]1F] | (R)(3S,4S) or (S)(3S,4S) or (R)(3R,4R) or (S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile | Calc'd 504, found 504 |

TABLE 6-continued

| Ex | Structure | Name | Exact Mass [M + H]+ |
|---|---|---|---|
| Ex-6.7 | 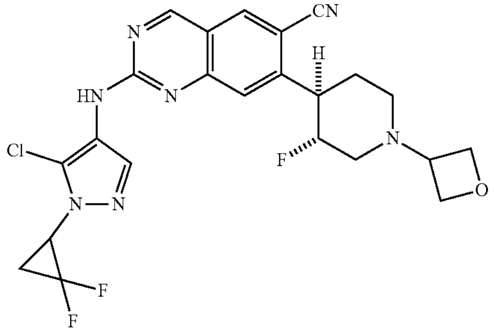 [SMILES: N#Cc1cc2cnc(Nc3cnn(C4CC4(F)F)c3Cl)nc2cc1[C@H]1CCN(C2COC2)C[C@@H]1F] | (R)(3S,4S) or (S)(3S,4S) or (R)(3R,4R) or (S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile | Calc'd 504, found 504 |

General Scheme 8.

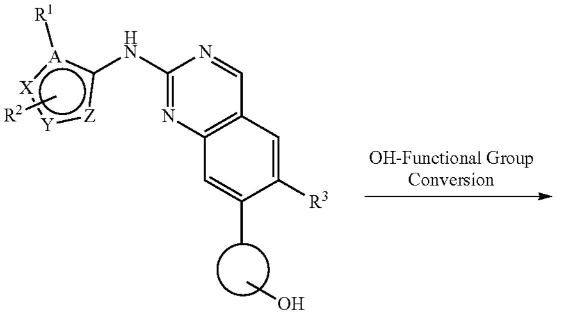

Gen-25

A = C,N
X = C,N
Y = C,N
Z = C,S
$R^1$ = Cl, H, alkyl
$R^2$ = alkyl
$R^3$ = Cl, $CH_3$

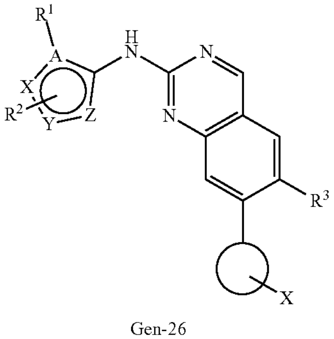

Gen-26
X = F, —OR

In General Scheme 8, compounds of the form Gen-25, which are encompassing of, but not limited to previously described intermediates of the form Gen-12/Gen-14/Gen-18/Gen-21, but specifically describes compounds bearing an alcohol group on the indicated fragment, were subjected reaction conditions which resulted in the conversion of the alcohol functional group to either an aliphatic fluorine, or alkyl ether, as represented by Gen-26. The representative compounds are described in more detail below.

Preparation of Examples 7.1 and 7.2

Scheme 65

Synthesis of (R)(3S,4S)(3S,4S) or (R)(3S,4S)(3R,4R) or (R)(3R,4R)(3S,4S) or (R)(3R,4R)(3R,4R) or (R)(3S,4S)(3S,4R) or (R)(3S,4S)(3R,4S) or (R)(3R,4R)(3S,4R) or (R)(3R,4R)(3R,4S) or (S)(3S,4S)(3S,4S) or (S)(3S,4S)(3R,4R) or (S)(3R,4R)(3S,4S) or (S)(3R,4R)(3R,4R) or (S)(3S,4S)(3S,4R) or (S)(3S,4S)(3R,4S) or (S)(3R,4R)(3S,4R) or (S)(3R,4R)(3R,4S) 6-chloro-N-(5-chloro-1-(2,2-difluorocyclopropyl)-1H-pyrazol-4-yl)-7-3-fluoro-1-(4-fluorotetrahydrofuran-3-yl)piperidin-4-yl)quinazolin-2-amine

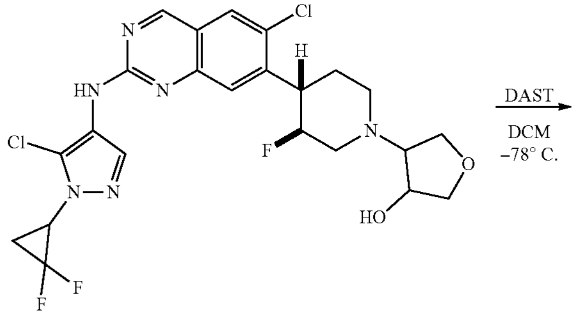

183

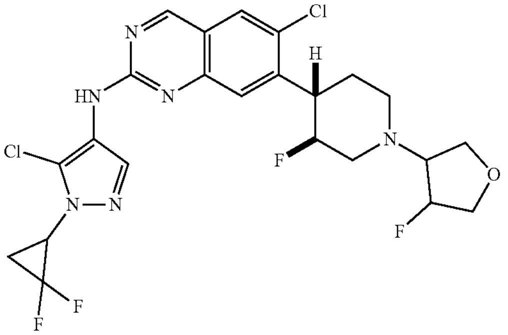

+

Ex-7.1

-continued

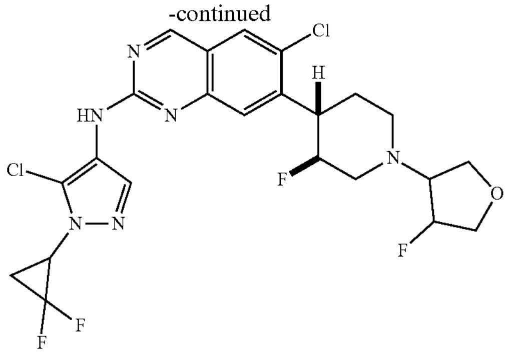

Ex-7.2 fluorotetrahydrofuran-3-yl)piperidin-4-yl)quinazolin-2-amine (Ex-7.1 and Ex-7.2)

Starting 183 was prepared using an identical sequence to that described in Scheme 58 for the preparation of Ex-4.9 with the following modification: racemic ketone 24 was substituted for chiral ketone 25, and therefore 183 was a mixture of two diastereomers. A 4 mL vial was charged with intermediate 183 (89 mg, 0.164 mmol) under inert atmosphere. DCM (850 μL) was added, and to the stirring mixture at −78° C. was added DAST (620 μL, 0.62 mmol). The resultant mixture was stirred at −78° C. for 2 hrs. At 2 hrs, the reaction was diluted with DCM (25 mL) and quenched by dropwise addition of sat. aq. $NH_4Cl$ (25 mL). The phases were separated and the aqueous phase extracted with DCM (3×25 mL). The combined organic phases were washed with $H_2O$(50 mL), dried over anhydrous $Na_2SO_4$, filtered, and solvent was removed from the collected filtrate under reduced pressure. The resultant crude residue was subjected to purification by silica gel chromatography (0-100% 3:1 EtOAc:EtOH in hexanes) to afford the title compound as a diastereomeric mixture. This material could be resolved to its component stereoisomers by chiral preparative SFC(Column & dimensions: CCA F4, 21 mm×250 mm; Mobile phase A: $CO_2$;

Mobile phase B: MeOH with 0.1% $NH_4OH$) to afford Ex-7.1 (tR=2.8 min) and Ex-7.2 (tR=5.0 min). MS (ESI) m/z calc'd for $C_{23}H_{23}Cl_2F_4N_6O$ [M+H]+: 545, found 545. $^1H$ NMR (400 MHz, DMSO-$d_6$, 25° C.) δ: 9.38 (s, 1H), 9.23 (s, 1H), 8.18 (s, 1H), 8.07 (s, 1H), 7.75 (s, 1H), 5.34 (d, J=54.1 Hz, 1H), 5.15-4.93 (m, 1H), 4.56-4.45 (m, 1H), 4.09 (dd, J=9.2, 7.2 Hz, 1H), 3.98-3.74 (m, 2H), 3.58 (dd, J=9.3, 6.9 Hz, 1H), 3.24 (m, 2H), 3.08 (d, J=10.7 Hz, 1H), 2.48-2.33 (m, 2H), 2.26 (t, J=10.8 Hz, 1H), 1.99-1.90 (m, 1H), 1.73-1.59 (m, 1H), 1.36-1.11 (m, 2H). MS (ESI) m/z calc'd for $C_{23}H_{23}Cl_2F_4N_6O$ [M+H]+: 545, found 545. $^1H$ NMR (400 MHz, DMSO-$d_6$, 25° C.) δ: 9.38 (s, 1H), 9.23 (s, 1H), 8.14 (s, 1H), 8.07 (s, 1H), 7.74 (s, 1H), 5.37 (d, J=54.3 Hz, 1H), 5.16-4.95 (m, 1H), 4.50 (q, J=8.7 Hz, 1H), 4.07 (dd, J=9.2, 7.2 Hz, 1H), 3.98-3.77 (m, 2H), 3.57 (dd, J=9.3, 6.9 Hz, 1H), 3.53-3.46 (m, 1H), 3.29-3.19 (m, 1H), 2.79 (d, J=10.4 Hz, 1H), 2.47-2.40 (m, 2H), 2.36-2.29 (m, 1H), 1.92 (d, J=9.3 Hz, 1H), 1.71-1.58 (m, 1H), 1.21 (m, 2H).

Preparation of Example 7.3

Scheme 66. Synthesis of (3S,4S) or (3R,4R) 6-chloro-N-(1-cyclopropyl-5-methyl-1H-pyrazol-4-yl)-7-(1-(4-methoxy-3-methyltetrahydrofuran-3-yl)piperidin-4-yl)quinazolin-2-amine

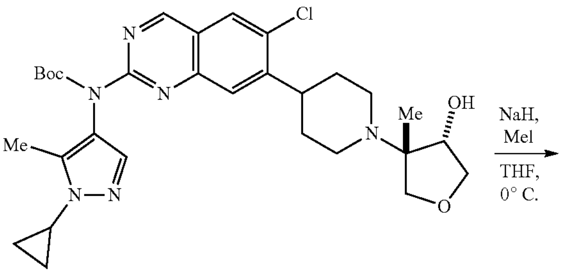

185

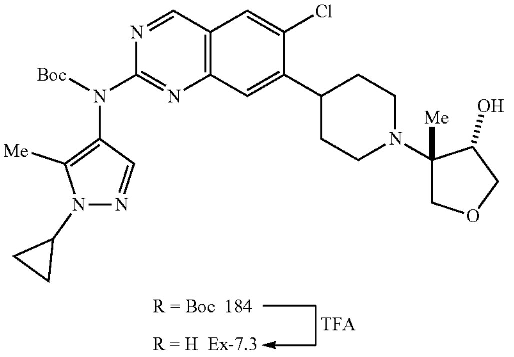

(3S,4S) or (3R,4R) tert-butyl (6-chloro-7-(1-(4-methoxy-3-methyltetrahydrofuran-3-yl)piperidin-4-yl)quinazolin-2-yl)(1-cyclopropyl-5-methyl-1H-pyrazol-4-yl)carbamate (184)

Starting 185 was prepared from intermediates 10 and 30 by the same methods used for the synthesis of 147 and 151. A 30 mL scintillation vial was charged with intermediate 185 (240 mg, 0.412 mmol) and NaH (60% dispersion in oil, 33 mg, 0.823 mmol) under inert atmosphere. THF (2.0 mL) was added and the resulting mixture was cooled to 0° C. and stirred for 5 min before iodomethane (52 μL, 0.823 mmol) was added. The reaction mixture was then stirred for 2 hrs at RT. The reaction was carefully quenched by addition of methanol. Solvent was removed under reduced pressure to afford the title compound 184, which was carried on as crude. MS (ESI) m/z calc'd for $C_{31}H_{42}ClN_6O_4$ $[M+H]^+$: 597, found 597.

(3S,4S) or (3R,4R) 6-chloro-N-(1-cyclopropyl-5-methyl-1H-pyrazol-4-yl)-7-(1-(4-methoxy-3-methyltetrahydrofuran-3-yl)piperidin-4-yl)quinazolin-2-amine (Ex-7.3)

A 30 mL scintillation vial was charged with crude intermediate 184. DCM (2.0 mL) was added, and to the stirring mixture at RT was added TFA (2.0 mL, 26.0 mmol). The resulting mixture was allowed to stir at RT for 2 hrs. Solvent was removed under reduced pressure, and the resultant crude residue was further purified by reversed phase HPLC, eluting with water (0.1% $NH_4OH$)-MeCN to afford afford the title compound Ex-7.3. MS (ESI): m/z calc'd for $C_{26}H_{34}ClN_6O_2$ $[M+H]^+$: 497, found 497. $^1H$ NMR (500

MHz, DMSO-d6) δ 9.12 (s, 1H), 9.06 (s, 1H), 7.96 (s, 1H), 7.73 (s, 1H), 7.42 (s, 1H), 3.92 (dd, J=10.2, 3.6 Hz, 1H), 3.82 (d, J=10.1 Hz, 1H), 3.61 (q, J=7.0 Hz, 2H), 3.52-3.47 (m, 2H), 3.26 (s, 3H), 2.97-2.86 (m, 2H), 2.55 (s, 1H), 2.41 (t, J=10.6 Hz, 1H), 2.31 (s, 3H), 1.82 (d, J=10.8 Hz, 2H), 1.76-1.64 (m, 2H), 1.07-1.02 (m, 3H), 1.01 (s, 3H), 1.00-0.97 (m, 2H).

Compounds in Table 7 below were prepared in accordance with the synthetic sequence illustrated in General Scheme 8 using the corresponding starting materials.

TABLE 7

| Ex | Structure | Name | Exact Mass $[M + H]^+$ |
|---|---|---|---|
| Ex-7.4 | 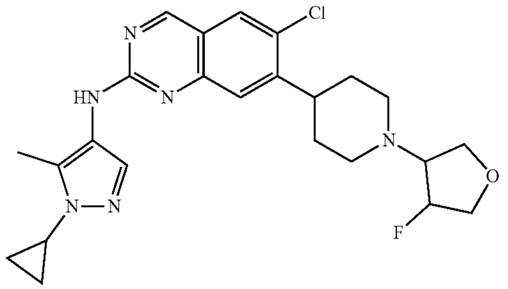 [SMILES: Cc1c(Nc2ncc3cc(Cl)c(C4CCN(C5COCC5F)CC4)cc3n2)cnn1C1CC1] | (3S,4S) or (3R,4R) or (3S,4R) or (3R,4S) 6-chloro-N-(1-cyclopropyl-5-methyl-1H-pyrazol-4-yl)-7-[1-(4-fluorooxolan-3-yl)piperidin-4-yl]quinazolin-2-amine | Calc'd 471, found 471 |
| Ex-7.5 | 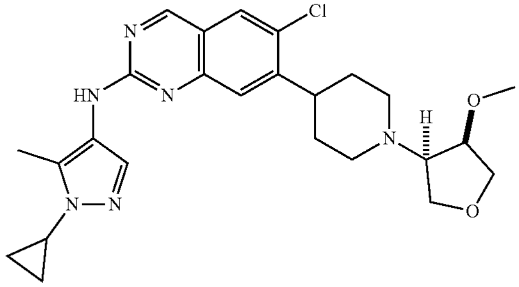 [SMILES: CO[C@H]1COC[C@H]1N1CCC(c2cc3nc(Nc4cnn(C5CC5)c4C)ncc3cc2Cl)CC1] | (3S,4S) or (3R,4R) 6-chloro-N-(1-cyclopropyl-5-methyl-1H-pyrazol-4-yl)-7-[1-(4-methoxyoxolan-3-yl)piperidin-4-yl]quinazolin-2-amine | Calc'd 483, found 483 |
| Ex-7.6 | 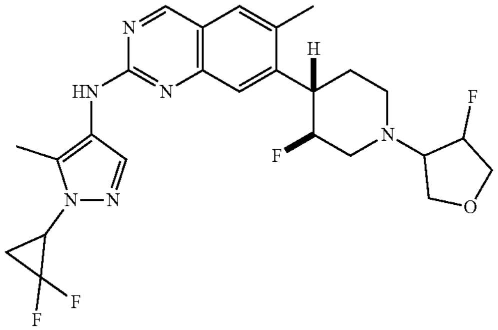 [SMILES: Cc1cc2cnc(Nc3cnn(C4CC4(F)F)c3C)nc2cc1[C@@H]1CCN(C2COCC2F)C[C@H]1F] | (S)(3S,4R)(3S,4S) or (S)(3R,4S)(3S,4S) or (S)(3R,4R)(3S,4S) or (S)(3S,4S)(3S,4S) or (S)(3S,4R)(3R,4R) or (S)(3R,4S)(3R,4R) or (S)(3R,4R)(3R,4R) or (S)(3S,4S)(3R,4R) or (R)(3S,4R)(3S,4S) or (R)(3R,4S)(3S,4S) or (R)(3R,4R)(3S,4S) or (R)(3S,4S)(3S,4S) or (R)(3S,4R)(3R,4R) or (R)(3R,4S)(3R,4R) or (R)(3R,4R)(3R,4R) or (R)(3S,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine | Calc'd 505, found 505 |

TABLE 7-continued

| Ex | Structure | Name | Exact Mass [M + H]+ |
|---|---|---|---|
| Ex-7.7 | 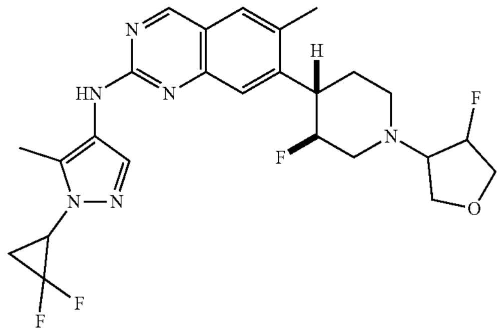 [SMILES: Cc1cc2cnc(Nc3cnn(C4CC4(F)F)c3C)nc2cc1[C@@H]1CCN(C2COCC2F)C[C@H]1F] | (S)(3S,4R)(3S,4S) or (S)(3R,4S)(3S,4S) or (S)(3R,4R)(3S,4S) or (S)(3S,4S)(3S,4S) or (S)(3S,4R)(3R,4R) or (S)(3R,4S)(3R,4R) or (S)(3R,4R)(3R,4R) or (S)(3S,4S)(3R,4R) or (R)(3S,4R)(3S,4S) or (R)(3R,4S)(3S,4S) or (R)(3R,4R)(3S,4S) or (R)(3S,4S)(3S,4S) or (R)(3S,4R)(3R,4R) or (R)(3R,4S)(3R,4R) or (R)(3R,4R)(3R,4R) or (R)(3S,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine | Calc'd 505, found 505 |
| Ex-7.8 | 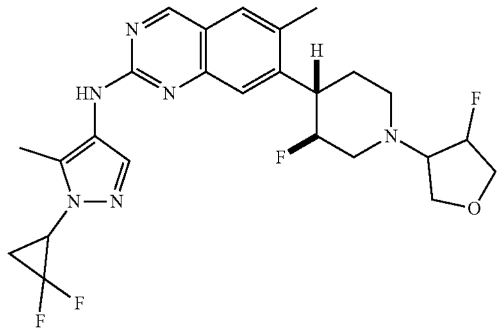 [SMILES: Cc1cc2cnc(Nc3cnn(C4CC4(F)F)c3C)nc2cc1[C@@H]1CCN(C2COCC2F)C[C@H]1F] | (S)(3S,4R)(3S,4S) or (S)(3R,4S)(3S,4S) or (S)(3R,4R)(3S,4S) or (S)(3S,4S)(3S,4S) or (S)(3S,4R)(3R,4R) or (S)(3R,4S)(3R,4R) or (S)(3R,4R)(3R,4R) or (S)(3S,4S)(3R,4R) or (R)(3S,4R)(3S,4S) or (R)(3R,4S)(3S,4S) or (R)(3R,4R)(3S,4S) or (R)(3S,4S)(3S,4S) or (R)(3S,4R)(3R,4R) or (R)(3R,4S)(3R,4R) or (R)(3R,4R)(3R,4R) or (R)(3S,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine | Calc'd 505, found 505 |
| Ex-7.9 | 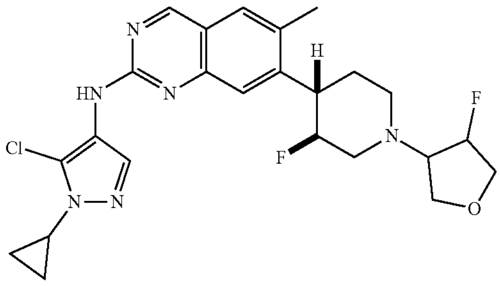 [SMILES: Cc1cc2cnc(Nc3cnn(C4CC4)c3Cl)nc2cc1[C@@H]1CCN(C2COCC2F)C[C@H]1F] | (3S,4R)(3S,4S) or (3R,4S)(3S,4S) or (3R,4R)(3S,4S) or (3S,4S)(3S,4S) or (3S,4R)(3R,4R) or (3R,4S)(3R,4R) or (3R,4R)(3R,4R) or (3S,4S)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine | Calc'd 489, found 489 |
| Ex-7.10 | 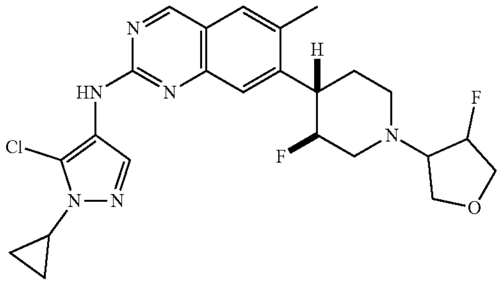 [SMILES: Cc1cc2cnc(Nc3cnn(C4CC4)c3Cl)nc2cc1[C@@H]1CCN(C2COCC2F)C[C@H]1F] | (3S,4R)(3S,4S) or (3R,4S)(3S,4S) or (3R,4R)(3S,4S) or (3S,4S)(3S,4S) or (3S,4R)(3R,4R) or (3R,4S)(3R,4R) or (3R,4R)(3R,4R) or (3S,4S)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine | Calc'd 489, found 489 |

General Scheme 9.

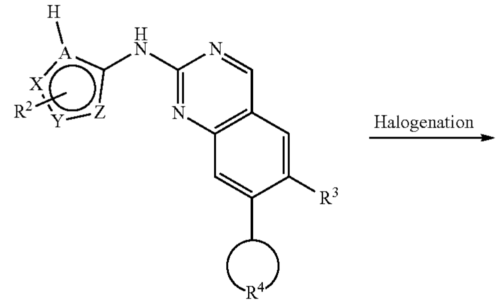

Gen-27

X = C,N
Y = C,N
Z = C,S
$R^2$ = alkyl
$R^3$ = Cl, $CH_3$
$R^4$ = alkyl, ——NR

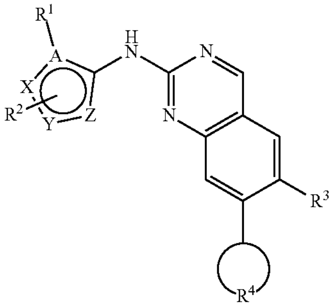

Gen-28
$R^1$ = Cl, Br

In General Scheme 9, compounds of the form Gen-27, which are encompassing of, but not limited to previously described intermediates of the form Gen-12/Gen-14/Gen-18/Gen-21, but specifically describes compounds bearing an unsubstituted heteroaromatic carbon at the indicated north-west fragment of the molecule, could be treated with an electrophilic halogenating agent to afford compounds of the form Gen-28. The representative compounds are described in more detail below.

Preparation of Example 8.1

Scheme 67. Synthesis of 6-chloro-N-(5-chloro-1-(2,2,2-trifluoroethyl)-1H-pyrazol-4-yl)-7-(1-(oxetan-3-yl)piperidin-4-yl)quinazolin-2-amine

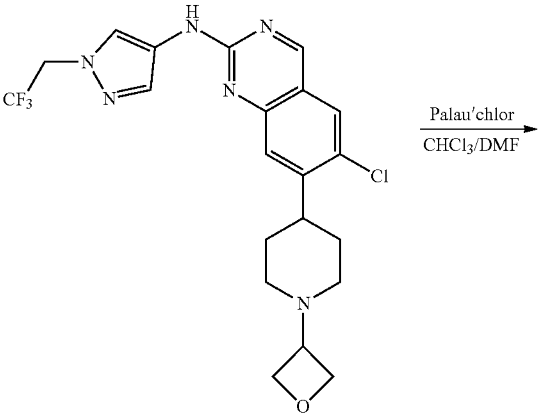

186

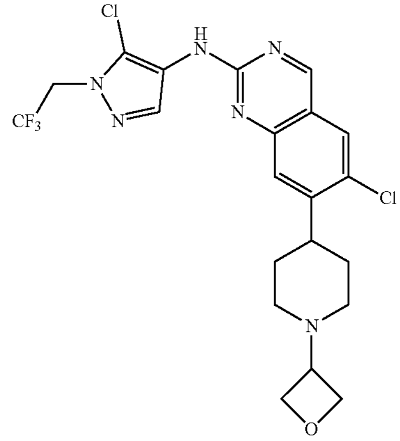

Ex-8.1

6-chloro-N-(5-chloro-1-(2,2,2-trifluoroethyl)-1H-pyrazol-4-yl)-7-(1-(oxetan-3-yl)piperidin-4-yl)quinazolin-2-amine (Ex-8.1)

Starting 6-chloro-7-(1-(oxetan-3-yl)piperidin-4-yl)-N-(1-(2,2,2-trifluoroethyl)-1H-pyrazol-4-yl)quinazolin-2-amine 186 was prepared from intermediates 16 and 110 according to General Scheme 5 via cross coupling, deprotection, and reductive amination procedures that have been described in Scheme, Scheme, and Scheme, respectively. A 4-mL scintillation vial was charged with intermediate 186 (34 mg, 0.073 mmol), under inert atmosphere. Chloroform (364 uL) and DMF (364 uL) was added, and to the stirring reaction mixture was added 2-chloro-1,3-bis(methoxycarbonyl)guanidine (23 mg, 0.11 mmol). The resultant mixture was stirred at RT for 3 hrs, at which point it was quenched by the addition of sat. aq. $Na_2S_2O_3$ and diluted with DCM and sat.

aq. $NaHCO_3$. The phases were separated, and the aqueous phase extracted with DCM (2×20 mL). The combined organic phases were dried over $Na_2SO_4$, filtered, and solvent was removed from the collected filtrate under reduced pressure. The resultant crude residue was subjected to purification by reversed phase HPLC, eluting with water (0.1% $NH_4OH$)-MeCN to afford the title compound Ex-8.1. MS (ESI): m/z calc'd for $C_{21}H_{21}Cl_2F_3N_{60}$ $[M+H]^+$: 501, found 501; $^1H$ NMR (400 MHz, DMSO-$d_6$, 25° C.) δ: 10.43 (s, 1H), 9.40 (s, 1H), 9.25 (s, 1H), 8.13 (s, 1H), 8.10 (s, 1H), 7.43 (s, 1H), 5.21-5.16 (m, 2H), 4.80-4.79 (m, 2H), 4.41 (m, 2H), 3.56-3.54 (m, 2H), 3.36 (m, 1H), 3.10 (m, 2H), 2.17-2.14 (m, 2H), 1.98-1.95 (m, 2H).

Preparation of Example 8

Scheme 68. Synthesis of N-(5-bromo-1-cyclopropyl-1H-pyrazol-4-yl)-6-chloro-7-(1-(oxetan-3-yl)piperidin-4-yl)quinazolin-2-amine

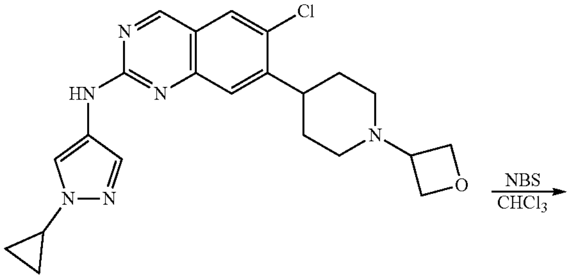

187

-continued

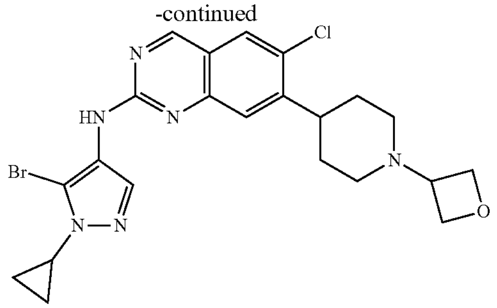

Ex-8.2

N-(5-bromo-1-cyclopropyl-1H-pyrazol-4-yl)-6-chloro-7-(1-(oxetan-3-yl)piperidin-4-yl)quinazolin-2-amine (Ex-8.)

Starting 6-chloro-N-(1-cyclopropyl-1H-pyrazol-4-yl)-7-(1-(oxetan-3-yl)piperidin-4-yl)quinazolin-2-amine 187 was prepared from intermediate 38 and commercial 4-bromo-1-cyclopropyl-1H-pyrazole according to General Scheme 3 via cross coupling using an analogous procedure to that described in Scheme. The title compound Ex-8. could be prepared by an identical procedure to that which was described for the preparation of Ex-8.1, substituting N-bromosuccinimide for 2-chloro-1,3-bis(methoxycarbonyl)guanidine. MS (ESI): m/z calc'd for $C_{22}H_{25}BrClN_6O$ $[M+H]^+$: 503, found 503; $^1H$ NMR (500 MHz, DMSO-$d_6$, 25° C.) δ: 9.18 (s, 1H), 9.06 (s, 1H), 8.02 (s, 1H), 7.85 (br s, 1H), 7.45 (s, 1H), 4.56 (m, 2H), 4.46 (m, 2H), 3.61 (m, 1H), 3.45 (m, 1H), 2.98 (m, 1H), 2.86 (m, 2H), 1.93 (m, 2H), 1.85 (m, 2H), 1.74 (m, 2H), 1.09 (m, 4H).

Compounds in Table 8 below were prepared in accordance with the synthetic sequence illustrated in General Scheme 9 using the corresponding starting materials.

TABLE 8

| Ex | Structure | Name | Exact Mass $[M + H]^+$ |
|---|---|---|---|
| Ex-8.2 | 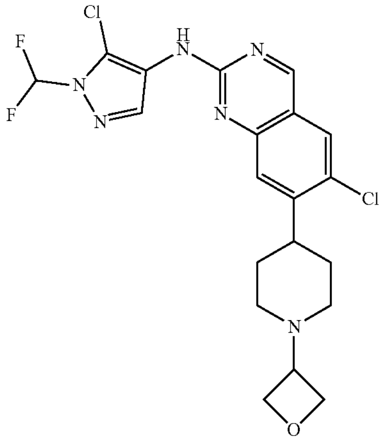 [SMILES: FC(F)n1ncc(Nc2ncc3cc(Cl)c(C4CCN(C5COC5)CC4)cc3n2)c1Cl] | 6-chloro-N-[5-chloro-1-(difluoromethyl)-1H-pyrazol-4-yl]-7-[1-(oxetan-3-yl)piperidin-4-yl]quinazolin-2-amine | Calc'd 469, found 469 |

TABLE 8-continued

| Ex | Structure | Name | Exact Mass [M + H]+ |
|---|---|---|---|
| Ex-8.3 | 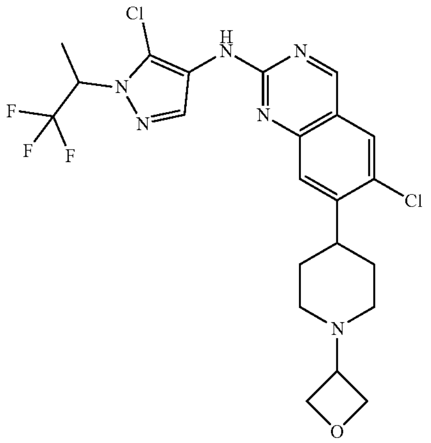 [SMILES: CC(n1ncc(Nc2ncc3cc(Cl)c(C4CCN(C5COC5)CC4)cc3n2)c1Cl)C(F)(F)F] | (S) or (R) 6-chloro-N-[5-chloro-1-(1,1,1-trifluoropropan-2-yl)-1H-pyrazol-4-yl]-7-[1-(oxetan-3-yl)piperidin-4-yl]quinazolin-2-amine | Calc'd 515, found 515 |
| Ex-8.4 | 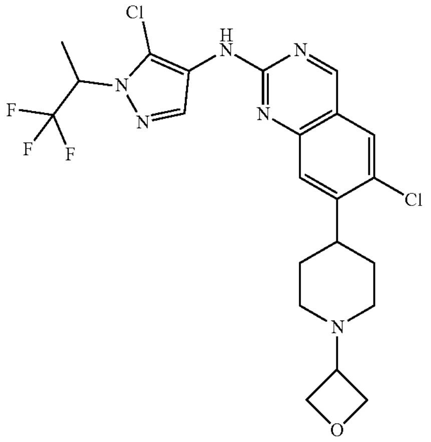 [SMILES: CC(n1ncc(Nc2ncc3cc(Cl)c(C4CCN(C5COC5)CC4)cc3n2)c1Cl)C(F)(F)F] | (S) or (R) 6-chloro-N-[5-chloro-1-(1,1,1-trifluoropropan-2-yl)-1H-pyrazol-4-yl]-7-[1-(oxetan-3-yl)piperidin-4-yl]quinazolin-2-amine | Calc'd 515, found 515 |
| Ex-8.5 | 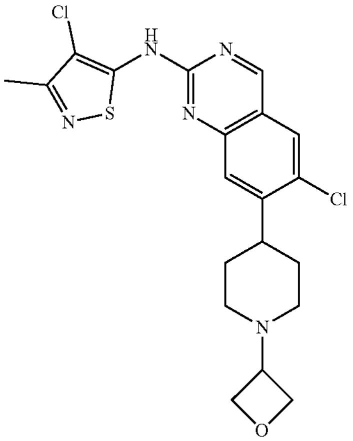 [SMILES: Cc1nsc(Nc2ncc3cc(Cl)c(C4CCN(C5COC5)CC4)cc3n2)c1Cl] | 6-chloro-N-(4-chloro-3-methyl-1,2-thiazol-5-yl)-7-[1-(oxetan-3-yl)piperidin-4-yl]quinazolin-2-amine | Calc'd 450, found 450 |
| Ex-8.6 | 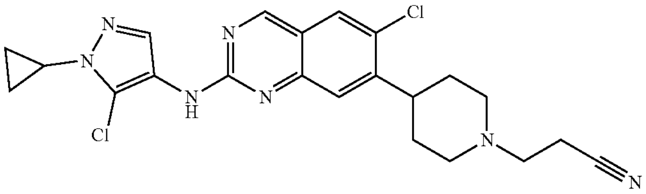 [SMILES: N#CCCN1CCC(c2cc3nc(Nc4cnn(C5CC5)c4Cl)ncc3cc2Cl)CC1] | 3-(4-{6-chloro-2-[(5-chloro-1-cyclopropyl-1H-pyrazol-4-yl)amino]quinazolin-7-yl}piperidin-1-yl)propanenitrile | Calc'd 456, found 456 |

TABLE 8-continued

| Ex | Structure | Name | Exact Mass [M + H]+ |
|---|---|---|---|
| Ex-8.7 | 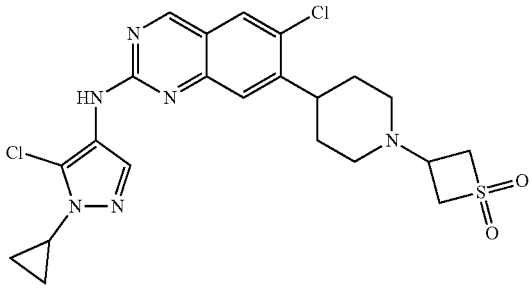 [SMILES: O=S1(=O)CC(N2CCC(c3cc4nc(Nc5cnn(C6CC6)c5Cl)ncc4cc3Cl)CC2)C1] | 3-(4-(6-chloro-2-((5-chloro-1-cyclopropyl-1H-pyrazol-4-yl)amino)quinazolin-7-yl)piperidin-1-yl)thietane 1,1-dioxide | Calc'd 507, found 507 |
| Ex-8.8 | 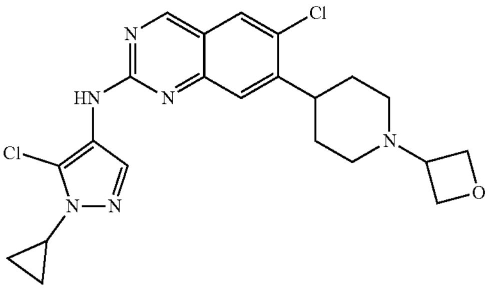 [SMILES: Clc1cc2cnc(Nc3cnn(C4CC4)c3Cl)nc2cc1C1CCN(C2COC2)CC1] | 6-chloro-N-(5-chloro-1-cyclopropyl-1H-pyrazol-4-yl)-7-[1-(oxetan-3-yl)piperidin-4-yl]quinazolin-2-amine | Calc'd 459, found 459 |
| Ex-8.9 | 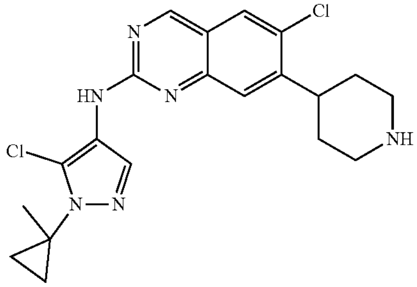 [SMILES: CC1(n2ncc(Nc3ncc4cc(Cl)c(C5CCNCC5)cc4n3)c2Cl)CC1] | 6-chloro-N-[5-chloro-1-(1-methylcyclopropyl)-1H-pyrazol-4-yl]-7-(piperidin-4-yl)quinazolin-2-amine | Calc'd 417, found 417 |
| Ex-8.10 | 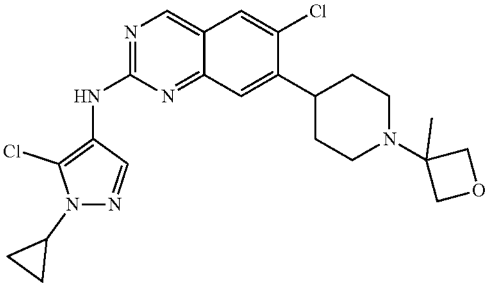 [SMILES: CC1(N2CCC(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-[1-(3-methyloxetan-3-yl)piperidin-4-yl]quinazolin-2-amine | Calc'd 473, found 473 |
| Ex-8.11 | 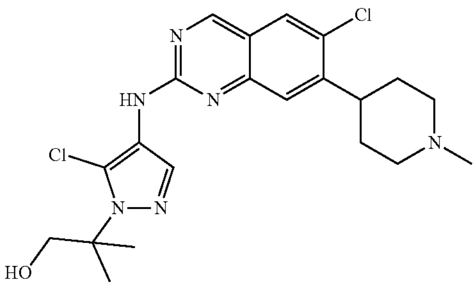 [SMILES: CN1CCC(c2cc3nc(Nc4cnn(C(C)(C)CO)c4Cl)ncc3cc2Cl)CC1] | 2-(5-chloro-4-{[6-chloro-7-(1-methylpiperidin-4-yl)quinazolin-2-yl]amino}-1H-pyrazol-1-yl)-2-methylpropan-1-ol | Calc'd 449, found 449 |

TABLE 8-continued

| Ex | Structure | Name | Exact Mass [M + H]$^+$ |
|---|---|---|---|
| Ex-8.12 | 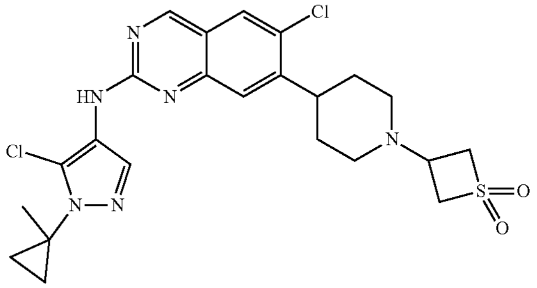 [SMILES: CC1(n2ncc(Nc3ncc4cc(Cl)c(C5CCN(C6CS(=O)(=O)C6)CC5)cc4n3)c2Cl)CC1] | 3-(4-(6-chloro-2-((5-chloro-1-(1-methylcyclopropyl)-1H-pyrazol-4-yl)amino)quinazolin-7-yl)piperidin-1-yl)thietane 1,1-dioxide | Calc'd 521, found 521 |
| Ex-8.13 | 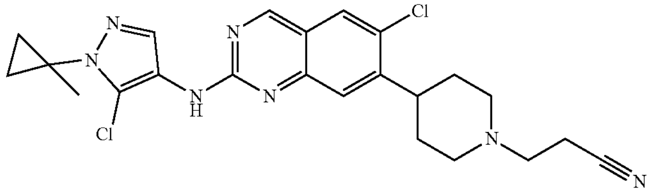 [SMILES: CC1(n2ncc(Nc3ncc4cc(Cl)c(C5CCN(CCC#N)CC5)cc4n3)c2Cl)CC1] | 3-[4-(6-chloro-2-{[5-chloro-1-(1-methylcyclopropyl)-1H-pyrazol-4-yl]amino}quinazolin-7-yl)piperidin-1-yl]propanenitrile | Calc'd 470, found 470 |
| Ex-8.14 | 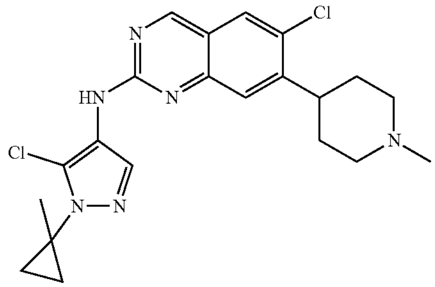 [SMILES: CN1CCC(c2cc3nc(Nc4cnn(C5(C)CC5)c4Cl)ncc3cc2Cl)CC1] | 6-chloro-N-[5-chloro-1-(1-methylcyclopropyl)-1H-pyrazol-4-yl]-7-(1-methylpiperidin-4-yl)quinazolin-2-amine | Calc'd 431, found 431 |
| Ex-8.15 | 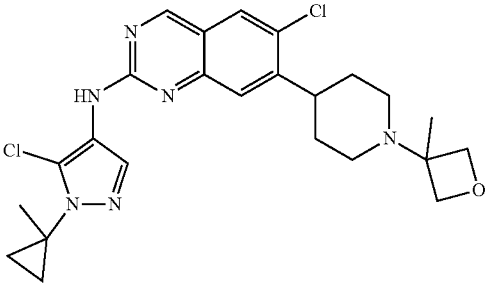 | 6-chloro-N-[5-chloro-1-(1-methylcyclopropyl)-1H-pyrazol-4-yl]-7-[1-(3-methyloxetan-3-yl)piperidin-4-yl]quinazolin-2-amine | Calc'd 487, found 487 |
| Ex-8.16 | 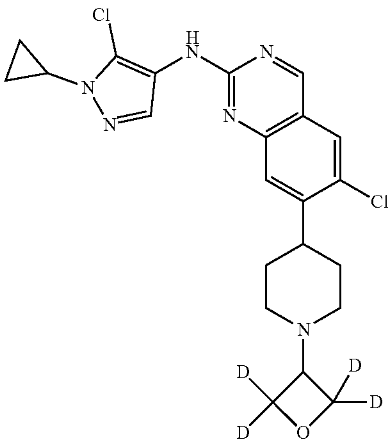 [SMILES: [2H]C1([2H])OC([2H])([2H])C1N1CCC(c2cc3nc(Nc4cnn(C5CC5)c4Cl)ncc3cc2Cl)CC1] | 6-chloro-N-(5-chloro-1-cyclopropyl-1H-pyrazol-4-yl)-7-(1-(oxetan-3-yl-2,2,4,4-d4)piperidin-4-yl)quinazolin-2-amine | Calc'd 463, found 463 |

TABLE 8-continued
| Ex | Structure | Name | Exact Mass [M + H]+ |
| --- | --- | --- | --- |
| Ex-8.17 | 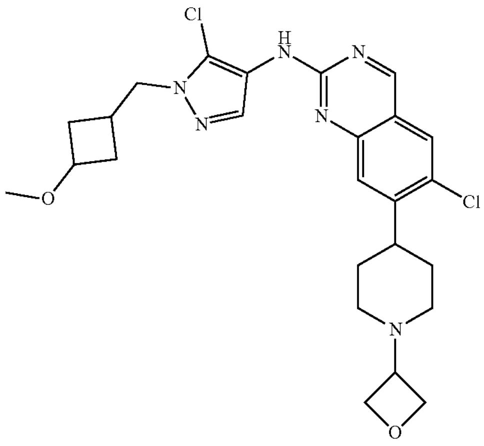 [SMILES: COC1CC(Cn2ncc(Nc3ncc4cc(Cl)c(C5CCN(C6COC6)CC5)cc4n3)c2Cl)C1] | 6-chloro-N-{5-chloro-1-[(3-methoxycyclobutyl)methyl]-1H-pyrazol-4-yl}-7-[1-(oxetan-3-yl)piperidin-4-yl]quinazolin-2-amine | Calc'd 517, found 517 |
| Ex-8.18 | 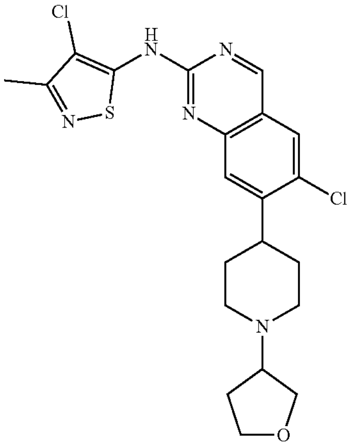 [SMILES: Cc1nsc(Nc2ncc3cc(Cl)c(C4CCN(C5CCOC5)CC4)cc3n2)c1Cl] | (S) or (R) 6-chloro-N-(4-chloro-3-methyl-1,2-thiazol-5-yl)-7-[1-(oxolan-3-yl)piperidin-4-yl]quinazolin-2-amine | Calc'd 464, found 464 |
| Ex-8.19 | 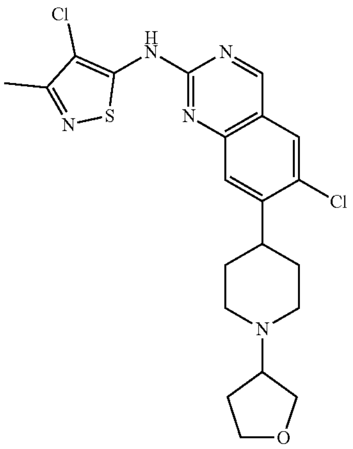 [SMILES: Cc1nsc(Nc2ncc3cc(Cl)c(C4CCN(C5CCOC5)CC4)cc3n2)c1Cl] | (S) or (R) 6-chloro-N-(4-chloro-3-methyl-1,2-thiazol-5-yl)-7-[1-(oxolan-3-yl)piperidin-4-yl]quinazolin-2-amine | Calc'd 464, found 464 |

TABLE 8-continued

| Ex | Structure | Name | Exact Mass [M + H]+ |
|---|---|---|---|
| Ex-8.20 | 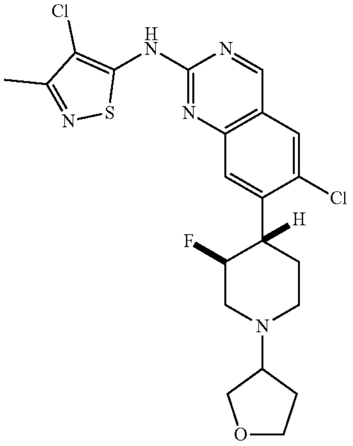 [SMILES: Cc1nsc(Nc2ncc3cc(Cl)c([C@@H]4CCN(C5CCOC5)C[C@H]4F)cc3n2)c1Cl] | (3S,4S)(S) or (3S,4S)(R) or (3R,4R)(S) or (3R,4R)(R) 6-chloro-N-(4-chloro-3-methyl-1,2-thiazol-5-yl)-7-[3-fluoro-1-(oxolan-3-yl)piperidin-4-yl]quinazolin-2-amine | Calc'd 482, found 482 |
| Ex-8.21 | 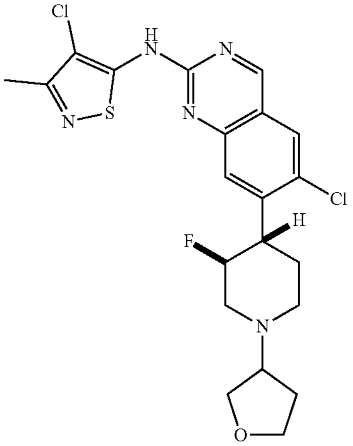 [SMILES: Cc1nsc(Nc2ncc3cc(Cl)c([C@@H]4CCN(C5CCOC5)C[C@H]4F)cc3n2)c1Cl] | (3S,4S)(S) or (3S,4S)(R) or (3R,4R)(S) or (3R,4R)(R) 6-chloro-N-(4-chloro-3-methyl-1,2-thiazol-5-yl)-7-[3-fluoro-1-(oxolan-3-yl)piperidin-4-yl]quinazolin-2-amine | Calc'd 482, found 482 |
| Ex-8.22 | 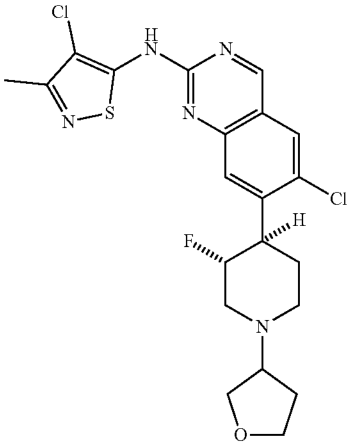 [SMILES: Cc1nsc(Nc2ncc3cc(Cl)c([C@H]4CCN(C5CCOC5)C[C@@H]4F)cc3n2)c1Cl] | (3S,4S)(S) or (3S,4S)(R) or (3R,4R)(S) or (3R,4R)(R) 6-chloro-N-(4-chloro-3-methyl-1,2-thiazol-5-yl)-7-[3-fluoro-1-(oxolan-3-yl)piperidin-4-yl]quinazolin-2-amine | Calc'd 482, found 482 |

TABLE 8-continued

| Ex | Structure | Name | Exact Mass [M + H]+ |
|---|---|---|---|
| Ex-8.23 | 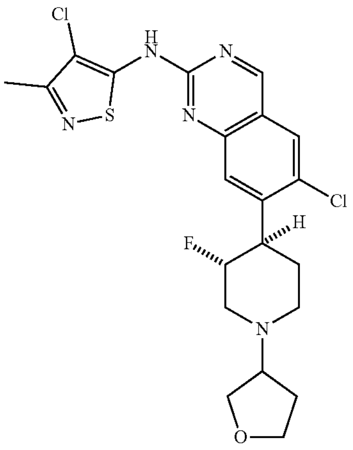 [SMILES: Cc1nsc(Nc2ncc3cc(Cl)c([C@H]4CCN(C5CCOC5)C[C@@H]4F)cc3n2)c1Cl] | (3S,4S)(S) or (3S,4S)(R) or (3R,4R)(S) or (3R,4R)(R) 6-chloro-N-(4-chloro-3-methyl-1,2-thiazol-5-yl)-7-[3-fluoro-1-(oxolan-3-yl)piperidin-4-yl]quinazolin-2-amine | Calc'd 482, found 482 |
| Ex-8.24 | 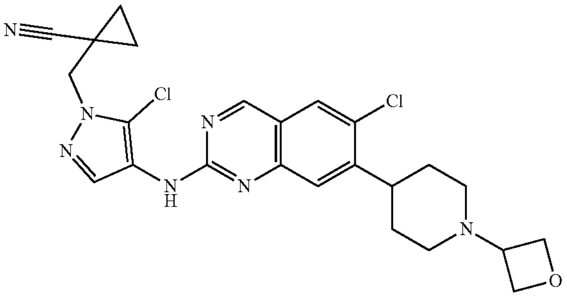 [SMILES: N#CC1(Cn2ncc(Nc3ncc4cc(Cl)c(C5CCN(C6COC6)CC5)cc4n3)c2Cl)CC1] | 1-{[5-chloro-4-({6-chloro-7-[1-(oxetan-3-yl)piperidin-4-yl]quinazolin-2-yl}amino)-1H-pyrazol-1-yl]methyl}cyclopropane-1-carbonitrile | Calc'd 498, found 498 |
| Ex-8.25 | 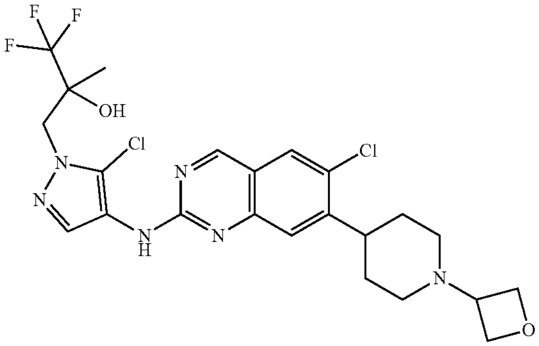 [SMILES: CC(O)(Cn1ncc(Nc2ncc3cc(Cl)c(C4CCN(C5COC5)CC4)cc3n2)c1Cl)C(F)(F)F] | (S) or (R) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol | Calc'd 545, found 545 |
| Ex-8.26 | 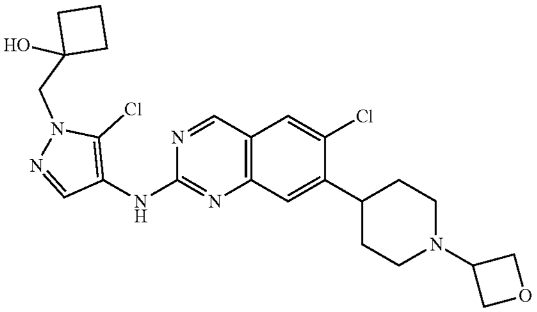 [SMILES: OC1(Cn2ncc(Nc3ncc4cc(Cl)c(C5CCN(C6COC6)CC5)cc4n3)c2Cl)CCC1] | 1-{[5-chloro-4-({6-chloro-7-[1-(oxetan-3-yl)piperidin-4-yl]quinazolin-2-yl}amino)-1H-pyrazol-1-yl]methyl}cyclobutan-1-ol | Calc'd 503, found 503 |

TABLE 8-continued

| Ex | Structure | Name | Exact Mass [M + H]+ |
|---|---|---|---|
| Ex-8.27 | 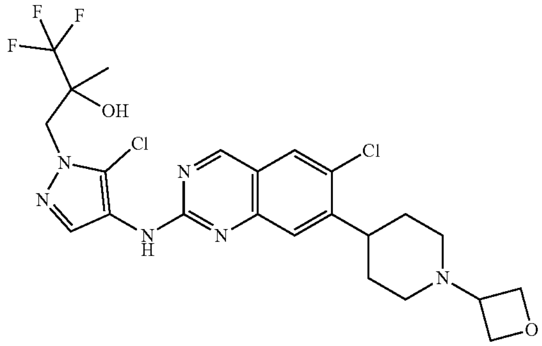 [SMILES: CC(O)(Cn1ncc(Nc2ncc3cc(Cl)c(C4CCN(C5COC5)CC4)cc3n2)c1Cl)C(F)(F)F] | (S) or (R) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol | Calc'd 545, found 545 |
| Ex-8.28 | 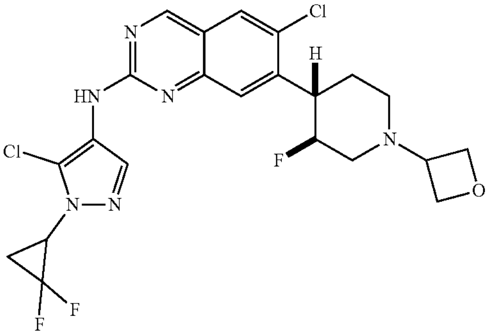 [SMILES: F[C@@H]1CN(C2COC2)CC[C@H]1c1cc2nc(Nc3cnn(C4CC4(F)F)c3Cl)ncc2cc1Cl] | (R)(3S,4S) or (S)(3S,4S) or (R)(3R,4R) or (S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine | Calc'd 513, found 513 |
| Ex-8.29 | 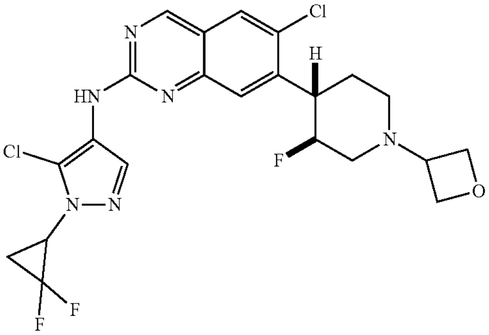 [SMILES: F[C@@H]1CN(C2COC2)CC[C@H]1c1cc2nc(Nc3cnn(C4CC4(F)F)c3Cl)ncc2cc1Cl] | (R)(3S,4S) or (S)(3S,4S) or (R)(3R,4R) or (S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine | Calc'd 513, found 513 |
| Ex-8.30 | 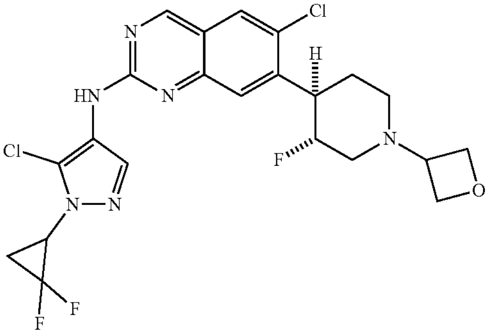 [SMILES: F[C@H]1CN(C2COC2)CC[C@@H]1c1cc2nc(Nc3cnn(C4CC4(F)F)c3Cl)ncc2cc1Cl] | (R)(3S,4S) or (S)(3S,4S) or (R)(3R,4R) or (S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine | Calc'd 513, found 513 |

TABLE 8-continued

| Ex | Structure | Name | Exact Mass [M + H]$^+$ |
|---|---|---|---|
| Ex-8.31 | 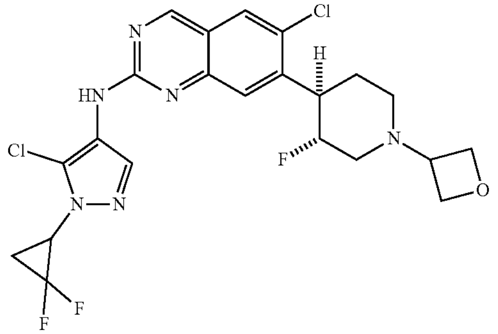 [SMILES: F[C@H]1CN(C2COC2)CC[C@@H]1c1cc2nc(Nc3cnn(C4CC4(F)F)c3Cl)ncc2cc1Cl] | (R)(3S,4S) or (S)(3S,4S) or (R)(3R,4R) or (S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine | Calc'd 513, found 513 |
| Ex-8.32 | 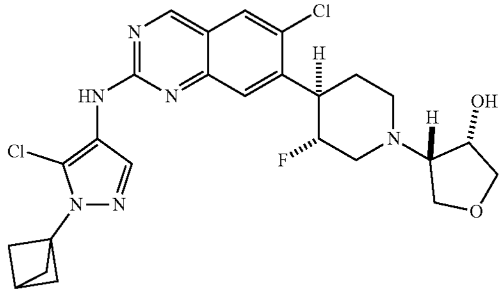 [SMILES: O[C@@H]1COC[C@@H]1N1CC[C@H](c2cc3nc(Nc4cnn(C56CC(C5)C6)c4Cl)ncc3cc2Cl)[C@@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol | Calc'd 533, found 533 |
| Ex-8.33 | 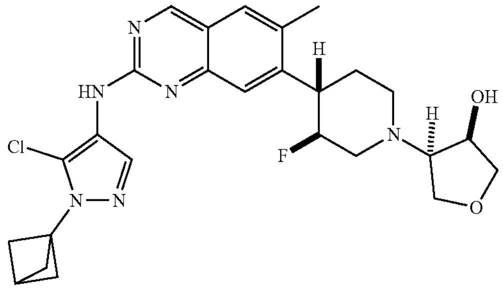 [SMILES: Cc1cc2cnc(Nc3cnn(C45CC(C4)C5)c3Cl)nc2cc1[C@@H]1CCN([C@@H]2COC[C@@H]2O)C[C@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol | Calc'd 513, found 513 |
| Ex-8.34 | 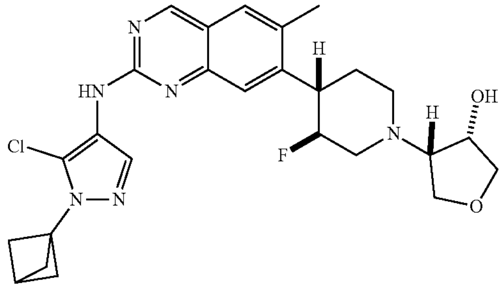 [SMILES: Cc1cc2cnc(Nc3cnn(C45CC(C4)C5)c3Cl)nc2cc1[C@@H]1CCN([C@H]2COC[C@H]2O)C[C@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol | Calc'd 513, found 513 |
| Ex-8.35 | 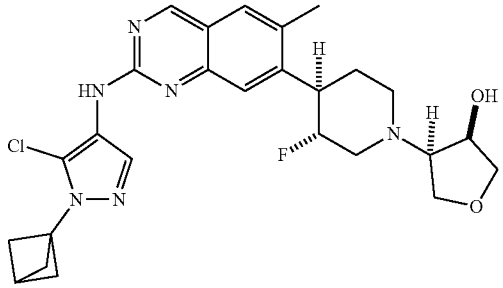 [SMILES: Cc1cc2cnc(Nc3cnn(C45CC(C4)C5)c3Cl)nc2cc1[C@H]1CCN([C@@H]2COC[C@@H]2O)C[C@@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol | Calc'd 513, found 513 |

TABLE 8-continued

| Ex | Structure | Name | Exact Mass [M + H]+ |
|---|---|---|---|
| Ex-8.36 | 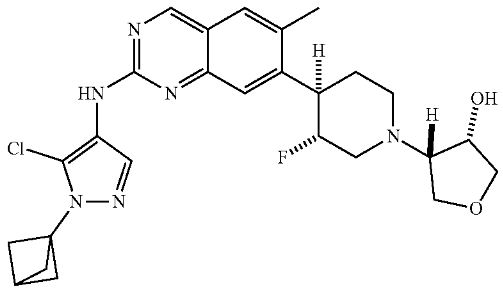 [SMILES: Cc1cc2cnc(Nc3cnn(C45CC(C4)C5)c3Cl)nc2cc1[C@H]1CCN([C@H]2COC[C@H]2O)C[C@@H]1F] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol | Calc'd 513, found 513 |
| Ex-8.37 | 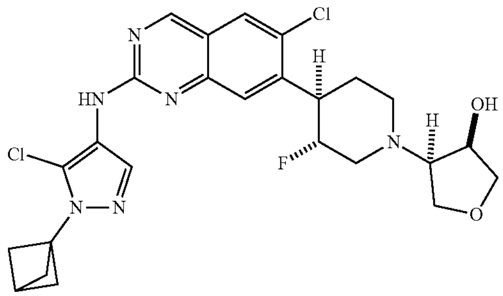 [SMILES: O[C@H]1COC[C@H]1N1CC[C@H](c2cc3nc(Nc4cnn(C56CC(C5)C6)c4Cl)ncc3cc2Cl)[C@@H](F)C1] | (3S,4S)(3S,4S) or (3S,4S)(3R,4R) or (3R,4R)(3S,4S) or (3R,4R)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol | Calc'd 533, found 533 |
| Ex-8.38 | 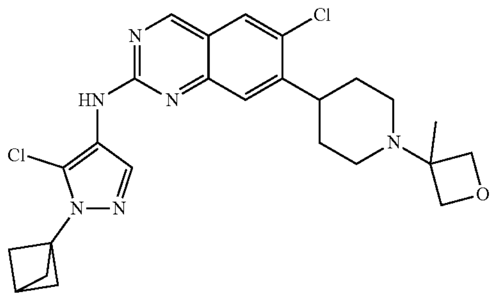 [SMILES: CC1(N2CCC(c3cc4nc(Nc5cnn(C67CC(C6)C7)c5Cl)ncc4cc3Cl)CC2)COC1] | N-[1-(bicyclo[1.1.1]pentan-1-yl)-5-chloro-1H-pyrazol-4-yl]-6-chloro-7-[1-(3-methyloxetan-3-yl)piperidin-4-yl]quinazolin-2-amine | Calc'd 499, found 499 |
| Ex-8.39 | 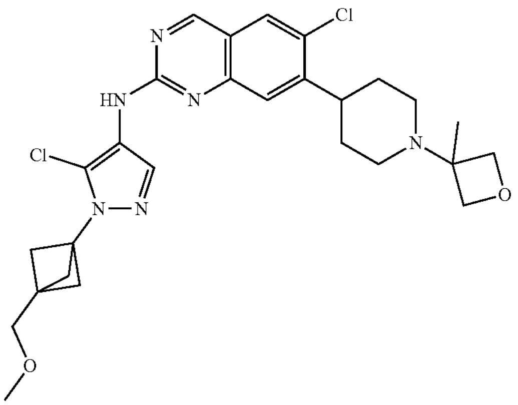 [SMILES: COCC12CC(n3ncc(Nc4ncc5cc(Cl)c(C6CCN(C7(C)COC7)CC6)cc5n4)c3Cl)(C1)C2] | 6-chloro-N-{5-chloro-1-[3-(methoxymethyl)bicyclo[1.1.1]pentan-1-yl]-1H-pyrazol-4-yl}-7-[1-(3-methyloxetan-3-yl)piperidin-4-yl]quinazolin-2-amine | Calc'd 543, found 543 |

General Scheme 10.

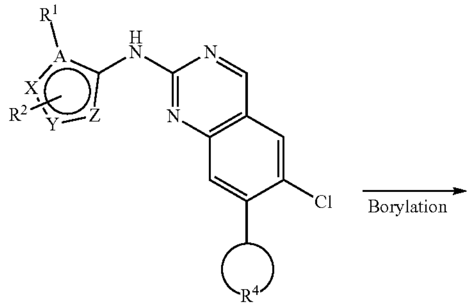

Gen-12/Gen-14/Gen-18/Gen-21

A = C,N
X = C,N
Y = C,N
Z = C,S
$R^1$ = Cl, H, alkyl
$R^2$ = alkyl
$R^4$ = alkyl, —NR

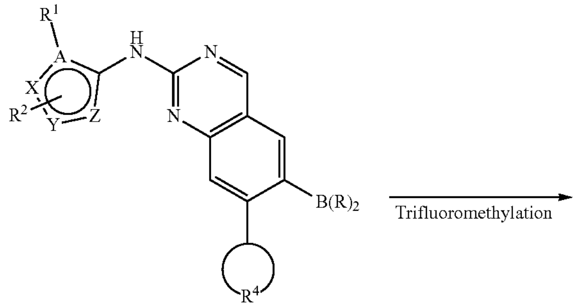

Gen-29

-continued

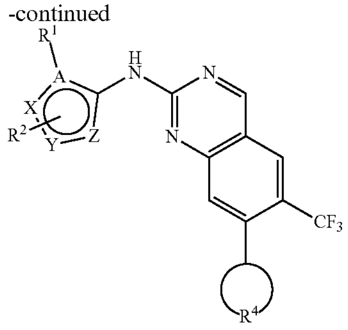

Gen-30

In General Scheme 10, previously described intermediates of the form Gen-12/Gen-14/Gen-18/Gen-21 were subjected to standard palladium catalyzed borylation conditions to afford intermediates of the form Gen-29. Compounds of the form Gen-29 could in turn be subjected to copper catalyzed trifluoromethylation to afford the corresponding trifluoromethyl-substituted compounds Gen-30. The representative compounds are described in more detail below.

Preparation of Example 9.1

Scheme 69. Synthesis of (3S,4S) or (3R,4R) 4-(4-(2-((1-cyclopropyl-5-methyl-1H-pyrazol-4-yl)amino)-6-(trifluoromethyl)quinazolin-7-yl)piperidin-1-yl)-4-methyltetrahydrofuran-3-ol

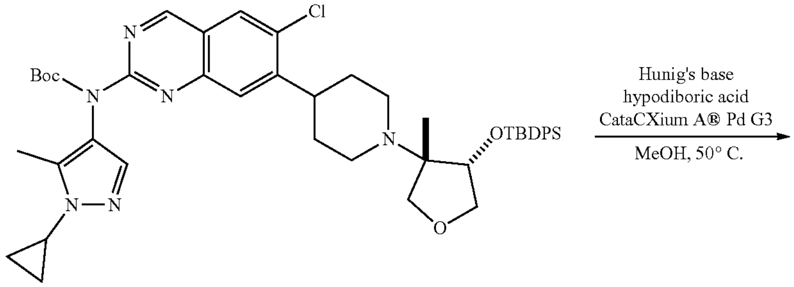

189

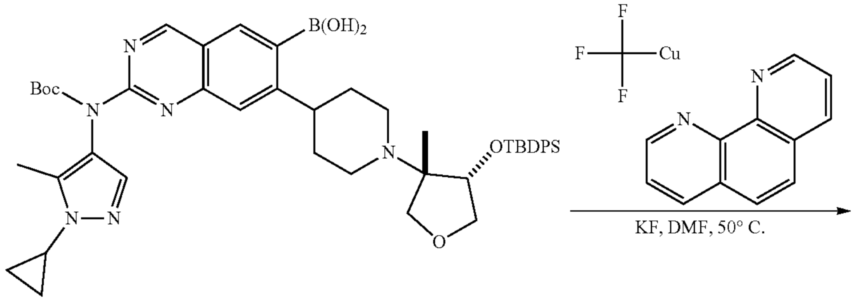

188

-continued

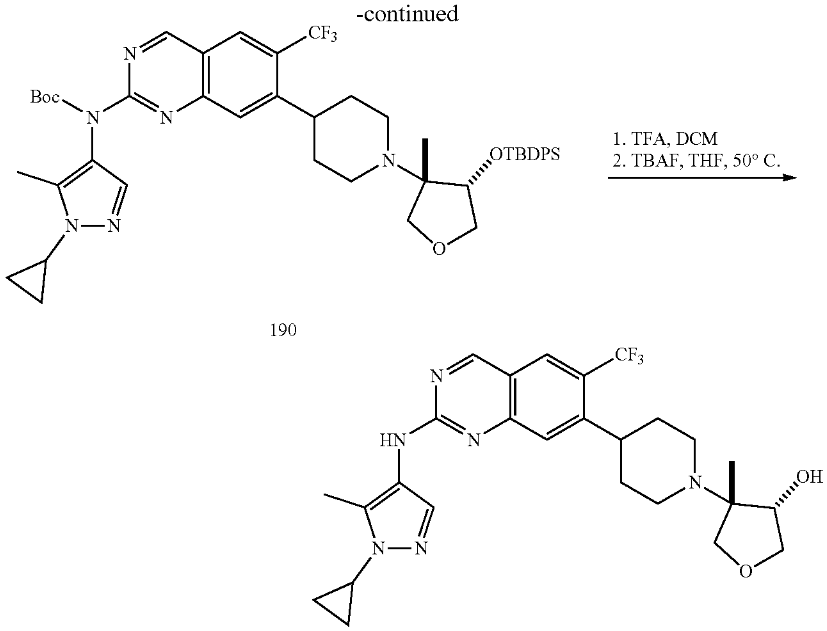

190

Ex-9.1

(3S,4S) or (3R,4R) (2-((tert-butoxycarbonyl)(1-cyclopropyl-5-methyl-1H-pyrazol-4-yl)amino)-7-(1-(4-((tert-butyldiphenylsilyl)oxy)-3-methyltetrahydrofuran-3-yl)piperidin-4-yl)quinazolin-6-yl)boronic acid (188)

Starting 189 was prepared from intermediates 10 and 30 by the same methods used for the synthesis of 147 and 151. A 30 mL scintillation vial was charged with intermediate 189 (290 mg, 0.353 mmol), hypodiboric acid (95 mg, 1.059 mmol), and CataCXium A® Pd G3 (23.60 mg, 0.035 mmol) under inert atmosphere. MeOH (6 mL), then DIPEA (185 μL, 1.059 mmol) were added, and the resultant mixture was warmed to 50° C. and stirred for 1 hr. The mixture was then filtered, and solvent was removed from the collected filtrate under reduced pressure. The resultant crude residue was subjected to purification by reversed phase HPLC, eluting with water (0.1% TFA)-MeCN to afford the title compound 188. MS (ESI): m/z calc'd for $C_{46}H_{60}BN_6O_6Si$ $[M+H]^+$: 831, found 831.

(3S,4S) or (3R,4R) tert-butyl (7-(1-(4-((tert-butyldiphenylsilyl)oxy)-3-methyltetrahydrofuran-3-yl)piperidin-4-yl)-6-(trifluoromethyl)quinazolin-2-yl)(1-cyclopropyl-5-methyl-1H-pyrazol-4-yl)carbamate (190)

A 4-dram vial was charged with intermediate 188 (35 mg, 0.042 mmol), Trifluoromethylator® ((1,10-Phenanthroline)(trifluoromethyl)copper(I), 30 mg, 0.097 mmol), and potassium fluoride (61.2 mg, 1.05 mmol) under inert atmosphere. DMF (1.0 mL) was added, and the resultant mixture was warmed to 50° C. and stirred for 1 hr at this temperature. The mixture was then poured into water (10 mL) and extracted with EtOAc (4×5.0 mL). The combined organic layers were dried over anhydrous $Na_2SO_4$, filtered, and solvent was removed from the collected filtrate under reduced pressure to afford the crude title compound 190, which was used for next step without further purification. MS (ESI): m/z calc'd for $C_{47}H_{58}F_3N_6O_4Si$ $[M+H]^+$: 855, found 855.

(3S,4S) or (3R,4R) 4-(4-(2-((1-cyclopropyl-5-methyl-1H-pyrazol-4-yl)amino)-6-(trifluoromethyl)quinazolin-7-yl)piperidin-1-yl)-4-methyltetrahydrofuran-3-ol (Ex-9.1)

A 4-dram vial was charged with intermediate 190 (25 mg, 0.029 mmol) under inert atmosphere. DCM (2 mL) was added, and to the stirring solution at RT was added TFA (23 μL, 0.29 mmol). The reaction mixture was stirred for 1 hr at RT. The mixture was quenched by carefully pouring into sat. aq. $NaHCO_3$ (30 mL), and extracted with EtOAc (3×10 mL). The combined organic layers were dried over anhydrous $Na_2SO_4$, filtered, and solvent was removed from the collected filtrate under reduced pressure to afford the corresponding crude des-Boc intermediate (not shown), which was used for next step without further purification. MS (ESI): m/z calc'd for $C_{42}H_{50}F_3N_6O_2Si$ $[M+H]^+$: 755, found 755. A 4-dram vial was charged with said crude des-Boc intermediate (20 mg, 0.026 mmol). THF (1 mL) was added, and to the stirring mixture at RT was added TBAF (1 M in THF, 53 μL, 0.053 mmol). The mixture was warmed to 50° C. and stirred at this temperature for 1 hr. The mixture was then filtered, and solvent was removed from the collected filtrate under reduced pressure. The resultant crude residue was subjected to purification by reversed phase HPLC, eluting with water (0.1% TFA)-MeCN to afford the title compound Ex-9.1. MS (ESI): m/z calc'd for $C_{26}H_{32}F_3N_6O_2$ $[M+H]^+$: 517, found 517. $^1H$ NMR (400 MHz, $CDCl_3$, 25° C.) δ: 9.12 (s, 1H), 8.08 (s, 1H), 7.85 (s, 1H), 7.66 (s, 1H), 4.39 (dd, J=10.6, 6.3 Hz, 1H), 4.22 (d, J=8.8 Hz, 1H), 4.13 (s, 1H), 3.98 (m, 1H), 3.71 (d, J=8.8 Hz, 1H), 3.38 (s, 1H), 3.26-3.12 (m, 3H), 3.05-2.97 (m, 1H), 2.89 (s, 1H), 2.49 (m, 2H), 2.38 (s, 2H), 2.09 (m, 2H), 1.62 (s, 1H), 1.46 (s, 3H), 1.20 (s, 2H), 1.09 (m, 2H).

General Scheme 11.

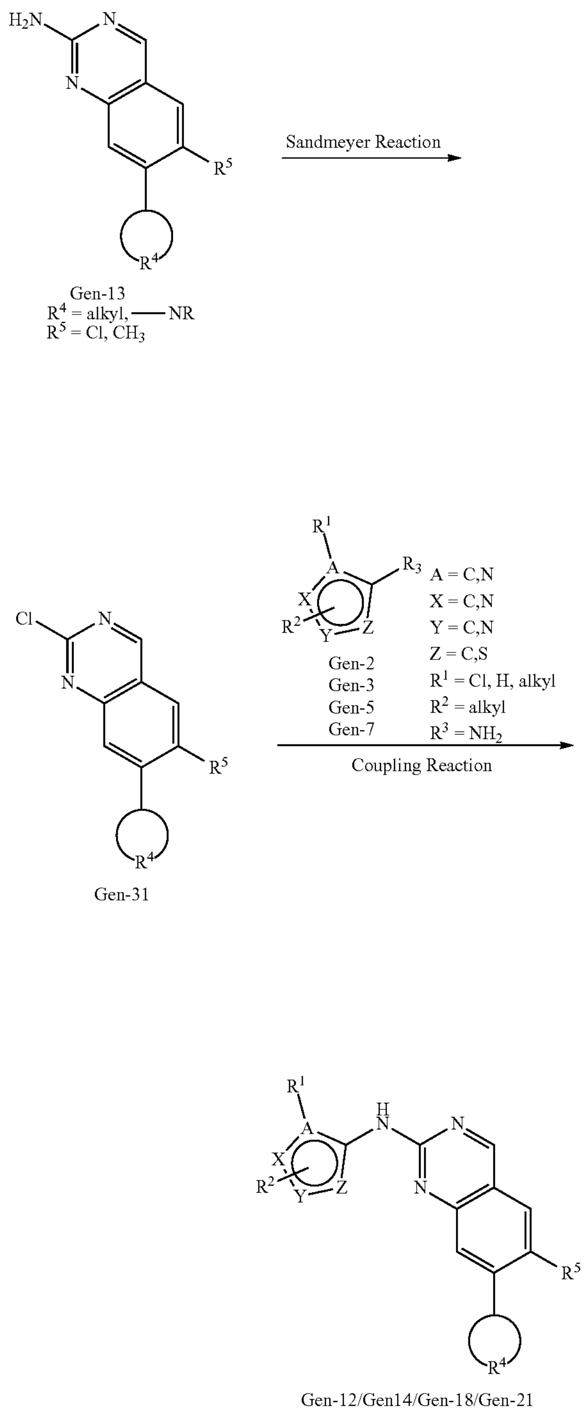

Gen-13

$R^4$ = alkyl, —NR $R^5$ = Cl, $CH_3$

Gen-31

Gen-2

Gen-3

Gen-5

Gen-7

Gen-12/Gen14/Gen-18/Gen-21

In General Scheme 11, aniline intermediates of type Gen-13, prepared as previously described (cf. General Scheme 3), could be converted to the corresponding aryl chlorides Gen-31 using Sandmeyer reaction conditions. Subjecting compounds Gen-31 to standard palladium-catalyzed amine arylation methodology afforded elaborated compounds of the form Gen-12/Gen-14/Gen-18/Gen-21. The representative compounds are described in more detail below.

Preparation of Example 10.1

Scheme 70. Synthesis of (3S,4S) or (3R,4R) 4-(4-(6-chloro-2-((3-chloro-1-methyl-1H-pyrazol-5-yl)amino)quinazolin-7-yl) piperidin-1-yl)-4-methyltetrahydrofuran-3-ol

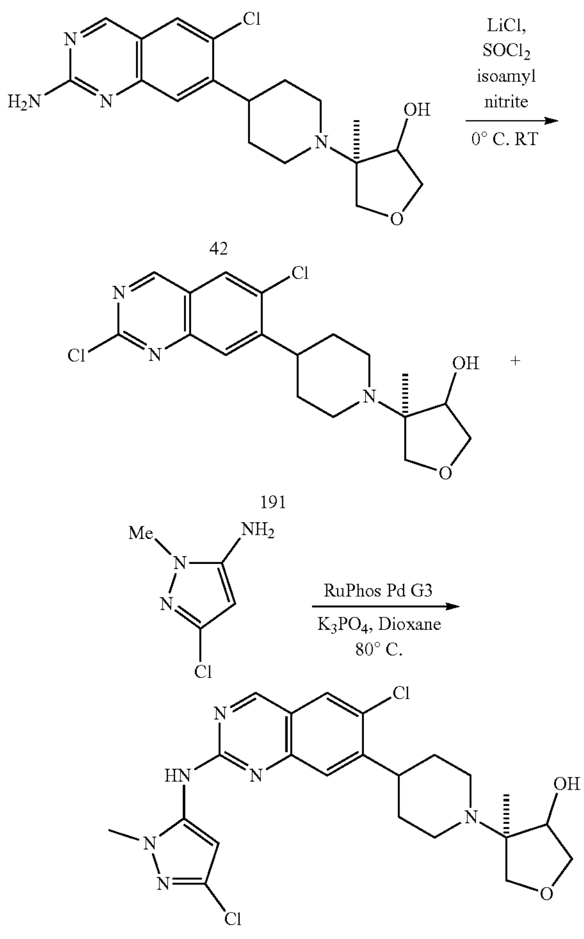

42

191

Ex-10.1

(3S,4S) or (3R,4R) 4-(4-(2,6-dichloroquinazolin-7-yl)piperidin-1-yl)-4-methyltetrahydrofuran-3-ol (191)

A 30 mL scintillation vial was charged with lithium chloride (58.4 mg, 1.38 mmol) and DMA (7 mL) under inert atmosphere. The vial was heated to 70° C. and stirred for 15 min after which intermediate 42 (500 mg, 1.38 mmol) was added. The vial was cooled to 0° C. and isoamyl nitrite (278 μL, 2.067 mmol) and thionyl chloride (111 μL, 1.52 mmol) were added. The reaction was allowed to slowly warm to RT with stirring under inert atmosphere overnight. At 16 hrs, the reaction was diluted with DCM (25 mL) and quenched by dropwise addition of saturated sodium bicarbonate (25 mL). The phases were separated, and the aqueous phase extracted with DCM (3×50 mL). The combined organic phases were washed with $H_2O$(50 mL), dried over $Na_2SO_4$, and the solvent removed under reduced pressure. The resultant crude residue was subjected to purification by silica gel chromatography (3:1 EtOAc/EtOH in Hexanes, 0-100%) to afford the title compound 191. MS (ESI) m/z calc'd for $C_{18}H_{22}Cl_2N_3O_2$ $[M+H]^+$: 383, found 383.

(3S,4S) or (3R,4R) 4-(4-(6-chloro-2-((3-chloro-1-methyl-1H-pyrazol-5-yl)amino)quinazolin-7-yl)piperidin-1-yl)-4-methyltetrahydrofuran-3-ol (Ex-10.1)

A 2 mL vial was charged with 3-chloro-1-methyl-1H-pyrazol-5-amine (26 mg, 0.21 mmol), intermediate 191 (31 mg, 0.08 mmol), $K_3PO_4$ (83 mg, 0.39 mmol), and RuPhos Pd G3 (21 mg, 0.025 mmol) under inert atmosphere. To the mixture at RT was added dioxane (400 μL). The resultant mixture was stirred at 80° C. overnight. At 16 hrs, the reaction mixture was diluted in DCM, filtered, and concentrated. The resultant crude residue was subjected to purification by silica gel chromatography (3:1 EtOAc/EtOH in Hexanes, 0-50%) to afford the title compound Ex-10.1. MS (ESI) m/z calc'd for $C22H_{27}Cl_2N_6O_2$ $[M+H]^+$: 478, found 478. $^1$H NMR (400 MHz, DMSO-$d_6$, 25° C.) δ: 10.03 (s, 1H), 9.30 (s, 1H), 8.11 (s, 1H), 7.70 (s, 1H), 6.61 (s, 1H), 5.47 (s, 1H), 4.39 (m, 1H), 3.95 (dd, J=9.5, 3.2 Hz, 1H), 3.79 (d, J=2.9 Hz, 1H), 3.72 (s, 4H), 3.62 (d, J=7.3 Hz, 1H), 3.54 (d, J=7.3 Hz, 1H), 3.45 (s, 1H), 3.03 (s, 1H), 2.85 (d, J=11.1 Hz, 1H), 2.42 (t, J=11.0 Hz, 1H), 1.88 (m, 4H), 1.04 (s, 3H).

The compounds of the invention, surprisingly and advantageously, exhibit good potency as inhibitors of LRRK2 kinase. The pIC50 values reported herein were measured as follows.

Biological Assay: LRRK2 Km ATP LanthaScreen™ Assay

Compound potency against LRRK2 kinase activity was determined using LanthaScreen™ technology from Life Technologies Corporation (Carlsbad, CA) using a GST20 tagged truncated human mutant G2019S LRRK2 in the presence of the fluorescein-labeled peptide substrate LRRKtide® (LRRK2 phosphorylated ezrin/radixin/moesin (ERM)), also from Life Technologies. The data presented for the $K_m$ ATP LanthaScreen™ Assay represents mean $IC_{50}$ values based on several test results and may have reasonable deviations depending on the specific conditions and reagents used. $K_m$ is the Michaelis constant of an enzyme and is defined as the concentration of native substrate (ATP for a kinase) which permits the enzyme to achieve half $V_{max}$ ($V_{max}$=rate of reaction when the enzyme is saturated with substrate). $IC_{50}$ (half-maximal inhibitory concentration) represents the concentration of inhibitor required to inhibit LRRK2 kinase activity by 50%. Assays were performed in the presence of 134 μM ATP ($K_m$ ATP). Upon completion, the assay was stopped, and phosphorylated substrate detected with a terbium (Tb)-labeled anti-pERM antibody (cat. no. PV4898). The compound dose response was prepared by diluting a 10 mM stock of compound to a maximum concentration of 9.99 μM in 100% DMSO, followed by custom fold serial dilution in DMSO nine times. 20 nL of each dilution was spotted via a Labcyte Echo onto a 384-well black-sided plate (Corning 3575) followed by 15 μl of a 1.25 nM enzyme solution in 1× assay buffer (50 mM Tris pH 8.5, 10 mM $MgCl_2$, 0.01% Brij-35, 1 mM EGTA, 2 mM dithiothreitol, 0.05 mM sodium orthovanadate). Following a 15-minute incubation period at RT, the kinase reaction was started with the addition of 5 μl of 400 nM fluorescein-labeled LRRKtide® (LRRK2 phosphorylated ezrin/radixin/moesin (ERM)) peptide substrate and 134 μM ATP solution in 1× assay buffer. The reaction was allowed to progress at ambient temperature for 90 minutes. The reaction was then stopped by the addition of 20 μl of TR-FRET Dilution Buffer (Life Technologies, Carlsbad, CA) containing 2 nM Tb-labeled anti-phospho LRRKtide® (LRRK2 phosphorylated ezrin/radixin/moesin (ERM)) antibody and 10 mM EDTA (Life Technologies, Carlsbad, CA). After an incubation period of 1 h at RT, the plate was read on an EnVision® multimode plate reader (Perkin Elmer, Waltham, MA) with an excitation wavelength of 337 nm (Laser) and a reading emission at both 520 and 495 nm. Compound $IC_{50}$ values were interpolated from nonlinear regression best-fits of the log of the final compound concentration, plotted as a function of the 520/495-nm emission ratio using activity base "Abase"). Abase uses a 4 parameter (4P) logistic fit based on the Levenberg-Marquardt algorithm. The $pIC_{50}$ values set forth in Table 9 below were derived from the $IC_{50}$ values (in molar concentration) and represent the negative logarithm of these values. "Ex" column in Table 7 corresponds to the example number of the compounds in the examples and tables above.

TABLE 9

| Ex | LRRK2 $pIC_{50}$ |
|---|---|
| Ex-1.1 | 7.93 |
| Ex-1.2 | 6.73 |
| Ex-1.3 | 7.05 |
| Ex-1.4 | 7.62 |
| Ex-1.5 | >9.20 |
| Ex-1.6 | >9.20 |
| Ex-1.7 | >9.20 |
| Ex-1.8 | 8.81 |
| Ex-1.9 | 7.52 |
| Ex-1.10 | 7.55 |
| Ex-1.11 | >9.20 |
| Ex-1.12 | 9.13 |
| Ex-1.13 | 9.11 |
| Ex-1.14 | >9.20 |
| Ex-1.15 | 8.16 |
| Ex-1.16 | >9.20 |
| Ex-1.17 | 8.58 |
| Ex-1.18 | 8.59 |
| Ex-1.19 | 7.59 |
| Ex-1.20 | 8.84 |
| Ex-1.21 | 8.73 |
| Ex-1.22 | 8.10 |
| Ex-1.23 | 9.00 |
| Ex-1.24 | 8.58 |
| Ex-1.25 | 8.99 |
| Ex-1.26 | >9.20 |
| Ex-1.27 | >9.20 |
| Ex-1.28 | 9.12 |
| Ex-2.1 | 8.79 |
| Ex-2.2 | >9.20 |
| Ex-2.3 | >9.20 |
| Ex-2.4 | >9.20 |
| Ex-2.5 | 8.66 |
| Ex-2.6 | >9.20 |
| Ex-2.7 | 9.09 |
| Ex-2.8 | 8.90 |
| Ex-2.9 | 7.44 |
| Ex-2.10 | >9.20 |
| Ex-2.11 | 9.10 |
| Ex-2.12 | >9.20 |
| Ex-2.13 | 9.15 |
| Ex-2.14 | 9.17 |
| Ex-2.15 | >9.20 |
| Ex-2.16 | 8.94 |
| Ex-2.17 | >9.20 |
| Ex-2.18 | >9.20 |
| Ex-2.19 | >9.20 |
| Ex-2.20 | >9.20 |
| Ex-2.21 | 9.17 |
| Ex-2.22 | >9.20 |
| Ex-2.23 | 8.94 |
| Ex-2.24 | 9.13 |
| Ex-2.25 | 9.05 |
| Ex-2.26 | >9.20 |
| Ex-2.27 | 8.87 |
| Ex-2.28 | >9.20 |
| Ex-2.29 | 8.78 |

TABLE 9-continued

| Ex | LRRK2 $pIC_{50}$ |
|---|---|
| Ex-2.30 | 9.19 |
| Ex-2.31 | >9.20 |
| Ex-2.32 | >9.20 |
| Ex-2.33 | >9.20 |
| Ex-2.34 | >9.20 |
| Ex-2.35 | 8.41 |
| Ex-2.36 | >9.20 |
| Ex-2.37 | 7.78 |
| Ex-2.38 | >9.20 |
| Ex-2.39 | 8.09 |
| Ex-2.40 | >9.20 |
| Ex-2.41 | 7.93 |
| Ex-2.42 | >9.20 |
| Ex-2.43 | >9.20 |
| Ex-2.44 | >9.20 |
| Ex-2.45 | 7.74 |
| Ex-2.46 | 8.22 |
| Ex-2.47 | 9.11 |
| Ex-2.48 | 8.77 |
| Ex-2.49 | 8.88 |
| Ex-2.50 | 9.13 |
| Ex-2.51 | >9.20 |
| Ex-2.52 | >9.20 |
| Ex-2.53 | 8.44 |
| Ex-2.54 | 8.48 |
| Ex-2.55 | >9.20 |
| Ex-2.56 | 8.75 |
| Ex-2.57 | >9.20 |
| Ex-2.58 | 9.17 |
| Ex-2.59 | >9.20 |
| Ex-2.60 | >9.20 |
| Ex-2.61 | 8.66 |
| Ex-2.62 | 7.88 |
| Ex-2.63 | 8.92 |
| Ex-2.64 | 9.02 |
| Ex-2.65 | 7.84 |
| Ex-2.66 | >9.20 |
| Ex-2.67 | >9.20 |
| Ex-2.68 | >9.20 |
| Ex-2.69 | 8.21 |
| Ex-2.70 | >9.20 |
| Ex-2.71 | 9.00 |
| Ex-2.72 | 8.90 |
| Ex-2.73 | 9.02 |
| Ex-2.74 | >9.20 |
| Ex-2.75 | 8.63 |
| Ex-2.76 | 7.76 |
| Ex-2.77 | 8.01 |
| Ex-2.78 | >9.20 |
| Ex-2.79 | >9.20 |
| Ex-2.80 | 7.14 |
| Ex-2.81 | 7.35 |
| Ex-2.82 | >9.20 |
| Ex-2.83 | 8.71 |
| Ex-2.84 | 8.80 |
| Ex-2.85 | 9.03 |
| Ex-2.86 | 8.05 |
| Ex-2.87 | 8.04 |
| Ex-2.88 | >9.20 |
| Ex-2.89 | 7.39 |
| Ex-2.90 | >9.20 |
| Ex-2.91 | >9.20 |
| Ex-3.1 | 7.54 |
| Ex-3.2 | 7.07 |
| Ex-4.1 | 9.08 |
| Ex-4.2 | >9.20 |
| Ex-4.3 | >9.20 |
| Ex-4.4 | 8.88 |
| Ex-4.5 | 8.79 |
| Ex-4.6 | >9.20 |
| Ex-4.7 | 7.74 |
| Ex-4.8 | 7.39 |
| Ex-4.9 | >9.20 |
| Ex-4.10 | >9.20 |
| Ex-4.11 | 8.73 |
| Ex-4.12 | >9.20 |
| Ex-4.13 | >9.20 |
| Ex-4.14 | >9.20 |

TABLE 9-continued

| Ex | LRRK2 $pIC_{50}$ |
|---|---|
| Ex-4.15 | >9.20 |
| Ex-4.16 | >9.20 |
| Ex-4.17 | >9.20 |
| Ex-4.18 | 9.16 |
| Ex-4.19 | 9.17 |
| Ex-4.20 | 8.11 |
| Ex-4.21 | >9.20 |
| Ex-4.22 | >9.20 |
| Ex-4.23 | 9.08 |
| Ex-4.24 | >9.20 |
| Ex-4.25 | 8.51 |
| Ex-4.26 | 8.31 |
| Ex-4.27 | >9.20 |
| Ex-4.28 | >9.20 |
| Ex-4.29 | 8.07 |
| Ex-4.30 | 7.32 |
| Ex-4.31 | 8.23 |
| Ex-4.32 | 7.78 |
| Ex-4.33 | 8.09 |
| Ex-4.34 | 9.12 |
| Ex-4.35 | >9.20 |
| Ex-4.36 | 8.29 |
| Ex-4.37 | 9.15 |
| Ex-4.38 | 9.11 |
| Ex-4.39 | >9.20 |
| Ex-4.40 | >9.20 |
| Ex-4.41 | 7.31 |
| Ex-4.42 | 7.21 |
| Ex-4.43 | 9.16 |
| Ex-4.44 | >9.20 |
| Ex-4.45 | >9.20 |
| Ex-4.46 | 9.13 |
| Ex-4.47 | 7.62 |
| Ex-4.48 | 9.05 |
| Ex-4.49 | >9.20 |
| Ex-4.50 | >9.20 |
| Ex-4.51 | >9.20 |
| Ex-4.52 | 9.06 |
| Ex-4.53 | >9.20 |
| Ex-4.54 | >9.20 |
| Ex-4.55 | >9.20 |
| Ex-4.56 | >9.20 |
| Ex-4.57 | >9.20 |
| Ex-4.58 | >9.20 |
| Ex-4.59 | >9.20 |
| Ex-4.60 | 8.69 |
| Ex-4.61 | 8.80 |
| Ex-4.62 | >9.20 |
| Ex-4.63 | 8.83 |
| Ex-4.64 | 8.85 |
| Ex-4.65 | 8.91 |
| Ex-4.66 | 8.70 |
| Ex-4.67 | >9.20 |
| Ex-4.68 | 8.92 |
| Ex-4.69 | 9.13 |
| Ex-4.70 | 7.92 |
| Ex-4.71 | 7.74 |
| Ex-4.72 | 8.92 |
| Ex-4.73 | 9.13 |
| Ex-4.74 | 9.19 |
| Ex-4.75 | 8.14 |
| Ex-4.76 | >9.20 |
| Ex-4.77 | 8.74 |
| Ex-4.78 | 7.95 |
| Ex-4.79 | >9.20 |
| Ex-4.80 | 8.87 |
| Ex-4.81 | 9.13 |
| Ex-4.82 | >9.20 |
| Ex-4.83 | 9.14 |
| Ex-4.84 | 9.01 |
| Ex-4.85 | 8.76 |
| Ex-4.86 | 8.09 |
| Ex-4.87 | 7.90 |
| Ex-4.88 | 8.42 |
| Ex-4.89 | 9.13 |
| Ex-4.90 | >9.20 |
| Ex-4.91 | >9.20 |
| Ex-4.92 | >9.20 |

TABLE 9-continued

| Ex | LRRK2 $pIC_{50}$ |
|---|---|
| Ex-4.93 | 8.70 |
| Ex-4.94 | 8.46 |
| Ex-4.95 | >9.20 |
| Ex-4.96 | 9.09 |
| Ex-4.97 | 8.57 |
| Ex-4.98 | >9.20 |
| Ex-4.99 | 8.01 |
| Ex-4.100 | 8.52 |
| Ex-4.101 | 9.02 |
| Ex-4.102 | >9.20 |
| Ex-4.103 | 8.49 |
| Ex-4.104 | >9.20 |
| Ex-4.105 | 8.51 |
| Ex-4.106 | >9.20 |
| Ex-4.107 | 8.52 |
| Ex-4.108 | 8.49 |
| Ex-4.109 | 7.99 |
| Ex-4.110 | 8.73 |
| Ex-4.111 | 8.55 |
| Ex-4.112 | >9.20 |
| Ex-4.113 | 8.11 |
| Ex-4.114 | 8.00 |
| Ex-4.115 | 9.07 |
| Ex-4.116 | 8.35 |
| Ex-4.117 | >9.20 |
| Ex-4.118 | 8.46 |
| Ex-4.119 | 7.96 |
| Ex-4.120 | 7.65 |
| Ex-4.121 | 8.92 |
| Ex-4.122 | >9.20 |
| Ex-4.123 | 8.37 |
| Ex-4.124 | 8.91 |
| Ex-4.125 | 8.16 |
| Ex-4.126 | 7.64 |
| Ex-4.127 | >9.20 |
| Ex-4.128 | 8.99 |
| Ex-4.129 | >9.20 |
| Ex-4.130 | 8.97 |
| Ex-4.131 | 8.62 |
| Ex-4.132 | >9.20 |
| Ex-4.133 | 8.92 |
| Ex-4.134 | >9.20 |
| Ex-4.135 | >9.20 |
| Ex-4.136 | 8.41 |
| Ex-4.137 | >9.20 |
| Ex-4.138 | 8.44 |
| Ex-4.139 | >9.20 |
| Ex-4.140 | 9.19 |
| Ex-4.141 | >9.20 |
| Ex-4.142 | 8.94 |
| Ex-4.143 | >9.20 |
| Ex-4.144 | 8.68 |
| Ex-4.145 | >9.20 |
| Ex-4.146 | >9.20 |
| Ex-4.147 | >9.20 |
| Ex-4.148 | >9.20 |
| Ex-4.149 | >9.20 |
| Ex-4.150 | >9.20 |
| Ex-4.151 | 8.98 |
| Ex-4.152 | >9.20 |
| Ex-4.153 | >9.20 |
| Ex-4.154 | 9.06 |
| Ex-4.155 | >9.20 |
| Ex-4.156 | >9.20 |
| Ex-4.157 | 8.38 |
| Ex-4.158 | 8.99 |
| Ex-4.159 | >9.20 |
| Ex-4.160 | >9.20 |
| Ex-4.161 | 8.92 |
| Ex-4.162 | >9.20 |
| Ex-4.163 | >9.20 |
| Ex-4.164 | >9.20 |
| Ex-4.165 | 8.67 |
| Ex-4.166 | 9.17 |
| Ex-4.167 | 8.14 |
| Ex-4.168 | 8.88 |
| Ex-4.169 | 8.25 |
| Ex-4.170 | 8.81 |

TABLE 9-continued

| Ex | LRRK2 $pIC_{50}$ |
|---|---|
| Ex-4.171 | 8.51 |
| Ex-4.172 | 7.53 |
| Ex-4.173 | 8.43 |
| Ex-4.174 | >9.20 |
| Ex-4.175 | 9.10 |
| Ex-4.176 | 8.73 |
| Ex-4.177 | 9.16 |
| Ex-4.178 | 8.58 |
| Ex-4.179 | >9.20 |
| Ex-4.180 | >9.20 |
| Ex-4.181 | >9.20 |
| Ex-4.182 | >9.20 |
| Ex-4.183 | >9.20 |
| Ex-4.184 | >9.20 |
| Ex-4.185 | 9.17 |
| Ex-4.186 | 7.95 |
| Ex-4.187 | 8.54 |
| Ex-4.188 | 7.83 |
| Ex-4.189 | >9.20 |
| Ex-4.190 | 8.73 |
| Ex-4.191 | >9.20 |
| Ex-4.192 | 8.76 |
| Ex-4.193 | 9.04 |
| Ex-4.194 | 8.28 |
| Ex-4.195 | 8.24 |
| Ex-4.196 | 8.87 |
| Ex-4.197 | 8.76 |
| Ex-4.198 | 7.88 |
| Ex-4.199 | 7.96 |
| Ex-4.200 | 8.76 |
| Ex-4.201 | 8.19 |
| Ex-4.202 | 8.47 |
| Ex-4.203 | 8.03 |
| Ex-4.204 | 7.67 |
| Ex-4.205 | 8.40 |
| Ex-4.206 | 7.90 |
| Ex-4.207 | 8.31 |
| Ex-4.208 | 7.96 |
| Ex-4.209 | 8.16 |
| Ex-4.210 | 8.55 |
| Ex-4.211 | 9.15 |
| Ex-4.212 | 8.75 |
| Ex-4.213 | 8.50 |
| Ex-4.214 | 8.62 |
| Ex-4.215 | 8.57 |
| Ex-4.216 | 9.05 |
| Ex-4.217 | 8.57 |
| Ex-4.218 | 7.86 |
| Ex-4.219 | 8.33 |
| Ex-4.220 | 8.21 |
| Ex-4.221 | >9.20 |
| Ex-4.222 | >9.20 |
| Ex-4.223 | 8.61 |
| Ex-4.224 | 7.86 |
| Ex-4.225 | 7.67 |
| Ex-4.226 | 8.43 |
| Ex-4.227 | >9.20 |
| Ex-4.228 | 8.81 |
| Ex-4.229 | 8.95 |
| Ex-4.230 | 9.13 |
| Ex-4.231 | >9.20 |
| Ex-4.232 | >9.20 |
| Ex-4.233 | >9.20 |
| Ex-4.234 | 7.23 |
| Ex-4.235 | 8.84 |
| Ex-4.236 | 6.61 |
| Ex-4.237 | >9.20 |
| Ex-4.238 | 7.40 |
| Ex-4.239 | >9.20 |
| Ex-4.240 | 7.57 |
| Ex-4.241 | >9.20 |
| Ex-4.242 | 7.67 |
| Ex-4.243 | >9.20 |
| Ex-4.244 | >9.20 |
| Ex-4.245 | >9.20 |
| Ex-4.246 | 8.22 |
| Ex-4.247 | >9.20 |
| Ex-4.248 | >9.20 |

TABLE 9-continued

| Ex | LRRK2 $pIC_{50}$ |
|---|---|
| Ex-4.249 | >9.20 |
| Ex-4.250 | 8.22 |
| Ex-4.251 | 9.05 |
| Ex-4.252 | 6.61 |
| Ex-4.253 | >9.20 |
| Ex-4.254 | >9.20 |
| Ex-4.255 | >9.20 |
| Ex-4.256 | >9.20 |
| Ex-4.257 | >9.20 |
| Ex-4.258 | 7.39 |
| Ex-4.259 | >9.20 |
| Ex-4.260 | 8.00 |
| Ex-4.261 | 7.51 |
| Ex-4.262 | 9.19 |
| Ex-5.1 | >9.20 |
| Ex-5.2 | >9.20 |
| Ex-5.3 | 8.96 |
| Ex-5.4 | 8.75 |
| Ex-5.5 | 8.37 |
| Ex-5.6 | 8.68 |
| Ex-5.7 | >9.20 |
| Ex-5.8 | >9.20 |
| Ex-5.9 | 8.49 |
| Ex-5.10 | 6.66 |
| Ex-5.11 | 8.57 |
| Ex-5.12 | 6.03 |
| Ex-5.13 | 9.00 |
| Ex-5.14 | 9.02 |
| Ex-5.15 | 8.42 |
| Ex-5.16 | >9.20 |
| Ex-6.1 | 8.72 |
| Ex-6.2 | >9.20 |
| Ex-6.3 | 9.07 |
| Ex-6.4 | 9.18 |
| Ex-6.5 | >9.20 |
| Ex-6.6 | 8.94 |
| Ex-6.7 | 9.01 |
| Ex-7.1 | 9.01 |
| Ex-7.2 | >9.20 |
| Ex-7.3 | 7.93 |
| Ex-7.4 | >9.20 |
| Ex-7.5 | >9.20 |
| Ex-7.6 | >9.20 |
| Ex-7.7 | >9.20 |
| Ex-7.8 | >9.20 |
| Ex-7.9 | 9.04 |
| Ex-7.10 | 9.04 |
| Ex-8.1 | >9.20 |
| Ex-8.2 | 8.83 |
| Ex-8.3 | >9.20 |
| Ex-8.4 | >9.20 |
| Ex-8.5 | >9.20 |
| Ex-8.6 | 8.17 |
| Ex-8.7 | >9.20 |
| Ex-8.8 | >9.20 |
| Ex-8.9 | >9.20 |
| Ex-8.10 | 9.08 |
| Ex-8.11 | 8.91 |
| Ex-8.12 | 8.92 |
| Ex-8.13 | >9.20 |
| Ex-8.14 | >9.20 |
| Ex-8.15 | >9.20 |
| Ex-8.16 | 9.18 |
| Ex-8.17 | >9.20 |
| Ex-8.18 | >9.20 |
| Ex-8.19 | 8.94 |
| Ex-8.20 | 8.53 |
| Ex-8.21 | 8.44 |
| Ex-8.22 | 8.68 |
| Ex-8.23 | 8.12 |
| Ex-8.24 | 8.92 |
| Ex-8.25 | >9.20 |
| Ex-8.26 | 8.78 |
| Ex-8.27 | 9.07 |
| Ex-8.28 | 9.04 |
| Ex-8.29 | 8.88 |
| Ex-8.30 | 8.96 |
| Ex-8.31 | >9.20 |
| Ex-8.32 | 9.05 |
| Ex-8.33 | >9.20 |
| Ex-8.34 | >9.20 |
| Ex-8.35 | 8.68 |
| Ex-8.36 | 8.38 |
| Ex-8.37 | >9.20 |
| Ex-8.38 | >9.20 |
| Ex-8.39 | 8.98 |
| Ex-8.40 | >9.20 |
| Ex-9.1 | 9.19 |
| Ex-10.1 | 9.11 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

We claim:

1. A compound represented by structural Formula I:

(I)

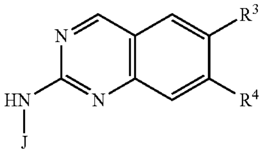

or a pharmaceutically acceptable salt thereof, wherein:

J is selected from:

a

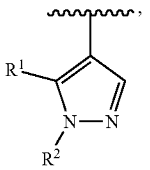

b

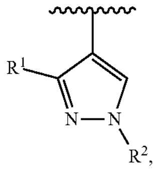

-continued c

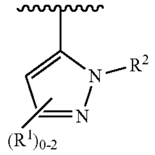

and d

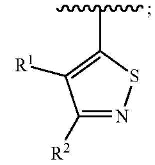

$R^1$ is independently selected from H, —$(C_1$-$C_6)$alkyl, —$(C_1$-$C_6)$haloalkyl, halogen, CN, and cyclopropyl;

$R^2$ is independently selected from —$(C_1$-$C_6)$alkyl, —$(C_1$-$C_6)$haloalkyl, —$((C_1$-$C_6)$alkyl$))_n(C_3$-$C_8)$cycloalkyl, bicyclopentanyl, spiroheptanyl, azaspiroheptanyl, $(CH_2)_n$oxetanyl, $(CH_2)_n$oxolanyl, thiazolyl, and piperidinyl, said alkyl, haloalkyl, cycloalkyl, and bicyclopentanyl optionally substituted with 1, 2, or 3 groups independently selected from halogen, OH, CN, —$(C_1$-$C_6)$alkyl, —$(C_1$-$C_6)$alkylOH, O-$(C_1$-$C_6)$alkyl, —$(C_1$-$C_6)$alkyl-O-$(C_1$-$C_6)$alkyl, and -O-$(C_1$-$C_6)$haloalkyl, and said spiroheptanyl, azaspiroheptanyl, oxetanyl, oxolanyl, thiazolyl, and piperidinyl optionally substituted with 1 to 2 groups independently selected from halogen, OH, CN, —$(C_1$-$C_6)$alkyl, —$(CH_2)_nO(C_1$-$C_6)$ alkyl, —$(C_1$-$C_6)$haloalkyl, oxolanyl, and oxetanyl, said oxolanyl and oxetanyl optionally substituted with 1 to 2 groups of $CH_3$;

$R^3$ is selected from $CH_3$, $CF_3$, $OCH_3$, Cl, CN, and cyclopropyl; and $R^4$ is selected from $(C_3$-$C_6)$cycloalkyl, piperidinyl, pyrrolidinyl, spiropentanyl, spirohexanyl, azaspiroheptanyl, azabicycloheptanyl, azabicylcooctanyl, and oxaazabicyclononanyl, said cycloalkyl, piperidinyl, pyrrolidinyl, spiropentanyl, spirohexanyl, azaspiroheptanyl, azabicycloheptanyl, azabicylcooctanyl, and oxaazabicyclononanyl optionally substituted with 1 to 3 groups of $R^b$, $R^b$ is selected from hydrogen, $(C_1$-$C_6)$alkyl, OH, $(CH_2)_n(C_3$-$C_6)$cycloalkyl, halogen, $(C_1$-$C_6)$haloalkyl, C(O)$(C_1$-$C_6)$alkyl, $(CH_2)_n$oxetanyl, $(CH_2)_n$oxolanyl, $(CH_2)_n$ oxanyl, tetrahydrothiophenedionyl, thietanedionyl, oxaspirooctanyl, and bicyclohexanyl, said alkyl, cycloalkyl, oxetanyl, oxolanyl, tetrahydrothiophenedionyl, thietanedionyl, oxaspirooctanyl, and bicyclohexanyl optionally substituted with 1 to 3 groups of $R^{b1}$;

$R^{b1}$ is selected from $(C_1$-$C_6)$alkyl, O$(C_1$-$C_6)$alkyl, $(C_3$-$C_6)$cycloalkyl, OH, halogen, CN, $CF_3$, phenyl, oxazolidinonyl, pyrrolidinonyl, and morpholinyl, said phenyl and alkyl optionally substituted with 1 to 2 groups of halogen and CN; and n is 0, 1, 2, 3, or 4.

2. A compound, or a pharmaceutically acceptable salt thereof represented by structural Formula I':

I'

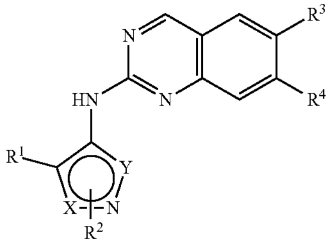

wherein X is N and Y is C, or X is C and Y is S, such that the moiety

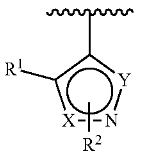

is selected from

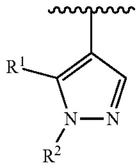

,

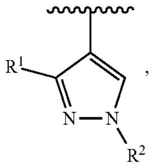

,

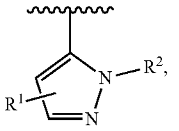

, and

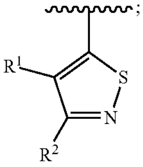

;

$R^1$ S $R^1$ is selected from H, Cl, and $CH_3$;

$R^2$ is selected from —$(C_1$-$C_6)$alkyl, —$(C_1$-$C_6)$haloalkyl, —$(C_1$-$C_6)$alkyl-OH, -$(C_1$-$C_6)$ haloalkyl-OH, —$(C_1$-$C_6)$alkyl-CN, —$(C_1$-$C_6)$alkyl-O-$(C_1$-$C_6)$alkyl, —$(C_1$-$C_6)$alkyl-O-$(C_1$-$C_6)$ haloalkyl, —$(C_3$-$C_6)$cycloalkyl, —$(C_3$-$C_6)$cycloalkyl which is substituted with 1, 2, or 3 groups independently selected from halogen, OH, CN, —$(C_1$-$C_6)$alkyl, and -O-$(C_1$-$C_6)$alkyl, —$(C_1$-$C_3)$alkyl $(C_3$-$C_6)$cycloalkyl, —$(C_1$-$C_3)$alkyl $(C_3$-$C_6)$cycloalkyl which is substituted with 1, 2, or 3 groups independently selected from halogen, OH, CN, and —$(C_1$-$C_6)$alkyl, bicycloalkyl;

bicycloalkyl which is substituted with 1 or 2 groups independently selected from halogen, C(O)$(C_1$-$C_6)$alkyl, C(O) O$(C_1$-$C_6)$alkyl, $(C_1$-$C_6)$alkyl-OH, $(C_1$-$C_6)$ alkyl-CN, C(O) NH $(C_1$-$C_6)$alkyl, C(O) N $((C_1$-$C_6)$ alkyl) 2, C(O) N $((C_1$-$C_6)$alkyl)-O-$((C_1$-$C_6)$alkyl), $(C_1$-$C_6)$haloalkyl, $(C_1$-$C_6)$alkyl-O-$(C_1$-$C_6)$alkyl, $(C_1$-$C_6)$ haloalkyl-O-$(C_1$-$C_6)$alkyl, $(C_1$-$C_6)$alkyl-O-$(C_1$-$C_6)$ haloalkyl, $(C_1$-$C_6)$haloalkyl-O-$(C_1$-$C_6)$haloalkyl, cyclopropyl, and cyclobutyl;

oxetanyl, oxetanyl which is substituted with 1, 2, or 3 groups independently selected from halogen, OH, CN, and —$(C_1$-$C_6)$alkyl, tetrahydrofuranyl, tetrahydrofuranyl which is substituted with 1, 2, or 3 groups independently selected from halogen, OH, CN, and —$(C_1\text{-}C_6)$alkyl, —$(C_1\text{-}C_3)$alkyl-oxetanyl, —$(C_1\text{-}C_3)$alkyl-oxetanyl which is substituted with 1, 2, or 3 groups independently selected from halogen, OH, CN, and —$(C_1\text{-}C_6)$alkyl, —$(C_1\text{-}C_3)$alkyl-tetrahydrofuranyl, —$(C_1\text{-}C_3)$alkyl-tetrahydrofuranyl which is substituted with 1, 2, or 3 groups independently selected from halogen, OH, CN, and —$(C_1\text{-}C_6)$alkyl,

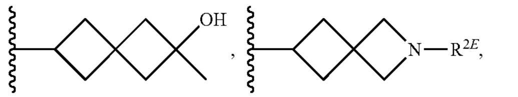

wherein $R^{2E}$ is selected from H, —$(C_1\text{-}C_6)$alkyl, —$(C_1\text{-}C_6)$ haloalkyl,

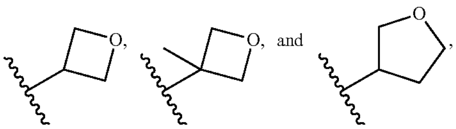

and

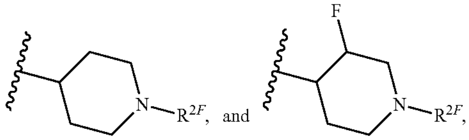

wherein:

$R^{2F}$ is selected from H, —$(C_1\text{-}C_6)$alkyl, —$(C_1\text{-}C_6)$ fluoroalkyl, —$(C_1\text{-}C_6)$alkyl-O-$(C_1\text{-}C_6)$alkyl,

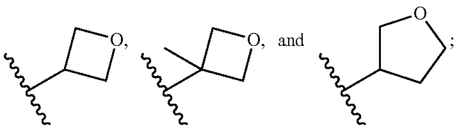

$R^3$ is selected from $CH_3$, $CF_3$, $OCH_3$, Cl, CN, and cyclopropyl; and $R^4$ is selected from $(C_1\text{-}C_6)$alkyl, $(C_3\text{-}C_6)$cycloalkyl, $(C_3\text{-}C_6)$cycloalkyl substituted with 1 or 2 fluorine atoms,

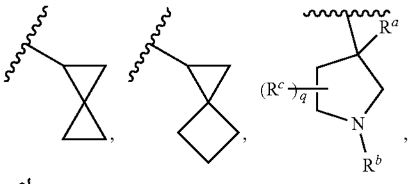

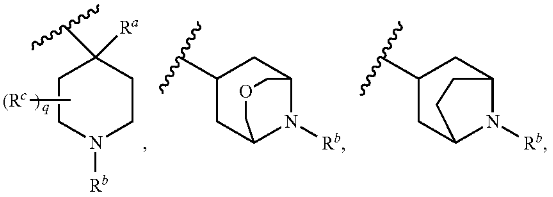

-continued

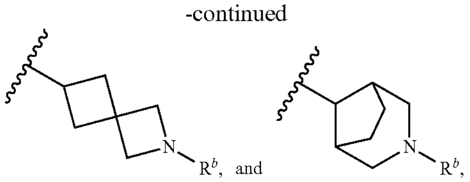

wherein:

q is 1 or 2;

$R^a$ is selected from H, F, and OH;

$R^c$ is selected from H, F, CN, OH, —$(C_1\text{-}C_6)$alkyl, and $O(C_1\text{-}C_4)$alkyl;

$R^b$ is selected from H, —$(C_1\text{-}C_6)$alkyl, —$(C_1\text{-}C_6)$haloalkyl, —$(C_1\text{-}C_6)$alkyl-OH, —$(C_1\text{-}C_6)$alkyl-CN, —$(C_1\text{-}C_6)$haloalkyl-OH, —$(C_1\text{-}C_6)$alkyl-O-$(C_1\text{-}C_6)$alkyl, —$(C_1\text{-}C_6)$alkyl-O-$(C_1\text{-}C_6)$haloalkyl, -$(C_3\text{-}C_6)$cycloalkyl, —$(C_3\text{-}C_6)$cycloalkyl which is substituted with 1, 2, or 3 groups independently selected from halogen, OH, CN, $(C_1\text{-}C_6)$alkyl, and $O(C_1\text{-}C_4)$alkyl, —$(C_1\text{-}C_3)$alkyl $(C_3\text{-}C_6)$cycloalkyl, —$(C_1\text{-}C_3)$alkyl $(C_3\text{-}C_6)$cycloalkyl which is substituted with 1, 2, or 3 groups independently selected from halogen, OH, CN, and —$(C_1\text{-}C_6)$alkyl, oxetanyl, oxetanyl which is substituted with 1, 2, or 3 groups independently selected from halogen, OH, CN, and —$(C_1\text{-}C_6)$alkyl, —$(C_1\text{-}C_3)$alkyl-oxetanyl, —$(C_1\text{-}C_3)$alkyl-oxetanyl which is substituted with 1, 2, or 3 groups independently selected from halogen, OH, CN, and —$(C_1\text{-}C_6)$alkyl, tetrahydrofuranyl, tetrahydrofuranyl which is substituted with 1, 2, or 3 groups independently selected from halogen, OH, CN, and —$(C_1\text{-}C_6)$alkyl, —$(C_1\text{-}C_3)$alkyl-tetrahydrofuranyl, —$(C_1\text{-}C_3)$alkyl-tetrahydrofuranyl which is substituted with 1, 2, or 3 groups independently selected from halogen, OH, CN, and —$(C_1\text{-}C_6)$alkyl,

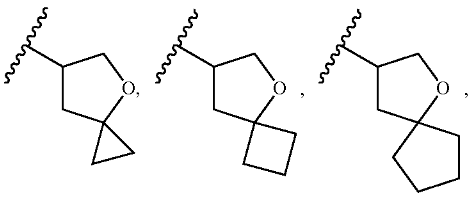 [SMILES: *C1COC2(CC2)C1 ; *C1COC2(CCC2)C1 ; *C1COC2(CCCC2)C1]

thietanyl, thietanyl which is substituted with 1, 2, or 3 groups independently selected from halogen, OH, CN, and —$(C_1\text{-}C_6)$alkyl, —$(C_1\text{-}C_3)$alkyl-thietanyl, —$(C_1\text{-}C_3)$alkyl-thietanyl which is substituted with 1, 2, or 3 groups independently selected from halogen, OH, CN, and —$(C_1\text{-}C_6)$alkyl, thietanyl 1,1-dioxide, thietanyl 1,1-dioxide which is substituted with 1, 2, or 3 groups independently selected from halogen, OH, CN, and —$(C_1\text{-}C_6)$alkyl, —$(C_1\text{-}C_3)$alkyl-thietanyl 1,1-dioxide, $-(C_1-C_3)$alkyl-thietanyl 1,1-dioxide which is substituted with 1, 2, or 3 groups independently selected from halogen, OH, CN, and $-(C_1-C_6)$alkyl, tetrahydrothiophenyl, tetrahydrothiophenyl which is substituted with 1, 2, or 3 groups independently selected from halogen, OH, CN, and $-(C_1-C_6)$alkyl, $-(C_1-C_3)$alkyl-tetrahydrothiophenyl, $-(C_1-C_3)$alkyl-tetrahydrothiophenyl which is substituted with 1, 2, or 3 groups independently selected from halogen, OH, CN, and $-(C_1-C_6)$alkyl, tetrahydrothiophenyl 1,1-dioxide, tetrahydrothiophenyl 1,1-dioxide which is substituted with 1, 2, or 3 groups independently selected from halogen, OH, CN, and $-(C_1-C_6)$alkyl, $-(C_1-C_3)$alkyl-tetrahydrothiophenyl 1,1-dioxide, and $-(C_1-C_3)$alkyl-tetrahydrothiophenyl 1,1-dioxide which is substituted with 1, 2, or 3 groups independently selected from halogen, OH, CN, and $-(C_1-C_6)$alkyl.

3. The compound according to claim 1, or a pharmaceutically acceptable salt thereof, wherein $R^3$ is selected from Cl, $CH_3$, and CN.

4. The compound according to claim 1, or a pharmaceutically acceptable salt thereof, wherein J is selected from:

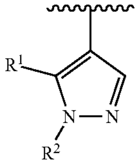
,
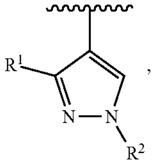
, and
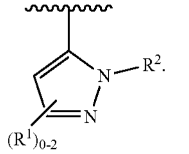

5. The compound according to claim 1, or a pharmaceutically acceptable salt thereof, wherein J is selected from:

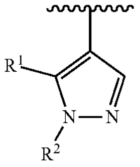
,
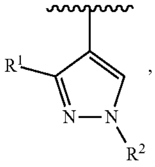
, and
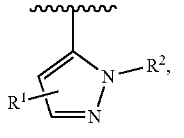

$R^1$ is selected from H, Cl, and $CH_3$; and $R^2$ is independently selected from $-(C_1-C_6)$alkyl, $-(C_1-C_6)$ haloalkyl, $-(C_1-C_6)$alkyl-O-$(C_1-C_6)$alkyl, $(CH_2)_n$cyclopropyl, $(CH_2)_n$cyclobutyl, bicyclopentanyl, spiroheptanyl, azaspiroheptanyl, $(CH_2)_n$oxetanyl, $(CH_2)_n$oxolanyl, thiazolyl, and piperidinyl, said alkyl, haloalkyl, cycloalkyl, and bicyclopentanyl optionally substituted with 1, 2, or 3 groups independently selected from halogen, OH, CN, $-(C_1-C_6)$alkyl, $-(C_1-C_6)$alkylOH, O-$(C_1-C_6)$alkyl, $-(C_1-C_6)$alkyl-O-$(C_1-C_6)$alkyl, and -O-$(C_1-C_6)$haloalkyl, said spiroheptanyl, azaspiroheptanyl, oxetanyl, oxolanyl, thiazolyl, and piperidinyl optionally substituted with 1 or 2 groups independently selected from halogen, OH, CN, $-(C_1-C_6)$alkyl, $-(CH_2)_nO(C_1-C_6)$alkyl, $-(C_1-C_6)$haloalkyl, oxolanyl, and oxetanyl, said oxolanyl and oxetanyl optionally substituted with 1 to 2 groups of $CH_3$.

6. The compound of claim 1, or a pharmaceutically acceptable salt thereof, wherein J is

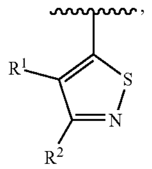

$R^1$ is selected from H, Cl, and $CH_3$; and $R^2$ is independently selected from $-(C_1-C_6)$alkyl, $-(C_1-C_6)$haloalkyl, $-(C_1-C_6)$alkyl-O-$(C_1-C_6)$alkyl, $(CH_2)_n$cyclopropyl, $(CH_2)_n$cyclobutyl, bicyclopentanyl, spiroheptanyl, azaspiroheptanyl, $(CH_2)_n$oxetanyl, $(CH_2)_n$oxolanyl, thiazolyl, and piperidinyl, said alkyl, haloalkyl, cycloalkyl, and bicyclopentanyl optionally substituted with 1, 2, or 3 groups independently selected from halogen, OH, CN, $-(C_1-C_6)$alkyl, $-(C_1-C_6)$alkylOH, O-$(C_1-C_6)$alkyl, $-(C_1-C_6)$alkyl-O-$(C_1-C_6)$alkyl, and -O-$(C_1-C_6)$haloalkyl, said spiroheptanyl, azaspiroheptanyl, oxetanyl, oxolanyl, thiazolyl, and piperidinyl optionally substituted with 1 to 2 groups independently selected from halogen, OH, CN, $-(C_1-C_6)$alkyl, $-(CH_2)_nO(C_1-C_6)$alkyl, $-(C_1-C_6)$haloalkyl, oxolanyl, and oxetanyl, said oxolanyl and oxetanyl optionally substituted with 1 to 2 groups of $CH_3$.

7. The compound according to claim 1, or a pharmaceutically acceptable salt thereof, wherein $R^4$ is selected from cyclopropyl, cyclohexyl, azaspiroheptanyl, spiropentanyl, spirohexanyl, azabicycloheptanyl, azabicyclooctanyl, oxaazabicyclononanyl, pyrrolidinyl, and piperidinyl, said cyclopropyl, cyclohexyl, azaspiroheptanyl, spiropentanyl, spirohexanyl, azabicycloheptanyl, azabicyclooctanyl, oxaazabicyclononanyl, pyrrolidinyl, and piperidinyl optionally substituted with 1 to 3 groups selected from $(C_1-C_6)$alkyl, OH, $(CH_2)_n(C_3-C_6)$cycloalkyl, halogen, $(C_1-C_6)$haloalkyl, $C(O)(C_1-C_6)$alkyl, $(CH_2)_n$oxetanyl, $(CH_2)_n$oxolanyl, $(CH_2)_n$oxanyl, tetrahydrothiophenedionyl, thietanedionyl, oxaspirooctanyl, and bicyclohexanyl, said alkyl, cycloalkyl, oxetanyl, oxolanyl, tetrahydrothiophenedionyl, thietanedionyl, oxaspirooctanyl, and bicyclohexanyl optionally substituted with 1 to 3 groups selected from $CH_3$, OH, $OCH_3$, $CF_3$, Fl, Cl, CN, $CH_2CN$, and cyclopropyl.

8. The compound according to claim 1 wherein $R^4$ is selected from azaspiroheptanyl, spiropentanyl, spirohexanyl, azabicycloheptanyl, azabicyclooctanyl, oxaazabicyclononanyl, pyrrolidinyl, and piperidinyl said azaspiroheptanyl, spiropentanyl, spirohexanyl, azabicycloheptanyl, azabicyclooctanyl, and oxaazabicyclononanyl, pyrrolidinyl, and piperidinyl optionally substituted with 1 to 3 groups selected from $CH_3$, $CH_2C(CH_3)_2OH$, oxetanyl, oxolanyl, and thietanedionyl, said oxetanyl, oxolanyl, and thietanedionyl optionally substituted with 1 to 3 groups selected from $CH_3$, OH, $OCH_3$, $CF_3$, Fl, Cl, CN, $CH_2CN$, and cyclopropyl.

9. The compound according to claim 1 wherein $R^4$ is selected from pyrrolidinyl, and piperidinyl, said pyrrolidinyl, and piperidinyl optionally substituted with 1 to 3 groups selected from $CH_3$, $CH_2C(CH_3)_2OH$, oxetanyl, oxolanyl, and thietanedionyl, said oxetanyl, oxolanyl, and thietanedionyl optionally substituted with 1 to 3 groups selected from $CH_3$, OH, $OCH_3$, $CF_3$, Fl, Cl, CN, $CH_2CN$, and cyclopropyl.

10. The compound according to claim 1 represented by structural Formula II:

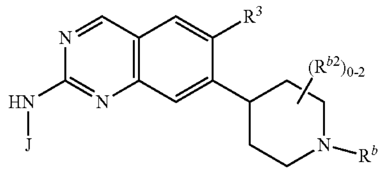

II or a pharmaceutically acceptable salt thereof, wherein J, $R^3$, and $R^b$ are as described and $R^{b2}$ is independently selected from $C_{1-6}$ alkyl and halogen.

11. The compound according to claim 10 wherein $R^{b2}$ is independently selected from $C_{1-6}$ alkyl and halogen, $R^3$ is selected from Cl, $CH_3$, $CF_3$, and CN, and J is selected from:

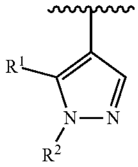
,
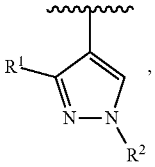
,
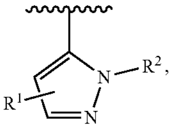
, and
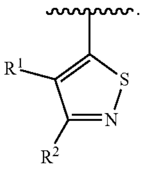
.

12. The compound according to claim 10 wherein $R^1$ is selected from H, $-CH_3$, $-C(CH_3)_3$, $-CHF_2$, $CF_3$, Br, Cl, CN, and cyclopropyl, and $R^2$ is selected from $—(C_1\text{-}C_6)$alkyl, $—(C_1\text{-}C_6)$haloalkyl, $—(C_1\text{-}C_6)$alkyl-O-$(C_1\text{-}C_6)$alkyl, $(CH_2)_n$ cyclopropyl, $(CH_2)_n$cyclobutyl, bicyclopentanyl, spiroheptanyl, azaspiroheptanyl, $(CH_2)_n$oxetanyl, $(CH_2)_n$ oxolanyl, thiazolyl, and piperidinyl, said alkyl, haloalkyl, cycloalkyl, and bicyclopentanyl optionally substituted with 1, 2, or 3 groups independently selected from halogen, OH, CN, $—(C_1\text{-}C_6)$alkyl, $—(C_1\text{-}C_6)$alkylOH, O-$(C_1\text{-}C_6)$alkyl, $—(C_1\text{-}C_6)$alkyl-O-$(C_1\text{-}C_6)$alkyl, and -O-$(C_1\text{-}C_6)$ haloalkyl, said spiroheptanyl, azaspiroheptanyl, oxetanyl, oxolanyl, thiazolyl, and piperidinyl optionally substituted with 1 to 2 groups independently selected from halogen, OH, CN, $—(C_1\text{-}C_6)$alkyl, $-(CH_2)_nO(C_1\text{-}C_6)$alkyl, $—(C_1\text{-}C_6)$haloalkyl, oxolanyl, and oxetanyl, said oxolanyl and oxetanyl optionally substituted with 1 to 2 groups of $CH_3$, wherein n is 0-3.

13. The compound according to claim 10 wherein $R^b$ is selected from $CH_3$, $CH_2C(CH_3)_2OH$, oxetanyl, oxolanyl, and thietanedionyl, said oxetanyl, oxolanyl, and thietanedionyl optionally substituted with 1 to 3 groups of $R^{b1}$ selected from $CH_3$, OH, $OCH_3$, $CF_3$, Fl, Cl, CN, $CH_2CN$, and cyclopropyl.

14. The compound of claim 1, or a pharmaceutically acceptable salt thereof selected from:

(S) 6-chloro-N-(1-ethyl-5-methyl-1H-pyrazol-4-yl)-7-(spiro[2.2]pentan-1-yl)quinazolin-2-amine
(R) 6-chloro-N-(1-ethyl-5-methyl-1H-pyrazol-4-yl)-7-(spiro[2.2]pentan-1-yl)quinazolin-2-amine
(S) 1-(3-(6-chloro-2-((1-cyclopropyl-1H-pyrazol-4-yl)amino)quinazolin-7-yl)pyrrolidin-1-yl)-2-methylpropan-2-ol
(R) 1-(3-(6-chloro-2-((1-cyclopropyl-1H-pyrazol-4-yl)amino)quinazolin-7-yl)pyrrolidin-1-yl)-2-methylpropan-2-ol
(1R,2S) 2-(4-(6-chloro-2-((1-cyclopropyl-5-methyl-1H-pyrazol-4-yl)amino)quinazolin-7-yl)piperidin-1-yl)cyclobutan-1-ol
(1R,2R) 2-(4-(6-chloro-2-((1-cyclopropyl-5-methyl-1H-pyrazol-4-yl)amino)quinazolin-7-yl)piperidin-1-yl)cyclobutan-1-ol
(1S,2S) 2-(4-(6-chloro-2-((1-cyclopropyl-5-methyl-1H-pyrazol-4-yl)amino)quinazolin-7-yl)piperidin-1-yl)cyclobutan-1-ol
(1S,2R) 2-(4-(6-chloro-2-((1-cyclopropyl-5-methyl-1H-pyrazol-4-yl)amino)quinazolin-7-yl)piperidin-1-yl)cyclobutan-1-ol
(3R,4R)-4-(4-(6-chloro-2-((5-chloro-1-cyclopropyl-1H-pyrazol-4-yl)amino)quinazolin-7-yl)piperidin-1-yl)-4-methyltetrahydrofuran-3-ol
(3S,4S)-4-(4-(6-chloro-2-((5-chloro-1-cyclopropyl-1H-pyrazol-4-yl)amino)quinazolin-7-yl)piperidin-1-yl)-4-methyltetrahydrofuran-3-ol
(S) 1-(3-{6-chloro-2-[(1-cyclopropyl-1H-pyrazol-4-yl)amino]quinazolin-7-yl}pyrrolidin-1-yl)-2-methylpropan-2-ol
(R) 1-(3-{6-chloro-2-[(1-cyclopropyl-1H-pyrazol-4-yl)amino]quinazolin-7-yl}pyrrolidin-1-yl)-2-methylpropan-2-ol
(S) 6-chloro-N-(5-chloro-1-cyclopropyl-1H-pyrazol-4-yl)-7-(2-methyl-1-(oxetan-3-yl)piperidin-4-yl)quinazolin-2-amine
(R) 6-chloro-N-(5-chloro-1-cyclopropyl-1H-pyrazol-4-yl)-7-(2-methyl-1-(oxetan-3-yl)piperidin-4-yl)quinazolin-2-amine
(S) 6-chloro-N-(5-chloro-1-cyclopropyl-1H-pyrazol-4-yl)-7-(2-methyl-1-(oxetan-3-yl)piperidin-4-yl)quinazolin-2-amine
(R) 6-chloro-N-(5-chloro-1-cyclopropyl-1H-pyrazol-4-yl)-7-(2-methyl-1-(oxetan-3-yl)piperidin-4-yl)quinazolin-2-amine
(S) 6-chloro-N-(1-cyclopropyl-5-methyl-1H-pyrazol-4-yl)-7-(2-methyl-1-(oxetan-3-yl)piperidin-4-yl)quinazolin-2-amine
(R) 6-chloro-N-(1-cyclopropyl-5-methyl-1H-pyrazol-4-yl)-7-(2-methyl-1-(oxetan-3-yl)piperidin-4-yl)quinazolin-2-amine
(S) 6-chloro-N-(1-cyclopropyl-5-methyl-1H-pyrazol-4-yl)-7-(2-methyl-1-(oxetan-3-yl)piperidin-4-yl)quinazolin-2-amine
(R) 6-chloro-N-(1-cyclopropyl-5-methyl-1H-pyrazol-4-yl)-7-(2-methyl-1-(oxetan-3-yl)piperidin-4-yl)quinazolin-2-amine -continued (3S,4S) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol
(3R,4R) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol
(3S,4S) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol
(3R,4R) 4-(4-(6-chloro-2-((1-cyclopropyl-5-methyl-1H-pyrazol-4-yl)amino)quinazolin-7-yl)piperidin-1-yl)-4-methyltetrahydrofuran-3-ol
cis or trans-4-(6-chloro-2-((5-chloro-1-cyclopropyl-1H-pyrazol-4-yl)amino)quinazolin-7-yl)-1-methylcyclohexan-1-ol
cis or trans-4-(6-chloro-2-((1-cyclopropyl-1H-pyrazol-4-yl)amino)quinazolin-7-yl)-1-methylcyclohexan-1-ol
(1R,2S) 2-(4-(6-chloro-2-((1-cyclopropyl-5-methyl-1H-pyrazol-4-yl)amino)quinazolin-7-yl)piperidin-1-yl)-2-methylcyclopentan-1-ol
(1S,2R) 2-(4-(6-chloro-2-((1-cyclopropyl-5-methyl-1H-pyrazol-4-yl)amino)quinazolin-7-yl)piperidin-1-yl)-2-methylcyclopentan-1-ol
(1S,2S) 2-(4-(6-chloro-2-((1-cyclopropyl-5-methyl-1H-pyrazol-4-yl)amino)quinazolin-7-yl)piperidin-1-yl)-2-methylcyclopentan-1-ol
(1R,2R) 2-(4-(6-chloro-2-((1-cyclopropyl-5-methyl-1H-pyrazol-4-yl)amino)quinazolin-7-yl)piperidin-1-yl)-2-methylcyclopentan-1-ol
(S) 6-chloro-N-(1-cyclopropyl-5-methyl-1H-pyrazol-4-yl)-7-[1-(2,2-difluorocyclopentyl)piperidin-4-yl]quinazolin-2-amine
(R) 6-chloro-N-(1-cyclopropyl-5-methyl-1H-pyrazol-4-yl)-7-[1-(2,2-difluorocyclopentyl)piperidin-4-yl]quinazolin-2-amine
(3S,4S) 4-(4-{6-chloro-2-[(3-cyclopropyl-1-methyl-1H-pyrazol-5-yl)amino]quinazolin-7-yl}piperidin-1-yl)oxolan-3-ol
(3R,4R) 4-(4-{6-chloro-2-[(3-cyclopropyl-1-methyl-1H-pyrazol-5-yl)amino]quinazolin-7-yl}piperidin-1-yl)oxolan-3-ol
(3S,4S) 4-[4-(6-chloro-2-{[1-methyl-3-(trifluoromethyl)-1H-pyrazol-5-yl]amino}quinazolin-7-yl)piperidin-1-yl]oxolan-3-ol
(3R,4R) 4-[4-(6-chloro-2-{[1-methyl-3-(trifluoromethyl)-1H-pyrazol-5-yl]amino}quinazolin-7-yl)piperidin-1-yl]oxolan-3-ol
(3S,4S) 4-(4-{6-chloro-2-[(1,3-dimethyl-1H-pyrazol-5-yl)amino]quinazolin-7-yl}piperidin-1-yl)-4-methyloxolan-3-ol
(3R,4R) 4-(4-{6-chloro-2-[(1,3-dimethyl-1H-pyrazol-5-yl)amino]quinazolin-7-yl}piperidin-1-yl)-4-methyloxolan-3-ol
(3S,4S)-4-(4-(6-chloro-2-((5-methyl-1-(methyl-d3)-1H-pyrazol-4-yl)amino)quinazolin-7-yl)piperidin-1-yl)-4-methyltetrahydrofuran-3-ol
(3R,4R)-4-(4-(6-chloro-2-((5-methyl-1-(methyl-d3)-1H-pyrazol-4-yl)amino)quinazolin-7-yl)piperidin-1-yl)-4-methyltetrahydrofuran-3-ol
(3S,4S)-4-(4-(6-chloro-2-((5-chloro-1-(methyl-d3)-1H-pyrazol-4-yl)amino)quinazolin-7-yl)piperidin-1-yl)-4-methyltetrahydrofuran-3-ol
(3R,4R)-4-(4-(6-chloro-2-((5-chloro-1-(methyl-d3)-1H-pyrazol-4-yl)amino)quinazolin-7-yl)piperidin-1-yl)-4-methyltetrahydrofuran-3-ol
(3S,4S) 4-(4-{6-chloro-2-[(1-cyclopropyl-3-methyl-1H-pyrazol-5-yl)amino]quinazolin-7-yl}piperidin-1-yl)-4-methyloxolan-3-ol
(3R,4R) 4-(4-{6-chloro-2-[(1-cyclopropyl-3-methyl-1H-pyrazol-5-yl)amino]quinazolin-7-yl}piperidin-1-yl)-4-methyloxolan-3-ol
(3S,4S) 1-(5-chloro-4-((6-chloro-7-(3-fluoro-1-(3-methyloxetan-3-yl)piperidin-4-yl)quinazolin-2-yl)amino)-1H-pyrazol-1-yl)-2-methylpropan-2-ol
(3R,4R) 1-(5-chloro-4-((6-chloro-7-(3-fluoro-1-(3-methyloxetan-3-yl)piperidin-4-yl)quinazolin-2-yl)amino)-1H-pyrazol-1-yl)-2-methylpropan-2-ol
6-chloro-N-(1-(3-(methoxymethyl)bicyclo[1.1.1]pentan-1-yl)-1H-pyrazol-4-yl)-7-(1-(3-methyloxetan-3-yl)piperidin-4-yl)quinazolin-2-amine
(3S,4S)-(4-(4-(2-((5-chloro-1-cyclopropyl-1H-pyrazol-4-yl)amino)-6-methylquinazolin-7-yl)piperidin-1-yl)tetrahydrofuran-3-ol
(3R,4R)-(4-(4-(2-((5-chloro-1-cyclopropyl-1H-pyrazol-4-yl)amino)-6-methylquinazolin-7-yl)piperidin-1-yl)tetrahydrofuran-3-ol
(S) 6-chloro-N-{1-[1-(3-methyloxetan-3-yl)piperidin-4-yl]-1H-pyrazol-4-yl}-7-(spiro[2.2]pentan-1-yl)quinazolin-2-amine
(R) 6-chloro-N-{1-[1-(3-methyloxetan-3-yl)piperidin-4-yl]-1H-pyrazol-4-yl}-7-(spiro[2.2]pentan-1-yl)quinazolin-2-amine
(S) 6-chloro-N-{1-[2-(3-methyloxetan-3-yl)-2-azaspiro[3.3]heptan-6-yl]-1H-pyrazol-4-yl}-7-(spiro[2.2]pentan-1-yl)quinazolin-2-amine
(R) 6-chloro-N-{1-[2-(3-methyloxetan-3-yl)-2-azaspiro[3.3]heptan-6-yl]-1H-pyrazol-4-yl}-7-(spiro[2.2]pentan-1-yl)quinazolin-2-amine
(S) 6-chloro-N-{5-chloro-1-[1-(3-methyloxetan-3-yl)piperidin-4-yl]-1H-pyrazol-4-yl}-7-(spiro[2.3]hexan-1-yl)quinazolin-2-amine
(R) 6-chloro-N-{5-chloro-1-[1-(3-methyloxetan-3-yl)piperidin-4-yl]-1H-pyrazol-4-yl}-7-(spiro[2.3]hexan-1-yl)quinazolin-2-amine
6-chloro-N-[5-chloro-1-(2-methoxy-2-methylpropyl)-1H-pyrazol-4-yl]-7-[1-(oxetan-3-yl)piperidin-4-yl]quinazolin-2-amine
(3S,4S) 6-chloro-N-[5-chloro-1-[(3-methyloxetan-3-yl)methyl]-1H-pyrazol-4-yl}-7-[3-fluoro-1-(oxetan-3-yl)piperidin-4-yl]quinazolin-2-amine
(3R,4R) 6-chloro-N-{5-chloro-1-[(3-methyloxetan-3-yl)methyl]-1H-pyrazol-4-yl}-7-[3-fluoro-1-(oxetan-3-yl)piperidin-4-yl]quinazolin-2-amine
(3S,4S) 6-chloro-N-[5-chloro-1-[(3-methyloxetan-3-yl)methyl]-1H-pyrazol-4-yl}-7-[3-fluoro-1-(oxetan-3-yl)piperidin-4-yl]quinazolin-2-amine -continued (3R,4R) 6-chloro-N-{5-chloro-1-[(3-methyloxetan-3-yl)methyl]-1H-pyrazol-4-yl}-7-[3-fluoro-1-(oxetan-3-yl)piperidin-4-yl]quinazolin-2-amine
6-chloro-N-{5-chloro-1-[2-(difluoromethoxy)-2-methylpropyl]-1H-pyrazol-4-yl}-7-[1-(oxetan-3-yl)piperidin-4-yl]quinazolin-2-amine
6-chloro-N-[1-(2-methoxy-2-methylpropyl)-5-methyl-1H-pyrazol-4-yl]-7-[1-(oxetan-3-yl)piperidin-4-yl]quinazolin-2-amine
1-{[4-({6-chloro-7-[1-(oxetan-3-yl)piperidin-4-yl]quinazolin-2-yl}amino)-5-methyl-1H-pyrazol-1-yl]methyl}cyclopropane-1-carbonitrile
6-chloro-N-[1-(2-methoxy-2-methylpropyl)-3-methyl-1H-pyrazol-4-yl]-7-[1-(oxetan-3-yl)piperidin-4-yl]quinazolin-2-amine
1-{[4-({6-chloro-7-[1-(oxetan-3-yl)piperidin-4-yl]quinazolin-2-yl}amino)-3-methyl-1H-pyrazol-1-yl]methyl}cyclopropane-1-carbonitrile
N-(1-(bicyclo[1.1.1]pentan-1-yl)-1H-pyrazol-4-yl)-6-chloro-7-(1-(3-methyloxetan-3-yl)piperidin-4-yl)quinazolin-2-amine
2-[4-({6-chloro-7-[1-(oxetan-3-yl)piperidin-4-yl]quinazolin-2-yl}amino)-5-methyl-1H-pyrazol-1-yl]-2-methylpropanenitrile
2-[4-({6-chloro-7-[1-(3-methyloxetan-3-yl)piperidin-4-yl]quinazolin-2-yl}amino)-5-methyl-1H-pyrazol-1-yl]-2-methylpropanenitrile
N-[1-(bicyclo[1.1.1]pentan-1-yl)-5-methyl-1H-pyrazol-4-yl]-6-chloro-7-[1-(oxetan-3-yl)piperidin-4-yl]quinazolin-2-amine
N-[1-(bicyclo[1.1.1]pentan-1-yl)-5-methyl-1H-pyrazol-4-yl]-6-chloro-7-[1-(3-methyloxetan-3-yl)piperidin-4-yl]quinazolin-2-amine
(S) 6-chloro-N-[5-methyl-1-(oxolan-3-yl)-1H-pyrazol-4-yl]-7-[1-(oxetan-3-yl)piperidin-4-yl]quinazolin-2-amine
(R) 6-chloro-N-[5-methyl-1-(oxolan-3-yl)-1H-pyrazol-4-yl]-7-[1-(oxetan-3-yl)piperidin-4-yl]quinazolin-2-amine
(S) 6-chloro-7-[1-(3-methyloxetan-3-yl)piperidin-4-yl]-N-[5-methyl-1-(oxolan-3-yl)-1H-pyrazol-4-yl]quinazolin-2-amine
(R) 6-chloro-7-[1-(3-methyloxetan-3-yl)piperidin-4-yl]-N-[5-methyl-1-(oxolan-3-yl)-1H-pyrazol-4-yl]quinazolin-2-amine
(3S,4S) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol
(3R,4R) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol
(3S,4S) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol
(3R,4R) 4-[4-(2-{[1-(bicyclo[1.1.1]pentan-1-yl)-5-methyl-1H-pyrazol-4-yl]amino}-6-chloroquinazolin-7-yl)piperidin-1-yl]oxolan-3-ol
(S) 6-chloro-N-[1-(2,2-difluorocyclopropyl)-5-methyl-1H-pyrazol-4-yl]-7-[1-(3-methyloxetan-3-yl)piperidin-4-yl]quinazolin-2-amine
(R) 6-chloro-N-[1-(2,2-difluorocyclopropyl)-5-methyl-1H-pyrazol-4-yl]-7-[1-(3-methyloxetan-3-yl)piperidin-4-yl]quinazolin-2-amine
6-chloro-N-{1-[3-(methoxymethyl)bicyclo[1.1.1]pentan-1-yl]-5-methyl-1H-pyrazol-4-yl}-7-[1-(oxetan-3-yl)piperidin-4-yl]quinazolin-2-amine
6-chloro-N-{1-[3-(methoxymethyl)bicyclo[1.1.1]pentan-1-yl]-5-methyl-1H-pyrazol-4-yl}-7-[1-(3-methyloxetan-3-yl)piperidin-4-yl]quinazolin-2-amine
(R)(3S,4S) 4-[4-(2-{[5-chloro-1-(2,2-difluorocyclopropyl)-1H-pyrazol-4-yl]amino}-6-methylquinazolin-7-yl)piperidin-1-yl]oxolan-3-ol
(R)(3R,4R) 4-[4-(2-{[5-chloro-1-(2,2-difluorocyclopropyl)-1H-pyrazol-4-yl]amino}-6-methylquinazolin-7-yl)piperidin-1-yl]oxolan-3-ol
(S)(3S,4S) 4-[4-(2-{[5-chloro-1-(2,2-difluorocyclopropyl)-1H-pyrazol-4-yl]amino}-6-methylquinazolin-7-yl)piperidin-1-yl]oxolan-3-ol
(S)(3R,4R) 4-[4-(2-{[5-chloro-1-(2,2-difluorocyclopropyl)-1H-pyrazol-4-yl]amino}-6-methylquinazolin-7-yl)piperidin-1-yl]oxolan-3-ol
4-[4-(2-{[5-chloro-1-(2,2-difluorocyclopropyl)-1H-pyrazol-4-yl]amino}-6-methylquinazolin-7-yl)piperidin-1-yl]oxolan-3-ol
(3S,4S) 4-[4-(2-{[1-(bicyclo[1.1.1]pentan-1-yl)-1H-pyrazol-4-yl]amino}-6-chloroquinazolin-7-yl)piperidin-1-yl]-4-methyloxolan-3-ol
(3R,4R) 4-[4-(2-{[1-(bicyclo[1.1.1]pentan-1-yl)-1H-pyrazol-4-yl]amino}-6-chloroquinazolin-7-yl)piperidin-1-yl]-4-methyloxolan-3-ol
(3S,4S) 4-(4-{2-[(5-chloro-1-cyclopropyl-1H-pyrazol-4-yl)amino]-6-methylquinazolin-7-yl}piperidin-1-yl)-4-methyloxolan-3-ol
(3R,4R) 4-(4-{2-[(5-chloro-1-cyclopropyl-1H-pyrazol-4-yl)amino]-6-methylquinazolin-7-yl}piperidin-1-yl)-4-methyloxolan-3-ol
(3S,4S) 4-(4-{2-[(5-chloro-1-cyclopropyl-1H-pyrazol-4-yl)amino]-6-methylquinazolin-7-yl}piperidin-1-yl)-4-methyloxolan-3-ol
(3R,4R) 4-(4-{2-[(5-chloro-1-cyclopropyl-1H-pyrazol-4-yl)amino]-6-methylquinazolin-7-yl}piperidin-1-yl)-4-methyloxolan-3-ol
(3S,4S) 4-(4-{2-[(1-cyclopropyl-5-methyl-1H-pyrazol-4-yl)amino]-6-methylquinazolin-7-yl}piperidin-1-yl)-4-methyloxolan-3-ol
(3R,4R) 4-(4-{2-[(1-cyclopropyl-5-methyl-1H-pyrazol-4-yl)amino]-6-methylquinazolin-7-yl}piperidin-1-yl)-4-methyloxolan-3-ol
(3S,4S) 4-(4-{2-[(1-cyclopropyl-5-methyl-1H-pyrazol-4-yl)amino]-6-methylquinazolin-7-yl}piperidin-1-yl)-4-methyloxolan-3-ol
(3R,4R) 4-(4-{2-[(1-cyclopropyl-5-methyl-1H-pyrazol-4-yl)amino]-6-methylquinazolin-7-yl}piperidin-1-yl)-4-methyloxolan-3-ol
(R)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol -continued (R)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(R)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(R)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(R)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(R)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3S,4S) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(S)(3R,4R) 4-[4-(2-{[5-chloro-1-(2,2-difluorocyclopropyl)-1H-pyrazol-4-yl]amino}-6-methylquinazolin-7-yl)piperidin-1-yl]-4-methyloxolan-3-ol
(R)(3S,4S) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(R)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(S)(3S,4S) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(R)(3S,4S) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(R)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(S)(3S,4S) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(S)(3R,4R) 4-[4-(2-{[1-(2,2-difluorocyclopropyl)-5-methyl-1H-pyrazol-4-yl]amino}-6-methylquinazolin-7-yl)piperidin-1-yl]-4-methyloxolan-3-ol
(3R,4S) 4-[5-chloro-4-({6-chloro-7-[1-(oxetan-3-yl)piperidin-4-yl]quinazolin-2-yl}amino)-1H-pyrazol-1-yl]oxolan-3-ol
(3S,4R) 4-[5-chloro-4-({6-chloro-7-[1-(oxetan-3-yl)piperidin-4-yl]quinazolin-2-yl}amino)-1H-pyrazol-1-yl]oxolan-3-ol
(3R,4R) 4-[5-chloro-4-({6-chloro-7-[1-(oxetan-3-yl)piperidin-4-yl]quinazolin-2-yl(amino)-1H-pyrazol-1-yl]oxolan-3-ol
(3S,4S) 4-[5-chloro-4-({6-chloro-7-[1-(oxetan-3-yl)piperidin-4-yl]quinazolin-2-yl}amino)-1H-pyrazol-1-yl]oxolan-3-ol
(3S,4S) 4-(4-{6-chloro-2-[(1-cyclopropyl-5-methyl-1H-pyrazol-4-yl)amino]quinazolin-7-yl}piperidin-1-yl)oxolane-3-carbonitrile
(3R,4R) 4-(4-{6-chloro-2-[(1-cyclopropyl-5-methyl-1H-pyrazol-4-yl)amino]quinazolin-7-yl}piperidin-1-yl)oxolane-3-carbonitrile
(3S,4R) 4-(4-{6-chloro-2-[(1-cyclopropyl-5-methyl-1H-pyrazol-4-yl)amino]quinazolin-7-yl}piperidin-1-yl)oxolane-3-carbonitrile
(3R,4S) 4-(4-{6-chloro-2-[(1-cyclopropyl-5-methyl-1H-pyrazol-4-yl)amino]quinazolin-7-yl}piperidin-1-yl)oxolane-3-carbonitrile
(R)(3S,4S) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(R)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(S)(3S,4S) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(S)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(S)(3S,4S) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(R)(3R,4R) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(R)(3S,4S) 4-[4-(6-chloro-2-{[1-(2,2-difluorocyclopropyl)-5-methyl-1H-pyrazol-4-yl]amino}quinazolin-7-yl)piperidin-1-yl]-4-methyloxolan-3-ol
(3S,4S) 4-(4-{6-chloro-2-[(3-methyl-1,2-thiazol-5-yl)amino]quinazolin-7-yl}piperidin-1-yl)oxolan-3-ol
(3R,4R) 4-(4-{6-chloro-2-[(3-methyl-1,2-thiazol-5-yl)amino]quinazolin-7-yl}piperidin-1-yl)oxolan-3-ol
6-chloro-N-[1-[3-(2-methoxypropan-2-yl)bicyclo[1.1.1]pentan-1-yl]-1H-pyrazol-4-yl}-7-[1-(3-methyloxetan-3-yl)piperidin-4-yl]quinazolin-2-amine
{3-[4-({6-chloro-7-[1-(3-methyloxetan-3-yl)piperidin-4-yl]quinazolin-2-yl}amino)-1H-pyrazol-1-yl]bicyclo[1.1.1]pentan-1-yl}methanol -continued 2-{3-[4-({6-chloro-7-[1-(3-methyloxetan-3-yl)piperidin-4-yl]quinazolin-2-yl}amino)-1H-pyrazol-1-yl]bicyclo[1.1.1]pentan-1-yl}propan-2-ol
6-chloro-N-(1-{3-[(dimethylamino)methyl]bicyclo[1.1.1]pentan-1-yl}-1H-pyrazol-4-yl)-7-[1-(3-methyloxetan-3-yl)piperidin-4-yl]quinazolin-2-amine
6-chloro-N-(1-{3-[(3,3-difluoroazetidin-1-yl)methyl]bicyclo[1.1.1]pentan-1-yl}-1H-pyrazol-4-yl)-7-[1-(3-methyloxetan-3-yl)piperidin-4-yl]quinazolin-2-amine
1-[4-({6-chloro-7-[1-(oxetan-3-yl)piperidin-4-yl]quinazolin-2-yl}amino)-3-methyl-1H-pyrazol-1-yl]-2-methylpropan-2-ol
6-chloro-N-(3-cyclopropyl-1-methyl-1H-pyrazol-5-yl)-7-[1-(oxetan-3-yl)piperidin-4-yl]quinazolin-2-amine
cis- or trans- 4-{6-chloro-2-[(1-cyclopropyl-5-methyl-1H-pyrazol-4-yl)amino]quinazolin-7-yl}-1-methylcyclohexan-1-ol
cis- or trans- 4-{2-[(5-chloro-1-cyclopropyl-1H-pyrazol-4-yl)amino]-6-methylquinazolin-7-yl}-1-methylcyclohexan-1-ol
(3S,4S) 4-(4-{6-chloro-2-[(1,5-dimethyl-1H-pyrazol-4-yl)amino]quinazolin-7-yl}piperidin-1-yl)-4-methyloxolan-3-ol
(3R,4R) 4-(4-{6-chloro-2-[(1,5-dimethyl-1H-pyrazol-4-yl)amino]quinazolin-7-yl}piperidin-1-yl)-4-methyloxolan-3-ol
(3S,4S) 4-(4-{6-chloro-2-[(5-chloro-1-methyl-1H-pyrazol-4-yl)amino]quinazolin-7-yl}piperidin-1-yl)oxolan-3-ol
(3S,4S) 4-(4-{6-chloro-2-[(5-chloro-1-methyl-1H-pyrazol-4-yl)amino]quinazolin-7-yl}piperidin-1-yl)oxolan-3-ol
(3S,4S) 4-(4-{6-chloro-2-[(1,5-dimethyl-1H-pyrazol-4-yl)amino]quinazolin-7-yl}piperidin-1-yl)oxolan-3-ol
(3R,4R) 4-(4-{6-chloro-2-[(1,5-dimethyl-1H-pyrazol-4-yl)amino]quinazolin-7-yl}piperidin-1-yl)oxolan-3-ol
(3S,4S) 4-(4-{6-chloro-2-[(1,3-dimethyl-1H-pyrazol-5-yl)amino]quinazolin-7-yl}piperidin-1-yl)oxolan-3-ol
(3R,4R) 4-(4-{6-chloro-2-[(1,3-dimethyl-1H-pyrazol-5-yl)amino]quinazolin-7-yl}piperidin-1-yl)oxolan-3-ol
(3S,4S) 4-(4-(6-chloro-2-((3-methyl-1-(methyl-$d_3$)-1H-pyrazol-5-yl)amino)quinazolin-7-yl)piperidin-1-yl)tetrahydrofuran-3-ol
(3R,4R) 4-(4-(6-chloro-2-((3-methyl-1-(methyl-$d_3$)-1H-pyrazol-5-yl)amino)quinazolin-7-yl)piperidin-1-yl)tetrahydrofuran-3-ol
(3S,4S) 4-(4-(6-chloro-2-((5-chloro-1-(methyl-$d_3$)-1H-pyrazol-4-yl)amino)quinazolin-7-yl)piperidin-1-yl)tetrahydrofuran-3-ol
(3R,4R) 4-(4-(6-chloro-2-((5-chloro-1-(methyl-$d_3$)-1H-pyrazol-4-yl)amino)quinazolin-7-yl)piperidin-1-yl)tetrahydrofuran-3-ol
(3S,4S) 4-(4-(6-chloro-2-((5-methyl-1-(methyl-$d_3$)-1H-pyrazol-4-yl)amino)quinazolin-7-yl)piperidin-1-yl)tetrahydrofuran-3-ol
(3R,4R) 4-(4-(6-chloro-2-((5-methyl-1-(methyl-$d_3$)-1H-pyrazol-4-yl)amino)quinazolin-7-yl)piperidin-1-yl)tetrahydrofuran-3-ol
6-chloro-N-(5-chloro-1-(methyl-$d_3$)-1H-pyrazol-4-yl)-7-(1-(3-methyloxetan-3-yl)piperidin-4-yl)quinazolin-2-amine
(S) 6-chloro-N-[1-(2,2-difluorocyclopropyl)-5-methyl-1H-pyrazol-4-yl]-7-[1-(oxetan-3-yl)piperidin-4-yl]quinazolin-2-amine
(R) 6-chloro-N-[1-(2,2-difluorocyclopropyl)-5-methyl-1H-pyrazol-4-yl]-7-[1-(oxetan-3-yl)piperidin-4-yl]quinazolin-2-amine
(3S,4S) 2-[4-({6-chloro-7-[1-(4-hydroxyoxolan-3-yl)piperidin-4-yl]quinazolin-2-yl}amino)-5-methyl-1H-pyrazol-1-yl]-2-methylpropanenitrile
(3R,4R) 2-[4-({6-chloro-7-[1-(4-hydroxyoxolan-3-yl)piperidin-4-yl]quinazolin-2-yl}amino)-5-methyl-1H-pyrazol-1-yl]-2-methylpropanenitrile
(3S,4S) 4-(4-{6-chloro-2-[(1-cyclopropyl-3-methyl-1H-pyrazol-5-yl)amino]quinazolin-7-yl}piperidin-1-yl)oxolan-3-ol
(3R,4R) 4-(4-{6-chloro-2-[(1-cyclopropyl-3-methyl-1H-pyrazol-5-yl)amino]quinazolin-7-yl}piperidin-1-yl)oxolan-3-ol
(3S,4S) 4-(4-(6-chloro-2-((5-chloro-1-methyl-1H-pyrazol-4-yl)amino)quinazolin-7-yl)piperidin-1-yl)-4-methyltetrahydrofuran-3-ol
(3R,4R) 4-(4-(6-chloro-2-((5-chloro-1-methyl-1H-pyrazol-4-yl)amino)quinazolin-7-yl)piperidin-1-yl)-4-methyltetrahydrofuran-3-ol
(3S,4S) 4-(4-{6-chloro-2-[(1,5-dimethyl-1H-pyrazol-4-yl)amino]quinazolin-7-yl}piperidin-1-yl)-4-methyloxolan-3-ol
(3R,4R) 4-(4-{6-chloro-2-[(1,5-dimethyl-1H-pyrazol-4-yl)amino]quinazolin-7-yl}piperidin-1-yl)-4-methyloxolan-3-ol
(3S,4S) 4-(4-{2-[(5-chloro-1-methyl-1H-pyrazol-4-yl)amino]-6-methylquinazolin-7-yl}piperidin-1-yl)oxolan-3-ol
(3R,4R) 4-(4-{2-[(5-chloro-1-methyl-1H-pyrazol-4-yl)amino]-6-methylquinazolin-7-yl}piperidin-1-yl)oxolan-3-ol
(3S,4S) 4-(4-{2-[(1,5-dimethyl-1H-pyrazol-4-yl)amino]-6-methylquinazolin-7-yl}piperidin-1-yl)oxolan-3-ol
(3R,4R) 4-(4-{2-[(1,5-dimethyl-1H-pyrazol-4-yl)amino]-6-methylquinazolin-7-yl}piperidin-1-yl)oxolan-3-ol
(3S,4S) 4-(4-{2-[(5-chloro-1-methyl-1H-pyrazol-4-yl)amino]-6-methylquinazolin-7-yl}piperidin-1-yl)-4-methyloxolan-3-ol
(3R,4R) 4-(4-{2-[(5-chloro-1-methyl-1H-pyrazol-4-yl)amino]-6-methylquinazolin-7-yl}piperidin-1-yl)-4-methyloxolan-3-ol
(3S,4S) 4-(4-{2-[(1,5-dimethyl-1H-pyrazol-4-yl)amino]-6-methylquinazolin-7-yl}piperidin-1-yl)-4-methyloxolan-3-ol -continued

| |
|---|
| (3R,4R) 4-(4-{2-[(1,5-dimethyl-1H-pyrazol-4-yl)amino]-6-methylquinazolin-7-yl}piperidin-1-yl)-4-methyloxolan-3-ol |
| (3S,4S) 4-[4-(6-chloro-2-{[5-(difluoromethyl)-1-methyl-1H-pyrazol-4-yl]amino}quinazolin-7-yl)piperidin-1-yl]-4-methyloxolan-3-ol |
| (3R,4R) 4-[4-(6-chloro-2-{[5-(difluoromethyl)-1-methyl-1H-pyrazol-4-yl]amino}quinazolin-7-yl)piperidin-1-yl]-4-methyloxolan-3-ol |
| (3S,4S) 4-(4-{2-[(3-tert-butyl-1-methyl-1H-pyrazol-5-yl)amino]-6-chloroquinazolin-7-yl}piperidin-1-yl)-4-methyloxolan-3-ol |
| (3R,4R) 4-(4-{2-[(3-tert-butyl-1-methyl-1H-pyrazol-5-yl)amino]-6-chloroquinazolin-7-yl}piperidin-1-yl)-4-methyloxolan-3-ol |
| (S)(3S,4S) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (S)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (R)(3S,4S) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (R)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (3S,4S) 4-(4-{6-chloro-2-[(1-cyclopropyl-1H-pyrazol-5-yl)amino]quinazolin-7-yl}piperidin-1-yl)-4-methyloxolan-3-ol |
| (3R,4R) 4-(4-{6-chloro-2-[(1-cyclopropyl-1H-pyrazol-5-yl)amino]quinazolin-7-yl}piperidin-1-yl)-4-methyloxolan-3-ol |
| (3S,4S) 5-({6-chloro-7-[1-(4-hydroxy-3-methyloxolan-3-yl)piperidin-4-yl]quinazolin-2-yl}amino)-1,3-dimethyl-1H-pyrazole-4-carbonitrile |
| (3R,4R) 5-({6-chloro-7-[1-(4-hydroxy-3-methyloxolan-3-yl)piperidin-4-yl]quinazolin-2-yl}amino)-1,3-dimethyl-1H-pyrazole-4-carbonitrile |
| (S)(3S,4S) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (S)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (R)(3S,4S)-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (R)(3R,4R) 4-[4-(6-chloro-2-{[1-(2,2-difluorocyclopropyl)-1H-pyrazol-5-yl]amino}quinazolin-7-yl)piperidin-1-yl]-4-methyloxolan-3-ol |
| (3S,4S) 4-[4-(6-chloro-2-{[5-chloro-1-(1-methylcyclopropyl)-1H-pyrazol-4-yl]amino}quinazolin-7-yl)piperidin-1-yl]-4-methyloxolan-3-ol |
| (3R,4R) 4-[4-(6-chloro-2-{[5-chloro-1-(1-methylcyclopropyl)-1H-pyrazol-4-yl]amino(quinazolin-7-yl)piperidin-1-yl]-4-methyloxolan-3-ol |
| (3S,4S) 4-[4-(6-chloro-2-{[1-methyl-3-(trifluoromethyl)-1H-pyrazol-5-yl]amino}quinazolin-7-yl)piperidin-1-yl]-4-methyloxolan-3-ol |
| (3S,4S) 4-[4-(6-chloro-2-{[1-methyl-3-(trifluoromethyl)-1H-pyrazol-5-yl]amino}quinazolin-7-yl)piperidin-1-yl]-4-methyloxolan-3-ol |
| (3S,4S) 4-(4-(6-chloro-2-((1-methyl-5-(trifluoromethyl)-1H-pyrazol-4-yl)amino)quinazolin-7-yl)piperidin-1-yl)-4-methyltetrahydrofuran-3-olyl)piperidin-1-yl]-4-methyloxolan-3-ol |
| (3R,4R) 4-(4-(6-chloro-2-((1-methyl-5-(trifluoromethyl)-1H-pyrazol-4-yl)amino)quinazolin-7-yl)piperidin-1-yl)-4-methyltetrahydrofuran-3-olyl)piperidin-1-yl]-4-methyloxolan-3-ol |
| (3S,4S) 4-[4-(6-chloro-2-{[1-cyclopropyl-5-(difluoromethyl)-1H-pyrazol-4-yl]amino}quinazolin-7-yl)piperidin-1-yl]-4-methyloxolan-3-ol |
| (3R,4R) 4-[4-(6-chloro-2-{[1-cyclopropyl-5-(difluoromethyl)-1H-pyrazol-4-yl]amino}quinazolin-7-yl)piperidin-1-yl]-4-methyloxolan-3-ol |
| (3S,4S)(7R) 6-chloro-N-(5-chloro-1-(3-fluoro-1-(3-methyloxetan-3-yl)piperidin-4-yl)-1H-pyrazol-4-yl)-7-(2,2-difluorocyclopropyl)quinazolin-2-amine |
| (3S,4S)(7S) 6-chloro-N-(5-chloro-1-(3-fluoro-1-(3-methyloxetan-3-yl)piperidin-4-yl)-1H-pyrazol-4-yl)-7-(2,2-difluorocyclopropyl)quinazolin-2-amine |
| (3R,4R)(7R) 6-chloro-N-(5-chloro-1-(3-fluoro-1-(3-methyloxetan-3-yl)piperidin-4-yl)-1H-pyrazol-4-yl)-7-(2,2-difluorocyclopropyl)quinazolin-2-amine |
| (3R,4R)(7S) 6-chloro-N-(5-chloro-1-(3-fluoro-1-(3-methyloxetan-3-yl)piperidin-4-yl)-1H-pyrazol-4-yl)-7-(2,2-difluorocyclopropyl)quinazolin-2-amine |
| (3S,4S) 6-chloro-N-(5-chloro-1-cyclopropyl-1H-pyrazol-4-yl)-7-(3-fluoropiperidin-4-yl)quinazolin-2-amine |
| (3R,4R) 6-chloro-N-(5-chloro-1-cyclopropyl-1H-pyrazol-4-yl)-7-(3-fluoropiperidin-4-yl)quinazolin-2-amine |
| 1-(5-chloro-4-((6-chloro-7-(1-(oxetan-3-yl)piperidin-4-yl)quinazolin-2-yl)amino)-1H-pyrazol-1-yl)-2-methylpropan-2-ol |
| (3S,4S) 1-(5-chloro-4-((6-chloro-7-(1-ethyl-3-fluoropiperidin-4-yl)quinazolin-2-yl)amino)-1H-pyrazol-1-yl)-2-methylpropan-2-ol |
| (3R,4R) 1-(5-chloro-4-((6-chloro-7-(1-ethyl-3-fluoropiperidin-4-yl)quinazolin-2-yl)amino)-1H-pyrazol-1-yl)-2-methylpropan-2-ol |
| (S) 3-(4-(6-chloro-2-((5-chloro-1-(2,2-difluoroethyl)-1H-pyrazol-4-yl)amino)quinazolin-7-yl)piperidin-1-yl)tetrahydrothiophene 1,1-dioxide |
| (S) 3-(4-(6-chloro-2-((5-chloro-1-(2,2-difluoroethyl)-1H-pyrazol-4-yl)amino)quinazolin-7-yl)piperidin-1-yl)tetrahydrothiophene 1,1-dioxide |
| 6-chloro-N-(5-chloro-1-(1-methylcyclopropyl)-1H-pyrazol-4-yl)-7-(1-(trifluoromethyl)piperidin-4-yl)quinazolin-2-amine |
| 1-((2S)-4-(6-chloro-2-((5-chloro-1-cyclopropyl-1H-pyrazol-4-yl)amino)quinazolin-7-yl)-2-methylpiperidin-1-yl)ethan-1-one |
| 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol |

-continued (R)(3S,4S)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(R)(3S,4S)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(R)(3R,4R)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahy drofuran-3-ol
(R)(3R,4R)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(S)(3S,4S)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(S)(3S,4S)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(S)(3R,4R)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
(S)(3R,4R)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)tetrahydrofuran-3-ol
4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3S,4S)(3S,4S) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3S,4S)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3R,4R)(3S,4S) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3R,4R)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3S,4S)(3S,4S) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3S,4S)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3R,4R)(3S,4S) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3R,4R)(3R,4R) 4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R) 3-(4-(6-chloro-2-((1-cyclopropyl-5-methyl-1H-pyrazol-4-yl)amino)quinazolin-7-yl)piperidin-1-yl)-1,1,1-trifluoropropan-2-ol
(S) 3-(4-(6-chloro-2-((1-cyclopropyl-5-methyl-1H-pyrazol-4-yl)amino)quinazolin-7-yl)piperidin-1-yl)-1,1,1-trifluoropropan-2-ol
3-(4-(6-chloro-2-((5-chloro-1-(2,2-difluoroethyl)-1H-pyrazol-4-yl)amino)quinazolin-7-yl)piperidin-1-yl)thietane 1,1-dioxide
6-chloro-N-(5-chloro-1-cyclobutyl-1H-pyrazol-4-yl)-7-[1-(oxetan-3-yl)piperidin-4-yl]quinazolin-2-amine
6-chloro-N-[5-chloro-1-(cyclopropylmethyl)-1H-pyrazol-4-yl]-7-[1-(oxetan-3-yl)piperidin-4-yl]quinazolin-2-amine
6-chloro-N-[5-chloro-1-(oxetan-3-yl)-1H-pyrazol-4-yl]-7-[1-(oxetan-3-yl)piperidin-4-yl]quinazolin-2-amine
6-chloro-N-[1-(difluoromethyl)-1H-pyrazol-4-yl]-7-[1-(oxetan-3-yl)piperidin-4-yl]quinazolin-2-amine
6-chloro-N-[5-chloro-1-(cyclobutylmethyl)-1H-pyrazol-4-yl]-7-[1-(oxetan-3-yl)piperidin-4-yl]quinazolin-2-amine
6-chloro-N-(5-chloro-1-cyclopropyl-1H-pyrazol-4-yl)-7-{1-[(3-methyloxetan-3-yl)methyl]piperidin-4-yl}quinazolin-2-amine
6-chloro-N-(5-chloro-1-cyclopropyl-1H-pyrazol-4-yl)-7-(1-(oxetan-3-yl-2,2,4,4-d4)piperidin-4-yl)quinazolin-2-amine
(3S,4S) 1-(5-chloro-4-{[6-chloro-7-(3-fluoro-1-methylpiperidin-4-yl)quinazolin-2-yl]amino}-1H-pyrazol-1-yl)-2-methylpropan-2-ol
3R,4R) 1-(5-chloro-4-{[6-chloro-7-(3-fluoro-1-methylpiperidin-4-yl)quinazolin-2-yl]amino}-1H-pyrazol-1-yl)-2-methylpropan-2-ol
6-chloro-N-[5-chloro-1-(1-methylcyclopropyl)-1H-pyrazol-4-yl]-7-[4-fluoro-1-(oxetan-3-yl)piperidin-4-yl]quinazolin-2-amine
(S) 6-chloro-N-[5-chloro-1-(1-methylcyclopropyl)-1H-pyrazol-4-yl]-7-[1-(oxetan-3-yl)pyrrolidin-3-yl]quinazolin-2-amine
(S) 6-chloro-N-[5-chloro-1-(1-methylcyclopropyl)-1H-pyrazol-4-yl]-7-[1-(oxetan-3-yl)pyrrolidin-3-yl]quinazolin-2-amine
(3S,4S) 6-chloro-N-[5-chloro-1-(1-methylcyclopropyl)-1H-pyrazol-4-yl]-7-[3-fluoro-1-(oxetan-3-yl)piperidin-4-yl]quinazolin-2-amine
(3R,4R) 6-chloro-N-[5-chloro-1-(1-methylcyclopropyl)-1H-pyrazol-4-yl]-7-[3-fluoro-1-(oxetan-3-yl)piperidin-4-yl]quinazolin-2-amine
(3S,4S) 4-(6-chloro-2-{[5-chloro-1-(1-methylcyclopropyl)-1H-pyrazol-4-yl]amino}quinazolin-7-yl)-1-methylpiperidin-3-ol
(3R,4R) 4-(6-chloro-2-{[5-chloro-1-(1-methylcyclopropyl)-1H-pyrazol-4-yl]amino}quinazolin-7-yl)-1-methylpiperidin-3-ol
6-chloro-N-(5-chloro-1-cyclopropyl-1H-pyrazol-4-yl)-7-[4-fluoro-1-(oxetan-3-yl)piperidin-4-yl]quinazolin-2-amine
(S) 6-chloro-N-(5-chloro-1-cyclopropyl-1H-pyrazol-4-yl)-7-[1-(oxetan-3-yl)pyrrolidin-3-yl]quinazolin-2-amine
(S) 6-chloro-N-(5-chloro-1-cyclopropyl-1H-pyrazol-4-yl)-7-[1-(oxetan-3-yl)pyrrolidin-3-yl]quinazolin-2-amine -continued

| |
|---|
| (3S,4S) 6-chloro-N-(5-chloro-1-cyclopropyl-1H-pyrazol-4-yl)-7-[3-fluoro-1-(oxetan-3-yl)piperidin-4-yl]quinazolin-2-amine |
| (3R,4R) 6-chloro-N-(5-chloro-1-cyclopropyl-1H-pyrazol-4-yl)-7-[3-fluoro-1-(oxetan-3-yl)piperidin-4-yl]quinazolin-2-amine |
| 6-chloro-N-(5-chloro-1-cyclopropyl-1H-pyrazol-4-yl)-7-(4-fluoro-1-methylpiperidin-4-yl)quinazolin-2-amine |
| (3S,4S) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine |
| (3R,4R) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine |
| (3S,4S) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine |
| (3R,4R) 6-chloro-N-[5-chloro-1-(2,2-difluoroethyl)-1H-pyrazol-4-yl]-7-[3-fluoro-1-(oxetan-3-yl)piperidin-4-yl]quinazolin-2-amine |
| (3S,4S) 6-chloro-N-(5-chloro-1-cyclopropyl-1H-pyrazol-4-yl)-7-(3-fluoro-1-methylpiperidin-4-yl)quinazolin-2-amine |
| (3R,4R) 6-chloro-N-(5-chloro-1-cyclopropyl-1H-pyrazol-4-yl)-7-(3-fluoro-1-methylpiperidin-4-yl)quinazolin-2-amine |
| (3S,4S) 6-chloro-N-(5-chloro-1-cyclopropyl-1H-pyrazol-4-yl)-7-(3-fluoro-1-methylpiperidin-4-yl)quinazolin-2-amine |
| (3R,4R) 6-chloro-N-(5-chloro-1-cyclopropyl-1H-pyrazol-4-yl)-7-(3-fluoro-1-methylpiperidin-4-yl)quinazolin-2-amine |
| (3S,4R) 6-chloro-N-(5-chloro-1-cyclopropyl-1H-pyrazol-4-yl)-7-[4-fluoro-1-(oxetan-3-yl)pyrrolidin-3-yl]quinazolin-2-amine |
| (3R,4S) 6-chloro-N-(5-chloro-1-cyclopropyl-1H-pyrazol-4-yl)-7-[4-fluoro-1-(oxetan-3-yl)pyrrolidin-3-yl]quinazolin-2-amine |
| (3S,4S) 1-[5-chloro-4-({6-chloro-7-[3-fluoro-1-(oxetan-3-yl)piperidin-4-yl]quinazolin-2-yl}amino)-1H-pyrazol-1-yl]-2-methylpropan-2-ol |
| (3R,4R) 1-[5-chloro-4-({6-chloro-7-[3-fluoro-1-(oxetan-3-yl)piperidin-4-yl]quinazolin-2-yl}amino)-1H-pyrazol-1-yl]-2-methylpropan-2-ol |
| 6-chloro-N-(3-methyl-1,2-thiazol-5-yl)-7-[1-(oxetan-3-yl)piperidin-4-yl]quinazolin-2-amine |
| (2R,3R) 6-chloro-N-(5-chloro-1-cyclopropyl-1H-pyrazol-4-yl)-7-[1-(2-methyloxetan-3-yl)piperidin-4-yl]quinazolin-2-amine |
| (2S,3S) 6-chloro-N-(5-chloro-1-cyclopropyl-1H-pyrazol-4-yl)-7-[1-(2-methyloxetan-3-yl)piperidin-4-yl]quinazolin-2-amine |
| (2S,3R) 6-chloro-N-(5-chloro-1-cyclopropyl-1H-pyrazol-4-yl)-7-[1-(2-methyloxetan-3-yl)piperidin-4-yl]quinazolin-2-amine |
| (2R,3S) 6-chloro-N-(5-chloro-1-cyclopropyl-1H-pyrazol-4-yl)-7-[1-(2-methyloxetan-3-yl)piperidin-4-yl]quinazolin-2-amine |
| (S) 6-chloro-N-(5-chloro-1-cyclopropyl-1H-pyrazol-4-yl)-7-[1-(oxolan-3-yl)piperidin-4-yl]quinazolin-2-amine |
| (R) 6-chloro-N-(5-chloro-1-cyclopropyl-1H-pyrazol-4-yl)-7-[1-(oxolan-3-yl)piperidin-4-yl]quinazolin-2-amine |
| (3S,4S) 6-chloro-7-[3-fluoro-1-(oxetan-3-yl)piperidin-4-yl]-N-(3-methyl-1,2-thiazol-5-yl)quinazolin-2-amine |
| (3R,4R) 6-chloro-7-[3-fluoro-1-(oxetan-3-yl)piperidin-4-yl]-N-(3-methyl-1,2-thiazol-5-yl)quinazolin-2-amine |
| (3S,4S) 6-chloro-7-(3-fluoro-1-methylpiperidin-4-yl)-N-(3-methyl-1,2-thiazol-5-yl)quinazolin-2-amine |
| (3R,4R) 6-chloro-7-(3-fluoro-1-methylpiperidin-4-yl)-N-(3-methyl-1,2-thiazol-5-yl)quinazolin-2-amine |
| 6-chloro-N-[1-(2-fluoroethyl)-5-methyl-1H-pyrazol-4-yl]-7-[1-(oxetan-3-yl)piperidin-4-yl]quinazolin-2-amine |
| 6-chloro-N-[5-chloro-1-(2,2-difluoroethyl)-1H-pyrazol-4-yl]-7-[1-(oxetan-3-yl)piperidin-4-yl]quinazolin-2-amine |
| 6-chloro-N-[5-chloro-1-(1-methylcyclopropyl)-1H-pyrazol-4-yl]-7-[1-(oxetan-3-yl)piperidin-4-yl]quinazolin-2-amine |
| 6-chloro-N-(5-chloro-1-cyclopropyl-1H-pyrazol-4-yl)-7-(1-(oxetan-3-yl-3-d)piperidin-4-yl)quinazolin-2-amine |
| 1-(5-chloro-4-((6-chloro-7-(1-(oxetan-3-yl-d5)piperidin-4-yl)quinazolin-2-yl)amino)-1H-pyrazol-1-yl)-2-methylpropan-2-ol |
| 1-(5-chloro-4-((6-chloro-7-(1-(oxetan-3-yl-3-d)piperidin-4-yl)quinazolin-2-yl)amino)-1H-pyrazol-1-yl)-2-methylpropan-2-ol |
| (R)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol |
| (R)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol |
| (S)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol |
| (S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol |
| (S) 3-[5-chloro-4-({6-chloro-7-[1-(oxetan-3-yl)piperidin-4-yl]quinazolin-2-yl}amino)-1H-pyrazol-1-yl]-2-methylbutan-2-ol |
| (R) 3-[5-chloro-4-({6-chloro-7-[1-(oxetan-3-yl)piperidin-4-yl]quinazolin-2-yl}amino)-1H-pyrazol-1-yl]-2-methylbutan-2-ol |
| (3S,4S) 1-[4-({6-chloro-7-[3-fluoro-1-(oxetan-3-yl)piperidin-4-yl]quinazolin-2-yl}amino)-5-methyl-1H-pyrazol-1-yl]-2-methylpropan-2-ol |

-continued (3R,4R) 1-[4-({6-chloro-7-[3-fluoro-1-(oxetan-3-yl)piperidin-4-yl]quinazolin-2-yl}amino)-5-methyl-1H-pyrazol-1-yl]-2-methylpropan-2-ol
(R)(3S,4S) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(R)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(S)(3S,4S) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(S)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(R)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(R)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(S)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(S) 3-[5-chloro-4-({6-chloro-7-[1-(oxetan-3-yl)piperidin-4-yl]quinazolin-2-yl}amino)-1H-pyrazol-1-yl]-2-methylbutan-2-ol
(R) 3-[5-chloro-4-({6-chloro-7-[1-(oxetan-3-yl)piperidin-4-yl]quinazolin-2-yl}amino)-1H-pyrazol-1-yl]-2-methylbutan-2-ol
(S)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(S)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(R)(3R,4R) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(R)(3S,4S) 3-(5-chloro-4-{[6-chloro-7-(3-fluoro-1-methylpiperidin-4-yl)quinazolin-2-yl]amino}-1H-pyrazol-1-yl)-2-methylbutan-2-ol
(S)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(S)(3S,4S) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(R)(3R,4R) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
(R)(3S,4S) 3-[5-chloro-4-({6-chloro-7-[3-fluoro-1-(oxetan-3-yl)piperidin-4-yl]quinazolin-2-yl}amino)-1H-pyrazol-1-yl]-2-methylbutan-2-ol
1-[5-chl oro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2S,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2R,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2S,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2S,3S) 1-[5-chloro-4-([6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2R,3R) l-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2S,3S) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2R,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
1-(5-chloro-4-{[6-chloro-7-(1-methylpiperidin-4-yl)quinazolin-2-yl]amino}-1H-pyrazol-1-yl)-2-methylpropan-2-ol
1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2R,3S)1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2S,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2R,3S) 1-[5-chloro-4-([6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2S,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2S,3S) 1-[5-chloro-4-([6-chloro-7-[3-fluoro-1-(2-methyloxetan-3-yl)piperidin-4-yl]quinazolin-2-yl}amino)-1H-pyrazol-1-yl]-2-methylpropan-2-ol
(3R,4R)(2R,3R) 1-[5-chloro-4-({6-chloro-7-[3-fluoro-1-(2-methyloxetan-3-yl)piperidin-4-yl]quinazolin-2-yl}amino)-1H-pyrazol-1-yl]-2-methylpropan-2-ol
(3S,4S)(2S,3S) 1-[5-chloro-4-({6-chloro-7-[3-fluoro-1-(2-methyloxetan-3-yl)piperidin-4-yl]quinazolin-2-yl(amino)-1H-pyrazol-1-yl]-2-methylpropan-2-ol
(3S,4S)(2R,3R) 1-[5-chloro-4-({6-chloro-7-[3-fluoro-1-(2-methyloxetan-3-yl)piperidin-4-yl]quinazolin-2-yl(amino)-1H-pyrazol-1-yl]-2-methylpropan-2-ol
(2R,3R) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol -continued (2S,3S) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol
(2S,3R) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol
(2R,3S) 1-[5-chloro-4-({6-chloro-7-[1-(2-methyloxetan-3-yl)piperidin-4-yl]quinazolin-2-yl}amino)-1H-pyrazol-1-yl]-2-methylpropan-2-ol
(S) 1-[5-chloro-4-({6-chloro-7-[1-(oxolan-3-yl)piperidin-4-yl]quinazolin-2-yl}amino)-1H-pyrazol-1-yl]-2-methylpropan-2-ol
(R) 1-[5-chloro-4-({6-chloro-7-[1-(oxolan-3-yl)piperidin-4-yl]quinazolin-2-yl}amino)-1H-pyrazol-1-yl]-2-methylpropan-2-ol
1-[(4-{6-chloro-2-[(5-chloro-1-cyclopropyl-1H-pyrazol-4-yl)amino]quinazolin-7-yl}piperidin-1-yl)methyl]cyclopropane-1-carbonitrile
(S) 1-[5-chloro-4-({6-chloro-7-[1-(oxolan-3-yl)piperidin-4-yl]quinazolin-2-yl}amino)-1H-pyrazol-1-yl]-2-methylpropan-2-ol
(R) 1-[5-chloro-4-({6-chloro-7-[1-(oxolan-3-yl)piperidin-4-yl]quinazolin-2-yl}amino)-1H-pyrazol-1-yl]-2-methylpropan-2-ol
1-[5-chloro-4-({6-methyl-7-[1-(oxetan-3-yl)piperidin-4-yl]quinazolin-2-yl}amino)-1H-pyrazol-1-yl]-2-methylpropan-2-ol
(3S,4S) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol
(3R,4R) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol
(3S,4S) N-(5-chloro-1-cyclopropyl-1H-pyrazol-4-yl)-7-[3-fluoro-1-(oxetan-3-yl)piperidin-4-yl]-6-methylquinazolin-2-amine
(3R,4R) N-(5-chloro-1-cyclopropyl-1H-pyrazol-4-yl)-7-[3-fluoro-1-(oxetan-3-yl)piperidin-4-yl]-6-methylquinazolin-2-amine
(3S,4S) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol
(3R,4R) 1-[5-chloro-4-({7-[3-fluoro-1-(oxetan-3-yl)piperidin-4-yl]-6-methylquinazolin-2-yl}amino)-1H-pyrazol-1-yl]-2-methylpropan-2-ol
N-(5-chloro-1-cyclopropyl-1H-pyrazol-4-yl)-6-methyl-7-[1-(oxetan-3-yl)piperidin-4-yl]quinazolin-2-amine
(3S,4S) N-(5-chloro-1-cyclopropyl-1H-pyrazol-4-yl)-7-[3-fluoro-1-(oxetan-3-yl)piperidin-4-yl]-6-methylquinazolin-2-amine
(3R,4R) N-(5-chloro-1-cyclopropyl-1H-pyrazol-4-yl)-7-[3-fluoro-1-(oxetan-3-yl)piperidin-4-yl]-6-methylquinazolin-2-amine
1-[5-chloro-4-({6-chloro-7-[4-fluoro-1-(oxetan-3-yl)piperidin-4-yl]quinazolin-2-yl(amino)-1H-pyrazol-1-yl]-2-methylpropan-2-ol
(3S,4S) 6-chloro-N-(4-chloro-3-methyl-1,2-thiazol-5-yl)-7-[3-fluoro-1-(oxetan-3-yl)piperidin-4-yl]quinazolin-2-amine
(3R,4R) 6-chloro-N-(4-chloro-3-methyl-1,2-thiazol-5-yl)-7-[3-fluoro-1-(oxetan-3-yl)piperidin-4-yl]quinazolin-2-amine
6-chloro-N-(5-chloro-1-cyclobutyl-1H-pyrazol-4-yl)-7-(piperidin-4-yl)quinazolin-2-amine
6-chloro-N-[5-chloro-1-(cyclopropylmethyl)-1H-pyrazol-4-yl]-7-(piperidin-4-yl)quinazolin-2-amine
(3S,4S) 6-chloro-N-[5-chloro-1-(1-methylcyclopropyl)-1H-pyrazol-4-yl]-7-(3-fluoropiperidin-4-yl)quinazolin-2-amine
(3R,4R) 6-chloro-N-[5-chloro-1-(1-methylcyclopropyl)-1H-pyrazol-4-yl]-7-(3-fluoropiperidin-4-yl)quinazolin-2-amine
6-chloro-N-[5-chloro-1-(2,2-difluoroethyl)-1H-pyrazol-4-yl]-7-(piperidin-4-yl)quinazolin-2-amine
1-(5-chloro-4-{[6-chloro-7-(piperidin-4-yl)quinazolin-2-yl]amino}-1H-pyrazol-1-yl)-2-methylpropan-2-ol
3-[4-(6-chloro-2-{[5-chloro-1-(2,2-difluoroethyl)-1H-pyrazol-4-yl]amino}quinazolin-7-yl)piperidin-1-yl]propanenitrile
3-(4-(6-chloro-2-((3-methylisothiazol-5-yl)amino)quinazolin-7-yl)piperidin-1-yl)thietane 1,1-dioxide
1-(5-chloro-4-{[6-chloro-7-(1-ethylpiperidin-4-yl)quinazolin-2-yl]amino}-1H-pyrazol-1-yl)-2-methylpropan-2-ol
6-chloro-N-[5-chloro-1-(2,2-difluoroethyl)-1H-pyrazol-4-yl]-7-[1-(3-methyloxetan-3-yl)piperidin-4-yl]quinazolin-2-amine
(3S,4S) 6-chloro-N-(5-chloro-1-cyclopropyl-1H-pyrazol-4-yl)-7-[3-fluoro-1-(3-methyloxetan-3-yl)piperidin-4-yl]quinazolin-2-amine
(3R,4R) 6-chloro-N-(5-chloro-1-cyclopropyl-1H-pyrazol-4-yl)-7-[3-fluoro-1-(3-methyloxetan-3-yl)piperidin-4-yl]quinazolin-2-amine
(3S,4S) 3-(4-{6-chloro-2-[(5-chloro-1-cyclopropyl-1H-pyrazol-4-yl)amino]quinazolin-7-yl}-3-fluoropiperidin-1-yl)thietane 1,1-dioxide
(3R,4R) 3-(4-{6-chloro-2-[(5-chloro-1-cyclopropyl-1H-pyrazol-4-yl)amino]quinazolin-7-yl}-3-fluoropiperidin-1-yl)thietane 1,1-dioxide
(3S,4S) 4-(4-(6-chloro-2-((5-chloro-1-cyclopropyl-1H-pyrazol-4-yl)amino)quinazolin-7-yl)piperidin-1-yl)tetrahydrofuran-3-carbonitrile
(3R,4R) 4-(4-(6-chloro-2-((5-chloro-1-cyclopropyl-1H-pyrazol-4-yl)amino)quinazolin-7-yl)piperidin-1-yl)tetrahydrofuran-3-carbonitrile
(3S,4R) 4-(4-(6-chloro-2-((5-chloro-1-cyclopropyl-1H-pyrazol-4-yl)amino)quinazolin-7-yl)piperidin-1-yl)tetrahydrofuran-3-carbonitrile
(3R,4S) 4-(4-(6-chloro-2-((5-chloro-1-cyclopropyl-1H-pyrazol-4-yl)amino)quinazolin-7-yl)piperidin-1-yl)tetrahydrofuran-3-carbonitrile
(3S,4S) 4-(4-(6-chloro-2-((5-chloro-1-cyclopropyl-1H-pyrazol-4-yl)amino)quinazolin-7-yl)piperidin-1-yl)tetrahydrofuran-3-ol -continued (3R,4R) 4-(4-(6-chloro-2-((5-chloro-1-cyclopropyl-1H-pyrazol-4-yl)amino)quinazolin-7-yl)piperidin-1-yl)tetrahydrofuran-3-ol (2S,4S) 6-chloro-N-(5-chloro-1-cyclopropyl-1H-pyrazol-4-yl)-7-(2-methyl-1-(oxetan-3-yl)piperidin-4-yl)quinazolin-2-amine (2R,4R) 6-chloro-N-(5-chloro-1-cyclopropyl-1H-pyrazol-4-yl)-7-(2-methyl-1-(oxetan-3-yl)piperidin-4-yl)quinazolin-2-amine (2S,4R) 6-chloro-N-(5-chloro-1-cyclopropyl-1H-pyrazol-4-yl)-7-(2-methyl-1-(oxetan-3-yl)piperidin-4-yl)quinazolin-2-amine (2R,4S) 6-chloro-N-(5-chloro-1-cyclopropyl-1H-pyrazol-4-yl)-7-(2-methyl-1-(oxetan-3-yl)piperidin-4-yl)quinazolin-2-amine (1R,3S)-3-((35,45) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1S,3R)-3-((3S,4S) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1R,3R)-3-((3S,4S) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1S,3S)-3-((3S,4S) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1R,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1S,3R)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile (1R,3R)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile 1S,3S)-3-((3R,4R) 4-(6-chloro-2-((5-chloro-1-cyclopropyl-1H-pyrazol-4-yl)amino)quinazolin-7-yl)-3-fluoropiperidin-1-yl)cyclopentane-1-carbonitrile cis or trans 6-chloro-N-(5-chloro-1-cyclopropyl-1H-pyrazol-4-yl)-7-(8-(oxetan-3-yl)-8-azabicyclo[3.2.1]octan-3-yl)quinazolin-2-amine cis or trans 6-chloro-N-(5-chloro-1-cyclopropyl-1H-pyrazol-4-yl)-7-(9-(oxetan-3-yl)-3-oxa-9-azabicyclo[3.3.1]nonan-7-yl)quinazolin-2-amine (R) 7-(1-(5-oxaspiro[3.4]octan-7-yl)piperidin-4-yl)-6-chloro-N-(5-chloro-1-cyclopropyl-1H-pyrazol-4-yl)quinazolin-2-amine (S) 7-(1-(5-oxaspiro[3.4]octan-7-yl)piperidin-4-yl)-6-chloro-N-(5-chloro-1-cyclopropyl-1H-pyrazol-4-yl)quinazolin-2-amine (S) 6-chloro-N-(5-chloro-1-cyclopropyl-1H-pyrazol-4-yl)-7-(1-(5,5-dimethyltetrahydrofuran-3-yl)piperidin-4-yl)quinazolin-2-amine (R) 6-chloro-N-(5-chloro-1-cyclopropyl-1H-pyrazol-4-yl)-7-(1-(5,5-dimethyltetrahydrofuran-3-yl)piperidin-4-yl)quinazolin-2-amine cis or trans 6-chloro-N-(5-chloro-1-cyclopropyl-1H-pyrazol-4-yl)-7-(2,6-dimethyl-1-(oxetan-3-yl)piperidin-4-yl)quinazolin-2-amine 6-chloro-N-(5-chloro-1-cyclopropyl-1H-pyrazol-4-yl)-7-(2-(oxetan-3-yl)-2-azaspiro[3.3]heptan-6-yl)quinazolin-2-amine 4-{6-chloro-2-[(4-chloro-3-methyl-1,2-thiazol-5-yl)amino]quinazolin-7-yl}-3-fluoropiperidin-1-yl]oxolan-3-ol (3S,4S)(3S,4S) 4-{6-chloro-2-[(4-chloro-3-methyl-1,2-thiazol-5-yl)amino]quinazolin-7-yl}-3-fluoropiperidin-1-yl]oxolan-3-ol (3S,4S)(3R,4R) 4-{6-chloro-2-[(4-chloro-3-methyl-1,2-thiazol-5-yl)amino]quinazolin-7-yl}-3-fluoropiperidin-1-yl]oxolan-3-ol (3R,4R)(3S,4S) 4-{6-chloro-2-[(4-chloro-3-methyl-1,2-thiazol-5-yl)amino]quinazolin-7-yl}-3-fluoropiperidin-1-yl]oxolan-3-ol (3R,4R)(3R,4R) 4-{6-chloro-2-[(4-chloro-3-methyl-1,2-thiazol-5-yl)amino]quinazolin-7-yl}-3-fluoropiperidin-1-yl]oxolan-3-ol (3S,4S)(3S,4S) 4-{6-chloro-2-[(4-chloro-3-methyl-1,2-thiazol-5-yl)amino]quinazolin-7-yl}-3-fluoropiperidin-1-yl]oxolan-3-ol (3S,4S)(3R,4R) 4-{6-chloro-2-[(4-chloro-3-methyl-1,2-thiazol-5-yl)amino]quinazolin-7-yl}-3-fluoropiperidin-1-yl]oxolan-3-ol (3R,4R)(3S,4S) 4-{6-chloro-2-[(4-chloro-3-methyl-1,2-thiazol-5-yl)amino]quinazolin-7-yl}-3-fluoropiperidin-1-yl]oxolan-3-ol (3R,4R)(3R,4R) 4-{6-chloro-2-[(4-chloro-3-methyl-1,2-thiazol-5-yl)amino]quinazolin-7-yl}-3-fluoropiperidin-1-yl]oxolan-3-ol 4-{6-chloro-2-[(5-chloro-1-cyclopropyl-1H-pyrazol-4-yl)amino]quinazolin-7-yl}-3-fluoropiperidin-1-yl]oxolan-3-ol (3S,4S)(3S,4S) 4-{6-chloro-2-[(5-chloro-1-cyclopropyl-1H-pyrazol-4-yl)amino]quinazolin-7-yl}-3-fluoropiperidin-1-yl]oxolan-3-ol (3S,4S)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol (3R,4R)(3S,4S) 4-{6-chloro-2-[(5-chloro-1-cyclopropyl-1H-pyrazol-4-yl)amino]quinazolin-7-yl}-3-fluoropiperidin-1-yl]oxolan-3-ol (3R,4R)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol (3S,4S)(3S,4S) 4-{6-chloro-2-[(5-chloro-1-cyclopropyl-1H-pyrazol-4-yl)amino]quinazolin-7-yl}-3-fluoropiperidin-1-yl]oxolan-3-ol (3S,4S)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol (3R,4R)(3S,4S) 4-{6-chloro-2-[(5-chloro-1-cyclopropyl-1H-pyrazol-4-yl)amino]quinazolin-7-yl}-3-fluoropiperidin-1-yl]oxolan-3-ol (3R,4R)(3R,4R) 4-{6-chloro-2-[(5-chloro-1-cyclopropyl-1H-pyrazol-4-yl)amino]quinazolin-7-yl}-3-fluoropiperidin-1-yl]oxolan-3-ol -continued 3-(4-(6-chloro-2-((5-chloro-1-cyclopropyl-1H-pyrazol-4-yl)amino)quinazolin-7-yl)piperidin-1-yl)thietane 1,1-dioxide
(R)(3S,4S) 3-[4-(6-chloro-2-{[5-chloro-1-(2,2-difluorocyclopropyl)-1H-pyrazol-4-yl]amino}quinazolin-7-yl)-3-fluoropiperidin-1-yl]thietane 1,1-dioxide
(S)(3R,4R) 3-[4-(6-chloro-2-{[5-chloro-1-(2,2-difluorocyclopropyl)-1H-pyrazol-4-yl]amino}quinazolin-7-yl)-3-fluoropiperidin-1-yl]thietane 1,1-dioxide
(S)(3S,4S) 3-[4-(6-chloro-2-{[5-chloro-1-(2,2-difluorocyclopropyl)-1H-pyrazol-4-yl]amino}quinazolin-7-yl)-3-fluoropiperidin-1-yl]thietane 1,1-dioxide
4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3S,4S)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3S,4S)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3R,4R)(3S,4S)4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3S,4S)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3S,4S)(3R,4R)4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3R,4R)(3S,4S)4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(1S,4S) 6-chloro-N-(1-cyclopropyl-5-methyl-1H-pyrazol-4-yl)-7-[2-(oxetan-3-yl)-2-azabicyclo[2.2.1]heptan-5-yl]quinazolin-2-amine
(1R,4R) 6-chloro-N-(1-cyclopropyl-5-methyl-1H-pyrazol-4-yl)-7-[2-(oxetan-3-yl)-2-azabicyclo[2.2.1]heptan-5-yl]quinazolin-2-amine
4-[4-{6-chloro-2-[(1-cyclopropyl-5-methyl-1H-pyrazol-4-yl)amino]quinazolin-7-yl}-3-fluoropiperidin-1-yl]oxolan-3-ol
(3S,4S)(3S,4S) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3S,4S)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3R,4R)(3S,4S) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3R,4R)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3S,4S)(3S,4S) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3S,4S)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3R,4R)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3R,4R)(3R,4R) 4-[4-{6-chloro-2-[(1-cyclopropyl-5-methyl-1H-pyrazol-4-yl)amino]quinazolin-7-yl}-3-fluoropiperidin-1-yl]oxolan-3-ol
(3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3S,4S)(2S,4R) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3S,4S)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3R,4R)(2S,4R) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3R,4R)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3S,4S)(2S,4R) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3S,4S)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3R,4R)(2S,4R) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3R,4R)(2S,4S) (3 4-[4-{6-chloro-2-[(1-cyclopropyl-5-methyl-1H-pyrazol-4-yl)amino]quinazolin-7-yl}-2-methylpiperidin-1-yl]oxolan-3-ol
(3S,4S) 4-(4-{6-chloro-2-[(1-cyclopropyl-5-methyl-1H-pyrazol-4-yl)amino]quinazolin-7-yl}piperidin-1-yl)oxolan-3-ol
(3R,4R) 4-(4-{6-chloro-2-[(1-cyclopropyl-5-methyl-1H-pyrazol-4-yl)amino]quinazolin-7-yl}piperidin-1-yl)oxolan-3-ol
(2R,3R) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile
(2S,3S) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile
(2S,3R) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile
(2R,3S) 2-[4-({6-chloro-7-[1-(2-methyloxetan-3-yl)piperidin-4-yl]quinazolin-2-yl}amino)-5-methyl-1H-pyrazol-1-yl]-2-methylpropanenitrile -continued

| |
|---|
| 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3S,4S) a4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |
| (S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol |

-continued (S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(R)(3S,4S) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(S)(3S,4S) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(R)(3R,4R) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(S)(3R4R) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(R)(3S,4S) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(S)(3S,4S) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
(R)(3R,4R) 4-[4-(2-{[1-(2,2-difluorocyclopropyl)-5-methyl-1H-pyrazol-4-yl]amino}-6-methylquinazolin-7-l)piperidin-1-yl]oxolan-3-ol
(S)(3R,4R) 4-[4-(2-{[1-(2,2-difluorocyclopropyl)-5-methyl-1H-pyrazol-4-yl]amino}-6-methylquinazolin-7-yl)piperidin-1-yl]oxolan-3-ol
4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3S,4S)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3R,4R) 4-[4-(2-{[1-(2,2-difluorocyclopropyl)-5-ethyl-1H-pyrazol-4-yl]amino}-6-methylquinazolin-7-yl)-3-fluoropiperidin-1-yl]oxolan-3-ol
(R)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3S,4S)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(S)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
(S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]oxolan-3-ol
4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol
(R)(3S,4S)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol -continued

| |
|---|
| (R)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (R)(3R,4R)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (S)(3S,4S)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (S)(3S,4S)(3R,4R) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (S)(3R,4R)(3S,4S) 4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (S)(3R,4R)(3R,4R)4-[4-(2-{[1-(2,2-difluorocyclopropyl)-5-methyl-1H-pyrazol-4-yl]amino}-6-methylquinazolin-7-yl)-3-fluoropiperidin-1-yl]oxolan-3-ol |
| (R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol |
| (3S,4S)(3S,4S) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3S,4S)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3R,4R)(3S,4S) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3S,4S)(3S,4S) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3S,4S)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3R,4R)(3S,4S) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| 3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)-4-methyloxolan-3-ol |
| (3S,4S)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3S,4S) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3R,4R)(3R,4R) 4-(4-{2-[(5-chloro-1-cyclopropyl-1H-pyrazol-4-yl)amino]-6-methylquinazolin-7-yl}-3-fluoropiperidin-1-yl)oxolan-3-ol |
| (3S,4S) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol |
| (3R,4R) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol |
| (3S,4S) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol |
| (3R,4R) 4-[4-(2-{[1-(bicyclo[1.1.1]pentan-1-yl)-1H-pyrazol-4-yl]amino}-6-chloroquinazolin-7-yl)piperidin-1-yl]oxolan-3-ol |
| (3S,4S)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-1H-pyrazol-4-yl]amino)-6-chloroquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol |

-continued (3S,4S)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(3R,4R)(3S,4S) 4-[4-(2-{[1-(bicyclo[1.1.1]pentan-1-yl)-1H-pyrazol-4-yl]amino)-6-chloroquinazolin-7-yl)-3-fluoropiperidin-1-yl]oxolan-3-ol
(3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(3S,4S)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(3S,4S)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(3R,4R)(3S,4S) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(3R,4R)(3R,4R) 4-[4-(2-{[1-(bicyclo[1.1.1]pentan-1-yl)-1H-pyrazol-4-yl]amino}-6-chloroquinazolin-7-yl)-3-fluoropiperidin-1-yl]oxolan-3-ol
(1S,2R)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2S)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2R)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2S)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2R)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2R)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2R)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2S)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2R)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2S)(3S,4S) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2R)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1R,2R)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2S)(3R,4R) 2-(4-{6-chloro-2-[(5-chloro-1-cyclopropyl-1H-pyrazol-4-yl)amino]quinazolin-7-yl}-3-fluoropiperidin-1-yl)cyclopentan-1-ol
(1S,2R)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2S)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2R)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2S)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2R)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2R)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2R)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2S)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2R)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2S)(3S,4S) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2R)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1R,2R)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol
(1S,2S)(3R,4R) 2-(4-{6-chloro-2-[(1-cyclopropyl-5-methyl-1H-pyrazol-4-yl)amino]quinazolin-7-yl}-3-fluoropiperidin-1-yl)cyclopentan-1-ol -continued (3S,4S)(3S,4S) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3S,4S)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3R,4R)(3S,4S) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3R,4R)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3S,4S)(3S,4S) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3S,4S)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3R,4R)(3S,4S) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(3R,4R)(3R,4R) 4-[4-(2-{[1-(bicyclo[1.1.1]pentan-1-yl)-5-methyl-1H-pyrazol-4-yl]amino}-6-chloroquinazolin-7-yl)-3-fluoropiperidin-1-yl]oxolan-3-ol
(R)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(R)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(R)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(R)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(S)(3S,4S)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(S)(3S,4S)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(S)(3R,4R)(3S,4S) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(S)(3R,4R)(3R,4R) 4-[4-(2-{[5-chloro-1-(2,2-difluorocyclopropyl)-1H-pyrazol-4-yl]amino}-6-methylquinazolin-7-yl)-3-fluoropiperidin-1-yl]-4-methyloxolan-3-ol
(3S,4S)(3S,4S) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3S,4S)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3R,4R)(3S,4S) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3R,4R)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3S,4S)(3S,4S) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3S,4S)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3R,4R)(3S,4S) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3R,4R)(3R,4R) 4-[4-(2-{[1-(bicyclo[1.1.1]pentan-1-yl)-5-methyl-1H-pyrazol-4-yl]amino}-6-methylquinazolin-7-yl)-3-fluoropiperidin-1-yl]oxolan-3-ol
(3R,5R) 6-chloro-N-(5-chloro-1-cyclopropyl-1H-pyrazol-4-yl)-7-[1-(5-cyclopropyloxolan-3-yl)piperidin-4-yl]quinazolin-2-amine
(3S,5R) 6-chloro-N-(5-chloro-1-cyclopropyl-1H-pyrazol-4-yl)-7-[1-(5-cyclopropyloxolan-3-yl)piperidin-4-yl]quinazolin-2-amine
(3R,5S) 6-chloro-N-(5-chloro-1-cyclopropyl-1H-pyrazol-4-yl)-7-[1-(5-cyclopropyloxolan-3-yl)piperidin-4-yl]quinazolin-2-amine
(3S,5S) 6-chloro-N-(5-chloro-1-cyclopropyl-1H-pyrazol-4-yl)-7-[1-(5-cyclopropyloxolan-3-yl)piperidin-4-yl]quinazolin-2-amine
(1R,3R) [3-(4-{6-chloro-2-[(1-cyclopropyl-5-methyl-1H-pyrazol-4-yl)amino]quinazolin-7-yl}piperidin-1-yl)cyclopentyl]acetonitrile
(1S,3R) [3-(4-{6-chloro-2-[(1-cyclopropyl-5-methyl-1H-pyrazol-4-yl)amino]quinazolin-7-yl}piperidin-1-yl)cyclopentyl]acetonitrile
(1R,3S) [3-(4-{6-chloro-2-[(1-cyclopropyl-5-methyl-1H-pyrazol-4-yl)amino]quinazolin-7-yl}piperidin-1-yl)cyclopentyl]acetonitrile
(1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile
(1R,3R) [3-(4-{6-chloro-2-[(1-cyclopropyl-5-methyl-1H-pyrazol-4-yl)amino]quinazolin-7-yl}piperidin-1-yl)cyclopentyl]acetonitrile
(1S,3R) [3-(4-{6-chloro-2-[(1-cyclopropyl-5-methyl-1H-pyrazol-4-yl)amino]quinazolin-7-yl}piperidin-1-yl)cyclopentyl]acetonitrile
(1R,3S) [3-(4-{6-chloro-2-[(1-cyclopropyl-5-methyl-1H-pyrazol-4-yl)amino]quinazolin-7-yl}piperidin-1-yl)cyclopentyl]acetonitrile
(1S,3S) [3-(4-{6-chloro-2-[(1-cyclopropyl-5-methyl-1H-pyrazol-4-yl)amino]quinazolin-7-yl}piperidin-1-yl)cyclopentyl]acetonitrile
7-{1-[(1S,5R)-bicyclo[3.1.0]hexan-2-yl]piperidin-4-yl}-6-chloro-N-(1-cyclopropyl-5-methyl-1H-pyrazol-4-yl)quinazolin-2-amine
(R) 6-chloro-N-(1-cyclopropyl-5-methyl-1H-pyrazol-4-yl)-7-[1-(5,5-dimethyloxolan-3-yl)piperidin-4-yl]quinazolin-2-amine
(S) 6-chloro-N-(1-cyclopropyl-5-methyl-1H-pyrazol-4-yl)-7-[1-(5,5-dimethyloxolan-3-yl)piperidin-4-yl]quinazolin-2-amine -continued (R)(3S,4S) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
((S)(3S,4S) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(R)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(R)(3S,4S) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(S)(3S,4S) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(R)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(S)(3R,4R) 6-chloro-N-[1-(2,2-difluorocyclopropyl)-5-methyl-1H-pyrazol-4-yl]-7-[(3R,4R)-3-fluoro-1-(oxetan-3-yl)piperidin-4-yl]quinazolin-2-amine
(R) 6-chloro-N-[1-(2,2-difluorocyclopropyl)-5-methyl-1H-pyrazol-4-yl]-7-[1-(oxetan-3-yl)piperidin-4-yl]quinazolin-2-amine
(S) 6-chloro-N-[1-(2,2-difluorocyclopropyl)-5-methyl-1H-pyrazol-4-yl]-7-[1-(oxetan-3-yl)piperidin-4-yl]quinazolin-2-amine
(R)(3S,4S)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3S,4S)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3R,4R)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3S,4S)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3S,4S)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3R,4R)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3S,4S)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3S,4S)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3R,4R)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3S,4S)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3S,4S)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3R,4R)(3S,4S) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(S)(3R,4R)(3R,4R) 4-(4-(6-chloro-2-((1-(2,2-difluorocyclopropyl)-5-methyl-1H-pyrazol-4-yl)amino)quinazolin-7-yl)-3-fluoropiperidin-1-yl)tetrahydrofuran-3-olyl]amino}quinazolin-7-yl)-3-fluoropiperidin-1-yl]oxolan-3-ol
(R)(3S,4S) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(S)(3S,4S) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(R)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(S)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(R)(3S,4S) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol -continued (S)(3S,4S) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(R)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(S)(3R,4R) 4-[4-(6-chloro-2-{[1-(2,2-difluorocyclopropyl)-5-methyl-1H-pyrazol-4-yl]amino}quinazolin-7-yl)piperidin-1-yl]oxolan-3-ol
(R)(3S,4S)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3S,4S)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3R,4R)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(R)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3S,4S)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3S,4S)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3R,4R)(3S,4S) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(S)(3R,4R)(3R,4R) 4-(6-chloro-2-{[5-chloro-1-(2,2-difluorocyclopropyl)-1H-pyrazol-4-yl]amino}quinazolin-7-yl)-3-fluoropiperidin-1-yl]oxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
((3R,4R)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(2R)(3S) 1-(3-{6-chloro-2-[(1-cyclopropyl-5-methyl-1H-pyrazol-4-yl)amino]quinazolin-7-yl}pyrrolidin-1-yl)-2-hydroxypropan-1-one
(2R)(3R) 1-(3-{6-chloro-2-[(1-cyclopropyl-5-methyl-1H-pyrazol-4-yl)amino]quinazolin-7-yl}pyrrolidin-1-yl)-2-hydroxypropan-1-one
(3S,4S)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)oxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)oxolan-3-ol
(2S)(3S) 1-(3-{6-chloro-2-[(1-cyclopropyl-5-methyl-1H-pyrazol-4-yl)amino]quinazolin-7-yl}pyrrolidin-1-yl)-2-hydroxypropan-1-one
(2S)(3R) 1-(3-{6-chloro-2-[(1-cyclopropyl-5-methyl-1H-pyrazol-4-yl)amino]quinazolin-7-yl}pyrrolidin-1-yl)-2-hydroxypropan-1-one
(S) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol
(R) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol
(S) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol
(R) 1-(4-{6-chloro-2-[(1-cyclopropyl-5-methyl-1H-pyrazol-4-yl)amino]quinazolin-7-yl}piperidin-1-yl)-4,4,4-trifluorobutan-2-ol
(1S)-2-(4-{6-chloro-2-[(1-cyclopropyl-5-methyl-1H-pyrazol-4-yl)amino]quinazolin-7-yl}piperidin-1-yl)-1-phenylethan-1-ol
(1R)-2-(4-{6-chloro-2-[(1-cyclopropyl-5-methyl-1H-pyrazol-4-yl)amino]quinazolin-7-yl}piperidin-1-yl)-1-(3-chlorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(3-fluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(3-fluorophenyl)ethan-1-ol -continued (1S)-2-(4-{6-chloro-2-[(1-cyclopropyl-5-methyl-1H-pyrazol-4-yl)amino]quinazolin-7-yl}piperidin-1-yl)-1-(3,5-difluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(3,5-difluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(3,4-difluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(2,4-difluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(2-fluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(2-fluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(2,5-difluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(2,5-difluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(2,3-difluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(2,3-difluorophenyl)ethan-1-ol
(1R)-2-(4-{6-chloro-2-[(1-cyclopropyl-5-methyl-1H-pyrazol-4-yl)amino]quinazolin-7-yl}piperidin-1-yl)-1-(2,6-difluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(2,6-difluorophenyl)ethan-1-ol
4-[(4-{6-chloro-2-[(1-cyclopropyl-5-methyl-1H-pyrazol-4-yl)amino]quinazolin-7-yl}piperidin-1-yl)methyl]oxan-4-ol
(2R)-1-(4-{6-chloro-2-[(1-cyclopropyl-5-methyl-1H-pyrazol-4-yl)amino]quinazolin-7-yl}piperidin-1-yl)-3-methoxypropan-2-ol
(2S)-1-(4-{6-chloro-2-[(1-cyclopropyl-5-methyl-1H-pyrazol-4-yl)amino]quinazolin-7-yl}piperidin-1-yl)-3-methoxypropan-2-ol
(1R)-2-(4-{6-chloro-2-[(1-cyclopropyl-5-methyl-1H-pyrazol-4-yl)amino]quinazolin-7-yl}piperidin-1-yl)-1-(4-fluorophenyl)ethan-1-ol
(1S)-2-(4-{6-chloro-2-[(1-cyclopropyl-5-methyl-1H-pyrazol-4-yl)amino]quinazolin-7-yl}piperidin-1-yl)-1-(4-fluorophenyl)ethan-1-ol
1-[(4-{6-chloro-2-[(1-cyclopropyl-5-methyl-1H-pyrazol-4-yl)amino]quinazolin-7-yl}piperidin-1-yl)methyl]cyclobutan-1-ol
1-[(2S)-3-(4-{6-chloro-2-[(1-cyclopropyl-5-methyl-1H-pyrazol-4-yl)amino]quinazolin-7-yl}piperidin-1-yl)-2-hydroxypropyl]pyrrolidin-2-one
1-(4-{6-chloro-2-[(1-cyclopropyl-5-methyl-1H-pyrazol-4-yl)amino]quinazolin-7-yl}piperidin-1-yl)-2-methylpropan-2-ol
(S) 1-(4-{6-chloro-2-[(1-cyclopropyl-5-methyl-1H-pyrazol-4-yl)amino]quinazolin-7-yl}piperidin-1-yl)-3-phenylpropan-2-ol
(R) 1-(4-{6-chloro-2-[(1-cyclopropyl-5-methyl-1H-pyrazol-4-yl)amino]quinazolin-7-yl}piperidin-1-yl)-3-phenylpropan-2-ol
(S) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile
(R) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile
(S) 3-[3-(4-{6-chloro-2-[(1-cyclopropyl-5-methyl-1H-pyrazol-4-yl)amino]quinazolin-7-yl}piperidin-1-yl)-2-hydroxypropyl]-1,3-oxazolidin-2-one
(R) 3-[3-(4-{6-chloro-2-[(1-cyclopropyl-5-methyl-1H-pyrazol-4-yl)amino]quinazolin-7-yl}piperidin-1-yl)-2-hydroxypropyl]-1,3-oxazolidin-2-one
(S) 1-(4-{6-chloro-2-[(1-cyclopropyl-5-methyl-1H-pyrazol-4-yl)amino]quinazolin-7-yl}piperidin-1-yl)-2-phenylpropan-2-ol
(R) 1-(4-{6-chloro-2-[(1-cyclopropyl-5-methyl-1H-pyrazol-4-yl)amino]quinazolin-7-yl}piperidin-1-yl)-2-phenylpropan-2-ol
(S) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol
(R) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol
(S) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol
(R) 2-(4-{6-chloro-2-[(1-cyclopropyl-5-methyl-1H-pyrazol-4-yl)amino]quinazolin-7-yl}piperidin-1-yl)-1-(4-chlorophenyl)ethan-1-ol
(S) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile
(R) 4-[2-(4-{6-chloro-2-[(1-cyclopropyl-5-methyl-1H-pyrazol-4-yl)amino]quinazolin-7-yl}piperidin-1-yl)-1-hydroxyethyl]benzonitrile
(S) 1-(4-{6-chloro-2-[(1-cyclopropyl-5-methyl-1H-pyrazol-4-yl)amino]quinazolin-7-yl}piperidin-1-yl)-3-(morpholin-4-yl)propan-2-ol
(R) 1-(4-{6-chloro-2-[(1-cyclopropyl-5-methyl-1H-pyrazol-4-yl)amino]quinazolin-7-yl}piperidin-1-yl)-3-(morpholin-4-yl)propan-2-ol
trans-3-[(4-{6-chloro-2-[(1-cyclopropyl-5-methyl-1H-pyrazol-4-yl)amino]quinazolin-7-yl}piperidin-1-yl)methyl]-3-hydroxycyclobutane-1-carbonitrile
4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3S,4S)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol -continued (R)(3S,4S)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3R,4R)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(R)(3R,4R)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3S,4S)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3S,4S)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3R,4R)(3S,4S) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(S)(3R,4R)(3R,4R) 4-(4-(6-chloro-2-((5-chloro-1-(2,2-difluorocyclopropyl)-1H-pyrazol-4-yl)amino)quinazolin-7-yl)-3-fluoropiperidin-1-yl)-4-methyltetrahydrofuran-3-ol
(3S,4S)(3S,4S) 4-[4-(6-chloro-2-{[5-chloro-1-(3-fluorobicyclo[1.1.1]pentan-1-yl)-1H-pyrazol-4-yl]amino}quinazolin-7-yl)-3-fluoropiperidin-1-yl]oxolan-3-ol
(3S,4S)(3R,4R) 4-[4-(6-chloro-2-{[5-chloro-1-(3-fluorobicyclo[1.1.1]pentan-1-yl)-1H-pyrazol-4-yl]amino}quinazolin-7-yl)-3-fluoropiperidin-1-yl]oxolan-3-ol
(3R,4R)(3S,4S) 4-[4-(6-chloro-2-{[5-chloro-1-(3-fluorobicyclo[1.1.1]pentan-1-yl)-1H-pyrazol-4-yl]amino}quinazolin-7-yl)-3-fluoropiperidin-1-yl]oxolan-3-ol
(3R,4R)(3R,4R) 4-[4-(6-chloro-2-{[5-chloro-1-(3-fluorobicyclo[1.1.1]pentan-1-yl)-1H-pyrazol-4-yl]amino}quinazolin-7-yl)-3-fluoropiperidin-1-yl]oxolan-3-ol
(3S,4S)(3S,4S) 4-[4-(2-{[5-chloro-1-(3-fluorobicyclo[1.1.1]pentan-1-yl)-1H-pyrazol-4-yl]amino}-6-methylquinazolin-7-yl)-3-fluoropiperidin-1-yl]oxolan-3-ol
(3S,4S)(3R,4R) 4-[4-(2-{[5-chloro-1-(3-fluorobicyclo[1.1.1]pentan-1-yl)-1H-pyrazol-4-yl]amino}-6-methylquinazolin-7-yl)-3-fluoropiperidin-1-yl]oxolan-3-ol
(3R,4R)(3S,4S) 4-[4-(2-{[5-chloro-1-(3-fluorobicyclo[1.1.1]pentan-1-yl)-1H-pyrazol-4-yl]amino}-6-methylquinazolin-7-yl)-3-fluoropiperidin-1-yl]oxolan-3-ol
(3R,4R)(3R,4R) 4-[4-(2-{[5-chloro-1-(3-fluorobicyclo[1.1.1]pentan-1-yl)-1H-pyrazol-4-yl]amino}-6-methylquinazolin-7-yl)-3-fluoropiperidin-1-yl]oxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-methyl-1H-pyrazol-4-yl)amino]quinazolin-7-yl]-3-fluoropiperidin-1-yl)-4-methyloxolan-3-ol
(3S,4S)(3S,4S) 4-(4-{6-chloro-2-[(1,3-dimethyl-1H-pyrazol-5-yl)amino]quinazolin-7-yl}-3-fluoropiperidin-1-yl)oxolan-3-ol
(3S,4S)(3R,4R) 4-(4-{6-chloro-2-[(1,3-dimethyl-1H-pyrazol-5-yl)amino]quinazolin-7-yl}-3-fluoropiperidin-1-yl)oxolan-3-ol
(3R,4R)(3S,4S) 4-(4-{6-chloro-2-[(1,3-dimethyl-1H-pyrazol-5-yl)amino]quinazolin-7-yl}-3-fluoropiperidin-1-yl)oxolan-3-ol
3R,4R)(3R,4R) 4-(4-{6-chloro-2-[(1,3-dimethyl-1H-pyrazol-5-yl)amino]quinazolin-7-yl}-3-fluoropiperidin-1-yl)oxolan-3-ol
(3S,4S)(3S,4S) 4-(4-{6-chloro-2-[(1,3-dimethyl-1H-pyrazol-5-yl)amino]quinazolin-7-yl}-3-fluoropiperidin-1-yl)oxolan-3-ol
(3S,4S)(3R,4R) 4-(4-{6-chloro-2-[(1,3-dimethyl-1H-pyrazol-5-yl)amino]quinazolin-7-yl}-3-fluoropiperidin-1-yl)oxolan-3-ol
(3R,4R)(3S,4S) 4-(4-{6-chloro-2-[(1,3-dimethyl-1H-pyrazol-5-yl)amino]quinazolin-7-yl}-3-fluoropiperidin-1-yl)oxolan-3-ol
(3R,4R)(3R,4R) 4-(4-{6-chloro-2-[(1,3-dimethyl-1H-pyrazol-5-yl)amino]quinazolin-7-yl}-3-fluoropiperidin-1-yl)oxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3S,4S)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-methyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-methyl-1H-pyrazol-4-yl)amino]quinazolin-7-yl}-3-fluoropiperidin-1-yl)-4-methyloxolan-3-ol -continued

| |
|---|
| (3S,4S)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3S,4S) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3R,4R)(3R,4R) 4-(4-{6-chloro-2-[(5-cyclopropyl-1-methyl-1H-pyrazol-4-yl)amino]quinazolin-7-yl}-3-fluoropiperidin-1-yl)oxolan-3-ol |
| (3S,4S)(2S) 4-[4-{2-[(5-chloro-1-cyclopropyl-1H-pyrazol-4-yl)amino]-6-methylquinazolin-7-yl}-2-methylpiperidin-1-yl]oxolan-3-ol |
| (3R,4R)(2S) 4-[4-{2-[(5-chloro-1-cyclopropyl-1H-pyrazol-4-yl)amino]-6-methylquinazolin-7-yl}-2-methylpiperidin-1-yl]oxolan-3-ol |
| (R)(3S,4S)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3S,4S)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3R,4R)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3S,4S)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3S,4S)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3R,4R)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (3S,4S)(3S,4S) 4-(4-{2-[(3-tert-butyl-1-methyl-1H-pyrazol-5-yl)amino]-6-chloroquinazolin-7-yl}-3-fluoropiperidin-1-yl)-4-methyloxolan-3-ol |
| (3S,4S)(3R,4R) 4-(4-{2-[(3-tert-butyl-1-methyl-1H-pyrazol-5-yl)amino]-6-chloroquinazolin-7-yl}-3-fluoropiperidin-1-yl)-4-methyloxolan-3-ol |
| (3R,4R)(3S,4S) 4-(4-{2-[(3-tert-butyl-1-methyl-1H-pyrazol-5-yl)amino]-6-chloroquinazolin-7-yl}-3-fluoropiperidin-1-yl)-4-methyloxolan-3-ol |
| (3R,4R)(3R,4R) 4-(4-{2-[(3-tert-butyl-1-methyl-1H-pyrazol-5-yl)amino]-6-chloroquinazolin-7-yl}-3-fluoropiperidin-1-yl)-4-methyloxolan-3-ol |
| (R)(3S,4S)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3S,4S)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3R,4R)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (R)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3S,4S)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3S,4S)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3R,4R)(3S,4S) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (S)(3R,4R)(3R,4R) N-[5-chloro-1-(2,2-difluorocyclopropyl)-1H-pyrazol-4-yl]-7-[3-fluoro-1-(4-methoxyoxolan-3-yl)piperidin-4-yl]-6-methylquinazolin-2-amine |
| (3S,4S)(3S,4S) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol |

-continued (3S,4S)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3S,4S)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3R,4R)N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3S,4S) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3S,4S)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3R,4R)(3S,4S) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3R,4R)(3R,4R) 4-(4-{6-chloro-2-[(5-chloro-1-cyclopropyl-1H-pyrazol-4-yl)amino]quinazolin-7-yl}-3-fluoropiperidin-1-yl)-4-methyloxolan-3-ol
(3S,4S)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3S,4S) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3S,4S)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3R,4R)(3S,4S) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3R,4R)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3S,4S)(3S,4S) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3S,4S)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3R,4R)(3S,4S) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3R,4R)(3R,4R) 4-[4-(6-chloro-2-{[1-methyl-3-(trifluoromethyl)-1H-pyrazol-5-yl]amino}quinazolin-7-yl)-3-fluoropiperidin-1-yl]-4-methyloxolan-3-ol
(3S,4S)(3S,4S) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3S,4S)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3R,4R)(3S,4S) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3R,4R)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3S,4S)(3S,4S) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3S,4S)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3R,4R)(3S,4S) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3R,4R)(3R,4R) 4-[4-(6-chloro-2-{[1-methyl-5-(trifluoromethyl)-1H-pyrazol-4-yl]amino}quinazolin-7-yl)-3-fluoropiperidin-1-yl]-4-methyloxolan-3-ol
(3S,4S)(3S,4S)) 4-(4-(6-chloro-2-((1,5-dimethyl-1H-pyrazol-4-yl)amino)quinazolin-7-yl)-3-fluoropiperidin-1-yl)tetrahydrofuran-3-ol
(3S,4S)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol
(3R,4R)(3S,4S) 4-(4-(6-chloro-2-((1,5-dimethyl-1H-pyrazol-4-yl)amino)quinazolin-7-yl)-3-fluoropiperidin-1-yl)tetrahydrofuran-3-ol
(3R,4R)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol
(3S,4S)(3S,4S) 4-(4-(6-chloro-2-((1,5-dimethyl-1H-pyrazol-4-yl)amino)quinazolin-7-yl)-3-fluoropiperidin-1-yl)tetrahydrofuran-3-ol
(3S,4S)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol
(3R,4R)(3S,4S) 4-(4-(6-chloro-2-((1,5-dimethyl-1H-pyrazol-4-yl)amino)quinazolin-7-yl)-3-fluoropiperidin-1-yl)tetrahydrofuran-3-ol
(3R,4R)(3R,4R) 4-(4-(6-chloro-2-((1,5-dimethyl-1H-pyrazol-4-yl)amino)quinazolin-7-yl)-3-fluoropiperidin-1-yl)tetrahydrofuran-3-ol -continued (3S,4S)(3S,4S) 4-(4-(2-((1,5-dimethyl-1H-pyrazol-4-yl)amino)-6-methylquinazolin-7-yl)-3-fluoropiperidin-1-yl)tetrahydrofuran-3-ol
(3S,4S)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol
(3R,4R)(3S,4S) 4-(4-(2-((1,5-dimethyl-1H-pyrazol-4-yl)amino)-6-methylquinazolin-7-yl)-3-fluoropiperidin-1-yl)tetrahydrofuran-3-ol
(3R,4R)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol
(3S,4S)(3S,4S) 4-(4-(2-((1,5-dimethyl-1H-pyrazol-4-yl)amino)-6-methylquinazolin-7-yl)-3-fluoropiperidin-1-yl)tetrahydrofuran-3-ol
(3S,4S)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol
(3R,4R)(3S,4S) 4-(4-(2-((1,5-dimethyl-1H-pyrazol-4-yl)amino)-6-methylquinazolin-7-yl)-3-fluoropiperidin-1-yl)tetrahydrofuran-3-ol
(3R,4R)(3R,4R) 4-(4-(2-((1,5-dimethyl-1H-pyrazol-4-yl)amino)-6-methylquinazolin-7-yl)-3-fluoropiperidin-1-yl)tetrahydrofuran-3-ol
(3S,4S)(3S,4S) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3S,4S)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3R,4R)(3S,4S) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3R,4R)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3S,4S)(3S,4S) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3S,4S)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3R,4R)(3S,4S) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3R,4R)(3R,4R) 4-(4-(2-((5-chloro-1-methyl-1H-pyrazol-4-yl)amino)-6-methylquinazolin-7-yl)-3-fluoropiperidin-1-yl)tetrahydrofuran-3-ol
(3S,4S)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3S,4S) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3R,4R)(3R,4R) N-(5-chloro-1-cyclopropyl-1H-pyrazol-4-yl)-7-[3-fluoro-1-(4-methoxyoxolan-3-yl)piperidin-4-yl]-6-methylquinazolin-2-amine
(3S,4S)(3S,4S) 4-(4-(6-chloro-2-((5-chloro-1-(3-methoxybicyclo[1.1.1]pentan-1-yl)-1H-pyrazol-4-yl)amino)quinazolin-7-yl)-3-fluoropiperidin-1-yl)tetrahydrofuran-3-ol
(3S,4S)(3R,4R) 4-(4-(6-chloro-2-((5-chloro-1-(3-methoxybicyclo[1.1.1]pentan-1-yl)-1H-pyrazol-4-yl)amino)quinazolin-7-yl)-3-fluoropiperidin-1-yl)tetrahydrofuran-3-ol
(3R,4R)(3S,4S) 4-(4-(6-chloro-2-((5-chloro-1-(3-methoxybicyclo[1.1.1]pentan-1-yl)-1H-pyrazol-4-yl)amino)quinazolin-7-yl)-3-fluoropiperidin-1-yl)tetrahydrofuran-3-ol
(3R,4R)(3R,4R) 4-(4-(6-chloro-2-((5-chloro-1-(3-methoxybicyclo[1.1.1]pentan-1-yl)-1H-pyrazol-4-yl)amino)quinazolin-7-yl)-3-fluoropiperidin-1-yl)tetrahydrofuran-3-ol
3-(4-(6-methyl-2-((5-methyl-1-(1-methylcyclopropyl)-1H-pyrazol4-yl)amino)quinazolin-7-yl)piperidin-1-yl)propanenitrile
3-(4-(2-((5-chloro-1-(1-methylcyclopropyl)-1H-pyrazol-4-yl)amino)-6-methylquinazolin-7-yl)piperidin-1-yl)propanenitrile
(3S,4S) N-(1-cyclopropyl-5-methyl-1H-pyrazol-4-yl)-7-[3-fluoro-1-(oxetan-3-yl)piperidin-4-yl]-6-methylquinazolin-2-amine
(3R,4R) N-(1-cyclopropyl-5-methyl-1H-pyrazol-4-yl)-7-[3-fluoro-1-(oxetan-3-yl)piperidin-4-yl]-6-methylquinazolin-2-amine
(3S,4S) N-(1-cyclopropyl-5-methyl-1H-pyrazol-4-yl)-7-[3-fluoro-1-(oxetan-3-yl)piperidin-4-yl]-6-methylquinazolin-2-amine
(3R,4R) N-(1-cyclopropyl-5-methyl-1H-pyrazol-4-yl)-7-[3-fluoro-1-(oxetan-3-yl)piperidin-4-yl]-6-methylquinazolin-2-amine
(3S,4S) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol
(3R,4R) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol
(3S,4S) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol
(3R,4R) 1-[4-({7-[3-fluoro-1-(oxetan-3-yl)piperidin-4-yl]-6-methylquinazolin-2-yl}amino)-5-methyl-1H-pyrazol-1-yl]-2-methylpropan-2-ol
(3S,4S) 4-(4-{2-[(1-cyclopropyl-5-methyl-1H-pyrazol-4-yl)amino]-6-methylquinazolin-7-yl}piperidin-1-yl)oxolan-3-ol
(3R,4R) 4-(4-{2-[(1-cyclopropyl-5-methyl-1H-pyrazol-4-yl)amino]-6-methylquinazolin-7-yl}piperidin-1-yl)oxolan-3-ol
N-[1-(bicyclo[1.1.1]pentan-1-yl)-5-methyl-1H-pyrazol-4-yl]-6-methyl-7-[1-(3-methyloxetan-3-yl)piperidin-4-yl]quinazolin-2-amine
(3S,4S)(3S,4S) 4-(4-{2-[(1,3-dimethyl-1H-pyrazol-5-yl)amino]-6-methylquinazolin-7-yl}-3-fluoropiperidin-1-yl)oxolan-3-ol
(3S,4S)(3R,4R) 4-(4-{2-[(1,3-dimethyl-1H-pyrazol-5-yl)amino]-6-methylquinazolin-7-yl}-3-fluoropiperidin-1-yl)oxolan-3-ol -continued (3R,4R)(3S,4S) 4-(4-{2-[(1,3-dimethyl-1H-pyrazol-5-yl)amino]-6-methylquinazolin-7-yl}-3-fluoropiperidin-1-yl)oxolan-3-ol
(3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol
(3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol
(3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol
(3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}-3-fluoropiperidin-1-yl)oxolan-3-ol
(3S,4S)(3S,4S) or (3S,4S)(3R,4R) or (3R,4R)(3S,4S) or (3R,4R)(3R,4R) 4-(4-{2-[(1,3-dimethyl-1H-pyrazol-5-yl)amino]-6-methylquinazolin-7-yl}piperidin-1-yl)-4-methyloxolan-3-ol
(3S,4S) or (3R,4R) 4-(4-{2-[(3-tert-butyl-1-methyl-1H-pyrazol-5-yl)amino]-6-methylquinazolin-7-yl}piperidin-1-yl)-4-methyloxolan-3-ol
(3S,4S) or (3R,4R) 4-methyl-4-[4-(6-methyl-2-{[1-methyl-3-(trifluoromethyl)-1H-pyrazol-5-yl]amino}quinazolin-7-yl)piperidin-1-yl]oxolan-3-ol
(3R,4R) 2-((5-chloro-1-cyclopropyl-1H-pyrazol-4-yl)amino)-7-(3-fluoro-1-(oxetan-3-yl)piperidin-4-yl)quinazoline-6-carbonitrile
(3S,4S) 2-((5-chloro-1-cyclopropyl-1H-pyrazol-4-yl)amino)-7-(3-fluoro-1-(oxetan-3-yl)piperidin-4-yl)quinazoline-6-carbonitrile
2-((5-chloro-1-cyclopropyl-1H-pyrazol-4-yl)amino)-7-(1-(oxetan-3-yl)piperidin-4-yl)quinazoline-6-carbonitrile
(R)(3S,4S) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(S)(3S,4S) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(R)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(R)(3S,4S) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(S)(3S,4S) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(R)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(S)(3R,4R) 2-((5-chloro-1-(2,2-difluorocyclopropyl)-1H-pyrazol-4-yl)amino)-7-(3-fluoro-1-(oxetan-3-yl)piperidin-4-yl)quinazoline-6-carbonitrile
(3S,4S) or (3R,4R) 4-methyl-4-(4-(6-methyl-2-((1-methyl-5-(trifluoromethyl)-1H-pyrazol-4-yl)amino)quinazolin-7-yl)piperidin-1-yl)tetrahydrofuran-3-ol
(R)(3S,4S)(3S,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3S,4S)(3R,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3R,4R)(3S,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3R,4R)(3R,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3S,4S)(3S,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3S,4S)(3R,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3R,4R)(3S,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(R)(3R,4R)(3R,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3S,4S)(3S,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3S,4S)(3R,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3R,4R)(3S,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3R,4R)(3R,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3S,4S)(3S,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3S,4S)(3R,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3R,4R)(3S,4R) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(S)(3R,4R)(3R,4S) 6-chloro-N-(5-chloro-1-(2,2-difluorocyclopropyl)-1H-pyrazol-4-yl)-7-(3-fluoro-1-(4-fluorotetrahydrofuran-3-yl)piperidin-4-yl)quinazolin-2-amine
(3S,4S) 6-chloro-N-(1-cyclopropyl-5-methyl-1H-pyrazol-4-yl)-7-(1-(4-methoxy-3-methyltetrahydrofuran-3-yl)piperidin-4-yl)quinazolin-2-amine -continued (3R,4R) 6-chloro-N-(1-cyclopropyl-5-methyl-1H-pyrazol-4-yl)-7-(1-(4-methoxy-3-methyltetrahydrofuran-3-yl)piperidin-4-yl)quinazolin-2-amine
(3S,4S) 6-chloro-N-(1-cyclopropyl-5-methyl-1H-pyrazol-4-yl)-7-[1-(4-fluorooxolan-3-yl)piperidin-4-yl]quinazolin-2-amine
(3R,4R) 6-chloro-N-(1-cyclopropyl-5-methyl-1H-pyrazol-4-yl)-7-[1-(4-fluorooxolan-3-yl)piperidin-4-yl]quinazolin-2-amine
(3S,4R) 6-chloro-N-(1-cyclopropyl-5-methyl-1H-pyrazol-4-yl)-7-[1-(4-fluorooxolan-3-yl)piperidin-4-yl]quinazolin-2-amine
(3R,4S) 6-chloro-N-(1-cyclopropyl-5-methyl-1H-pyrazol-4-yl)-7-[1-(4-fluorooxolan-3-yl)piperidin-4-yl]quinazolin-2-amine
(3S,4S) 6-chloro-N-(1-cyclopropyl-5-methyl-1H-pyrazol-4-yl)-7-[1-(4-methoxyoxolan-3-yl)piperidin-4-yl]quinazolin-2-amine
(3S,4S) 6-chloro-N-(1-cyclopropyl-5-methyl-1H-pyrazol-4-yl)-7-[1-(4-methoxyoxolan-3-yl)piperidin-4-yl]quinazolin-2-amine
(S)(3S,4R)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3R,4S)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3R,4R)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3S,4S)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3S,4R)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3R,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3R,4R)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(S)(3S,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3S,4R)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3R,4S)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3R,4R)(3S,4S) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3S,4S)(3S,4S) (N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3S,4R)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3R,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3R,4R)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(R)(3S,4S)(3R,4R) N-[1-(2,2-difluorocyclopropyl)-5-methyl-1H-pyrazol-4-yl]-7-[3-fluoro-1-(4-fluorooxolan-3-yl)piperidin-4-yl]-6-methylquinazolin-2-amine
(3S,4S)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3S,4R)(3S,4S) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3R,4S)(3S,4S) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3R,4R)(3S,4S) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3S,4S)(3S,4S) or N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3S,4R)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3R,4S)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3R,4R)(3R,4R) N-(5-chloro-1-cyclopropyl-1H-pyrazol-4-yl)-7-[3-fluoro-1-(4-fluorooxolan-3-yl)piperidin-4-yl]-6-methylquinazolin-2-amine
(3S,4S)(3R,4R)N-(5-chloro-1-cyclopropyl-1H-pyrazol-4-yl)-7-[3-fluoro-1-(4-fluorooxolan-3-yl)piperidin-4-yl]-6-methylquinazolin-2-amine
6-chloro-N-(5-chloro-1-(2,2,2-trifluoroethyl)-1H-pyrazol-4-yl)-7-(1-(oxetan-3-yl)piperidin-4-yl)quinazolin-2-amine
N-(5-bromo-1-cyclopropyl-1H-pyrazol-4-yl)-6-chloro-7-(1-(oxetan-3-yl)piperidin-4-yl)quinazolin-2-amine
6-chloro-N-[5-chloro-1-(difluoromethyl)-1H-pyrazol-4-yl]-7-[1-(oxetan-3-yl)piperidin-4-yl]quinazolin-2-amine
(S) 6-chloro-N-[5-chloro-1-(1,1,1-trifluoropropan-2-yl)-1H-pyrazol-4-yl]-7-[1-(oxetan-3-yl)piperidin-4-yl]quinazolin-2-amine
(R) 6-chloro-N-[5-chloro-1-(1,1,1-trifluoropropan-2-yl)-1H-pyrazol-4-yl]-7-[1-(oxetan-3-yl)piperidin-4-yl]quinazolin-2-amine
6-chloro-N-(4-chloro-3-methyl-1,2-thiazol-5-yl)-7-[1-(oxetan-3-yl)piperidin-4-yl]quinazolin-2-amine
3-(4-{6-chloro-2-[(5-chloro-1-cyclopropyl-1H-pyrazol-4-yl)amino]quinazolin-7-yl}piperidin-1-yl)propanenitrile -continued 3-(4-(6-chloro-2-((5-chloro-1-cyclopropyl-1H-pyrazol-4-yl)amino)quinazolin-7-yl)piperidin-1-yl)thietane 1,1-dioxide
6-chloro-N-(5-chl oro-1-cyclopropyl-1H-pyrazol-4-yl)-7-[1-(oxetan-3-yl)piperidin-4-yl]quinazolin-2-amine
6-chloro-N-[5-chloro-1-(1-methylcyclopropyl)-1H-pyrazol-4-yl]-7-(piperidin-4-yl)quinazolin-2-amine
6-chloro-N-(5-chloro-1-cyclopropyl-1H-pyrazol-4-yl)-7-[1-(3-methyloxetan-3-yl)piperidin-4-yl]quinazolin-2-amine
2-(5-chloro-4-{[6-chloro-7-(1-methylpiperidin-4-yl)quinazolin-2-yl]amino}-1H-pyrazol-1-yl)-2-methylpropan-1-ol
3-(4-(6-chloro-2-((5-chl oro-1-(1-methylcyclopropyl)-1H-pyrazol-4-yl)amino)quinazolin-7-yl)piperidin-1-yl)thietane 1,1-dioxide
3-[4-(6-chloro-2-[[5-chloro-1-(1-methylcyclopropyl)-1H-pyrazol-4-yl]amino}quinazolin-7-yl)piperidin-1-yl]propanenitrile
6-chloro-N-[5-chloro-1-(1-methylcyclopropyl)-1H-pyrazol-4-yl]-7-(1-methylpiperidin-4-yl)quinazolin-2-amine
6-chloro-N-[5-chloro-1-(1-methylcyclopropyl)-1H-pyrazol-4-yl]-7-[1-(3-methyloxetan-3-yl)piperidin-4-yl]quinazolin-2-amine
6-chloro-N-(5-chloro-1-cyclopropyl-1H-pyrazol-4-yl)-7-(1-(oxetan-3-yl-2,2,4,4-d4)piperidin-4-yl)quinazolin-2-amine
6-chloro-N-{5-chloro-1-[(3-methoxycyclobutyl)methyl]-1H-pyrazol-4-yl}-7-[1-(oxetan-3-yl)piperidin-4-yl]quinazolin-2-amine
(S) 6-chloro-N-(4-chloro-3-methyl-1,2-thiazol-5-yl)-7-[1-(oxolan-3-yl)piperidin-4-yl]quinazolin-2-amine
(R) 6-chloro-N-(4-chloro-3-methyl-1,2-thiazol-5-yl)-7-[1-(oxolan-3-yl)piperidin-4-yl]quinazolin-2-amine
(3S,4S)(S) 6-chloro-N-(4-chloro-3-methyl-1,2-thiazol-5-yl)-7-[3-fluoro-1-(oxolan-3-yl)piperidin-4-yl]quinazolin-2-amine
(3S,4S)(R) 6-chloro-N-(4-chloro-3-methyl-1,2-thiazol-5-yl)-7-[3-fluoro-1-(oxolan-3-yl)piperidin-4-yl]quinazolin-2-amine
(3R,4R)(S) 6-chloro-N-(4-chloro-3-methyl-1,2-thiazol-5-yl)-7-[3-fluoro-1-(oxolan-3-yl)piperidin-4-yl]quinazolin-2-amine
(3R,4R)(R) 6-chloro-N-(4-chloro-3-methyl-1,2-thiazol-5-yl)-7-[3-fluoro-1-(oxolan-3-yl)piperidin-4-yl]quinazolin-2-amine
(3S,4S)(S) 6-chloro-N-(4-chloro-3-methyl-1,2-thiazol-5-yl)-7-[3-fluoro-1-(oxolan-3-yl)piperidin-4-yl]quinazolin-2-amine
(3S,4S)(R) 6-chloro-N-(4-chloro-3-methyl-1,2-thiazol-5-yl)-7-[3-fluoro-1-(oxolan-3-yl)piperidin-4-yl]quinazolin-2-amine
(3R,4R)(S) 6-chloro-N-(4-chloro-3-methyl-1,2-thiazol-5-yl)-7-[3-fluoro-1-(oxolan-3-yl)piperidin-4-yl]quinazolin-2-amine
(3R,4R)(R) 6-chloro-N-(4-chloro-3-methyl-1,2-thiazol-5-yl)-7-[3-fluoro-1-(oxolan-3-yl)piperidin-4-yl]quinazolin-2-amine
1-{[5-chloro-4-({6-chloro-7-[1-(oxetan-3-yl)piperidin-4-yl]quinazolin-2-yl}amino)-1H-pyrazol-1-yl]methyl}cyclopropane-1-carbonitrile
(S) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol
(R) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol
1-{[5-chloro-4-({6-chloro-7-[1-(oxetan-3-yl)piperidin-4-yl]quinazolin-2-yl}amino)-1H-pyrazol-1-yl]methyl}cyclobutan-1-ol
(S) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol
(R) 3-[5-chloro-4-({6-chloro-7-[1-(oxetan-3-yl)piperidin-4-yl]quinazolin-2-yl}amino)-1H-pyrazol-1-yl]-1,1,1-trifluoro-2-methylpropan-2-ol
(R)(3S,4S) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(S)(3S,4S) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(R)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(R)(3S,4S) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(S)(3S,4S) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(R)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(S)(3R,4R) 6-chloro-N-[5-chloro-1-(2,2-difluorocyclopropyl)-1H-pyrazol-4-yl]-7-[3-fluoro-1-(oxetan-3-yl)piperidin-4-yl]quinazolin-2-amine
(3S,4S)(3S,4S) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol
(3S,4S)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol
(3R,4R)(3S,4S) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol
(3R,4R)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol -continued

| |
|---|
| (3S,4S)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-5-chloro-1H-pyrazol-4-yl]amino}-6-methylquinazolin-7-yl)-3-fluoropiperidin-1-yl]oxolan-3-ol |
| (3S,4S)(3S,4S) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol |
| (3S,4S)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol |
| (3R,4R)(3S,4S) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol |
| (3R,4R)(3R,4R) 4-[4-(2-{[1-(bicyclo[1.1.1]pentan-1-yl)-5-chloro-1H-pyrazol-4-yl]amino}-6-chloroquinazolin-7-yl)-3-fluoropiperidin-1-yl]oxolan-3-ol |
| N-[1-(bicyclo[1.1.1]pentan-1-yl)-5-chloro-1H-pyrazol-4-yl]-6-chloro-7-[1-(3-methyloxetan-3-yl)piperidin-4-yl]quinazolin-2-amine |
| 6-chloro-N-{5-chloro-1-[3-(methoxymethyl)bicyclo[1.1.1]pentan-1-yl]-1H-pyrazol-4-yl}-7-[1-(3-methyloxetan-3-yl)piperidin-4-yl]quinazolin-2-amine |
| (3S,4S) 4-(4-(2-((1-cyclopropyl-5-methyl-1H-pyrazol-4-yl)amino)-6-(trifluoromethyl)quinazolin-7-yl)piperidin-1-yl)-4-methyltetrahydrofuran-3-ol |
| (3R,4R) 4-(4-(2-((1-cyclopropyl-5-methyl-1H-pyrazol-4-yl)amino)-6-(trifluoromethyl)quinazolin-7-yl)piperidin-1-yl)-4-methyltetrahydrofuran-3-ol |
| (3S,4S) 4-(4-(6-chloro-2-((3-chloro-1-methyl-1H-pyrazol-5-yl)amino)quinazolin-7-yl)piperidin-1-yl)-4-methyltetrahydrofuran-3-ol, and |
| 3R,4R) 4-(4-(6-chloro-2-((3-chloro-1-methyl-1H-pyrazol-5-yl)amino)quinazolin-7-yl)piperidin-1-yl)-4-methyltetrahydrofuran-3-ol. |

15. A compound according to claim 14, or a pharmaceutically acceptable salt thereof selected from:

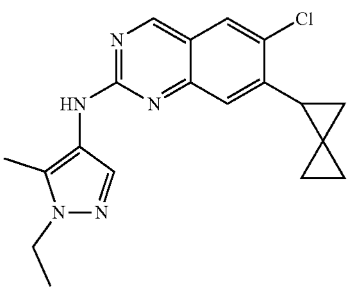

-continued

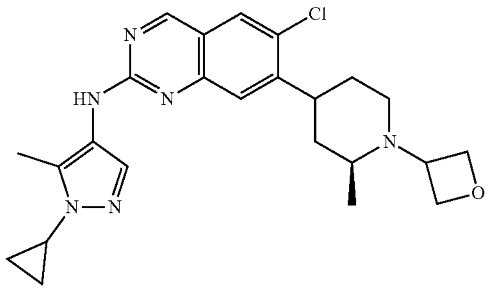

-continued
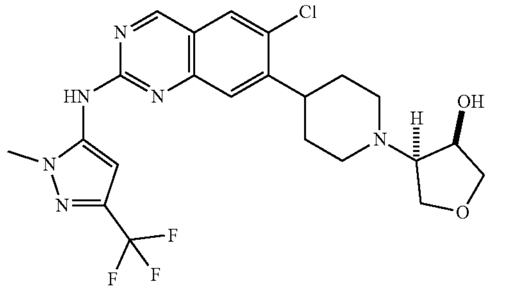
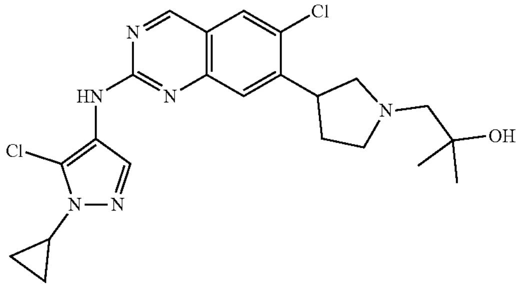
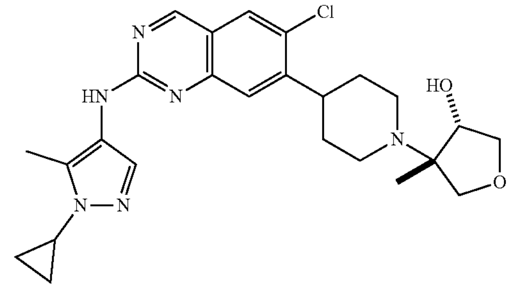
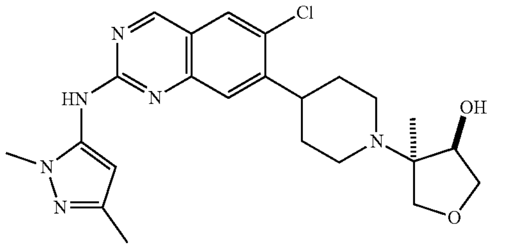
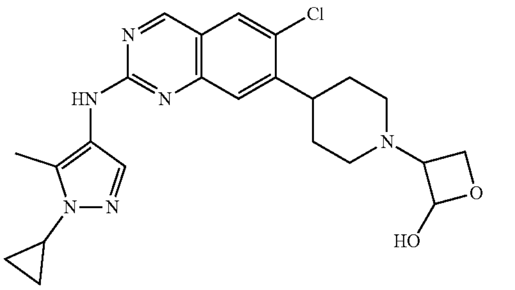
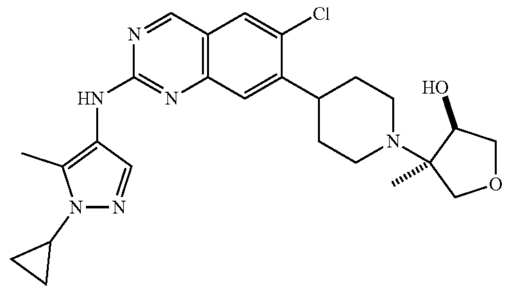
-continued
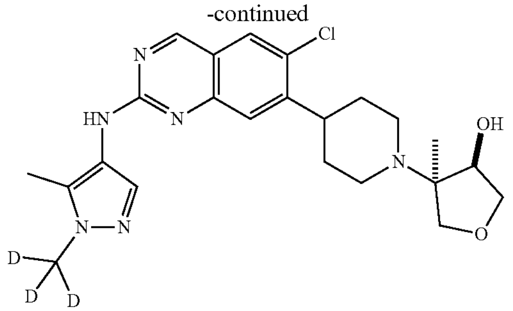
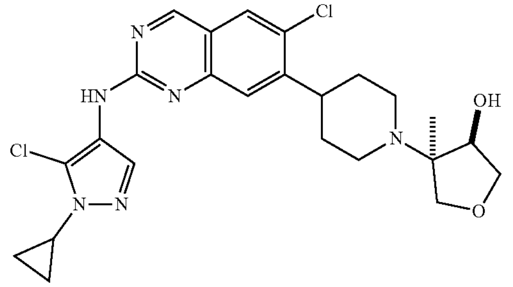
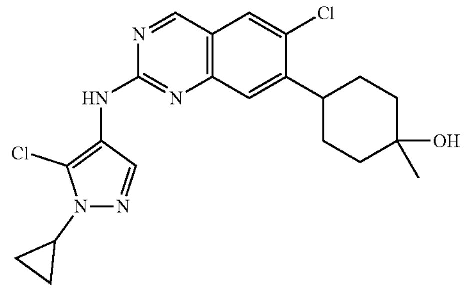
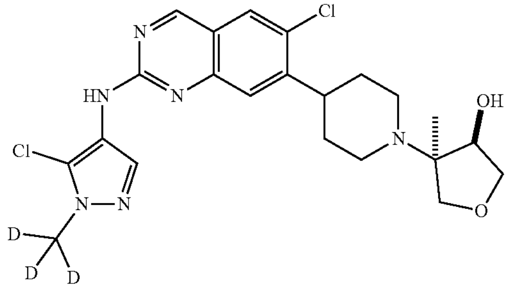
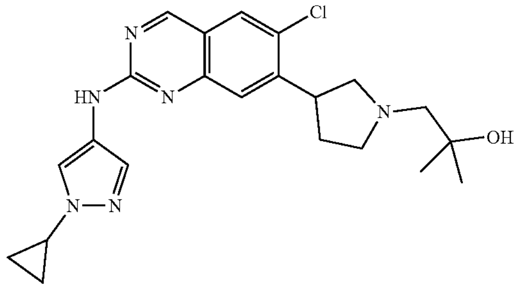
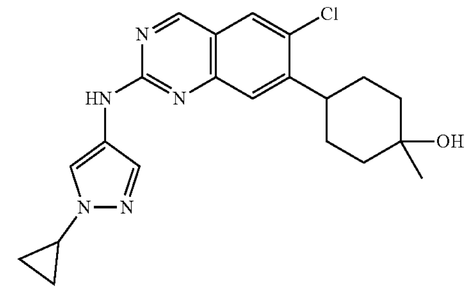

-continued
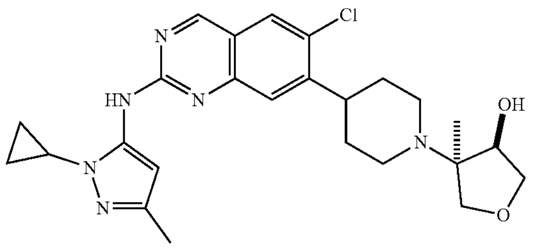
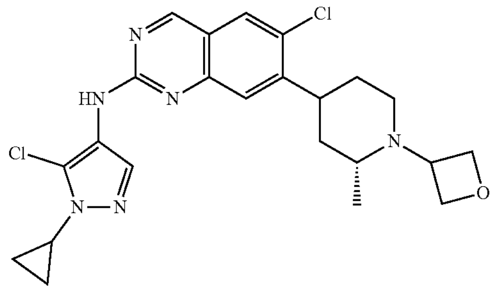
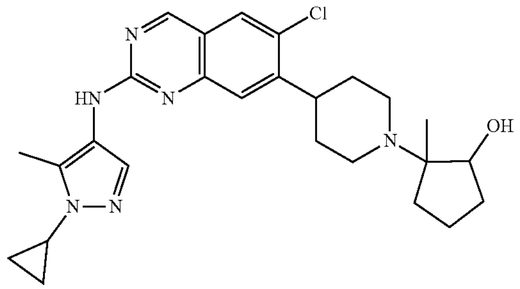
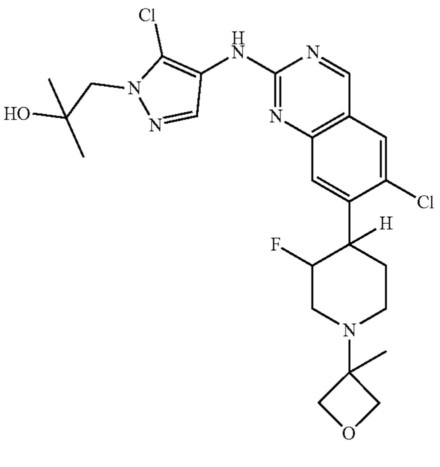
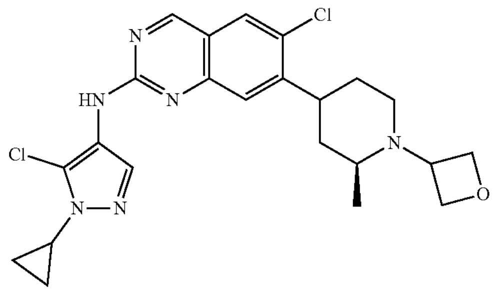
-continued
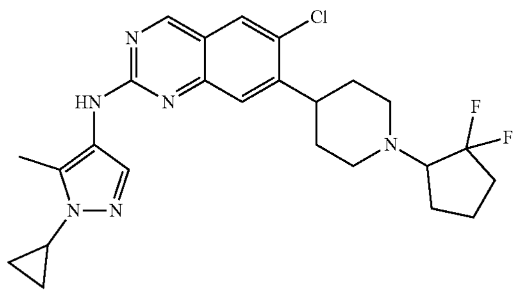
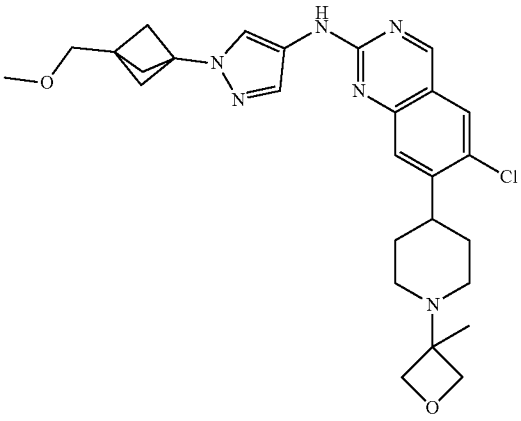
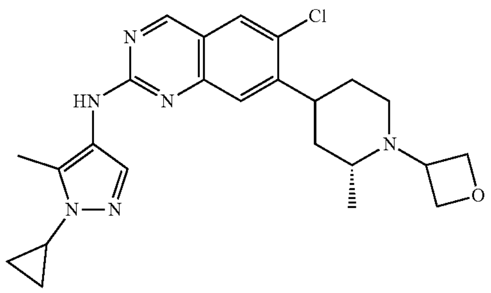
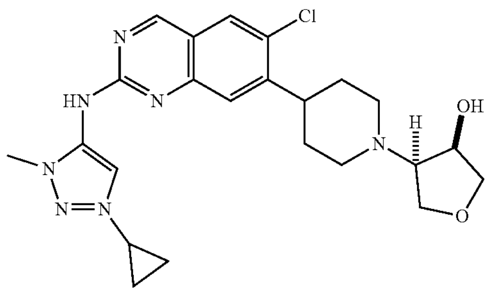
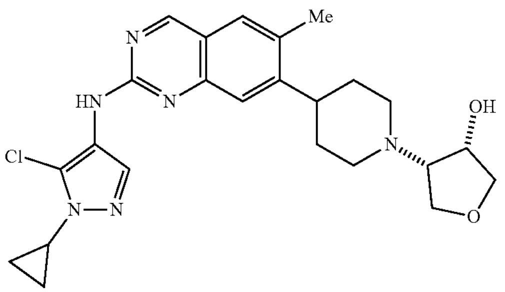

-continued
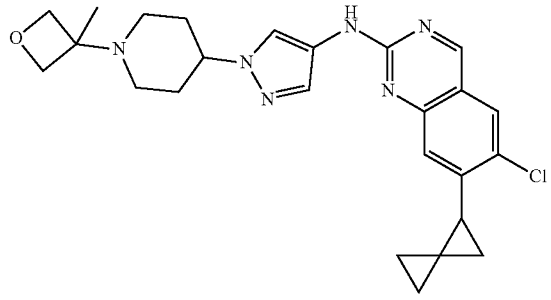
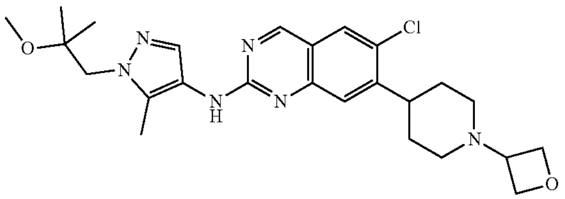
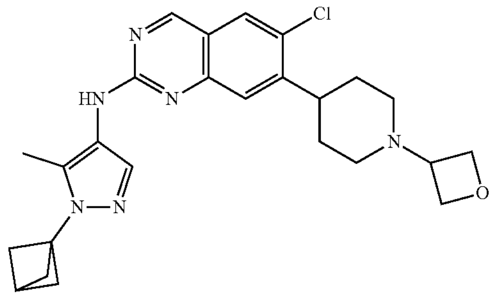
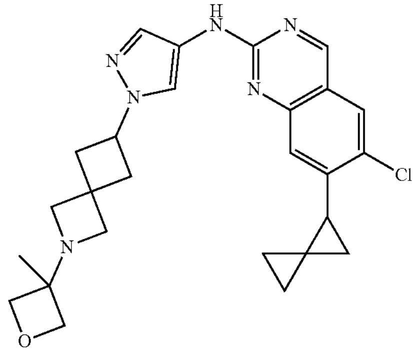
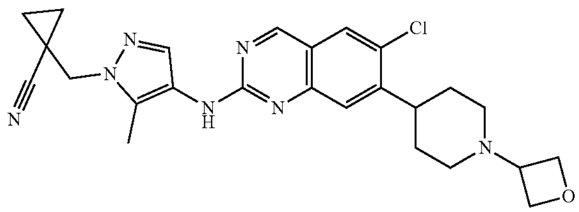
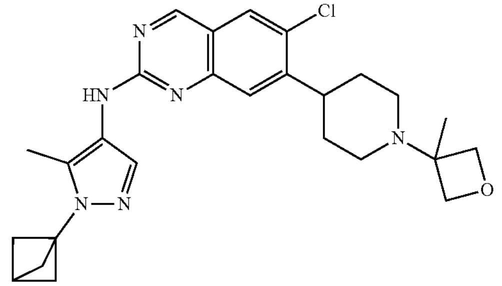
-continued
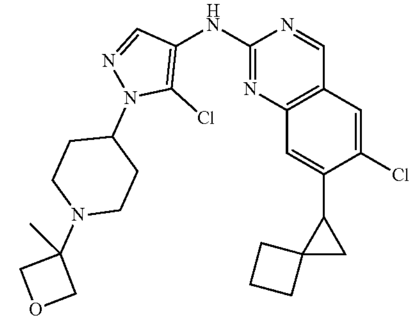
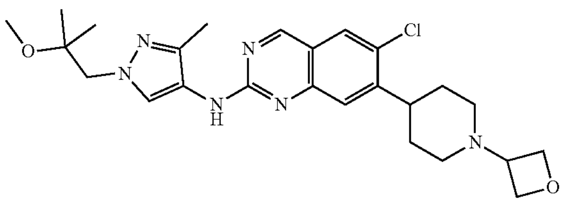
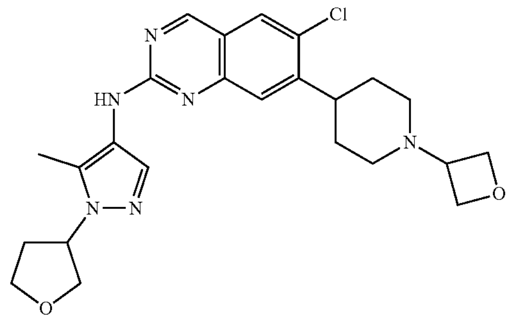
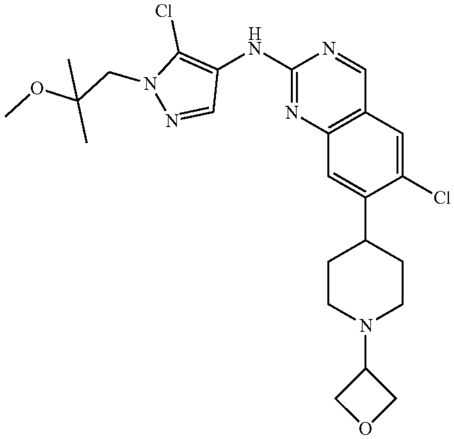
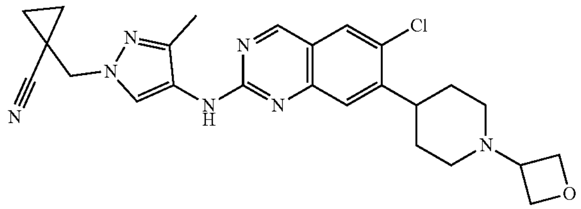

-continued
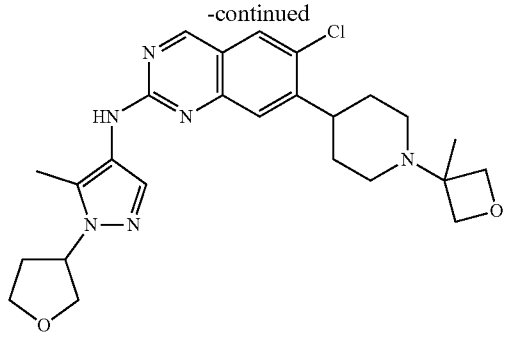
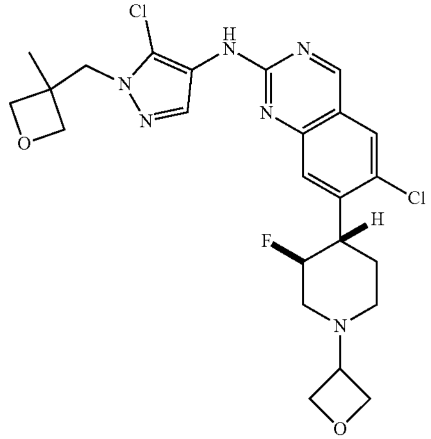
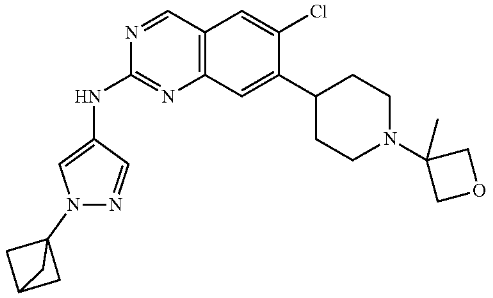
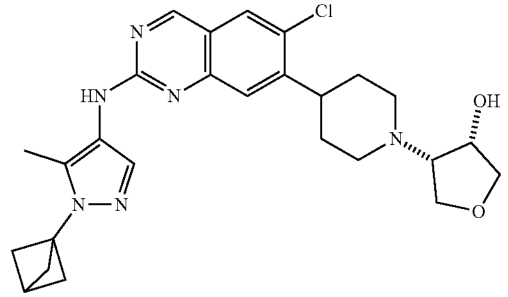
-continued
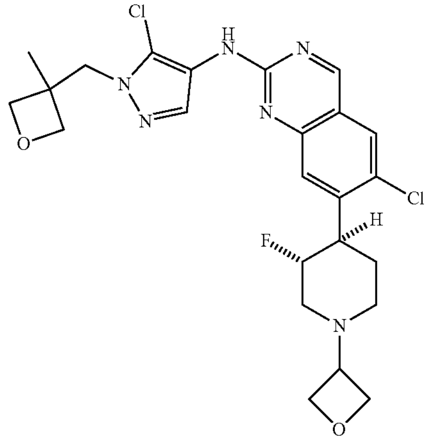
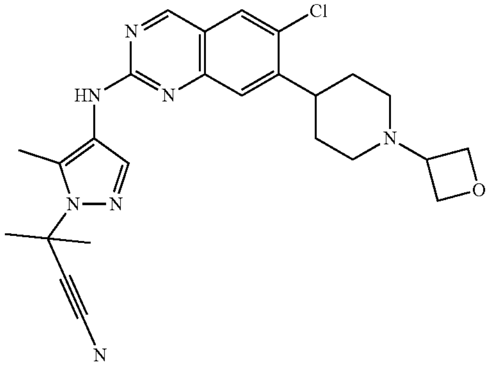
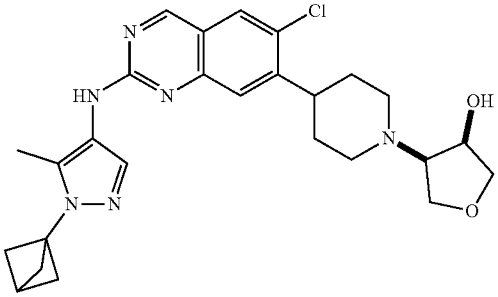
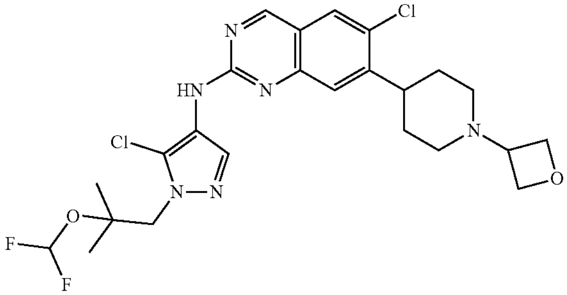
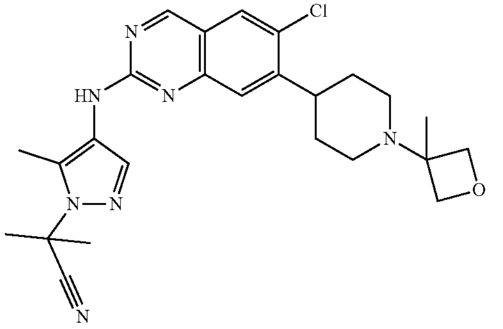

-continued
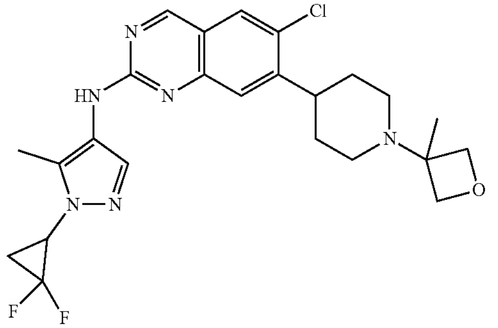
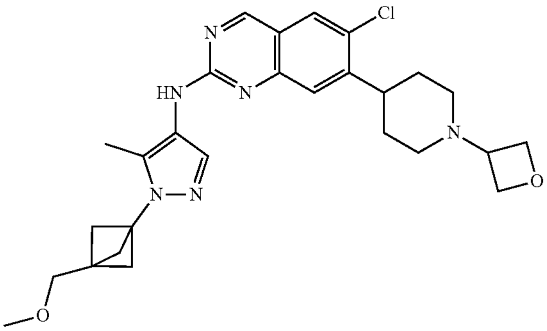
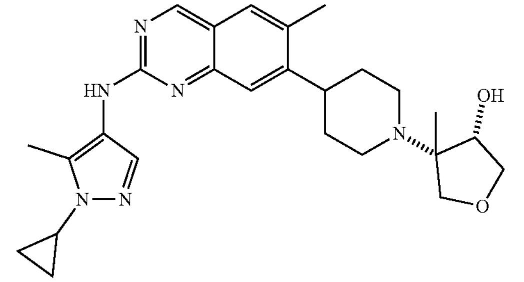
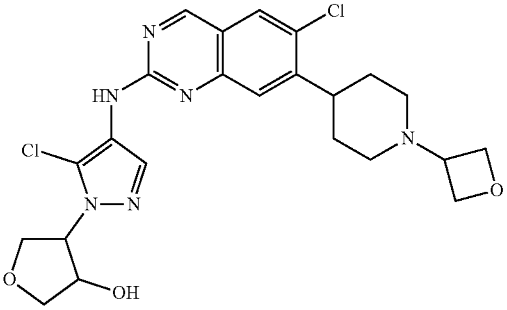
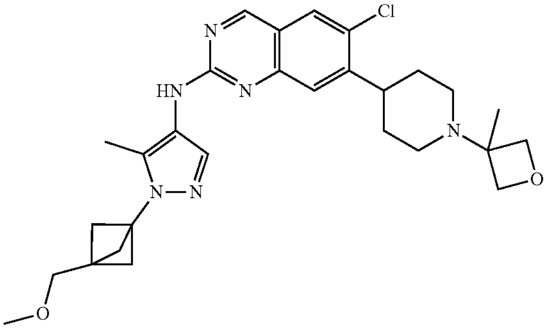
-continued
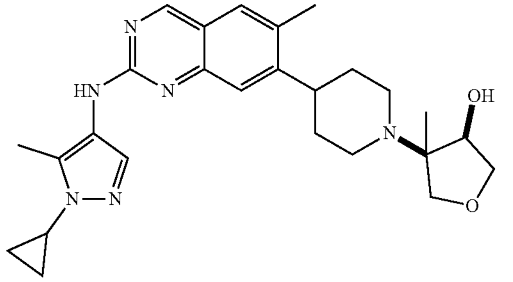
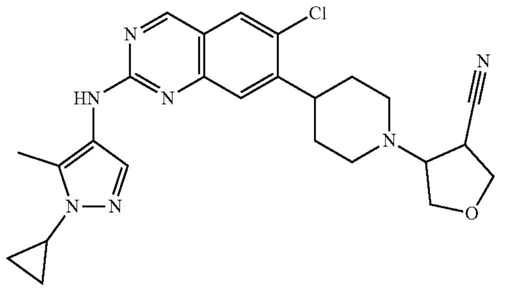
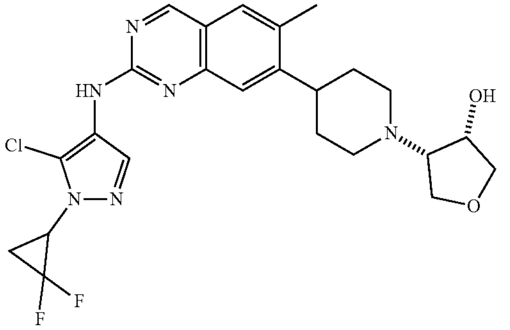
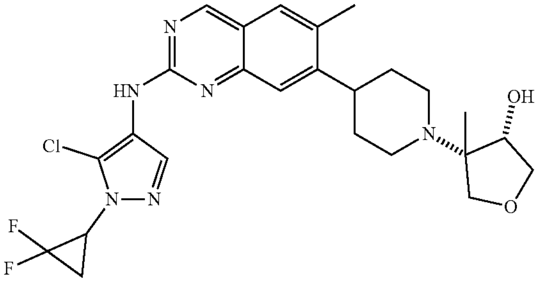
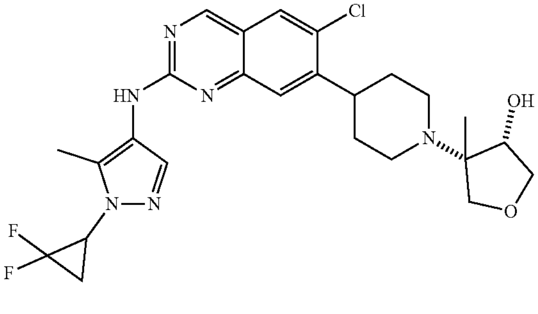

-continued
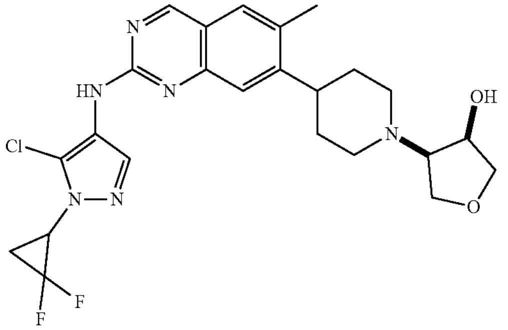
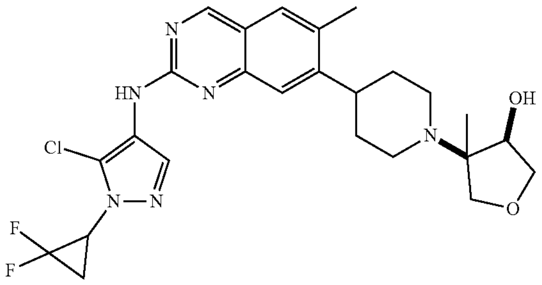
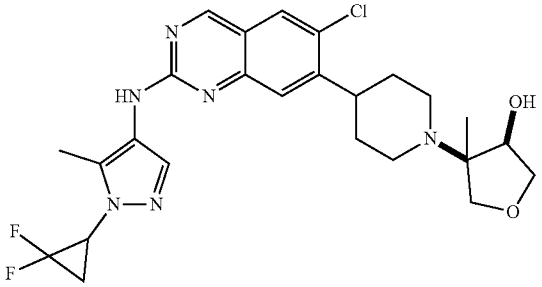
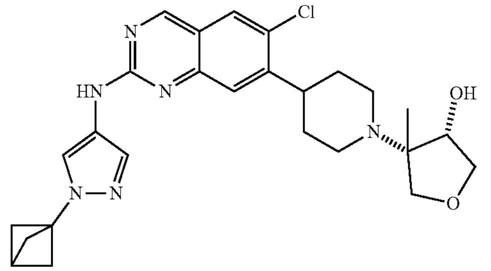
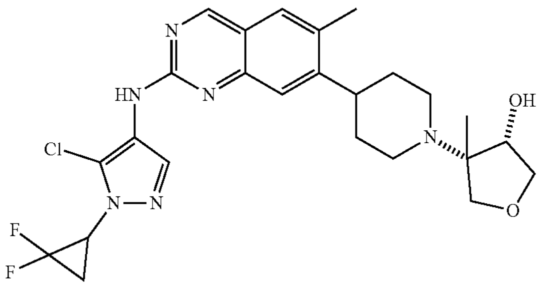
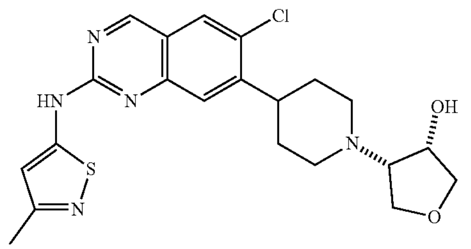
-continued
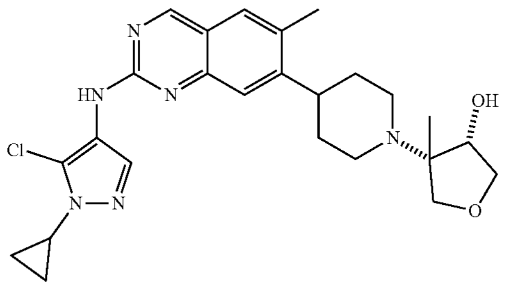
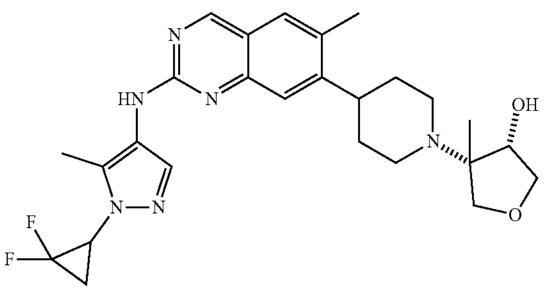
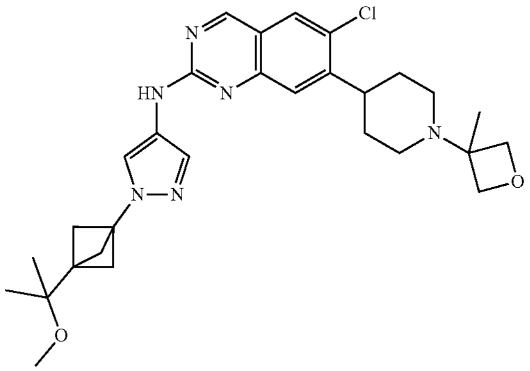
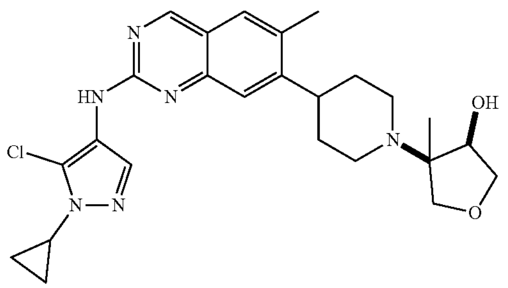
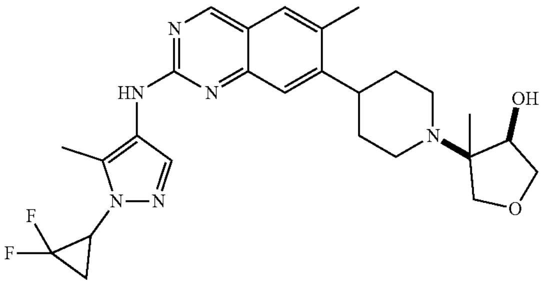

-continued
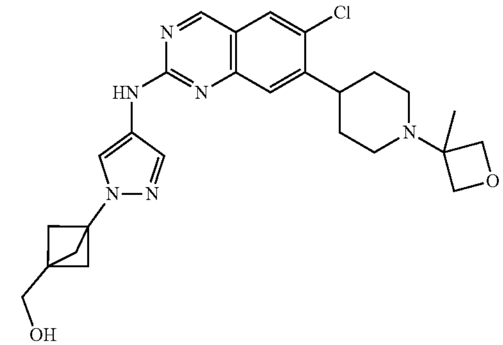
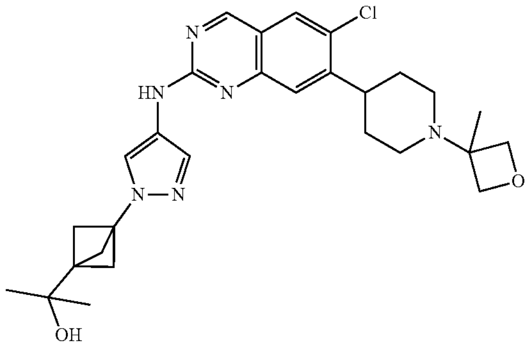
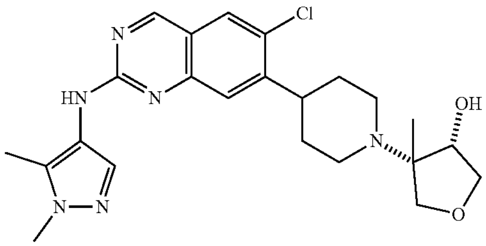
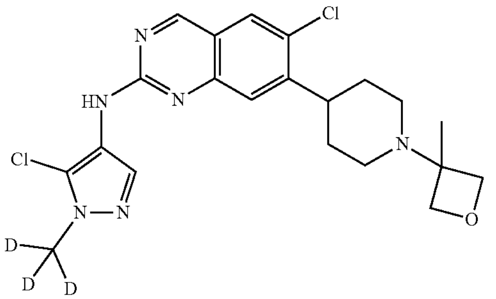
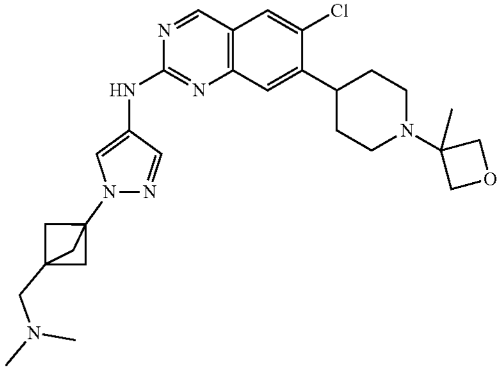
-continued
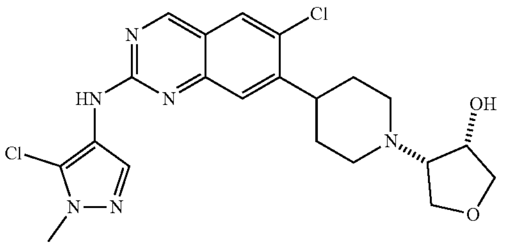
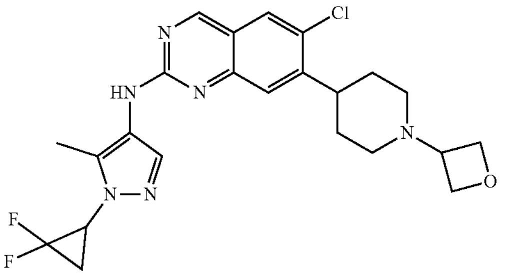
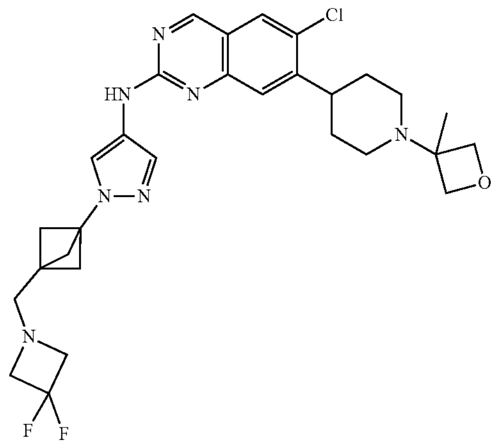
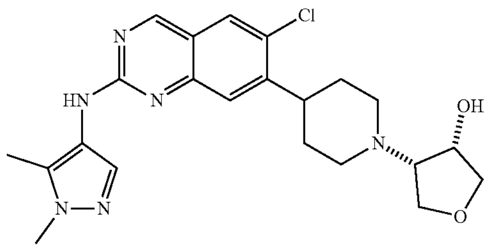
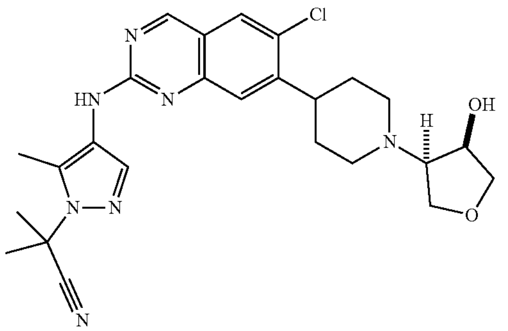

-continued
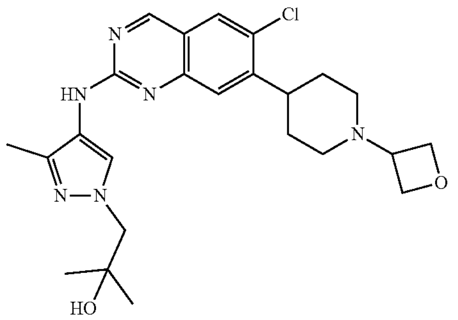
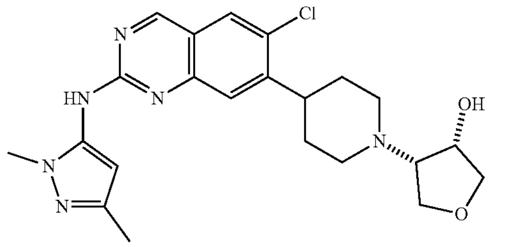
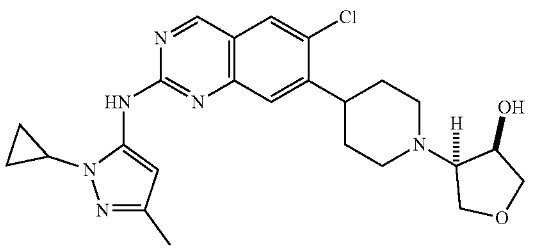
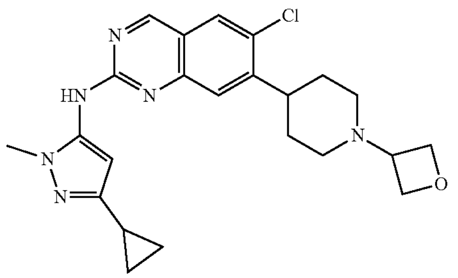
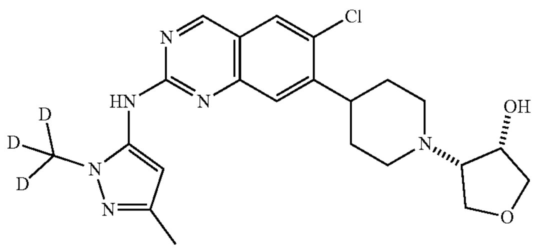
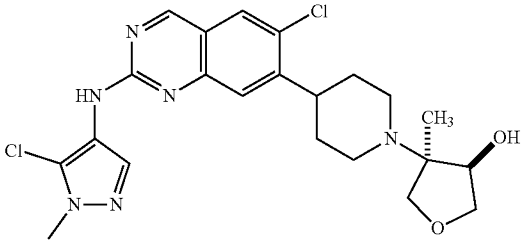
-continued
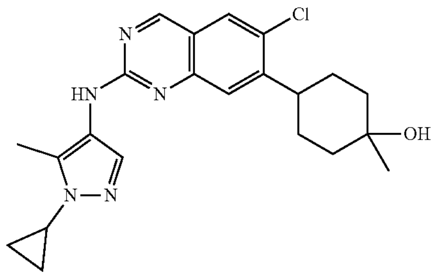
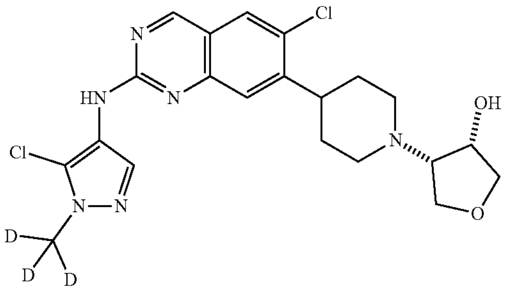
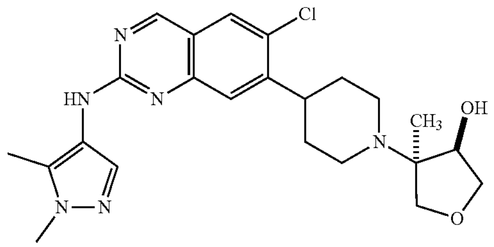
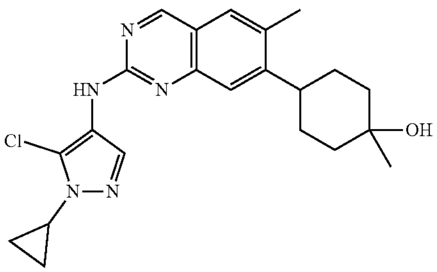
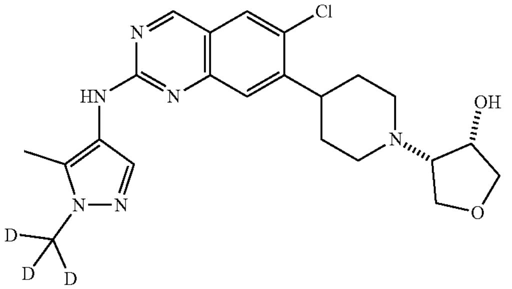
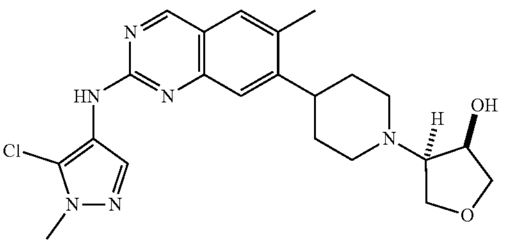

-continued
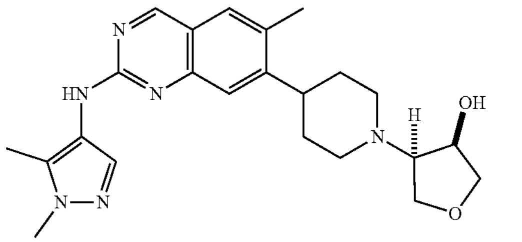
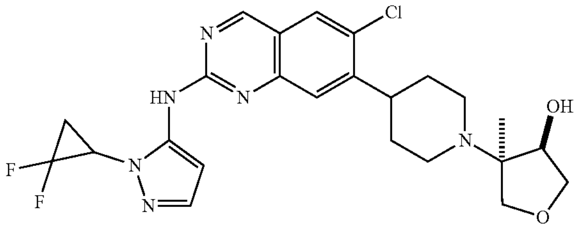
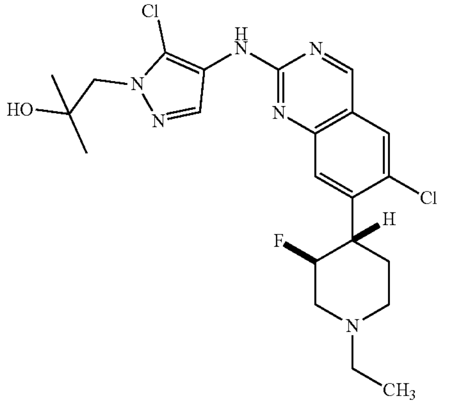
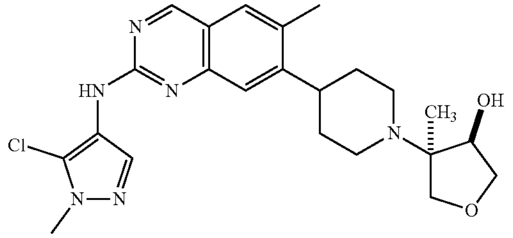
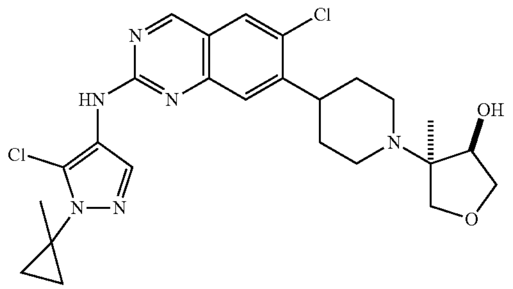
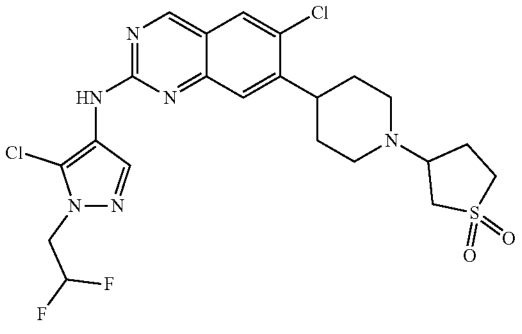
-continued
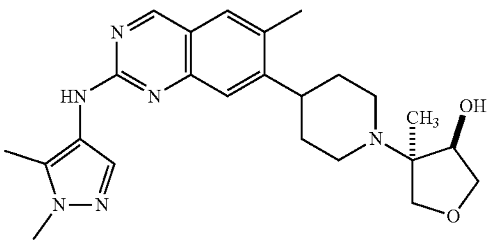
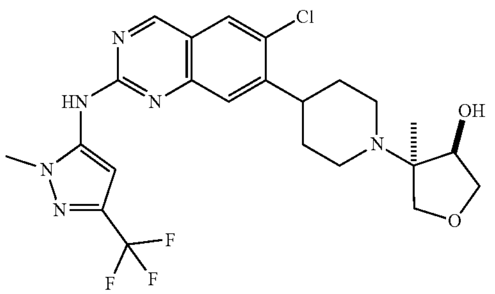
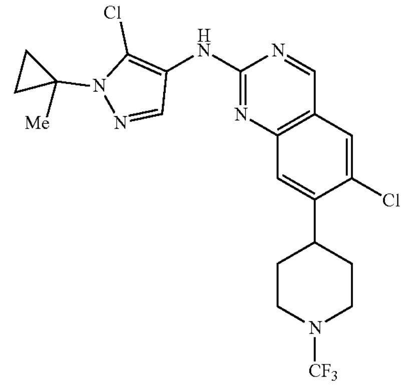
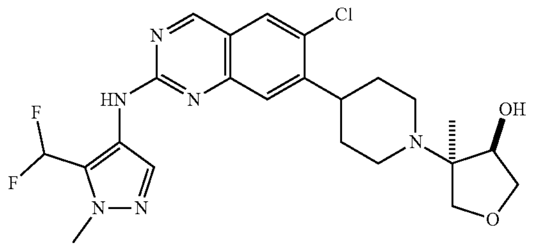
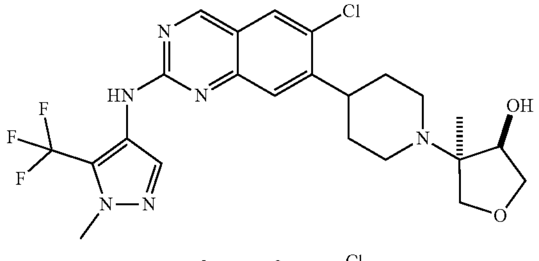
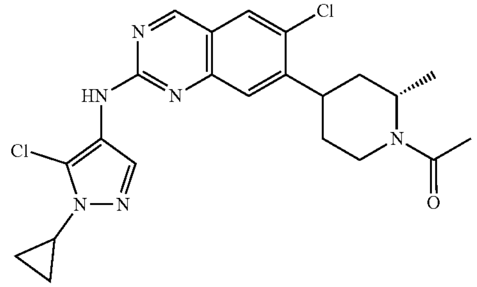

-continued
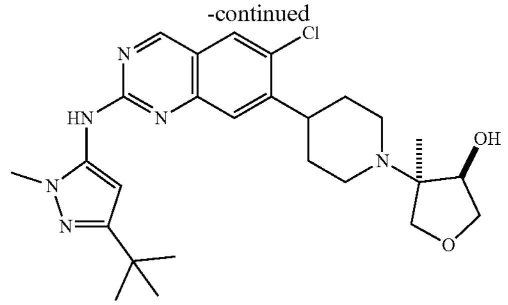
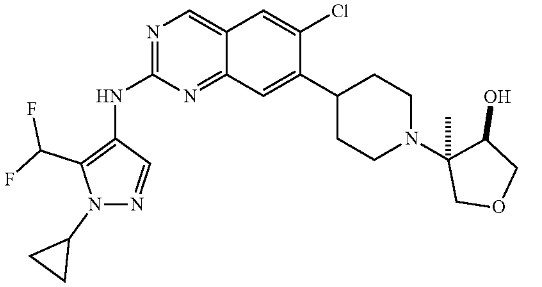
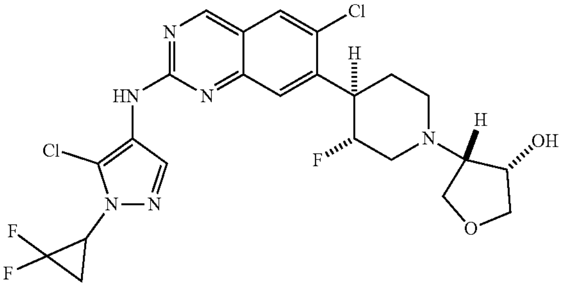
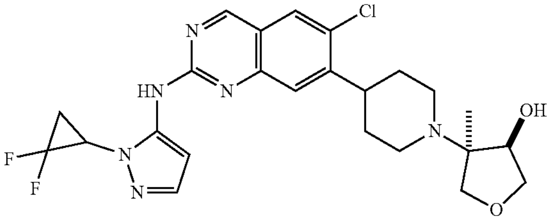
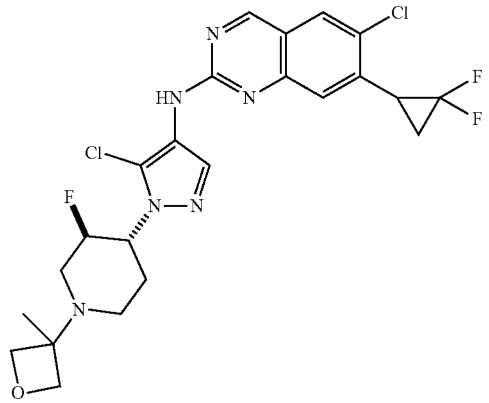
-continued
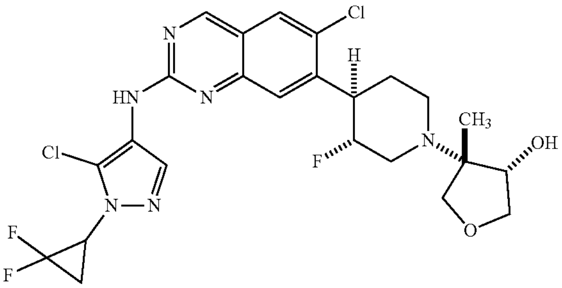
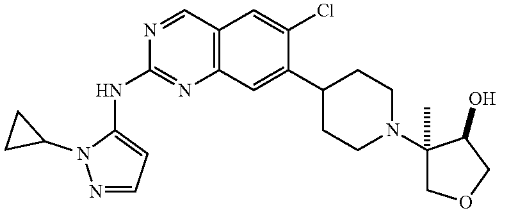
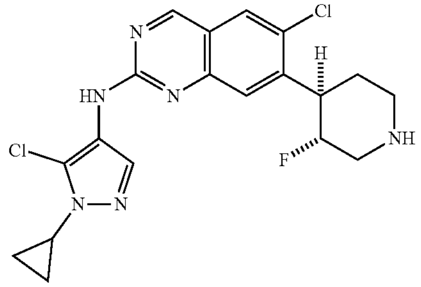
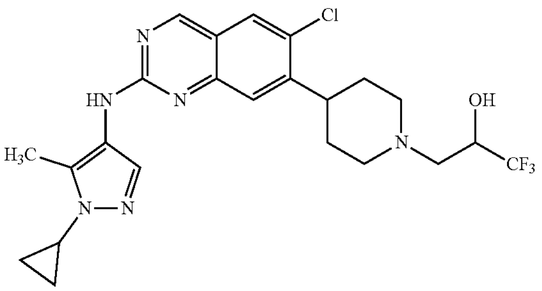
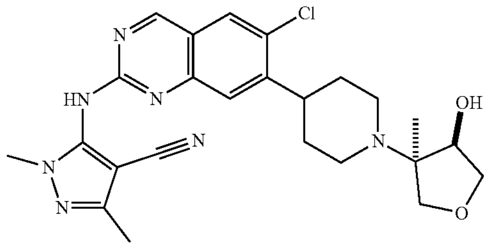

-continued
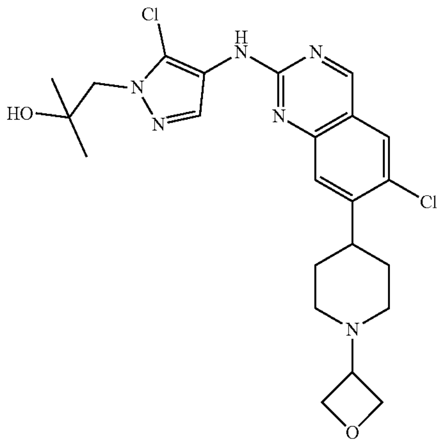
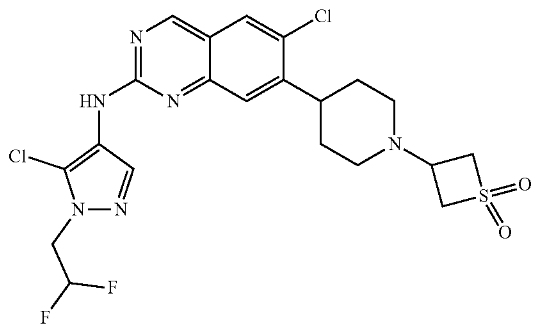
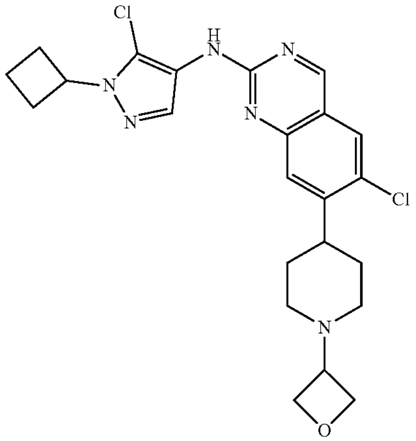
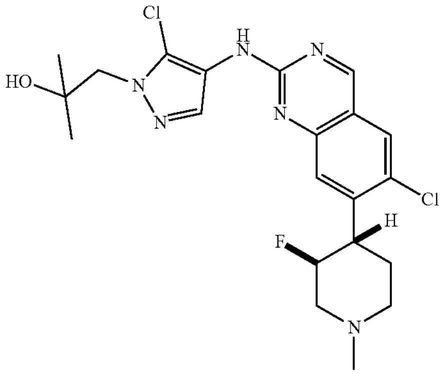
-continued
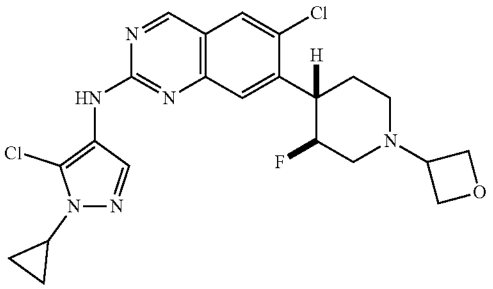
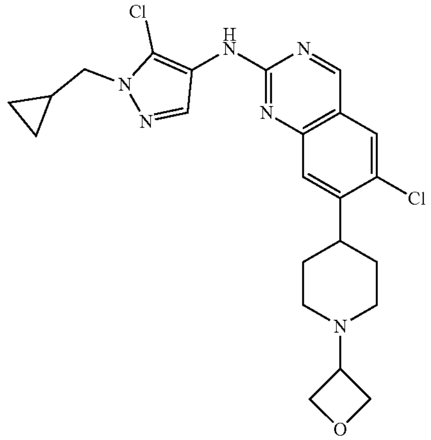
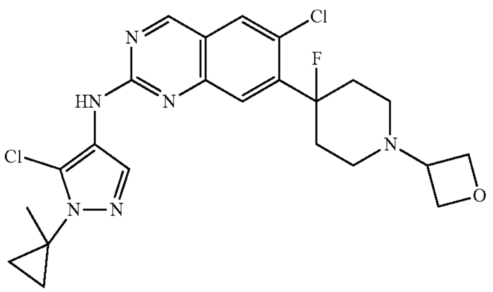
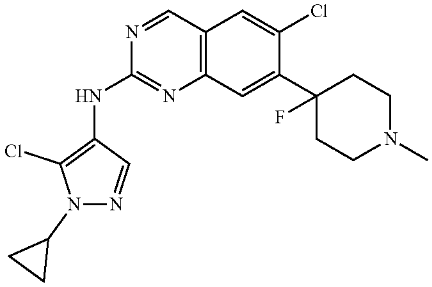

-continued
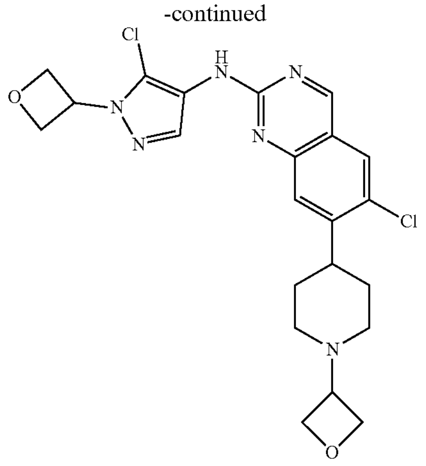
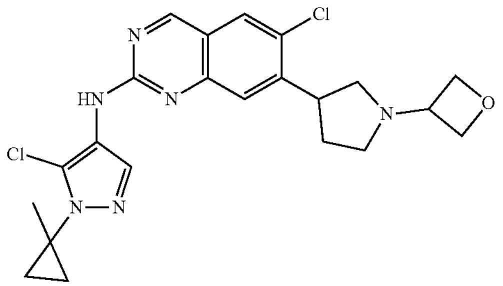
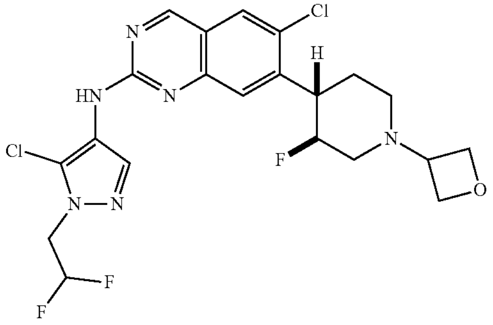
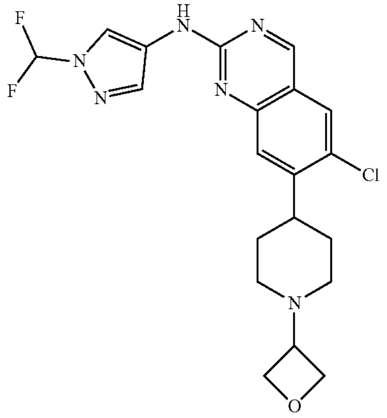
-continued
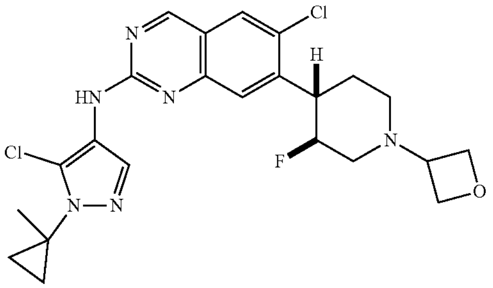
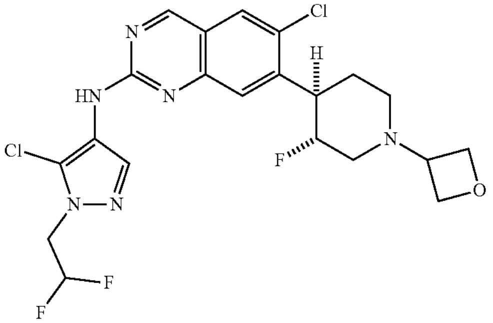
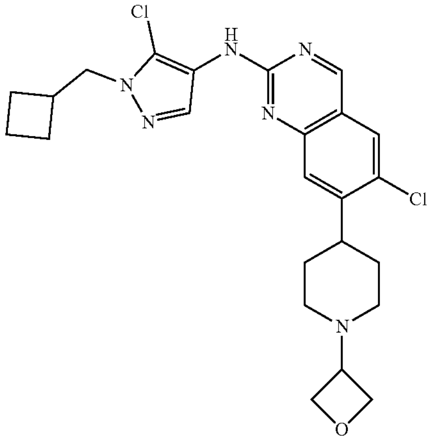
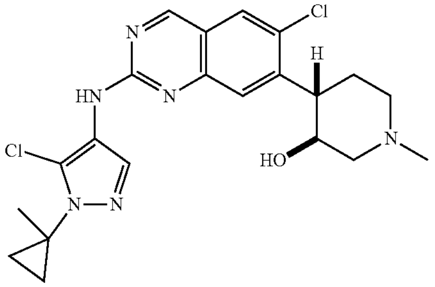
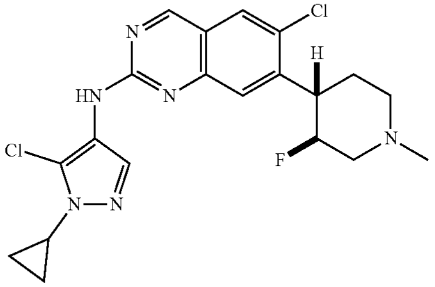

-continued
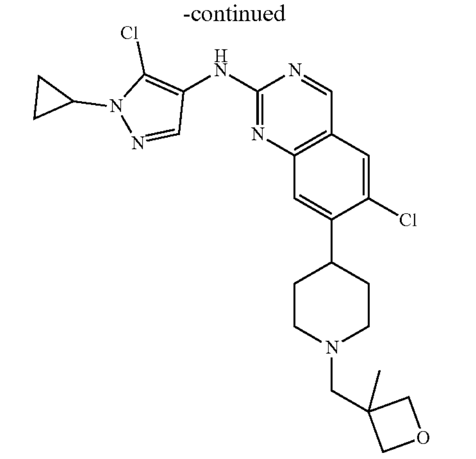
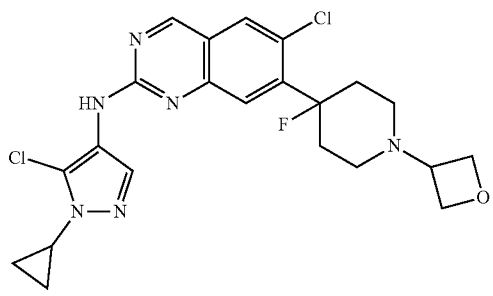
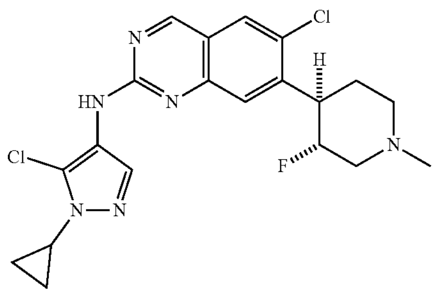
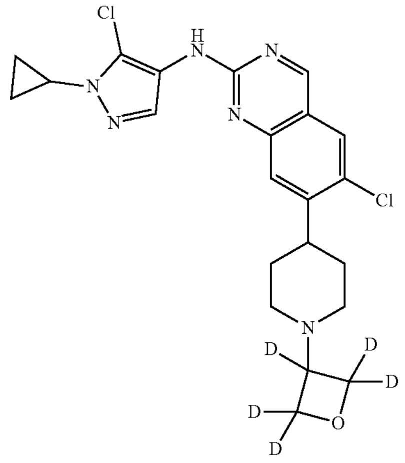
-continued
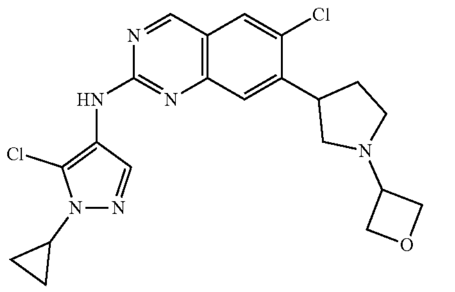
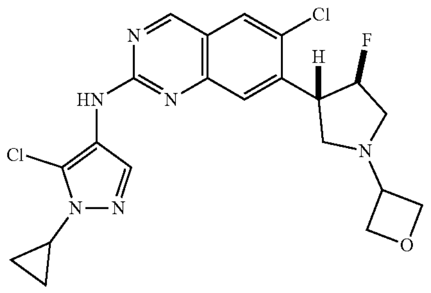
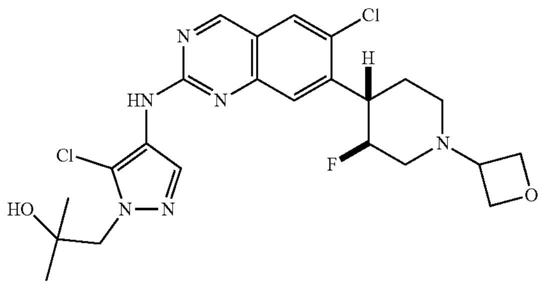
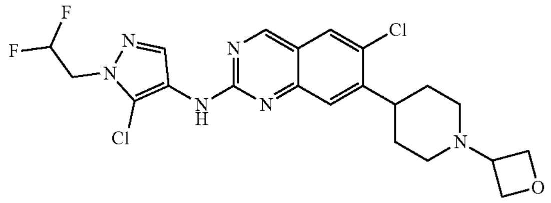
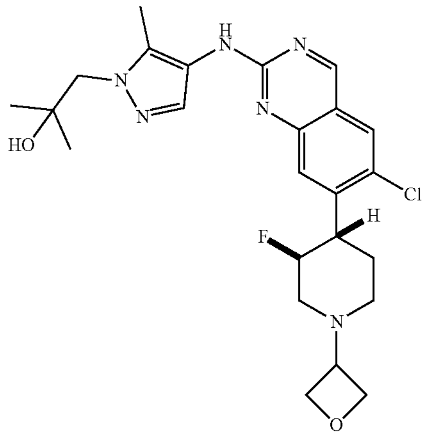

-continued
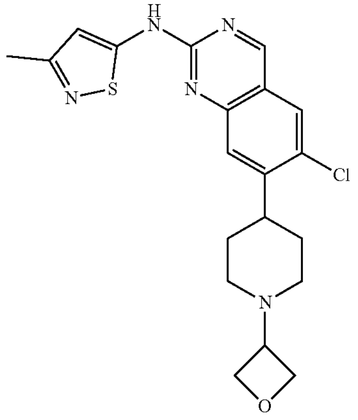
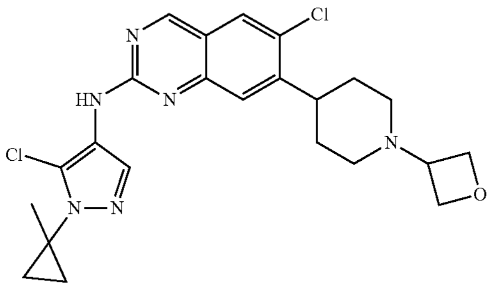
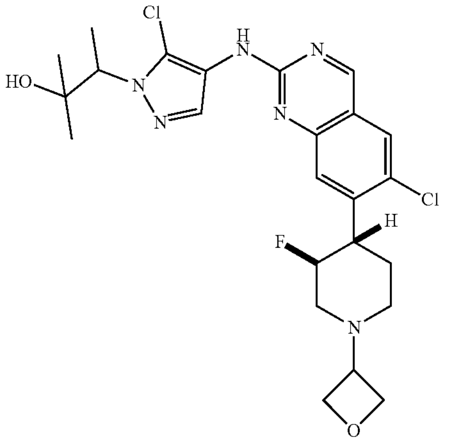
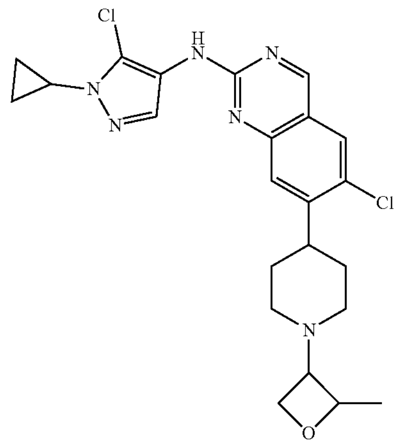
-continued
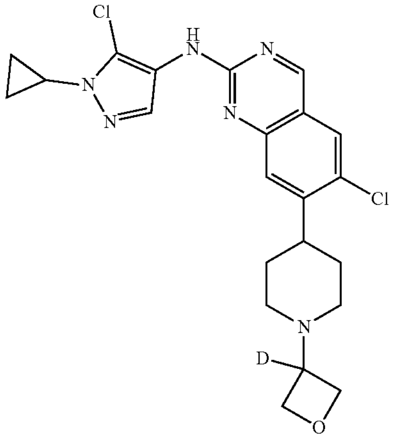
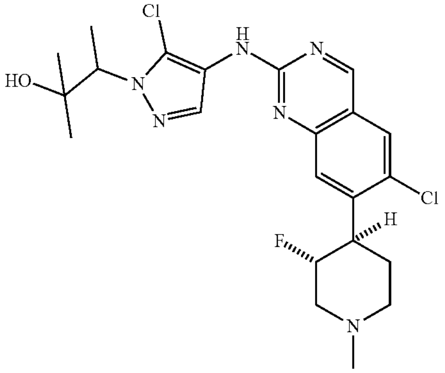
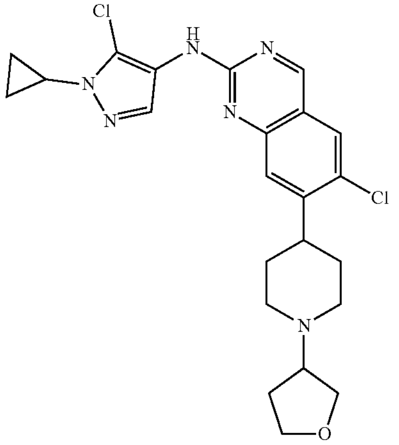
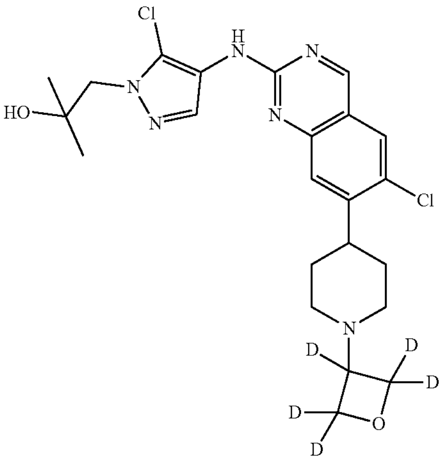

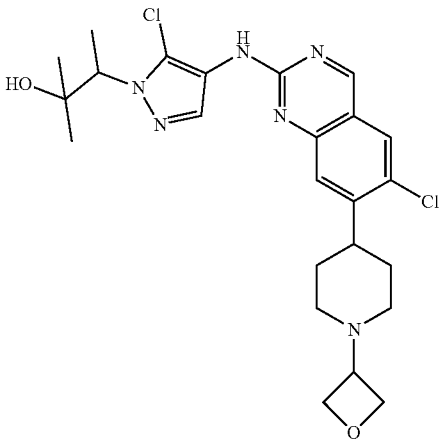
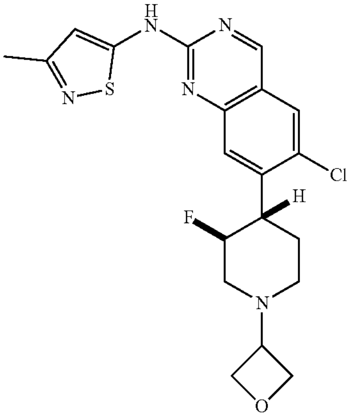
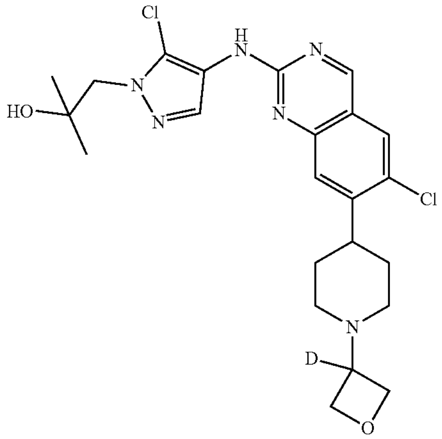
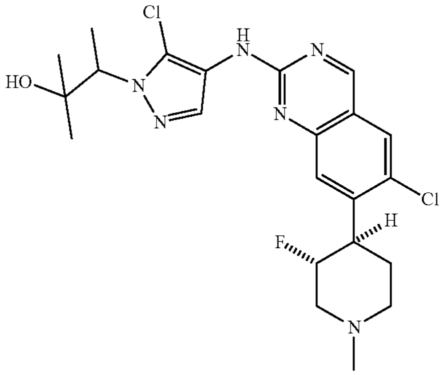
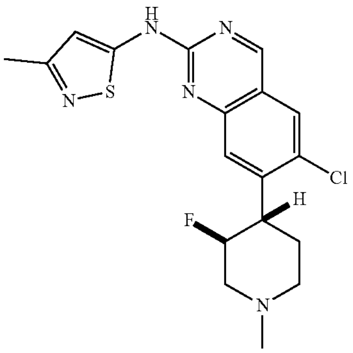
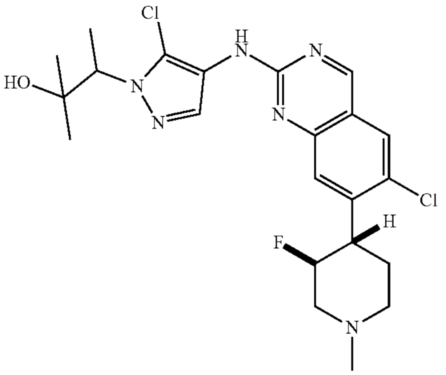
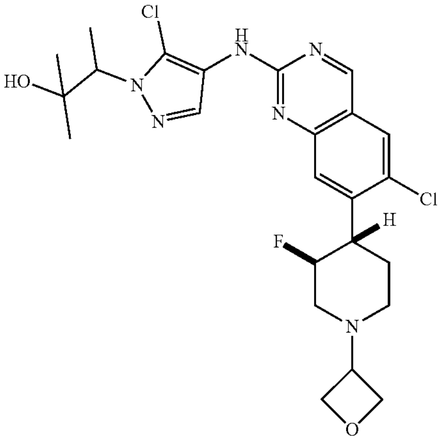
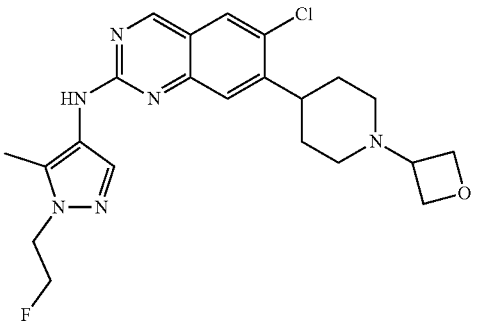

-continued
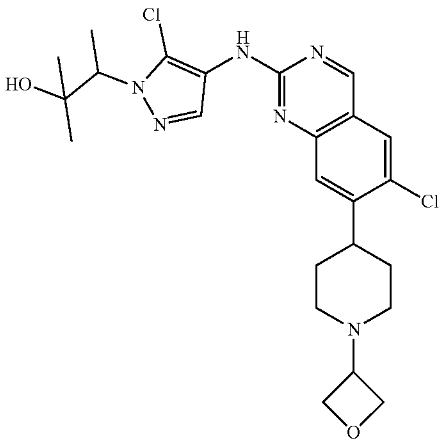
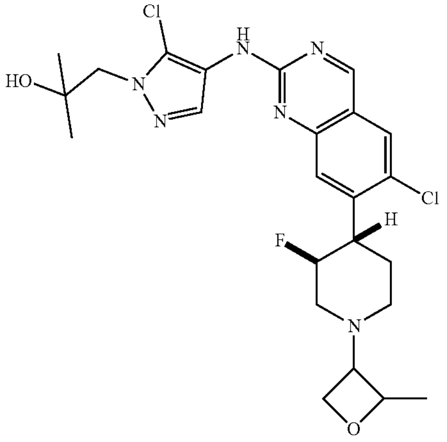
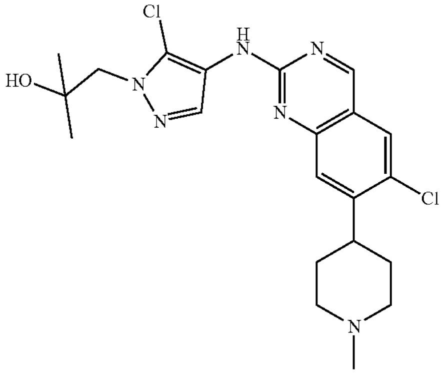
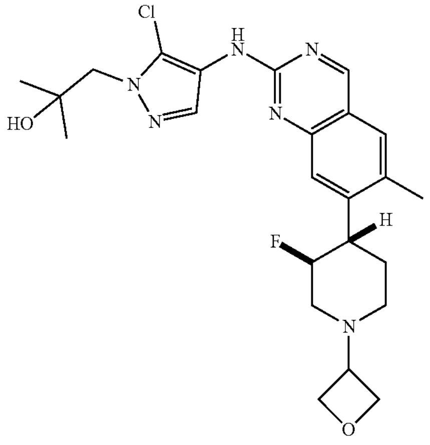
-continued
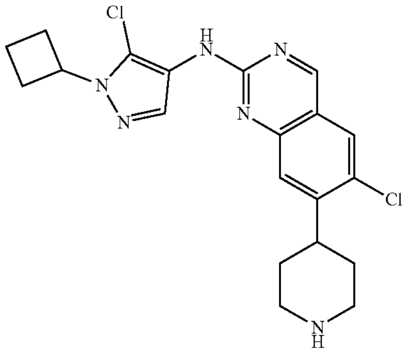
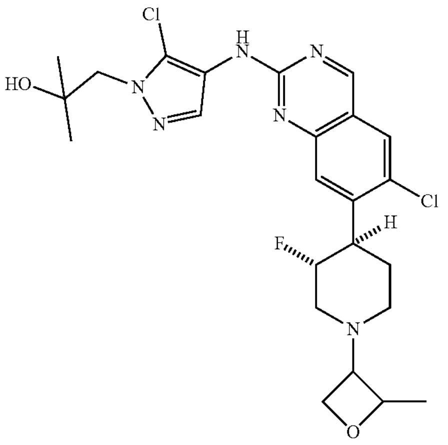
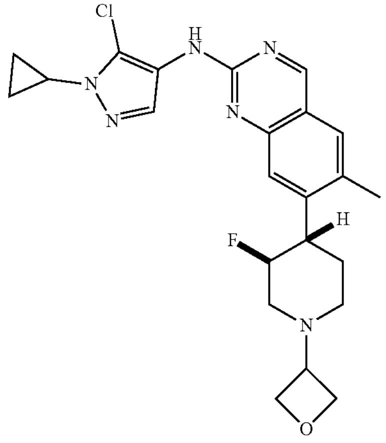
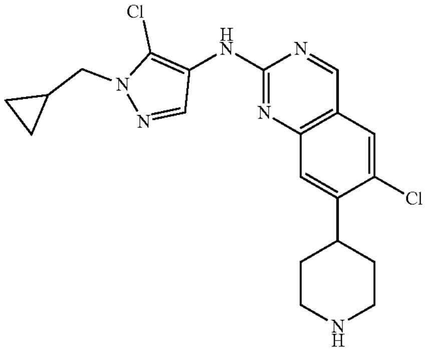

-continued
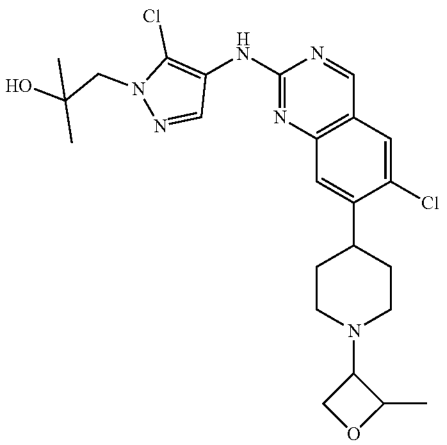
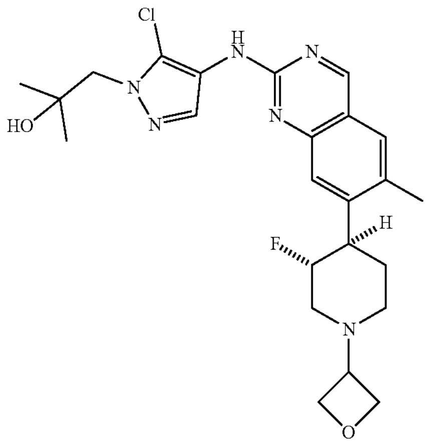
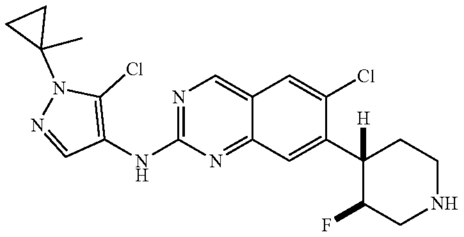
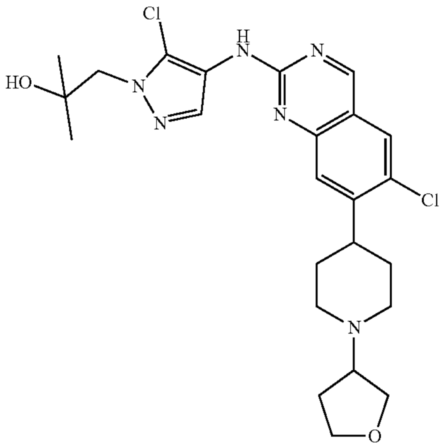
-continued
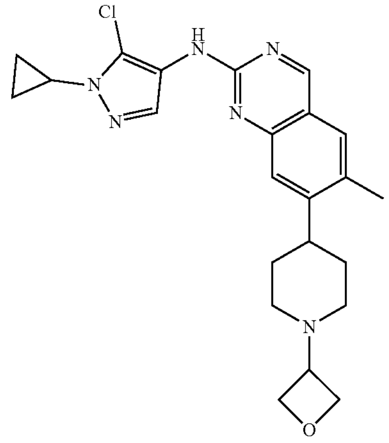
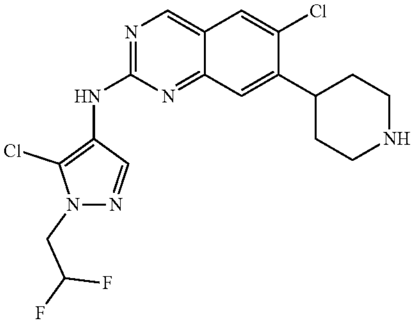
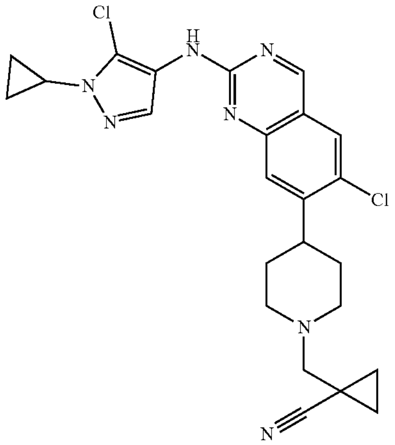
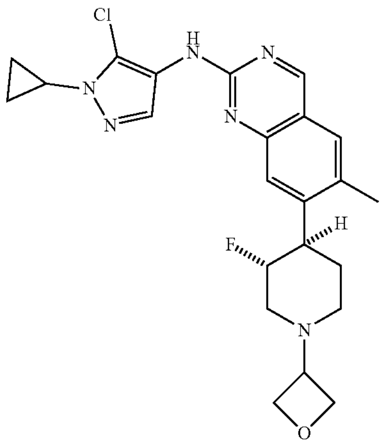

-continued
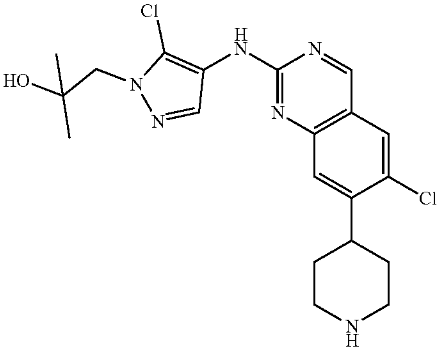
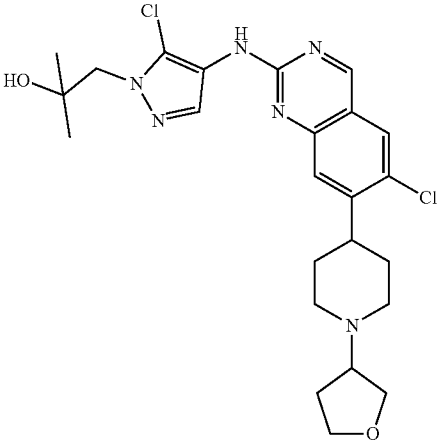
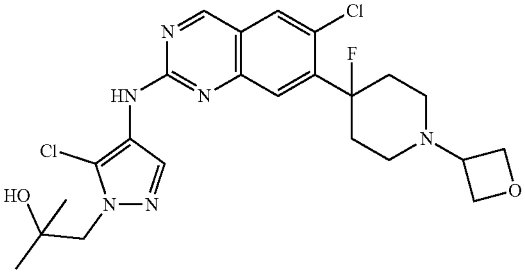
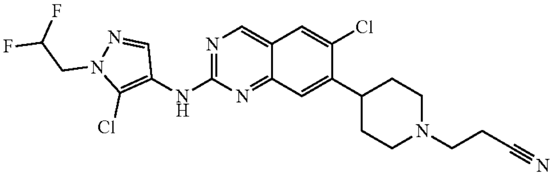
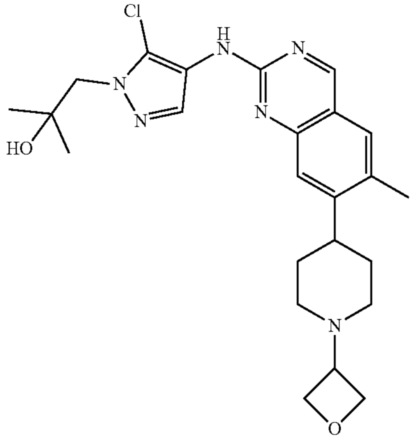
-continued
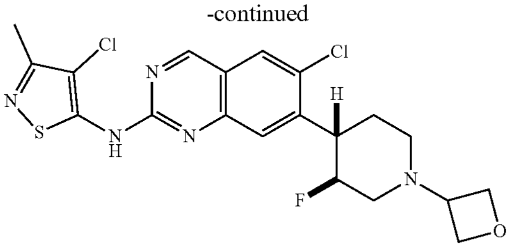
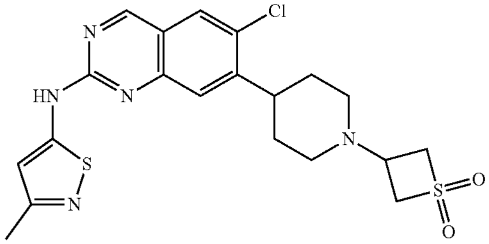
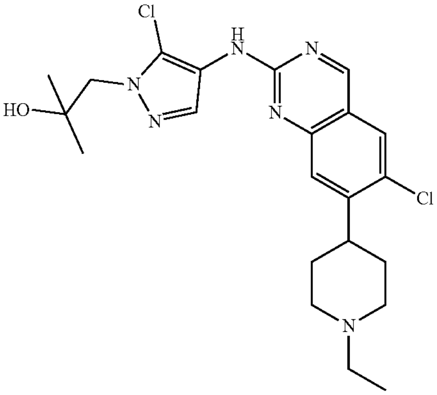
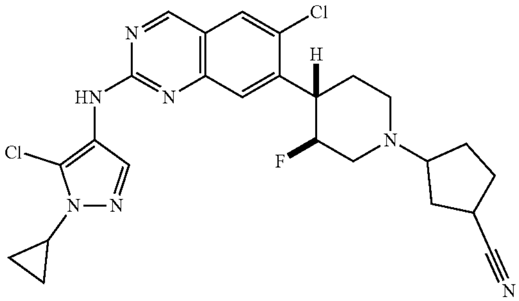
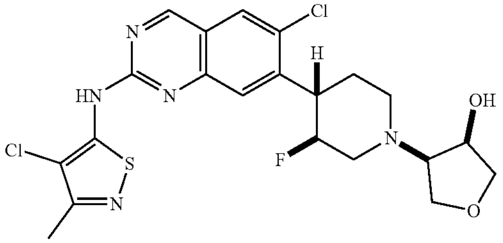
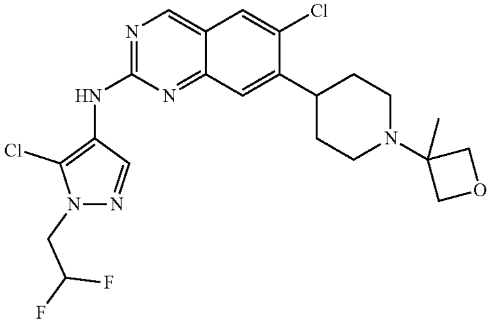

-continued
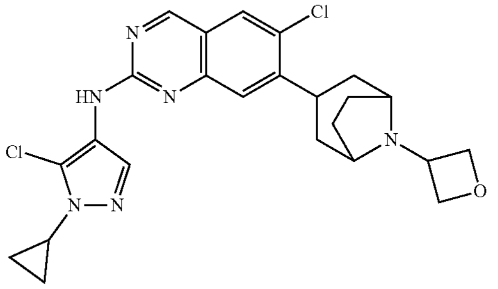
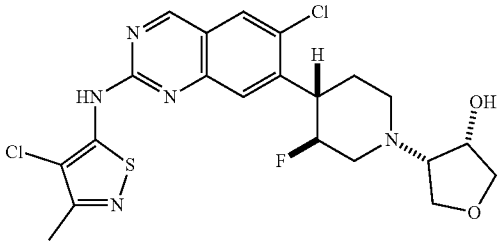
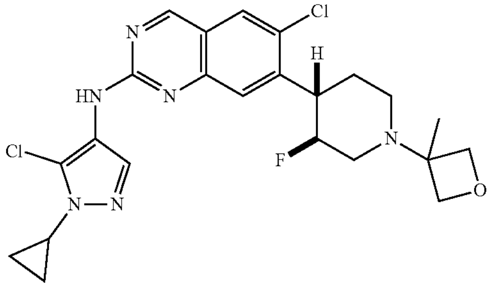
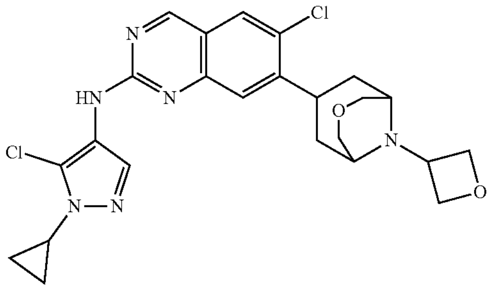
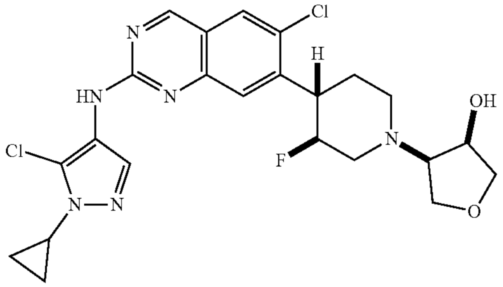
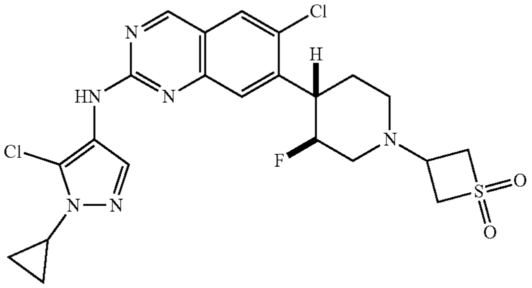
-continued
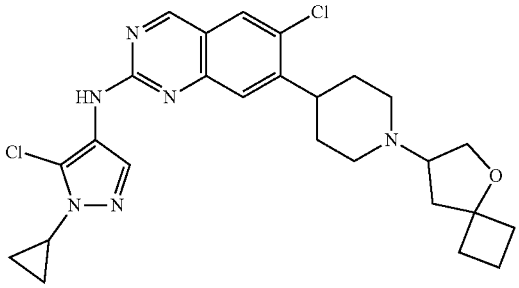
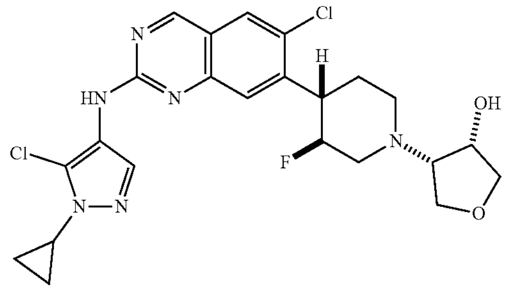
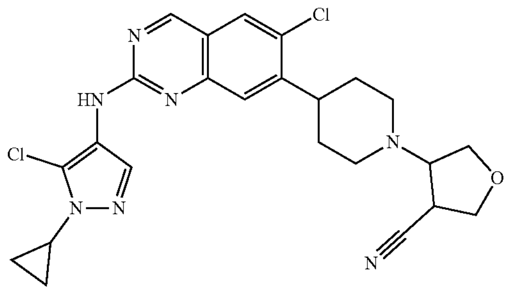
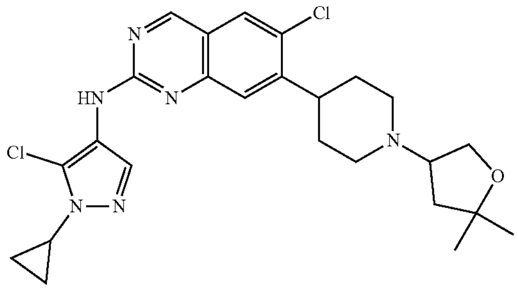
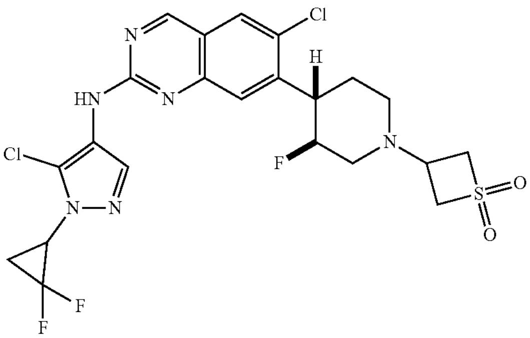

-continued
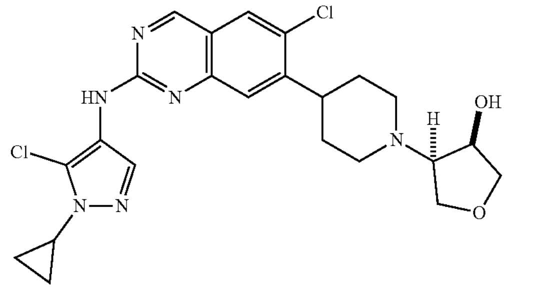
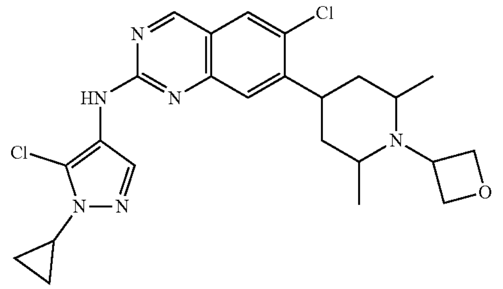
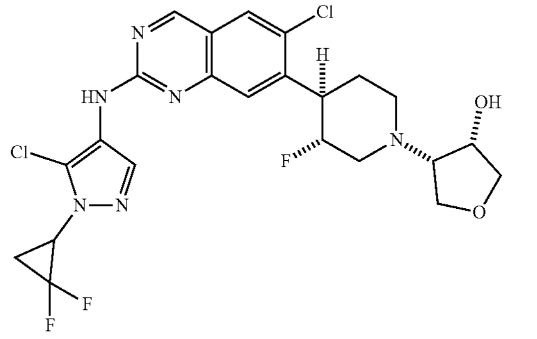
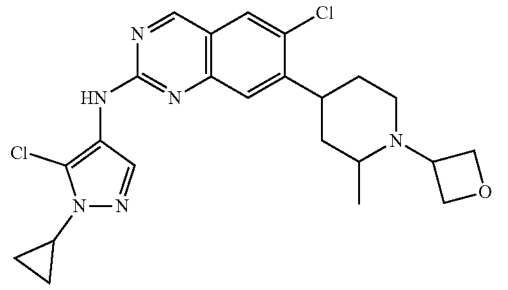
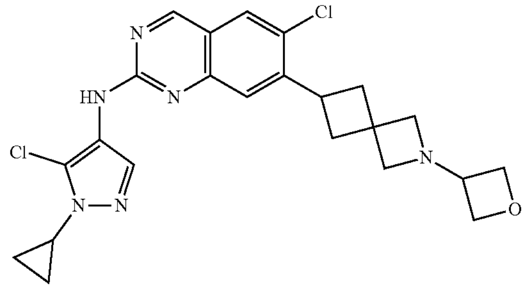
-continued
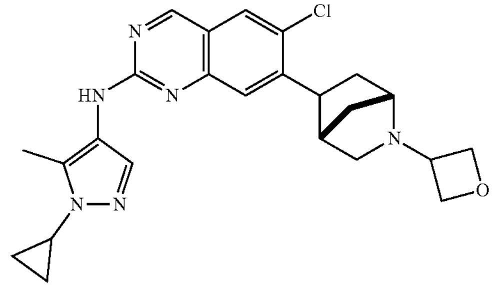
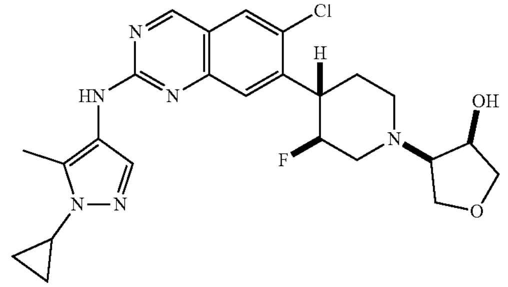
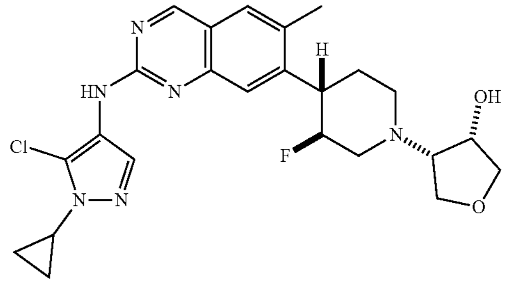
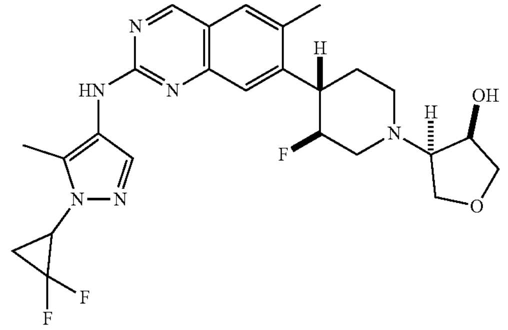
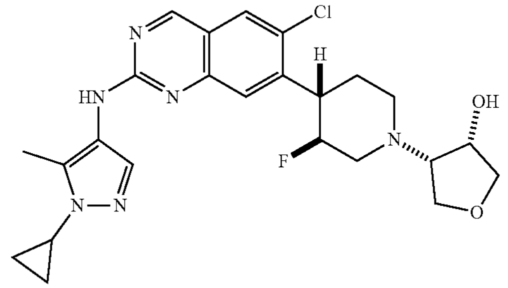

-continued
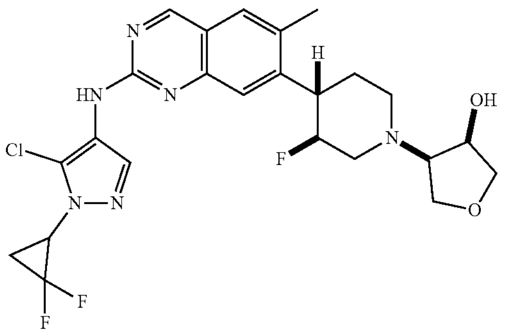
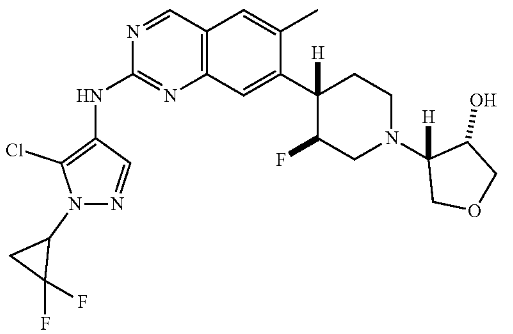
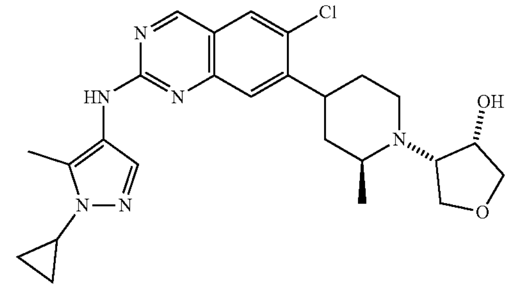
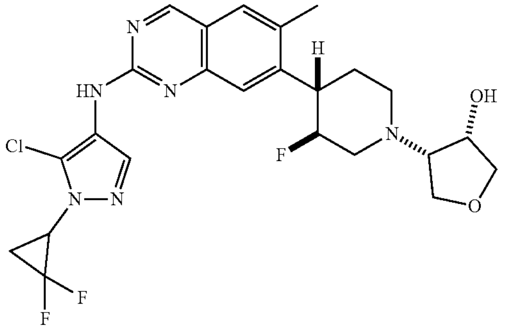
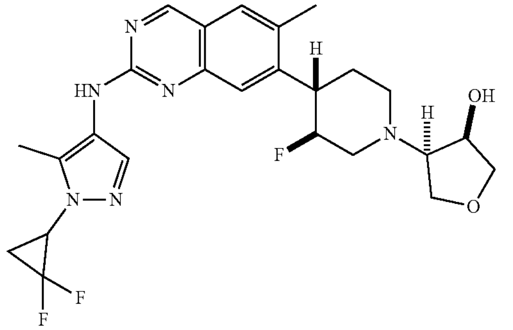
-continued
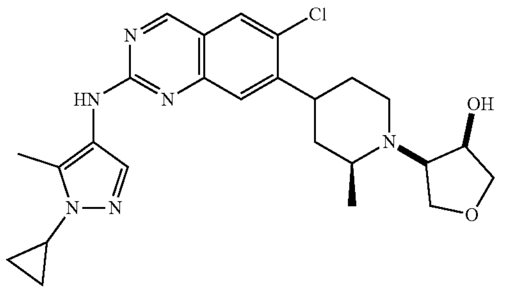
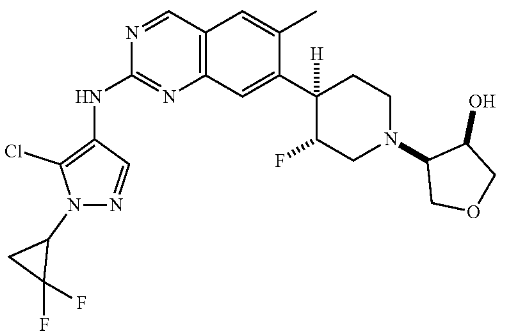
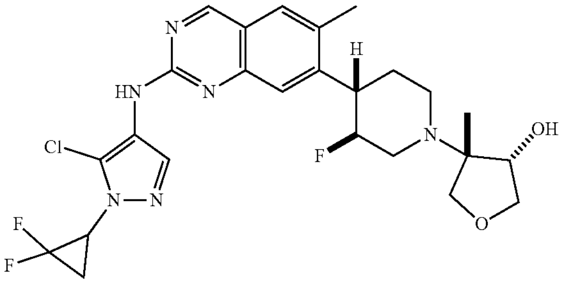
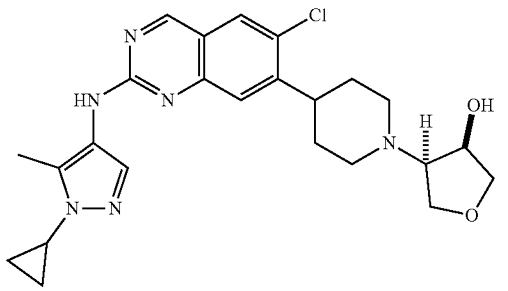
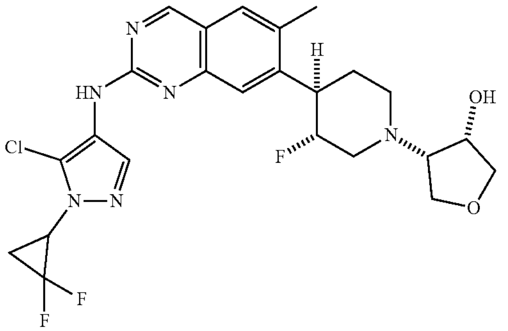

-continued
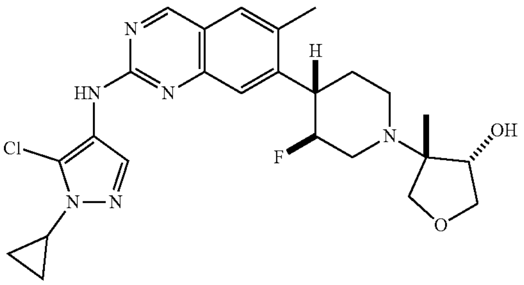
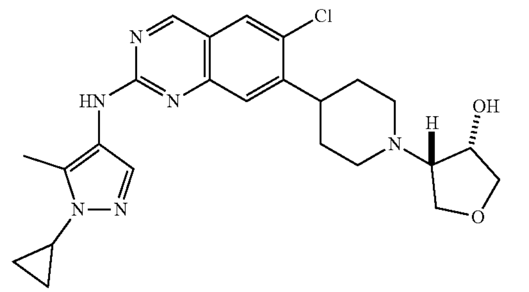
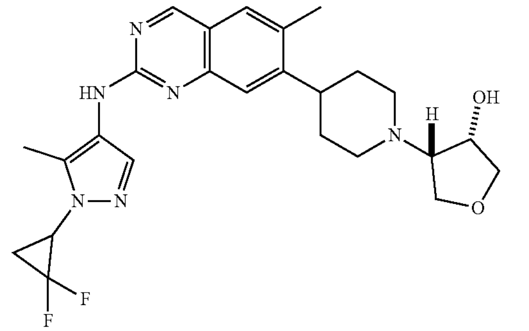
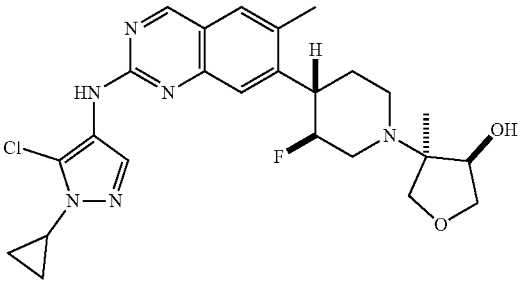
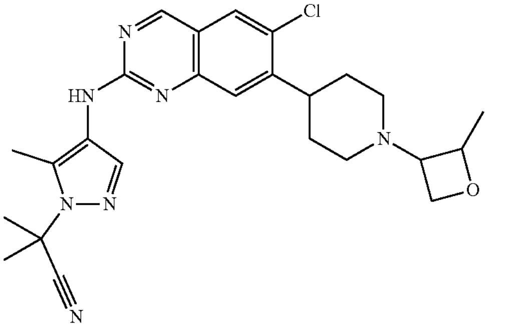
-continued
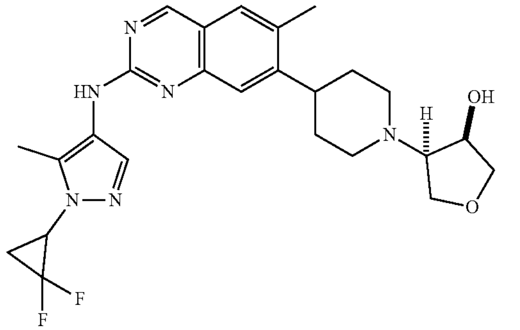
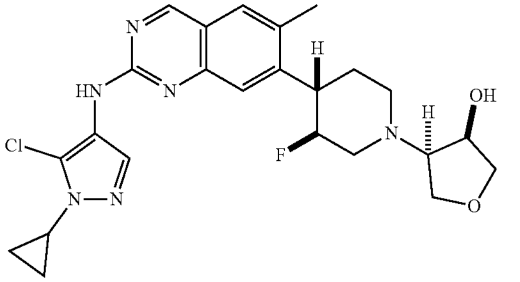
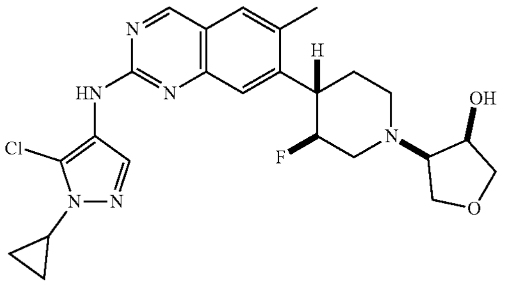
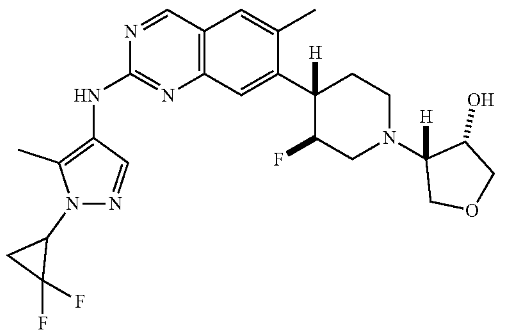
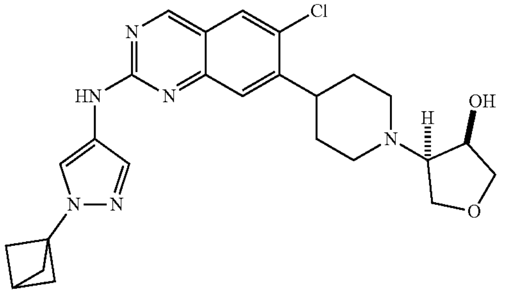

-continued
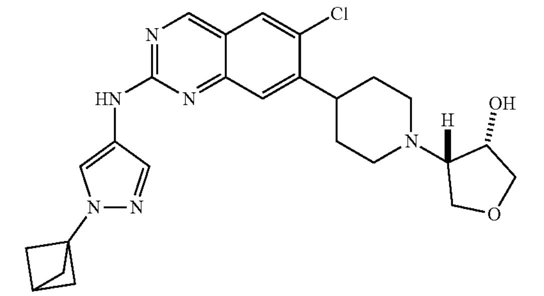
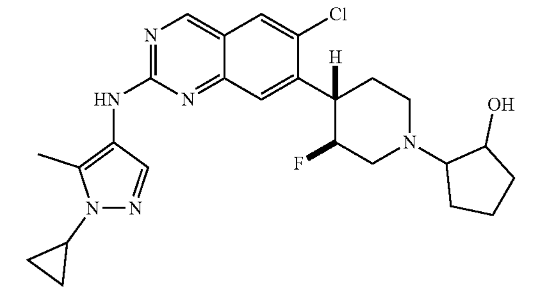
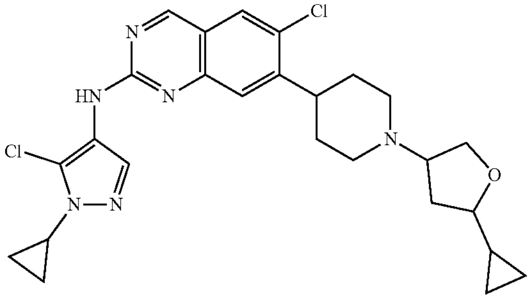
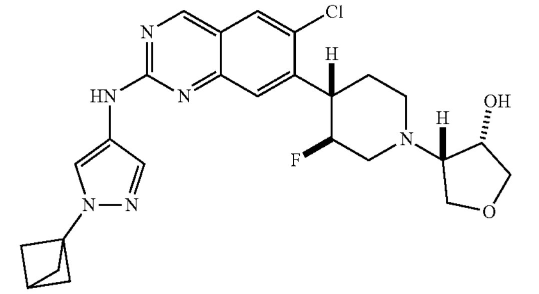
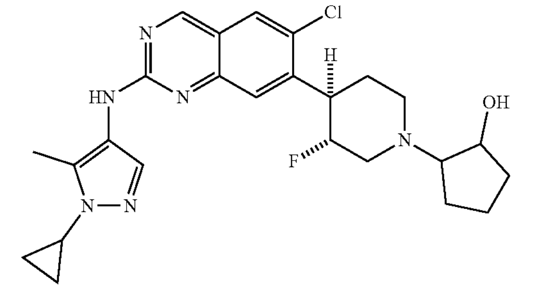
-continued
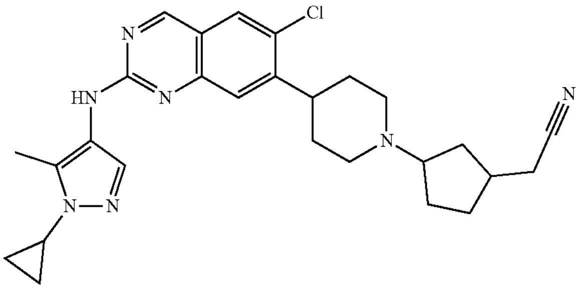
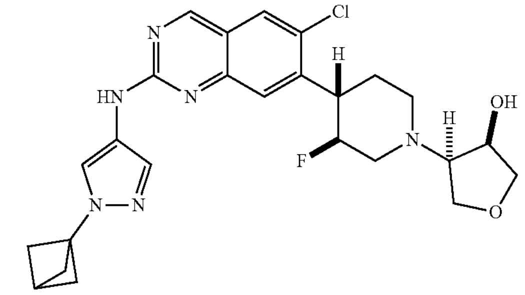
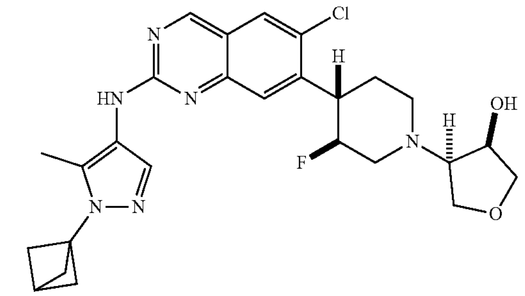
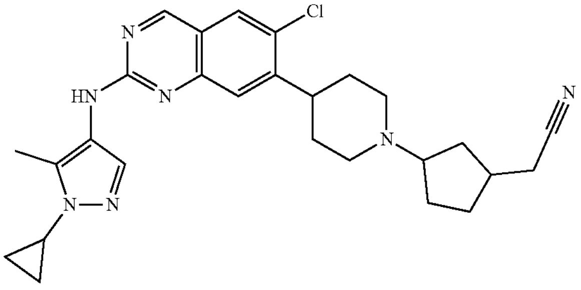
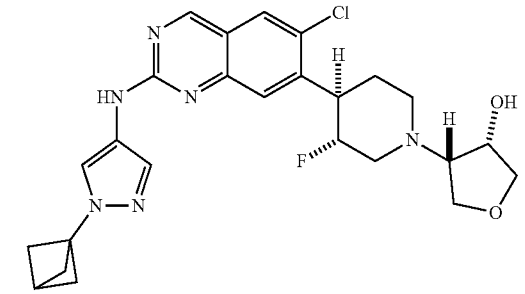

-continued
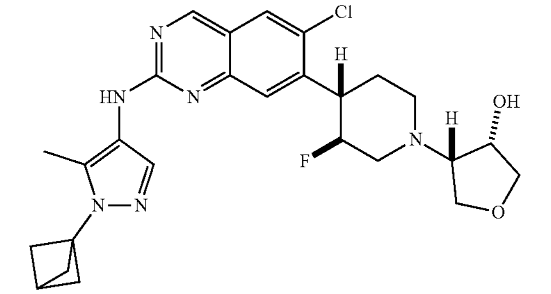
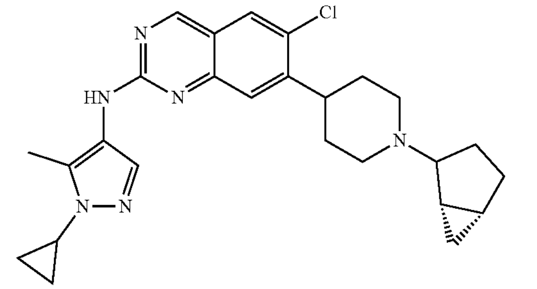
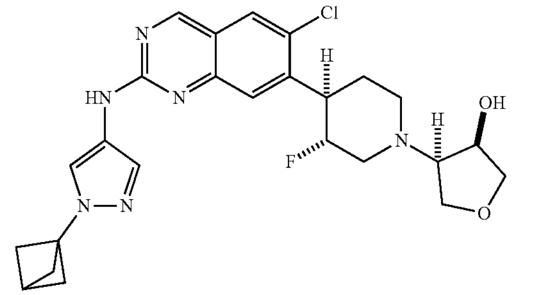
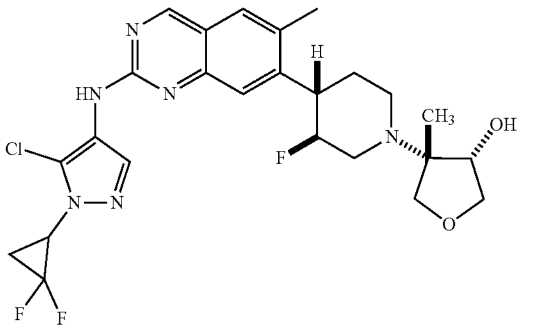
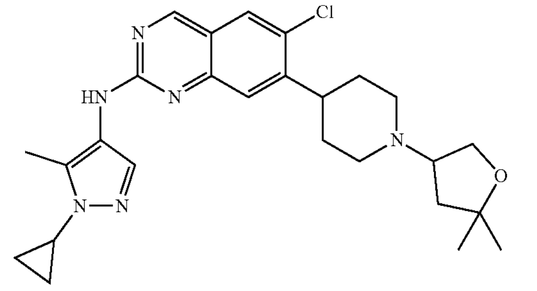
-continued
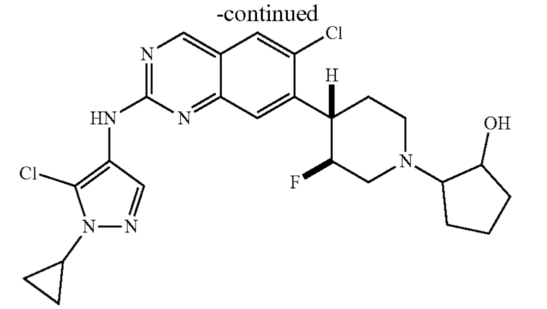
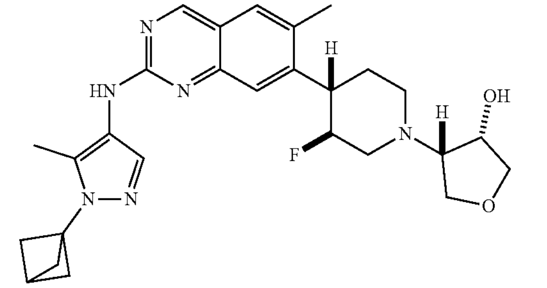
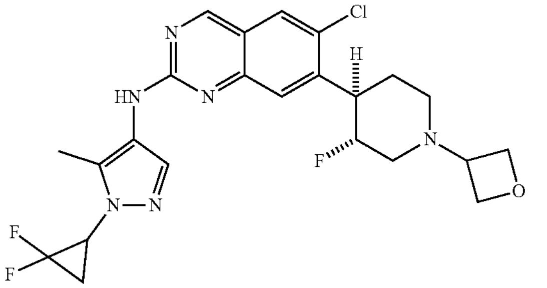
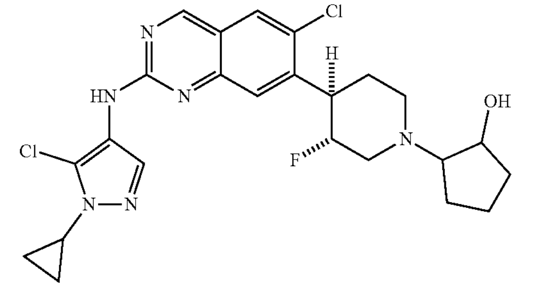
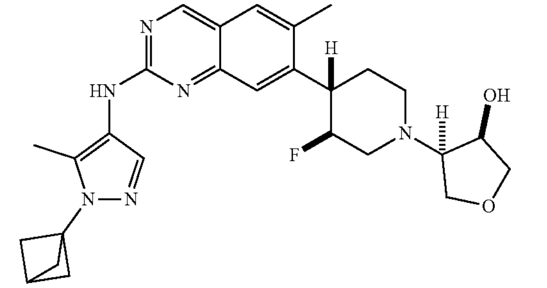
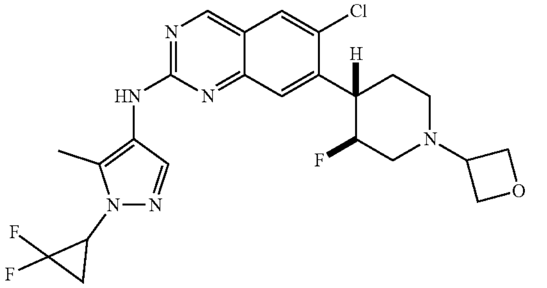

-continued
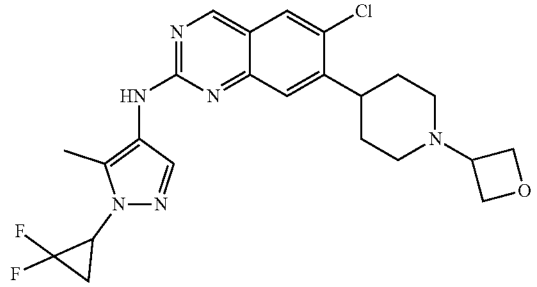
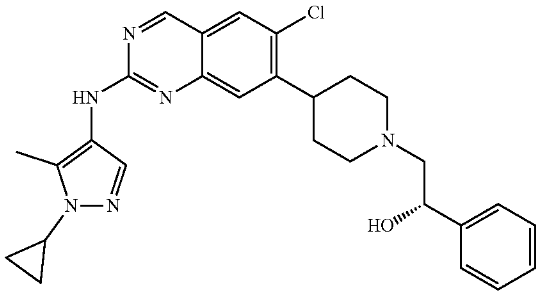
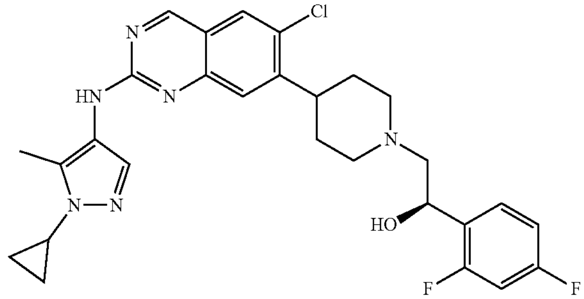
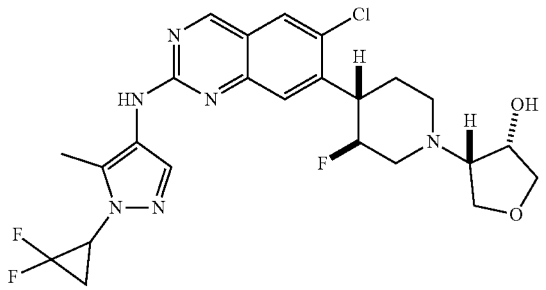
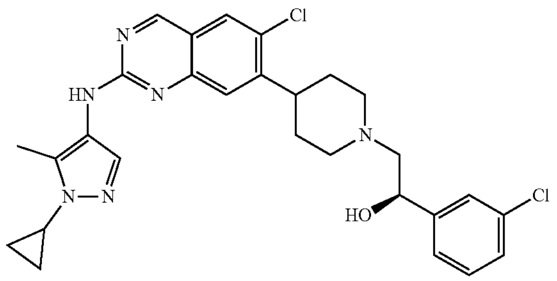
-continued
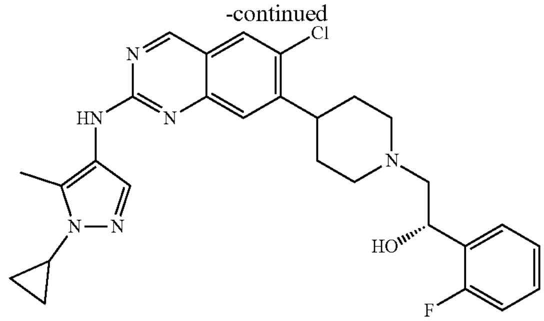
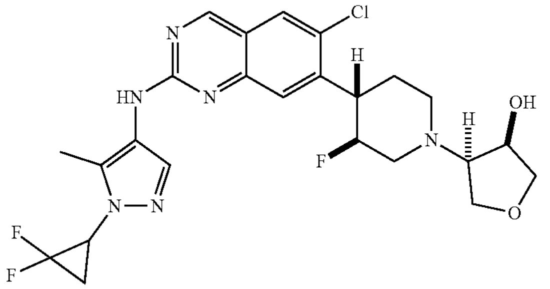
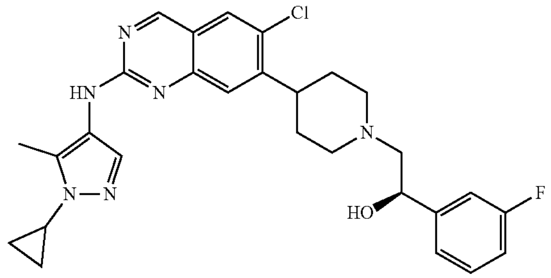
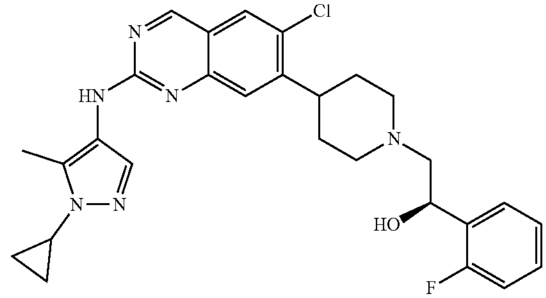
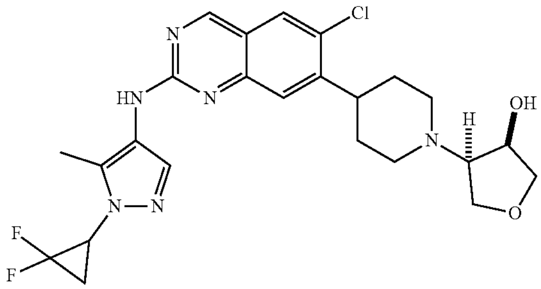
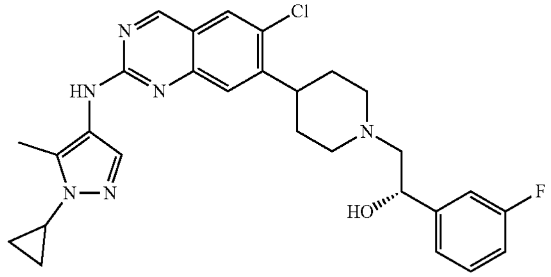

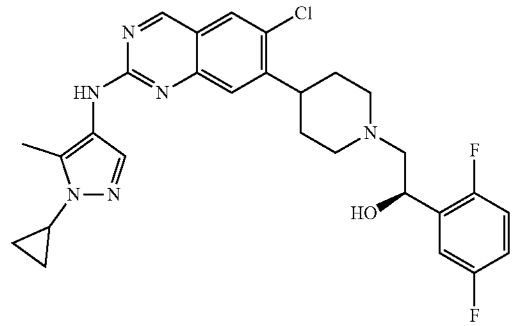
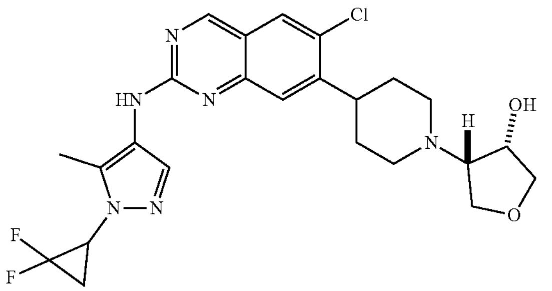
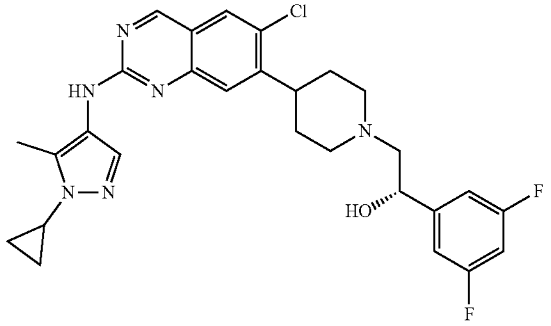
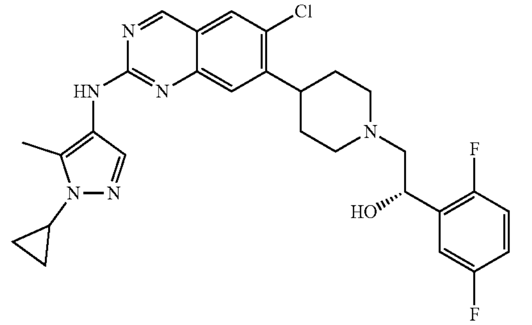
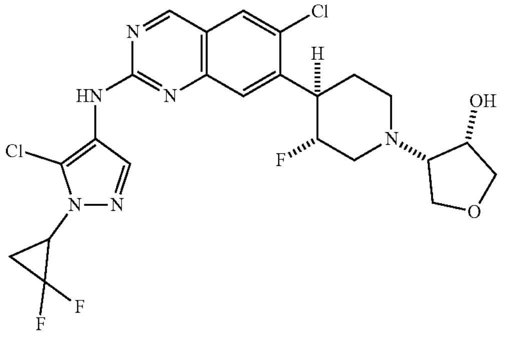
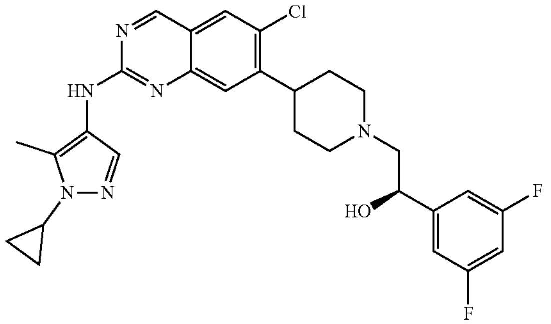
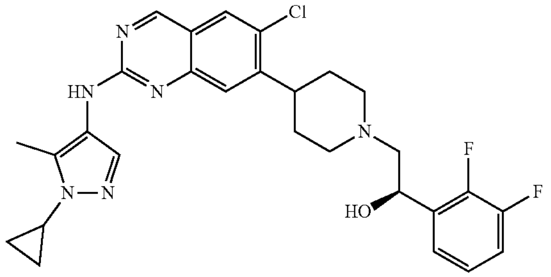
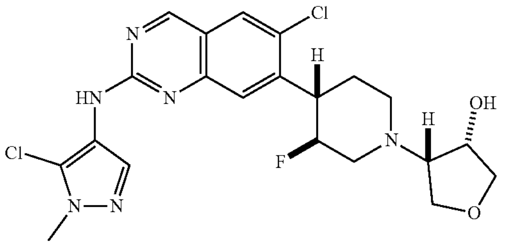
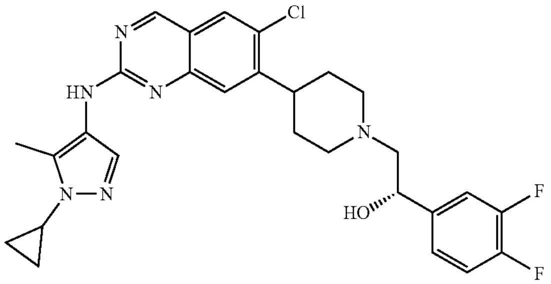
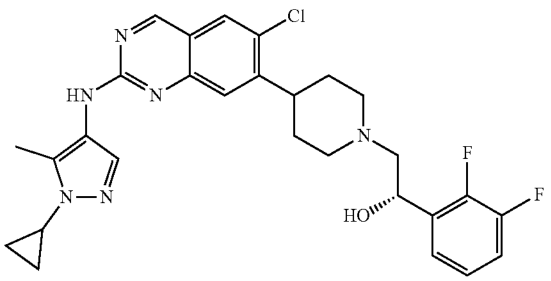
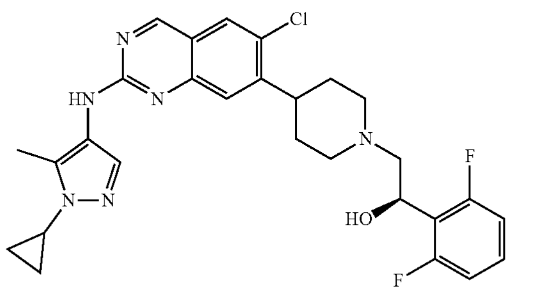

-continued
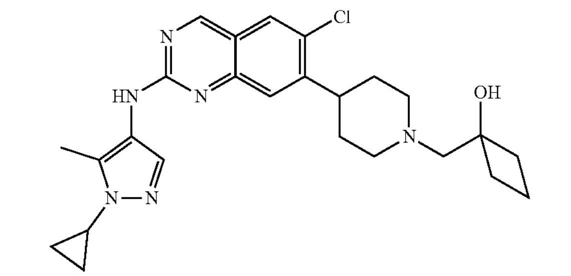
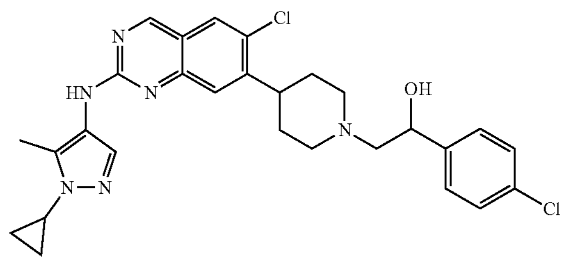
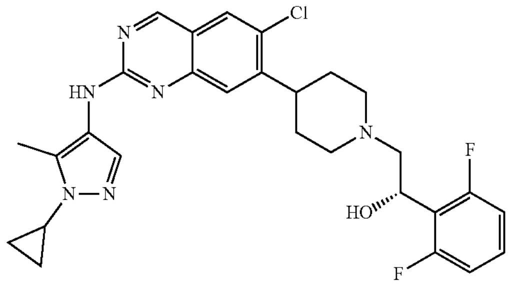
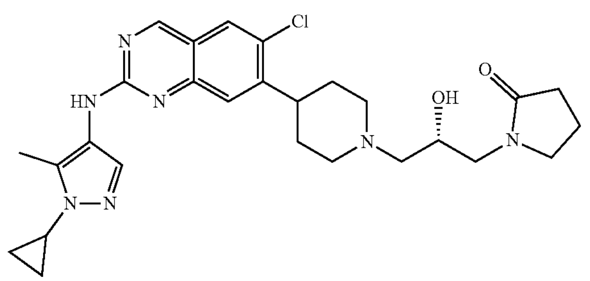
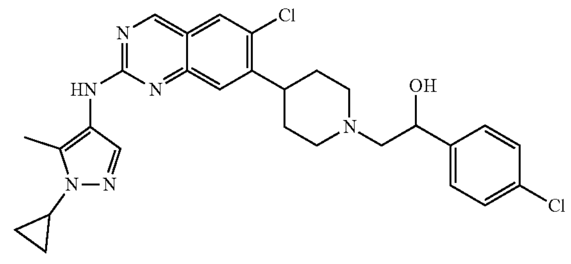
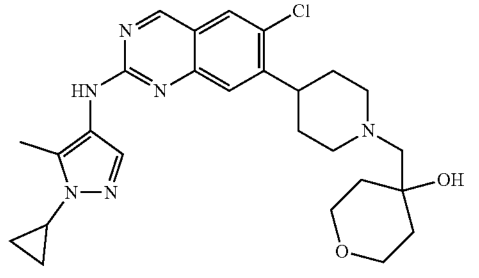
-continued
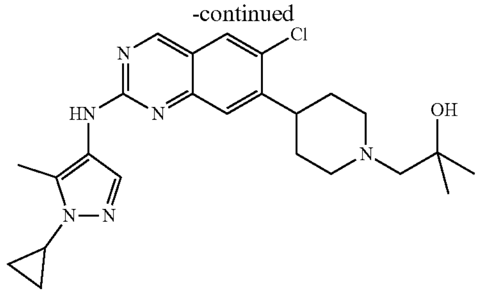
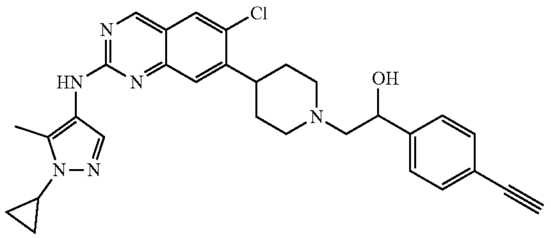
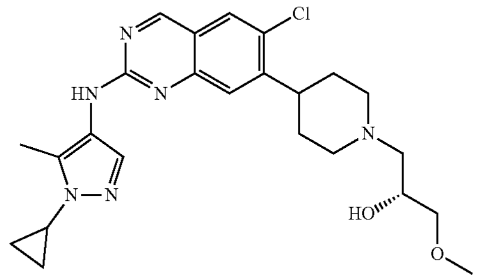
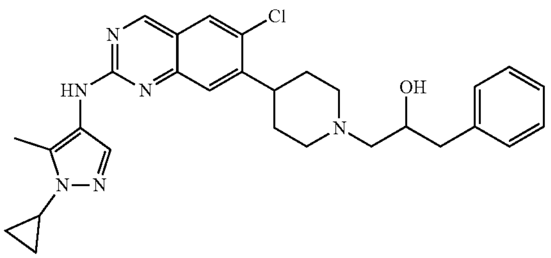
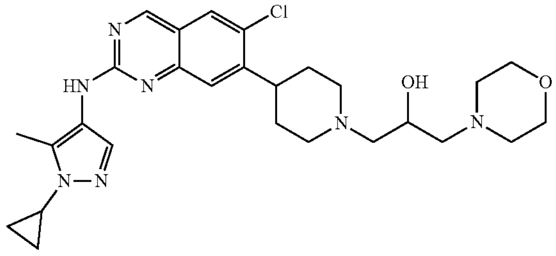
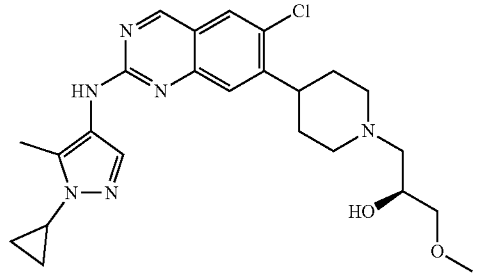

-continued
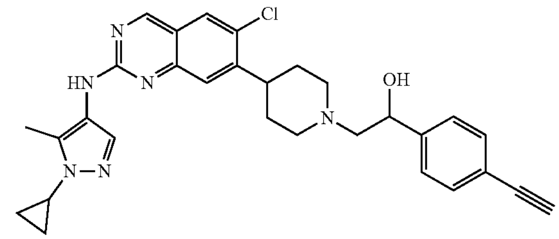
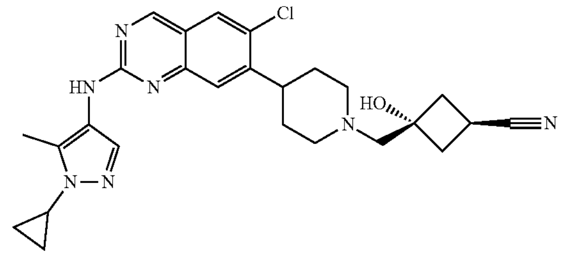
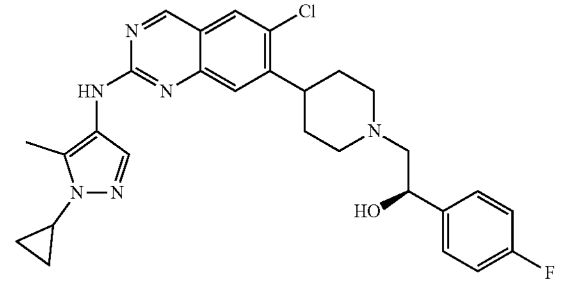
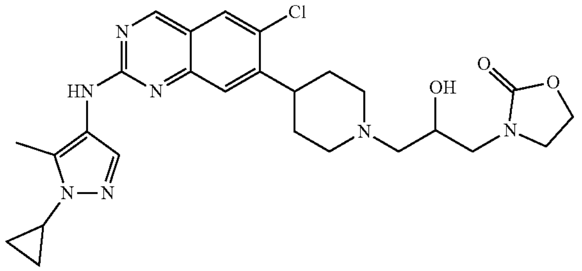
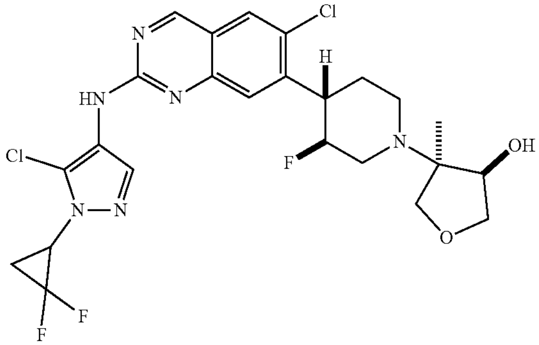
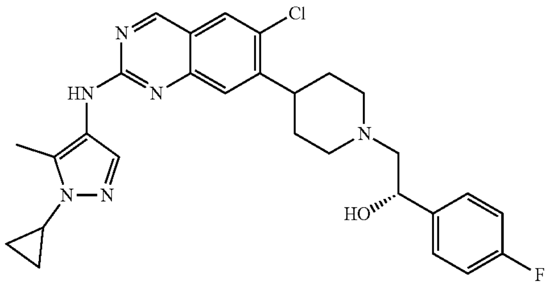
-continued
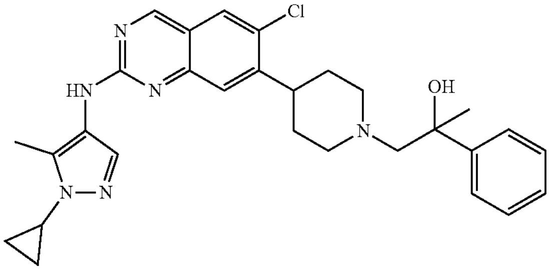
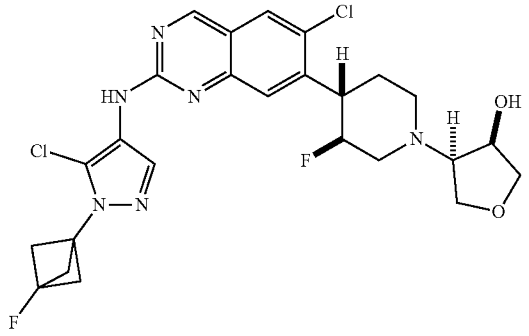
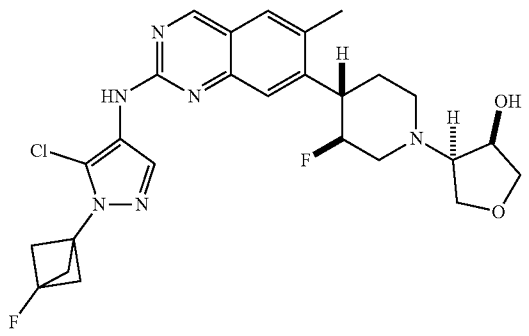
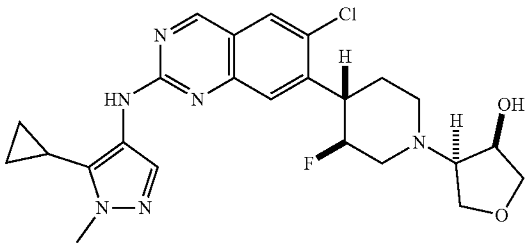
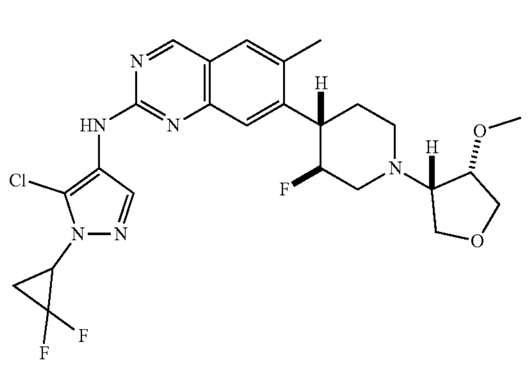

-continued
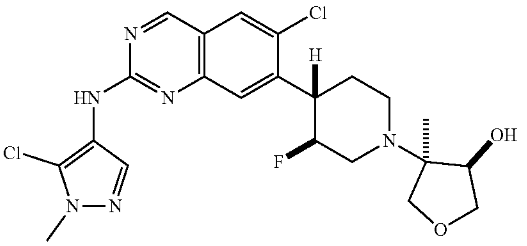
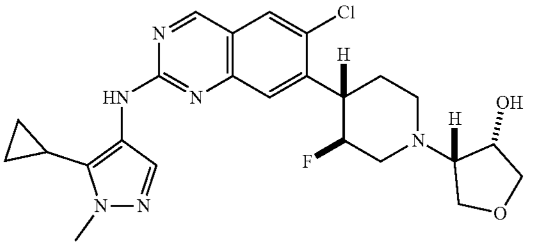
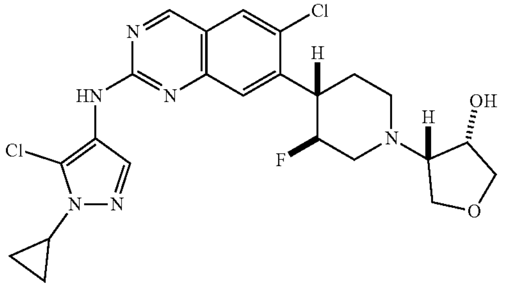
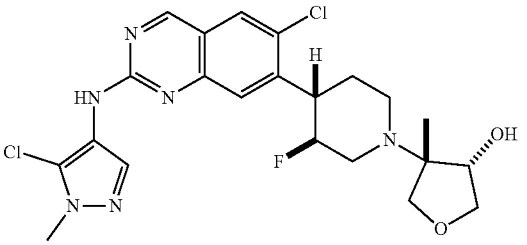
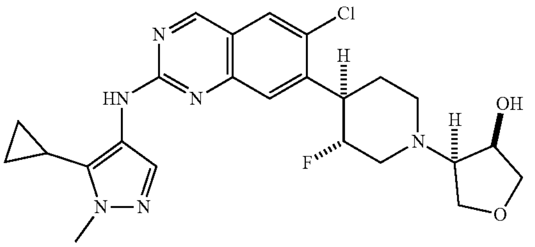
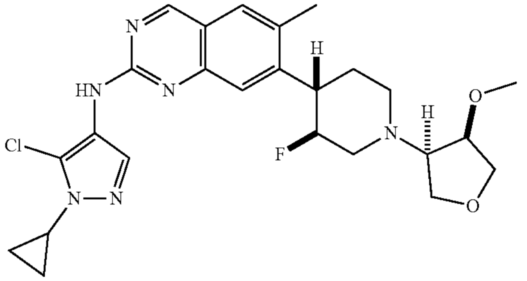
-continued
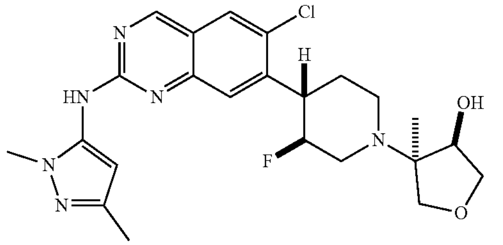
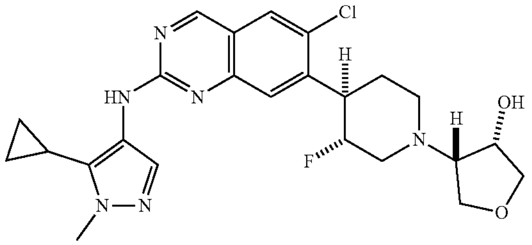
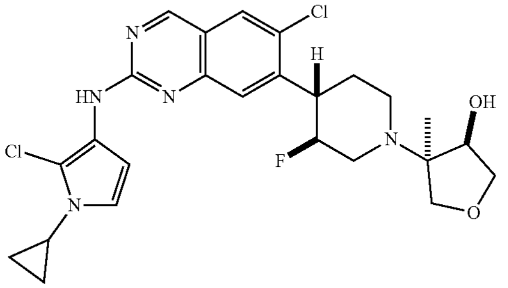
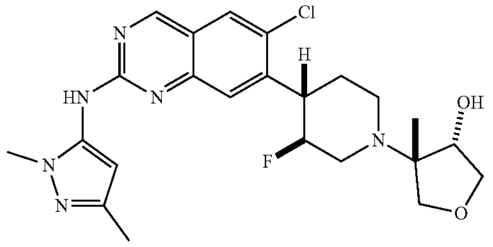
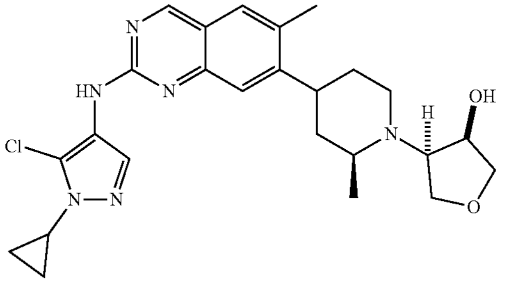
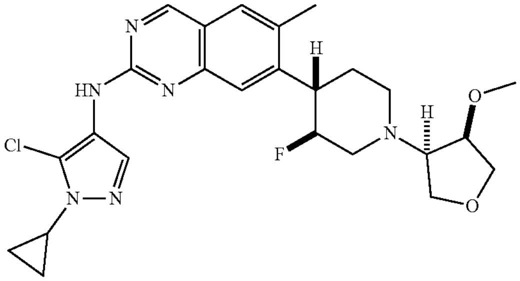

-continued
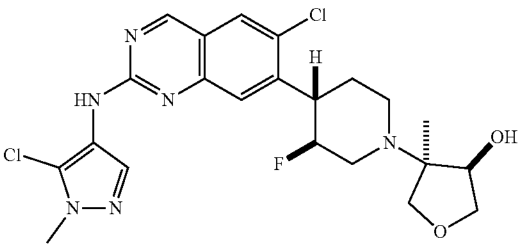
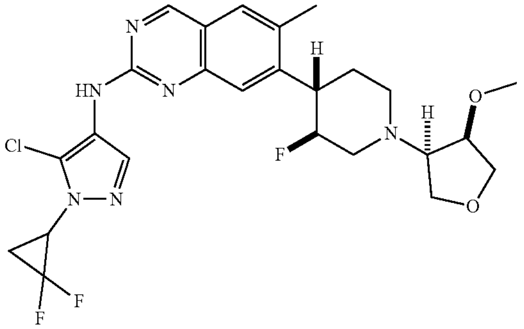
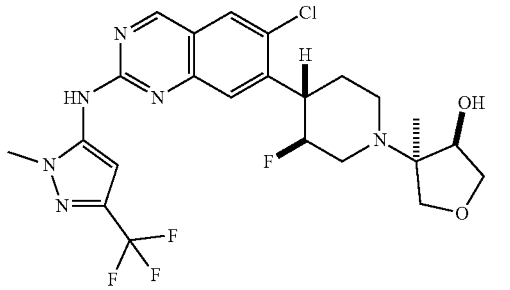
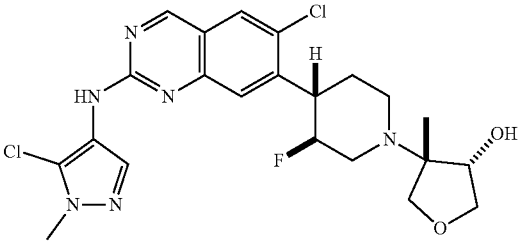
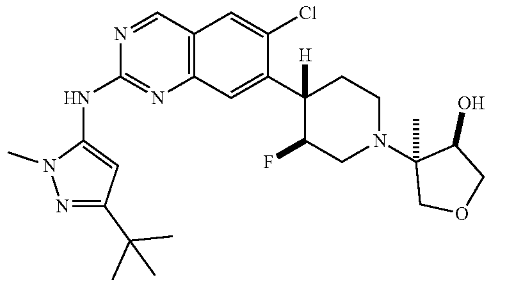
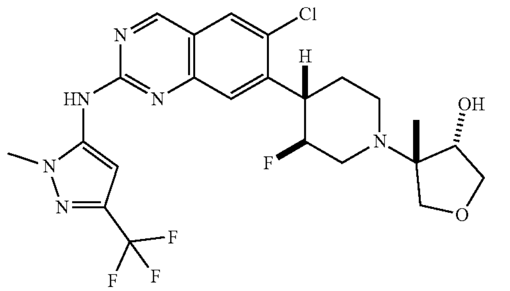
-continued
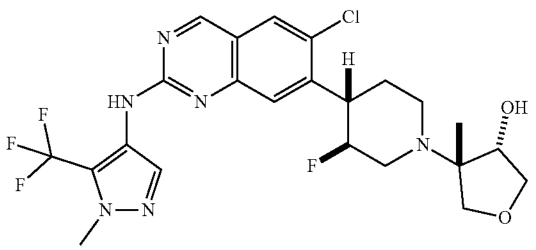
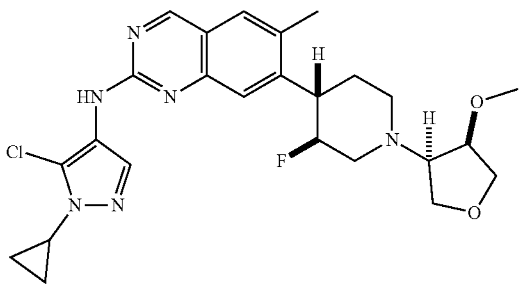
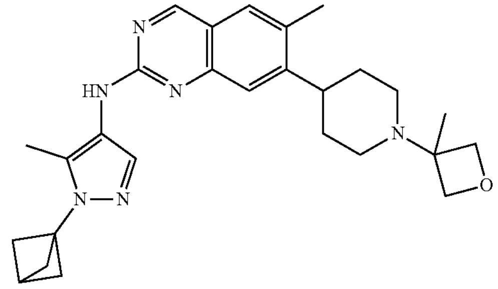
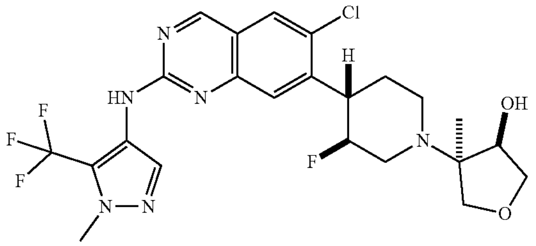
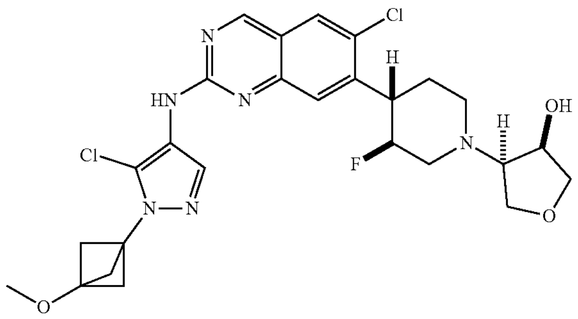
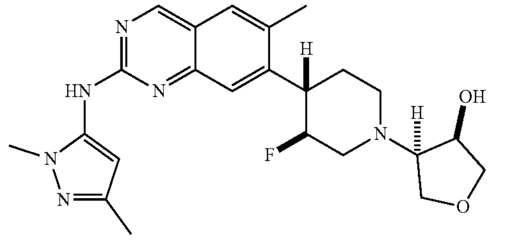

-continued
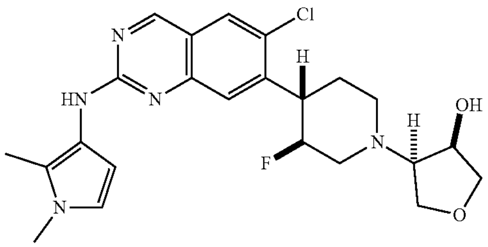
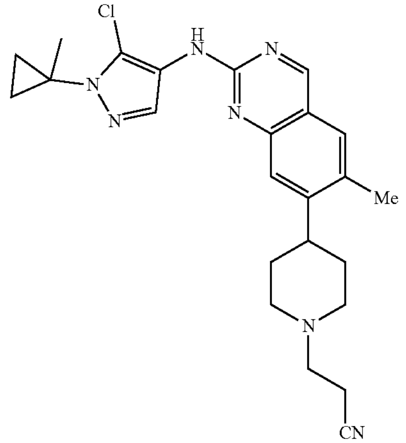
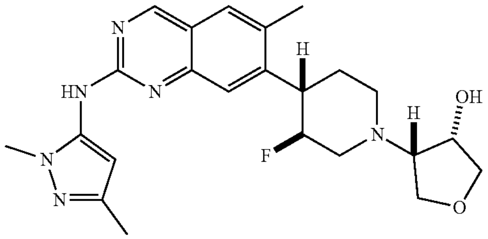
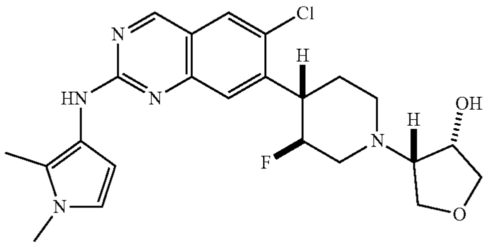
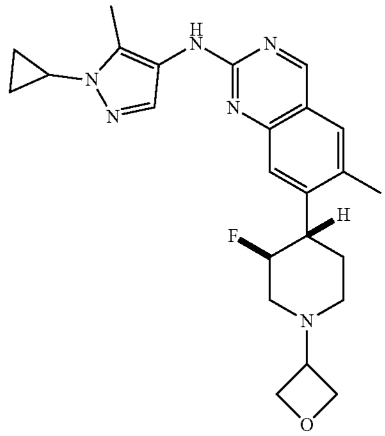
-continued
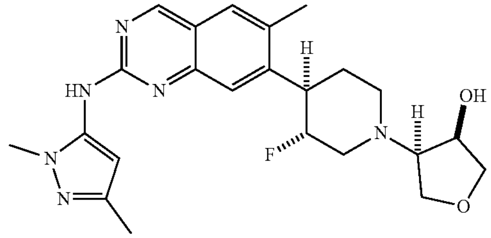
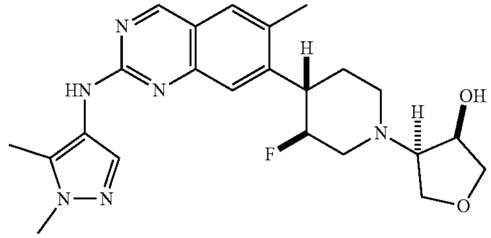
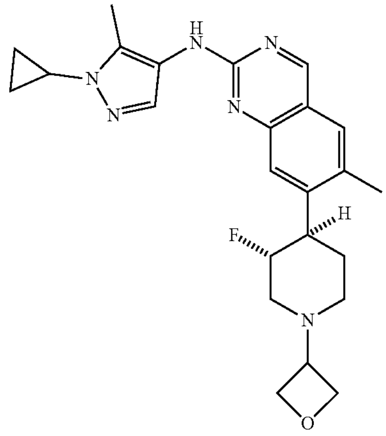
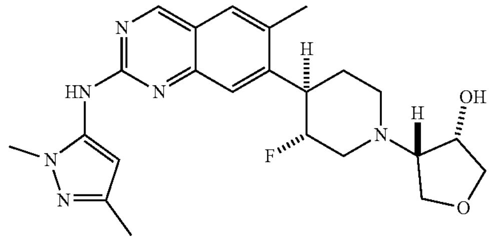
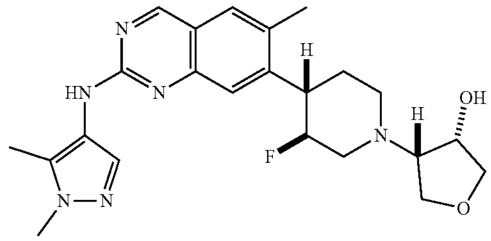
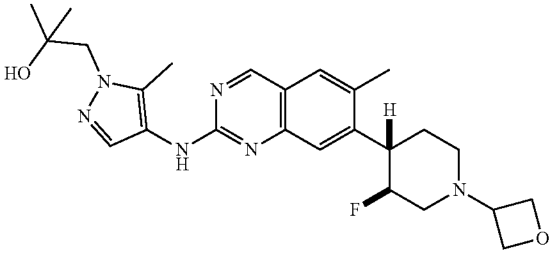

-continued
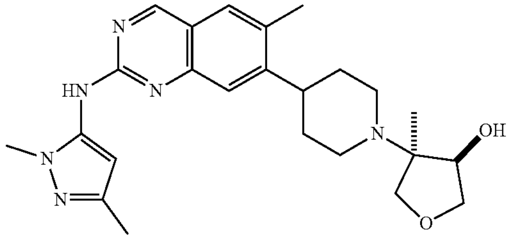
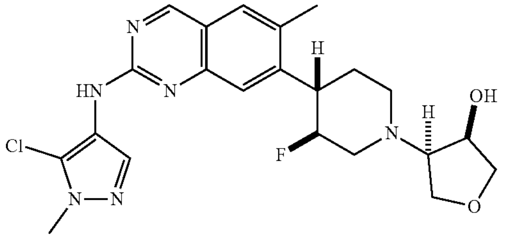
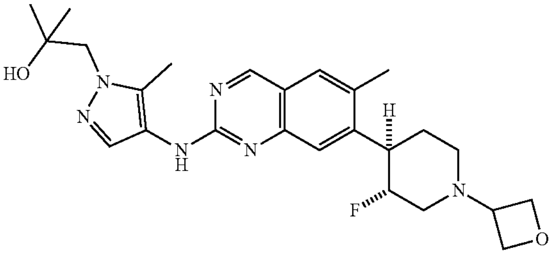
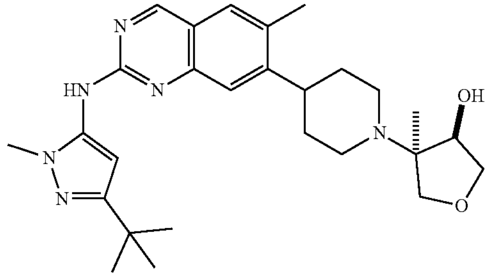
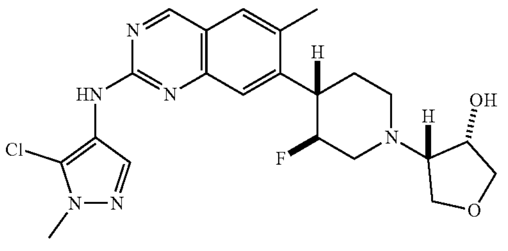
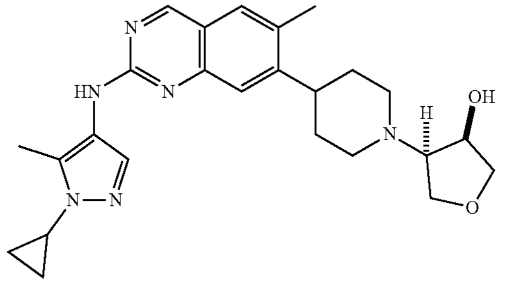
-continued
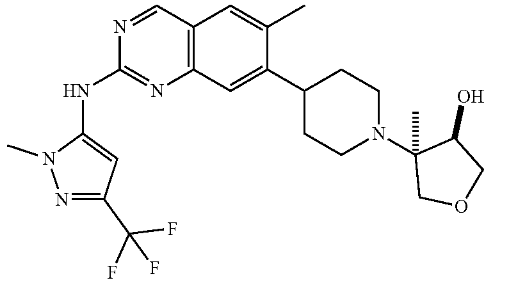
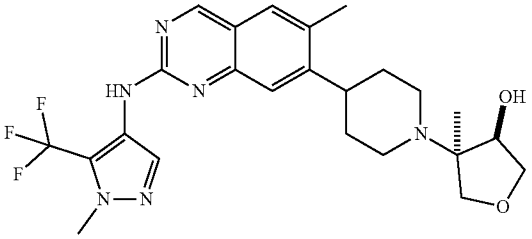
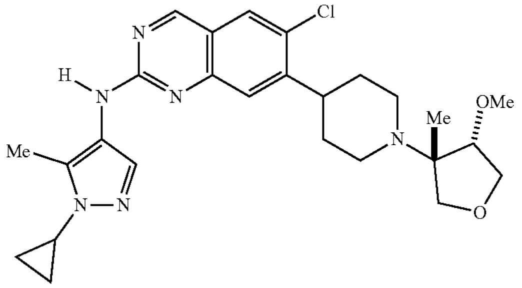
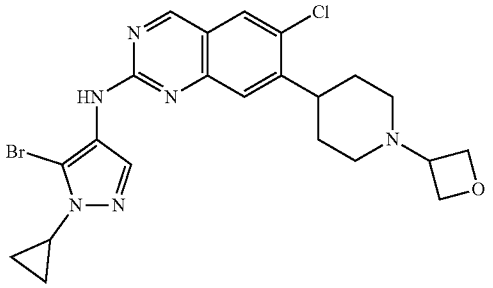
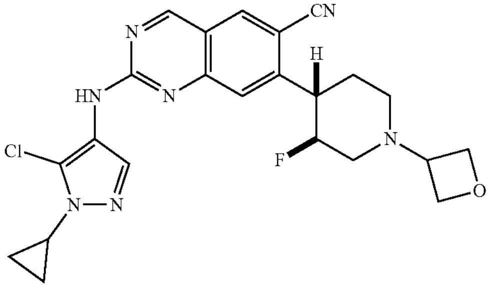
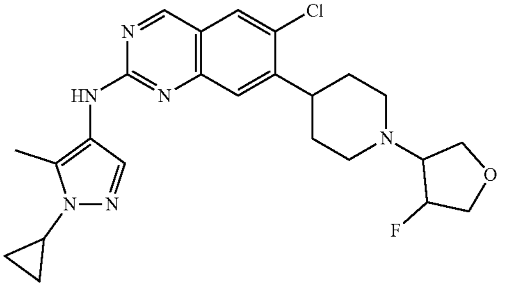

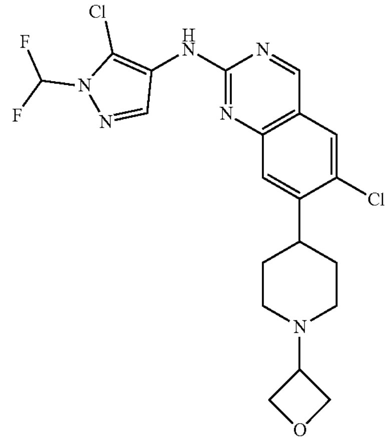
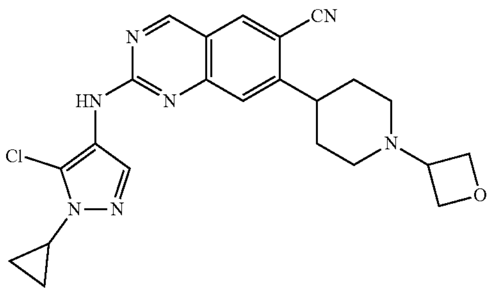
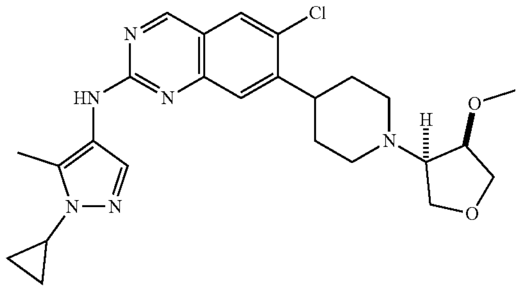
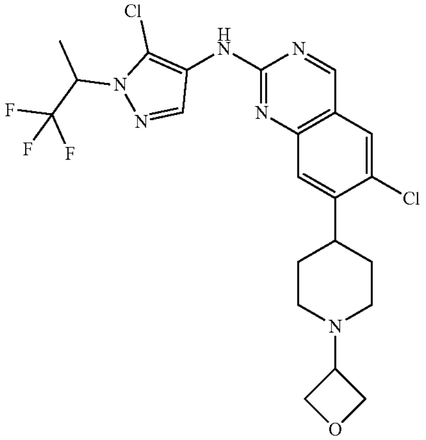
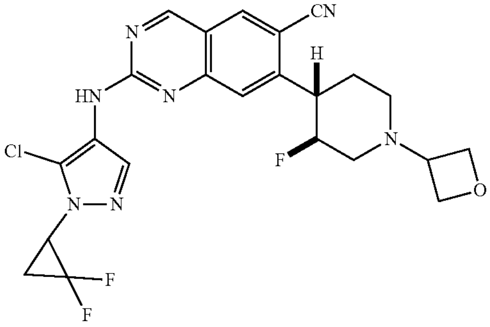
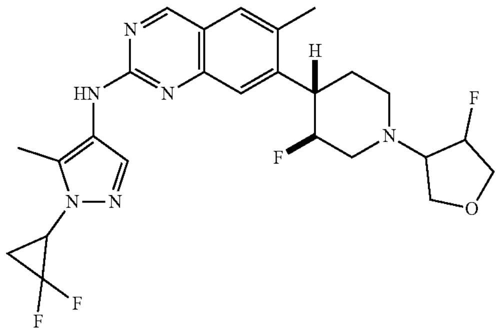
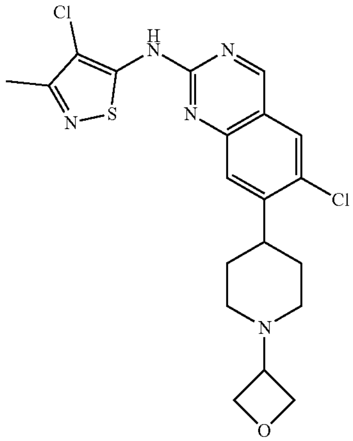
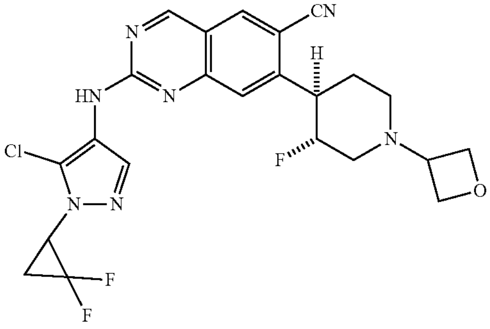
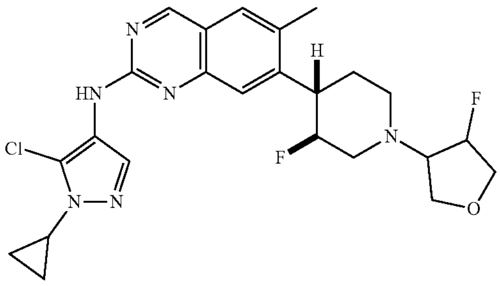

-continued
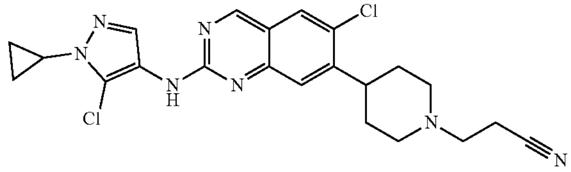
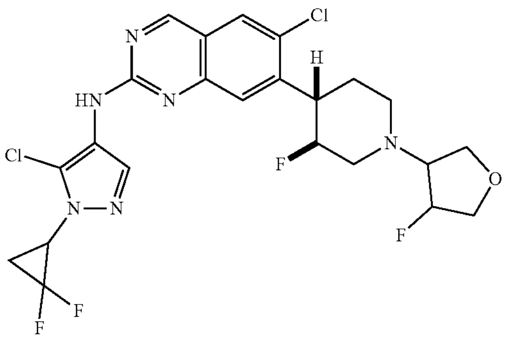
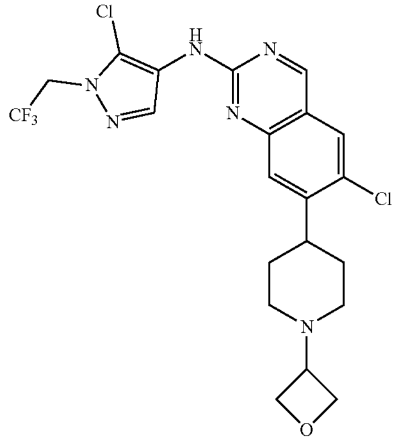
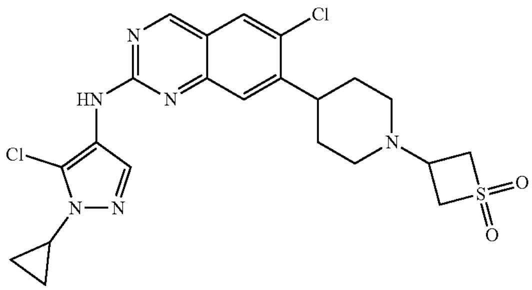
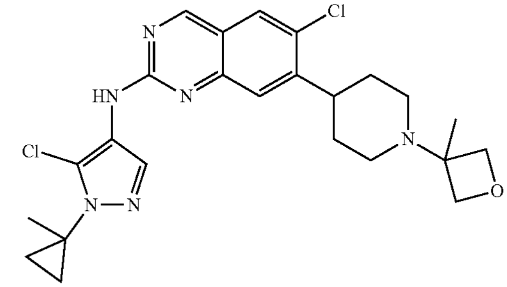
-continued
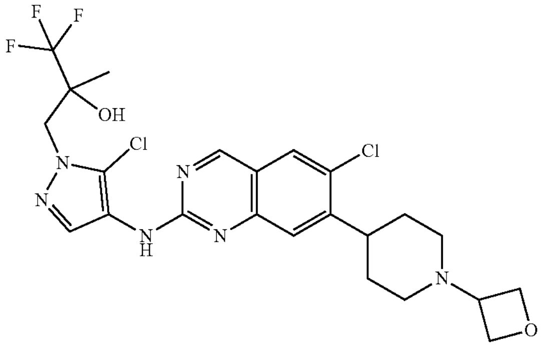
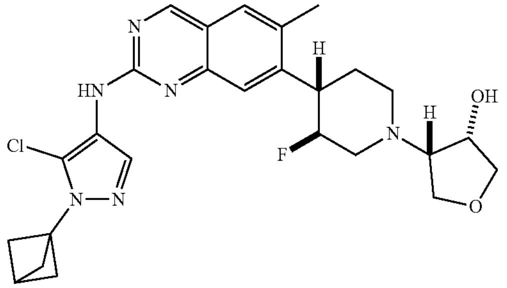
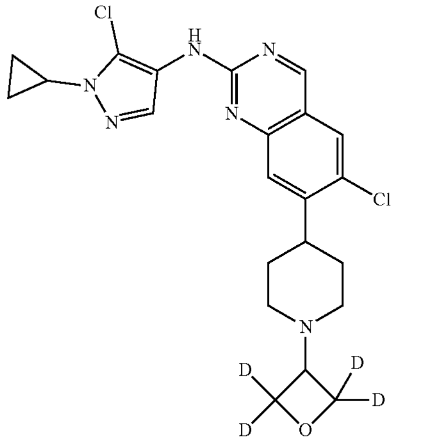
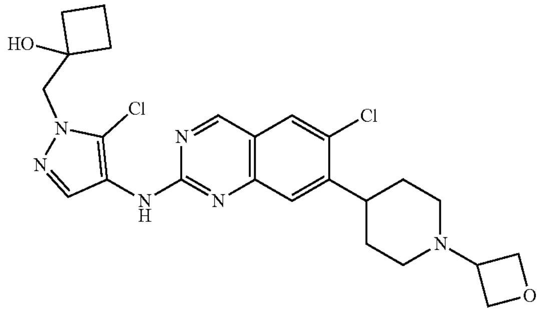
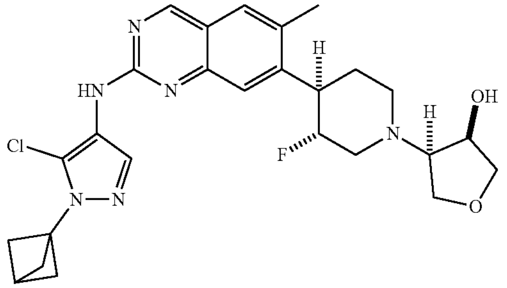

-continued
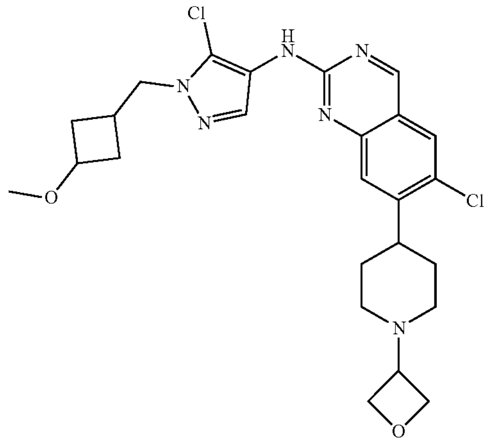
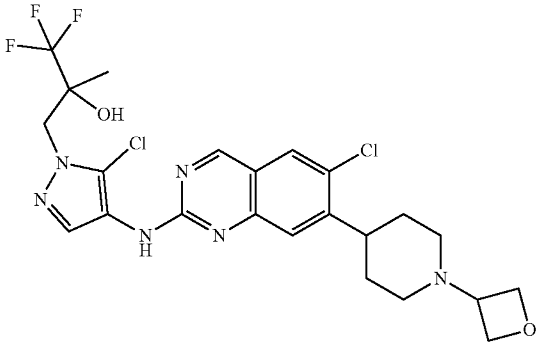
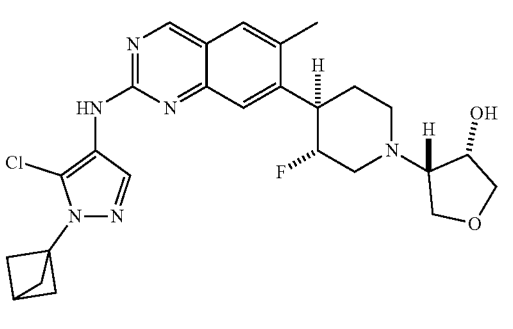
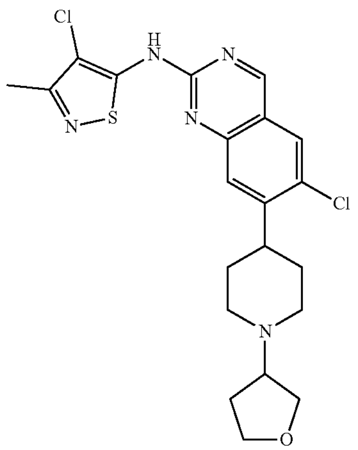
-continued
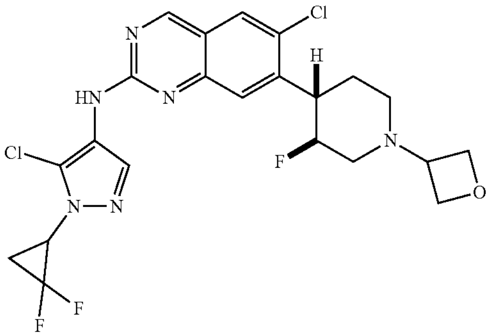
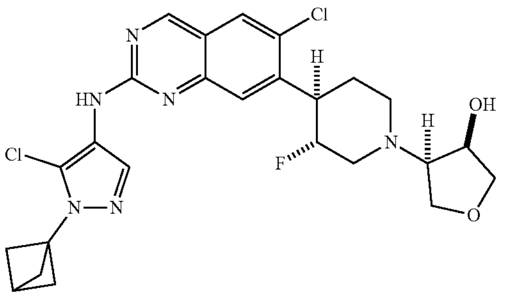
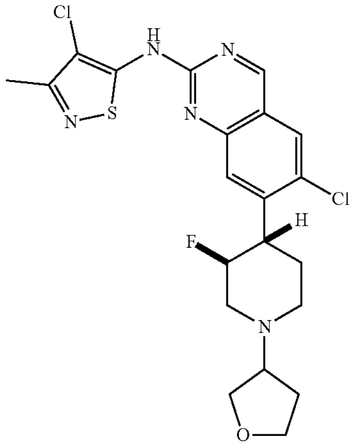
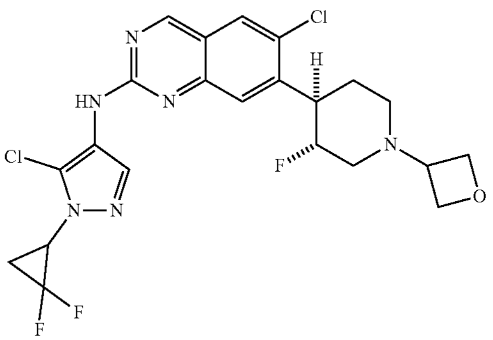
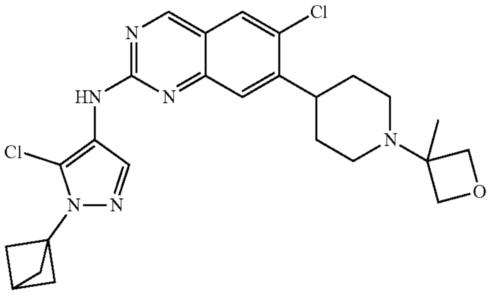

-continued

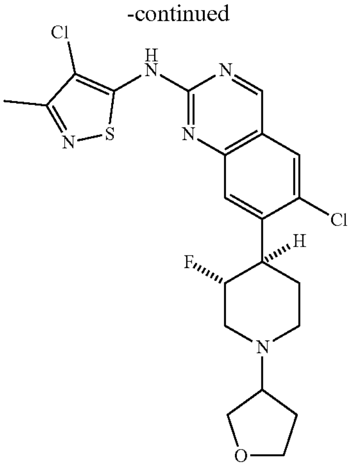

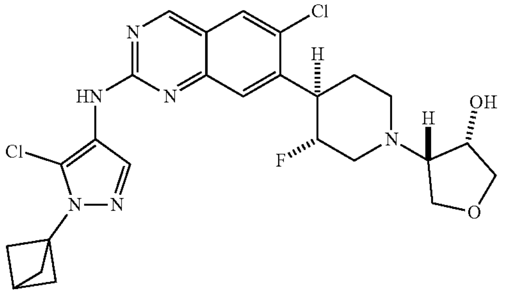

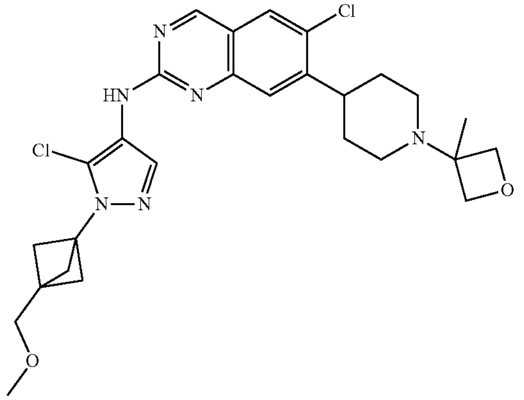

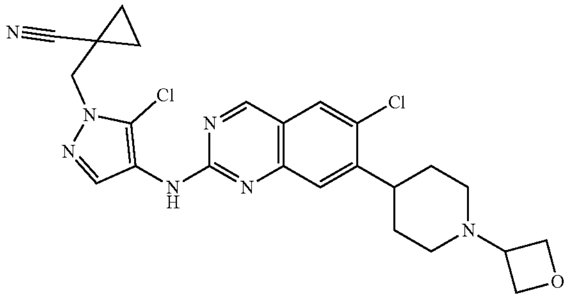

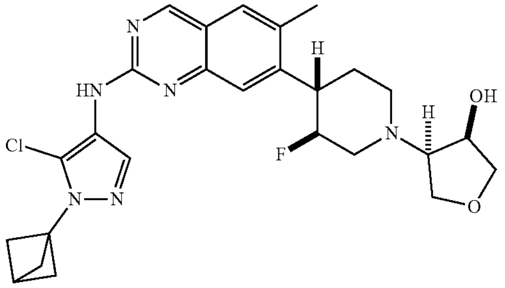

-continued

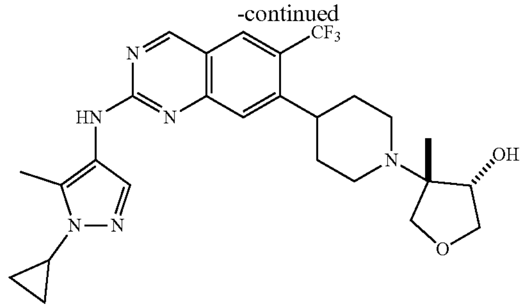

and

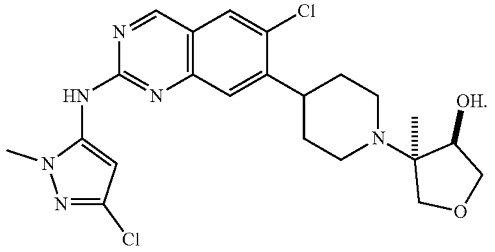

16. A pharmaceutical composition comprising a compound of claim 1, or a pharmaceutically acceptable salt thereof, and a pharmaceutically acceptable carrier.

17. A method of treating Parkinson's Disease comprising administering an effective amount of a compound of claim 1, or a pharmaceutically acceptable salt thereof, or a pharmaceutically acceptable composition of the same to a person in need thereof.

18. A method for the treatment of an indication in which LRRK2 kinase is involved comprising administering to a subject in need thereof an effective amount of a compound according to claim 1, or a pharmaceutically acceptable salt thereof, or a pharmaceutically acceptable composition of the same, said indication selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tauopathy disorders characterized by hyperphosphorylation of tau, and Parkinson's disease linked to chromosome 17, neuroinflammation associated with of microglial inflammatory responses associated with multiple sclerosis, HIV-induced dementia, ALS, ischemic stroke, traumatic brain injury and spinal cord injury, lymphomas, leukemias, multiple sclerosis, rheumatoid arthritis, systemic lupus erythematosus, autoimmune hemolytic anemia, pure red cell aplasia, idiopathic thrombocytopenia pupura (ITP), Evans Syndrome, vasculitis, bullous skin disorder, type I diabetes mellitus, Sjogren's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

* * * * *